US010415015B2

(12) United States Patent
Veerapathran et al.

(10) Patent No.: US 10,415,015 B2
(45) Date of Patent: Sep. 17, 2019

(54) ENGINEERED ARTIFICIAL ANTIGEN PRESENTING CELLS FOR TUMOR INFILTRATING LYMPHOCYTE EXPANSION

(71) Applicant: Iovance Biotherapeutics, Inc., San Carlos, CA (US)

(72) Inventors: Anand Veerapathran, Tampa, FL (US); Aishwarya Gokuldass, Chennai (IN); Brian Rabinovich, Winchester, MA (US); Michael T. Lotze, Pittsburgh, PA (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 0 days.

(21) Appl. No.: 15/800,967

(22) Filed: Nov. 1, 2017

(65) Prior Publication Data
US 2018/0127715 A1 May 10, 2018

Related U.S. Application Data

(63) Continuation of application No. PCT/US2017/059271, filed on Oct. 31, 2017.

(60) Provisional application No. 62/415,274, filed on Oct. 31, 2016, provisional application No. 62/438,600, filed on Dec. 23, 2016, provisional application No. 62/475,053, filed on Mar. 22, 2017, provisional application No. 62/481,831, filed on Apr. 5, 2017.

(51) Int. Cl.
| | |
|---|---|
| *A61K 39/00* | (2006.01) |
| *C12N 5/0781* | (2010.01) |
| *C12N 5/0784* | (2010.01) |
| *C12N 5/078* | (2010.01) |
| *A61P 35/00* | (2006.01) |
| *C07K 14/705* | (2006.01) |
| *C07K 16/42* | (2006.01) |

(52) U.S. Cl.
CPC ........ *C12N 5/0635* (2013.01); *A61K 39/0011* (2013.01); *A61P 35/00* (2018.01); *C07K 14/70532* (2013.01); *C07K 14/70575* (2013.01); *C07K 16/4283* (2013.01); *C12N 5/065* (2013.01); *C12N 5/0639* (2013.01); *A61K 2039/515* (2013.01); *A61K 2039/5158* (2013.01); *C07K 2317/622* (2013.01); *C12N 2501/06* (2013.01); *C12N 2501/2302* (2013.01); *C12N 2501/25* (2013.01); *C12N 2501/51* (2013.01); *C12N 2501/515* (2013.01); *C12N 2501/998* (2013.01); *C12N 2502/11* (2013.01); *C12N 2502/99* (2013.01)

(58) Field of Classification Search
None
See application file for complete search history.

(56) References Cited

U.S. PATENT DOCUMENTS

| | | |
|---|---|---|
| 4,370,338 A | 1/1983 | Mizoule |
| 4,766,106 A | 8/1988 | Katre et al. |
| 4,820,516 A | 4/1989 | Sawyer et al. |
| 4,902,502 A | 2/1990 | Nitecki et al. |
| 5,089,261 A | 2/1992 | Nitecki et al. |
| 5,177,017 A | 1/1993 | Lin et al. |
| 5,206,344 A | 4/1993 | Katre et al. |
| 5,279,833 A | 1/1994 | Rose |
| 5,422,261 A | 6/1995 | Lee et al. |
| 5,593,875 A | 1/1997 | Wurm et al. |
| 5,593,877 A | 1/1997 | King |
| 5,601,819 A | 2/1997 | Wong et al. |
| 5,648,260 A | 7/1997 | Winter et al. |
| 5,714,350 A | 2/1998 | Co et al. |
| 5,739,277 A | 4/1998 | Presta et al. |
| 5,766,902 A | 6/1998 | Craig et al. |
| 5,783,433 A | 7/1998 | Frenz et al. |
| 5,824,778 A | 10/1998 | Ishikawa et al. |
| 5,827,642 A | 10/1998 | Riddell et al. |
| 5,834,250 A | 11/1998 | Wells et al. |

(Continued)

FOREIGN PATENT DOCUMENTS

| | | |
|---|---|---|
| EP | 0154316 | 11/1985 |
| EP | 0401384 | 6/1990 |

(Continued)

OTHER PUBLICATIONS

Pini et al Design and use of a phage display library. Human antibodies with subnanomolar affinity against a marker of angiogenesis eluted from a two-dimensional gel J. Biol. Chem. 273:21769-21776(1998).*

(Continued)

*Primary Examiner* — Maria G Leavitt

(74) *Attorney, Agent, or Firm* — Morgan, Lewis & Bockius, LLP

(57) ABSTRACT

In some embodiments, compositions and methods relating to isolated artificial antigen presenting cells (aAPCs) are disclosed, including aAPCs comprising a myeloid cell transduced with one or more viral vectors, such as a MOLM-14 or a EM-3 myeloid cell, wherein the myeloid cell endogenously expresses HLA-AB/C, ICOS-L, and CD58, and wherein the one or more viral vectors comprise a nucleic acid encoding CD86 and a nucleic acid encoding 4-1BBL and/or OX40L and transduce the myeloid cell to express CD86 and 4-1BBL and/or OX40L proteins. In some embodiments, methods of expanding tumor infiltrating lymphocytes (TILs) with aAPCs and methods of treating cancers using TILs after expansion with aAPCs are also disclosed.

12 Claims, 98 Drawing Sheets
Specification includes a Sequence Listing.

(56) References Cited

U.S. PATENT DOCUMENTS

| | | | |
|---|---|---|---|
| 5,869,046 A | 2/1999 | Presta et al. | |
| 5,877,293 A | 3/1999 | Adair et al. | |
| 5,886,152 A | 3/1999 | Nakatani et al. | |
| 5,908,635 A | 6/1999 | Thierry | |
| 5,928,893 A | 7/1999 | Kang et al. | |
| 5,962,320 A | 10/1999 | Robinson | |
| 5,989,888 A | 11/1999 | Dwulet et al. | |
| 6,025,337 A | 2/2000 | Truong et al. | |
| 6,040,177 A | 3/2000 | Riddell et al. | |
| 6,054,297 A | 4/2000 | Carter et al. | |
| 6,056,938 A | 5/2000 | Unger et al. | |
| 6,096,871 A | 8/2000 | Presta et al. | |
| 6,110,490 A | 8/2000 | Thierry | |
| 6,121,022 A | 9/2000 | Presta et al. | |
| 6,123,938 A | 9/2000 | Stern et al. | |
| 6,194,551 B1 | 2/2001 | Idusogie et al. | |
| 6,210,669 B1 | 4/2001 | Aruffo et al. | |
| 6,242,195 B1 | 6/2001 | Idusogie et al. | |
| 6,277,375 B1 | 8/2001 | Ward | |
| 6,303,121 B1 | 10/2001 | Kwon | |
| 6,312,700 B1 | 11/2001 | Starr | |
| 6,350,861 B1 | 2/2002 | Co et al. | |
| 6,362,325 B1 | 3/2002 | Kwon | |
| 6,391,607 B1 | 5/2002 | Lazarus et al. | |
| 6,410,517 B1 | 6/2002 | Truong et al. | |
| 6,475,994 B2 | 11/2002 | Tomalia et al. | |
| 6,489,458 B2 | 12/2002 | Hackett et al. | |
| 6,528,624 B1 | 3/2003 | Idusogie et al. | |
| 6,534,484 B1 | 3/2003 | Wheeler et al. | |
| 6,538,124 B1 | 3/2003 | Idusogie et al. | |
| 6,569,997 B1 | 5/2003 | Kwon | |
| 6,627,442 B1 | 9/2003 | Humeau et al. | |
| 6,706,289 B2 | 3/2004 | Lewis et al. | |
| 6,737,056 B1 | 5/2004 | Presta | |
| 6,821,505 B2 | 11/2004 | Ward | |
| 6,887,673 B2 | 5/2005 | Kunkel et al. | |
| 6,905,685 B2 | 6/2005 | Kwon | |
| 6,974,863 B2 | 12/2005 | Kwon | |
| 6,998,253 B1 | 2/2006 | Presta et al. | |
| 7,070,995 B2 | 7/2006 | Jensen | |
| 7,083,784 B2 | 8/2006 | Dall'Acqua et al. | |
| 7,118,742 B2 | 10/2006 | Ware | |
| 7,189,705 B2 | 3/2007 | Lam et al. | |
| 7,214,493 B2 | 5/2007 | Kunkel et al. | |
| 7,288,638 B2 | 10/2007 | Jure-Kunkel et al. | |
| 7,297,526 B2 | 11/2007 | Shak | |
| 7,407,785 B2 | 8/2008 | Lazarus et al. | |
| 7,446,190 B2 | 11/2008 | Sadelain et al. | |
| 7,504,101 B2 | 3/2009 | Weinberg | |
| 7,550,140 B2 | 6/2009 | Bakker et al. | |
| 7,569,664 B2 | 8/2009 | Jakobsen et al. | |
| 7,622,444 B2 | 11/2009 | Weinberg | |
| 7,638,325 B2 * | 12/2009 | June ............... | C12N 5/0634 435/325 |
| 7,687,070 B2 | 3/2010 | Gebeyehu et al. | |
| 7,696,175 B2 | 4/2010 | Epstein et al. | |
| 7,754,482 B2 | 7/2010 | Riley et al. | |
| 7,767,429 B2 | 8/2010 | Bookbinder et al. | |
| 7,812,135 B2 | 10/2010 | Smith et al. | |
| 7,943,743 B2 | 5/2011 | Korman et al. | |
| 7,960,515 B2 | 6/2011 | Min et al. | |
| 7,961,515 B2 | 6/2011 | Kato et al. | |
| 8,008,449 B2 | 8/2011 | Korman et al. | |
| 8,133,983 B2 | 3/2012 | Bakker et al. | |
| 8,168,757 B2 | 5/2012 | Finnefrock et al. | |
| 8,202,517 B2 | 6/2012 | Bookbinder et al. | |
| 8,217,149 B2 | 7/2012 | Irving et al. | |
| 8,236,930 B2 | 8/2012 | Min et al. | |
| 8,287,856 B2 | 10/2012 | Li et al. | |
| 8,337,850 B2 | 12/2012 | Ahrens et al. | |
| 8,354,509 B2 | 1/2013 | Carven et al. | |
| 8,367,804 B2 | 2/2013 | Boulter et al. | |
| 8,388,967 B2 | 3/2013 | Smith et al. | |
| 8,399,645 B2 | 3/2013 | Campana et al. | |
| 8,431,124 B2 | 4/2013 | Bookbinder et al. | |
| 8,431,380 B2 | 4/2013 | Bookbinder et al. | |
| 8,450,460 B2 | 5/2013 | Hill et al. | |
| 8,580,247 B2 | 11/2013 | Li et al. | |
| 8,686,119 B2 | 4/2014 | Rotem-Yehudar et al. | |
| 8,709,424 B2 | 4/2014 | Schebye et al. | |
| 8,722,400 B2 | 5/2014 | Riley et al. | |
| 8,735,553 B1 | 5/2014 | Li et al. | |
| 8,779,108 B2 | 7/2014 | Queva et al. | |
| 8,809,050 B2 | 9/2014 | Vera et al. | |
| 8,821,867 B2 | 9/2014 | Ahrens et al. | |
| 8,907,053 B2 | 12/2014 | Sasikumar et al. | |
| 8,916,381 B1 | 12/2014 | June et al. | |
| 8,921,519 B2 | 12/2014 | Hill et al. | |
| 8,956,860 B2 | 2/2015 | Vera et al. | |
| 8,962,804 B2 | 2/2015 | Williams et al. | |
| 9,006,399 B2 | 4/2015 | Liu et al. | |
| 9,028,823 B2 | 5/2015 | Smith et al. | |
| 9,028,824 B2 | 5/2015 | Min et al. | |
| 9,044,442 B2 | 6/2015 | Sasikumar et al. | |
| 9,096,642 B2 | 8/2015 | Sasikumar et al. | |
| 9,163,085 B2 | 10/2015 | Liu et al. | |
| 9,211,316 B2 | 12/2015 | Munoz Montano | |
| 9,328,156 B2 | 5/2016 | June et al. | |
| 9,340,599 B2 | 5/2016 | Hill et al. | |
| 9,359,420 B2 | 6/2016 | Hill et al. | |
| 9,468,678 B2 | 10/2016 | Ahrens et al. | |
| 9,555,105 B2 | 1/2017 | Riley et al. | |
| 2004/0110704 A1 | 6/2004 | Yamaune et al. | |
| 2005/0095244 A1 | 5/2005 | Jure-Kunkel et al. | |
| 2005/0106717 A1 | 5/2005 | Wilson et al. | |
| 2005/0177518 A1 | 8/2005 | Michener | |
| 2006/0034810 A1 | 2/2006 | Riley et al. | |
| 2009/0028857 A1 | 1/2009 | Li et al. | |
| 2010/0136030 A1 | 6/2010 | Salah-Eddine et al. | |
| 2010/0203056 A1 | 8/2010 | Irving et al. | |
| 2010/0266617 A1 | 10/2010 | Carven et al. | |
| 2010/0285013 A1 | 11/2010 | Li et al. | |
| 2011/0008369 A1 | 1/2011 | Finnefrock et al. | |
| 2011/0027218 A1 | 2/2011 | Hill et al. | |
| 2011/0052530 A1 | 3/2011 | Dudley et al. | |
| 2011/0111494 A1 | 5/2011 | Hill et al. | |
| 2011/0136228 A1 | 6/2011 | Vera et al. | |
| 2011/0274685 A1 | 11/2011 | Keler et al. | |
| 2012/0015888 A1 * | 1/2012 | Rosenberg ............ | C07K 14/705 514/19.3 |
| 2012/0189639 A1 | 7/2012 | Schebye et al. | |
| 2012/0213771 A1 | 8/2012 | Keler et al. | |
| 2012/0244133 A1 | 9/2012 | Rosenberg et al. | |
| 2013/0022600 A1 | 1/2013 | Li et al. | |
| 2013/0034559 A1 | 2/2013 | Queva et al. | |
| 2013/0045200 A1 | 2/2013 | Irving et al. | |
| 2013/0045201 A1 | 2/2013 | Irving et al. | |
| 2013/0045202 A1 | 2/2013 | Irving et al. | |
| 2013/0102075 A1 | 4/2013 | Vera et al. | |
| 2013/0108641 A1 | 5/2013 | Baurin et al. | |
| 2013/0108651 A1 | 5/2013 | Carven et al. | |
| 2013/0109843 A1 | 5/2013 | Carven et al. | |
| 2013/0115617 A1 | 5/2013 | Wilson | |
| 2014/0065135 A1 | 3/2014 | Irving et al. | |
| 2014/0112942 A1 | 4/2014 | Van Eenennaam et al. | |
| 2014/0227237 A1 | 8/2014 | June et al. | |
| 2014/0294898 A1 | 10/2014 | Miller et al. | |
| 2014/0328791 A1 | 11/2014 | Bossard et al. | |
| 2014/0341917 A1 | 11/2014 | Nastri et al. | |
| 2014/0348841 A1 | 11/2014 | Schebye et al. | |
| 2014/0377284 A1 | 12/2014 | Simons et al. | |
| 2014/0377739 A1 | 12/2014 | Welch et al. | |
| 2015/0064204 A1 | 3/2015 | Beers et al. | |
| 2015/0073024 A1 | 3/2015 | Sasikumar et al. | |
| 2015/0073042 A1 | 3/2015 | Sasikumar et al. | |
| 2015/0087581 A1 | 3/2015 | Sasikumar et al. | |
| 2015/0110734 A1 | 4/2015 | Hill et al. | |
| 2015/0119923 A1 | 4/2015 | Liberatore et al. | |
| 2015/0125419 A1 | 5/2015 | Hill et al. | |
| 2015/0125491 A1 | 5/2015 | Sasikumar et al. | |
| 2015/0126709 A1 | 5/2015 | Hill et al. | |
| 2015/0126710 A1 | 5/2015 | Hill et al. | |
| 2015/0132288 A1 | 5/2015 | Simons et al. | |
| 2015/0175966 A1 | 6/2015 | Vera et al. | |

(56) References Cited

U.S. PATENT DOCUMENTS

| | | | |
|---|---|---|---|
| 2015/0190506 A1 | 7/2015 | Cheung et al. | |
| 2016/0010058 A1 | 1/2016 | Gros et al. | |
| 2016/0051698 A1 | 2/2016 | Schneck et al. | |
| 2016/0144018 A1 | 5/2016 | Hinrichs et al. | |
| 2016/0176941 A1 | 6/2016 | Hill et al. | |
| 2016/0208216 A1 | 7/2016 | Vera et al. | |
| 2016/0272695 A1 | 9/2016 | Hill et al. | |
| 2017/0152478 A1 | 6/2017 | Rosenberg et al. | |
| 2017/0160269 A1* | 6/2017 | Linnemann | G01N 33/505 |

FOREIGN PATENT DOCUMENTS

| | | |
|---|---|---|
| EP | 0404097 | 9/1996 |
| EP | 1176195 | 1/2002 |
| EP | 0672141 | 5/2003 |
| WO | 88/07089 | 9/1988 |
| WO | 93/11161 | 6/1993 |
| WO | WO94/26290 * | 11/1994 |
| WO | 95/12673 | 5/1995 |
| WO | 95/21925 | 8/1995 |
| WO | 95/27735 | 10/1995 |
| WO | 1995027735 | 10/1995 |
| WO | 96/14339 | 5/1996 |
| WO | 98/05787 | 2/1998 |
| WO | 98/10088 | 3/1998 |
| WO | 98/23289 | 6/1998 |
| WO | 99/42585 | 8/1999 |
| WO | 99/51642 | 10/1999 |
| WO | 99/54342 | 10/1999 |
| WO | 99/58572 | 11/1999 |
| WO | 00/09560 | 2/2000 |
| WO | 00/32767 | 6/2000 |
| WO | 00/42072 | 7/2000 |
| WO | WO2001/88097 * | 11/2001 |
| WO | 02/44215 | 6/2002 |
| WO | 02/060919 | 8/2002 |
| WO | 03/035835 | 5/2003 |
| WO | 03/057171 | 7/2003 |
| WO | 03/074569 | 9/2003 |
| WO | 2004/016750 | 2/2004 |
| WO | 2004/029207 | 4/2004 |
| WO | 2004/035752 | 4/2004 |
| WO | 2004/063351 | 7/2004 |
| WO | 2004/074455 | 9/2004 |
| WO | 2004/099249 | 11/2004 |
| WO | 2005/040217 | 5/2005 |
| WO | 2005/070963 | 8/2005 |
| WO | 2005/077981 | 8/2005 |
| WO | 2005/092925 | 10/2005 |
| WO | 2005/103077 | 11/2005 |
| WO | 2005103077 | 11/2005 |
| WO | 2005/123780 | 12/2005 |
| WO | 2006/019447 | 2/2006 |
| WO | 2006/047350 | 5/2006 |
| WO | 2006/085967 | 8/2006 |
| WO | 2006/121810 | 11/2006 |
| WO | 2008/025516 | 3/2008 |
| WO | 2008025516 | 3/2008 |
| WO | 2008/156712 | 12/2008 |
| WO | 2009/007120 | 1/2009 |
| WO | 2009007120 | 1/2009 |
| WO | 2010/003766 | 1/2010 |
| WO | 2010/010051 | 1/2010 |
| WO | 2010003766 | 1/2010 |
| WO | 2010010051 | 1/2010 |
| WO | 2010/042433 | 4/2010 |
| WO | 2010/0126766 | 4/2010 |
| WO | 2010/078966 | 7/2010 |
| WO | 2011/028683 | 3/2011 |
| WO | 2011072088 | 6/2011 |
| WO | 2012/004367 | 1/2012 |
| WO | 2012/027328 | 3/2012 |
| WO | 2012/032433 | 3/2012 |
| WO | 2012065086 | 5/2012 |
| WO | 2012129201 | 9/2012 |
| WO | 2012/177788 | 12/2012 |
| WO | 2013/028231 | 2/2013 |
| WO | 2013/038191 | 3/2013 |
| WO | 2013/039954 | 3/2013 |
| WO | 2013173835 | 11/2013 |
| WO | 2013188427 | 12/2013 |
| WO | 2014/148895 | 9/2014 |
| WO | 2014210036 | 12/2014 |
| WO | 2015/026684 | 2/2015 |
| WO | 2015/031667 | 3/2015 |
| WO | 2015/033301 | 3/2015 |
| WO | 2015/036927 | 3/2015 |
| WO | 2015/119923 | 8/2015 |
| WO | 2016/145085 | 9/2015 |
| WO | 2015/164816 | 10/2015 |
| WO | 2015/189356 | 12/2015 |
| WO | 2015/189357 | 12/2015 |
| WO | 2016/108244 | 7/2016 |

OTHER PUBLICATIONS

Ngo, in the Protein Folding Problem and Tertiary Structure Prediction, Merz et al. (eds.), Birkhauser Boston: Boston, MA, pp. 433 and 492-495, 1994.*

Axelsson et al., "Cryopreserved peripheral blood mononuclear cells are suitable for the assessment of immunological markers in type 1 diabetic children", Cryobiology, Aug. 2008, 57, 201-208.

Bierer et al., "Cyclosporin A and FK506: molecular mechanisms of immunosuppression and probes for transplantation of biology", Current Opinion in Immunology, 1993, 57, 763-773.

Bird et al., "Single-Chain Antigen-Binding Proteins", Reports, Oct. 1988, 423-426.

Boshart et al., "A Very Strong Enhancer is located upstream of an immediate early gene cytomegalovirus", Cell, Jun. 1995, 41, 521-530.

Cawthon, "Telomere measurements by quantitative PCR", Nucleic Acids, Mar. 2002, 30(10), 6 pages.

Eton et al., "A Phase II Study of "Decrescendo" Interleukin-2 plus Interferon-a-2a in Patients with Progressive Metastatic Melanoma after chemotherapy", Cancer, Apr. 2000, 88(7), 1703-1709.

Goff et al., "Tumor Infiltrating Lymphocyte Therapy for Metastatic Melanoma: Analysis of Tumors Resected for TIL", J. Immunother, Oct. 2010, 33(8), 840-847.

Goff et al., "Randomized, Prospective Evaluation Comparing Intensity of Lymphodepletion before adoptive transfer of tumor-infiltrating lymphocytes for patients with metastatic melanoma", Journal of Clinical Oncology, Jul. 2016, 34(20), 71 pages.

Gossen et al., "Transcriptional Activation by Tetracyclines in Mammalian Cells", Science, Jun. 1995, 268, 1766-1769.

Gribskov et al., "Sigma Factors from E. coli, B subtilis, phage SP01, and phage T4 homologous proteins", Nucleic Acids Research, Mar. 1986, 14(16), 19 pages.

Grussenmeyer et al., "Complexes of Polyoma virus medium T antigen and cellular proteins", Proc Natl. Acad. Sci., USA Dec. 1985, 82, 7952-7954.

Harvey et al., "Inducible Control of Gene Expression: Prospects for Gene Therapy", Current Opinion in Chemical Biology, 1998, 2, 512-518.

Holliger, et al., "Diabodies": Small bivalent and biospecific antibody fragments, Proc. Natl. Acad. Sci. USA, Jul. 1993, 90, 6444-6448.

Houot et al., "Therapeutic effect of CD137 immunomodulation in lymphoma and its enhancement by Treg depletion", Blood, Oct. 2009, 114(16), 3431-3438.

Huston et al., "Protein engineering of antibody binding sites: recovery of specific activity in an anti-digoxin single-chain Fv analogue produced in *Escherichia coli*", Proc. Natl. Acad. Sci., USA, Aug. 1988, 85, 5879-5883.

Jones et al., "Lentiviral Vector Design for Optimal T Cell Receptor Gene Expression in the transduction of peripheral blood lymphocytes and tumor-infiltrating lymphocytes", Human Gene Therapy, Jun. 2009, 20, 630-640.

(56) References Cited

OTHER PUBLICATIONS

Katzen, "Gateway Recombinational cloning: a biological operating system" Expert Opin. Drug Discov. 2007, 2(4), 571-589.

Kohrt et al., "CD137 stimulation enhances the antilymphoma activity of anti-CD20 antibodies", Blood, Feb. 2011, 117(8), 2423-2432.

Lee et al., "4-1BB Signaling Activates the T Cell Factor 1 Effector /B-Catenin Pathway with Delayed Kinetics via ERK Signaling and Delayed PI3K/AKT Activation to Promote the Proliferation of CD8+ T Cells", PLOS, Jul. 2013, 11 pages.

Lee et al., "Tumor-Infiltrating Lymphocytes in Melanoma", Curr Oncol Rep. Aug. 2012, 14, 468-474.

Liu et al., "Calcineurin is a Common Target of Cyclophilin-Cyclosporin A and FKBp-FK506 Complexes", Cell, Aug. 1991, 66, 807-815.

Lynch, "The Promise of 4-1-BB (CD137_-mediated immunomodulation and immunotherapy of Cancer", Immunological Reviews, 2008, 277-286.

Magari et al., "Pharmacological Control of a Humanized Gene Therapy System Implanted into Nude Mice", J. Clin. Invest. Dec. 1997, 100(11), 2865-2872.

Nilsson et al., "Immobilization and Purification of Enzymes with Staphyloccal Protein A Gene Fusions", The EMBO Journal ,1985, 4(4), 1075-1080.

Nilsson et al., "Expression and Purification of Recombinant Insulin-Like growth factors from *Escherichia coli*", Methods in Enzymology, 1991, 198, 14 pages.

No et al., "Ecdysone-inducible gene expression in mammalian cells and transgeneic Mice", Proc Natl. Acad. Sci. USA, Apr. 1996, 93, 3346-3351.

O'Day et al., "Advantages of Concurrent Biochemotherapy Modified by Decrescendo Interleukin-2, Granulocyte Colony-Stimulating Factor, and Tamoxifen for Patients with Metastatic Melanoma", Journal of Oncology, Sep. 1999, 17(9), 2752-2761.

Poljak, "Production and Structure of Diabodies", Structure, Dec. 1994, 2, 1121-1123.

Rosenberg et al., "Use of Tumor-Infiltrating Lymphocytes and Interleukin-2 in the Immunotherapy of Patients with Metastatic Melanoma", The New England Journal of Medicine, Dec. 1988, 5 pages.

Sabbagh et al., "ERK-Dependent Bim Modulation Downstream of 4-1BB-TRAF1 Signaling Axis is a Crital Mediator of CD8 T Cell Survival in Vivo", The Journal of Immunology, 2008, 8093-8101.

Sallusto et al., "Central Memory and Effector Memory T Cell Subsets: Function, Generation, and Maintenance", Annu. Rev. Immunol., 2004, 22, 745-763.

Scharping et al., "The Turmor Microenvironment Represses T Cell Mitochondrial Biogenesis to Drive Intratumoral T Cell Metabolic Insufficiency and Dysfunction", Immunity, Aug. 2016, 45, 374-388.

Smith et al., "Single-Step Purification of Polypeptides Expressed in *Escherichia coli* as fusions with glutathione S-Transferase", Gene, Mar. 1988, 67, 31-40.

Smith et al., "Comparison of Biosequences" Advances in Applied Mathematics, 1981, 2, 482-489.

Steinke et al., "Th2 Cytokines and asthma Interleukin-4: Its role in the parthenogenesis of asthma, and targeting it for asthma treatment with interleukin-4 receptor antagonists", Respir Res, Feb. 2001, 2, 66-70.

Swartz et al., "Tumor Microenvironment Complexity: Emerging Roles in Cancer Therapy", American Association for Cancer Research, May 2012, 72(10), 2473-2480.

Turtle, "Artificial Antigen-Presenting Cells for Use in Adoptive Immunotherapy", The Cancer Journal, Jul.-Aug. 2010, 16(4), 374-381.

Vinay et al., "Dual Immunoregulatory pathways of 4-1BB Signaling", J. Mol Med., Feb. 2006, 84, 726-736.

Wang et at., "Positive and Negative regulation of gene expression in eukaryotic cells with an inducible transcriptional regulator", Gene Therapy, 1997, 4, 432-441.

Wang et al., "Ligand-Inducible and liver specific target gene expression in transgenic mice", Nature Biotechnology, Mar. 1997, 15, 239-243.

Wang et al., "Development of a Hypoxia-inducible cytosine deaminase expression vector for gene-directed prodrug cancer therapy", Cancer Gene Therapy, Jan. 2005, 12, 276-283.

Wang et al., "In Vitro Characterization of the Anti-PD-1 Antibody Nivolumab, BMS-936558, and in Vivo Toxicology in Non-Human primates", Cancer Immunol. Res., Sep. 2014, 2(9), 846-856.

Watts, "TNF/TNFR Family Members in Costimulation of T Cell Responses", Annu. Rev. Immunol. 2005, 23, 23-68.

Weber et al., "Safety, Efficacy, and Biomarkers of Nivolumab with Vaccine in Ipilimumab-Refractory or Naive-Melanoma", Journal of Clinical Oncology, Dec. 2013, 31(34), 10 pages.

Weinberg et al., "Engagement of the OX-40 Receptor in Vivo Enhances Antitumor Immunity", The Journal of Immunology, 2000, 2160-2169.

Yang et al., "Naive T-Cells in myelodysplastic syndrome display intrinsic human telomerase reverse transcriptase (hTERT) Deficiency", Leukemia, 2013, 27, 897-906.

Yi et al., "T-Cell exhaustion: Characteristics, causes and conversion", Immunology, 2010, 129, 474-481.

Donia et al., "Simplified protocol for clinical-grade tumor-infiltrating lymphocyte manufacturing with use of the Wave bioreactor"; Cythotherapy, Aug. 2014;16(8):1117-20.

Henning et al., "Measurement of T-Cell Telomere Length UNIT 7.47 Using Amplified-Signal FISH Staining and Flow Cytometry Curr Protoc Cytom."; Jan. 5, 2017; 79:7.1-47.10.

Kelesidis et al. "Assessment of Telomere Length, UNIT 7.26 Phenotype, and DNA Conten"; Curr Protoc Cytom. Jan. 5, 2017; 79:7.26.1-7.26.23.

Gardner et al., "Gender and telomere length: Systematic review and meta-analysis"; Exp Gerontol. Mar. 2014 51:15-27.

Carbonari et al., "Correlation between terminal restriction fragments and flow-FISH measures in samples over wide range telomere lengths"; Cell Prolif. Feb. 2014;47(1):20-7.

Rufer et al.; "Telomere length dynamics in human lymphocyte subpopulations measured by flow cytometry"; Nat Biotechnol. Aug. 1998;16(8):743-7.

Li et al., "MART-1—Specific Melanoma Tumor-Infiltrating Lymphocytes Maintaining CD28 Expression Have Improved Survival and Expansion Capability Following Antigenic Restimulation In Vitro"; J. Immunol. Jan. 1, 2010;184(1):452-65.

Rosenberg et al., "Adoptive cell therapy for the treatment of patients with metastatic melanoma"; Curr Opin Immunol. Apr. 2009;21(2)233-40.

Shen et al., "Persistence of Tumor Infiltrating Lymphocytes in AdoptiveImmunotherapy Correlates With Telomere Length"; J Immunother. Jan. 2007;30(1):123-9.

Zhou et al.; "Persistence of Multiple Tumor-Specific T-Cell Clones is Associated with Complete Tumor Regression in a Melanoma Patient Receiving Adoptive Cell Transfer Therapy"; J. Immunol. Nov. 15, 2005;175(10):7046-52.

Goff et al., "Randomized, Prospective Evaluation Comparing Intensity of Lymphodepletion Before Adoptive Transfer of Tumor-Infiltrating Lymphocytes for Patients With Metastatic Melanoma"; J. Clin Oncol. Jul. 10, 2016;34(2):2389-97.

Erdel et al.; "Telomere Recognition and Assembly Mechanism of Mammalian Shelterin"; Cell Rep Jan. 3, 2017;18(1)41-53.

Cardenas et al., "A Xenopus egg factor with DNA-binding properties characteristic of terminus-specific telomeric proteins"; Genes Dev. May 1993;7(5):883-94.

de Lange; "Activation of telomerase in a human tumor"; Proc Natl Acad Sci USA Apr. 12, 1994;91(8):2882-5.

de Lange; "Structure and Variability of Human Chromosome Ends"; Mol Cell Biol. Feb. 1990;10(2):518-27.

Buck et al., "T cell metabolism drives immunity"; JEM 212: 1345-1360; 2015.

Tran, KQ, Zhou, J., Durflinger KH, et al., "Minimally Cultured Tumor-infiltrating Lymphocytes Display Optimal Characteristics for Adoptive Cell Therapy"; 2008, J. Immunother, 31, 742-751.

Chandran et al., "Treatment of metastatic uveal melanoma with adoptive transfer of tumour-infiltrating lymphocytes: a single-

(56) References Cited

OTHER PUBLICATIONS centre, two-stage, single-arm, phase 2 study"; Lancet Oncol, doi: 10:1016/S1470-2045(17)30251-6 (2017).
Stevanovic et al., "Complete Regression of Metastatic Cervical Cancer After Treatment With Human Papillomavirus—Targeted Tumor—Infiltrating T Cells"; J Clin Oncol 33, doi: 10.1200/jco.2014.58.9093 (2015).
Dayhoff, "Atlas of Protein Sequences and Structure", M.O. Dayhoff ed., 5 suppl., 3, 353-358, National Biomedical Research Foundation, Washington D.C. USA.
U.S. National Institutes of Health, "A Study of Varlilumab and Atezolizuamb in Patients with Advanced Cancer", U.S. National Library of Medicine, Sep. 2015, clinicaltrials.gov identifier NCT02543645, 6 pages.
U.S. National Institutes of Health, A Study of Varlilumab (Anti-CD27) and Ipilimumab and CDX-1401 in Patients with Unresectable Stage III or IV Melanoma, U.S. National Library of Medicine, Apr. 2015, clinicaltrials.gov identifier NCT02413827, 6 pages.
U.S. National Institutes of Health, "A Study of Varlilumab (Anti-CD27) and Sunitinib in Patients with Metastatic Clear Cell Renal Cell Carcinoma", U.S. National Library of Medicine, Mar. 2015, clinicaltrials.gov identifier NCT2386111, 6 pages.
U.S. National Institutes of Health, "A Dose of Escalation and Cohort Expansion of Anti-CD27 (Varlilumab) and Anti-PD-1 (Nivolumab) in Advanced Refractory Solid Tumors", U.S. National Library of Medicine, Jan. 2015, clinicaltrials.gov identifier NCT02335918, 6 pages.
U.S. National Institutes of Health, Combination Study of Urelumab and Rituximsb in Patients with b-cell Non-Hodgkins Lymphoma, U.S. National Library of Medicine, Jan. 2015, clinicaltrials.gov identifier NCT01775631, 6 pages.
U.S. National Institutes of Health, Combination Study of Urelumab and Cetuximab in Patients with Advanced/ Metastatic Colorectal Cancer or Advanced/Metastatic Head and Neck Cancer, U.S. National Library of Medicine, Apr. 2014, clinicaltrials.gov identifier NCT02110082, 6 pages.
U.S. National Institutes of Health, "An Investigational Immunotherapy Study to Determine the Safety of Urelumab given in Combination with Nivoluamb in Solid Tumors and B-Cell Non-Hodgkins Lymphoma", U.S. National Library of Medicine, Oct. 2014, clinicaltrials.gov identifier NCT02253992, 7 pages.
U.S. National Institutes of Health, Safety Tolerability, Pharmacokinetics, and Immunoregulatory Study of Urelumab ) BMS-663513) in Subjects with Advanced / Metastatic Solid Tumors and Relapsed/ Refractory B-Cell Non-Hodgkin's Lymphoma National Library of Medicine, Nov. 2011, clinicaltrials.gov identifier NCT01471210, 8 pages.
Segal, et al., "Results from an Integrated Safety Analysis of Urelumab, an Agonist Anti CD-137 Monoclonal Antibody", Clin. Cancer Res., Apr. 2017, 23(8), 1929-1936.
Samaik et al., "Developmental Therapeutics", J Clin Oncology, May 27, 2017, 35(155), 6 pages.
Curti, et al., "OX40 is a Potent Immune-Stimulating Target in Late-Stage Cancer Patients", Cancer Res., Dec. 2013, 73(24), 7189-98.
Oshima, et al., "Characterization of Murine CD70 by Molecular cloning and mAb", Int. Immunol. Jan. 1998, 10(4), 517-26.
Claus, et al., "CD27 Signaling Increases the Frequency of Regulatory T Cells and Promotes Tumor Growth", Cancer Res. Jul. 2012, 72(14), 3664-76.
Aulwurm, et al., "Immune Stimulatory effects of CD70 override CD70—mediated immune cell apoptosis in rodent glioma models and confer long-lasting antiglimoa immunity in vivo", Int. J. Cancer 2006, 118, 1728-35.
He, et al., Agonist Anti-Human CD27 Monoclonal Antibody induces T Cell Activation and Tumor Immunity in human CD27—Transgenic Mice, J. Immunol. 2013, 191, 4174-83.
Nocentini and Riccardi, "GITR: A multifaceted regulator of immunity belonging to the tumor necrosis factor receptor superfamily", Eur. J. Immunol., Feb. 2005, 35, 1016-1022.

Ko, et al., "Treatment of Advanced Tumors with Agonistic anti-GITR mAb and its effects on tumor-infiltrating foxp3 +CD4+ regulatory T cells", J. Exp. Med., Oct. 2005, 202(7), 885-91.
Shimizu, et al., "Stimulation of CD25+CD4 regulatory T cells through GITR breaks immunological self-tolerance", Nature Immunology, Jan. 2002, 3, 135-142.
Cohen, et al., "Agonist Antibody Enhances Vaccine-induced CD8+ T-Cell Responses and Tumor Immunity", Cancer Res., May 2006, 66(9), 4904-12.
Azuma, "Role of the Glucocorticoid-Induced TNFR-Related Protein (GITR)-GITR Ligand Pathway in Innate and Adaptive Immunity", Crit. Rev. Immunol. 2010, 30(6), 547-57.
Schaer, et al., "Modulation of GITR for Cancer Immunotherapy", Curr. Opin. Immunol. 2012, 24, 217-224.
Montgomery, et al., "Herpes Simplex Virus-1 Entry into Cells Mediated by a novel member of the TNF/NGF Receptor Family", Cell, Nov. 1996, 87, 427-36.
Mauri, et al., "LIGHT, a New Member of the TNF Superfamily, and Lymphotoxin a Are ligands for Herpesvirus Entry mediator", Immunity, Jan. 1998, 8, 21-30.
Tamada, et al., "Reciprocal Expression of the TNF Family Receptor Herpes Virus Entry Mediator and its ligand LIGHT on activated T Cells: LIGHT down-regulates its own receptor", J. Immunol. 2000, 165, 4397-404.
Harrop, et al., "Herpesvirus entry mediator ligand (HVEM-L), a novel ligand for HVEM/TR2, Stimulates Proliferation of T Cells and Inhibits HT29 Cell Growth", J. Biol. Chem., Oct. 1998, 273(42), 27548-56.
Linch et al., "OX40 agonists and combination immunotherapy: putting the pedal to the metal", Front. Oncol., Feb. 2015, 34, 1-14.
Ward, et al., "Binding activities of a repertoire of a single immunoglobulin variable domains secreted from *Escherichia coli*", Nature, Oct. 1989, 341, 544-546.
Jones, et al., "Replacing the complementarity—determining regions in a human antibody with those from a mouse", Nature, May 1986, 321, 522-525.
Riechmann, et al., "Reshaping human antibodies for therapy", Nature, Mar. 1988, 332, 323-329.
Presta, "Antibody engineering", Curr. Op. Struct. Biol. 1992, 2, 593-596.
Yamane-Ohnuki, et al., "Establishment of FUT8 knockout Chinese hamster ovary cells: an ideal host cell line for producing completely defucosylated antibodies wth enhanced antibody-dependent cellular cytotoxicity", Biotechnol. Bioeng., Mar. 2004, 87, 614-622.
Shields, et al., "Lack of fucose on Human IgG1 N-Linked Oligosaccharide improves binding to human FcγRIII and antibody-dependent cellular toxicity", J. Biol. Chem., Jul. 2002, 277(30), 26733-26740.
Umana, et al., "Engineered glycoforms of an antineuro-blastoma IgG1 with Optimized antibody-dependent cellular cytotoxic activity", Nat. Biotech., Feb. 1999, 17, 176-180.
Tarentino, et al., "The Isolation and Structure of the Core Oligosaccharide Sequences of IgM" Biochem. 1975, 14(25), 5516-5523.
Muranski, et al., "Increased intensity lymphodepletion and adoptive immunotherapy—how far can we go?", Nat. Clin. Pract. Oncol., Dec. 2006, 3, 668-681.
Gassner, et al., "Fludarabine modulates composition and function of the T Cell pool in patients with chronic lymphocytic leukaemia", Cancer• Immunol. Immunother., 2011, 60, 75-85.
Brummell, et al., "Probing the Combining Site of an Anti-Carbohydrate antibody by saturation—mutagenesis: Role of the heavy-chain CDR3 Residues", Biochemistry 1993, 32(4), 1180-1187.
Kobayashi, et al., "Tryptophan H33 plays an important role in pyrimidine (6-4) pyrimidone photoproduct binding by a high-affinity antibody", Protein Engineering, 1999, 12(10), 879-884 (1999).
Sano et al., "Xenograft models of head and neck cancers", Head Neck Oncol., Aug. 2009, 1(32), 6 pages.
Batzer, et al., "Enhanced evolutionary PCR using olignucleotides with inosine at the 3'-terminus", Nucleic Acid Res. Jul. 1991, 19(18), 1 page.

(56) References Cited

OTHER PUBLICATIONS

Ohtsuka, et al., "An Alternative approach to Deoxyoligonucleotides as hybridization probes by insertion of deoxyinosine at ambiguous codon positions", J. Biol. Chem. 1985, 260(5), 2605-2608.

Rossolini, et al., "Use of deoxyinosine-containing primers vs degenerate primers for polymerase chain reaction based on ambiguous sequence information", Mol. Cell. Probes 1994, 8, 91-98.

Gieffers et al., "APG350 induces Superior Clustering of TRAIL receptors and shows therapeutic antitumor efficacy independent of Cross-linking via Fcγ receptors", Mol. Cancer Therapeutics, Dec. 2013, 12(12), 2735-47.

Fisher, et al., "Targeting of 4-1BB by monoclonal antibody PF-05082566 enhances T-Cell function and promotes anti-tumor activity", Cancer Immunolog. & Immunother. 2012, 61, 1721-33.

Jin et al. "Simplified Method of the Growth of Human Tumor Infiltrating Lymphocytes in Gas-Permeable Flasks to Numbers needed for patient treatment", J Immunother., Apr. 2012, 35(3), 283-92.

U.S. National Institutes of Health, "A study of PF-05082566 in combination with Mogamulizumab in Patients with Advanced Solid Tumors", U.S. National Library of Medicine, May 2015, clinicaltrials.gov identifier NCT02444793, 8 pages.

U.S. National Institutes of Health, "A Study of PF-05082566 as a Single Agent and in Combination with Rituximab", U.S. National Library of Medicine, Mar. 2011, clinicaltrials.gov identifier NCT001307267, 6 pages.

U.S. National Institutes of Health, Study of OX40 Agonist PF-04518600 Alone and in Combination with 4-1BB Agonist PF-05082566, U.S. National Library of Medicine, Dec. 2014, clinicaltrials.gov identifier NCT02315066, 6 pages.

U.S. National Institutes of Health, A Study of CDX-1127 (Varlilumab) in Patients with Select Solid Tumor Types or Hematologic Cancer, U.S. National Library of Medicine, Oct. 2011, clinicaltrials.gov identifier NCT01460134, 7 pages.

Gattinoni, et al., "Adoptive immunotherapy for cancer: building on success", Nat. Rev. Immunol. May 2006, 6(5), 383-393.

Dudley, et al.,"Cancer Regression and Autoimmunity in Patients After Clonal Repopulation with Antitumor Lymphocytes", Science, Oct. 2002, 298, 850-54.

Dudley, et at., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley, et al., "Adoptive Cell Therapy for Patients with Metastatic Melanoma: Evaluation of Intensive Myeloablative Chemoradiation Preparative Regimens", J. Clin. Oncol., Nov. 2008, 26(32), 5233-39.

Riddell, et al., "Restoration of Viral Immunity in Immunodeficient Humans by the Adoptive Transfer of T Cell Clones", Science, Jul. 1992, 257, 238-41.

Dudley, et al., "Generation of Tumor-Infiltrating Lymphocyte Cultures for USe in Adoptive Transfer Therapy for Melanoma Patients", J. Immunother., 2003, 26(4), 332-42.

Butler et al., "Human cell-based artificial antigen-presenting cells for cancer immunotherapy", Immunol. Rev. Jan. 2014, 257(1), 191-209.

Friedman,et al., "Augmented Lymphocyte expansion from solid tumors with engineered cells for costimulatory enhancement", J. Immunother. Nov. 2011, 34(9), 651-661.

Ye, et al., "Engineered Artificial antigen presenting cells facilitate direct and efficient expansion of tumor infiltrating lymphocytes", J. Translat. Med. 2011, 9(131), 13 pages.

Forget, et al., "Activation and propagation of tumor infiltrating lymphocytes on clinical-grade designer antigen presenting cells for adoptive immunotherapy of melanmoa", J Immunother. 2014, 37(9), 448-60.

Maus, et al., Ex Vivo expansion of polyclonal and antigen-specific cytotoxic T lymphocytes by artificial APCs expressing ligands for the T-cell receptor, CD28 abd 4-1BB Nat. Biotechnol. 2002, 20, 143-148.

Suhoski, et al., "Engineering Artificial Antigen-presenting cells to express a diverse array of co-stimulatory molecules", Mol. Ther., May 2007, 15(5), 981-988.

Matsuo et al., Two acute monocytic leukemia (AML-M5a) cells lines, (MOLM-13 and MOLM-14) with interclonal phenotypic heterogeneity showing MLL-AF9 fusion resulting from an occult chromosome insertion, ins(11;9) (q23;p22p23) Leukemia 1997, 11, 1469-77.

Konopka, et al., "Cell lines and clinical isolates derived from PH1-positive chronic myelogenous leukemia patients express c-abl proteins with a common structural alteration", Proc. Nat'l Acad. Sci. USA, Mar. 1985, 82, 1810-4.

International Search Report for PCT/US2017/059271 dated Feb. 3, 2018, 9 pages.

Written Opinion for PCT/US2017/059271 dated Feb. 3, 2018, 13 pages.

Burks, et al., "In vitro scanning saturation mutagenesis of an antibody binding pocket", Proc. Natl. Acad. Sci. USA Jan. 1997, 94, 412-417.

Gordon et al., "Gene Therapy using Retroviral Vectors", Curr. Op. Biotechnol., 1994, 5, 611-616.

Miller, et al., "Use of Retroviral Vectors for Gene Transfer and Expression", Meth. Enzymol., 1993, 217, 581-599.

Nelson, "IL-2, Regulatory T Cells and Tolerance", J. Immunol., Feb. 2004, 172, 3983-88.

Malek, "The Biology of Interleukin-2", Annu. Rev. Immunol. 2008, 26, 453-79.

Fry et al., "Interleukin-7: from bench to clinic", Blood, Jan. 2002, 99(11), 3892-904.

Fehniger et al., "Interleukin 15: biology and relevance to human disease", Blood, Jan. 2001, 97(1), 14-32.

Spolski et al., "Interleukin-21: a double-edged sword with therapeutic potential",, Nat. Rev. Drug. Disc., May 2014, 13, 379-95.

Levine, et al., "Gene Transfer in humans using a conditionally replicating lentiviral vector" Proc. Nat 'l, Acad. Sci., Nov. 2006, 103, 17372-77.

Zufferey, et al., "Multiply attenuated lenivrial vector achieves efficient gene delivery in vivo", Nat. Biotechnol., Jul. 1997, 15, 871-75.

Dull, et al.,"A Third-Generation Lentivirus Vector with a Conditional Packaging System", J. Virology, Nov. 1998, 72(11), 8463-71.

Cepko et al., "Transduction of Genes Using Retrovirus Vectors", Cur. Prot. Mol. Biol. 1996, 9.9.1-9.9.16.

Hackett, et al., "A Transposon and Transposase System for Human Application", Mol. Therapy, Jan. 2010, 18(4), 674-83.

Tsong, "Electroporation of Cell Membranes", Biophys. J., Aug. 1991, 60, 297-306.

Graham et al., "A New Technique for the Assay of Infectivity of Human Adenovirus 5 DNA", Virology, Jan. 1973, 52, 456-467.

Wigler, et al. "DNA-meditated transfer of the adenine phosphoribosyltransferase locus into mammalian cells", Proc. Natl. Acad. Sci., Mar. 1979, 76, 1373-1376.

Chen et al., "High-Efficiency Transformation of Mammalian Cells by Plasmid DNA", Mol. Cell. Biol., Aug. 1987, 7(8), 2745-2752.

Rose, et al., "A New Cationic Liposome Reagent Mediating Nearly Quantitative Transfection of Animal Cells", Biotechniques, 1991, 10(4), 520-525.

Felgner, et al., "Lipofection: A Highly efficient, lipid-mediated DNA-transfection procedure", Proc. Natl. Acad. Sci. USA, Nov. 1987, 84, 7413-7417.

Jin, et al., "Simplified Method of the Growth of Human Tumor Infiltrating Lymphocytes (TIL) in Gas-Permeable Flasks to Numbers Needed for Patient Treatment", J. Immunotherapy, Apr. 2012, 35(3), 283-292.

Mullany, et al, "Minireview: Animal Models and Mechanisms of Ovarian Cancer Development", Endocrinology, Apr. 2012, 153(4), 1585-92.

Fong, et al., "Ovarian Cancer mouse models: a summary of current models and their limitations", J. Ovarian Res. Sep. 2009, 2(12), 8 pages.

Herreros-Villanueva, et al., "Mouse models of pancreatic Cancer", World J. Gastroenterol., Mar. 2012, 18(12), 1286-1294.

(56) References Cited

OTHER PUBLICATIONS

Fantozzi et al., "Mouse Models of breast cancer metastasis", Breast Cancer Res., Jul. 2006, 8(212), 11 pages.
Damsky, et al., "Mouse Melanoma models and cells lines", Pigment Cell & Melanoma Res. 2010, 23, 853-859.
Meuwissen, et al., "Mouse models for human lung cancer", Genes & Development, 2005, 19, 643-664.
Kim, "Animal Models of Cancer in the head and neck region", Clin. Exp. Otorhinolaryngol., Jun. 2009, 2(2), 55-60.
Raskind W. H. etal., "Correlation between cytogenetic and molecular findings in human chronic myelogenous leukemia lines EM-2 and EM-3", Cancer Genetics and Cytogenetics, Elsevier Science Publishing, New York, NY, US, vol. 25, No. 2, Apr. 1, 1987, pp. 271-284.
Gajewski T. F. et al., "The P815 Mastocytoma Tumor Model", Curr. Protoc. Immunol., Chapter 20, Unit 20.4, May 31, 2001.
Deniger D. C. et a., "Activating and Propagating Polyclonal Gamma Delta T Cells with Broad Specificity for Malignancies", Clinical Cancer Research, vol. 20, No. 22, Nov. 15, 2014, pp. 5708-5719.
Sadehghi, et al., "Rapid expansion of T cells: Effects of culture and cryopreservation and importance of short-term cell recovery" Acta Oncologica 2013, 52, 978-986.
Tsoukas et al., "Activation of resting T lymphocytes by anti-CD3 (T3) antibodies in the absence of monocytes", J. Immunol. 1985, 135, 1719.
Tran et al., "Minimally Cultured tumor-infiltrating lymphocytes display optimal characteristics for adoptive cell therapy", 2008, J. Immunother., Oct. 2008 31(8), 742-751.
Chang et al., "Emerging concepts in immunotherapt T-cell metabolism as a therapeutic target", Nat. Immunol., Apr. 2016, 17(4), 364-368.
Radvanyi, et al., "Specific Lymphocyte Subsets Predict Response to Adoptive Cell Therapy Using Expanded Autologous Tumor-Infiltrating Lymphocytes in Metastatic Melanoma Patients"; Clin Cancer Res 2012, 18, 6758-6770.
Gruijl, et al., "IL-21 promotes the expansion of CD27+CD28+tumor infiltrating lymphocytes with high cytotoxic potential and low collateral expansionof regulatory T cells"; J. Transl . Med. 2013, 11, 37.
Maciejowski et al., "Telomeres in cancer: tumour suppression and genome instability"; Nat Rev Mol Cell Biol. Mar. 2017; 18(3):175-186.
de Lange T, Shiue L, Myers RM, Cox DR, Naylor SL, Killery AM, Varmus HE. "Structure and variability of human chromosome ends"; Mol Cell Biol. 1990;10:518-527.
Santegoets, S. J., "IL-21 promotes the expansion of CD27+CD28+ tumor infiltrating lymphocytes with high cytotoxic potential and low collateral expansion of regulatory T cells"; J Transl Med., 2013, 11:37 (https://nwww.ncbi.nlm.nih.gov/pmc/articles/PMC3626797/).
Musin, "The problem of the twenty-five spheres"; (2003). Russ. Math Surv. 58(4): 794-795.
Batzer, "Enhanced evolutionary PCR using oligonucleotides with inosine at the 3'-terminus"; Nucleic Acids Research, vol. 19, 18, 5081.
Sethuraman et al., "Successful expansion and characterization of tumor infiltrating lymphocytes (TILs) from non-melanoma tumors"; Journal for ImmunoTherapy of Cancer, vol. 4, Supp. 1, 2016, P41-42.
Richards et al., "Flow Cytometry Assessment of Residual Melanoma Cells in Tumor-Infiltrating Lymphocyte Cultures"; Cytometry A 2012; 81:374-81.
Dudley ME, Wunderlich Jr, Shelton TE, et al., "Generation of Tumor-Infiltrating Lymphocyte Cultures for Use in Adoptive Transfer Therapy for Melanoma Patients"; 2003, J. Immunother, 26, 332-342.
Thomas, et al., "Targeting human CD27 with an agonist antibody stimulates T-cell activation and antitumor immunity"; Oncolummunology 2014, 3, e27255.

Jung, et al., "Bypassing glycosylation: engineering aglycosylated full-length IgG antibodies for human therapy"; Cur. Opin. Biotechnology 2011, 22, 858-867.
Roth, et al., "Immune Response against Tumors"; Adv. Immunol. 1994, 57, 281-351.
Fearon, et al., "Induction in a Murine Tumor of Immunogenic Tumor Variants by Transfection with a Foreign Gene"; Cancer Res. 1988, 48, 2975-2980.
Keir, et al., "PD-1 and Its Ligands in Tolerance and Immunity"; Annu. Rev. Immunol. 2008, 26, 677-704.
Topalian, et al., "Safety, Activity, and Immune Correlates of Anti-PD-1 Antibody in Cancer"; N. Eng. J. Med. 2012, 366, 2443-54.
Page, et al., "Immune Modulation in Cancer with Antibodies"; Ann. Rev. Med., 2014, 65, 185-202.
Fuerst, "Metastatic Melanoma: Immunotherapy with Pembrolizumab Induces Durable Responses"; Oncology Times, 2014, 36, 35-56.
Robert, et al., "Anti-programmed-death-receptor-1 treatment with pembrolizumab in ipilimumab-refractory advanced melanoma: a randomised dose-comparison cohort of a phase 1 trial"; Lancet, 2014, 384, 1109-17.
Thomas, et al., "Immunotherapy for non-small-cell lung cancer"; Exp. Opin. Biol. Ther., 2014, 14, 1061-1064.
Brahmer, et al. "Clinical activity and biomarkers of MEDI4736, an anti-PD-L1 antibody, in patients with NSCLC"; Journal of Clinical Oncology 32, No. 15-suppl (May 2014) 8021-8021.
McDermott, et al., "Durable benefit and the potential for long-term survival with immunotherapy in advanced melanoma"; Cancer Treatment Rev., 2014, 40, 1056-64.
Chacon, et al., "Manipulating the Tumor Microenvironment Ex Vivo for Enhanced Expansion of Tumor-Infiltrating Lymphocytes for Adoptive Cell Therapy"; Clin. Cancer Res. 2015, 21, 611-21.
Joseph, et al., "Impact of Clinical and Pathologic Features on Tumor-Infiltrating Lymphocyte Expansion from Surgically Excised Melanoma Metastases for Adoptive T-cell Therapy"; Clin. Cancer Res. 2011, 17, 4882-91.
Tran, et al., "T-Cell Transfer Therapy Targeting Mutant KRAS in Cancer"; N. Engl. J. Med. 2016, 375, 2255-62.
Tran, et al., "Cancer Immunotherapy Based on Mutation-Specific CD4+ T Cells in a Patient with Epithelial Cancer"; Science 2014, 344, 641-45.
Paulsen, et al., "Modulation of CD4+ T-cell activation by CD95 co-stimulation"; Cell Death Differ. 2011, 18, 619-31.
Monnier, et al., "In Vivo Applications of Single Chain Fv (Variable Domain) (scFv) FragmentsAntibodies"; 2013, 2, 193-208.
Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).
Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):OF1-OF9 (2013).
Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).
Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.
Shen et al., "Persistence of Tumor Infiltrating Lymphocytes in Adoptive Immunotherapy Correlates With Telomere Length"; J. Immunother, 30, 123-129 (2007).
Zhou, et al. "Persistence of Multiple Tumor-Specific T-Cell Clones Is Associated with Complete Tumor Regression in a Melanoma Patient Receiving Adoptive Cell Transfer Therapy"; J. Immunother, 28, 53-62 (2005).
Eil R, Vodnala SK, et al., "Ionic immune suppression within the tumour microenvironment limits T cell effector function"; Nature, 2016; 537, 539-543.
Feske, et al., "Ion Channels in Innate and Adaptive Immunity"; Annu. Rev. Immunol. 2015, 33, 291-353.

(56) References Cited

OTHER PUBLICATIONS

Di, et al., "Inhibition of the K+ channel KCa3.1 ameliorates T cell-mediated colitis"; Proc. Nat'l Acad. Sci. USA 2010, 107, 1541-46.

Sankaranarayanan, et al., "Naphtho[1,2-d]thiazol-2-ylamine (SKA-31), a New Activator of KCa2 and KCa3.1 Potassium Channels, Potentiates the Endothelium-Derived Hyperpolarizing Factor Response and Lowers Blood Pressure"; Mol. Pharmacol. 2009, 75, 281-95.

Strobaek, et al., "Activation of human IK and SK Ca2+-activated K+ channels by NS309 (6,7-dichloro-1H-indole-2,3-dione 3-oxime)"; Biochim. Biophys. Acta 2004, 1665, 1-5.

Abeagbo, "1-Ethyl-2-benzimidazolinone stimulates endothelial K channels and Ca nitric oxide formation in rat mesenteric vessels"; Eur. J. Pharmacol. 1999, 379, 151-59.

Devor, et al., "Modulation of Cl-secretion by benzimidazolones.I. Direct activation of a Ca2+-dependent K+ channel"; Am. J. Physiol. 1996, 271, L775-L784.

Singh, et al., "Benzimidazolone Activators of Chloride Secretion: Potential Therapeutics for Cystic Fibrosis and Chronic Obstructive Pulmonary Disease"; J. Pharmacol. Exp. Ther. 2001, 296, 600-611.

Grunnet, et al., "Pharmacological modulation of SK3 channels"; Neuropharmacology 2001, 40, 879-887.

Coleman, et al., "New Positive Ca21-Activated K1 Channel Gating Modulators with Selectivity for KCa3.1 s"; Mol. Pharmacol. 2014, 86, 342-57.

Hinrichs et al.; "Exploiting the curative potential of adoptive T-cell therapy for cancer"; Immunol Rev. Jan. 2014; 257 (1):56-71.

Somerville et al., "Clinical scale rapid expansion of lymphocytes for adoptive cell transfer therapy in the WAVE® bioreactor"; J Transl Med. Apr. 4, 2012;0-69.

Campbell, et al., "CCR7 Expression and Memory T Cell Diversity in Humans"; J. Immunol. 2001, 166, 877-84.

Huang et al., "Survival, Persistence, and Progressive Differentiation of Adoptively Transferred Tumor-Reactive T Cells Associated with Tumor Regression"; J. Immunother, 28(3), 258-267 (2005).

Fatozzi, "Mouse models of breast cancer metastasis"; Breast Cancer Res. 2006, 8, 212.

* cited by examiner

| | Event Count | % of Total | % of Parent |
|---|---|---|---|
| Ungated | 10000 | | |
| Open Gate | 2848 | 28.48% | 28.48% of Ungated |
| Singlets | 2845 | 28.45% | 99.89% of Open Gate |
| Live cells | 2697 | 26.97% | 94.8% of Singlets |
| NK cells | 3 | 0.03% | 0.11% of Live cells |
| Non T cells | 160 | 1.6% | 5.93% of Live cells |
| TCR alpha beta+ | 2371 | 23.71% | 87.91% of Live cells |
| CD4+ | 785 | 7.85% | 33.11% of TCR alpha beta+ |
| CD4+CD27+ | 32 | 0.32% | 4.08% of CD4+ |
| CD4+CD28+ | 769 | 7.69% | 97.96% of CD4+ |
| CD4+CD57+ | 119 | 1.19% | 15.16% of CD4+ |
| CD8+ | 1475 | 14.75% | 62.21% of TCR alpha beta+ |
| CD8+CD27+ | 42 | 0.42% | 2.85% of CD8+ |
| CD8+CD28+ | 1376 | 13.76% | 93.29% of CD8+ |
| CD8+CD57+ | 291 | 2.91% | 19.73% of CD8+ |

M1053T

M1030T

M1053T

M1030T

M1053T

M1030T

ENGINEERED ARTIFICIAL ANTIGEN PRESENTING CELLS FOR TUMOR INFILTRATING LYMPHOCYTE EXPANSION

CROSS-REFERENCE TO RELATED APPLICATIONS

This application is a continuation of International Application No. PCT/US17/59271, filed Oct. 31, 2017, which claims the benefit of priority to U.S. Provisional Application No. 62/481,831, filed Apr. 5, 2017, U.S. Provisional Application No. 62/475,053, filed Mar. 22, 2017, U.S. Provisional Application No. 62/438,600, filed Dec. 23, 2016, and U.S. Provisional Application No. 62/415,274, filed Oct. 31, 2016, the entireties of which are incorporated herein by reference.

FIELD OF THE INVENTION

Engineered artificial antigen presenting cells (aAPCs) for expansion of tumor infiltrating lymphocytes are disclosed.

BACKGROUND OF THE INVENTION

Treatment of bulky, refractory cancers using adoptive autologous transfer of tumor infiltrating lymphocytes (TILs) represents a powerful approach to therapy for patients with poor prognoses. Gattinoni, et al., Nat. Rev. Immunol. 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., Science 2002, 298, 850-54; Dudley, et al., J. Clin. Oncol. 2005, 23, 2346-57; Dudley, et al., J. Clin. Oncol. 2008, 26, 5233-39; Riddell, et al., Science 1992, 257, 238-41; Dudley, et al., J. Immunother. 2003, 26, 332-42. However, although REP can result in a 1,000-fold expansion of TILs over a 14-day period, it requires a large excess (e.g., 200-fold) of irradiated allogeneic peripheral blood mononuclear cells (PBMCs), often from multiple donors, as feeder cells, as well as anti-CD3 antibody (OKT-3) and high doses of IL-2. Dudley, et al., J. Immunother. 2003, 26, 332-42. Despite their high performance, PBMCs have multiple drawbacks, including the large numbers of allogeneic PBMCs required, the need to obtain PBMCs by leukapheresis from multiple healthy donors, the resulting interdonor variability in PBMC viability after cryopreservation and variable TIL expansion results, the risk of undetected viral pathogens causing downstream patient infections, and the extensive and costly laboratory testing of each individual donor cell product to confirm sterility and quality (including viral contaminant testing) and to test expansion properties.

Unfortunately, aAPCs developed for use in the expansion of TILs have suffered from poor performance when compared to PBMCs, including alterations of the phenotypic properties of the input TILs, as well as poor expansion performance and/or high variability in expansion results. Because of the large number of potential cells that might be adapted for use as aAPCs and the unpredictability of identifying suitable candidates, the focus of aAPC development for polyclonal TILs to date has been solely on the well-established K562 cell line. Butler and Hirano, Immunol. Rev. 2014, 257, 191-209. For example, K562 cells modified to express 4-1BBL (CD137L) were tested in pre-REP culture (but not in REP culture) to determine enhancement of TIL expansion from tumor digest, but PBMCs were still required to be used in conjunction with K562 cells to obtain TIL expansion. Friedman, et al., J. Immunother. 2011, 34, 651-661. Other engineered K562 cells modified to express CD64, CD86, and 4-1BBL were tested and achieved TIL expansion that was at best comparable to PBMCs, and most likely less than PBMCs, and also suffered from skewing of the polyclonal TIL phenotype to a less favorable $CD8^+$/$CD4^+$ T cell ratio. Ye, et al., J. Translat. Med. 2011, 9, 131. Recently, K562 cells modified to express CD86, 4-1BBL (CD137L), high affinity Fc receptor (CD64) and membrane-bound IL-15 have also been shown to propagate TIL (post-REP) at equivalent numbers compared to PBMC feeders, but with the additional complexity of membrane-bound IL-15. Forget, et al., J. Immunother. 2014, 37, 448-60. Other systems developed have lacked critical costimulatory molecules, have led to unfavorable T cell phenotypic skewing, or have required additional interleukins (such as IL-21). Butler and Hirano, Immunol. Rev. 2014, 257, 191-209. Overall, K562 modified aAPCs have not been shown to provide for consistent expansion of TILs with acceptable variability while also performing better than PBMCs in other measures including overall expansion cell counts. Alternative aAPCs besides K562 cells have been successful in other cell expansion methods, but have not achieved the same performance as PBMCs with the unique polyclonal subset of cells that make up TILs. Maus, et al., Nat. Biotechnol. 2002, 20, 143-148; Suhoski, et al., Mol. Ther. 2007, 15, 981-988.

The MOLM-14 human leukemia cell line was established from the peripheral blood of a patient with relapsed acute monocytic leukemia, and initial phenotypic characterization indicated the presence of at least the following markers: CD4, CD9, CD11a, CD13, CD14, CD15, CD32, CD33, CD64, CD65, CD87, CD92, CD93, CD116, CD118, and CD155. Matsuo, et al., Leukemia 1997, 11, 1469-77. Additional phenotypic characterization of MOLM-14 found higher levels of HLA-A/B/C, CD64, CD80, ICOS-L, CD58, and lower levels of CD86. MOLM-14 cells and the closely-related MOLM-13 cells have not been previously reported as useful aAPCs for the expansion of cells for tumor immunotherapy applications.

The EM-3 human cell line was established from the bone marrow of a patient with Philadelphia chromosome-positive CML. Konopka, et al., Proc. Nat'l Acad. Sci. USA 1985, 82, 1810-4. EM-3 cells and the closely-related EM-2 cell line have not been previously reported as useful aAPCs for the expansion of cells for tumor immunotherapy applications. Phenotypic characterization for EM-3 cells indicates the presence of at least the following markers: CD13, CD15, and CD33.

The present invention provides the unexpected finding that engineered myeloid lineage cells, including MOLM-13, MOLM-14, EM-3, and EM-2 cells, transduced with additional costimulatory molecules, including CD86 (B7-2), 4-1BBL (CD137L), and OX40L (CD134L), provide for superior and highly efficient expansions of TILs in large numbers with minimal variability, reduced cost, and no reliance on human blood samples as a source of PBMCs, with the benefit of using an aAPC which can be produced efficiently from a master cell bank. CD86 and 4-1BBL are costimulatory molecules that provide costimulatory signals for T cell activation. The MOLM-14, MOLM-13, EM-3, and/or EM-2 cells transduced with additional costimulatory molecules are useful, for example, in the expansion of TILs for use in cancer immunotherapy and other therapies.

SUMMARY OF THE INVENTION

In an embodiment, the invention provides an artificial antigen presenting cell (aAPC) comprising a myeloid cell transduced with one or more vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein.

In an embodiment, each of the CD86 protein and the 4-1BBL protein are human proteins.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the aAPC can stimulate and expand a tumor infiltrating lymphocyte (TIL) contacted with the aAPC.

It will be apparent that in certain embodiments of the invention, the nucleic acid molecule encoding CD86 may be comprised in a different viral vector to the nucleic acid molecule encoding 4-1BBL or the same viral vector.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the aAPC expands a population of TILs by at least 50-fold over a period of 7 days in a cell culture medium comprising IL-2 at a concentration of about 3000 IU/mL and OKT-3 antibody at a concentration of about 30 ng/mL.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the aAPC can stimulate and expand a T cell contacted with the aAPC.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell endogenously expresses HLA-A/B/C, ICOS-L, and CD58.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is essentially devoid of membrane-bound IL-15.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is a MOLM-14 cell.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is a MOLM-13 cell.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is a EM-3 cell.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is a EM-2 cell.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the CD86 protein comprises an amino acid sequence as set forth in SEQ ID NO:8, or an amino acid sequence comprising one or more conservative amino acid substitutions thereof, and the 4-1BBL protein comprises SEQ ID NO:9, or an amino acid sequence comprising one or more conservative amino acid substitutions thereof.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the nucleic acid molecule encoding CD86 comprises a nucleic acid sequence as set forth in SEQ ID NO:16 and the nucleic acid molecule encoding 4-1BBL comprises a nucleic acid sequence as set forth in SEQ ID NO:19.

In an embodiment, the invention provides a method of expanding tumor infiltrating lymphocytes (TILs), the method comprising the step of contacting a population of TILs with an aAPC comprising a myeloid cell transduced with one or more viral vectors, wherein the one or more viral vectors comprise a nucleic acid molecule encoding CD86 and a nucleic acid molecule encoding 4-1BBL, wherein the myeloid cell expresses a CD86 protein and a 4-1BBL protein, and wherein the population of TILs is expanded. In an embodiment, the method is an in vitro or an ex vivo method.

In an embodiment, the invention provides a method of expanding a population of tumor infiltrating lymphocytes (TILs), the method comprising the steps of:
 (a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
 (b) contacting the population of TILs with the population of aAPCs in a cell culture medium.

In an embodiment, the foregoing method is an in vitro or an ex vivo method.

In an embodiment, the invention provides a method of expanding a population of tumor infiltrating lymphocytes (TILs), the method comprising the steps of:
(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
(b) contacting the population of TILs with the population of aAPCs in a cell culture medium, wherein the cell culture medium further comprises IL-2 at an initial concentration of about 3000 IU/mL and OKT-3 antibody at an initial concentration of about 30 ng/mL.

In an embodiment, the foregoing method is an in vitro or an ex vivo method.

In an embodiment, the invention provides a method of expanding a population of tumor infiltrating lymphocytes (TILs), the method comprising the steps of:
(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
(b) contacting the population of TILs with the population of aAPCs in a cell culture medium, wherein the population of APCs expands the population of TILs by at least 50-fold over a period of 7 days in a cell culture medium.

In an embodiment, the foregoing method is an in vitro or an ex vivo method.

In an embodiment, the invention provides a method of expanding a population of tumor infiltrating lymphocytes (TILs), the method comprising the steps of:
(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
(b) contacting the population of TILs with the population of aAPCs in a cell culture medium, wherein the myeloid cell endogenously expresses HLA-A/B/C, ICOS-L, and CD58.

In an embodiment, the foregoing method is an in vitro or an ex vivo method.

In an embodiment, the invention provides a method of expanding a population of tumor infiltrating lymphocytes (TILs), the method comprising the steps of:
(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
(b) contacting the population of TILs with the population of aAPCs in a cell culture medium, wherein the myeloid cell is a MOLM-14 cell.

In an embodiment, the foregoing method is an in vitro or an ex vivo method.

In an embodiment, the invention provides a method of expanding a population of tumor infiltrating lymphocytes (TILs), the method comprising the steps of:
(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
(b) contacting the population of TILs with the population of aAPCs in a cell culture medium, wherein the myeloid cell is a MOLM-13 cell.

In an embodiment, the foregoing method is an in vitro or an ex vivo method.

In an embodiment, the invention provides a method of expanding a population of tumor infiltrating lymphocytes (TILs), the method comprising the steps of:
(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
(b) contacting the population of TILs with the population of aAPCs in a cell culture medium, wherein the myeloid cell is a EM-3 cell.

In an embodiment, the foregoing method is an in vitro or an ex vivo method.

In an embodiment, the invention provides a method of expanding a population of tumor infiltrating lymphocytes (TILs), the method comprising the steps of:
(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
(b) contacting the population of TILs with the population of aAPCs in a cell culture medium, wherein the myeloid cell is a EM-2 cell.

In an embodiment, the foregoing method is an in vitro or an ex vivo method.

In an embodiment, the invention provides a method of expanding a population of tumor infiltrating lymphocytes (TILs), the method comprising the steps of:
(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and
(b) contacting the population of TILs with the population of aAPCs in a cell culture medium, wherein the CD86 protein comprises an amino acid sequence as set forth in SEQ ID NO:8, or comprises an amino acid sequence comprising one or more conservative amino acid substitutions thereof, and the 4-1BBL protein comprises an amino acid sequence as set forth in SEQ ID NO:9, or comprises an amino acid sequence comprising one or conservative amino acid substitutions thereof.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the nucleic acid encoding CD86 comprises a nucleic acid sequence as set forth in SEQ ID NO:16 and the nucleic acid encoding 4-1BBL comprises a nucleic acid sequence as set forth in SEQ ID NO:19.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the expansion is performed using a gas permeable container.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the ratio of the population of TILs to the population of aAPCs is between 1 to 200 and 1 to 400.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the ratio of the population of TILs to the population of aAPCs is about 1 to 300.

In an embodiment, the invention provides a method of expanding tumor infiltrating lymphocytes (TILs), the method comprising contacting a population of TILs comprising a population of TILs with a myeloid artificial antigen presenting cell (aAPC), wherein the myeloid aAPC comprises at least two co-stimulatory ligands that specifically bind with at least two co-stimulatory molecules on the TILs, wherein binding of the co-stimulatory molecules with the co-stimulatory ligand induces proliferation of the TILs, thereby specifically expanding TILs, and wherein the at least two co-stimulatory ligands comprise CD86 and 4-1BBL. In an embodiment, the foregoing method is an in vitro or ex vivo method.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer;

wherein the myeloid aAPCs endogenously expresses HLA-A/B/C, ICOS-L, and CD58, and wherein the myeloid aAPCs are transduced to express a CD86 protein and a 4-1BBL protein.

In an embodiment, the invention provides a population of tumor infiltrating lymphocytes (TILs) for use in treating cancer, wherein the TILs are a second population of TILs and are obtainable from a method comprising the steps of:

(a) performing a rapid expansion of a first population of TILs using a population of myeloid artificial antigen presenting cells (myeloid aAPCs) in a cell culture medium to obtain the second population of TILs, wherein the TILs are/have been obtained from a tumor resected from a patient, and wherein the second population of TILs is at least 50-fold greater in number than the first population of TILs after 7 days from the start of the rapid expansion; and wherein the myeloid aAPCs endogenously expresses HLA-A/B/C, ICOS-L, and CD58, and wherein the myeloid aAPCs are transduced to express a CD86 protein and a 4-1BBL protein.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer;

wherein the myeloid aAPCs endogenously expresses HLA-A/B/C, ICOS-L, and CD58, wherein the myeloid aAPCs are transduced to express a CD86 protein and a 4-1BBL protein, wherein the myeloid aAPCs comprise MOLM-14 cells transduced with one or more viral vectors, and wherein the one or more viral vectors comprise a nucleic acid encoding CD86 and a nucleic acid encoding 4-1BBL, and wherein the MOLM-14 cells express a CD86 protein and a 4-1BBL protein.

In an embodiment, the invention provides a population of tumor infiltrating cells (TILs) for use in treating a cancer, wherein the population of TILs is a second population of TILs and is obtainable by a process comprising:

(a) performing a rapid expansion of a first population of TILs using a population of myeloid artificial antigen presenting cells (myeloid aAPCs) in a cell culture medium to obtain the second population of TILs, wherein the first population of TILs are/have been obtained from a tumor resected from a patient, wherein the second population of TILs is at least 50-fold greater in number than the first population of TILs after 7 days from the start of the rapid expansion;

wherein the myeloid aAPCs endogenously expresses HLA-A/B/C, ICOS-L, and CD58, wherein the myeloid aAPCs are transduced to express a CD86 protein and a 4-1BBL protein, wherein the myeloid aAPCs comprise MOLM-14 cells transduced with one or more viral vectors, and wherein the one or more viral vectors comprise a nucleic acid encoding CD86 and a nucleic acid encoding 4-1BBL, and wherein the MOLM-14 cells express a CD86 protein and a 4-1BBL protein.

In an embodiment, the invention provides a method of treating a cancer with a population of tumor infiltrating lymphocytes (TILs) comprising the steps of:
(a) obtaining a first population of TILs from a tumor resected from a patient;
(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and
(c) administering a therapeutically effective portion of the second population of TILs to a patient with the cancer; wherein the myeloid aAPCs endogenously expresses HLA-A/B/C, ICOS-L, and CD58, wherein the myeloid aAPCs are transduced to express a CD86 protein and a 4-1BBL protein, wherein the myeloid aAPCs comprise EM-3 cells transduced with one or more viral vectors, and wherein the one or more viral vectors comprise a nucleic acid encoding CD86 and a nucleic acid encoding 4-1BBL, and wherein the EM-3 cells express a CD86 protein and a 4-1BBL protein.

In an embodiment, the invention provides a population of tumor infiltrating lymphocytes (TILs) for use in treating a cancer, the population of TILs being a second population of TILs and obtainable by a process comprising:
(a) performing a rapid expansion of a first population of TILs using a population of myeloid artificial antigen presenting cells (myeloid aAPCs) in a cell culture medium to obtain the second population of TILs, wherein the first population of TILs are/have been obtained from a tumor resected from a patient, and wherein the second population of TILs is at least 50-fold greater in number than the first population of TILs after 7 days from the start of the rapid expansion; and
wherein the myeloid aAPCs endogenously expresses HLA-A/B/C, ICOS-L, and CD58, wherein the myeloid aAPCs are transduced to express a CD86 protein and a 4-1BBL protein, wherein the myeloid aAPCs comprise EM-3 cells transduced with one or more viral vectors, and wherein the one or more viral vectors comprise a nucleic acid encoding CD86 and a nucleic acid encoding 4-1BBL, and wherein the EM-3 cells express a CD86 protein and a 4-1BBL protein.

In an embodiment, the invention provides a method of treating a cancer with a population of tumor infiltrating lymphocytes (TILs) comprising the steps of:
(a) obtaining a first population of TILs from a tumor resected from a patient;
(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and
(c) administering a therapeutically effective portion of the second population of TILs to a patient with the cancer; wherein the myeloid aAPCs endogenously expresses HLA-A/B/C, ICOS-L, and CD58, wherein the myeloid aAPCs are transduced to express a CD86 protein and a 4-1BBL protein, and wherein the rapid expansion is performed over a period not greater than 14 days.

In an embodiment, the invention provides a population of tumor infiltrating lymphocytes (TILs) for use in treating a cancer, wherein the population of TILs is a second population and is obtainable by a method comprising the steps of:
(a) performing a rapid expansion of the first population of TILs using a population of myeloid artificial antigen presenting cells (myeloid aAPCs) in a cell culture medium to obtain the second population of TILs, wherein the second population of TILs is at least 50-fold greater in number than the first population of TILs after 7 days from the start of the rapid expansion, wherein the myeloid aAPCs endogenously express HLA-A/B/C, ICOS-L and CD58, wherein the myeloid aAPCs are transduced to express a CD86 protein and a 4-1BBL protein, and wherein the rapid expansion is performed over a period not greater than 14 days.

In an embodiment, the invention provides a method of treating a cancer with a population of tumor infiltrating lymphocytes (TILs) comprising the steps of:
(a) obtaining a first population of TILs from a tumor resected from a patient;
(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and
(c) administering a therapeutically effective portion of the second population of TILs to a patient with the cancer; wherein the myeloid aAPCs endogenously expresses HLA-A/B/C, ICOS-L, and CD58, wherein the myeloid aAPCs are transduced to express a CD86 protein and a 4-1BBL protein, and wherein the cell culture medium further comprises IL-2 at an initial concentration of about 3000 IU/mL and OKT-3 antibody at an initial concentration of about 30 ng/mL.

In an embodiment, the invention provides a population of tumor infiltrating lymphocytes (TILs) for use in treating a cancer, the population of TILs being a second population of TILs and obtainable by a process comprising:
(a) performing a rapid expansion of a first population of TILs using a population of myeloid artificial antigen presenting cells (myeloid aAPCs) in a cell culture medium to obtain the second population of TILs, wherein the first population of TILs are/have been obtained from a tumor resected from a patient, and wherein the second population of TILs is at least 50-fold greater in number than the first population of TILs after 7 days from the start of the rapid expansion; and wherein the myeloid aAPCs endogenously express HLA-A/B/C, ICOS-L, and CD58, wherein the myeloid aAPCs are transduced to express a CD86 protein and a 4-1BBL protein, and wherein the cell culture medium further comprises IL-2 at an initial concentration of about 3000 IU/mL and OKT-3 antibody at an initial concentration of about 30 ng/mL.

In an embodiment, the invention provides a method of treating a cancer with a population of tumor infiltrating lymphocytes (TILs) comprising the steps of:
(a) obtaining a first population of TILs from a tumor resected from a patient;
(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and
(c) administering a therapeutically effective portion of the second population of TILs to a patient with the cancer;
wherein the myeloid aAPCs endogenously expresses HLA-A/B/C, ICOS-L, and CD58, wherein the myeloid aAPCs are transduced to express a CD86 protein and a 4-1BBL protein, and wherein the expansion is performed using a gas permeable container.

In an embodiment, the invention provides a population of tumor infiltrating lymphocytes (TILs) for use in treating a cancer, the population of TILs being a second population of TILs and obtainable by a process comprising:
(a) performing a rapid expansion of a first population of TILs using a population of myeloid artificial antigen presenting cells (myeloid aAPCs) in a cell culture medium to obtain the second population of TILs, wherein the first population of TILs are/have been obtained from a tumor resected from a patient, and wherein the second population of TILs is at least 50-fold greater in number than the first population of TILs after 7 days from the start of the rapid expansion; and wherein the myeloid aAPCs endogenously express HLA-A/B/C, ICOS-L, and CD58, wherein the myeloid aAPCs are transduced to express a CD86 protein and a 4-1BBL protein, and wherein the expansion is performed using a gas permeable container.

In an embodiment, the invention provides a method of treating a cancer with a population of tumor infiltrating lymphocytes (TILs) comprising the steps of:
(a) obtaining a first population of TILs from a tumor resected from a patient;
(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and
(c) administering a therapeutically effective portion of the second population of TILs to a patient with the cancer;
wherein the myeloid aAPCs endogenously expresses HLA-A/B/C, ICOS-L, and CD58, wherein the myeloid aAPCs are transduced to express a CD86 protein and a 4-1BBL protein, and wherein the ratio of the second population of TILs to the population of aAPCs is between 1 to 200 and 1 to 400.

In an embodiment, the invention provides a population of tumor infiltrating cells (TILs) for use in treating a cancer, the population of TILs being a second population of TILs and obtainable by a process comprising the steps of:
(a) performing a rapid expansion of a first population of TILs using a population of myeloid artificial antigen presenting cells (myeloid aAPCs) in a cell culture medium to obtain the second population of TILs, wherein the first population of TILs is/has been obtained from a tumor resected from a patient, and wherein the second population of TILs is at least 50-fold greater in number than the first population of TILs after 7 days from the start of the rapid expansion; and
wherein the myeloid aAPCs endogenously expresses HLA-A/B/C, ICOS-L, and CD58, wherein the myeloid aAPCs are transduced to express a CD86 protein and a 4-1BBL protein, and wherein the ratio of the second population of TILs to the population of aAPCs is between 1 to 200 and 1 to 400. In certain embodiments, the ratio of the second population of TILs to the population of aAPCs is about 1 to 300.

In an embodiment, the invention provides a method of treating a cancer with a population of tumor infiltrating lymphocytes (TILs) comprising the steps of:
(a) obtaining a first population of TILs from a tumor resected from a patient;
(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and
(c) administering a therapeutically effective portion of the second population of TILs to a patient with the cancer;
wherein the myeloid aAPCs endogenously expresses HLA-A/B/C, ICOS-L, and CD58, wherein the myeloid aAPCs are transduced to express a CD86 protein and a 4-1BBL protein, and wherein the ratio of the second population of TILs to the population of aAPCs is about 1 to 300.

In an embodiment, the invention provides a method of treating a cancer with a population of tumor infiltrating lymphocytes (TILs) comprising the steps of:
(a) obtaining a first population of TILs from a tumor resected from a patient;
(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and
(c) administering a therapeutically effective portion of the second population of TILs to a patient with the cancer;
wherein the myeloid aAPCs endogenously expresses HLA-A/B/C, ICOS-L, and CD58, wherein the myeloid aAPCs are transduced to express a CD86 protein and a 4-1BBL protein, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma.

In an embodiment, the invention provides a population of tumor infiltrating lymphocytes (TILs) for use in treating a cancer, the population of TILs being a second population of TILs and obtainable by a method comprising the steps of:
(a) performing a rapid expansion of a first population of TILs using a population of myeloid artificial antigen presenting cells (myeloid aAPCs) in a cell culture medium to obtain the second population of TILs, wherein the first population of TILs is/has been obtained from a tumor resected from a patient, and wherein the second population of TILs is at least 50-fold greater in number than the first population of TILs after 7 days from the start of the rapid expansion; and wherein the myeloid aAPCs endogenously expresses HLA-A/B/C, ICOS-L, and CD58, wherein the myeloid aAPCs are transduced to express a CD86 protein and a 4-1BBL protein, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma.

In an embodiment, the invention provides a method of treating a cancer with a population of tumor infiltrating lymphocytes (TILs) comprising the steps of:
(a) obtaining a first population of TILs from a tumor resected from a patient;
(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;
(d) administering a therapeutically effective portion of the third population of TILs to a patient with the cancer.

In an embodiment, the invention provides a method of treating a cancer with a population of tumor infiltrating lymphocytes (TILs) comprising the steps of:
(a) obtaining a first population of TILs from a tumor resected from a patient;
(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;
(d) administering a therapeutically effective portion of the third population of TILs to a patient with the cancer, wherein the myeloid aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein.

In an embodiment, the invention provides a method of treating a cancer with a population of tumor infiltrating lymphocytes (TILs) comprising the steps of:
(a) obtaining a first population of TILs from a tumor resected from a patient;
(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;
(d) administering a therapeutically effective portion of the third population of TILs to a patient with the cancer, wherein the myeloid aAPCs comprise EM-3 cells transduced with one or more viral vectors, wherein the one or more viral vectors comprise a nucleic acid encoding CD86 and a nucleic acid encoding 4-1BBL, and wherein the EM-3 cells express a CD86 protein and a 4-1BBL protein.

In an embodiment, the invention provides a population of tumor infiltrating lymphocytes (TILs) for use in treating a cancer, wherein the population of TILs is a third population of TILs and obtainable by a method comprising the steps of:
(a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2;
(b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3.

In an embodiment, the myeloid aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. In an embodiment, the myeloid cells comprise MOLM-13 cells transduced with one or more viral vectors, wherein the one or more viral vectors comprise a nucleic acid encoding CD86 and a nucleic acid encoding 4-1BBL, and wherein the MOLM-13 cells express a CD86 protein and a 4-1BBL protein. In certain embodiments, the myeloid cells comprise EM-3 cells transduced with one or more viral vectors, wherein the one or more viral vectors comprise a nucleic acid encoding CD86 and a nucleic acid encoding 4-1BBL, and wherein the EM-3 cells express a CD86 protein and a 4-1BBL protein. In certain embodiments, the myeloid cells comprise EM-2 cells transduced with one or more viral vectors, wherein the one or more viral vectors comprise a nucleic acid encoding CD86 and a nucleic acid encoding 4-1BBL, and wherein the EM-2 cells express a CD86 protein and a 4-1BBL protein.

In an embodiment, the invention provides a method of treating a cancer with a population of tumor infiltrating lymphocytes (TILs) comprising the steps of:
- (a) obtaining a first population of TILs from a tumor resected from a patient;
- (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
- (c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;
- (d) treating the patient with a non-myeloablative lymphodepletion regimen, wherein the non-myeloablative lymphodepletion regimen comprises the steps of administration of cyclophosphamide at a dose of 60 mg/m²/day for two days followed by administration of fludarabine at a dose of 25 mg/m²/day for five days;
- (e) administering a therapeutically effective portion of the third population of TILs to a patient with the cancer; and
- (f) treating the patient with a high-dose IL-2 regimen, wherein the high-dose IL-2 regimen comprises 600,000 or 720,000 IU/kg of aldesleukin administered as a 15-minute bolus intravenous infusion every eight hours until tolerance;

wherein the myeloid aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein.

In an embodiment, the invention provides a method of treating a cancer with a population of tumor infiltrating lymphocytes (TILs) comprising the steps of:
- (a) obtaining a first population of TILs from a tumor resected from a patient;
- (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
- (c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;
- (d) treating the patient with a non-myeloablative lymphodepletion regimen, wherein the non-myeloablative lymphodepletion regimen comprises the steps of administration of cyclophosphamide at a dose of 60 mg/m²/day for two days followed by administration of fludarabine at a dose of 25 mg/m²/day for five days;
- (e) administering a therapeutically effective portion of the third population of TILs to a patient with the cancer; and
- (f) treating the patient with a high-dose IL-2 regimen, wherein the high-dose IL-2 regimen comprises 600,000 or 720,000 IU/kg of aldesleukin administered as a 15-minute bolus intravenous infusion every eight hours until tolerance;

wherein the myeloid aAPCs comprise EM-3 cells transduced with one or more viral vectors, wherein the one or more viral vectors comprise a nucleic acid encoding CD86 and a nucleic acid encoding 4-1BBL, and wherein the EM-3 cells express a CD86 protein and a 4-1BBL protein.

In an embodiment, the invention provides a population of tumor infiltrating lymphocytes (TILs) for use in treating a cancer, wherein the population of TILs are a third population of TILs and obtainable by a method comprising the steps of:
- (a) an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2; and
- (b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3;

and further wherein the population of TILs is for administration to a patient in combination with a non-myeloablative lymphodepletion regimen, wherein the non-myeloablative lymphodepletion regimen comprises cyclophosphamide which is for administration at a dose of 60 mg/m²/day for two days followed by fludarabine which is for administration at a dose of 25 mg/m²/day for five days and further wherein the population of TILs is for administration in combination with a high-dose IL-2 regimen, wherein the high-dose IL-2 regimen comprises 600,000 or 720,000 IU/kg of aldesleukin for administration as a 15-minute bolus intravenous infusion every eight hours until tolerance. In certain embodiments, the population of TILs is for administration prior to the high-dose IL-2 regimen and subsequent to the non-myeloablative lymphodepletion regimen.

In certain embodiments, the myeloid aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. the myeloid aAPCs comprise MOLM-13 cells transduced with one or more viral vectors, wherein the one or more viral vectors comprise a nucleic acid encoding CD86 and a nucleic acid encoding 4-1BBL, and wherein the MOLM-13 cells express a CD86 protein and a 4-1BBL protein. In certain embodiments, the myeloid aAPCs comprise EM-3 cells transduced with one or more viral vectors, wherein the one or more viral vectors comprise a nucleic acid encoding CD86 and a nucleic acid encoding 4-1BBL, and wherein the EM-3 cells express a CD86 protein and a 4-1BBL protein.

In an embodiment, the population of TILs is for use in the treating of a cancer selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma.

In an embodiment, the invention provides a method of treating a cancer with a population of tumor infiltrating lymphocytes (TILs) comprising the steps of:
  (a) obtaining a first population of TILs from a tumor resected from a patient;
  (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
  (c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; and
  (d) administering a therapeutically effective portion of the third population of TILs to a patient with the cancer,
  wherein IL-2 is present at an initial concentration of about 3000 IU/mL and OKT-3 antibody is present at an initial concentration of about 30 ng/mL in the second cell culture medium.

In an embodiment, the invention provides a population of tumor infiltrating lymphocytes (TILs) for use in treating a cancer, wherein the population of TILs is a third population of TILs and is obtainable by a method comprising the steps:
  (a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2; and
  (b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3; wherein IL-2 is present at an initial concentration of about 3000 IU/mL and OKT-3 antibody is present at an initial concentration of about 30 ng/mL in the second cell culture medium.

In an embodiment, the invention provides a method of treating a cancer with a population of tumor infiltrating lymphocytes (TILs) comprising the steps of:
  (a) obtaining a first population of TILs from a tumor resected from a patient;
  (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
  (c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; and
  (d) administering a therapeutically effective portion of the third population of TILs to a patient with the cancer,
  wherein the rapid expansion is performed over a period not greater than 14 days.

In an embodiment, the invention provides a population of tumor infiltrating lymphocytes (TILs) for use in treating a cancer, wherein the population of TILs is a third population of TILs and is obtainable by a method comprising the steps:
  (a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2; and
  (b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3; wherein the rapid expansion is performed over a period not greater than 14 days.

In embodiment, the invention provides a method of treating a cancer with a population of tumor infiltrating lymphocytes (TILs) comprising the steps of:
  (a) obtaining a first population of TILs from a tumor resected from a patient;
  (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
  (c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; and
  (d) administering a therapeutically effective portion of the third population of TILs to a patient with the cancer,
  wherein the initial expansion is performed using a gas permeable container.

In an embodiment, the invention provides a method of treating a cancer with a population of tumor infiltrating lymphocytes (TILs) comprising the steps of:
  (a) obtaining a first population of TILs from a tumor resected from a patient;
  (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; and
(d) administering a therapeutically effective portion of the third population of TILs to a patient with the cancer, wherein the rapid expansion is performed using a gas permeable container.

In an embodiment, the invention provides a population of tumor infiltrating lymphocytes (TILs) for use in treating a cancer, wherein the population of TILs is a third population of TILs and is obtainable by a method comprising the steps:
(a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2;
(b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3; wherein the initial expansion and/or the rapid expansion is performed using a gas-permeable container.

In an embodiment, the invention provides a method of treating a cancer with a population of tumor infiltrating lymphocytes (TILs) comprising the steps of:
(a) obtaining a first population of TILs from a tumor resected from a patient;
(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;
(d) administering a therapeutically effective portion of the third population of TILs to a patient with the cancer, wherein the ratio of the second population of TILs to the population of aAPCs in the rapid expansion is between 1 to 80 and 1 to 400.

In an embodiment, the invention provides a method of treating a cancer with a population of tumor infiltrating lymphocytes (TILs) comprising the steps of:
(a) obtaining a first population of TILs from a tumor resected from a patient;
(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;
(d) administering a therapeutically effective portion of the third population of TILs to a patient with the cancer, wherein the ratio of the second population of TILs to the population of aAPCs in the rapid expansion is about 1 to 300.

In an embodiment, the invention provides a population of tumor infiltrating lymphocytes (TILs) for use in treating a cancer, wherein the population of TILs is a third population of TILs and is obtainable by a method comprising the steps:
(a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2;
(b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3, and wherein the ratio of the second population of TILs to the population of aAPCs in the rapid expansion is between 1 to 80 and 1 to 400.

In an embodiment, the the ratio of the second population of TILs to the population of aAPCs in the rapid expansion is about 1 to 300.

In an embodiment, the invention provides a method of treating a cancer with a population of tumor infiltrating lymphocytes (TILs) comprising the steps of:
(a) obtaining a first population of TILs from a tumor resected from a patient;
(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;
(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) administering a therapeutically effective portion of the third population of TILs to a patient with the cancer, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma.

In an embodiment, the invention provides a kit for specifically inducing proliferation of a tumor infiltrating lymphocyte expressing a known co-stimulatory molecule, the kit comprising an effective amount of an aAPC, wherein said aAPC comprises a MOLM-14 cell or a EM-3 cell transduced using a lentiviral vector (LV), wherein the LV comprises a nucleic acid encoding at least one co-stimulatory ligand that specifically binds said known co-stimulatory molecule, wherein binding of the known co-stimulatory molecule with said co-stimulatory ligand stimulates and expands said T cell, the kit further comprising an applicator and an instructional material for the use of said kit.

In an embodiment, the invention provides a method for assessing the potency of tumor infiltrating lymphocytes (TILs) comprising the steps of:

(a) providing a plurality of mouse mastocytoma P815 cells expressing the endogenous CD16 Fc receptor, wherein the P815 cells are transduced with a lentiviral vector based on enhanced green fluorescent protein (GFP) and Firefly Luciferase;
(b) co-culturing the plurality of P815 cells TILs with and without OKT-3 to assess T cell receptor (TCR) activation (specific killing) or lymphokine activated killing (LAK, non-specific killing), respectively;
(c) incubating for four hours;
(d) adding Luciferin and incubating for 5 minutes;
(e) reading bioluminescence intensity using a luminometer; and
(f) and calculating percent cytotoxicity and survival.

BRIEF DESCRIPTION OF THE DRAWINGS

The foregoing summary, as well as the following detailed description of the invention, will be better understood when read in conjunction with the appended drawings.

FIG. 86 illustrates the total cell counts for experiment one and FIG. 87 illustrates the total cell counts for experiment two.

BRIEF DESCRIPTION OF THE SEQUENCE LISTING

Figure 1:
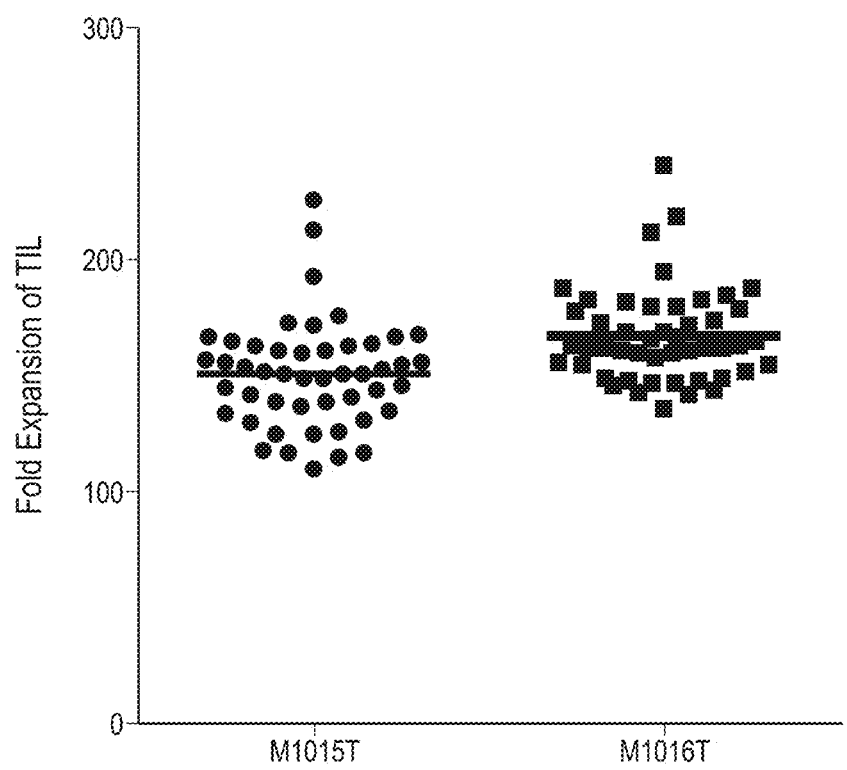
FIG. 1 illustrates the results of rapid expansion of TILs using irradiated allogeneic PBMC feeder cells. Each TIL line (M1015T and M1016T) ($1.3 \times 10^5$ cells) was co-cultured with 46 different irradiated feeders ($1.3 \times 10^7$ cells), IL-2 (3000 IU/mL) and OKT-3 (30 ng/mL) in a T25 flask for 7 days. The fold expansion value for TILs was calculated on Day 7. The figure shows the number of fold expansions for two TIL lines in separate stimulation experiments, with 46 different feeder lots tested, and highlights the variability of expansion results using PBMC feeder cells.

SEQ ID NO:1 is an amino acid sequence for the heavy chain of muromonab.

SEQ ID NO:2 is an amino acid sequence for the light chain of muromonab.

SEQ ID NO:3 is an amino acid sequence for recombinant human IL-2.

SEQ ID NO:4 is an amino acid sequence for aldesleukin.

SEQ ID NO:5 is an amino acid sequence for recombinant human IL-7.

SEQ ID NO:6 is an amino acid sequence for recombinant human IL-15.

SEQ ID NO:7 is an amino acid sequence for recombinant IL-21.

SEQ ID NO:8 is the amino acid sequence of human CD86.

SEQ ID NO:9 is the amino acid sequence of human 4-1BBL (CD137L).

SEQ ID NO:10 is the amino acid sequence of human OX40L (CD134L).

SEQ ID NO:11 is the amino acid sequence of human CD28.

SEQ ID NO:12 is the amino acid sequence of human CTLA-4.

SEQ ID NO:13 is the amino acid sequence of human 4-1BB (CD137).

SEQ ID NO:14 is the amino acid sequence of human OX40 (CD134).

SEQ ID NO:15 is a nucleotide sequence for the pLV430G 4-1BBL empty vector.

SEQ ID NO:16 is a nucleotide sequence for the 4-1BBL CoOP portion of the pLV430G human 4-1BBL vector.

SEQ ID NO:17 is a nucleotide sequence for the 4-1BBL PCRP.

SEQ ID NO:18 is a nucleotide sequence for the pLV430G hCD86 empty vector.

SEQ ID NO:19 is a nucleotide sequence for the hCD86 CoOP portion of the pLV430G human hCD86 vector.

SEQ ID NO:20 is a nucleotide sequence for the hCD86 CoOP B1 B2 PCRP portion of the pLV430G human hCD86 vector.

SEQ ID NO:21 is a nucleotide sequence for the pDONR221 hCD86 vector.

SEQ ID NO:22 is a nucleotide sequence for the pDONR221 4-1BBL vector.

SEQ ID NO:23 is a nucleotide sequence for the pLV430G vector.

SEQ ID NO:24 is a nucleotide sequence for the pDONR221 vector.

SEQ ID NO:25 is a nucleotide sequence for the psPAX2 helper plasmid for lentiviral production.

SEQ ID NO:26 is a nucleotide sequence for the pCIGO-VSV.G helper plasmid for lentiviral production.

SEQ ID NO:27 is the amino acid sequence of the mFc-7C12 scFv clone.

SEQ ID NO:28 is the amino acid sequence of the mFc-8B3 scFv clone.

SEQ ID NO:29 is a nucleotide sequence for the mFC-7C12 scFv.

SEQ ID NO:30 is a nucleotide sequence for the mFC-8B3 scFv.

SEQ ID NO:31 is a nucleotide sequence for the destination vector pLV4301G.

SEQ ID NO:32 is a nucleotide sequence for the donor vector 1, pMK 7c12 anti mFC scFv CoOp ECORV SacII L1R5.

SEQ ID NO:33 is a nucleotide sequence for the donor vector 2, pMK hCD8a scaffold TN L5 L2.

SEQ ID NO:34 is a nucleotide sequence for the final vector used for lentiviral production, pLV4301G 7C12 scFv mIgG hCD8 flag.

SEQ ID NO:35 is a nucleotide sequence for the destination vector, pLV4301G.

SEQ ID NO:36 is a nucleotide sequence for the donor vector 1, pMK 8B3 anti mFC scFv CoOp ECORV SacII L1R5.

SEQ ID NO:37 is a nucleotide sequence for the donor vector 2, pMK hCD8a scaffold TN L5 L2.

SEQ ID NO:38 is a nucleotide sequence for the final vector used for lentiviral production, pLV4301G 8B3 scFv mIgG hCD8 flag.

SEQ ID NO:39 is a nucleotide sequence for pLenti-C-Myc-DDK OX40L vector for lentiviral production.

SEQ ID NO:40 is a nucleotide sequence for Tel-1b primer used for quantitative polymerase chain reaction measurements of telomere length.

SEQ ID NO:41 is a nucleotide sequence for Tel-2b primer used for quantitative polymerase chain reaction measurements of telomere length.

SEQ ID NO:42 is a nucleotide sequence for Tel-1b primer used for quantitative polymerase chain reaction measurements of telomere length.

SEQ ID NO:43 is a nucleotide sequence for Tel-1b primer used for quantitative polymerase chain reaction measurements of telomere length.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

The terms "co-administration," "co-administering," "administered in combination with," "administering in combination with," "simultaneous," and "concurrent," as used herein, encompass administration of two or more active pharmaceutical ingredients to a human subject so that both active pharmaceutical ingredients and/or their metabolites are present in the human subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present is also encompassed in the methods of the invention.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "antigen" refers to a substance that induces an immune response. In some embodiments, an antigen is a molecule capable of being bound by an antibody or a T cell receptor (TCR) if presented by major histocompatibility complex (MEW) molecules. The term "antigen", as used herein, also encompasses T cell epitopes. An antigen is additionally capable of being recognized by the immune system. In some embodiments, an antigen is capable of inducing a humoral immune response or a cellular immune response leading to the activation of B lymphocytes and/or T lymphocytes. In some cases, this may require that the antigen contains or is linked to a Th cell epitope. An antigen can also have one or more epitopes (e.g., B- and T-epitopes). In some embodiments, an antigen will preferably react, typically in a highly specific and selective manner, with its corresponding antibody or TCR and not with the multitude of other antibodies or TCRs which may be induced by other antigens.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the human subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit in a human subject. A prophylactic effect includes delaying or eliminating the appearance of a disease or condition, delaying or eliminating the onset of symptoms of a disease or condition, slowing, halting, or reversing the progression of a disease or condition, or any combination thereof.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are described herein.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to herein as "freshly harvested" or "a first population of TILs"), and "secondary TILs" are any TIL cell populations that have been expanded or proliferated as discussed herein, including, but not limited to bulk TILs and expanded TILs ("REP TILs" or "post-REP TILs", or "second population of TILs" or "third population of TILs" where appropriate).

TILs can generally be defined either biochemically, using cell surface markers, or functionally, by their ability to infiltrate tumors and effect treatment. TILs can be generally categorized by expressing one or more of the following biomarkers: CD4, CD8, TCR $\alpha\beta$, CD27, CD28, CD56, CCR7, CD45Ra, CD95, PD-1, and CD25. Additionally, and alternatively, TILs can be functionally defined by their ability to infiltrate solid tumors upon reintroduction into a patient.

By "cryopreserved TILs" herein is meant that TILs are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

By "population of cells" (including TILs) herein is meant a number of cells that share common traits.

The term "central memory T cell" refers to a subset of T cells that in the human are CD45R0+ and constitutively express CCR7 ($CCR7^{hi}$) and CD62L ($CD62^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 (CCR7$^{lo}$) and are heterogeneous or low for CD62L expression (CD62L$^{lo}$). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin.

The terms "sequence identity," "percent identity," and "sequence percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, Calif.) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

The term "conservative amino acid substitutions" means amino acid sequence modifications which do not abrogate the binding of an antibody to an antigen or a protein to its ligand. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in a 4-1BBL or CD86 protein is preferably replaced with another amino acid residue from the same class. Methods of identifying amino acid conservative substitutions which do not eliminate antigen or ligand binding are well-known in the art (see, e.g., Brummell, et al., *Biochemistry* 1993, 32, 1180-1187; Kobayashi, et al., Protein Eng. 1999, 12, 879-884 (1999); and Burks, et al., *Proc. Natl. Acad. Sci. USA* 1997, 94, 412-417).

The term "retrovirus" refers to RNA viruses that utilize reverse transcriptase during their replication cycle, wherein retroviral genomic RNA is converted into double-stranded DNA by reverse transcriptase. The double-stranded DNA form is integrated into the chromosome of the infected cell (a "provirus"). The provirus serves as a template for RNA polymerase II and directs the expression of RNA molecules which encode the structural proteins and enzymes needed to produce new viral particles. At each end of the provirus are structures called "long terminal repeats" or "LTRs." The LTR contains numerous regulatory signals including transcriptional control elements, polyadenylation signals and sequences needed for replication and integration of the viral genome. Several genera included within the family Retroviridae, including *Cisternavirus A, Oncovirus A, Oncovirus B, Oncovirus C, Oncovirus D, Lentivirus, Gammaretrovirus*, and *Spumavirus*. Some of the retroviruses are oncogenic (i.e., tumorigenic), while others are not. The oncoviruses induce sarcomas, leukemias, lymphomas, and mammary carcinomas in susceptible species. Retroviruses infect a wide variety of species, and may be transmitted both horizontally and vertically. Because they are integrated into the host DNA, they are capable of transmitting sequences of host DNA from cell to cell. Example gammaretroviral vectors include those derived from the amphotropic Moloney murine leukemia virus (MLV-A), which use cell surface phosphate transporter receptors for entry and then permanently integrate into proliferating cell chromosomes. The amphotropic MLV vector system has been well established and is a popular tool for gene delivery (See, e.g., Gordon and Anderson, *Curr. Op. Biotechnol.*, 1994, 5, 611-616 and Miller, et al., *Meth. Enzymol.*, 1993, 217, 581-599, the disclosures of which are incorporated herein by reference.

The term "lentivirus" refers to a genus that includes HIV (human immunodeficiency virus; including HIV type 1, and HIV type 2), visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T cells).

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotec GmbH, Bergisch Gladbach, Germany) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the

TABLE 1

Amino acid sequences of muromonab.

| Identifier (Description) | Sequence (One-Letter Amino Acid Symbols) | | | | | |
|---|---|---|---|---|---|---|
| SEQ ID NO: 1 (Muromonab heavy chain) | QVQLQQSGAE NQHFKDKATL KTTAPSVYPL YTLSSSVTVT PSVFLFPPKP STYRVVSVLT LTKNQVSLTC QQGNVFSCSV | LARPGASVKM TTDKSSSTAY APVCGGTTGS SSTWPSQSIT KDTLMISRTP VLHQDWLNGK LVEGFYPSDI MHEALHNHYT | SCHASGYTFT MQLSSLTSED SVTLGCLVKG CNVAHPASST EVTCVVVDVS EYKCKVSNKA AVEWESNGQP QKSLSLSPGK | RYTMHWVKQR SAVYYCARYY YFPEPVTLTW KVDKKIEPRP HEDPEVKFNW LPAPIEKTIS ENNYKTTPPV | PGQGLEWIGY DDHYCLDYWG NSGSLSSGVH KSCDKTHTCP YVDGVEVHNA KARGQPREPQ LDSDGSFFLY | INPSRGYTNY QGTTLTVSSA TFPAVLQSDL PCPAPELLGG KTKPREEQYN VYTLPPSRDE SKLTVDKSRW | 60 120 180 240 300 360 420 450 |
| SEQ ID NO: 2 (Muromonab light chain) | QIVLTQSPAI FRGSGSGTSY SEQLTSGGAS TKDEYERHNS | MSASPGEKVT SLTISGMEAE VVCFLNNFYP YTCEATHKTS | MTCSASSSVS DAATYYCQQW KDINVKWKID TSPIVKSFNR | YMNWYQQKSG SSNPFTFGSG GSERQNGVLN NEC | TSPKRWIYDT TKLEINRADT SWTDQDSKDS | SKLASGVPAH APTVSIFPPS TYSMSSTLTL | 60 120 180 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, N.H., USA (CELLGRO GMP) or ProSpec-Tany TechnoGene Ltd., East Brunswick, N.J., USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, Calif., USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. Formulations of IL-2 suitable for use in the invention are described in U.S. Pat. No. 6,706,289, the disclosure of which is incorporated by reference herein.

invention is commercially available from multiple suppliers, including ProSpec-Tany TechnoGene Ltd., East Brunswick, N.J., USA (Cat. No. CYT-254) and ThermoFisher Scientific, Inc., Waltham, Mass., USA (human IL-7 recombinant protein, Cat. No. Gibco PHC0071). The amino acid sequence of recombinant human IL-7 suitable for use in the invention is given in Table 2 (SEQ ID NO:5).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, N.J., USA (Cat. No. CYT-230-b) and Thermo-Fisher Scientific, Inc., Waltham, Mass., USA (human IL-15 recombinant protein, Cat. No. 34-8159-82). The amino acid sequence of recombinant human IL-15 suitable for use in the invention is given in Table 2 (SEQ ID NO:6).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human CD4+ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, N.J., USA (Cat. No. CYT-408-b) and ThermoFisher Scientific, Inc., Waltham, Mass., USA (human IL-21 recombinant protein, Cat. No. 14-8219-80). The amino acid sequence of recombinant human IL-21 suitable for use in the invention is given in Table 2 (SEQ ID NO:7).

closely related EM-2 cell line is deposited at DSMZ under Accession No. ACC135. As used herein the term "EM-3 cell" refers to a EM-3 cell and/or a cell derived from the deposited EM-3 parental cell line.

As used herein, the term "a CD86 protein" may refer to a protein comprising an amino acid sequence as set forth in

TABLE 2

Amino acid sequences of interleukins.

| Identifier (Description) | Sequence (One-Letter Amino Acid Symbols) | | | | | | |
|---|---|---|---|---|---|---|---|
| SEQ ID NO: 3 (recombinant human IL-2 (rhIL-2)) | MAPTSSSTKK EEELKPLEEV RWITFCQSII | TQLQLEHLLL LNLAQSKNFH STLT | DLQMILNGIN LRPRDLISNI | NYKNPKLTRM NVIVLELKGS | LTFKFYMPKK ETTFMCEYAD | ATELKHLQCL ETATIVEFLN | 60 120 134 |
| SEQ ID NO: 4 (aldesleukin) | PTSSSTKKTQ ELKPLEEVLN ITFSQSIIST | LQLEHLLLDL LAQSKNFHLR LT | QMILNGINNY PRDLISNINV | KNPKLTRMLT IVLELKGSET | FKFYMPKKAT TFMCEYADET | ELKHLQCLEE ATIVEFLNRW | 60 120 132 |
| SEQ ID NO: 5 (recombinant human IL-7 (rhIL-7)) | MDCDIEGKDG ARKLRQFLKM KEQKKLNDLC | KQYESVLMVS NSTGDFDLHL FLKRLLQEIK | IDQLLDSMKE LKVSEGTTIL TCWNKILMGT | IGSNCLNNEF LNCTGQVKGR KEH | NFFKRHICDA KPAALGEAQP | NKEGMFLFRA THSLEENKSL | 60 120 153 |
| SEQ ID NO: 6 (recombinant human IL-15 (rhIL-15)) | MNWVNVISDL HDTVENLIIL | KKIEDLIQSM ANNSLSSNGN | HIDATLYTES VTESGCKECE | DVHPSCKVTA ELEEKNIKEF | MKCFLLELQV LQSFVHIVQM | ISLESGDASI FINTS | 60 115 |
| SEQ ID NO: 7 (recombinant human IL-21 (rhIL-21)) | MQDRHMIRMR NNERIINVSI HLSSRTHGSE | QLIDIVDQLK KKLKRKPPST DS | NYVNDLVPEF NAGRRQKHRL | LPAPEDVETN TCPSCDSYEK | CEWSAFSCFQ KPPKEFLERF | KAQLKSANTG KSLLQHMIHQ | 60 120 132 |

The term "myeloid cell" as used herein refers to cells of the myeloid lineage or derived therefrom. The myeloid lineage includes a number of morphologically, phenotypically, and functionally distinct cell types including different subsets of granulocytes (neutrophils, eosinophils, and basophils), monocytes, macrophages, erythrocytes, megakaryocytes, and mast cells. In certain embodiments, the myeloid cell is a cell derived from a cell line of myeloid lineage.

"MOLM-14" refers to a human leukemia cell line which was established from the peripheral blood of a patient with relapsed acute monocytic leukemia, and initial phenotypic characterization indicated the presence of at least the following markers: CD4, CD9, CD11a, CD13, CD14, CD15, CD32, CD33, CD64, CD65, CD87, CD92, CD93, CD116, CD118, and CD155. Matsuo, et al., *Leukemia* 1997, 11, 1469-77. Additional phenotypic characterization of MOLM-14 found higher levels of HLA-A/B/C, CD64, CD80, ICOS-L, CD58, and lower levels of CD86. The MOLM-14 cell line is deposited at DSMZ under Accession No. ACC777. The closely related MOLM-13 cell line is deposited at DSMZ under Accession No. ACC554. As used herein the term "MOLM-14 cell" refers to a MOLM-14 cell and/or a cell derived from the deposited MOLM-14 parental cell line. As used herein the term "MOLM-13 cell" refers to a MOLM-13 cell and/or a cell derived from the deposited MOLM-13 parental cell line.

"EM-3" refers to a human cell line was established from the bone marrow of a patient with Philadelphia chromosome-positive CIVIL. Konopka, et al., *Proc. Nat'l Acad. Sci. USA* 1985, 82, 1810-4. Phenotypic characterization for EM-3 cells indicates the presence of at least the following markers: CD13, CD15, and CD33. The EM-3 cell line is deposited at DSMZ under Accession No. ACC134 whilst the SEQ ID NO:8 or a protein comprising an amino acid sequence having at least 90% sequence identity to the amino acid sequence depicted in SEQ ID NO:8, e.g., 91%, 92%, 93%, 94%, 95%, 96%, 97%, 98% or 99%.

As used herein, the term "4-1BBL" or "CD137L" may refer to a protein comprising an amino acid sequence as set forth in SEQ ID NO:9 or a protein comprising an amino acid sequence having at least 90% sequence identity to the amino acid sequence depicted in SEQ ID NO:9, e.g., 91%, 92%, 93%, 94%, 95%, 96%, 97%, 98% or 99%.

As used herein, the term "OX40L" or "CD137L" may refer to a protein comprising an amino acid sequence as set forth in SEQ ID NO:10 or a protein comprising an amino acid sequence having at least 90% sequence identity to the amino acid sequence depicted in SEQ ID NO:10, e.g., 91%, 92%, 93%, 94%, 95%, 96%, 97%, 98% or 99%.

The term "biosimilar" means a biological product, including a monoclonal antibody or fusion protein, that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference IL-2 protein is aldesleukin (PROLEUKIN), a protein approved by drug regulatory authorities with reference to aldesleukin is a "biosimilar to" aldesleukin or is a "biosimilar thereof" of aldesleukin. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorized, approved for authorization or subject of an application for authorization under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorized by the EMA. However, in some instances, the biosimilar may be compared to a biological medicinal product which has been authorized outside the European Economic Area (a non-EEA authorized "comparator") in certain studies. Such studies include for example certain clinical and in vivo non-clinical studies. As used herein, the term "biosimilar" also relates to a biological medicinal product which has been or may be compared to a non-EEA authorized comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorized or considered suitable for authorization. In certain circumstances, the biosimilar exhibits different binding characteristics as compared to the reference medicinal product, wherein the different binding characteristics are considered by a Regulatory Authority such as the EMA not to be a barrier for authorization as a similar biological product. The term "biosimilar" is also used synonymously by other national and regional regulatory agencies.

As used herein, the term "variant" encompasses but is not limited to proteins, antibodies or fusion proteins which comprise an amino acid sequence which differs from the amino acid sequence of a reference protein or antibody by way of one or more substitutions, deletions and/or additions at certain positions within or adjacent to the amino acid sequence of the reference protein or antibody. The variant may comprise one or more conservative substitutions in its amino acid sequence as compared to the amino acid sequence of a reference protein or antibody. Conservative substitutions may involve, e.g., the substitution of similarly charged or uncharged amino acids. The variant retains the ability to specifically bind to the antigen of the reference protein or antibody. The term "variant" also includes pegylated antibodies or proteins.

"Pegylation" refers to a modified antibody, or a fragment thereof, or protein that typically is reacted with polyethylene glycol (PEG), such as a reactive ester or aldehyde derivative of PEG, under conditions in which one or more PEG groups become attached to the antibody, antibody fragment, or protein. Pegylation may, for example, increase the biological (e.g., serum) half life of the antibody or protein. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The antibody or protein to be pegylated may be an aglycosylated antibody. Methods for pegylation are known in the art and can be applied to the antibodies and proteins described herein, as described for example in European Patent Nos. EP 0154316 and EP 0401384.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

Artificial Antigen Presenting Cells

In an embodiment, the invention includes an isolated artificial antigen presenting cell (aAPC) comprising a cell that expresses HLA-A/B/C, CD64, CD80, ICOS-L, and CD58, and is modified to express one or more costimulatory molecules. In an embodiment, the invention includes an aAPC comprising a MOLM-14 cell that is modified to express one or more costimulatory molecules. In an embodiment, the invention includes an aAPC comprising a MOLM-13 cell that is modified to express one or more costimulatory molecules.

In an embodiment, the invention includes an aAPC comprising a MOLM-14 cell that endogenously expresses HLA-A/B/C, CD64, CD80, ICOS-L, and CD58, wherein the cell is modified to express a CD86 protein comprising an amino acid sequence as set forth in SEQ ID NO:8, and conservative amino acid substitutions thereof, and a 4-1BBL protein comprising an amino acid sequence as set forth in SEQ ID NO:9, and conservative amino acid substitutions thereof, and wherein the CD86 protein and the 4-1BBL protein are expressed on the surface of the MOLM-14 cell.

In an embodiment, the invention includes an aAPC comprising a MOLM-14 cell transduced with one or more viral vectors, wherein the one or more viral vectors comprise a nucleic acid encoding CD86 and a nucleic acid encoding 4-1BBL, and wherein the MOLM-14 cell expresses CD86 and 4-1BBL. In an embodiment, the invention includes an aAPC comprising a MOLM-13 cell transduced with one or more viral vectors, wherein the one or more viral vectors comprise a nucleic acid encoding CD86 and a nucleic acid encoding 4-1BBL, and wherein the MOLM-13 cell expresses CD86 and 4-1BBL. In an embodiment, the invention includes a method of preparing any of the foregoing embodiments of aAPCs.

In an embodiment, the invention includes an aAPC comprising a MOLM-14 cell modified to express a CD86 protein comprising an amino acid sequence as set forth in SEQ ID NO:8 and a 4-1BBL protein comprising an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-13 cell modified to express a CD86 protein comprising an amino acid sequence as set forth in SEQ ID NO:8, and conservative amino acid substitutions thereof, and a 4-1BBL protein comprising an amino acid sequence as set forth in SEQ ID NO:9, and conservative amino acid substitutions thereof, wherein the CD86 protein and the 4-1BBL protein are expressed on the surface of the MOLM-13 cell. In an embodiment, the invention includes a method of preparing any of the foregoing embodiments of aAPCs.

In an embodiment, the invention includes an aAPC comprising a MOLM-14 cell modified to express a CD86 protein comprising a sequence with greater than 99% identity to an amino acid sequence as set forth in SEQ ID NO:8 and a 4-1BBL protein comprising a sequence with greater than 99% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 98% identity to an amino acid sequence as set forth in SEQ ID NO:8 and a 4-1BBL protein comprising a sequence with greater than 98% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 97% identity to an amino acid sequence as set forth in SEQ ID NO:8 and a 4-1BBL protein comprising a sequence with greater than 97% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 96% identity to an amino acid sequence as set forth in SEQ ID NO:8 and a 4-1BBL protein comprising a sequence with greater than 96% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 95% identity to an amino acid sequence as set forth in SEQ ID NO:8 and a 4-1BBL protein comprising a sequence with greater than 95% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 90% identity to an amino acid sequence as set forth in SEQ ID NO:8 and a 4-1BBL protein comprising a sequence with greater than 90% identity to an amino acid sequence as set forth in SEQ ID NO:9, wherein the CD86 protein and the 4-1BBL protein are expressed on the surface of the MOLM-14 cell. In an embodiment, the invention includes a method of preparing any of the foregoing embodiments of aAPCs.

In an embodiment, the invention includes an aAPC comprising a MOLM-13 cell modified to express a CD86 protein comprising an amino acid sequence as set forth in SEQ ID NO:8 and a 4-1BBL protein comprising an amino acid sequence as set forth in SEQ ID NO:9, wherein the CD86 protein and the 4-1BBL protein are expressed on the surface of the MOLM-13 cell. In an embodiment, the invention includes an aAPC comprising a MOLM-13 cell modified to express a CD86 protein comprising an amino acid sequence as set forth in SEQ ID NO:8, and conservative amino acid substitutions thereof, and a 4-1BBL protein comprising an amino acid sequence as set forth in SEQ ID NO:9, and conservative amino acid substitutions thereof, wherein the CD86 protein and the 4-1BBL protein are expressed on the surface of the MOLM-13 cell. In an embodiment, the invention includes a method of preparing any of the foregoing embodiments of aAPCs.

In an embodiment, the invention includes an aAPC comprising a MOLM-13 cell modified to express a CD86 protein comprising a sequence with greater than 99% identity to an amino acid sequence as set forth in SEQ ID NO:8 and a 4-1BBL protein comprising a sequence with greater than 99% identity to an amino acid sequence as set forth in SEQ ID NO:9, wherein the CD86 protein and the 4-1BBL protein are expressed on the surface of the MOLM-13 cell. In an embodiment, the invention includes an aAPC comprising a MOLM-13 cell modified to express a CD86 protein comprising a sequence with greater than 98% identity to an amino acid sequence as set forth in SEQ ID NO:8 and a 4-1BBL protein comprising a sequence with greater than 98% identity to an amino acid sequence as set forth in SEQ ID NO:9, wherein the CD86 protein and the 4-1BBL protein are expressed on the surface of the MOLM-13 cell. In an embodiment, the invention includes an aAPC comprising a MOLM-13 cell modified to express a CD86 protein comprising a sequence with greater than 97% identity to an amino acid sequence as set forth in SEQ ID NO:8 and a 4-1BBL protein comprising a sequence with greater than 97% identity to an amino acid sequence as set forth in SEQ ID NO:9, wherein the CD86 protein and the 4-1BBL protein are expressed on the surface of the MOLM-13 cell. In an embodiment, the invention includes an aAPC comprising a MOLM-13 cell modified to express a CD86 protein comprising a sequence with greater than 96% identity to an amino acid sequence as set forth in SEQ ID NO:8 and a 4-1BBL protein comprising a sequence with greater than 96% identity to an amino acid sequence as set forth in SEQ ID NO:9, wherein the CD86 protein and the 4-1BBL protein are expressed on the surface of the MOLM-13 cell. In an embodiment, the invention includes an aAPC comprising a MOLM-13 cell modified to express a CD86 protein comprising a sequence with greater than 95% identity to an amino acid sequence as set forth in SEQ ID NO:8 and a 4-1BBL protein comprising a sequence with greater than 95% identity to an amino acid sequence as set forth in SEQ ID NO:9, wherein the CD86 protein and the 4-1BBL protein are expressed on the surface of the MOLM-13 cell. In an embodiment, the invention includes an aAPC comprising a MOLM-13 cell modified to express a CD86 protein comprising a sequence with greater than 90% identity to an amino acid sequence as set forth in SEQ ID NO:8 and a 4-1BBL protein comprising a sequence with greater than 90% identity to an amino acid sequence as set forth in SEQ ID NO:9, wherein the CD86 protein and the 4-1BBL protein are expressed on the surface of the MOLM-13 cell. In an embodiment, the invention includes a method of preparing any of the foregoing embodiments of aAPCs.

In an embodiment, the invention includes an aAPC comprising a MOLM-14 cell transduced with one or more viral vectors, wherein the one or more viral vectors comprise a nucleic acid encoding CD86 and a nucleic acid encoding OX40L, and wherein the MOLM-14 cell expresses CD86 and OX40L. In an embodiment, the invention includes an aAPC comprising a MOLM-13 cell transduced with one or more viral vectors, wherein the one or more viral vectors comprise a nucleic acid encoding CD86 and a nucleic acid encoding OX40L, and wherein the MOLM-13 cell expresses CD86 and OX40L. In an embodiment, the invention includes a method of preparing any of the foregoing embodiments of aAPCs.

In an embodiment, the invention includes an aAPC comprising a MOLM-14 cell modified to express a CD86 protein comprising an amino acid sequence as set forth in SEQ ID NO:8 and a OX40L protein comprising an amino acid sequence as set forth in SEQ ID NO:10, wherein the CD86 protein and the OX40L protein are expressed on the surface of the MOLM-14 cell. In an embodiment, the invention includes an aAPC comprising a MOLM-13 cell modified to express a CD86 protein comprising an amino acid sequence as set forth in SEQ ID NO:8, and conservative amino acid substitutions thereof, and a OX40L protein comprising an amino acid sequence as set forth in SEQ ID NO:10, and conservative amino acid substitutions thereof, wherein the CD86 protein and the OX40L protein are expressed on the surface of the MOLM-13 cell. In an embodiment, the invention includes a method of preparing any of the foregoing embodiments of aAPCs.

In an embodiment, the invention includes an aAPC comprising a MOLM-14 cell modified to express a CD86 protein comprising a sequence with greater than 99% identity to an amino acid sequence as set forth in SEQ ID NO:8 and a OX40L protein comprising a sequence with greater than 99% identity to an amino acid sequence as set forth in SEQ ID NO:10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 98% identity to an amino acid sequence as set forth in SEQ ID NO:8 and a OX40L protein comprising a sequence with greater than 98% identity to an amino acid sequence as set forth in SEQ ID NO:10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 97% identity to an amino acid sequence as set forth in SEQ ID NO:8 and a OX40L protein comprising a sequence with greater than 97% identity to an amino acid sequence as set forth in SEQ ID NO:10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 96% identity to an amino acid sequence as set forth in SEQ ID NO:8 and a OX40L protein comprising a sequence with greater than 96% identity to an amino acid sequence as set forth in SEQ ID NO:10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 95% identity to an amino acid sequence as set forth in SEQ ID NO:8 and a OX40L protein comprising a sequence with greater than 95% identity to an amino acid sequence as set forth in SEQ ID NO:10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 90% identity to an amino acid sequence as set forth in SEQ ID NO:8 and a OX40L protein comprising a sequence with greater than 90% identity to an amino acid sequence as set forth in SEQ ID NO:10, wherein the CD86 protein and the OX40L protein are expressed on the surface of the MOLM-14 cell. In an embodiment, the invention includes a method of preparing any of the foregoing embodiments of aAPCs.

In any of the foregoing embodiments, it will be understood that an aAPC comprising a MOLM-14 or MOLM-13 cell may be modified to express both OX40L and 4-1BBL.

The sequences for human CD86, human 4-1BBL (CD137L), and human OX40L (CD134L) are given in Table 3.

TABLE 3

Amino acid sequences for human CD86, human 4-1BBL, and human OX40L.

| Identifier (Description) | Sequence (One-Letter Amino Acid Symbols) | |
|---|---|---|
| SEQ ID NO: 8 (human CD86) | MGLSNILFVM AFLLSGAAPL KIQAYFNETA DLPCQFANSQ NQSLSELVVF WQDQENLVLN | 60 |
| | EVYLGKEKED SVHSKYMGRT SFDSDSWTLR LHNLQIKDKG LYQCIIHHKK PTGMIRIHQM | 120 |
| | NSELSVLANF SQPEIVPISN ITENVYINLT CSSIHGYPEP KKMSVLLRTK NSTIEYDGIM | 180 |
| | QESQDNVTEL YDVSISLSVS FPDVTSNMTI FCILETDKTR LLSSPFSIEL EDPQPPPDHI | 240 |
| | PWITAVLPTV IICVMVFCLI LWKWKKKKRP RNSYKCGTNT MEREESEQTK KREKIHIPER | 300 |
| | SDEAQRVFKS SKTSSCDKSD TCF | 323 |
| SEQ ID NO: 9 (human 4-1BBL, CD137) | MEYASDASLD PEAPWPPAPR ARACRVLPWA LVAGLLLLLL LAAACAVFLA CPWAVSGARA | 60 |
| | SPGSAASPRL REGPELSPDD PAGLLDLRQG MFAQLVAQNV LLIDGPLSWY SDPGLAGVSL | 120 |
| | TGGLSYKEDT KELVVAKAGV YYVFFQLELR RVVAGEGSGS VSLALHLQPL RSAAGAAALA | 180 |
| | LTVDLPPASS EARNSAFGFQ GRLLHLSAGQ RLGVHLHTEA RARHAWQLTQ GATVLGLFRV | 240 |
| | TPEIPAGLPS PRSE | 254 |
| SEQ ID NO: 10 (human OX40L, CD134L) | MERVQPLEEN VGNAARPRFE RNKLLLVASV IQGLGLLLCF TYICLHFSAL QVSHRYPRIQ | 60 |
| | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVNGGEL ILIHQNPGEF | 180 |
| | CVL | 183 |

In an embodiment, the invention includes an aAPC comprising a MOLM-14 cell modified to express a first protein that binds to a second protein comprising an amino acid sequence as set forth in SEQ ID NO:13, and conservative amino acid substitutions thereof, and a third protein that binds to a fourth protein comprising an amino acid sequence as set forth in SEQ ID NO:11 or SEQ ID NO:12, and conservative amino acid substitutions thereof. In an embodiment, the invention includes an aAPC comprising a MOLM-13 cell modified to express a first protein that binds to a second protein comprising an amino acid sequence as set forth in SEQ ID NO:13, and conservative amino acid substitutions thereof, and a third protein that binds to a fourth protein comprising an amino acid sequence as set forth in SEQ ID NO:11 or SEQ ID NO:12, and conservative amino acid substitutions thereof. In an embodiment, the invention includes a method of preparing any of the foregoing embodiments of aAPCs.

In an embodiment, the invention includes an aAPC comprising a MOLM-14 cell modified to express a first protein that binds to a second protein comprising a sequence with greater than 99% identity to an amino acid sequence as set forth in SEQ ID NO:13 and a third protein that binds to a fourth protein comprising a sequence with greater than 99% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 98% identity to an amino acid sequence as set forth in SEQ ID NO:13 and a third protein that binds to a fourth protein comprising a sequence with greater than 98% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 97% identity to an amino acid sequence as set forth in SEQ ID NO:13 and a third protein that binds to a fourth protein comprising a sequence with greater than 97% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 96% identity to an amino acid sequence as set forth in SEQ ID NO:13 and a third protein that binds to a fourth protein comprising a sequence with greater than 96% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 95% identity to an amino acid sequence as set forth in SEQ ID NO:13 and a third protein that binds to a fourth protein comprising a sequence with greater than 95% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 90% identity to an amino acid sequence as set forth in SEQ ID NO:13 and a third protein that binds to a fourth protein comprising a sequence with greater than 90% identity to an amino acid sequence as set forth in SEQ ID NO:11 or SEQ ID NO:12. In an embodiment, the invention includes a method of preparing any of the foregoing embodiments of aAPCs.

In an embodiment, the invention includes an aAPC comprising a MOLM-13 cell modified to express a first protein that binds to a second protein comprising a sequence with greater than 99% identity to an amino acid sequence as set forth in SEQ ID NO:13 and a third protein that binds to a fourth protein comprising a sequence with greater than 99% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 98% identity to an amino acid sequence as set forth in SEQ ID NO:13 and a third protein that binds to a fourth protein comprising a sequence with greater than 98% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 97% identity to an amino acid sequence as set forth in SEQ ID NO:13 and a third protein that binds to a fourth protein comprising a sequence with greater than 97% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 96% identity to an amino acid sequence as set forth in SEQ ID NO:13 and a third protein that binds to a fourth protein comprising a sequence with greater than 96% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 95% identity to an amino acid sequence as set forth in SEQ ID NO:13 and a third protein that binds to a fourth protein comprising a sequence with greater than 95% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 90% identity to an amino acid sequence as set forth in SEQ ID NO:13 and a third protein that binds to a fourth protein comprising a sequence with greater than 90% identity to an amino acid sequence as set forth in SEQ ID NO:11 or SEQ ID NO:12. In an embodiment, the invention includes a method of preparing any of the foregoing embodiments of aAPCs.

In an embodiment, the invention includes an aAPC comprising a MOLM-14 cell modified to express a first protein that binds to a second protein comprising an amino acid sequence as set forth in SEQ ID NO:14, and conservative amino acid substitutions thereof, and a third protein that binds to a fourth protein comprising an amino acid sequence as set forth in SEQ ID NO:11 or SEQ ID NO:12, and conservative amino acid substitutions thereof. In an embodiment, the invention includes an aAPC comprising a MOLM-13 cell modified to express a first protein that binds to a second protein comprising an amino acid sequence as set forth in SEQ ID NO:14, and conservative amino acid substitutions thereof, and a third protein that binds to a fourth protein comprising an amino acid sequence as set forth in SEQ ID NO:11 or SEQ ID NO:12, and conservative amino acid substitutions thereof. In an embodiment, the invention includes a method of preparing any of the foregoing embodiments of aAPCs.

In an embodiment, the invention includes an aAPC comprising a MOLM-14 cell modified to express a first protein that binds to a second protein comprising a sequence with greater than 99% identity to an amino acid sequence as set forth in SEQ ID NO:14 and a third protein that binds to a fourth protein comprising a sequence with greater than 99% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 98% identity to an amino acid sequence as set forth in SEQ ID NO:14 and a third protein that binds to a fourth protein comprising a sequence with greater than 98% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 97% identity to an amino acid sequence as set forth in SEQ ID NO:14 and a third protein that binds to a fourth protein comprising a sequence with greater than 97% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 96% identity to an amino acid sequence as set forth in SEQ ID NO:14 and a third protein that binds to a fourth protein comprising a sequence with greater than 96% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 95% identity to an amino acid sequence as set forth in SEQ ID NO:14 and a third protein that binds to a fourth protein comprising a sequence with greater than 95% identity to an amino acid sequence as set forth in SEQ ID NO:11 or SEQ ID NO:12. In an embodiment, the invention includes an aAPC comprising a MOLM-14 cell modified to express a first protein that binds to a second protein comprising a sequence with greater than 90% identity to an amino acid sequence as set forth in SEQ ID NO:14 and a third protein that binds to a fourth protein comprising a sequence with greater than 90% identity to an amino acid sequence as set forth in SEQ ID NO:11 or SEQ ID NO:12. In an embodiment, the invention includes a method of preparing any of the foregoing embodiments of aAPCs.

In an embodiment, the invention includes an aAPC comprising a MOLM-13 cell modified to express a first protein that binds to a second protein comprising a sequence with greater than 99% identity to an amino acid sequence as set forth in SEQ ID NO:14 and a third protein that binds to a fourth protein comprising a sequence with greater than 99% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 98% identity to an amino acid sequence as set forth in SEQ ID NO:14 and a third protein that binds to a fourth protein comprising a sequence with greater than 98% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 97% identity to an amino acid sequence as set forth in SEQ ID NO:14 and a third protein that binds to a fourth protein comprising a sequence with greater than 97% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 96% identity to an amino acid sequence as set forth in SEQ ID NO:14 and a third protein that binds to a fourth protein comprising a sequence with greater than 96% identity to an amino acid sequence as set forth in SEQ ID NO:11 or SEQ ID NO:12.

In an embodiment, the invention includes an aAPC comprising a MOLM-13 cell modified to express a first protein that binds to a second protein comprising a sequence with greater than 95% identity to an amino acid sequence as set forth in SEQ ID NO:14 and a third protein that binds to a fourth protein comprising a sequence with greater than 95% identity to an amino acid sequence as set forth in SEQ ID NO:11 or SEQ ID NO:12. In an embodiment, the invention includes an aAPC comprising a MOLM-13 cell modified to express a first protein that binds to a second protein comprising a sequence with greater than 90% identity to an amino acid sequence as set forth in SEQ ID NO:14 and a third protein that binds to a fourth protein comprising a sequence with greater than 90% identity to an amino acid sequence as set forth in SEQ ID NO:11 or SEQ ID NO:12. In an embodiment, the invention includes a method of preparing any of the foregoing embodiments of aAPCs.

The sequences for the ligands to which human CD86 binds (CD28 and CTLA-4), the ligand to which human 4-1BBL binds (4-1BB), and the ligand to which human OX40L binds (OX40) are given in Table 4.

In an embodiment, the invention includes an aAPC comprising an EM-3 cell transduced with one or more viral vectors, wherein the one or more viral vectors comprise a nucleic acid encoding CD86 and a nucleic acid encoding 4-1BBL, and wherein the EM-3 cell expresses CD86 and 4-1BBL. In an embodiment, the invention includes a method of preparing any of the foregoing embodiments of aAPCs.

In an embodiment, the invention includes an aAPC comprising an EM-3 cell modified to express a CD86 protein comprising an amino acid sequence as set forth in SEQ ID NO:8 and a 4-1BBL protein comprising an amino acid sequence as set forth in SEQ ID NO:9, wherein the CD86 protein and the 4-1BBL protein are expressed on the surface of the EM-3 cell. In an embodiment, the invention includes a method of preparing any of the foregoing embodiments of aAPCs.

In an embodiment, the invention includes an aAPC comprising an EM-3 cell modified to express a CD86 protein comprising a sequence with greater than 99% identity to an amino acid sequence as set forth in SEQ ID NO:8 and a 4-1BBL protein comprising a sequence with greater than

TABLE 4

Amino acid sequences for human CD28,
human CTLA-4, human 4-1BB, and human OX40.

| Identifier (Description) | Sequence (One-Letter Amino Acid Symbols) | | | | | |
|---|---|---|---|---|---|---|
| SEQ ID NO: 11 (human CD28) | MLRLLLALNL | FPSIQVTGNK | ILVKQSPMLV | AYDNAVNLSC | KYSYNLFSRE | FRASLHKGLD | 60 |
| | SAVEVCVVYG | NYSQQLQVYS | KTGFNCDGKL | GNESVTFYLQ | NLYVNQTDIY | FCKIEVMYPP | 120 |
| | PYLDNEKSNG | TIIHVKGKHL | CPSPLFPGPS | KPFWVLVVVG | GVLACYSLLV | TVAFIIFWVR | 180 |
| | SHRSRLLHSD | YMNMTPRRPG | PTRKHYQPYA | PPRDFAAYRS | | | 220 |
| SEQ ID NO: 12 (human CTLA-4) | MACLGFQRHK | AQLNLATRTW | PCTLLFFLLF | IPVFCKAMHV | AQPAVVLASS | RGIASFVCEY | 60 |
| | ASPGKATEVR | VTVLRQADSQ | VTEVCAATYM | MGNELTFLDD | SICTGTSSGN | QVNLTIQGLR | 120 |
| | AMDTGLYICK | VELMYPPPYY | LGIGNGTQIY | VIDPEPCPDS | DFLLWILAAV | SSGLFFYSFL | 180 |
| | LTAVSLSKML | KKRSPLTTGV | YVKMPPTEPE | CEKQFQPYFI | PIN | | 223 |
| SEQ ID NO: 13 (human 4-1BB) | MGNSCYNIVA | TLLLVLNFER | TRSLQDPCSN | CPAGTFCDNN | RNQICSPCPP | NSFSSAGGQR | 60 |
| | TCDICRQCKG | VFRTRKECSS | TSNAECDCTP | GFHCLGAGCS | MCEQDCKQGQ | ELTKKGCKDC | 120 |
| | CFGTFNDQKR | GICRPWTNCS | LDGKSVLVNG | THERDVVCGP | SPADLSPGAS | SVTPPAPARE | 180 |
| | PGHSPQIISF | FLALTSTALL | FLLFFLTLRF | SVVKRGRKKL | LYIFKQPFMR | PVQTTQEEDG | 240 |
| | CSCRFPEEEE | GGCEL | | | | | 255 |
| SEQ ID NO: 14 (human OX40) | MCVGARRLGR | GPCAALLLLG | LGLSTVTGLH | CVGDTYPSND | RCCHECRPGN | GMVSRCSRSQ | 60 |
| | NTVCRPCGPG | FYNDVVSSKP | CKPCTWCNLR | SGSERKQLCT | ATQDTVCRCR | AGTQPLDSYK | 120 |
| | PGVDCAPCPP | GHFSPGDNQA | CKPWTNCTLA | GKHTLQPASN | SSDAICEDRD | PPATQPQETQ | 180 |
| | GPPARPITVQ | PTEAWPRTSQ | GPSTRPVEVP | GGRAVAAILG | LGLVLGLLGP | LAILLALYLL | 240 |
| | RRDQRLPPDA | FKPPGGGSFR | TPIQEEQADA | HSTLAKI | | | 277 |

In an embodiment, the invention includes an isolated artificial antigen presenting cell (aAPC) comprising a cell that expresses HLA-A/B/C, ICOS-L, and CD58, and is modified to express one or more costimulatory molecules, wherein the aAPC is derived from an EM-3 parental cell line. In an embodiment, the invention includes an aAPC comprising an EM-3 cell that is modified to express one or more costimulatory molecules. In an embodiment, the invention includes an aAPC comprising an EM-2 cell that is modified to express one or more costimulatory molecules.

In an embodiment, the invention includes an aAPC comprising an EM-3 cell that expresses HLA-A/B/C, ICOS-L, and CD58, wherein the cell is modified to express a CD86 protein comprising an amino acid sequence as set forth in SEQ ID NO:8, and conservative amino acid substitutions thereof, and a 4-1BBL protein comprising an amino acid sequence as set forth in SEQ ID NO:9, and conservative amino acid substitutions thereof, and wherein the CD86 protein and the 4-1BBL protein are expressed on the surface of the EM-3 cell.

99% identity to an amino acid sequence as set forth in SEQ ID NO:9, wherein the CD86 protein and the 4-1BBL protein are expressed on the surface of the EM-3 cell. In an embodiment, the invention includes an aAPC comprising a EM-3 cell modified to express a CD86 protein comprising a sequence with greater than 98% identity to an amino acid sequence as set forth in SEQ ID NO:8 and a 4-1BBL protein comprising a sequence with greater than 98% identity to an amino acid sequence as set forth in SEQ ID NO:9, wherein the CD86 protein and the 4-1BBL protein are expressed on the surface of the EM-3 cell. In an embodiment, the invention includes an aAPC comprising a EM-3 cell modified to express a CD86 protein comprising a sequence with greater than 97% identity to an amino acid sequence as set forth in SEQ ID NO:8 and a 4-1BBL protein comprising a sequence with greater than 97% identity to an amino acid sequence as set forth in SEQ ID NO:9, wherein the CD86 protein and the 4-1BBL protein are expressed on the surface of the EM-3 cell. In an embodiment, the invention includes an aAPC comprising a EM-3 cell modified to express a CD86 protein comprising a sequence with greater than 96% identity to an amino acid sequence as set forth in SEQ ID NO:8 and a 4-1BBL protein comprising a sequence with greater than 96% identity to an amino acid sequence as set forth in SEQ ID NO:9, wherein the CD86 protein and the 4-1BBL protein are expressed on the surface of the EM-3 cell. In an embodiment, the invention includes an aAPC comprising a EM-3 cell modified to express a CD86 protein comprising a sequence with greater than 95% identity to an amino acid sequence as set forth in SEQ ID NO:8 and a 4-1BBL protein comprising a sequence with greater than 95% identity to an amino acid sequence as set forth in SEQ ID NO:9, wherein the CD86 protein and the 4-1BBL protein are expressed on the surface of the EM-3 cell. In an embodiment, the invention includes an aAPC comprising a EM-3 cell modified to express a CD86 protein comprising a sequence with greater than 90% identity to an amino acid sequence as set forth in SEQ ID NO:8 and a 4-1BBL protein comprising a sequence with greater than 90% identity to an amino acid sequence as set forth in SEQ ID NO:9, wherein the CD86 protein and the 4-1BBL protein are expressed on the surface of the EM-3 cell. In an embodiment, the invention includes a method of preparing any of the foregoing embodiments of aAPCs.

In an embodiment, the invention includes an aAPC comprising an EM-3 cell modified to express a first protein that binds to a second protein comprising an amino acid sequence as set forth in SEQ ID NO:13, and conservative amino acid substitutions thereof, and a third protein that binds to a fourth protein comprising an amino acid sequence as set forth in SEQ ID NO:11 or SEQ ID NO:12, and conservative amino acid substitutions thereof. In an embodiment, the invention includes a method of preparing any of the foregoing embodiments of aAPCs.

In an embodiment, the invention includes an aAPC comprising an EM-3 cell modified to express a first protein that binds to a second protein comprising a sequence with greater than 99% identity to an amino acid sequence as set forth in SEQ ID NO:13 and a third protein that binds to a fourth protein comprising a sequence with greater than 99% identity to an amino acid sequence as set forth in SEQ ID NO:11 or SEQ ID NO:12. In an embodiment, the invention includes an aAPC comprising an EM-3 cell modified to express a first protein that binds to a second protein comprising a sequence with greater than 98% identity to an amino acid sequence as set forth in SEQ ID NO:13 and a third protein that binds to a fourth protein comprising a sequence with greater than 98% identity to an amino acid sequence as set forth in SEQ ID NO:11 or SEQ ID NO:12. In an embodiment, the invention includes an aAPC comprising an EM-3 modified to express a first protein that binds to a second protein comprising a sequence with greater than 97% identity to an amino acid sequence as set forth in SEQ ID NO:13 and a third protein that binds to a fourth protein comprising a sequence with greater than 97% identity to an amino acid sequence as set forth in SEQ ID NO:11 or SEQ ID NO:12. In an embodiment, the invention includes an aAPC comprising an EM-3 cell modified to express a first protein that binds to a second protein comprising a sequence with greater than 96% identity to an amino acid sequence as set forth in SEQ ID NO:13 and a third protein that binds to a fourth protein comprising a sequence with greater than 96% identity to an amino acid sequence as set forth in SEQ ID NO:11 or SEQ ID NO:12. In an embodiment, the invention includes an aAPC comprising an EM-3 cell modified to express a first protein that binds to a second protein comprising a sequence with greater than 95% identity to an amino acid sequence as set forth in SEQ ID NO:13 and a third protein that binds to a fourth protein comprising a sequence with greater than 95% identity to an amino acid sequence as set forth in SEQ ID NO:11 or SEQ ID NO:12. In an embodiment, the invention includes an aAPC comprising an EM-3 cell modified to express a first protein that binds to a second protein comprising a sequence with greater than 90% identity to an amino acid sequence as set forth in SEQ ID NO:13 and a third protein that binds to a fourth protein comprising a sequence with greater than 90% identity to an amino acid sequence as set forth in SEQ ID NO:11 or SEQ ID NO:12. In an embodiment, the invention includes a method of preparing any of the foregoing embodiments of aAPCs.

In an embodiment, the invention includes an aAPC comprising an EM-3 cell modified to express a single chain fragment variable (scFv) binding domain, such as clones 7C12 and 8B3 described herein, to bind the Fc domain of a monoclonal antibody, such as OKT-3, providing an additional proliferative signal.

In an embodiment, the invention includes an aAPC comprising an EM-2 cell modified to express a CD86 protein comprising an amino acid sequence as set forth in SEQ ID NO:8 and a 4-1BBL protein comprising an amino acid sequence as set forth in SEQ ID NO:9, wherein the CD86 protein and the 4-1BBL protein are expressed on the surface of the EM-2 cell. In an embodiment, the invention includes a method of preparing any of the foregoing embodiments of aAPCs.

In an embodiment, the invention includes an aAPC comprising an EM-2 cell modified to express a CD86 protein comprising a sequence with greater than 99% identity to an amino acid sequence as set forth in SEQ ID NO:8 and a 4-1BBL protein comprising a sequence with greater than 99% identity to an amino acid sequence as set forth in SEQ ID NO:9, wherein the CD86 protein and the 4-1BBL protein are expressed on the surface of the EM-2 cell. In an embodiment, the invention includes an aAPC comprising a EM-2 cell modified to express a CD86 protein comprising a sequence with greater than 98% identity to an amino acid sequence as set forth in SEQ ID NO:8 and a 4-1BBL protein comprising a sequence with greater than 98% identity to an amino acid sequence as set forth in SEQ ID NO:9, wherein the CD86 protein and the 4-1BBL protein are expressed on the surface of the EM-2 cell. In an embodiment, the invention includes an aAPC comprising a EM-2 cell modified to express a CD86 protein comprising a sequence with greater than 97% identity to an amino acid sequence as set forth in SEQ ID NO:8 and a 4-1BBL protein comprising a sequence with greater than 97% identity to an amino acid sequence as set forth in SEQ ID NO:9, wherein the CD86 protein and the 4-1BBL protein are expressed on the surface of the EM-2 cell. In an embodiment, the invention includes an aAPC comprising a EM-2 cell modified to express a CD86 protein comprising a sequence with greater than 96% identity to an amino acid sequence as set forth in SEQ ID NO:8 and a 4-1BBL protein comprising a sequence with greater than 96% identity to an amino acid sequence as set forth in SEQ ID NO:9, wherein the CD86 protein and the 4-1BBL protein are expressed on the surface of the EM-2 cell. In an embodiment, the invention includes an aAPC comprising a EM-2 cell modified to express a CD86 protein comprising a sequence with greater than 95% identity to an amino acid sequence as set forth in SEQ ID NO:8 and a 4-1BBL protein comprising a sequence with greater than 95% identity to an amino acid sequence as set forth in SEQ ID NO:9, wherein the CD86 protein and the 4-1BBL protein are expressed on the surface of the EM-2 cell. In an embodiment, the invention includes an aAPC comprising a EM-2 cell modified to express a CD86 protein comprising a sequence with greater than 90% identity to an amino acid sequence as set forth in SEQ ID NO:8 and a 4-1BBL protein comprising a sequence with greater than 90% identity to an amino acid sequence as set forth in SEQ ID NO:9, wherein the CD86 protein and the 4-1BBL protein are expressed on the surface of the EM-2 cell. In an embodiment, the invention includes a method of preparing any of the foregoing embodiments of aAPCs.

In an embodiment, the invention includes an aAPC comprising an EM-2 cell modified to express a first protein that binds to a second protein comprising an amino acid sequence as set forth in SEQ ID NO:13, and conservative amino acid substitutions thereof, and a third protein that binds to a fourth protein comprising an amino acid sequence as set forth in SEQ ID NO:11 or SEQ ID NO:12, and conservative amino acid substitutions thereof. In an embodiment, the invention includes a method of preparing any of the foregoing embodiments of aAPCs.

In an embodiment, the invention includes an aAPC comprising an EM-2 cell modified to express a first protein that binds to a second protein comprising a sequence with greater than 99% identity to an amino acid sequence as set forth in SEQ ID NO:13 and a third protein that binds to a fourth protein comprising a sequence with greater than 99% identity to an amino acid sequence as set forth in SEQ ID NO:11 or SEQ ID NO:12. In an embodiment, the invention includes an aAPC comprising an EM-2 cell modified to express a first protein that binds to a second protein comprising a sequence with greater than 98% identity to an amino acid sequence as set forth in SEQ ID NO:13 and a third protein that binds to a fourth protein comprising a sequence with greater than 98% identity to an amino acid sequence as set forth in SEQ ID NO:11 or SEQ ID NO:12. In an embodiment, the invention includes an aAPC comprising an EM-2 modified to express a first protein that binds to a second protein comprising a sequence with greater than 97% identity to an amino acid sequence as set forth in SEQ ID NO:13 and a third protein that binds to a fourth protein comprising a sequence with greater than 97% identity to an amino acid sequence as set forth in SEQ ID NO:11 or SEQ ID NO:12. In an embodiment, the invention includes an aAPC comprising an EM-2 cell modified to express a first protein that binds to a second protein comprising a sequence with greater than 96% identity to an amino acid sequence as set forth in SEQ ID NO:13 and a third protein that binds to a fourth protein comprising a sequence with greater than 96% identity to an amino acid sequence as set forth in SEQ ID NO:11 or SEQ ID NO:12. In an embodiment, the invention includes an aAPC comprising an EM-2 cell modified to express a first protein that binds to a second protein comprising a sequence with greater than 95% identity to an amino acid sequence as set forth in SEQ ID NO:13 and a third protein that binds to a fourth protein comprising a sequence with greater than 95% identity to an amino acid sequence as set forth in SEQ ID NO:11 or SEQ ID NO:12. In an embodiment, the invention includes an aAPC comprising an EM-2 cell modified to express a first protein that binds to a second protein comprising a sequence with greater than 90% identity to an amino acid sequence as set forth in SEQ ID NO:13 and a third protein that binds to a fourth protein comprising a sequence with greater than 90% identity to an amino acid sequence as set forth in SEQ ID NO:11 or SEQ ID NO:12. In an embodiment, the invention includes a method of preparing any of the foregoing embodiments of aAPCs.

In an embodiment, the invention includes an aAPC comprising an EM-2 cell modified to express a single chain fragment variable (scFv) binding domain, such as clones 7C12 and 8B3 described herein, to bind the Fc domain of a monoclonal antibody, such as OKT-3, providing an additional proliferative signal.

Figure 96:
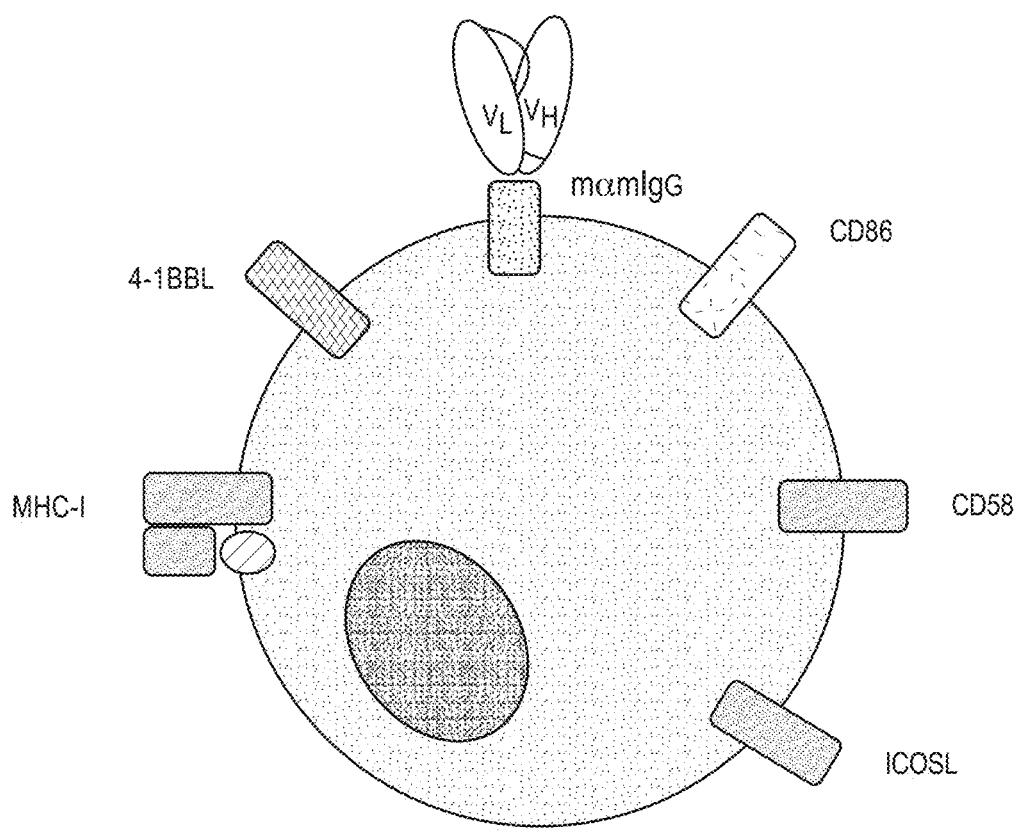
FIG. 96 illustrates a schematic diagram of an embodiment of an aAPC of the present invention.
Figure 97:
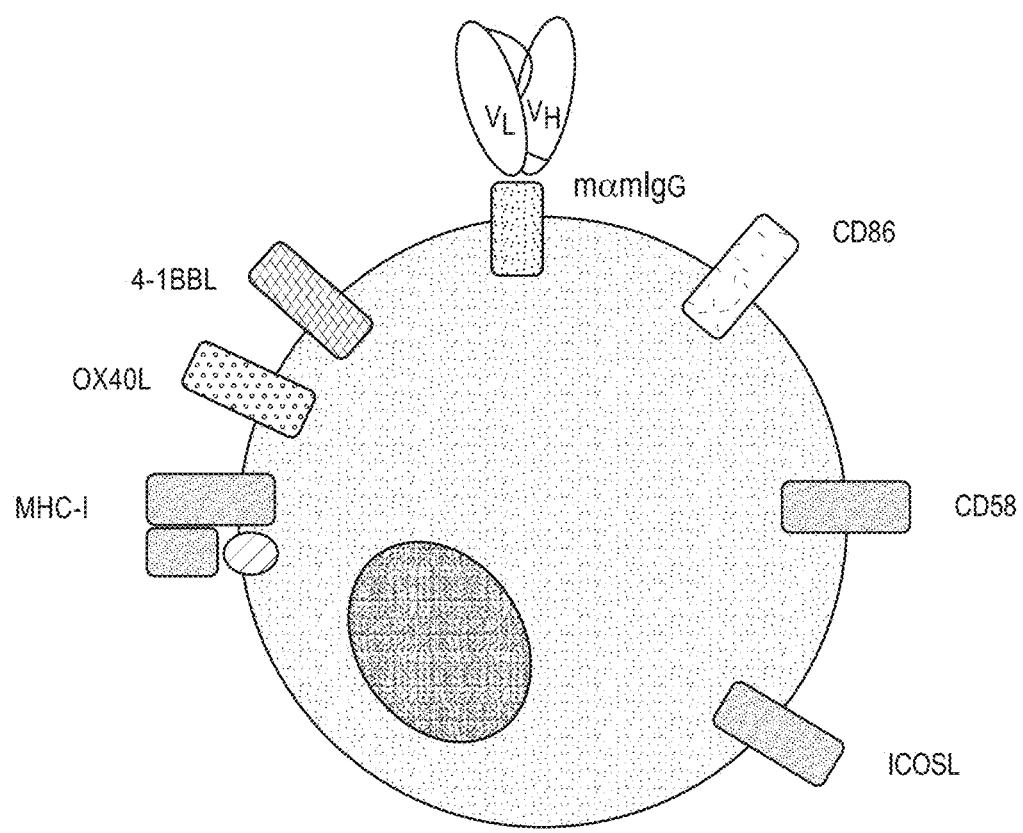
FIG. 97 illustrates a schematic diagram of an embodiment of an aAPC of the present invention.
Figure 98:
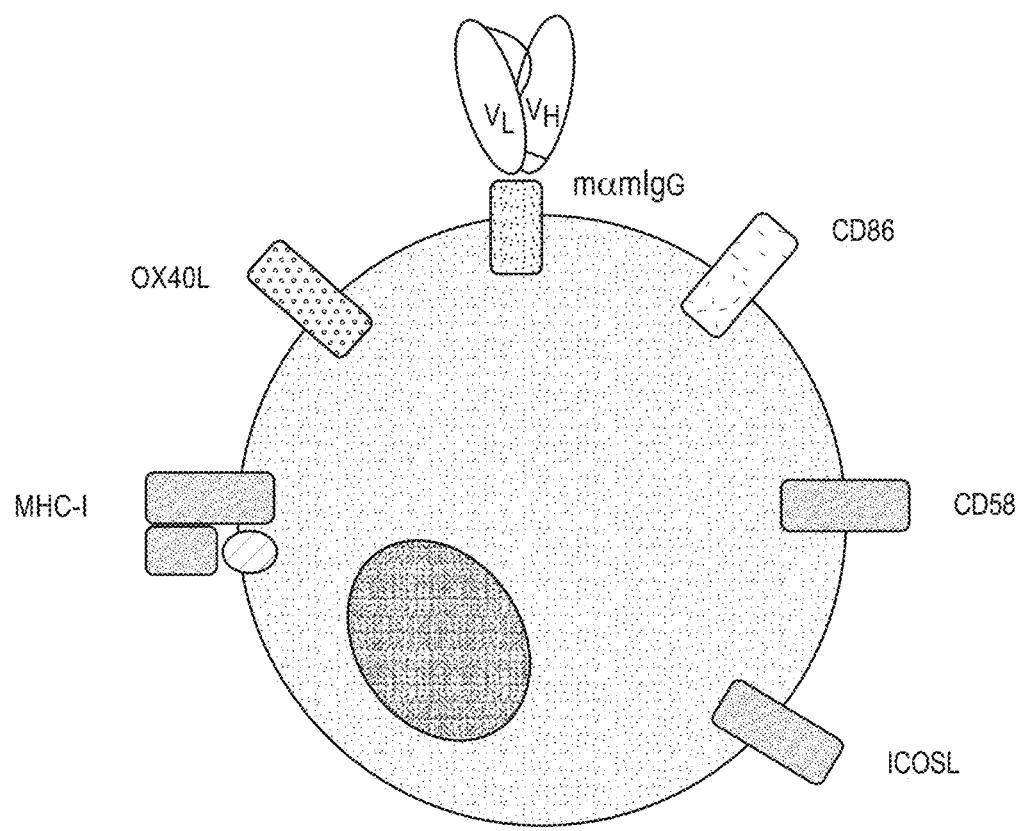
FIG. 98 illustrates a schematic diagram of an embodiment of an aAPC of the present invention.

In an embodiment, the invention includes an aAPC comprising an EM-3 or an EM-2 cell modified as depicted in FIG. 96. In an embodiment, the invention includes an aAPC comprising an EM-3 or an EM-2 cell modified as depicted in FIG. 97. In an embodiment, the invention includes an aAPC comprising an EM-3 or an EM-2 cell modified as depicted in FIG. 98.

In an embodiment, the invention includes an aAPC comprising an EM-3 cell that expresses HLA-A/B/C, ICOS-L, and CD58, wherein the cell is modified to express a CD86 protein comprising an amino acid sequence as set forth in SEQ ID NO:8, and conservative amino acid substitutions thereof, and a OX40L protein comprising an amino acid sequence as set forth in SEQ ID NO:10, and conservative amino acid substitutions thereof, and wherein the CD86 protein and the OX40L protein are expressed on the surface of the EM-3 cell.

In an embodiment, the invention includes an aAPC comprising an EM-3 cell transduced with one or more viral vectors, wherein the one or more viral vectors comprise a nucleic acid encoding CD86 and a nucleic acid encoding OX40L, and wherein the EM-3 cell expresses CD86 and OX40L. In an embodiment, the invention includes a method of preparing any of the foregoing embodiments of aAPCs.

In an embodiment, the invention includes an aAPC comprising an EM-3 cell modified to express a CD86 protein comprising an amino acid sequence as set forth in SEQ ID NO:8 and a OX40L protein comprising an amino acid sequence as set forth in SEQ ID NO:10, wherein the CD86 protein and the OX40L protein are expressed on the surface of the EM-3 cell. In an embodiment, the invention includes a method of preparing any of the foregoing embodiments of aAPCs.

In an embodiment, the invention includes an aAPC comprising an EM-3 cell modified to express a CD86 protein comprising a sequence with greater than 99% identity to an amino acid sequence as set forth in SEQ ID NO:8 and a OX40L protein comprising a sequence with greater than 99% identity to an amino acid sequence as set forth in SEQ ID NO:10, wherein the CD86 protein and the OX40L protein are expressed on the surface of the EM-3 cell. In an embodiment, the invention includes an aAPC comprising a EM-3 cell modified to express a CD86 protein comprising a sequence with greater than 98% identity to an amino acid sequence as set forth in SEQ ID NO:8 and a OX40L protein comprising a sequence with greater than 98% identity to an amino acid sequence as set forth in SEQ ID NO:10, wherein the CD86 protein and the OX40L protein are expressed on the surface of the EM-3 cell. In an embodiment, the invention includes an aAPC comprising a EM-3 cell modified to express a CD86 protein comprising a sequence with greater than 97% identity to an amino acid sequence as set forth in SEQ ID NO:8 and a OX40L protein comprising a sequence with greater than 97% identity to an amino acid sequence as set forth in SEQ ID NO:10, wherein the CD86 protein and the OX40L protein are expressed on the surface of the EM-3 cell. In an embodiment, the invention includes an aAPC comprising a EM-3 cell modified to express a CD86 protein comprising a sequence with greater than 96% identity to an amino acid sequence as set forth in SEQ ID NO:8 and a OX40L protein comprising a sequence with greater than 96% identity to an amino acid sequence as set forth in SEQ ID NO:10, wherein the CD86 protein and the OX40L protein are expressed on the surface of the EM-3 cell. In an embodiment, the invention includes an aAPC comprising a EM-3 cell modified to express a CD86 protein comprising a sequence with greater than 95% identity to an amino acid sequence as set forth in SEQ ID NO:8 and a OX40L protein comprising a sequence with greater than 95% identity to an amino acid sequence as set forth in SEQ ID NO:10, wherein the CD86 protein and the OX40L protein are expressed on the surface of the EM-3 cell. In an embodiment, the invention includes an aAPC comprising a EM-3 cell modified to express a CD86 protein comprising a sequence with greater than 90% identity to an amino acid sequence as set forth in SEQ ID NO:8 and a OX40L protein comprising a sequence with greater than 90% identity to an amino acid sequence as set forth in SEQ ID NO:10, wherein the CD86 protein and the OX40L protein are expressed on the surface of the EM-3 cell. In an embodiment, the invention includes a method of preparing any of the foregoing embodiments of aAPCs.

In an embodiment, the invention includes an aAPC comprising an EM-3 cell modified to express a first protein that binds to a second protein comprising an amino acid sequence as set forth in SEQ ID NO:14, and conservative amino acid substitutions thereof, and a third protein that binds to a fourth protein comprising an amino acid sequence as set forth in SEQ ID NO:11 or SEQ ID NO:12, and conservative amino acid substitutions thereof. In an embodiment, the invention includes a method of preparing any of the foregoing embodiments of aAPCs.

In an embodiment, the invention includes an aAPC comprising an EM-3 cell modified to express a first protein that binds to a second protein comprising a sequence with greater than 99% identity to an amino acid sequence as set forth in SEQ ID NO:14 and a third protein that binds to a fourth protein comprising a sequence with greater than 99% identity to an amino acid sequence as set forth in SEQ ID NO:11 or SEQ ID NO:12. In an embodiment, the invention includes an aAPC comprising an EM-3 cell modified to express a first protein that binds to a second protein comprising a sequence with greater than 98% identity to an amino acid sequence as set forth in SEQ ID NO:14 and a third protein that binds to a fourth protein comprising a sequence with greater than 98% identity to an amino acid sequence as set forth in SEQ ID NO:11 or SEQ ID NO:12. In an embodiment, the invention includes an aAPC comprising an EM-3 modified to express a first protein that binds to a second protein comprising a sequence with greater than 97% identity to an amino acid sequence as set forth in SEQ ID NO:14 and a third protein that binds to a fourth protein comprising a sequence with greater than 97% identity to an amino acid sequence as set forth in SEQ ID NO:11 or SEQ ID NO:12. In an embodiment, the invention includes an aAPC comprising an EM-3 cell modified to express a first protein that binds to a second protein comprising a sequence with greater than 96% identity to an amino acid sequence as set forth in SEQ ID NO:14 and a third protein that binds to a fourth protein comprising a sequence with greater than 96% identity to an amino acid sequence as set forth in SEQ ID NO:11 or SEQ ID NO:12. In an embodiment, the invention includes an aAPC comprising an EM-3 cell modified to express a first protein that binds to a second protein comprising a sequence with greater than 95% identity to an amino acid sequence as set forth in SEQ ID NO:14 and a third protein that binds to a fourth protein comprising a sequence with greater than 95% identity to an amino acid sequence as set forth in SEQ ID NO:11 or SEQ ID NO:12. In an embodiment, the invention includes an aAPC comprising an EM-3 cell modified to express a first protein that binds to a second protein comprising a sequence with greater than 90% identity to an amino acid sequence as set forth in SEQ ID NO:14 and a third protein that binds to a fourth protein comprising a sequence with greater than 90% identity to an amino acid sequence as set forth in SEQ ID NO:11 or SEQ ID NO:12. In an embodiment, the invention includes a method of preparing any of the foregoing embodiments of aAPCs.

In an embodiment, the invention includes an aAPC comprising an EM-3 cell modified to express a single chain fragment variable (scFv) binding domain, such as clones 7C12 and 8B3 described herein, to bind the Fc domain of a monoclonal antibody, such as OKT-3, providing an additional proliferative signal.

In an embodiment, the invention includes an aAPC comprising an EM-2 cell modified to express a CD86 protein comprising an amino acid sequence as set forth in SEQ ID NO:8 and a OX40L protein comprising an amino acid sequence as set forth in SEQ ID NO:10, wherein the CD86 protein and the OX40L protein are expressed on the surface of the EM-2 cell. In an embodiment, the invention includes a method of preparing any of the foregoing embodiments of aAPCs.

In an embodiment, the invention includes an aAPC comprising an EM-2 cell modified to express a CD86 protein comprising a sequence with greater than 99% identity to an amino acid sequence as set forth in SEQ ID NO:8 and a OX40L protein comprising a sequence with greater than 99% identity to an amino acid sequence as set forth in SEQ ID NO:10, wherein the CD86 protein and the OX40L protein are expressed on the surface of the EM-2 cell. In an embodiment, the invention includes an aAPC comprising a EM-2 cell modified to express a CD86 protein comprising a sequence with greater than 98% identity to an amino acid sequence as set forth in SEQ ID NO:8 and a OX40L protein comprising a sequence with greater than 98% identity to an amino acid sequence as set forth in SEQ ID NO:10, wherein the CD86 protein and the OX40L protein are expressed on the surface of the EM-2 cell. In an embodiment, the invention includes an aAPC comprising a EM-2 cell modified to express a CD86 protein comprising a sequence with greater than 97% identity to an amino acid sequence as set forth in SEQ ID NO:8 and a OX40L protein comprising a sequence with greater than 97% identity to an amino acid sequence as set forth in SEQ ID NO:10, wherein the CD86 protein and the OX40L protein are expressed on the surface of the EM-2 cell. In an embodiment, the invention includes an aAPC comprising a EM-2 cell modified to express a CD86 protein comprising a sequence with greater than 96% identity to an amino acid sequence as set forth in SEQ ID NO:8 and a OX40L protein comprising a sequence with greater than 96% identity to an amino acid sequence as set forth in SEQ ID NO:10, wherein the CD86 protein and the OX40L protein are expressed on the surface of the EM-2 cell. In an embodiment, the invention includes an aAPC comprising a EM-2 cell modified to express a CD86 protein comprising a sequence with greater than 95% identity to an amino acid sequence as set forth in SEQ ID NO:8 and a OX40L protein comprising a sequence with greater than 95% identity to an amino acid sequence as set forth in SEQ ID NO:10, wherein the CD86 protein and the OX40L protein are expressed on the surface of the EM-2 cell. In an embodiment, the invention includes an aAPC comprising a EM-2 cell modified to express a CD86 protein comprising a sequence with greater than 90% identity to an amino acid sequence as set forth in SEQ ID NO:8 and a OX40L protein comprising a sequence with greater than 90% identity to an amino acid sequence as set forth in SEQ ID NO:10, wherein the CD86 protein and the OX40L protein are expressed on the surface of the EM-2 cell. In an embodiment, the invention includes a method of preparing any of the foregoing embodiments of aAPCs.

In an embodiment, the invention includes an aAPC comprising an EM-2 cell modified to express a first protein that binds to a second protein comprising an amino acid sequence as set forth in SEQ ID NO:14, and conservative amino acid substitutions thereof, and a third protein that binds to a fourth protein comprising an amino acid sequence as set forth in SEQ ID NO:11 or SEQ ID NO:12, and conservative amino acid substitutions thereof. In an embodiment, the invention includes a method of preparing any of the foregoing embodiments of aAPCs.

In an embodiment, the invention includes an aAPC comprising an EM-2 cell modified to express a first protein that binds to a second protein comprising a sequence with greater than 99% identity to an amino acid sequence as set forth in SEQ ID NO:14 and a third protein that binds to a fourth protein comprising a sequence with greater than 99% identity to an amino acid sequence as set forth in SEQ ID NO:11 or SEQ ID NO:12. In an embodiment, the invention includes an aAPC comprising an EM-2 cell modified to express a first protein that binds to a second protein comprising a sequence with greater than 98% identity to an amino acid sequence as set forth in SEQ ID NO:14 and a third protein that binds to a fourth protein comprising a sequence with greater than 98% identity to an amino acid sequence as set forth in SEQ ID NO:11 or SEQ ID NO:12. In an embodiment, the invention includes an aAPC comprising an EM-2 modified to express a first protein that binds to a second protein comprising a sequence with greater than 97% identity to an amino acid sequence as set forth in SEQ ID NO:14 and a third protein that binds to a fourth protein comprising a sequence with greater than 97% identity to an amino acid sequence as set forth in SEQ ID NO:11 or SEQ ID NO:12. In an embodiment, the invention includes an aAPC comprising an EM-2 cell modified to express a first protein that binds to a second protein comprising a sequence with greater than 96% identity to an amino acid sequence as set forth in SEQ ID NO:14 and a third protein that binds to a fourth protein comprising a sequence with greater than 96% identity to an amino acid sequence as set forth in SEQ ID NO:11 or SEQ ID NO:12. In an embodiment, the invention includes an aAPC comprising an EM-2 cell modified to express a first protein that binds to a second protein comprising a sequence with greater than 95% identity to an amino acid sequence as set forth in SEQ ID NO:14 and a third protein that binds to a fourth protein comprising a sequence with greater than 95% identity to an amino acid sequence as set forth in SEQ ID NO:11 or SEQ ID NO:12. In an embodiment, the invention includes an aAPC comprising an EM-2 cell modified to express a first protein that binds to a second protein comprising a sequence with greater than 90% identity to an amino acid sequence as set forth in SEQ ID NO:14 and a third protein that binds to a fourth protein comprising a sequence with greater than 90% identity to an amino acid sequence as set forth in SEQ ID NO:11 or SEQ ID NO:12. In an embodiment, the invention includes a method of preparing any of the foregoing embodiments of aAPCs.

In an embodiment, the invention includes an aAPC comprising an EM-2 cell modified to express a single chain fragment variable (scFv) binding domain, such as clones 7C12 and 8B3 described herein, to bind the Fc domain of a monoclonal antibody, such as OKT-3, providing an additional proliferative signal.

In an embodiment, the invention includes an aAPC comprising an EM-3 or an EM-2 cell modified as depicted in FIG. 96. In an embodiment, the invention includes an aAPC comprising an EM-3 or an EM-2 cell modified as depicted in FIG. 97. In an embodiment, the invention includes an aAPC comprising an EM-3 or an EM-2 cell modified as depicted in FIG. 98.

In any of the foregoing embodiments, it is understood that an aAPC comprising an EM-3 or EM-2 cell may be modified to express both OX40L and 4-1BBL.

In an embodiment, the invention includes an isolated artificial antigen presenting cell (aAPC) comprising a cell that expresses CD58, and is modified to express one or more costimulatory molecules, wherein the aAPC is derived from a K562-lineage parental cell line. In an embodiment, the invention includes an aAPC comprising a K562-lineage cell that is modified to express one or more costimulatory molecules. In an embodiment, the K562 lineage parental cell line is deposited under accession no. ATCC CCL-243 and also at European Collection of Authenticated Cell Cultures (ECACCCECACC 89121407).

In an embodiment, the invention includes an aAPC comprising a K562-lineage cell that expresses CD58, wherein the cell is modified to express a CD86 protein comprising an amino acid sequence as set forth in SEQ ID NO:8, and conservative amino acid substitutions thereof, and a 4-1BBL protein comprising an amino acid sequence as set forth in SEQ ID NO:9, and conservative amino acid substitutions thereof, and wherein the CD86 protein and the 4-1BBL protein are expressed on the surface of the K562-lineage cell.

In an embodiment, the invention includes an aAPC comprising a K562-lineage cell transduced with one or more viral vectors, wherein the one or more viral vectors comprise a nucleic acid encoding CD86 and a nucleic acid encoding 4-1BBL, and wherein the K562-lineage cell expresses CD86 and 4-1BBL. In an embodiment, the invention includes a method of preparing any of the foregoing embodiments of aAPCs.

In an embodiment, the invention includes an aAPC comprising a K562-lineage cell modified to express a CD86 protein comprising an amino acid sequence as set forth in SEQ ID NO:8 and a 4-1BBL protein comprising an amino acid sequence as set forth in SEQ ID NO:9, wherein the CD86 protein and the 4-1BBL protein are expressed on the surface of the K562-lineage cell. In an embodiment, the invention includes a method of preparing any of the foregoing embodiments of aAPCs.

In an embodiment, the invention includes an aAPC comprising a K562-lineage cell modified to express a CD86 protein comprising a sequence with greater than 99% identity to an amino acid sequence as set forth in SEQ ID NO:8 and a 4-1BBL protein comprising a sequence with greater than 99% identity to an amino acid sequence as set forth in SEQ ID NO:9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 98% identity to an amino acid sequence as set forth in SEQ ID NO:8 and a 4-1BBL protein comprising a sequence with greater than 98% identity to an amino acid sequence as set forth in SEQ ID NO:9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 97% identity to an amino acid sequence as set forth in SEQ ID NO:8 and a 4-1BBL protein comprising a sequence with greater than 97% identity to an amino acid sequence as set forth in SEQ ID NO:9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 96% identity to an amino acid sequence as set forth in SEQ ID NO:8 and a 4-1BBL protein comprising a sequence with greater than 96% identity to an amino acid sequence as set forth in SEQ ID NO:9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 95% identity to an amino acid sequence as set forth in SEQ ID NO:8 and a 4-1BBL protein comprising a sequence with greater than 95% identity to an amino acid sequence as set forth in SEQ ID NO:9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 90% identity to an amino acid sequence as set forth in SEQ ID NO:8 and a 4-1BBL protein comprising a sequence with greater than 90% identity to an amino acid sequence as set forth in SEQ ID NO:9, wherein the CD86 protein and the 4-1BBL protein are expressed on the surface of the K562-lineage cell. In an embodiment, the invention includes a method of preparing any of the foregoing embodiments of aAPCs.

In an embodiment, the invention includes an aAPC comprising a K562-lineage cell modified to express a first protein that binds to a second protein comprising an amino acid sequence as set forth in SEQ ID NO:11, and conservative amino acid substitutions thereof, and a third protein that binds to a fourth protein comprising an amino acid sequence as set forth in SEQ ID NO:12 or SEQ ID NO:13, and conservative amino acid substitutions thereof. In an embodiment, the invention includes a method of preparing any of the foregoing embodiments of aAPCs.

In an embodiment, the invention includes an aAPC comprising a K562-lineage cell modified to express a first protein that binds to a second protein comprising a sequence with greater than 99% identity to an amino acid sequence as set forth in SEQ ID NO:11 and a third protein that binds to a fourth protein comprising a sequence with greater than 99% identity to an amino acid sequence as set forth in SEQ ID NO:12 or SEQ ID NO:13. In an embodiment, the invention includes an aAPC comprising a K562-lineage cell modified to express a first protein that binds to a second protein comprising a sequence with greater than 98% identity to an amino acid sequence as set forth in SEQ ID NO:11 and a third protein that binds to a fourth protein comprising a sequence with greater than 98% identity to an amino acid sequence as set forth in SEQ ID NO:12 or SEQ ID NO:13. In an embodiment, the invention includes an aAPC comprising a K562-lineage modified to express a first protein that binds to a second protein comprising a sequence with greater than 97% identity to an amino acid sequence as set forth in SEQ ID NO:11 and a third protein that binds to a fourth protein comprising a sequence with greater than 97% identity to an amino acid sequence as set forth in SEQ ID NO:12 or SEQ ID NO:13. In an embodiment, the invention includes an aAPC comprising a K562-lineage cell modified to express a first protein that binds to a second protein comprising a sequence with greater than 96% identity to an amino acid sequence as set forth in SEQ ID NO:11 and a third protein that binds to a fourth protein comprising a sequence with greater than 96% identity to an amino acid sequence as set forth in SEQ ID NO:12 or SEQ ID NO:13. In an embodiment, the invention includes an aAPC comprising a K562-lineage cell modified to express a first protein that binds to a second protein comprising a sequence with greater than 95% identity to an amino acid sequence as set forth in SEQ ID NO:11 and a third protein that binds to a fourth protein comprising a sequence with greater than 95% identity to an amino acid sequence as set forth in SEQ ID NO:12 or SEQ ID NO:13. In an embodiment, the invention includes an aAPC comprising a K562-lineage cell modified to express a first protein that binds to a second protein comprising a sequence with greater than 90% identity to an amino acid sequence as set forth in SEQ ID NO:11 and a third protein that binds to a fourth protein comprising a sequence with greater than 90% identity to an amino acid sequence as set forth in SEQ ID NO:12 or SEQ ID NO:13. In an embodiment, the invention includes a method of preparing any of the foregoing embodiments of aAPCs.

In an embodiment, the invention includes an aAPC comprising an K562-lineage cell modified to express a single chain fragment variable (scFv) binding domain, such as clones 7C12 and 8B3 described herein, to bind the Fc domain of a monoclonal antibody, such as OKT-3, providing an additional proliferative signal.

Methods of Preparing Artificial Antigen Presenting Cells

In an embodiment, a method of preparing an aAPC includes the step of stable incorporation of genes for production of CD86 and 4-1BBL. In an embodiment, a method of preparing an aAPC includes the step of retroviral transduction. In an embodiment, a method of preparing an aAPC includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of preparing an aAPC includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of preparing an aAPC includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tc1-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In an embodiment, a method of preparing an aAPC includes the step of stable incorporation of genes for transient production of CD86 and 4-1BBL. In an embodiment, a method of preparing an aAPC includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. In an embodiment, a method of preparing an aAPC includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of preparing an aAPC includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of preparing an aAPC includes the step of transfection using methods described in U.S. Pat. Nos. 5,766,902; 6,025,337; 6,410,517; 6,475,994; and 7,189,705; the disclosures of each of which are incorporated by reference herein.

In an embodiment, the aAPC is transduced by first using the Gateway cloning method (commercially available from ThermoFisher, Inc.) to prepare vector for lentiviral transduction, followed by lentiviral transduction using the vector and one or more associated helper plasmids, as is also described elsewhere herein. In the Gateway cloning method, a gene is selected (such as CD86) and is then provided with primers and amplified using PCR technology with the help of an attB tagged primer pair. The PCR fragment is then combined with a donor vector (pDONR, such as pDONR221) that includes attP sites to provide an entry clone, using the BP reaction. An integration reaction between the attB and the attP sites combines the PCR fragment with the donor vector. The resulting entry clone contains the gene of interest flanked by attL sites. The LR reaction is then used to combine the entry clone with a destination vector to produce an expression vector. In the LR reaction, a recombination reaction is used to link the entry clone with the destination vector (such as pLV430G) using the attL and attR sites and a clonase enzyme. The attL sites are already found in the entry clone, while the destination vector includes the attR sites. The LR reaction is carried out to transfer the sequence of interest into one or more destination vectors in simultaneous reactions.

In some embodiments, the aAPCs described herein may be grown and maintained under serum-based media and/or serum free media. According to an exemplary method, aAPCs may be cultured in 24 well plates at a cell density of about $1\times10^6$ cells per well for 3 to 5 days. The cells may then be isolated and/or washed by centrifugation and resuspended in media or cryopreserved in an appropriate cryopreservation media (e.g., CryoStor 10 (BioLife Solutions)) and stored in a −80° C. freezer.

In some embodiments, the aAPCs described herein may be grown in the presence of serum-based media. In some embodiments, the aAPCs described herein by may be grown in the presence of serum-based media that includes human serum (hSerum) containing media (e.g., cDMEM with 10% hSerum). In some embodiments, the aAPCs grown in the presence of serum-based media may be selected from the group consisting of aMOLM-13 cells, aMOLM-14 cells, and aEM3 cells.

In some embodiments, the aAPCs described herein may be grown in the presence of serum free media. In some embodiments, the serum free media may be selected from the group consisting of CTS Optmizer (ThermoFisher), Xvivo-20 (Lonza), Prime T Cell CDM (Irvine), XFSM (MesenCult), and the like. In some embodiments, the aAPCs grown in the presence of serum free media may be selected from the group consisting of aMOLM-13 cells, aMOLM-14 cells, and aEM3 cells.

Methods of Expanding Tumor Infiltrating Lymphocytes and T Cells

In an embodiment, the invention includes a method of expanding tumor infiltrating lymphocytes (TILs), the method comprising contacting a population of TILs comprising at least one TIL with an aAPC described herein, wherein said aAPC comprises at least one co-stimulatory ligand that specifically binds with a co-stimulatory molecule expressed on the cellular surface of the TILs, wherein binding of said co-stimulatory molecule with said co-stimulatory ligand induces proliferation of the TILs, thereby specifically expanding TILs.

In an embodiment, the invention provides a method of expanding a population of tumor infiltrating lymphocytes (TILs) using any of the aAPCs of the present disclosure, the method comprising the steps as described in Jin, et al., *J. Immunotherapy* 2012, 35, 283-292, the disclosure of which is incorporated by reference herein. For example, the tumor may be placed in enzyme media and mechanically dissociated for approximately 1 minute. The mixture may then be incubated for 30 minutes at 37° C. in 5% $CO_2$ and then mechanically disrupted again for approximately 1 minute. After incubation for 30 minutes at 37° C. in 5% $CO_2$, the tumor may be mechanically disrupted a third time for approximately 1 minute. If after the third mechanical disruption, large pieces of tissue are present, 1 or 2 additional mechanical dissociations may be applied to the sample, with or without 30 additional minutes of incubation at 37° C. in 5% $CO_2$. At the end of the final incubation, if the cell suspension contains a large number of red blood cells or dead cells, a density gradient separation using Ficoll may be performed to remove these cells. TIL cultures were initiated in 24-well plates (Costar 24-well cell culture cluster, flat bottom; Corning Incorporated, Corning, N.Y.), each well may be seeded with $1\times10^6$ tumor digest cells or one tumor fragment approximately 1 to 8 mm$^3$ in size in 2 mL of complete medium (CM) with IL-2 (6000 IU/mL; Chiron Corp., Emeryville, Calif.). CM consists of RPMI 1640 with GlutaMAX, supplemented with 10% human AB serum, 25 mM Hepes, and 10 mg/mL gentamicin. Cultures may be initiated in gas-permeable flasks with a 40 mL capacity and a 10 cm$^2$ gas-permeable silicon bottom (G-Rex 10; Wilson Wolf Manufacturing, New Brighton, each flask may be loaded with 10-40×10$^6$ viable tumor digest cells or 5-30 tumor fragments in 10-40 mL of CM with IL-2. G-Rex 10 and 24-well plates may be incubated in a humidified incubator at 37° C. in 5% $CO_2$ and 5 days after culture initiation, half the media may be removed and replaced with fresh CM and IL-2 and after day 5, half the media may be changed every 2-3 days. Rapid expansion protocol (REP) of TILs may be performed using T-175 flasks and gas-permeable bags or gas-permeable G-Rex flasks, as described elsewhere herein, using the aAPCs of the present disclosure. For REP in T-175 flasks, $1\times10^6$ TILs may be suspended in 150 mL of media in each flask. The TIL may be cultured with aAPCs of the present disclosure at a ratio described herein, in a 1 to 1 mixture of CM and AIM-V medium (50/50 medium), supplemented with 3000 IU/mL of IL-2 and 30 ng/mL of anti-CD3 antibody (OKT-3). The T-175 flasks may be incubated at 37° C. in 5% $CO_2$. Half the media may be changed on day 5 using 50/50 medium with 3000 IU/mL of IL-2. On day 7, cells from 2 T-175 flasks may be combined in a 3 L bag and 300 mL of AIM-V with 5% human AB serum and 3000 IU/mL of IL-2 may be added to the 300 mL of TIL suspension. The number of cells in each bag may be counted every day or two days, and fresh media may be added to keep the cell count between 0.5 and $2.0\times10^6$ cells/mL. For REP in 500 mL capacity flasks with 100 $cm^2$ gas-permeable silicon bottoms (e.g., G-Rex 100, Wilson Wolf Manufacturing, as described elsewhere herein), $5\times10^6$ or $10\times10^6$ TILs may be cultured with aAPCs at a ratio described herein (e.g., 1 to 100) in 400 mL of 50/50 medium, supplemented with 3000 IU/mL of IL-2 and 30 ng/mL of anti-CD3 antibody (OKT-3). The G-Rex 100 flasks may be incubated at 37° C. in 5% $CO_2$. On day five, 250 mL of supernatant may be removed and placed into centrifuge bottles and centrifuged at 1500 rpm (491 g) for 10 minutes. The obtained TIL pellets may be resuspended with 150 mL of fresh 50/50 medium with 3000 IU/mL of IL-2 and added back to the G-Rex 100 flasks. When TIL are expanded serially in G-Rex 100 flasks, on day seven the TIL in each G-Rex100 are suspended in the 300 mL of media present in each flask and the cell suspension may be divided into three 100 mL aliquots that may be used to seed 3 G-Rex100 flasks. About 150 mL of AIM-V with 5% human AB serum and 3000 IU/mL of IL-2 may then be added to each flask. G-Rex100 flasks may then be incubated at 37° C. in 5% $CO_2$, and after four days, 150 mL of AIM-V with 3000 IU/mL of IL-2 may be added to each G-Rex100 flask. After this, the REP may be completed by harvesting cells on day 14 of culture.

As described herein, TILs may be expanded advantageously in the presence of serum free media. In some embodiments, the TIL expansion methods described herein may include the use of serum free media rather than serum-based media (e.g., complete media or CM1). In some embodiments, the TIL expansion methods described herein may use serum free media rather than serum-based media. In some embodiments, the serum free media may be selected from the group consisting of CTS Optmizer (ThermoFisher), Xvivo-20 (Lonza), Prime T Cell CDM (Irvine), and the like.

In an embodiment, the invention provides a method of expanding a population of tumor infiltrating lymphocytes (TILs), the method comprising the steps of:
  (a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and
  (b) contacting the population of TILs with the population of aAPCs in a cell culture medium.

In an embodiment, the invention provides a method of expanding a population of tumor infiltrating lymphocytes (TILs), the method comprising the steps of:
  (a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and
  (b) contacting the population of TILs with the population of aAPCs in a cell culture medium,
  wherein the cell culture medium further comprises IL-2 at an initial concentration of about 3000 IU/mL and OKT-3 antibody at an initial concentration of about 30 ng/mL.

In an embodiment, the invention provides a method of expanding a population of tumor infiltrating lymphocytes (TILs), the method comprising the steps of:
  (a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and
  (b) contacting the population of TILs with the population of aAPCs in a cell culture medium,
  wherein the population of APCs expands the population of TILs by at least 50-fold over a period of 7 days in a cell culture medium.

In an embodiment, the invention provides a method of expanding a population of tumor infiltrating lymphocytes (TILs), the method comprising the steps of:
  (a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and
  (b) contacting the population of TILs with the population of aAPCs in a cell culture medium,
  wherein the myeloid cell endogenously expresses HLA-A/B/C, ICOS-L, and CD58.

In an embodiment, the invention provides a method of expanding a population of tumor infiltrating lymphocytes (TILs), the method comprising the steps of:
  (a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and
  (b) contacting the population of TILs with the population of aAPCs in a cell culture medium,
  wherein the myeloid cell is a MOLM-14 cell.

In an embodiment, the invention provides a method of expanding a population of tumor infiltrating lymphocytes (TILs), the method comprising the steps of:
  (a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and
  (b) contacting the population of TILs with the population of aAPCs in a cell culture medium,
  wherein the myeloid cell is a MOLM-13 cell.

In an embodiment, the invention provides a method of expanding a population of tumor infiltrating lymphocytes (TILs), the method comprising the steps of:
  (c) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (d) contacting the population of TILs with the population of aAPCs in a cell culture medium, wherein the myeloid cell is a EM-3 cell.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the CD86 protein comprises an amino acid sequence as set forth in SEQ ID NO:8, or conservative amino acid substitutions thereof, and the 4-1BBL protein comprises an amino acid sequence as set forth in SEQ ID NO:9, or conservative amino acid substitutions thereof.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the nucleic acid encoding CD86 comprises a nucleic acid sequence as set forth in SEQ ID NO:19 and the nucleic acid encoding 4-1BBL comprises a nucleic acid sequence as set forth in SEQ ID NO:16.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the expansion is performed using a gas permeable container.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the ratio of the population of TILs to the population of aAPCs is between 1 to 200 and 1 to 400.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the ratio of the population of TILs to the population of aAPCs is about 1 to 300.

In an embodiment, the invention provides a method of expanding tumor infiltrating lymphocytes (TILs), the method comprising contacting a population of TILs comprising a population of TILs with a myeloid artificial antigen presenting cell (aAPC), wherein the myeloid aAPC comprises at least two co-stimulatory ligands that specifically bind with at least two co-stimulatory molecule on the TILs, wherein binding of the co-stimulatory molecules with the co-stimulatory ligand induces proliferation of the TILs, thereby specifically expanding TILs, and wherein the at least two co-stimulatory ligands comprise CD86 and 4-1BBL.

In any of the foregoing embodiments, the aAPC may further comprise OX40L in addition to 4-1BBL, or may comprise OX40L instead of 4-1BBL.

In an embodiment, a method of expanding or treating a cancer includes a step wherein TILs are obtained from a patient tumor sample. A patient tumor sample may be obtained using methods known in the art. For example, TILs may be cultured from enzymatic tumor digests and tumor fragments (about 1 to about 8 $mm^3$ in size) from sharp dissection. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In an embodiment, REP can be performed in a gas permeable container using the aAPCs of the present disclosure by any suitable method. For example, TILs can be rapidly expanded using non-specific T cell receptor stimulation in the presence of interleukin-2 (IL-2) or interleukin-15 (IL-15). The non-specific T cell receptor stimulus can include, for example, about 30 ng/mL of an anti-CD3 antibody, e.g. OKT-3, a monoclonal anti-CD3 antibody (commercially available from Ortho-McNeil, Raritan, N.J., USA or Miltenyi Biotech, Auburn, Calif., USA) or UHCT-1 (commercially available from BioLegend, San Diego, Calif., USA). TILs can be rapidly expanded by further stimulation of the TILs in vitro with one or more antigens, including antigenic portions thereof, such as epitope(s), of the cancer, which can be optionally expressed from a vector, such as a human leukocyte antigen A2 (HLA-A2) binding peptide, e.g., 0.3 µM MART-1:26-35 (27 L) or gpl 00:209-217 (210M), optionally in the presence of a T cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2.

In an embodiment, a method for expanding TILs may include using about 5000 mL to about 25000 mL of cell culture medium, about 5000 mL to about 10000 mL of cell culture medium, or about 5800 mL to about 8700 mL of cell culture medium. In an embodiment, a method for expanding TILs may include using about 1000 mL to about 2000 mL of cell medium, about 2000 mL to about 3000 mL of cell culture medium, about 3000 mL to about 4000 mL of cell culture medium, about 4000 mL to about 5000 mL of cell culture medium, about 5000 mL to about 6000 mL of cell culture medium, about 6000 mL to about 7000 mL of cell culture medium, about 7000 mL to about 8000 mL of cell culture medium, about 8000 mL to about 9000 mL of cell culture medium, about 9000 mL to about 10000 mL of cell culture medium, about 10000 mL to about 15000 mL of cell culture medium, about 15000 mL to about 20000 mL of cell culture medium, or about 20000 mL to about 25000 mL of cell culture medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad, Calif., USA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the rapid expansion is performed using a gas permeable container. Such embodiments allow for cell populations to expand from about $5 \times 10^5$ cells/cm$^2$ to between $10 \times 10^6$ and $30 \times 10^6$ cells/cm$^2$. In an embodiment, this expansion occurs without feeding. In an embodiment, this expansion occurs without feeding so long as medium resides at a height of about 10 cm in a gas-permeable flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739 A1, International Patent Application Publication No. WO 2014/210036 A1, U.S. Patent Application Publication No. US 2013/0115617 A1, International Publication No. WO 2013/188427 A1, U.S. Patent Application Publication No. US 2011/0136228 A1, U.S. Pat. No. 8,809,050, International Patent Application Publication No. WO 2011/072088 A2, U.S. Patent Application Publication No. US 2016/0208216 A1, U.S. Patent Application Publication No. US 2012/0244133 A1, International Patent Application Publication No. WO 2012/129201 A1, U.S. Patent Application Publication No. US 2013/0102075 A1, U.S. Pat. No. 8,956,860, International Patent Application Publication No. WO 2013/173835 A1, and U.S. Patent Application Publication No. US 2015/0175966 A1, the disclosures of which are incorporated herein by reference. Such processes are also described in Jin, et al., *J. Immunotherapy* 2012, 35, 283-292, the disclosure of which is incorporated by reference herein.

In an embodiment, the gas permeable container is a G-Rex 10 flask (Wilson Wolf Manufacturing Corporation, New Brighton, Minn., USA). In an embodiment, the gas permeable container includes a 10 cm$^2$ gas permeable culture surface. In an embodiment, the gas permeable container includes a 40 mL cell culture medium capacity. In an embodiment, the gas permeable container provides 100 to 300 million TILs after 2 medium exchanges.

In an embodiment, the gas permeable container is a G-Rex 100 flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 450 mL cell culture medium capacity. In an embodiment, the gas permeable container provides 1 to 3 billion TILs after 2 medium exchanges.

In an embodiment, the gas permeable container is a G-Rex 100M flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 1000 mL cell culture medium capacity. In an embodiment, the gas permeable container provides 1 to 3 billion TILs without medium exchange.

In an embodiment, the gas permeable container is a G-Rex 100 L flask (Wilson Wolf Manufacturing Corporation, New Brighton, Minn., USA). In an embodiment, the gas permeable container includes a 100 cm$^2$ gas permeable culture surface. In an embodiment, the gas permeable container includes a 2000 mL cell culture medium capacity. In an embodiment, the gas permeable container provides 1 to 3 billion TILs without medium exchange.

In an embodiment, the gas permeable container is a G-Rex 24 well plate (Wilson Wolf Manufacturing Corporation, New Brighton, Minn., USA). In an embodiment, the gas permeable container includes a plate with wells, wherein each well includes a 2 cm$^2$ gas permeable culture surface. In an embodiment, the gas permeable container includes a plate with wells, wherein each well includes a 8 mL cell culture medium capacity. In an embodiment, the gas permeable container provides 20 to 60 million cells per well after 2 medium exchanges.

In an embodiment, the gas permeable container is a G-Rex 6 well plate (Wilson Wolf Manufacturing Corporation, New Brighton, Minn., USA). In an embodiment, the gas permeable container includes a plate with wells, wherein each well includes a 10 cm$^2$ gas permeable culture surface. In an embodiment, the gas permeable container includes a plate with wells, wherein each well includes a 40 mL cell culture medium capacity. In an embodiment, the gas permeable container provides 100 to 300 million cells per well after 2 medium exchanges.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using aAPCs for a duration of about 14 to about 42 days, e.g., about 28 days.

In an embodiment, the rapid expansion uses about $1 \times 10^9$ to about $1 \times 10^{11}$ aAPCs. In an embodiment, the rapid expansion uses about $1 \times 10^9$ aAPCs. In an embodiment, the rapid expansion uses about $1 \times 10^{10}$ aAPCs. In an embodiment, the rapid expansion uses about $1 \times 10^{11}$ aAPCs.

In an embodiment, the ratio of TILs to aAPCs (TIL:aAPC) is selected from the group consisting of 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, 1:225, 1:250, 1:275, 1:300, 1:350, 1:400, 1:450, and 1:500. In a preferred embodiment, the ratio of TILs to aAPCs (TIL:aAPC) is about 1:90. In a preferred embodiment, the ratio of TILs to aAPCs (TIL:aAPC) is about 1:95. In a preferred embodiment, the ratio of TILs to aAPCs (TIL:aAPC) is about 1:100. In a preferred embodiment, the ratio of TILs to aAPCs (TIL:aAPC) is about 1:105. In a preferred embodiment, the ratio of TILs to aAPCs (TIL:aAPC) is about 1:110.

In an embodiment, the ratio of TILs to aAPCs in the rapid expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to aAPCs in the rapid expansion is between 1 to 50 and 1 to 300. In an embodiment, the ratio of TILs to aAPCs in the rapid expansion is between 1 to 100 and 1 to 200.

In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises an OKT-3 antibody. In a preferred embodiment, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody.

In an embodiment, a rapid expansion process for TILs may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks, commercially available from Wilson Wolf Manufacturing Corporation, New Brighton, Minn., USA). For TIL rapid expansion in T-175 flasks, $1 \times 10^6$ TILs suspended in 150 mL of media may be added to each T-175 flask. The TILs may be cultured with aAPCs at a ratio of 1 TIL to 100 aAPCs and the cells were cultured in a 1 to 1 mixture of CM and AIM-V medium, supplemented with 3000 IU (international units) per mL of IL-2 and 30 ng per ml of anti-CD3 antibody (e.g., OKT-3). The T-175 flasks may be incubated at 37° C. in 5% $CO_2$. Half the media may be exchanged on day 5 using 50/50 medium with 3000 IU per mL of IL-2. On day 7 cells from two T-175 flasks may be combined in a 3 liter bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

In an embodiment, for TIL rapid expansions in 500 mL capacity gas permeable flasks with 100 cm gas-permeable silicon bottoms (G-Rex 100, commercially available from Wilson Wolf Manufacturing Corporation, New Brighton, Minn., USA), $5 \times 10^6$ or $10 \times 10^6$ TIL may be cultured with aAPCs at a ratio of 1 to 100 in 400 mL of 50/50 medium, supplemented with 5% human AB serum, 3000 IU per mL of IL-2 and 30 ng per mL of anti-CD3 (OKT-3). The G-Rex 100 flasks may be incubated at 37° C. in 5% $CO_2$. On day 5, 250 mL of supernatant may be removed and placed into centrifuge bottles and centrifuged at 1500 rpm (revolutions per minute; 491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-Rex 100 flask. The cells may be harvested on day 14 of culture.

In an embodiment, TILs may be prepared as follows. 2 $mm^3$ tumor fragments are cultured in complete media (CM) comprised of AIM-V medium (Invitrogen Life Technologies, Carlsbad, Calif.) supplemented with 2 mM glutamine (Mediatech, Inc. Manassas, Va.), 100 U/mL penicillin (Invitrogen Life Technologies), 100 μg/mL streptomycin (Invitrogen Life Technologies), 5% heat-inactivated human AB serum (Valley Biomedical, Inc. Winchester, Va.) and 600 IU/mL rhIL-2 (Chiron, Emeryville, Calif.). For enzymatic digestion of solid tumors, tumor specimens were diced into RPMI-1640, washed and centrifuged at 800 rpm for 5 minutes at 15-22° C., and resuspended in enzymatic digestion buffer (0.2 mg/mL Collagenase and 30 units/ml of DNase in RPMI-1640) followed by overnight rotation at room temperature. TILs established from fragments may be grown for 3-4 weeks in CM and expanded fresh or cryopreserved in heat-inactivated HAB serum with 10% dimethylsulfoxide (DMSO) and stored at −180° C. until the time of study. Tumor associated lymphocytes (TAL) obtained from ascites collections were seeded at 3×10$^6$ cells/well of a 24 well plate in CM. TIL growth was inspected about every other day using a low-power inverted microscope.

In an embodiment, TILs are expanded in gas-permeable containers. Gas-permeable containers have been used to expand TILs using PBMCs using methods, compositions, and devices known in the art, including those described in U.S. Patent Application Publication No. U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, about 10 L, about 11 L, about 12 L, about 13 L, about 14 L, about 15 L, about 16 L, about 17 L, about 18 L, about 19 L, about 20 L, about 25 L, and about 30 L. In an embodiment, the cell expansion system includes a gas permeable cell bag with a volume range selected from the group consisting of between 50 and 150 mL, between 150 and 250 mL, between 250 and 350 mL, between 350 and 450 mL, between 450 and 550 mL, between 550 and 650 mL, between 650 and 750 mL, between 750 and 850 mL, between 850 and 950 mL, and between 950 and 1050 mL. In an embodiment, the cell expansion system includes a gas permeable cell bag with a volume range selected from the group consisting of between 1 L and 2 L, between 2 L and 3 L, between 3 L and 4 L, between 4 L and 5 L, between 5 L and 6 L, between 6 L and 7 L, between 7 L and 8 L, between 8 L and 9 L, between 9 L and 10 L, between 10 L and 11 L, between 11 L and 12 L, between 12 L and 13 L, between 13 L and 14 L, between 14 L and 15 L, between 15 L and 16 L, between 16 L and 17 L, between 17 L and 18 L, between 18 L and 19 L, and between 19 L and 20 L. In an embodiment, the cell expansion system includes a gas permeable cell bag with a volume range selected from the group consisting of between 0.5 L and 5 L, between 5 L and 10 L, between 10 L and 15 L, between 15 L and 20 L, between 20 L and 25 L, and between 25 L and 30 L. In an embodiment, the cell expansion system utilizes a rocking time of about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, and about 28 days. In an embodiment, the cell expansion system utilizes a rocking time of between 30 minutes and 1 hour, between 1 hour and 12 hours, between 12 hours and 1 day, between 1 day and 7 days, between 7 days and 14 days, between 14 days and 21 days, and between 21 days and 28 days. In an embodiment, the cell expansion system utilizes a rocking rate of about 2 rocks/minute, about 5 rocks/minute, about 10 rocks/minute, about 20 rocks/minute, about 30 rocks/minute, and about 40 rocks/minute. In an embodiment, the cell expansion system utilizes a rocking rate of between 2 rocks/minute and 5 rocks/minute, 5 rocks/minute and 10 rocks/minute, 10 rocks/minute and 20 rocks/minute, 20 rocks/minute and 30 rocks/minute, and 30 rocks/minute and 40 rocks/minute. In an embodiment, the cell expansion system utilizes a rocking angle of about 2°, about 3°, about 4°, about 5°, about 6°, about 7°, about 8°, about 9°, about 10°, about 11°, and about 12°. In an embodiment, the cell expansion system utilizes a rocking angle of between 2° and 3°, between 3° and 4°, between 4° and 5°, between 5° and 6°, between 6° and 7°, between 7° and 8°, between 8° and 9°, between 9° and 10°, between 10° and 11°, and between 11° and 12°.

In an embodiment, a method of expanding TILs using aAPCs further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

In an embodiment, the aAPCs of the present invention may be used to expand T cells. Any of the foregoing embodiments of the present invention described for the expansion of TILs may also be applied to the expansion of T cells. In an embodiment, the aAPCs of the present invention may be used to expand CD8$^+$ T cells. In an embodiment, the aAPCs of the present invention may be used to expand CD4$^+$ T cells. In an embodiment, the aAPCs of the present invention may be used to expand T cells transduced with a chimeric antigen receptor (CAR-T). In an embodiment, the aAPCs of the present invention may be used to expand T cells comprising a modified T cell receptor (TCR). The CAR-T cells may be targeted against any suitable antigen, including CD19, as described in the art, e.g., in U.S. Pat. Nos. 7,070,995; 7,446,190; 8,399,645; 8,916,381; and 9,328,156; the disclosures of which are incorporated by reference herein. The modified TCR cells may be targeted against any suitable antigen, including NY-ESO-1, TRP-1, TRP-2, tyrosinase cancer antigen, MAGE-A3, SSX-2, and VEGFR2, or antigenic portions thereof, as described in the art, e.g., in U.S. Pat. Nos. 8,367,804 and 7,569,664, the disclosures of which are incorporated by reference herein.

Methods of Treating Cancers and Other Diseases

The compositions and methods described herein can be used in a method for treating diseases. In an embodiment, they are for use in treating hyperproliferative disorders. They may also be used in treating other disorders as described herein and in the following paragraphs. The TILs, populations and compositions thereof described herein may be for use in the treatment of a disease. In an embodiment, the TILs, populations and compositions described herein are for use in the treatment of a hyperproliferative disorder.

In some embodiments, the hyperproliferative disorder is cancer. In some embodiments, the hyperproliferative disorder is a solid tumor cancer. In some embodiments, the solid tumor cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma, pancreatic cancer, and glioblastoma. In some embodiments, the hyperproliferative disorder is a hematological malignancy. In some embodiments, the hematological malignancy is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma.

In an embodiment, the invention includes a method of treating a cancer with a population of tumor infiltrating lymphocytes (TILs) comprising the steps of: (a) obtaining a first population of TILs from a tumor resected from a patient; (b) performing a rapid expansion of the first population of TILs using a population of artificial antigen presenting cells (aAPCs) in a cell culture medium to obtain a second population of TILs, wherein the second population of TILs is at least 50-fold greater in number than the first population of TILs; and (c) administering a therapeutically effective portion of the second population of TILs to a patient with the cancer. In an embodiment, the aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. In an embodiment, the rapid expansion is performed over a period not greater than 14 days.

In an embodiment, the invention includes a method of treating a cancer with a population of tumor infiltrating lymphocytes (TILs) comprising the steps of: (a) obtaining a first population of TILs from a tumor resected from a patient; (b) performing an initial expansion of the first population of TILs using a first population of artificial antigen presenting cells (aAPCs) in a first cell culture medium to obtain a second population of TILs, wherein the second population of TILs is at least 10-fold greater in number than the first population of TILs, and wherein the first cell culture medium comprises IL-2; (c) performing a rapid expansion of the second population of TILs using a second population of aAPCs in a second cell culture medium to obtain a third population of TILs, wherein the third population of TILs is at least 50-fold greater in number than the first population of TILs; and wherein the second cell culture medium comprises IL-2 and OKT-3; (d) administering a therapeutically effective portion of the third population of TILs to a patient with the cancer. In an embodiment, the aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. In an embodiment, the rapid expansion is performed over a period not greater than 14 days. In an embodiment, the initial expansion is performed using a gas permeable container.

In an embodiment, the invention includes a method of treating a cancer with a population of tumor infiltrating lymphocytes (TILs) comprising the steps of: (a) obtaining a first population of TILs from a tumor resected from a patient; (b) performing an initial expansion of the first population of TILs in a first cell culture medium to obtain a second population of TILs, wherein the second population of TILs is at least 10-fold greater in number than the first population of TILs, and wherein the first cell culture medium comprises IL-2; (c) performing a rapid expansion of the second population of TILs using a population of artificial antigen presenting cells (aAPCs) in a second cell culture medium to obtain a third population of TILs, wherein the third population of TILs is at least 50-fold greater in number than the first population of TILs; and wherein the second cell culture medium comprises IL-2 and OKT-3; (d) administering a therapeutically effective portion of the third population of TILs to a patient with the cancer. In an embodiment, the aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. In an embodiment, the rapid expansion is performed over a period not greater than 14 days.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development*, 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32.

Non-Myeloablative Lymphodepletion with Chemotherapy

In an embodiment, the invention includes a method of treating a cancer with a population of TILs, wherein a patient is pre-treated with non-myeloablative chemotherapy prior to an infusion of TILs according to the present disclosure. In an embodiment, the invention provides a population of TILs obtainable by a method described herein for use in treating a cancer, wherein the population of TILs is for treating a patient which is pre-treated with non-myeloablative chemotherapy. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the aAPC-expanded TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.,* 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 µg/mL-10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/ml-10 µg/ml by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide are together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

Pharmaceutical Compositions, Dosages, and Dosing Regimens

In an embodiment, TILs expanded using aAPCs of the present disclosure are administered to a patient as a pharmaceutical composition. In an embodiment, the pharmaceutical composition is a suspension of TILs in a sterile buffer. TILs expanded using aAPCs of the present disclosure may be administered by any suitable route as known in the art. Preferably, the TILs are administered as a single infusion, such as an intra-arterial or intravenous infusion, which preferably lasts approximately 30 to 60 minutes. Other suitable routes of administration include intraperitoneal, intrathecal, and intralymphatic administration.

Any suitable dose of TILs can be administered. Preferably, from about $2.3 \times 10^{10}$ to about $13.7 \times 10^{10}$ TILs are administered, with an average of around $7.8 \times 10^{10}$ TILs, particularly if the cancer is melanoma. In an embodiment, about $1.2 \times 10^{10}$ to about $4.3 \times 10^{10}$ of TILs are administered.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $2 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the TILs provided in the pharmaceutical compositions of the invention is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of embodiments of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Variability in Expansion of Tumor Infiltrating Lymphocytes Using PBMC Feeder Cells The variability in TIL expansion obtained by use of PBMC feeder cells may be demonstrated by comparing the results of multiple TIL expansions on the same line of TILs obtained from a patient. FIG. 1 illustrates typical results of rapid expansion of TILs using irradiated allogeneic PBMC feeder cells (PBMC feeders). Two TIL lines labeled M1015T and M1016T ($1.3 \times 10^5$ cells) were co-cultured with 46 different irradiated feeder cell lots ($1.3 \times 10^7$), IL-2 (3000 IU/mL, recombinant human IL-2 (e.g., aldesleukin or equivalent), CellGenix, Inc., Portsmouth, N.H., USA) and OKT-3 (30 ng/mL, MACS GMP CD3 pure, Miltenyi Biotec GmbH, Bergisch Gladbach, Germany) in a T25 flask for 7 days. The fold expansion value for TILs was calculated on Day 7. The figure shows the number of fold expansions for the two TIL lines in separate stimulation experiments. For each TIL line, 46 different PBMC feeder lots were tested. The results range over more than 100-fold for each TIL line, and highlight the variability of expansion results using PBMC feeder cells. The aAPCs of the present invention offer reduced variability in expansion performance compared to PBMC feeders, as well as other advantages, as shown in the following examples.

Example 2—Selection of Myeloid Cells for aAPC Development

Phenotypic characterization was performed on various myeloid-lineage cell lines to identify potential candidates for further modification into aAPCs for TIL expansion. The results are summarized in Table 5. The MOLM-14 cell line exhibited endogenous expression of CD64, and was selected for further development. The EM-3 cell line was selected based on the observation of endogenous expression of ICOS-L (which was not observed for the EM-2 cell line, despite being taken from the same patient).

Example 3—Preparation of MOLM-14 Artificial Antigen Presenting Cells (aMOLM14 aAPCs)

MOLM-14 cells were obtained from Leibniz-Institut DSMZ-Deutsche Sammlung von Mikroorganismen and Zellkulturen GmbH. To develop MOLM-14 based aAPCs, MOLM-14 cells were engineered with the costimulatory molecules CD86 and 4-1BBL (CD137L). Human CD86 (hCD86) and human 4-1BBL (h4-1BBL) genes were cloned into commercially-available PLV430G and co-transfected with PDONR221 vectors (Invitrogen/Thermo Fisher Scientific, Carlsbad, Calif., USA) using a lentiviral transduction method. The gateway cloning method was used as described in Katzen, *Expert Opin. Drug Disc.* 2007, 4, 571-589, to clone hCD86 and hCD137L genes onto the PLV430G and PDONR221 vectors. The 293T cell line (human embryonic kidney cells transformed with large T antigen) was used for lentiviral production, transduced to MOLM-14 cells. The transfected cells were sorted (S3e Cell Sorter, Bio-Rad, Hercules, Calif., USA) using APC-conjugated CD86 and PE-conjugated CD137L to isolate and enrich the cells. The enriched cells were checked for purity by flow cytometry.

Figure 2:
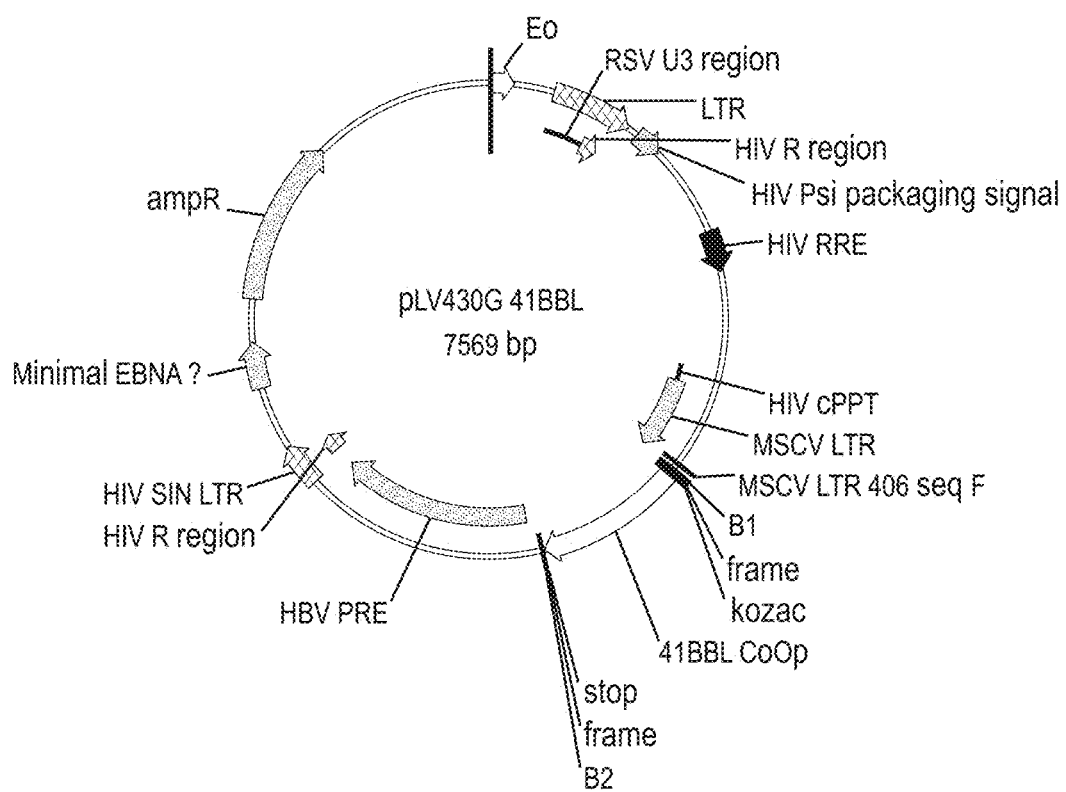
FIG. 2 illustrates a vector diagram of the pLV430G human 4-1BBL vector.
Figure 3:
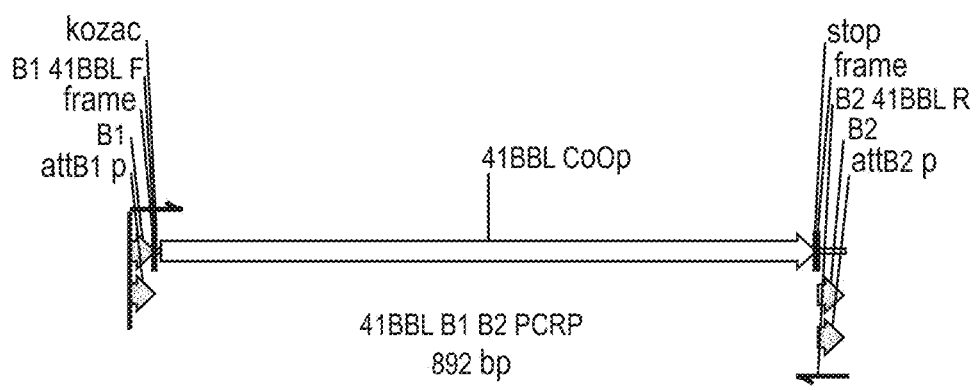
FIG. 3 illustrates a diagram of the 4-1BBL PCRP (polymerase chain reaction product) portion of the pLV430G human 4-1BBL vector.
Figure 4:
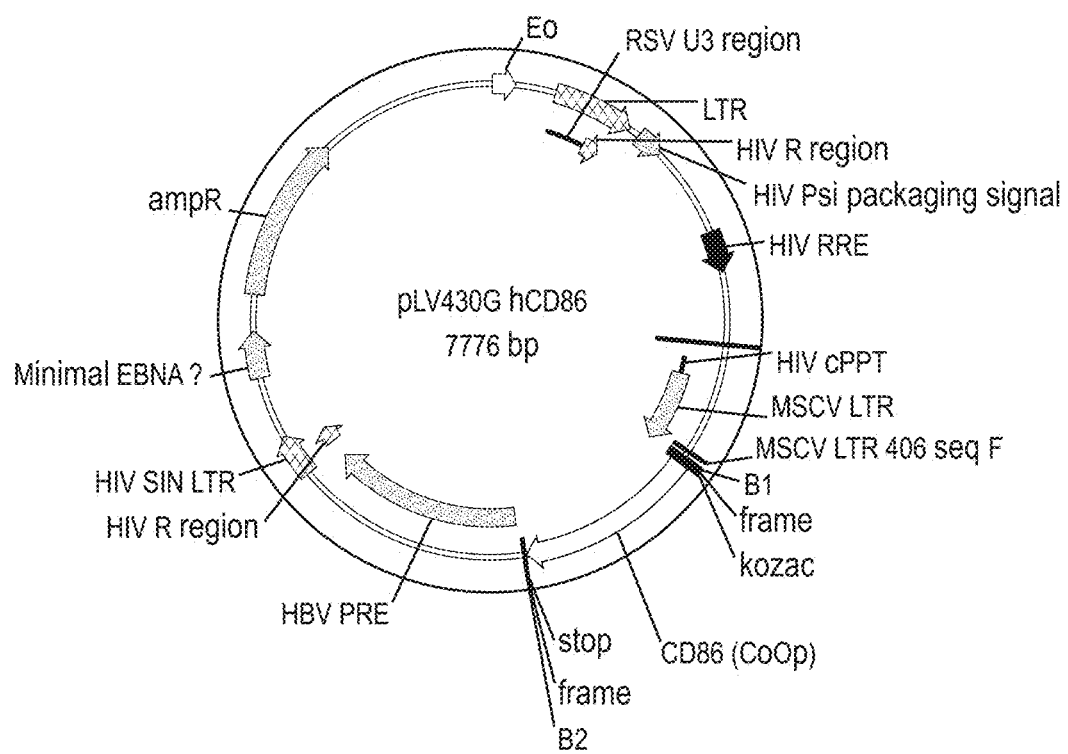
FIG. 4 illustrates a vector diagram of the pLV430G human CD86 vector.
Figure 5:
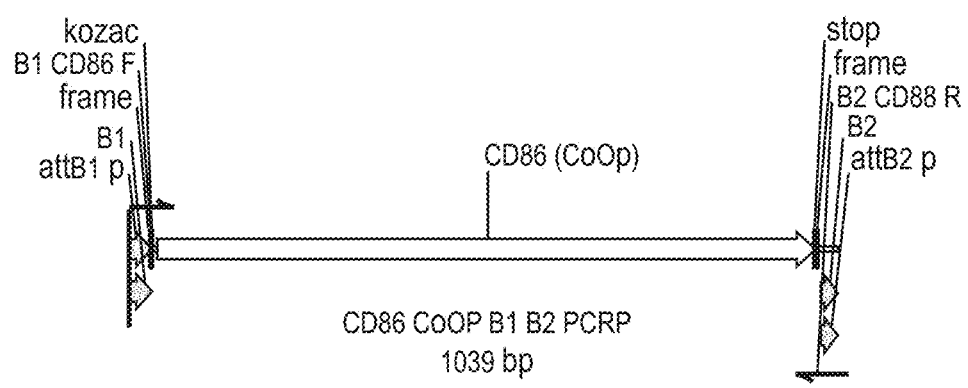
FIG. 5 illustrates a diagram of the CD86 PCRP portion of the pLV430G human CD86 vector.
Figure 6:
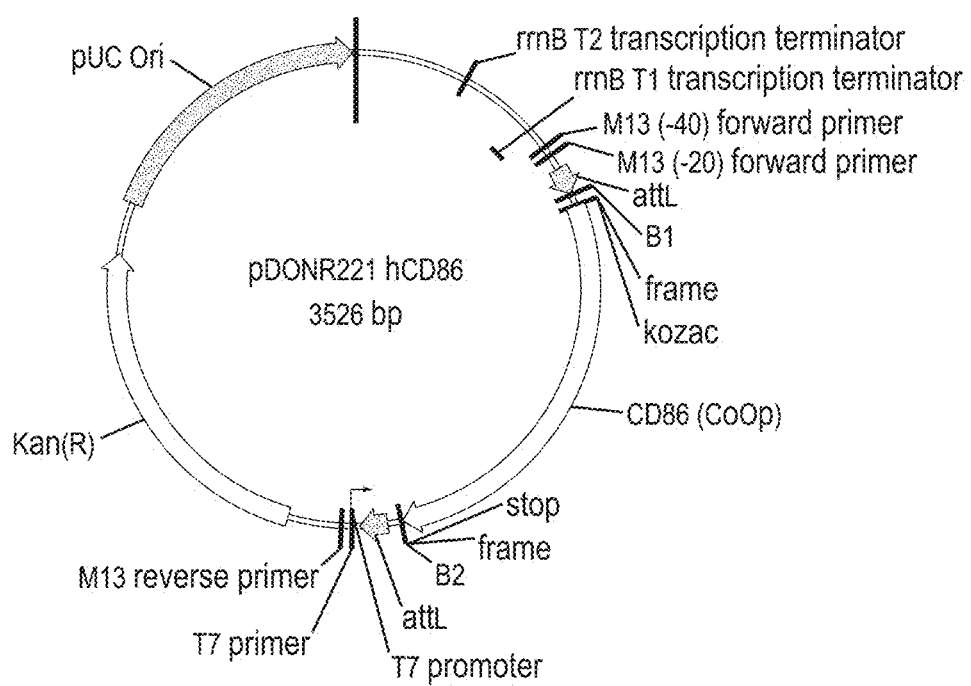
FIG. 6 illustrates a vector diagram of the pDONR221 human CD86 donor vector.
Figure 7:
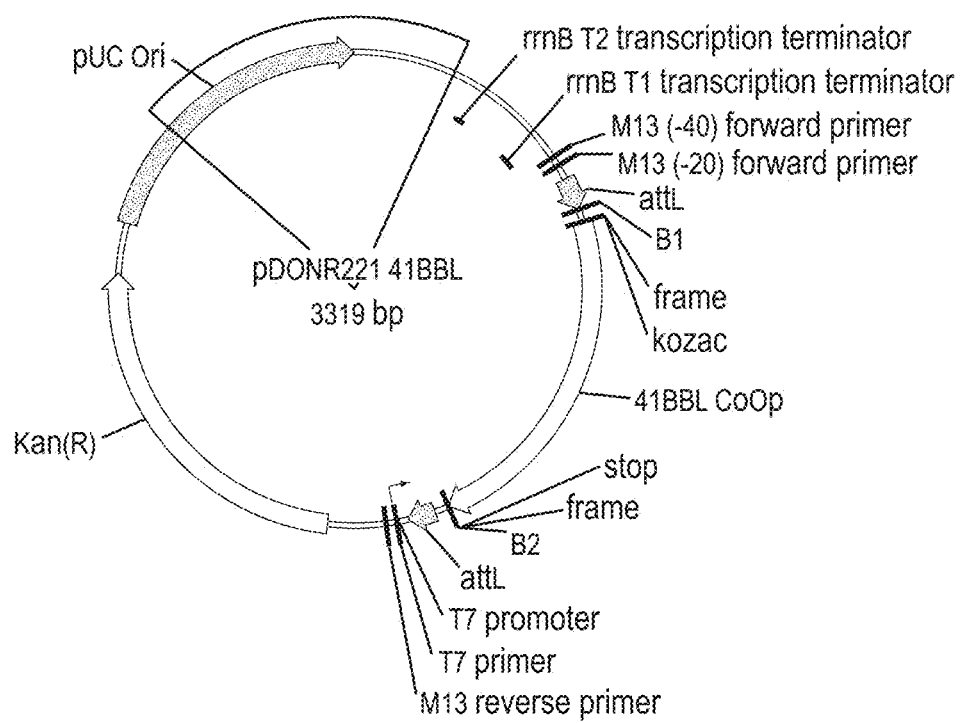
FIG. 7 illustrates a vector diagram of the pDONR221 human 4-1BBL donor vector.
Figure 8:
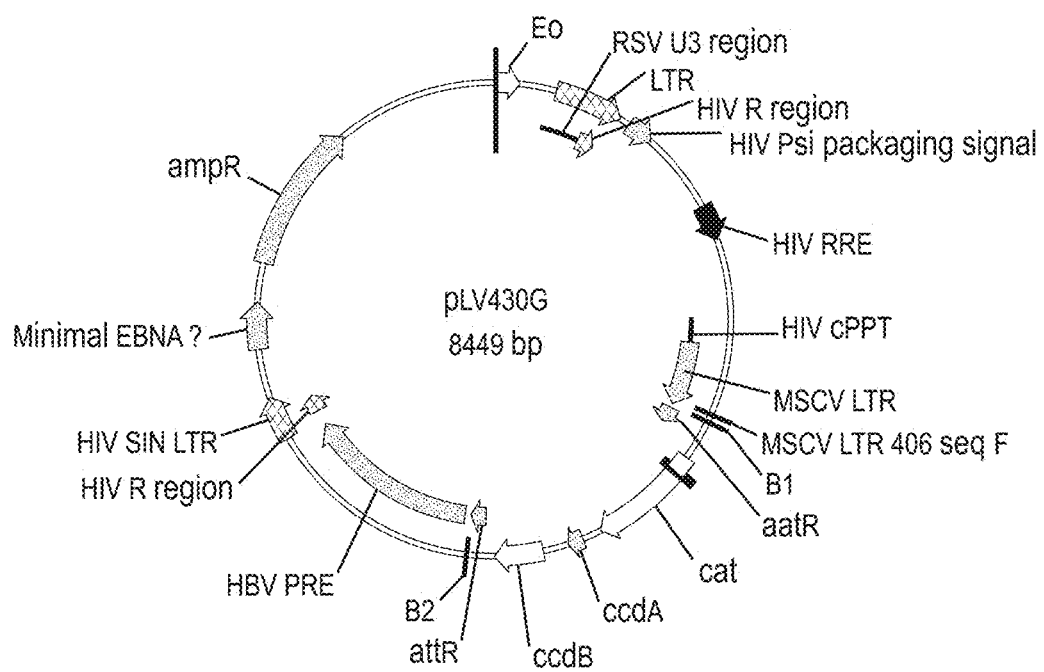
FIG. 8 illustrates a vector diagram of the pLV430G empty vector.
Figure 9:
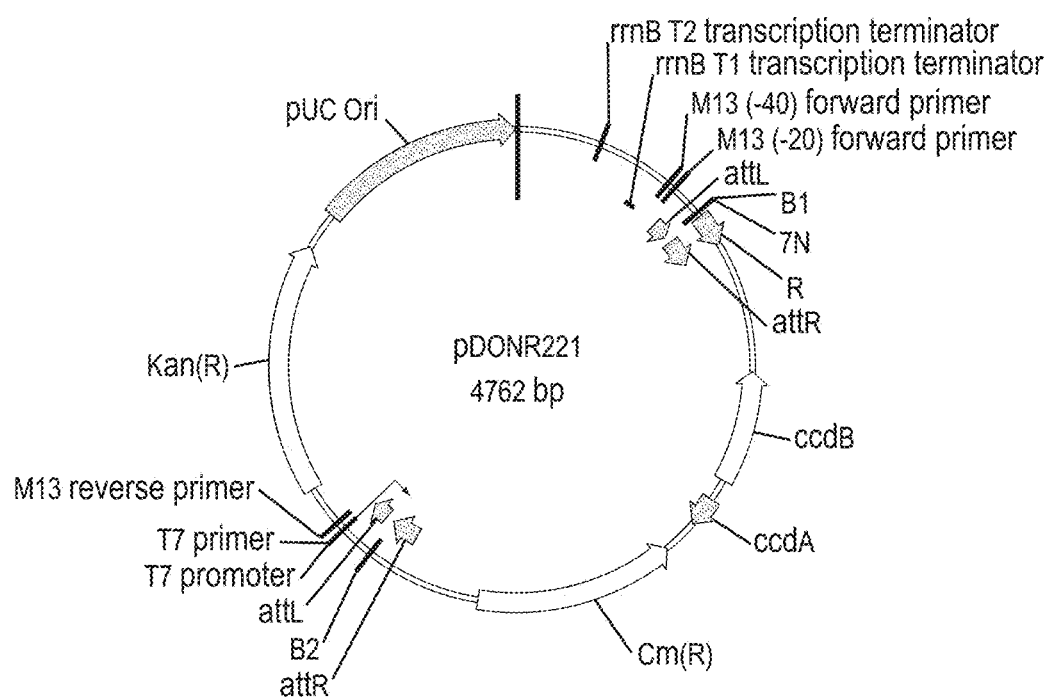
FIG. 9 illustrates a vector diagram of the pDONR221 empty vector.
Figure 10:
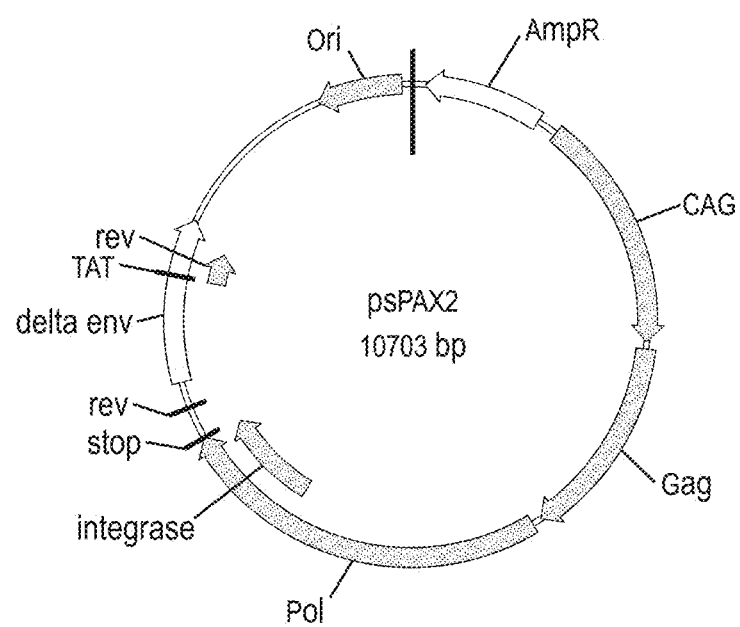
FIG. 10 illustrates a vector diagram of the psPAX2 helper plasmid for lentivirus production.
Figure 11:
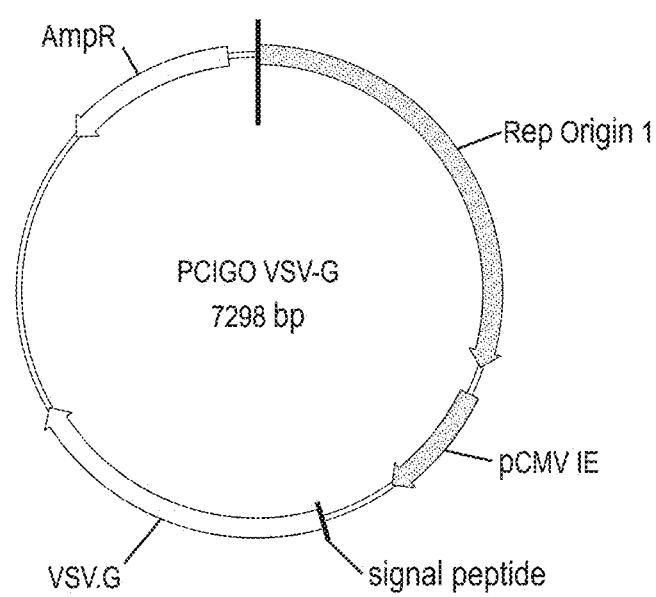
FIG. 11 illustrates a vector diagram of the pCIGO-VSV.G helper plasmid for lentivirus production.

The vectors and portions thereof used for cloning are depicted in FIG. 2 to FIG. 11, and the nucleotide sequences for each vector are given in Table 6. The pLV430G human 4-1BBL vector is illustrated in FIG. 2, with the polymerase chain reaction product (PCRP) portion shown in FIG. 3. The pLV430G human CD86 vector is illustrated in FIG. 4, with the PCRP portion shown in FIG. 5. The pDONR221 human CD86 donor and human 4-1BBL donor vectors are shown in FIG. 6 and FIG. 7, respectively. Diagrams of the empty pLV430G destination vector and empty pDONR221 donor vector for the Gateway cloning method are shown in FIG. 8 and FIG. 9, respectively. FIG. 10 and FIG. 11 illustrate vector diagrams of the psPAX2 and pCIGO-VSV.G helper plasmids used for lentivirus production.

TABLE 5

Summary of costimulatory molecules expressed endogenously on candidate cell lines for aAPCs. CML refers to chronic myeloid leukemia, and AML refers to acute myeloid leukemia. "Pop" refers to the population of cells observed to express the marker (½ pop = 50%).

| Origin | Cell line | | | | | |
|---|---|---|---|---|---|---|
| | EM-2 Myeloid blast crisis, CML | EM-3 Myeloid blast crisis, CML | KG1-246 AML | KG1-8031 AML | K562 myeloid erythro-leukemia, CML | MOLM-14 AML |
| HLA-A/B/C | + | + | + | + | − | + |
| CD64 | − | − | − | − | − | + |
| CD80 | − | − | − | − | − | + |
| ICOS-L | − | + | − | − | − | + |
| 4-1BBL | − | − | − | − | − | − |
| PD-L1 | − | − | − | − | − | − |
| CD58 | + | + | + | + | + | + |
| CD86 | − | − | − | − | − | + (½ pop) |

TABLE 6

Nucleotide sequences for preparation of
lentivirus for transduction of aAPCs.

| Identifier (Description) | Sequence | |
|---|---|---|
| SEQ ID NO: 15 (pLV430G human 4-1BBL vector) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga agcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg gggagaatt agatcgcgat gggaaaaaat | 960 |
| | tcggttaagg ccagggggaa agaaaaaata taattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca aagaagaag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggat ttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac agagacagat | 2100 |
| | ccattcgatt agtgaacgga tctcgacggt atcggtttta aagaaaaagg gggattggg | 2160 |
| | gggtacagtg caggggaaag aatagtagac ataatagcaa cagacataca aactaaagaa | 2220 |
| | ttacaaaaac aaattacaaa aattcaaaat tttatcgatt ttatttagtc tccagaaaaa | 2280 |
| | ggggggaatg aaagacccca cctgtaggtt tggcaagcta gcttaagtaa cgccattttg | 2340 |
| | caaggcatgg aaaatacata actgagaata aggaagtca gatcaaggtt aggaacagga | 2400 |
| | agacaggaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga atgacccctg tccttatttt gaactaacca | 2580 |
| | atcagttcgc ttctcgcttc tgttcgcgcg cttctgctcc ccgagctcaa taaaagagcc | 2640 |
| | cacaacccct cactcggcgc gccagtcctc cgatagactg cgtcgcccgg gtaccgatat | 2700 |
| | caacaagttt gtacaaaaaa gcaggcttcg ccaccatgga atacgcctct gatgccagcc | 2760 |
| | tggaccccga agctccttgg cctcctgccc ctagagccag agcctgtaga gtgctgcctt | 2820 |
| | gggctctggt ggctggcctt ctccttctgc tgctgctggc cgctgcctgc gctgtgtttc | 2880 |
| | tggcttgtcc ttgggcgtg tcaggcgcca gagcttctct tggatctgcc gccagcccca | 2940 |
| | gactgagaga gggacctgag ctgagccccg atgatcctgc cggactgctg gatctgagac | 3000 |
| | agggcatgtt cgcccagctg gtgccccaga acgtgctgct gatcgatggc cccctgagct | 3060 |
| | ggtacagcga tcctggactg gctggcgtgt cactgacagg cggcctgagc tacaaagagg | 3120 |
| | acaccaaaga actggtggtg gccaaggccg gcgtgtacta cgtgttcttt cagctggaac | 3180 |
| | tgcggagagt ggtggccggc gaaggatccg gctctgtgtc tctggcactg catctgcagc | 3240 |
| | ccctgagatc tgctgcaggc gctgctgcac tggccctgac agtggacctg cctccagcct | 3300 |
| | ctagcgaggc cagaaactcc gcattcgggt tcaaggcag actgctgcac ctgtctgccg | 3360 |
| | gccagagact gggagtgcat ctgcacacag aggccagcac cagacgcctg tggcagctga | 3420 |
| | cagggcgc tacagtgctg gcctgttca gagtgaccc cgaaattcca gccggcctgc | 3480 |
| | ccagccctag aagcgagtag gacccagctt tcttgtacaa agtggtgatt cgagttaatt | 3540 |
| | aagctagcct agtgccattt gttcagtggt tcgtagggct ttccccact gtttggcttt | 3600 |
| | cagttatatg gatgatgtgg tattggggc caagtctgta cagcatcttg agtcccttt | 3660 |
| | taccgctgtt accaatttc ttttgtcttt gggtatacat ttaaacccta acaaacaaaa | 3720 |
| | gagatggggt tactctctaa attttatggg ttatgtcatt ggatgttatg ggtccttgcc | 3780 |
| | acaagaacac atcatacaaa aaatcaaaga atgtttaga aaacttccta ttaacaggcc | 3840 |
| | tattgattgg aaagtatgtc aacgaattgt gggttttctg gttttttgctg cccctttttac | 3900 |
| | acaatgtggt tatcctgcgt tgatgccttt gtatgtcatgt attcaatcta agcaggcttt | 3960 |
| | cactttctcg ccaacttaca aggcctttct gtgtaaacaa tacctgaacc tttaccccgt | 4020 |
| | tgcccggcaa cggccaggtc tgtgccaagt gtttgctgac gcaacccca ctggctgggg | 4080 |
| | cttggtcatg ggccatcagc gcatggtgtg aatcctttgc gctcctctgc atccatac | 4140 |
| | tgcggaactc ctagccgctt gttttgctcg cagcaggtct ggagcaaaca ttatcggaac | 4200 |
| | tgataactct gttgtcctat cccgcaaata tacatgtttt ccatgctgc taggctgtgc | 4260 |
| | tgccaactgg atcctgcgcg gacgtccttt gtttacgtc ccgtcggcgc tgaatcctgc | 4320 |
| | ggacgaccct tctcgggtc gcttgggact ctcgtcccc cttctccgtc tgccgttccg | 4380 |
| | accgaccacg gggcgcacct ctctttacgc ggactcccg tctgtgcctt ctcatctgcc | 4440 |

TABLE 6-continued

Nucleotide sequences for preparation of
lentivirus for transduction of aAPCs.

| Identifier (Description) | Sequence | |
|---|---|---|
| | ggaccgtgtg cacttcgctt cacctctgca cgtcgcatgg agaccaccgt gaacgcccac | 4500 |
| | caaatattgc ccaaggtctt acataagagg actcttggac tctcagcaat gtcaacgacc | 4560 |
| | gaccttgagg catacttcaa agactgtttg tttaaagact gggaggagtt gggggaggag | 4620 |
| | attaggttaa aggtctttgt actaggaggc tgtaggcata aattggtctg cgcaccagca | 4680 |
| | ccatggcgca atcactagag cggggtacct ttaagaccaa tgacttacaa ggcagctgta | 4740 |
| | gatcttagcc acttttttaaa agaaaagggg ggactggaag ggctaattca ctcccaacga | 4800 |
| | agacaagatc tgcttttttgc ttgtactggg tctctctggt tagaccagat ctgagcctgg | 4860 |
| | gagctctctg gctaactagg gaacccactg cttaagcctc aataaagctt gccttgagtg | 4920 |
| | cttcaagtag tgtgtgcccg tctgttgtgt gactctggta actagagatc cctcagaccc | 4980 |
| | ttttagtcag tgtggaaaat ctctagcagt agtagttcat gtcatcttat tattcagtat | 5040 |
| | ttataacttg caaagaaatg aatatcagag agtgagagga acttgtttat tgcagcttat | 5100 |
| | aatggttaca aataaagcaa tagcatcaca aatttcacaa ataaagcatt tttttcactg | 5160 |
| | cattctagtt gtggtttgtc caaactcatc aatgtatctt atcatgtctg gctctagcta | 5220 |
| | tcccgcccct aactccgccc atcccgcccc taactccgcc cagttccgcc cattctccgc | 5280 |
| | cccatggctg actaattttt tttatttatg cagaggccga ggccggatcc cttgagtggc | 5340 |
| | tttcatcctg gagcagactt tgcagtctgt ggactgcaac acaacattgc cttatatgtgt | 5400 |
| | aactcttggc tgaagctctt acaccaatgc tgggggacat gtacctccca ggggcccagg | 5460 |
| | aagactacgg gaggctacac caacgtcaat cagaggggcc tgtgtagcta ccgataagcg | 5520 |
| | gaccctcaag agggcattag caatagtgtt tataaggccc ccttgttaat tcttgaagac | 5580 |
| | gaaagggcct cgtgatacgc ctatttttat aggttaatgt catgataata atggtttctt | 5640 |
| | agacgtcagg tggcactttt cggggaaatg tgcgcggaac ccctatttgt ttattttttct | 5700 |
| | aaatacattc aaatatgtat ccgctcatga cagtaacc ctgataaatg cttcaataat | 5760 |
| | attgaaaaag gaagagtatg agtattcaac atttccgtgt cgcccttatt ccctttttttg | 5820 |
| | cggcattttg ccttcctgtt tttgctcacc cagaaacgct ggtgaaagta aaagatgctg | 5880 |
| | aagatcagtt gggtgcacga gtgggttaca tcgaactgga tctcaacagc ggtaagatcc | 5940 |
| | ttgagagttt tcgccccgaa gaacgttttc caatgatgag cacttttaaa gttctgctat | 6000 |
| | gtggcgcggt attatcccgt gttgacgccg ggcaagagca actcggtcgc cgcatacact | 6060 |
| | attctcagaa tgacttggtt gagtactcac cagtcacaga aaagcatctt acggatggca | 6120 |
| | tgacagtaag agaattatgc agtgctgcca taaccatgag tgataacact gcggccaact | 6180 |
| | tacttctgac aacgatcgga ggaccgaagg agctaaccgc ttttttgcac aacatggggg | 6240 |
| | atcatgtaac tcgccttgat cgttgggaac cggagctgaa tgaagccata ccaaacgacg | 6300 |
| | agcgtgacac cacgatgcct gcagcaatgg caacaacgtt gcgcaaacta ttaactggcg | 6360 |
| | aactacttac tctagcttcc cggcaacaat taatagactg gatggaggcg gataaagttg | 6420 |
| | caggaccact tctgcgctcg gcccttccgg ctggctggtt tattgctgat aaatctggag | 6480 |
| | ccggtgagcg tgggtctcgc ggtatcattg cagcactggg gccagatggt aagccctccc | 6540 |
| | gtatcgtagt tatctacacg acggggagtc aggcaactat ggatgaacga aatagacaga | 6600 |
| | tcgctgagat aggtgcctca ctgattaagc attggtaact gtcagaccaa gtttactcat | 6660 |
| | atatacttta gattgattta aaacttcatt tttaatttaa aaggatctag gtgaagatcc | 6720 |
| | tttttgataa tctcatgacc aaaatccctt aacgtgagtt ttcgttccac tgagcgtcag | 6780 |
| | accccgtaga aaagatcaaa ggatcttctt gagatccttt tttctgcgcg taatctgct | 6840 |
| | gcttgcaaac aaaaaaacca ccgctaccag cggtggtttg tttgccggat caagagctac | 6900 |
| | caactctttt tccgaaggta actggcttca gcagagcgca gataccaaat actgtccttc | 6960 |
| | tagtgtagcc gtagttaggc caccacttca agaactctgt agcaccgcct acatacctcg | 7020 |
| | ctctgctaat cctgttacca gtggctgctg ccagtggcga taagtcgtgt cttaccgggt | 7080 |
| | tggactcaag acgatagtta ccggataagg cgcagcggtc gggctgaacg gggggttcgt | 7140 |
| | gcacacagcc cagcttggag cgaacgacct acaccgaact gagataccta cagcgtgagc | 7200 |
| | attgagaaag cgccacgctt cccgaaggga aaagcggca caggtatccg gtaagcggca | 7260 |
| | gggtcggaac aggagagcgc acgagggagc ttccaggggg aaacgcctgg tatctttata | 7320 |
| | gtcctgtcgg gtttcgccac ctctgacttg agcgtcgatt tttgtgatgc tcgtcagggg | 7380 |
| | ggcggagcct atggaaaaac gccagcaacg cggccttttt acggttcctg gccttttgct | 7440 |
| | ggccttttttg aagctgtccc tgatggtcgt catctacctg cctggacagc atggcctgca | 7500 |
| | acgcgggcat cccgatgccg ccgaagcga gaagaatcat aatggggaag gccatccagc | 7560 |
| | ctcgcgtcg | 7569 |
| SEQ ID NO: 16 (4-1BBL CoOP) | atggaatacg cctctgatgc cagcctggac cccgaagctc cttggcctcc tgcccctaga | 60 |
| | gccagagcct gtagagtgct gccttgggct ctggtggctg gccttctcct tctgctgctg | 120 |
| | ctggccgctg cctgcgctga gtttctggct tgtccttgga ccgtgtcagg cgcagagct | 180 |
| | tctcctggat ctgccgccaa cccagactg agagagggac ctgagctgag cccgatgat | 240 |
| | cctgccggac tgctggatct gagacagggc atgttcgccc agctggtggc ccagaacgtg | 300 |
| | ctgctgatcg atggcccct gagctggtac agcgatcctg gactggctgg cgtgtcactg | 360 |
| | acaggcggcc tgagctacaa agaggacacc aaagaactgg tggtggccaa ggccggcgtg | 420 |
| | tactacgtgt tctttcagct ggaactgcgg agagtggtgg ccggcgaagg atccggctct | 480 |
| | gtgtctctgg cactgcatct gcagcccctg agatctgctg caggcgctgc tgcactggcc | 540 |
| | ctgacagtgg acctgcctcc agcctctagc gaggccgaaa ctccgcatt cgggtttcaa | 600 |
| | ggcagctgc tgcacctgtc tgccggcag agactgggag tgcatctgca cacagaggcc | 660 |
| | agagccagac acgcctggca gctgacacag gccgctacag tgctgggcct gttcagagtg | 720 |
| | accccgaaa ttccagccgg cctgcccagc cctagaagcg agtag | 765 |
| SEQ ID NO: 17 (4-1BBL PRCP) | ggggacaagt ttgtacaaaa aagcaggctt cgccaccatg aatacgcct ctgatgcag | 60 |
| | cctggacccc gaagctcctt ggcctcctgc cctagagcc agagcctgta gagtgctgcc | 120 |
| | ttgggctctg gtggctggcc ttctccttct gctgctgctg gccgctgcct gcgctgtgtt | 180 |
| | tctggcttgt ccttgggccg tgtcaggcgc cagagcttct cctggatctg ccgccagccc | 240 |
| | cagactgaga gagggacctg agctgagccc cgatgatcct gccggactgc tggatctgag | 300 |
| | acagggcatg ttcgcccagc tggtggccca gaacgtgctg ctgatcgatg gccccctgag | 360 |

TABLE 6-continued

Nucleotide sequences for preparation of
lentivirus for transduction of aAPCs.

| Identifier (Description) | Sequence | |
|---|---|---|
| | ctggtacagc gatcctggac tggctggcgt gtcactgaca ggcggcctga gctacaaaga | 420 |
| | ggacaccaaa gaactggtgg tggccaaggc cggcgtgtac tacgtgttct ttcagctgga | 480 |
| | actgcggaga gtggtggccg gcgaaggatc cggctctgtg tctctggcac tgcatctgca | 540 |
| | gcccctgaga tctgctgcag gcgctgctgc actggccctg acagtggacc tgcctccagc | 600 |
| | ctctagcgag gccagaaact ccgcattcgg gtttcaaggc agactgctgc acctgtctgc | 660 |
| | cggccagaga ctgggagtgc atctgcacac agaggccaga gccagacacg cctggcagct | 720 |
| | gacacagggc gctacagtgc tgggcctgtt cagagtgacc cccgaaattc cagccggcct | 780 |
| | gcccagccct agaagcgagt aggacccagc tttcttgtac aaagtggtcc cc | 832 |
| SEQ ID NO: 18 (pLV430G human CD86 vector) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagtctaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg gggagaatt agatcgcgat gggaaaaaat | 960 |
| | tcggttaagg ccagggggaa agaaaaaata taattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataagt agtagcaaaa gaaccattag gagtagcacc caccaaggca aagagaagag | 1380 |
| | tggtcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaataggaa gagagagaca agacagat | 2100 |
| | ccattcgatt agtgaacgga tctcgacggt atcggtttta aaagaaaagg ggggattggg | 2160 |
| | gggtacagtg caggggaaag aatagtagac ataatagcaa cagacataca aactaaagaa | 2220 |
| | ttacaaaaac aaattacaaa aattcaaaat tttatcgatt ttatttagtc tccagaaaaa | 2280 |
| | gggggaatg aaagacccca cctgtaggtt tggcaagcta gcttaagtaa cgcatttttg | 2340 |
| | caaggcatgg aaaatacata actgagaata gagaagttca gatcaaggtt aggaacagag | 2400 |
| | agacagcaga atatgggcca acaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga atgacctgt gccttatttt gaactaacca | 2580 |
| | atcagttcgc ttctcgcttc tgttcgcgcg cttctgctcc ccgagctcaa taaaagagcc | 2640 |
| | cacaacccct cactcggcgc gccagtcctc cgatagactg cgtcgcccgg gtaccgatat | 2700 |
| | caacaagttt gtacaaaaaa gcaggcttcg ccaccatggg cctgagcaac atcctgttcg | 2760 |
| | tgatggcctt cctgctgtcc ggagccgccc ctctgaagat ccaggctac ttcaacgaga | 2820 |
| | ccgccgacct gccctgccag ttcgcaaaca gccagaacca gcctgagc gaactggtga | 2880 |
| | tgttctggca ggaccaggaa aacctggtcc tgaacgaggt gtacctgggc aaagaaaagt | 2940 |
| | tcgacagcgt gcacagcaag tacatgggcc ggaccagctt cgacagcgac agctggacc | 3000 |
| | tgcggctgca caacctgcag atcaaggaca agggcctgta ccagtgcatc atccaccaca | 3060 |
| | agaaacccac cggcatgatc agaatccacc agatgaacag cgagctgtcc gtgctggcca | 3120 |
| | acttcagcca gcccgagatc gtgcccatca gcaacatcac cgagaacgtg tacatcaacc | 3180 |
| | tgacctgcag cagcatccac ggctacccg agcccaagaa atgagcgtg ctgctgcgga | 3240 |
| | ccaagaacag caccatcgag tacgacggcg tgatgcagaa agccaggac aacgtgaccg | 3300 |
| | agctgtacga cgtgagcatc agcctgagcg tgagcttccc cgacgtgacc agcaacatga | 3360 |
| | ccatcttttg catcctggaa accgacaaga cccggctgct gtccagcccc ttcagcatcg | 3420 |
| | agctggaaga tccccagccc cctcccgacc acatccctg atcaccgcc gtgctgccca | 3480 |
| | ccgtgatcat ctgcgtgatg gtgttctgcc tgatcctgtg aagtggaag aagaagaagc | 3540 |
| | ggctagggaa cagtcacaag tgcggcacca acggggagaa acggagcagc gagcagcaga | 3600 |
| | ccaagagcgc ggagaagatc cacatccccg agcggagcga cgaggcccag cgggtgttca | 3660 |
| | agagcagcaa gaccagcagc tgcgacaaga gcgacaccctg cttctaggac ccagctttct | 3720 |
| | tgtacaaagt ggtgattcga gttaattaag ctagcctagt gccatttgtt cagtggttcg | 3780 |
| | tagggctttc ccccactgtt tggctttcag ttatatggat gatgtgtat tggggccaa | 3840 |
| | gtctgtacag catcttgagt cccttttttac cgctgttacc aattttcttt tgtctttggg | 3900 |

TABLE 6-continued

Nucleotide sequences for preparation of
lentivirus for transduction of aAPCs.

| Identifier (Description) | Sequence | |
|---|---|---|
| | tatacattta aaccctaaca aaacaaagag atggggttac tctctaaatt ttatgggtta | 3960 |
| | tgtcattgga tgttatgggt cctgccaca agaacacatc atacaaaaaa tcaaagaatg | 4020 |
| | ttttagaaaa cttcctatta acaggcctat tgattggaaa gtatgtcaac gaattgtggg | 4080 |
| | tcttttgggt tttgctgccc cttttacaca atgtggttat cctgcgttga tgcctttgta | 4140 |
| | tgcatgtatt caatcaagc aggctttcac tttctcgcca acttacaagg cctttctgtg | 4200 |
| | taaacaatac ctgaacctt accccgttgc ccggcaacgg ccaggtctgt gccaagtgtt | 4260 |
| | tgctgacgca acccccactg gctggggctt ggtcatgggc catcagcgca tgcgtggaac | 4320 |
| | cttttcggct cctctgccga tccatactgc ggaactccta gccgcttgtt ttgctcgcag | 4380 |
| | caggtctgga gcaaacatta tcgggactga taactctgtt gtcctatccc gcaaatatac | 4440 |
| | atcgtttcca tggctgctag gctgtgctgc caactggatc ctgcgcggga cgtcctttgt | 4500 |
| | ttacgtcccg tcggcgctga atcctgcgga cgacccttct cggggtcgct tgggactctc | 4560 |
| | tcgtcccctt ctccgtctgc cgttccgacc gaccacgggg cgcacctctc tttacgcgga | 4620 |
| | ctcccgtct gtgccttctc atctgccgga ccgtgtgcac ttcgcttcac ctctgcacgt | 4680 |
| | cgcatggaga ccaccgtgaa cgcccaccaa atattgccca aggtcttaca taagaggact | 4740 |
| | cttggactct cagcaatgtc aacgaccgac cttgaggcat acttcaaaga ctgtttgttt | 4800 |
| | aaagactggg aggagttggg ggaggagatt aggttaaagg tctttgtact aggaggctgt | 4860 |
| | aggcataaat tggtctgcgc accagcacca tggcgcaatc actagagcgg ggtacctta | 4920 |
| | agaccaatga cttacaaggc agctgtagat cttagccact ttttaaaaga aaaggggga | 4980 |
| | ctggaagggc taattcactc ccaacgaaga caagatctgc tttttgcttg tactgggtct | 5040 |
| | ctctggttag accagatctg agcctgggag ctctctggct aactagggaa cccactgctt | 5100 |
| | aagcctcaat aaagcttgcc ttgagtgctt caagtagtgt gtgcccgtct gttgtgtgac | 5160 |
| | tctggtaact agagatccct cagacccttt tagtcagtgt ggaaaatctc tagcagtagt | 5220 |
| | agttcatgtc atcttattat tcagtattta taacttgcaa agaaatgaat atcagagagt | 5280 |
| | gagaggaact tgtttattgc agcttataat ggttacaaat aaagcaatag catcacaaat | 5340 |
| | ttcacaaata aagcatttt ttcactgcat tctagttgtg gtttgtccaa actcatcaat | 5400 |
| | gtatcttatc atgtctggct ctagctatcc cgcccctaac tccgcccatc ccgcccctaa | 5460 |
| | ctccgcccag ttccgcccat tctccgcccc atggctgact aatttttttt atttatgcag | 5520 |
| | aggccgaggc cggatccctt gagtggcttt catcctgcag cagactttgc agtctgtgga | 5580 |
| | ctgcaacaca acattgcctt tatgtgtaac tcttggctga agctcttaca ccaatgctgg | 5640 |
| | gggacatgta cctcccaggg gcccaggaag actacgggag gctacaccaa cgtcaatcag | 5700 |
| | aggggcctgt gtagctaccg ataagcggac cctcaagagg gcattagcaa tagtgtttat | 5760 |
| | aaggcccct tgttaattct tgaagacgaa agggcctcgt gatacgccta tttttatagg | 5820 |
| | ttaatgtcat gataataatg gtttcttaga cgtcaggtgg cacttttcgg ggaaatgtgc | 5880 |
| | gcggaacccc tatttgttta tttttctaaa tacattcaaa tatgtatccg ctcatgagac | 5940 |
| | aataaccctg ataaatgctt caataatatt gaaaaggaa gagtatgagt attcaacatt | 6000 |
| | tccgtgtcgc cctttattccc ttttttgcgg catttttgcct tcctgttttt gctcacccag | 6060 |
| | aaacgctggt gaaagtaaaa gatgctgaag atcagttggg tgcacgagtg ggttacatcg | 6120 |
| | aactggatct caacagcggt aagatccttg agagttttcg ccccgaagaa cgttttccaa | 6180 |
| | tgatgagcac ttttaaagtt ctgctatgtg gcgcggtatt atcccgtgtt gacgccgggc | 6240 |
| | aagagcaact cggtcgccgc atacactatt ctcagaatga cttggttgag tactcaccag | 6300 |
| | tcacagaaaa gcatcttacg gatggcatga cagtaagaga attatgcagt gctgccataa | 6360 |
| | ccatgagtga taacactgcg gccaacttac ttctgacaac gatcggagga ccgaaggagc | 6420 |
| | taaccgcttt tttgcacaac atgggggatc atgtaactcg ccttgatcgt tgggaaccgg | 6480 |
| | agctgaatga agccatacca aacgacgagc gtgacaccac gatgcctgca gcaatggaca | 6540 |
| | caacgttgcg caaactatta actggcgaac tacttactct agcttcccgg caacaattaa | 6600 |
| | tagactggat ggaggcggat aaagttgcag gaccacttct gcgctcggcc cttccggctg | 6660 |
| | gctggtttat tgctgataaa tctggagccg gtgagcgtgg gtctcgcggt atcattgcag | 6720 |
| | cactggggcc agatggtaag ccctcccgta tcgtagttat ctacacgacg gggagtcagg | 6780 |
| | caactatgga tgaacgaaat agacagatcg ctgagatagg tgcctcactg attaagcatt | 6840 |
| | ggtaactgtc agaccaagtt tactcatata ctttagat tgatttaaaa cttcattttt | 6900 |
| | aatttaaaag gatctaggtg aagatccttt ttgataatct catgaccaaa atcccttaac | 6960 |
| | gtgagttttc gttccactga gcgtcagacc ccgtagaaaa gatcaaagga tcttcttgag | 7020 |
| | atccttttttt tctgcgcgta atctgctgct tgcaaacaaa aaaaccaccg ctaccagcgg | 7080 |
| | tggtttgttt gccggatcaa gagctaccaa ctcttttttcc gaaggtaact ggcttcagca | 7140 |
| | gagcgcagat accaaatact gtccttctag tgtagccgta gttaggccac cacttcaaga | 7200 |
| | actctgtagc accgcctaca tacctcgctc tgctaatcct gttaccagtg gctgctgcca | 7260 |
| | gtggcgataa gtcgtgtctt accgggttgg actcaagacg atagttaccg gataaggcgc | 7320 |
| | agcggtcggg ctgaacgggg ggttcgtgca cacagcccag cttggagcga acgacctaca | 7380 |
| | ccgaactgag atacctacag cgtgagcatt gagaaagcgc cacgcttccc gaagggagaa | 7440 |
| | aggcggacag gtatccggta agcggcaggg tcggaacagg agagcgcacg agggagcttc | 7500 |
| | caggggaaa cgcctggtat ctttatagtc ctgtcgggtt tcgccacctc tgacttgagc | 7560 |
| | gtcgatttt gtgatgctcg tcaggggggc ggagcctatg gaaaaacgcc agcaacgcgg | 7620 |
| | ccttttttacg gttcctggcc ttttgctggc cttttgaag cgtccctga tggtcgtcat | 7680 |
| | ctacctgcct ggacagcatg gcctgcaacg cgggcatccc gatgccgccg gaagcgagaa | 7740 |
| | gaatcataat ggggaaggcc atccagcctc gcgtcg | 7776 |
| SEQ ID NO: 19 (CD86 CoOP) | atgggcctga gcaacatcct gttcgtgatg gccttcctgc tgtccggagc cgcccctctg | 60 |
| | aagatccagg cctacttcaa cgagaccgcc gacctgccct gccagttcgc caacagccag | 120 |
| | aaccagagcc tgagcgaact ggtggttgttc tggcaggacc aggaaaacct ggtcctgaac | 180 |
| | gaggtgtacc tgggcaaaga aaagttcgac agcgtgcaca gcaagtacat gggccggacc | 240 |
| | agcttcgaca gcgacagctg gaccctgcgg ctgcacaacc tgcagatcaa ggacaagggc | 300 |
| | ctgtaccagt gcatcatcca ccacaagaaa cccaccggca tgatcagaat ccaccagatg | 360 |
| | aacagcgagc tgtccgtgct ggccaacttc agccagcccg agatcgtgcc catcagcaac | 420 |
| | atcaccgaga acgtgtacat caacctgacc tgcagcagca tccacggcta cccccgagccc | 480 |

TABLE 6-continued

Nucleotide sequences for preparation of
lentivirus for transduction of aAPCs.

| Identifier (Description) | Sequence | |
|---|---|---|
| | aagaaaatga gcgtgctgct gcggaccaag aacagcacca tcgagtacga cggcgtgatg | 540 |
| | cagaaaagcc aggacaacgt gaccgagctg tacgacgtga gcatcagcct gagcgtgagc | 600 |
| | ttccccgacg tgaccagcaa catgaccatc ttttgcatcc tggaaaccga caagacccgg | 660 |
| | ctgctgtcca gcccttcag catcgagctg gaagatcccc agccccctcc cgaccacatc | 720 |
| | ccctggatca ccgccgtgct gccccaccgt gatcatctgcg tgatggtgtt ctgcctgatc | 780 |
| | ctgtggaagt ggaagaagaa gaagcggcct aggaacagct acaagtgcgg caccaacacc | 840 |
| | atggaacggg aggaaagcga gcagaccaag aagcgggaga gatccacat ccccgagcgg | 900 |
| | agcgacgagg cccagcgggt gttcaagagc agcaagacca gcagctgcga caagagcgac | 960 |
| | acctgcttc | 969 |
| SEQ ID NO: 20 (CD86 PCRP) | ggggacaagt ttgtacaaaa aagcaggctt cgccaccatg gcctgagca acatcctgtt | 60 |
| | cgtgatggcc ttcctgctgt ccggagccgc ccctctgaag atccaggcct acttcaacga | 120 |
| | gaccgccgac ctgccctgcc agttcgccaa cagccagaac cagagcctga gcgaactggt | 180 |
| | ggtgttctgg caggaccagg aaaacctggt cctgaacgag gtgtacctgg gcaaagaaaa | 240 |
| | gttcgacagc gtgcacagca agtacatggg ccggaccgac ttcgacagcg acagctggac | 300 |
| | cctgcggctg cacaacctgc agatcaagga caagggcctg taccagtgca tcatccacca | 360 |
| | caagaaaccc accggcatga tcagaatcca ccagatgaac agcgagctgt ccgtgctggc | 420 |
| | caacttcagc cagcccgaga tcgtgcccat cagcaacatc accgagaacg tgtacatcaa | 480 |
| | cctgacctgc agcagcatcc acggctaccc cgagcccaag aaaatgagcg tgctgctgcg | 540 |
| | gaccaagaac agcaccatcg agtacgacgg cgtgatgcag aaaagccagg acaacgtgac | 600 |
| | cgagctgtac gacgtgagca tcagcctgag cgtgagcttc cccgacgtga ccagcaacat | 660 |
| | gaccatcttt tgcatcctgg aaaccgacaa gacccggctg ctgtccagcc ccttcagcat | 720 |
| | cgagctggaa gatccccagc cccctcccga ccacatcccc tggatcaccg ccgtgctgcc | 780 |
| | caccgtgatc atctgcgtga tggtgttctg cctgatcctg tggaagtgga agaagaagaa | 840 |
| | gcggcctagg aacagctaca agtgcggcac caacaccatg gaacgggagg aaagcgagca | 900 |
| | gaccaagaag cgggagaaga tccacatccc cgagcggagc gacgaggccc agcgggtgtt | 960 |
| | caagagcagc aagaccagca gctgcgacaa gagcgacacc tgcttctagg acccagcttt | 1020 |
| | cttgtacaaa gtggtcccc | 1039 |
| SEQ ID NO: 21 (pDONR221 CD86 vector) | ctttcctgcg ttatcccctg attctgtgga taaccgtatt accgcctttg agtgagctga | 60 |
| | taccgctcgc cgcagccgaa cgaccgagcg cagcgagtca gtgagcgagg aagcggaaga | 120 |
| | gcgcccaata cgcaaaccgc ctctccccgc gcgttggccg attcattaat gcagctggca | 180 |
| | cgacaggttt cccgactgga agcgggcag tgagcgcaac gcaattaata cgcgtaccgc | 240 |
| | tagccaggaa gagtttgtag aaacgcaaaa aggccatccg tcaggatggc cttctgctta | 300 |
| | gtttgatgcc tggcagttta tggcgggcgt cctgcccgcc accctccggg ccgttgcttc | 360 |
| | acaacgttca aatccgctcc cggcggattt gtcctactca ggagagcgtt caccgacaaa | 420 |
| | caacagataa aacgaaaggc ccagtcttcc gactgagcct ttcgttttat ttgatgcctg | 480 |
| | gcagttcct actctcgcgt taacgctagc atggatgttt cccagtcac gacgttgtaa | 540 |
| | aacgacggcc agtcttaagc tcgggcccca ataatgatt ttattttgac tgatagtgac | 600 |
| | ctgttcgttg caacacattg atgagcaatg cttttttata atgccacaagt ttgtacaaaa | 660 |
| | aagcaggctt cgccaccatg gcctgagca acatcctgtt cgtgatggcc ttcctgctgt | 720 |
| | ccggagccgc ccctctgaag atccaggcct acttcaacga gaccgccgac ctgccctgcc | 780 |
| | agttcgccaa cagccagaac cagagcctga gcgaactggt ggtgttctgg caggaccagg | 840 |
| | aaaacctggt cctgaacgag gtgtacctgg gcaaagaaaa gttcgacagc gtgcacagca | 900 |
| | agtacatggg ccggaccagc ttcgacagcg acagctggac cctgcggctg cacaacctgc | 960 |
| | agatcaagga caagggcctg taccagtgca tcatccacca caagaaaccc accggcatga | 1020 |
| | tcagaatcca ccagatgaac agcgagctgt ccgtgctggc caacttcagc cagcccgaga | 1080 |
| | tcgtgcccat cagcaacatc accgagaacg tgtacatcaa cctgacctgc agcagcatcc | 1140 |
| | acggctaccc cgagcccaag aaaatgagcg tgctgctgcg gaccaagaac agcaccatcg | 1200 |
| | agtacgacgg cgtgatgcag aaaagccagg acaacgtgac cgagctgtac gacgtgagca | 1260 |
| | tcagcctgag cgtgagcttc cccgacgtga ccagcaacat gaccatcttt tgcatcctgg | 1320 |
| | aaaccgacaa gacccggctg ctgtccagcc ccttcagcat cgagctggaa gatccccagc | 1380 |
| | cccctcccga ccacatcccc tggatcaccg ccgtgctgcc caccgtgatc atctgcgtga | 1440 |
| | tggtgttctg cctgatcctg tggaagtgga agaagaagaa gcggcctagg aacagctaca | 1500 |
| | agtgcggcac caacaccatg gaacgggagg aaagcgagca gaccaagaag cgggagaaga | 1560 |
| | tccacatccc cgagcggagc gacgaggccc agcgggtgtt caagagcagc aagaccagca | 1620 |
| | gctgcgacaa gagcgacacc tgcttctagg acccagcttt cttgtacaaa gtggtcatta | 1680 |
| | taagaaagca ttgcttatca atttgttgca acgaacaggt cactatcagt caaaataaaa | 1740 |
| | tcattatttg ccatccagct gatatcccct atagtgagtc gtattacatg gtcatagctg | 1800 |
| | tttcctgca gctctggccc gtgtctcaaa atctctgatg ttacattgca caagataaaa | 1860 |
| | taatatcatc atgaacaata aaactgtctg cttacataaa cagtaataca aggggtgtta | 1920 |
| | tgagccatat tcaacgggaa acgtcgaggc cgcgattaaa ttccaacatg gatgctgatt | 1980 |
| | tatatgggta taaatggct cgcgataatg tcggcaatc aggtgcgaca atctatcgct | 2040 |
| | tgtatgggaa gcccgatgcg ccagagttgt ttctgaaaca tggcaaaggt agcgttgcca | 2100 |
| | atgatgttac agatgagatg gtcagactaa actggctgac ggaatttatg cctcttccga | 2160 |
| | ccatcaagca ttttatccgt actcctgatg atgcatggtt actcaccact gcgatccccg | 2220 |
| | gaaaaacagc attccaggta ttagaagaat atcctgattc aggtgaaaat attgttgatg | 2280 |
| | cgctggcagt gttcctgcgc cggttgcatt cgattcctgt ttgtaattgt cctttaaca | 2340 |
| | gcgatcgcgt atttcgtctc gctcaggcgc aatcacgaat gaataacggt ttggttgatg | 2400 |
| | cgagtgattt tgatgacgag cgtaatggct ggcctgttga acaagtctgg aaagaaatgc | 2460 |
| | ataaactttt gccattctca ccggattcag tcgtcactca tggtgatttc tcacttgata | 2520 |
| | accttatttt tgacgagggg aaattaatag gttgtattga tgttggacga gtcggaatcg | 2580 |
| | cagaccgata ccaggatctt gccatcctat ggaactgcct cggtgagttt tctccttcat | 2640 |
| | tacagaaacg gctttttcaa aaatatggta ttgataatcc tgatatgaat aaattgcagt | 2700 |

TABLE 6-continued

Nucleotide sequences for preparation of
lentivirus for transduction of aAPCs.

| Identifier (Description) | Sequence | |
|---|---|---|
| | ttcatttgat gctcgatgag tttttctaat cagaattggt taattggttg taacactggc | 2760 |
| | agagcattac gctgacttga cgggacggcg caagctcatg accaaaatcc cttaacgtga | 2820 |
| | gttacgcgtc gttccactga gcgtcagacc ccgtagaaaa gatcaaagga tcttcttgag | 2880 |
| | atccttttt tctgcgcgta atctgctgct tgcaaacaaa aaaaccaccg ctaccagcgg | 2940 |
| | tggtttgttt gccggatcaa gagctaccaa ctcttttcc gaaggtaact ggcttcagca | 3000 |
| | gagcgcagat accaaatact gttcttctag tgtagccgta gttaggccac cacttcaaga | 3060 |
| | actctgtagc accgcctaca tacctcgctc tgctaatcct gttaccagtg gctgctgcca | 3120 |
| | gtggcgataa gtcgtgtctt accgggttgg actcaagacg atagttaccg gataaggcgc | 3180 |
| | agcggtcggg ctgaacgggg ggttcgtgca cacagcccag cttggagcga acgacctaca | 3240 |
| | ccgaactgag atacctacag cgtgagctat gagaaagcgc cacgcttccc gaagggagaa | 3300 |
| | aggcggacag gtatccggta agcggcaggg tcggaacagg agagcgcacg agggagcttc | 3360 |
| | cagggggaaa cgcctggtat ctttatagtc ctgtcgggtt tcgccacctc tgacttgagc | 3420 |
| | gtcgattttt gtgatgctcg tcagggggggc ggagcctatg gaaaaacgcc agcaacgcgg | 3480 |
| | ccttttacg gttcctggcc ttttgctggc cttttgctca catgtt | 3526 |
| SEQ ID NO: 22 (pDONR221 4-1BBL vector) | ctttcctgcg ttatcccctg attctgtgga taaccgtatt accgcctttg agtgagctga | 60 |
| | taccgctcgc cgcagccgaa cgaccgagcg cagcgagtca gtgagcgagg aagcggaaga | 120 |
| | gcgcccaata cgcaaaccgc ctctccccgc gcgttggccg attcattaat gcagctggca | 180 |
| | cgacaggttt cccgactgga aagcgggcag tgagcgcaac gcaattaata cgcgtaccgc | 240 |
| | tagccaggaa gagtttgtag aaacgcaaaa aggccatccg tcaggatggc cttctgctta | 300 |
| | gtttgatgcc tggcagttta tggcgggcgt cctgcccgcc accctccggg ccgttgcttc | 360 |
| | acaacgttca aatccgctcc cggcggattt gtcctactca ggagagcgtt caccgacaaa | 420 |
| | caacagataa aacgaaaggc ccagtcttcc gactgagcct ttcgttttat ttgatgcctg | 480 |
| | gcagttccct actctcgcgt taacgctagc atggatgttt tcccagtcac gacgttgtaa | 540 |
| | aacgacggcc agtcttaagc tcgggcccca ataatgatt ttattttgac tgatagtgac | 600 |
| | ctgttcgttg caacacattg atgagcaatg ctttttata atgcacaagt ttgtacaaaa | 660 |
| | aagcaggctt cgccaccatg aatacgcct ctgatgccag cctggacccc gaagctcctt | 720 |
| | ggcctcctgc ccctagagca agagcctgta gagtgctgcc ttgggctctg gtggctggcc | 780 |
| | ttctccttct gctgctgctg gccgctgcct gcgctgtgtt tctggcttgt ccttgggccg | 840 |
| | tgtcaggcgc cagagcttct cctggatctg ccgccagccc cagactgaga gagggacctg | 900 |
| | agctgagccc cgatgatcct gccggactgc tggatctgag acagggcatg ttcgcccagc | 960 |
| | tggtggccca gaacgtgctg ctgatcgatg gccccctgag ctggtacagc gatcctggac | 1020 |
| | tggctggcgt gtcactgaca ggcggcctga gctacaaaga ggacaccaaa gaactggtgg | 1080 |
| | tggccaaggc cggcgtgtac tacgtgttct ttcagctgga actgcggaga gtggtggccg | 1140 |
| | gcgaaggatc cggctctgtg tctctggcac tgcatctgca gcccctgaga tctgctgcag | 1200 |
| | gcgctgctgc actgggcctg acagtggacc tgcctccagc ctctagcgag gccagaaact | 1260 |
| | ccgcattcgg gttccaaggc agactgctgc acctctctgc cggccagaa ctgggagtgc | 1320 |
| | atctgcacac agaggccaga gccagacacg cctggcagct gacacagggc gctacagtgc | 1380 |
| | tgggcctgtt cagagtgacc cccgaaattc cagccggcct gccagcccct agaagcgagt | 1440 |
| | aggacccagc tttcttgtac aaagtggtca ttataagaaa gcattgctta tcaatttgtt | 1500 |
| | gcaacgaaca ggtcactatc agtcaaaata aaatcattat ttgccatcca gctgatatcc | 1560 |
| | cctatagtga gtcgtattac atggtcatag ctgtttcctg gcagctctgg cccgtgtctc | 1620 |
| | aaaatctctg atgttacatt gcacaagata aaataatatc atcatgaaca ataaaactgt | 1680 |
| | ctgcttacat aaacagtaat acaaggggtg ttatgagcca tattcaacgg gaaacgtcga | 1740 |
| | ggccgcgatt aaattccaac atggatgctg atttatatgg gtataaatgg ctcgcgata | 1800 |
| | atgtcgggca atcaggtgcg acaatctatc gcttgtatgg gaagcccgat gcgccagagt | 1860 |
| | tgtttctgaa acatggcaaa ggtagcgttg ccaatgatgt tacagatgag atggtcagac | 1920 |
| | taaactggct gacggaattt atgcctcttc cgaccatcaa gcatttatc cgtactcctg | 1980 |
| | atgatgcatg gttactcacc actgcgatcc ccggaaaaac agcattccag gtattagaag | 2040 |
| | aatatcctga ttcaggtgaa aatattgttg atgcgctggc agtgttcctg cgccggttgc | 2100 |
| | attcgattcc tgtttgtaat tgtcctttta acagcgatcg cgtatttcgt ctcgctcagg | 2160 |
| | cgcaatcacg aatgaataac ggtttggttg atgcgagtga ttttgatgac gagcgtaatg | 2220 |
| | gctggcctgt tgaacaagtc tggaaagaaa tgcataaact tttgccattc tcaccggatt | 2280 |
| | cagtcgtcac tcatggtgat ttctcacttg ataaccttat ttttgacgag gggaaattaa | 2340 |
| | taggttgtat tgatgttgga cgagtcggaa tcgcagaccg ataccaggat cttgccatcc | 2400 |
| | tatggaactg cctcggtgag ttttctcctt cattacagaa acggcttttt caaaaatatg | 2460 |
| | gtattgataa tcctgatatg aataaattgc agtttcattt gatgctcgat gagttttttct | 2520 |
| | aatcagaatt ggttaattgg ttgtaacact ggcagagcat tacgctgact tgagggggagg | 2580 |
| | gcgcaagctc atgaccaaaa tcccttaacg tgagttacgc gtcgttccac tgagcgtcag | 2640 |
| | accccgtaga aaagatcaaa ggatcttctt gagatccttt ttttctgcgc gtaatctgct | 2700 |
| | gcttgcaaac aaaaaaacca ccgctaccag cggtggtttg tttgccggat caagagctac | 2760 |
| | caactctttt tccgaaggta actggcttca gcagagcgca gataccaaat actgttcttc | 2820 |
| | tagtgtagcc gtagttaggc caccacttca agaactctgt agcaccgcct acatacctcg | 2880 |
| | ctctgctaat cctgttacca gtggctgctg ccagtggcga taagtcgtgt cttaccgggt | 2940 |
| | tggactcaag acgatagtta ccggataagg cgcagcggtc gggctgaacg gggggttcgt | 3000 |
| | gcacacagcc cagcttggag cgaacgacct acaccgaact gagatacctta cagcgtgagc | 3060 |
| | tatgagaaag cgccacgctt cccgaaggga gaaaggcgga caggtatccg gtaagcggca | 3120 |
| | gggtcggaac aggagagcgc acgagggagc ttccagggg aaacgcctgg tatctttata | 3180 |
| | gtcctgtcgg gtttcgccac ctctgacttg agcgtcgatt tttgtgatgc tcgtcagggg | 3240 |
| | gcggagcct atggaaaaac gccagcaacg cggccttttt acgttcctgg ccttttgct | 3300 |
| | ggccttttgc tcacatgtt | 3319 |

TABLE 6-continued

Nucleotide sequences for preparation of
lentivirus for transduction of aAPCs.

| Identifier (Description) | Sequence | |
|---|---|---|
| SEQ ID NO: 23 (pLV430G vector) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga agcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg gggagaatt agatcgcgat gggaaaaaat | 960 |
| | tcggttaagg ccaggggaa agaaaaaata taattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcaac caccaaggca aagaagaagag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggg tttctggaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggttaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac agagacagat | 2100 |
| | ccattcgatt agtgaacgga tctcgacggt atcggtttta aagaaaaagg gggattggg | 2160 |
| | gggtacagtg caggggaaag aatagtagac ataatagcaa cagacataca aactaaagaa | 2220 |
| | ttacaaaaac aaattacaaa aattcaaaat tttatcgatt ttatttagtc tccagaaaaa | 2280 |
| | ggggggaatg aaagacccca cctgtaggtt tggcaagcta gcttaagtaa cgccattttg | 2340 |
| | caaggcatgg aaaatacata actgagaata ggaaagttca gatcaaggtt aggaacagag | 2400 |
| | agacaggaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga atgaccctg tgccttattt gaactaacca | 2580 |
| | atcagttcgc ttctcgcttc tgttcgcgcg cttctgctcc ccgagctcaa taaaagagcc | 2640 |
| | cacaacccct cactcggcgc gccagtcctc cgatagactg cgtcgcccgg gtaccgtatat | 2700 |
| | cacaagtttg tacaaaaaag ctgaacgaga acgtaaaat gatataaata tcaatatatt | 2760 |
| | aaattagatt ttgcataaaa aacagactac ataatactgt aaaacacaac atatccagtc | 2820 |
| | actatggcgg ccgcattagg caccccaggc tttacacttt atgcttccgg ctcgtataat | 2880 |
| | gtgtggattt tgagttagga tccgtcgaga ttttcaggag ctaaggaagc taaaatggag | 2940 |
| | aaaaaaatca ctggatatac caccgttgat atatcccaat ggcatcgtaa agaacatttt | 3000 |
| | gaggcatttc agtcagttgc tcaatgtacc tataaccaga ccgttcagct ggatattacg | 3060 |
| | gcctttttaa agaccgtaaa gaaaaataag cacaagtttt atccggcctt tattcacatt | 3120 |
| | cttgcccgcc tgatgaatgc tcatccggaa ttccgtatgg caatgaaaga cggtgagctg | 3180 |
| | gtgatatggg atagtgttca cccttgttac accgttttcc atgagcaaac tgaaacgttt | 3240 |
| | tcatcgctct ggagtgaata ccacgacgat ttccggcagt ttctacacat atattcgcaa | 3300 |
| | gatgtggcgt gttacggtga aaacctggcc tatttcccta aagggtttat tgagaatatg | 3360 |
| | tttttcgtct cagccaatcc ctgggtgagt ttcaccagtt ttgatttaaa cgtggccaat | 3420 |
| | atggacaact tcttcgcccc cgttttcacc atgggcaaat attatacgca aggcgacaag | 3480 |
| | gtgctgatgc cgctggcgat tcaggttcat catgccgttt gtgatggctt ccatgtcggc | 3540 |
| | agaatgctta atgaattaca acagtactgc gatgagtggc agggcggggc gtaaacgcgt | 3600 |
| | ggatccgcct tactaaaagc cagataacag tatgcgctga tttttgcggt | 3660 |
| | ataagaatat atactgatat gtatacccga agtatgtcaa aaagaggtat gctatgaagc | 3720 |
| | agcgtattac agtgacagtt gacagcgaca gctatcagtt gctcaaggca tatatgatgt | 3780 |
| | caatatctcc ggtctggtaa gcacaaccat gcagaatgaa gcccgtcgtc tgcgtgccga | 3840 |
| | acgctggaaa gcggaaaatc aggaagggat ggctgaggtc gcccggttta ttgaaatgaa | 3900 |
| | cggctctttt gctgacgaga caggggctg tgaaatgca gtttaaggtt tacacctata | 3960 |
| | aaagagagag ccgttatcgt ctgtttgtgg atgtacagag tgatattatt gacacgcccg | 4020 |
| | ggcgacggat ggtgatcccc ctggccagtg cacgtctgct gtcagataaa gtctcccgtg | 4080 |
| | aactttaccc ggtggtgcat gcggggatg aagctggcgc catgatgacc accgatatgg | 4140 |
| | ccagtgtgcc ggtctccgtt atcggggaag aagtggctga tctcagccac cgcgaaaatg | 4200 |
| | acatcaaaaa cgccattaac ctgatgttct gggaatata atgtcaggc tccttatac | 4260 |
| | acagccagtc tgcaggtcga ccatagtgac tggatatgtt gtgttttaca gtattatgta | 4320 |
| | gtctgttttt tatgcaaaat ctaatttaat atattgatat ttatatcatt ttacgtttct | 4380 |
| | cgttcagctt tcttgtacaa agtggtgatt cgagttaatt aagctagcct agtgccattt | 4440 |

TABLE 6-continued

Nucleotide sequences for preparation of
lentivirus for transduction of aAPCs.

| Identifier (Description) | Sequence | |
|---|---|---|
| | gttcagtggt tcgtagggct ttcccccact gtttggcttt cagttatatg gatgatgtgg | 4500 |
| | tattgggggc caagtctgta cagcatcttg agtccctttt taccgctgtt accaatttc | 4560 |
| | ttttgtcttt gggtatacat ttaaaccta acaaaacaaa gagatggggt tactctctaa | 4620 |
| | attttatggg ttatgtcatt ggatgttatg ggtccttgcc acaagaacac atcatacaaa | 4680 |
| | aaatcaaaga atgttttaga aaacttccta ttaacaggcc tattgattgg aaagtatgtc | 4740 |
| | aacgaattgt gggtcttttg ggttttgctg ccccttttac acaatgtggt tatcctgcgt | 4800 |
| | tgatgccttt gtatgcatgt attcaatcta agcaggcttt cactttctcg ccaacttaca | 4860 |
| | aggcctttct gtgtaaacaa tacctgaacc tttaccccgt tgcccggcaa cggccaggtc | 4920 |
| | tgtgccaagt gtttgctgac gcaaccccca ctggctgggg cttggtcatg ggccatcagc | 4980 |
| | gcatgcgtgg aaccttttcg gctcctctgc cgatccatac tgcggaactc ctagccgctt | 5040 |
| | gttttgctcg cagcaggtct ggagcaaaca ttatcgggac tgataactct gttgtcctat | 5100 |
| | cccgcaaata tacatcgttt ccatggctgc taggctgtgc tgccaactgg atcctgcgcg | 5160 |
| | ggacgtcctt tgtttacgtc ccgtcggcgc tgaatcctgc ggacgaccct tctcggggtc | 5220 |
| | gcttgggact ctctcgtccc cttctccgtc tgccgttccg accgaccacg gggcgcacct | 5280 |
| | ctctttacgc ggactcccg tctgtgcctt tcatctgcc ggaccgtgtg cacttcgctt | 5340 |
| | cacctctgca cgtcgcatgg agaccaccgt gaacgccac caaatattgc ccaaggtctt | 5400 |
| | acataagagg actcttggac tctcagcaat gtcaacgacc gaccttgagg catacttcaa | 5460 |
| | agactgtttg tttaaagact gggaggagtt gggggaggag attaggttaa aggtctttgt | 5520 |
| | actaggaggc tgtaggcata aattggtctg cgcaccagga ccatgcgca atcactagag | 5580 |
| | cggggtacct ttaagaccaa tgacttacaa ggcagctgta gatcttagcc actttttaaa | 5640 |
| | agaaaagggg ggactggaag ggctaattca ctcccaacga agacaagatc tgcttttgc | 5700 |
| | ttgtactggg tctctctggt tagaccagat ctgagcctgg gagctctctg gctaactagg | 5760 |
| | gaacccactg cttaagcctc aataaagctt gccttgagtg cttcaagtag tgtgtgcccg | 5820 |
| | tctgttgtgt gactctggta actagagatc cctcagaccc ttttagtcag tgtggaaaat | 5880 |
| | ctctagcagt agtagttcat gtcatcttat tattcagtat ttataacttg caaagaaatg | 5940 |
| | aatatcagag agtgagagga acttgtttat tgcagcttat aatggttaca aataaagcaa | 6000 |
| | tagcatcaca aatttcacaa ataaagcatt ttttcactg cattctagtt gtggtttgtc | 6060 |
| | caaactcatc aatgtatctt atcatgtctg gctctagcta tcccgcccct aactccgccc | 6120 |
| | atcccgcccc taactccgcc cagttccgcc cattctccgc cccatggctg actaatttt | 6180 |
| | tttatttatg cagaggccga ggccggatcc cttgagtggc tttcatcctg gagcagactt | 6240 |
| | tgcagtctgt ggactgcaac acaacattgc ctttatgtgt aactcttggc tgaagctctt | 6300 |
| | acaccaatgc tgggggacat gtacctccca ggggcccaag aagactacgg gaggctacac | 6360 |
| | caacgtcaat cagagggggc tgtgtagcta ccgataagcg gaccctcaag agggcattag | 6420 |
| | caatagtgtt tataaggccc ccttgttaat tcttgaagac gaaagggcct cgtgatacgc | 6480 |
| | ctatttttat aggttaatgt catgataata atggtttctt agacgtcagg tggcactttt | 6540 |
| | cggggaaatg tgcgcggaac ccctatttgt ttatttttct aaatacattc aaatatgtat | 6600 |
| | ccgctcatga gacaataacc ctgataaatg cttcaataat attgaaaaag gaagagtatg | 6660 |
| | agtattcaac atttccgtgt cgcccttatt cccttttttg cggcatttg ccttcctgtt | 6720 |
| | tttgctcacc cagaaacgct ggtgaaagta aaagatgctg aagatcagtt gggtgcacga | 6780 |
| | gtgggttaca tcgaactgga tctcaacagc ggtaagatcc ttgagagttt tcgccccgaa | 6840 |
| | gaacgttttc caatgatgag cacttttaaa gttctgctat gtggcgcggt attatcccgt | 6900 |
| | gttgacgccg ggcaagagca actcggtcgc cgcatacact attctcagaa tgacttggtt | 6960 |
| | gagtactcac cagtcacaga aaagcatctt acggatggca tgacagtaag agaattatgc | 7020 |
| | agtgctgcca taaccatgag tgataacact gcggccaact tacttctgac aacgatcgga | 7080 |
| | ggaccgaagg agctaaccgc ttttttgcac aacatggggg atcatgtaac tcgccttgat | 7140 |
| | cgttgggaac cggagctgaa tgaagccata ccaaacgacg agcgtgacac cacgatgcct | 7200 |
| | gcagcaatgg caacaacgtt gcgcaaacta ttaactggcg aactacttac tctagcttcc | 7260 |
| | cggcaacaat taatagactg gatggaggcg gataaagttg caggaccact tctgcgctcg | 7320 |
| | gcccttccgg ctggctggtt tattgctgat aaatctggag ccggtgagcg tgggtctcgc | 7380 |
| | ggtatcattg cagcactggg gccagatggt aagccctccc gtatcgtagt tatctacacg | 7440 |
| | acggggagtc aggcaactat ggatgaacga aatagacaga tcgctgagat aggtgcctca | 7500 |
| | ctgattaagc attggtaact gtcagaccaa gtttactcat atatacttta gattgattta | 7560 |
| | aaacttcatt tttaatttaa aaggatctag gtgaagatcc tttttgataa tctcatgacc | 7620 |
| | aaaatccctt aacgtgagtt ttcgttccac tgagcgtcag accccgtaga aaagatcaaa | 7680 |
| | ggatcttctt gagatccttt tttctgcgc gtaatctgct gcttgcaaac aaaaaaacca | 7740 |
| | ccgctaccag cggtggtttg tttgccggat caagagctac caactctttt tccgaaggta | 7800 |
| | actggcttca gcagagcgca gataccaaat actgtccttc tagtgtagcc gtagttaggc | 7860 |
| | caccacttca agaactctgt agcaccgcct acatacctcg ctctgctaat cctgttacca | 7920 |
| | gtggctgctg ccagtggcga taagtcgtgt cttaccgggt tggactcaag acgatagtta | 7980 |
| | ccggataagg cgcagcggtc gggctgaacg gggggttcgt gcacacagcc cagcttggag | 8040 |
| | cgaacgacct acaccgaact gagatacccta cagcgtgagc attgagaaag cgccacgctt | 8100 |
| | cccgaaggga gaaaggcgga caggtatccg gtaagcggca gggtcggaac aggagagcgc | 8160 |
| | acgagggagc ttccaggggg aaacgcctgg tatctttata gtcctgtcgg gtttcgccac | 8220 |
| | ctctgacttg agcgtcgatt tttgtgatgc tcgtcagggg gcggagcct atgaaaaac | 8280 |
| | gccagcaacg cggcctttt acggttcctg gccttttg gcctttttg aagctgtccc | 8340 |
| | tgatggtcgt catctacctg cctggacagc atggcctgca acgcgggcat ccgatgccg | 8400 |
| | ccggaagcga gaagaatcat aatggggaag gccatccagc ctcgcgtcg | 8449 |
| SEQ ID NO: 24 (pDONR221 vector) | cttttcctgcg ttatccctg attctgtgga taaccgtatt accgcctttg agtgagctga | 60 |
| | taccgctcgc cgcagccgaa cgaccgagcg cagcgagtca gtgagcgagg aagcggaaga | 120 |
| | gcgcccaata cgcaaaccgc ctctccccgc gcgttggccg attcattaat gcagctggca | 180 |
| | cgacaggttt cccgactgga aagcgggcag tgagcgcaac gcaattaata cgcgtaccgc | 240 |
| | tagccaggaa gagtttgtag aaacgcaaaa aggccatccg tcaggatggc cttctgctta | 300 |
| | gtttgatgcc tggcagttta tggcgggcgt cctgcccgcc accctccggg ccgttgcttc | 360 |

TABLE 6-continued

Nucleotide sequences for preparation of
lentivirus for transduction of aAPCs.

| Identifier (Description) | Sequence | |
|---|---|---|
| | acaacgttca aatccgctcc cggcggattt gtcctactca ggagagcgtt caccgacaaa | 420 |
| | caacagataa aacgaaaggc ccagtcttcc gactgagcct ttcgtttat ttgatgcctg | 480 |
| | gcagttccct actctcgcgt taacgctagc atggatgttt tcccagtcac gacgttgtaa | 540 |
| | aacgacggcc agtcttaagc tcgggcccca aataatgatt ttattttgac tgatagtgac | 600 |
| | ctgttcgttg caacacattg atgagcaatg cttttttata atgccaactt tgtacaaaaa | 660 |
| | agctgaacga gaaacgtaaa atgatataaa tatcaatata ttaaattaga ttttgcataa | 720 |
| | aaaacagact acataatact gtaaaacaca acatatccag tcactatgaa tcaactactt | 780 |
| | agatggtatt agtgacctgt agtcgaccga cagccttcca aatgttcttc gggtgatgct | 840 |
| | gccaacttag tcgaccgaca gccttccaaa tgttcttctc aaacggaatc gtcgtatcca | 900 |
| | gcctactcgc tattgtcctc aatgccgtat taaatcataa aaagaaataa gaaaaagagg | 960 |
| | tgcgagcctc tttttttgtgt gacaaaataa aaacatctac ctattcatat acgctagtgt | 1020 |
| | catagtcctg aaaatcatct gcatcaagaa caatttcaca actcttatac tttctctta | 1080 |
| | caagtcgttc ggcttcatct ggattttcag cctctatact tactaaacgt gataaagttt | 1140 |
| | ctgtaatttc tactgtatcg acctgcagac tggctgtgta taagggagcc tgacatttat | 1200 |
| | attcccaga acatcaggtt aatggcgttt ttgatgtcat tttcgcggtg gctgagatca | 1260 |
| | gccacttctt ccccgataac ggagaccggc acactggcca tatcggtggt catcatgcgc | 1320 |
| | cagctttcat ccccgatatg caccaccggg taaagttcac gggagacttt atctgacagc | 1380 |
| | agacgtgcac tggccagggg gatcaccatc cgtcgcccgg gcgtgtcaat aatatcactc | 1440 |
| | tgtacatcca caaacagacg ataacggctc tctcttttat aggtgtaaac cttaaactgc | 1500 |
| | atttcaccag cccctgttct cgtcagcaaa agagccgttc atttcaataa accgggcgac | 1560 |
| | ctcagccatc ccttcctgat tttccgcttt ccagcgttcg gcacgcagac gacgggcttc | 1620 |
| | attctgcatg gttgtgctta ccagaccgga gatattgaca tcatatatgc cttgagcaac | 1680 |
| | tgatagctgt cgctgtcaac tgtcactgta atacgctgct tcatagcata cctcttttg | 1740 |
| | acatacttcg ggtatacata tcagtatata ttccttatacc gcaaaaatca gcgcgcaaat | 1800 |
| | acgcatactg ttatctggct tttagtaagc cggatccacg cggcgtttac gccccgccct | 1860 |
| | gccactcatc gcagtactgt tgtaattcat taagcattct gccgacatgg aagccatcac | 1920 |
| | agacggcatg atgaacctga atcgccagcg gcatcagcac cttgtcgcct tgcgtataat | 1980 |
| | atttgcccat ggtgaaaacg ggggcgaaga agttgtccat attggccacg tttaaatcaa | 2040 |
| | aactggtgaa actcacccag ggattggctg agacgaaaaa catattctca ataaaccctt | 2100 |
| | tagggaaata ggccaggttt tcaccgtaac acgccacatc ttgcgaatat atgtgtagaa | 2160 |
| | actgccggaa atcgtcgtgg tattcactcc agagcgatga aaacgtttca gtttgctcat | 2220 |
| | ggaaaacggt gtaacaaggg tgaacactat cccatatcac cagctcaccg tctttcattg | 2280 |
| | ccatacggaa ttccggatga gcattcatca ggcgggcaag aatgtgaata aaggccggat | 2340 |
| | aaaacttgtg cttattttt tttacggtct ttaaaaaggc cgtaatatcc agctgaacgg | 2400 |
| | tctggttata ggtacattga gcaactgact gaaatgcctc aaaatgttct ttacgatgcc | 2460 |
| | attgggatat atcaacggtg gtatatccag tgatttttt ctccattta gcttccttag | 2520 |
| | ctcctgaaaa tctcgataac tcaaaaaata cgcccggtag tgatcttatt tcattatggt | 2580 |
| | gaaagttgga acctcttacg tgccgatcaa cgtctcattt tcgccaaaag ttggcccagg | 2640 |
| | gcttcccggt atcaacaggg acaccaggat ttatttattc tgcgaagtga tcttccgtca | 2700 |
| | caggtattta ttcggcgcaa agtgcgtcgg gtgatgctgc caacttagtc gactacaggt | 2760 |
| | cactaatacc atctaagtag ttgattcata gtgactggat atgttgtgtt ttacagtatt | 2820 |
| | atgtagtctg tttttatgc aaaatctaat ttaatatatt gatatttata tcatttttacg | 2880 |
| | tttctcgttc agctttcttg tacaaagttg gcattataag aaagcattgc ttatcaattt | 2940 |
| | gttgcaacga acaggtcact atcagtcaaa ataaaatcat tatttgccat ccagctgata | 3000 |
| | tcccctatag tgagtcgtat tacatggtca tagctgtttc ctggcagctc tggcccgtgt | 3060 |
| | ctcaaaatct ctgatgttac attgcacaag ataaaataat atcatcatga acaataaaac | 3120 |
| | tgtctgctta cataaacagt aatacaaggg gtgttatgag ccatattcaa cgggaaacgt | 3180 |
| | cgaggccgcg attaaattcc aacatggatg ctgatttata tgggtataaa tgggctcgcg | 3240 |
| | ataatgtcgg gcaatcaggt gcgacaatct atcgcttgta tgggaagccc gatgcgccag | 3300 |
| | agttgtttct gaaacatggc aaaggtagcg ttgccaatga tgttacagat gagatggtca | 3360 |
| | gactaaactg gctgacggaa tttatgcctc ttccgaccat caagcatttt atccgtactc | 3420 |
| | ctgatgatgc atggttactc accactgcga tccccggaaa aacagcattc caggtattag | 3480 |
| | aagaatatcc tgattcaggt gaaaatattg ttgatgctg ggcagtgttc ctgcgccggt | 3540 |
| | tgcattcgat tcctgtttgt aattgtcctt ttaacagcga tcgcgtattt cgtctcgctc | 3600 |
| | aggcgcaatc acgaatgaat aacggtttgg ttgatgcgag tgattttgat gacgagcgta | 3660 |
| | atggctggcc tgttaacaa gtctggaaag aaatgcataa acttttgcca ttctcaccgg | 3720 |
| | attcagtcgt cactcatggt gatttctcac ttgataacct tattttgac gaggggaaat | 3780 |
| | taataggttg tattgatgtt ggacgagtcg gaatcgcaga ccgataccag gatcttgcca | 3840 |
| | tcctatgaa ctgcctcggt gagttttctc cttcattaca gaaacggctt tttcaaaaat | 3900 |
| | atggtattga taatcctgat atgaataaat tgcagtttca tttgatgctc gatgagtttt | 3960 |
| | tctaatcaga attggttaat tggttgtaac actggcagag cattacgctg acttgacggg | 4020 |
| | acggcgcaag ctcatgacca aaatccctta acgtgagtta cgcgtcgttc cactgagcgt | 4080 |
| | cagacccgt agaaaagatc aaaggatctt cttgagatcc tttttttctg cgcgtaatct | 4140 |
| | gctgcttgca aacaaaaaaa ccaccgctac cagcggtggt ttgtttgccg gatcaagagc | 4200 |
| | taccaactct ttttccgaag gtaactggct tcagcagagc gcagatacca aatactgttc | 4260 |
| | ttctagtgta gccgtagtta ggccaccact tcaagaactc tgtagcaccg cctacatacc | 4320 |
| | tcgctctgct aatcctgtta ccagtggctg ctgccagtgg cgataagtcg tgtcttaccg | 4380 |
| | ggttggactc aagacgatag ttaccggata aggcgcagcg gtcgggctga acgggggtt | 4440 |
| | cgtgcacaca gcccagcttg gagcgaacga cctacaccga actgagatac ctacagcgtg | 4500 |
| | agctatgaga aagcgccacg cttcccgaag ggagaaaggc ggacaggtat ccggtaagcg | 4560 |
| | gcagggtcgg aacaggagag cgcacgaggg agcttccagg gggaaacgcc tggtatcttt | 4620 |
| | atagtcctgt cgggtttcgc cacctctgac ttgagcgtcg atttttgtga tgctcgtcag | 4680 |
| | gggggcggag cctatgaaa aacgccagca acgcggcctt ttacggttc ctggccttt | 4740 |
| | gctggccttt tgctcacatg t | 4761 |

TABLE 6-continued

Nucleotide sequences for preparation of
lentivirus for transduction of aAPCs.

| Identifier (Description) | Sequence | |
|---|---|---|
| SEQ ID NO: 25 (psPAX2 plasmid) | aaaaggatct tcacctagat cctttaaat taaaaatgaa gttttaaatc aatctaaagt | 60 |
| | atatatgagt aaacttggtc tgacagttac caatgcttaa tcagtgaggc acctatctca | 120 |
| | gcgatctgtc tatttcgttc atccatagtt gcctgactcc ccgtcgtgta gataactacg | 180 |
| | atacgggagg gcttaccatc tggccccagt gctgcaatga taccgcgaga cccacgctca | 240 |
| | ccggctccag atttatcagc aataaaccag ccagccggaa gggccgagcg cagaagtggt | 300 |
| | cctgcaactt tatccgcctc catccagtct attaattgtt gccgggaagc tagagtaagt | 360 |
| | agttcgccag ttaatagttt cgcaacgtt gttgccattg ctacaggcat cgtggtgtca | 420 |
| | cgctcgtcgt ttggtatggc ttcattcagc tccggttccc aacgatcaag gcgagttaca | 480 |
| | tgatccccca tgttgtgcaa aaaagcggtt agctccttcg gtcctccgat cgttgtcaga | 540 |
| | agtaagttgg ccgcagtgtt atcactcatg gttatggcag cactgcataa ttctcttact | 600 |
| | gtcatgccat ccgtaagatg ctttctgtg actggtgagt actcaaccaa gtcattctga | 660 |
| | gaatagtgta tgcggcgacc gagttgctct tgcccggcgt caatacggga taataccgcg | 720 |
| | ccacatagca gaactttaaa agtgctcatc attggaaaac gttcttcggg gcgaaaactc | 780 |
| | tcaaggatct taccgctgtt gagatccagt tcgatgtaac ccactcgtgc acccaactga | 840 |
| | tcttcagcat cttttacttt caccagcgtt tctgggtgag caaaaacagg aaggcaaaat | 900 |
| | gccgcaaaaa agggaataag ggcgacacgg aaatgttgaa tactcatact cttccttttt | 960 |
| | caatattatt gaagcattta tcagggttat tgtctcatga gcggatacat atttgaatgt | 1020 |
| | atttagaaaa ataaacaaat aggggttccg cgcacatttc cccgaaaagt gccacctggt | 1080 |
| | cgacattgat tattgactag ttattaatag taatcaatta cggggtcatt agttcatagc | 1140 |
| | ccatatatgg agttccgcgt tacataactt acggtaaatg gcccgcctgg ctgaccgccc | 1200 |
| | aacgaccccc gcccattgac gtcaataatg acgtatgttc ccatagtaac gccaatagggg | 1260 |
| | actttccatt gacgtcaatg ggtggactat ttacggtaaa ctgcccactt ggcagtacat | 1320 |
| | caagtgtatc atatgccaag tacgccccct attgacgtca atgacggtaa atggcccgcc | 1380 |
| | tggcattatg cccagtacat gaccttatgg gactttccta cttggcagta catctacgta | 1440 |
| | ttagtcatcg ctattaccat gggtcgaggt gagccccacg ttctgcttca ctctccccat | 1500 |
| | ctccccccc tccccacccc caattttgta tttatttatt ttttaattat tttgtgcagc | 1560 |
| | gatgggggcg ggggggggcg ggcgcgcg caggcgggcg gggcgggc gaggggcggg | 1620 |
| | gcggggcgag gcggagaggt gcggcggcag ccaatcagag cggcgcgctc cgaaagtttc | 1680 |
| | cttttatggc gaggcggcgg cggcggcggc cctataaaaa gcgaagcgcg cggcgggcgg | 1740 |
| | gagtcgctgc gttgccttcg ccccgtgccc cgctccgcgc cgcctcgcgc cgcccgcccc | 1800 |
| | ggctctgact gaccgcgtta ctcccacagg tgagcgggcg ggacggccct tctcctccgg | 1860 |
| | gctgtaatta gcgcttggtt taatgacggc tcgtttcttt tctgtggctg cgtgaaagcc | 1920 |
| | ttaaagggct ccgggagggc cctttgtgcg ggggggagcg gctcggggg tgcgtgcgtg | 1980 |
| | tgtgtgtgcg tggggagcgc cgcgtgcggc ccgcgctgcc cggcggctgt gagcgctgcg | 2040 |
| | ggcgcggcgc ggggcttttgt gcgctccgcg tgtgcgcgag gggagcgcgg ccggggcgg | 2100 |
| | tgccccgcgc tgcggggggg ctgcgagggg aacaaaggct gcgtgcgggg tgtgtgcgtg | 2160 |
| | gggggggtgag caggggggtgt gggcgcggcg gtcggctgt aaccccccc tgcaccgccc | 2220 |
| | tccccgagtt gctgagcacg gcccggcttc gggtgcgggg ctccgtgcgg ggcgtggcgc | 2280 |
| | gggctcgcc gtgccgggcg ggggttggcg gcaggtgggg gtgccgggcg gggcgggcc | 2340 |
| | gcctcgggcc gggggagggct cggggagggg gcggcggcgg cccggagcgc cggcggctgt | 2400 |
| | cgaggcgcgg cgagccgcag ccattgcctt ttatggtaat cgtgcgagag ggcgcaggga | 2460 |
| | cttcctttgt cccaaatctg cgcgagccga atctgggag gcgccgccgc acccccctcta | 2520 |
| | gcgggcgcgg gcgaagcggt gcggcgcgg caggaaggaa atgggcgggg aggccttcg | 2580 |
| | tgcgtcgccg cgccgccgtc ccccttctcca tctccagcct cggggctgcc gcaggggac | 2640 |
| | ggctgccttc gggggggacg gggcagggcg gggttcggct tctggcgtgt gaccggcggc | 2700 |
| | tctagagcct ctgctaacca tgttcatgcc ttcttctttt cctacagct cctgggcaac | 2760 |
| | gtgctggtta ttgtgctgtc tcatcatttt ggcaaagaat tcgggccggc cgcgttgaca | 2820 |
| | cgcacggcaa gaggcgaggg gcggcgactg gtgagagatg ggtgcgagag cgtcagtatt | 2880 |
| | aagcggggga gaattagatc gatgggaaaa aattcggtta aggccagggg gaaagaaaaa | 2940 |
| | atataaatta aaacatatag tatgggcaag cagggagcta gaacgattcg cagttaatcc | 3000 |
| | tggcctgtta gaaacatcag aaggctgtag acaaatactg ggacagctac aaccatccct | 3060 |
| | tcagacagga tcagaagaac ttagatcatt atataataca gtagcaaccc tctattgtgt | 3120 |
| | gcatcaaagg atagagataa aagacaccaa ggaagcttta gacaagatag aggaagagca | 3180 |
| | aaacaaaagt aagaaaaaag cacagcaagc agcagctgac acaggacaca gcaatcaggt | 3240 |
| | cagccaaaat tacccctatag tgcagaacat ccaggggcaa atggtacatc aggccatatc | 3300 |
| | acctagaact ttaaatgcat gggtaaaagt agtagaagag aaggctttca gcccagaagt | 3360 |
| | gatacccatg ttttcagcat tatcagaagg agccaccca caagatttaa acaccatgct | 3420 |
| | aaacacagtg ggggacatc aagcagccat gcaaatgtta aagagacca tcaatgagga | 3480 |
| | agctgcagaa tgggatagag tgcatccagt gcatgcaggg cctattgcac caggccagat | 3540 |
| | gagagaacca aggggaagtg acatagcagg aactactagt acccttcagg aacaaatagg | 3600 |
| | atggatgaca cataatccac ctatcccagt aggagaaatc tataaaagat ggataatcct | 3660 |
| | gggattaaat aaaatagtaa gaatgtatag ccctaccagc attctggaca taagacaagg | 3720 |
| | accaaaggaa ccctttagag actatgtaga ccggttctat aaaactctaa gagccgagca | 3780 |
| | agcttcacaa gaggtaaaaa attggatgac agcgaaccc ttgtccaaa atgcgaaccc | 3840 |
| | agattgtaag actattttaa aagcattggg accaggagcg acactagaag aaatgatgac | 3900 |
| | agcatgtcag ggagtggggg gacccggcca taagcaaga gttttggctg aagcaatgag | 3960 |
| | ccaagtaaca aatccagcta ccataatgat acagaaaggc aattttagga accaagaaa | 4020 |
| | gactgttaag tgtttcaatt gtggcaaaga agggcacata gccaaaaatt gcagggcccc | 4080 |
| | taggaaaaag ggctgttgga aatgtggaaa ggaaggacac caaatgaaag attgtactga | 4140 |
| | gagacaggct aattttttag ggaagatctg gccttcccac aagggaaggc cagggaattt | 4200 |
| | tcttcagagc agaccagagc caacagcccc accagaagag agcttcaggt ttggggaaga | 4260 |
| | gacaacaact ccctctcaga aggaggagcc gatagacaag gaactgtatc ctttagcttc | 4320 |
| | cctcagatca ctctttggca gcgaccccct cgtcacaataa agatagggg gcaattaaag | 4380 |

TABLE 6-continued

Nucleotide sequences for preparation of lentivirus for transduction of aAPCs.

| Identifier (Description) | Sequence | |
|---|---|---|
| | gaagctctat tagatacagg agcagatgat acagtattag aagaaatgaa tttgccagga | 4440 |
| | agatggaaac caaaaatgat aggggggaatt ggaggtttta tcaaagtagg acagtatgat | 4500 |
| | cagatactca tagaaatctg cggacataaa gctataggta cagtattagt aggacctaca | 4560 |
| | cctgtcaaca taattggaag aaatctgttg actcagattg gctgcactt aaatttccc | 4620 |
| | attagtccta ttgagactgt accagtaaaa ttaaagccag gaatggatgg cccaaaagtt | 4680 |
| | aaacaatggc cattgacaga agaaaaaata aaagcattag tagaaatttg tacagaaatg | 4740 |
| | gaaaaggaag gaaaaatttc aaaaattggg cctgaaaatc catacaatac tccagtattt | 4800 |
| | gccataaaga aaaaagacag tactaaatgg agaaaattag tagatttcag agaacttaat | 4860 |
| | aagagaactc aagatttctg ggaagttcaa ttaggaatac cacatcctgc agggttaaaa | 4920 |
| | cagaaaaaat cagtaacagt actggatgtg ggcgatgcat atttttcagt tcccttagat | 4980 |
| | aaagacttca ggaagtatac tgcatttacc atacctagta taaacaatga gacaccaggg | 5040 |
| | attagatatc agtacaatgt gcttccacag ggatggaaag gatcaccagc aatattccag | 5100 |
| | tgtagcatga caaaaatctt agagcctttt agaaaacaaa atccagacat agtcatctat | 5160 |
| | caatacatgg atgatttgta tgtaggatct gacttagaaa tagggcagca tagaacaaaa | 5220 |
| | atagaggaac tgagacaaca tctgttgagg tggggattta ccacaccaga caaaaaacat | 5280 |
| | cagaaagaac ctccattcct ttggatgggt tatgaactcc atcctgataa atggacagta | 5340 |
| | cagcctatag tgctgccaga aaaggacagc tggactgtca atgacataca gaaattagtg | 5400 |
| | ggaaaattga attgggcaag tcagatttat gcagggatta agtaaggca attatgtaaa | 5460 |
| | cttcttaggg gaaccaaagc actaacagaa gtagtaccac taacagaaga agcagagctn | 5520 |
| | gaactggcag aaaacaggga gattctaaaa gaaccggtac atggagtgta ttatgaccca | 5580 |
| | tcaaaagact taatagcaga aatacagaag caggggcaag gccaatggac atatcaaatt | 5640 |
| | tatcaagagc catttaaaaa tctgaaaaca ggaaaatatg caagaatgag gggtgcccac | 5700 |
| | actaatgatg tgaaacaatt aacagaggca gtacaaaaaa tagccacaga aagcatagta | 5760 |
| | atatggggaa agactcctaa atttaaatta cccatacaaa aggaaacatg ggaagcatgg | 5820 |
| | tggacagagt attggcaagc cacctggatt cctgagtggg agtttgtcaa tacccctccc | 5880 |
| | ttagtgaagt tatggtacca gttagagaaa gaacccataa taggagcaga aactttctat | 5940 |
| | gtagatgggg cagccaatag ggaaactaaa ttaggaaaag caggatatgt aactgacaga | 6000 |
| | ggaagacaaa aagttgtccc cctaacggac acaacaaatc agaagactga gttacaagca | 6060 |
| | attcatctag ctttgcagga ttcgggatta gaagtaaaca tagtacagga ctcacaatat | 6120 |
| | gcattggaa tcattcaagc acaaccagat aagagtgaat cagagttagt cagtcaaata | 6180 |
| | atagagcagt taataaaaaa ggaaaaagtc tacctggcat gggtaccagc acacaaagga | 6240 |
| | attggaggaa atgaacagt agatggggtg gtcagtgctg gaatcaggaa agtactattt | 6300 |
| | ttagatggaa tagataaggc ccaagaagaa catgagaaat atcacagtaa ttggagagca | 6360 |
| | atggctagtg attttaacct accacctgta gtagcaaaag aaatagtagc cagctgtgat | 6420 |
| | aaatgtcagc taaaagggga agccatgcat ggacaagtag actgtagccc aggaatatgg | 6480 |
| | cagctagatt gtacacattt agaaggaaaa gttatcttgg tagcagttca tgtagccagt | 6540 |
| | ggatatatag aagcagaagt tattccagca gagacagggc aagaaacagc atacttcctc | 6600 |
| | ttaaaattag caggaagatg gccagtaaaa acagtacata gacaatggc agcaatttc | 6660 |
| | accagtacta cagttaaggc cgcctgttgg tgggcgggga tcaagcagga atttggcatt | 6720 |
| | ccctacaatc cccaaagtca aggagtaata gaatctatga taaagaatt aaagaaaatt | 6780 |
| | ataggacagg taagagatca ggctgaacat cttaagacag cagtacaaat ggcagtattc | 6840 |
| | atccacaatt ttaaaagaaa agggggggatt ggggggtaca gtgcagggga agaatagta | 6900 |
| | gacataatag caacagacat acaaactaaa gaattacaaa aacaaattac aaaaattcaa | 6960 |
| | aattttcggg tttattacag ggacaggaga gatccagttt ggaaaggacc agcaaagctc | 7020 |
| | ctctggaaag gtgaagggc agtagtaata caagataata gtgacataaa agtagtgcca | 7080 |
| | agaagaaaag caaagatcat cagggattat ggaaaacaga tggcaggtga tgattgtgtg | 7140 |
| | gcaagtagac aggatgagga ttaacacatg gaattctgca acaactgctg tttatccatt | 7200 |
| | tcagaattgg gtgtcgacat agcagaatag gcgttactcg acagaggaga gcaagaaatg | 7260 |
| | gagccagtag atcctagact agagccctgg aagcatccag gaagtcagcc taaaactgct | 7320 |
| | tgtaccaatt gctattgtaa aaagtgttgc tttcattgcc aagtttgttt catgacaaaa | 7380 |
| | gccttaggca tctcctatgg caggaagaag cggagacagc gacgaagagc tcatcagaac | 7440 |
| | agtcagactc atcaagcttc tctatcaaag cagtaagtag tacatgtaat gcaacctata | 7500 |
| | atagtagcaa tagtagcatt agtagtagca ataataatag caatagttgt gtggtccata | 7560 |
| | gtaatcatag aatataggaa aatggccgct gatcttcaga cctggaggag gagatatgag | 7620 |
| | ggacaattgg agaagtgaat tatataaata taagtagta aaaattgaac cattaggagt | 7680 |
| | agcacccacc aaggcaaaga gaagagtggt gcagagaaa aaaagacag tgggaatagg | 7740 |
| | agctttgttc cttgggttct tgggagcagc aggaagcact atgggcgcag cctcaatgac | 7800 |
| | gctgacggta caggccagac aattattgtc tggtatagtg caggaggaga acaatttgct | 7860 |
| | gagggctatt gaggcgcaac agcatctgtt gcaactcaca gtctgggca tcaagcagct | 7920 |
| | ccaagcaaga atcctagctg tggaaagata cctaaaggat caacagctcc tagggatttg | 7980 |
| | gggttgctct ggaaaactca tttgcaccac tgctgtgcct tggaatgcta gttggagtaa | 8040 |
| | taaatctctg gaacagatct ggaatcacac gacctggatg gagtgggaca gagaaattaa | 8100 |
| | caattacaca agcttaatac actccttaat tgaagaatcg caaaaccagc aagaaaagaa | 8160 |
| | tgaacaagaa ttattggaat tagataaatg gcaagtttg tggaattggt ttaacataac | 8220 |
| | aaattggctg tggtatataa aattattcat aatgatagta ggaggcttgg taggtttaag | 8280 |
| | aatagttttt gctgtacttt ctatagtgaa tagagttagg cagggatatt caccattatc | 8340 |
| | gtttcagacc cacctcccaa tcccgagggg acccgacagg cccgaaggaa tagaagaaga | 8400 |
| | aggtggagag agagacagag acagatccat tcgattagtg aacggatcct tggcacttat | 8460 |
| | ctgggacgat ctgcggagcc tgtgcctctt cagctaccgc cgcttgagag acttactctt | 8520 |
| | gattgtaacg aggattgtgg aacttctggg acgcaggggg tgggaagccc tcaaatattg | 8580 |
| | gtggaatctc ctacaatatt ggagtcagga gctaaagaat agtgctgtta gcttgctcaa | 8640 |
| | tgccacagcc atagcagtag ctgaggggac agatagggtt ataagaagtag tacaaggagc | 8700 |
| | ttgtagagct attcgccaca tacctagaag aataagacag ggcttggaaa ggattttgct | 8760 |
| | ataagctcga aacaaccggt acctctagaa ctatagctag cagatcttttt ccctctgcc | 8820 |

TABLE 6-continued

Nucleotide sequences for preparation of
lentivirus for transduction of aAPCs.

| Identifier (Description) | Sequence | |
|---|---|---|
| | aaaaattatg gggacatcat gaagcccctt gagcatctga cttctggcta ataaaggaaa | 8880 |
| | tttattttca ttgcaatagt gtgttggaat tttttgtgtc tctcactcgg aaggacatat | 8940 |
| | gggagggcaa atcatttaaa acatcagaat gagtatttgg tttagagttt ggcaacatat | 9000 |
| | gccatatgct ggctgccatg aacaaaggtg gctataaaga ggtcatcagt atatgaaaca | 9060 |
| | gcccctgct gtccattcct tattccatag aaaagccttg acttgaggtt agatttttt | 9120 |
| | tatattttgt tttgtgttat ttttttcttt aacatcccta aaatttcct tacatgtttt | 9180 |
| | actagccaga tttttcctcc tctcctgact actcccagtc atagctgtcc ctcttctctt | 9240 |
| | atgaagatcc ctcgacctgc agcccaagct tggcgtaatc atggtcatag ctgtttcctg | 9300 |
| | tgtgaaattg ttatccgctc acaattccac acaacatacg agccggaagc ataaagtgta | 9360 |
| | aagcctgggg tgcctaatga gtgagctaac tcacattaat tgcgttgcgc tcactgcccg | 9420 |
| | ctttccagtc gggaaacctg tcgtgccagc tgcattaat cgcaacaat | 9480 |
| | agtcccgccc ctaactccgc ccatcccgcc cctaactccg cccagttccg cccattctcc | 9540 |
| | gccccatggc tgactaattt ttttattta tgcagaggcc gaggccgcct cggcctctga | 9600 |
| | gctattccag aagtagtgag gaggcttttt tggaggccta ggcttttgca aaaagctaac | 9660 |
| | ttgtttattg cagcttataa tggttacaaa taaagcaata gcatcacaaa tttcacaaat | 9720 |
| | aaagcatttt tttcactgca ttctagttgt ggtttgtcca aactcatcaa tgtatcttat | 9780 |
| | catgtctgga tccgctgcat taatgaatcg gccaacgcgc ggggagaggc ggtttgcgta | 9840 |
| | ttgggcgctc ttccgcttcc tcgctcactg actcgctgcg ctcggtcgtt cggctgcggc | 9900 |
| | gagcggtatc agctcactca aaggcggtaa tacggttatc cacagaatca ggggataacg | 9960 |
| | caggaaagaa catgtgagca aaaggccagc aaaaggccag gaaccgtaaa aaggccgcgt | 10020 |
| | tgctggcgtt tttccatagg ctccgccccc ctgacgagca tcacaaaaat cgacgctcaa | 10080 |
| | gtcagaggtg gcgaaacccg acaggactat aaagatacca ggcgtttccc cctggaagct | 10140 |
| | ccctcgtgcg ctctcctgtt ccgaccctgc cgcttaccgg atacctgtcc gcctttctcc | 10200 |
| | cttcgggaag cgtggcgctt tctcaatgct cacgctgtag gtatctcagt tcggtgtagg | 10260 |
| | tcgttcgctc caagctgggc tgtgtgcacg aaccccccgt tcagcccgac cgctgcgcct | 10320 |
| | tatccggtaa ctatcgtctt gagtccaacc cggtaagaca cgacttatcg ccactggcag | 10380 |
| | cagccactgg taacaggatt agcagagcga ggtatgtagg cggtgctaca gagttcttga | 10440 |
| | agtggtggcc taactacggc tacactagaa ggacagtatt tggtatctgc gctctgctga | 10500 |
| | agccagttac cttcggaaaa agagttggta gctcttgatc cggcaaacaa accaccgctg | 10560 |
| | gtagcggtgg tttttttgtt tgcaagcagc agattacgcg cagaaaaaaa ggatctcaag | 10620 |
| | aagatccttt gatcttttct acggggtctg acgctcagtg gaacgaaaac tcacgttaag | 10680 |
| | ggattttggt catgagatta tca | 10703 |
| SEQ ID NO: 26 (pCIGO-VSV.G plasmid) | gtcgacggat cgggagatca attccggcac ctgtcctacg agttgcatga taaagaagac | 60 |
| | agtcataagt gcggcgacga tagtcatgcc ccgcgcccac cggaaggagc tgactgggtt | 120 |
| | gaaggctctc aagggctcgc gtcgtgcag gaaaaggaca agcagcgaaa attcacgccc | 180 |
| | ccttgggagg tggcggcata tgcaaaggat agcactccca ctctactact gggtatcata | 240 |
| | tgctgactgt atatgcatga ggatagcata tgctacccgg atacagatta ggatagcata | 300 |
| | tactacccag atatagatta ggatagcata tgctacccag atatagatta ggatagccta | 360 |
| | tgctacccag atataaatta ggatagcata tactacccag atatagatta ggatagcata | 420 |
| | tgctacccag atatagatta ggatagccta tgctacccag atatagatta ggatagcata | 480 |
| | tgctacccag atatagatta ggatagcata tgctatccag atatttgggt agtatatgct | 540 |
| | acccagatat aaattaggat agcatatact accctaatct ctattaggat agcatatgct | 600 |
| | acccggatac agattaggat agcatatgct acccagatat agattaggat agcatatgct | 660 |
| | acccagatat agattaggat agccatatgct acccagatat aaattaggat agcatatact | 720 |
| | acccagatat agattaggat agcatatgct acccagatat agattaggat agcctatgct | 780 |
| | acccagatat agattaggat agcatatgct atccagatat ttgggtagta tatgctaccc | 840 |
| | atggcaacat tagcccaccg tgctctcagc gacctgtga atatgaggac caacaaccct | 900 |
| | gtgcttggcg ctcaggcgca agtgtgtgta atttgtcctc cagatcgcag caatcgcgcc | 960 |
| | cctatcttgg cccgcccacc tacttatgca ggtattcccc gggggtgccat tagtggtttt | 1020 |
| | gtgggcaagt ggtttgaccg cagtggttag cggggttaca atcagccaag ttattacacc | 1080 |
| | cttatttac agtccaaaac cgcagggcgg cgtgtggggg ctgacgcgtg cccccactcc | 1140 |
| | acaatttcaa aaaaaagagt ggccacttgt cttttgttta gggcccatt ggcgtgggag | 1200 |
| | cccgtttaat tttcgggggt gttagagaca accagtggag tccgctgctg tcgcgtcca | 1260 |
| | ctctctttcc ccttgttaca aatagagtgt aacaacatg ttcacctgtc ttggtccctg | 1320 |
| | cctgggacac atcttaataa ccccagtatc atattgcact aggattatgt gttgcccata | 1380 |
| | gccataaatt cgtgtgagat ggacatccag tctttacggc ttgtcccac cccatgaatt | 1440 |
| | tctattgtta aagatattca gaatgtttca ttcctacact agtatttatt gcccaagggg | 1500 |
| | tttgtgaggg ttatatttggt gtcatagcac aatgccacca ctgaaccccc cgtccaaatt | 1560 |
| | ttattctggg ggcgtcacct gaaaccttgt tttcgagcac ctcacataca ccttactgtt | 1620 |
| | cacaactcag cagttattct attagctaaa cgaaggaaga tgaagaagca caggagaagtt | 1680 |
| | caggagagtt cactgcccgc tccttgatct tcagccactg cccttgtgac taaatggtt | 1740 |
| | cactaccctc gtggaatcct gaccccatgt aaataaaacc gtgacagctc atggggtggg | 1800 |
| | agatatcgct gttccttagg acccttttac taacctaat tcgatagcat atgcttcccg | 1860 |
| | ttgggtaaca tatgctattg aattagggtt agtctggata gtatatacta ctacccggga | 1920 |
| | agcatatgct acccgtttag ggttaacaag ggggccttat aaacactatt gctaatgccc | 1980 |
| | tcttgagggt ccgcttatcg gtagctacac aggcccctct gattgacgtt ggtgtagcct | 2040 |
| | cccgtagtct tcctgggccc ctgggaggta catgtccccc agcattggtg taagagcttc | 2100 |
| | agccaagatt tacacataaa ggcaatgttg tgttgcagtc cacagactga aaagtctgct | 2160 |
| | ccaggatgaa agccactcaa gggatcttca atattggcca ttagccatat tattcattgg | 2220 |
| | ttatatagca taaatcaata ttggctattg gccattgcat acgttgtatc tatatcataa | 2280 |
| | tatgtacatt tatattggct catgtccaat atgaccgcca tgttggcatt gattattgac | 2340 |
| | tagttattaa tagtaatcaa ttacggggtc attagttcat agcccatata tggagttccg | 2400 |
| | cgttacataa cttacggtaa atggcccgcc tggctgaccg cccaacgacc cccgcccatt | 2460 |

TABLE 6-continued

Nucleotide sequences for preparation of
lentivirus for transduction of aAPCs.

| Identifier (Description) | Sequence | |
|---|---|---|
| | gacgtcaata atgacgtatg ttcccatagt aacgccaata gggactttcc attgacgtca | 2520 |
| | atgggtggag tatttacggt aaactgccca cttggcagta catcaagtgt atcatatgcc | 2580 |
| | aagtccgccc cctattgacg tcaatgacgg taaatggccc gcctggcatt atgcccagta | 2640 |
| | catgacctta cgggactttc ctacttggca gtacatctac gtattagtca tcgctattac | 2700 |
| | catggtgatg cggttttggc agtacaccaa tgggcgtgga tagcggtttg actcacgggg | 2760 |
| | atttccaagt ctccacccca ttgacgtcaa tgggagtttg ttttggcacc aaaatcaacg | 2820 |
| | ggactttcca aaatgtcgta ataaccccgc cccgttgacg caaatgggcg gtaggcgtgt | 2880 |
| | acggtgggag gtctatataa gcagagctcg tttagtgaac cgtcagatca ctagaagctt | 2940 |
| | tattgcggta gtttatcaca gttaaattgc taacgcagtc agtgcttctg acacaacagt | 3000 |
| | ctcgaactta agctgcagaa gttggtcgtg aggcactggg caggtaagta tcaaggttac | 3060 |
| | aagacaggtt taaggagacc aatagaaact gggcttgtcg agacagagaa gactcttgcg | 3120 |
| | tttctgatag gcacctattg gtcttactga catccacttt gcctttctct ccacaggtgt | 3180 |
| | ccactcccag ttcaattaca gctcttaagg ctagagtact taatacgact cactataggc | 3240 |
| | tagcggtacc gagctcggat ccactagtaa cggccgccag tgtgctggaa ttcaacgag | 3300 |
| | atcgatctgt ttccttgaca ctatgaagtg cctttttgac ttagccttt tattcattgg | 3360 |
| | ggtgaattgc aagttcacca tagttttcc acacaaccaa aaaggaaact ggaaaaatgt | 3420 |
| | tccttctaat taccattatt gcccgtcaag ctcagattta aattggcata atgacttaat | 3480 |
| | aggcacagcc atacaagtca aaatgcccaa gagtcacaag gctattcaag cagacggttg | 3540 |
| | gatgtgtcat gcttccaaat gggtcactac ttgtgatttc cgctggtatg gaccgaagta | 3600 |
| | tataacacag tccatccgat ccttcactcc atctgtagaa caatgcaagg aaagcattga | 3660 |
| | acaaacgaaa caaggaactt ggctgaatcc aggcttccct cctcaaagtt gtggatatgc | 3720 |
| | aactgtgacg gatgccgaag cagtgattgt ccaggtgact cctccaccatg tgctggttga | 3780 |
| | tgaatacaca ggagaatggg ttgattcaca gttcatcaac ggaaaatgca gcaattacat | 3840 |
| | atgccccact gtccataact ctacaacctg gcattctgac tataaggtca aagggctatg | 3900 |
| | tgattctaac ctcatttcca tggacatcac cttcttctca gaggacggag agctatcatc | 3960 |
| | cctgggaaag gagggcacag ggttcagaag taactacttt gcttatgaaa ctggaggcaa | 4020 |
| | ggcctgcaaa atgcaatact gcaagcattg gggagtcaga ctcccatcag gtgtctggtt | 4080 |
| | cgagatggct gataaggatc tctttgctgc agccagattc cctgaatgcc cagaagggtc | 4140 |
| | aagtatctct gctccatctc agacctcagt ggatgtaagt ctaattcagg acgttgagag | 4200 |
| | gatcttggat tattccctct gccaagaaac ctggagcaaa atcagagcgg gtcttccaat | 4260 |
| | ctctccagtg gatctcagct atcttgctcc taaaaaccca ggaaccggtc ctgctttcac | 4320 |
| | cataatcaat ggtaccctaa aatactttga gaccagatac atcagagtcg atattgctgc | 4380 |
| | tccaatcctc tcaagaatgg tcggaatgat cagtggaact accacagaaa gggaactgtg | 4440 |
| | ggatgactgg gcaccatatg aagacgtgga aattggaccc aatggagttc tgaggaccag | 4500 |
| | ttcaggatat aagtttcctt tatacatgat tggacatggt atgttggact ccgatcttca | 4560 |
| | tcttagctca aaggctcagg tgttcgaaca tcctcacatt caagacgctg cttcgcaact | 4620 |
| | tcctgatgat gagagtttat tttttggtga tactgggcta tccaaaaatc caatcgagct | 4680 |
| | tgtagaaggt tggttcagta gttggaaaag ctctattgcc tctttttct ttatcatagg | 4740 |
| | gttaatcatt ggactattct tggttctccg agttggtatc catctttgca ttaaattaaa | 4800 |
| | gcacaccaag aaaagacaga tttatacaga catagagtg aaccgacttg gaaagtaact | 4860 |
| | caaatcctgc acaacagatt cttcatgttt ggaccaaatc aacttgtgat accatgctca | 4920 |
| | aagaggcctc aattatattt gagttttaa tttttatgga attctgcaga tatccatcac | 4980 |
| | actggcggcc gctcgagcat gcatctagag ggcccctattc tatagtgtca cctaaatgct | 5040 |
| | agagctcgct gatcagcctc gactgtgcct tctagttgcc agccatctgt tgtttgccc | 5100 |
| | tccccccgtgc cttccttgac cctggaaggt gccactccca ctgtcctttc ctaataaaat | 5160 |
| | gaggaaattg catcgcattg tctgagtagg tgtcattcta ttctgggggg tggggtgggg | 5220 |
| | caggacagca agggggagga ttgggaagac aatagcaggc atgctgggga tgcggtgggc | 5280 |
| | tctatgcgct ctgaggcgga aagaaccagc tgcattaatg aatcggccaa cgcgcgggga | 5340 |
| | gaggcggttt gcgtattggg cgctcttccg cttcctcgct cactgactcg ctgcgctcgg | 5400 |
| | tcgttcggct gcggcgagcg gtatcagctc actcaaaggc ggtaatacgg ttatccacag | 5460 |
| | aatcagggga taacgcagga agaacatgt gagcaaaagg ccagcaaaag gccaggaacc | 5520 |
| | gtaaaaaggc cgcgttgctg gcgtttttcc ataggctccg cccccctgac gagcatcaca | 5580 |
| | aaaatcgacg ctcaagtcag aggtggcgaa acccgacagg actataaaga taccaggcgt | 5640 |
| | ttccccctgg aagctccctc gtgcgctctc ctgttccgac cctgccgctt accggatacc | 5700 |
| | tgtccgcctt tctcccttcg ggaagcgtgg cgctttctca atgctcacgc tgtaggtatc | 5760 |
| | tcagttcggt gtaggtcgtt cgctccaagc tgggctgtgt gcacgaaccc cccgttcagc | 5820 |
| | ccgaccgctg cgccttatcc ggtaactatc gtcttgagtc caacccggta agacacgact | 5880 |
| | tatcgccact ggcagcagcc actggtaaca ggattagcag agcgaggtat gtaggcggtg | 5940 |
| | ctacagagtt cttgaagtgg tggcctaact acggctacac tagaaggaca gtatttggta | 6000 |
| | tctgcgctct gctgaagcca gttaccttcg gaaaaagagt tggtagctct tgatccggca | 6060 |
| | aacaaaccac cgctggtagc ggtggttttt tgtttgcaa gcagcagatt acgcgcagaa | 6120 |
| | aaaaaggatc tcaagaagat cctttgatct tttctacggg gtctgacgct cagtggaacg | 6180 |
| | aaaactcacg ttaagggatt ttggtcatga gattatcaaa aaggatcttc acctagatcc | 6240 |
| | ttttaaatta aaaatgaagt tttaaatcaa tctaaagtat atatgagtaa acttggtctg | 6300 |
| | acagttacca atgcttaatc agtgaggcac ctatctcagc gatctgtcta tttcgttcat | 6360 |
| | ccatagttgc ctgactcccc gtcgtgtaga taactacgat acgggagggc ttaccatctg | 6420 |
| | gccccagtgc tgcaatgata ccgcgagacc cacgctcacc ggctccagat ttatcagcaa | 6480 |
| | taaaccagcc agccggaagg gccgagcgca gaagtggtcc tgcaacttta tccgcctcca | 6540 |
| | tccagtctat taattgttgc cgggaagcta gagtaagtag ttcgccagtt aatagtttgc | 6600 |
| | gcaacgttgt tgccattgct acaggcatcg tggtgtcacg ctcgtcgttt ggtatggctt | 6660 |
| | cattcagctc cggttcccaa cgatcaaggc gagttacatg atccccatg ttgtgcaaaa | 6720 |
| | aagcggttag ctccttcggt cctccgatcg ttgtcagaag taagttggcc gcagtgttat | 6780 |
| | cactcatggt tatggcagca ctgcataatt ctcttactgt catgccatcc gtaagatgct | 6840 |
| | tttctgtgac tggtgagtac tcaaccaagt cattctgaga atagtgtatg cggcgaccga | 6900 |

TABLE 6-continued

Nucleotide sequences for preparation of
lentivirus for transduction of aAPCs.

| Identifier (Description) | Sequence | |
|---|---|---|
| | gttgctcttg cccggcgtca atacgggata ataccgcgcc acatagcaga actttaaaag | 6960 |
| | tgctcatcat tggaaaacgt tcttcggggc gaaaactctc aaggatctta ccgctgttga | 7020 |
| | gatccagttc gatgtaaccc actcgtgcac ccaactgatc ttcagcatct tttactttca | 7080 |
| | ccagcgtttc tgggtgagca aaaacaggaa ggcaaaatgc cgcaaaaaag ggaataaggg | 7140 |
| | cgacacggaa atgttgaata ctcatactct tcctttttca atattattga agcatttatc | 7200 |
| | agggttattg tctcatgagc ggatacatat ttgaatgtat ttagaaaaat aaacaaatag | 7260 |
| | gggttccgcg cacatttccc cgaaaagtgc cacctgac | 7298 |

Figure 12:
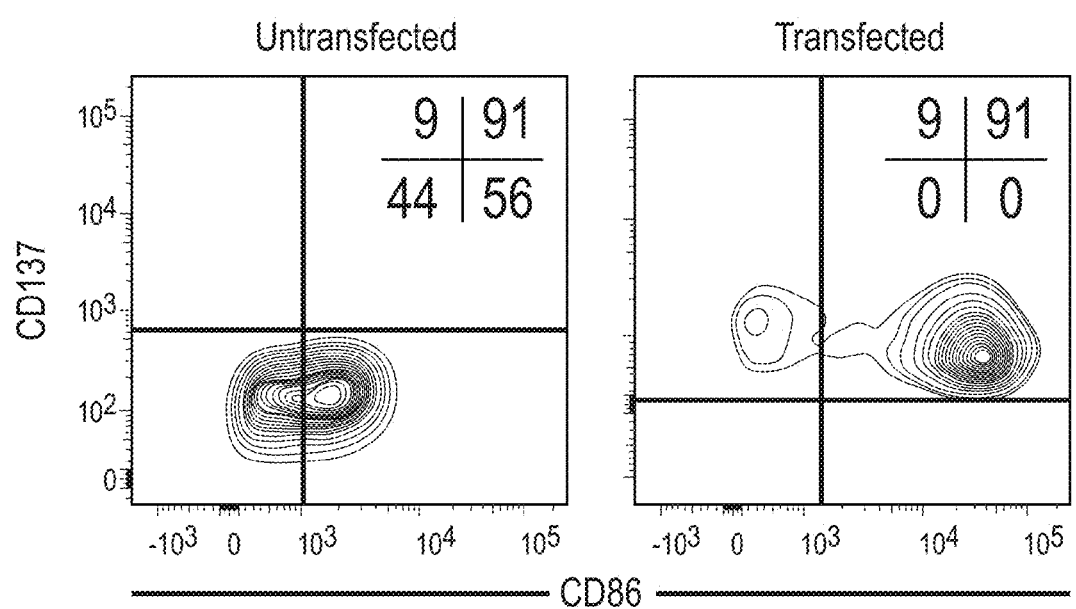
FIG. 12 illustrates the results of flow cytometry experiments on MOLM-14 cells before lentiviral transfection ("Untransfected") and after transfection ("Transfected"), confirming the expression of CD137 and CD86 on engineered MOLM-14 cells.
Figure 13:
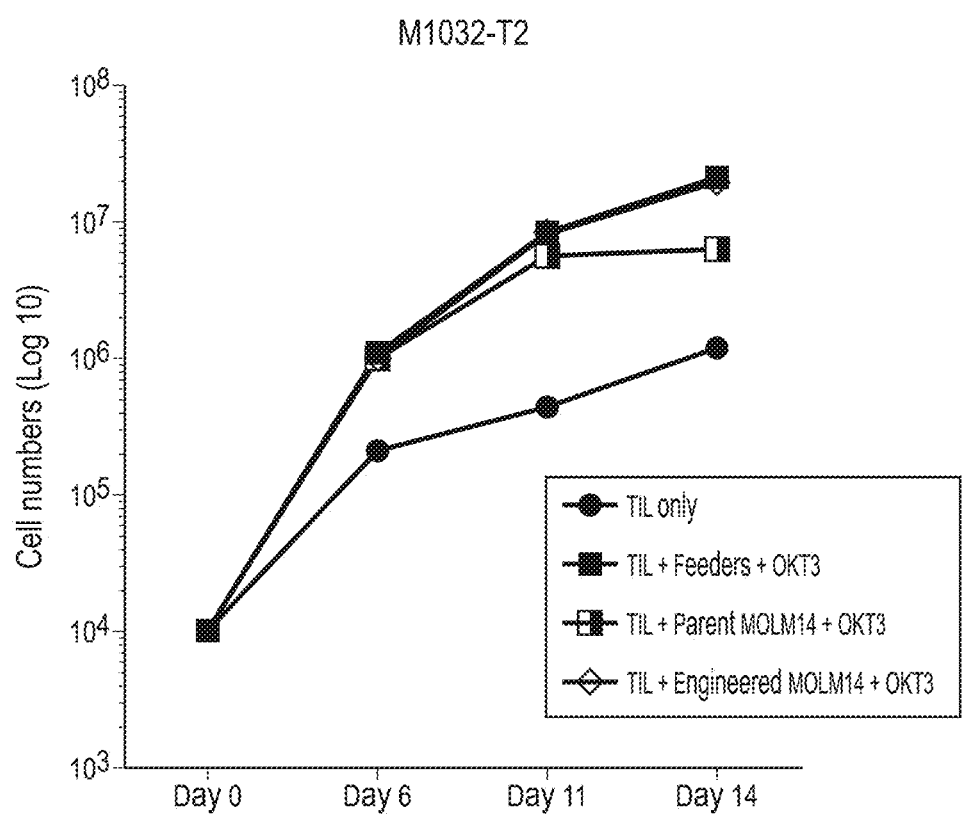
FIG. 13 illustrates the results of rapid expansion of TILs using irradiated parental unmodified MOLM-14 cells ("Parent MOLM14"), engineered MOLM-14 cells (CD86/4-1BBL, "Engineered MOLM14"), or PBMC feeders ("Feeders") for TIL lot M1032-T2. TIL were co-cultured with PBMC feeders or parental or engineered MOLM14 cells at 1:100 ratios with OKT-3 (30 ng/mL) and IL-2 (3000 IU/mL). Cells were counted and split on Day 6 and 11. Each dot represents cell numbers determined on Day 0, 6, 11 and 14 respectively. A logarithmic scale is used.
Figure 14:
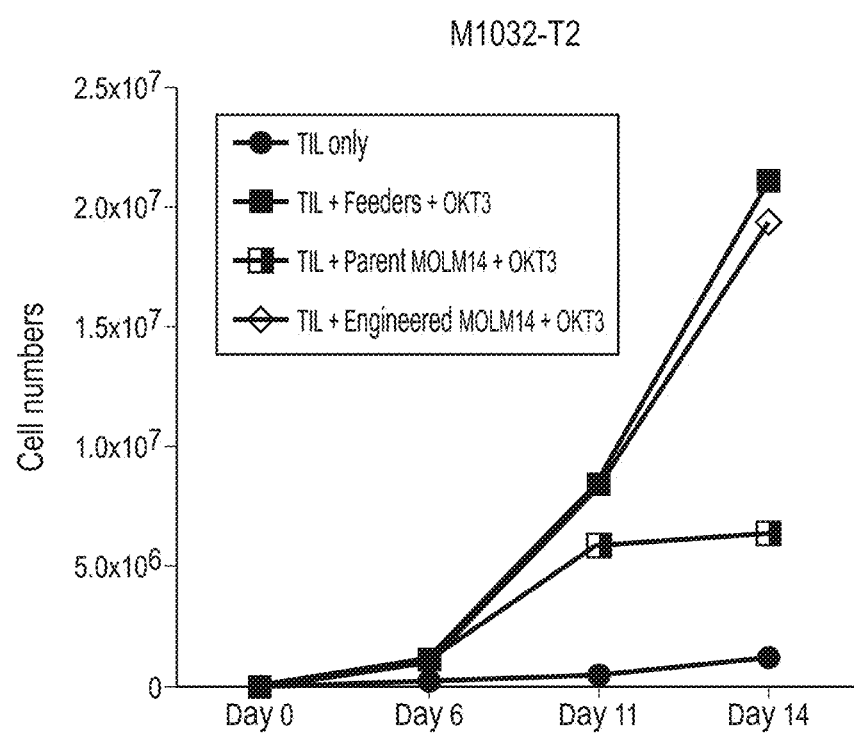
FIG. 14 illustrates results as shown in FIG. 13, depicted using a linear scale.
Figure 15:
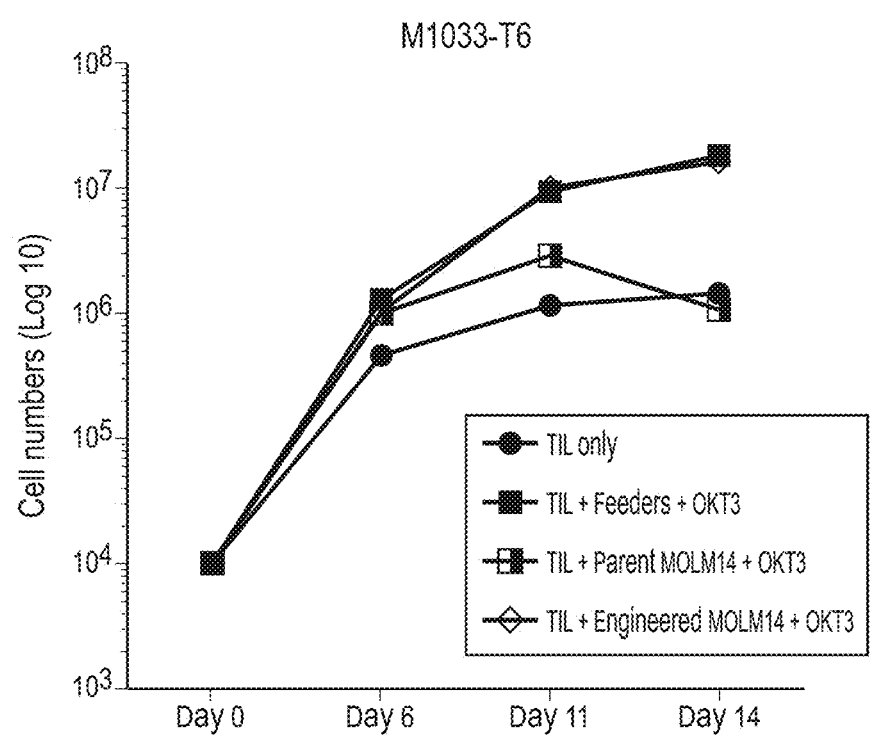
FIG. 15 illustrates results for TIL lot M1033-T6 with other parameters as given in FIG. 13, using a logarithmic scale.
Figure 16:
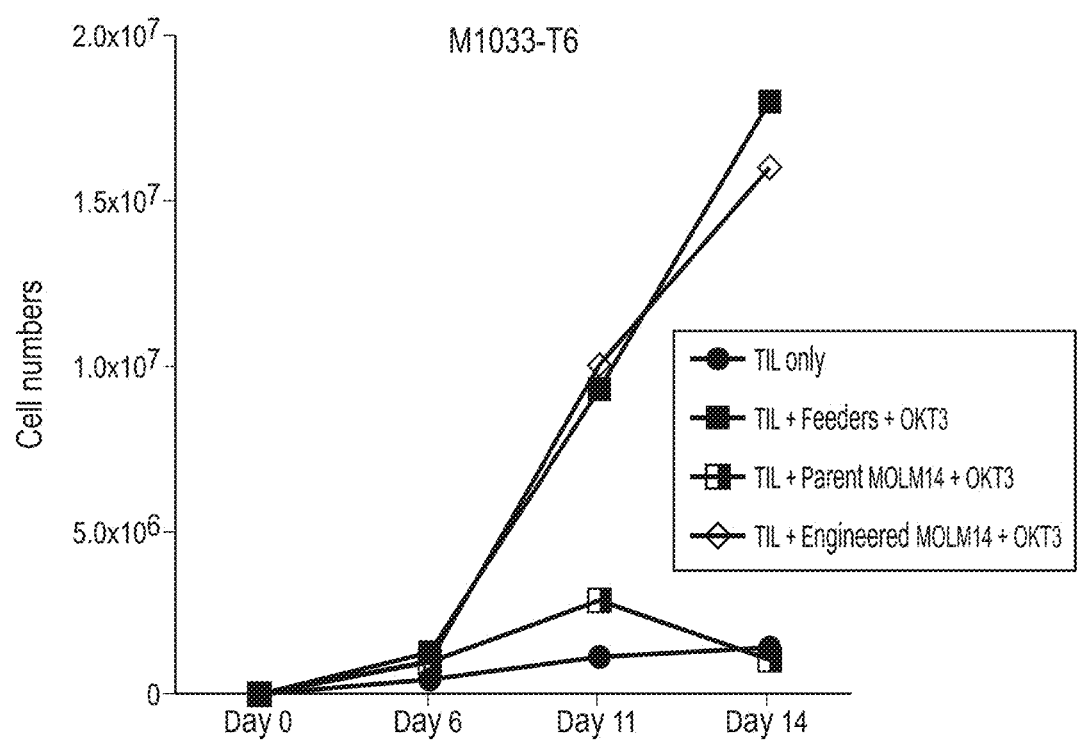
FIG. 16 illustrates results as shown in FIG. 14, depicted using a linear scale.

Expression of CD86 and 4-1BBL on engineered MOLM-14 aAPCs (also referred to herein as aMOLM14 aAPCs) was confirmed using flow cytometry (Canto II flow cytometer, Becton, Dickinson, and Co., Franklin Lakes, N.J., USA), with results shown in FIG. 12. aMOLM-14 aAPCs were γ-irradiated at 100 Gy and frozen.

Example 4—Expansion of Tumor Infiltrating Lymphocytes Using MOLM-14 Artificial Antigen Presenting Cells Engineered MOLM-14 cells were gamma-irradiated at 100 Gy before co-culturing with TILs. REPs were initiated by culturing TILs with irradiated, engineered MOLM-14 cells at 1:100 ratios in CM2 media containing OKT-3 (30 ng/mL) and IL-2 (3000 IU/mL) for 14 days. At REP harvest, the TIL expansion rates, phenotype for activation and differentiation stage markers, metabolism rate, cytotoxicity and re-rapid expansion protocol (re-REP) assay were measured.

The results are shown in FIG. 13, FIG. 14, FIG. 15, and FIG. 16, where two expansions for two sets of patient TILs are compared. The results with the CD86/4-1BBL modified MOLM-14 cells (labeled "TIL+Engineered MOLM14+OKT3") are comparable to the PBMC feeders (labeled "TIL+Feeders+OKT3").

Figure 17:
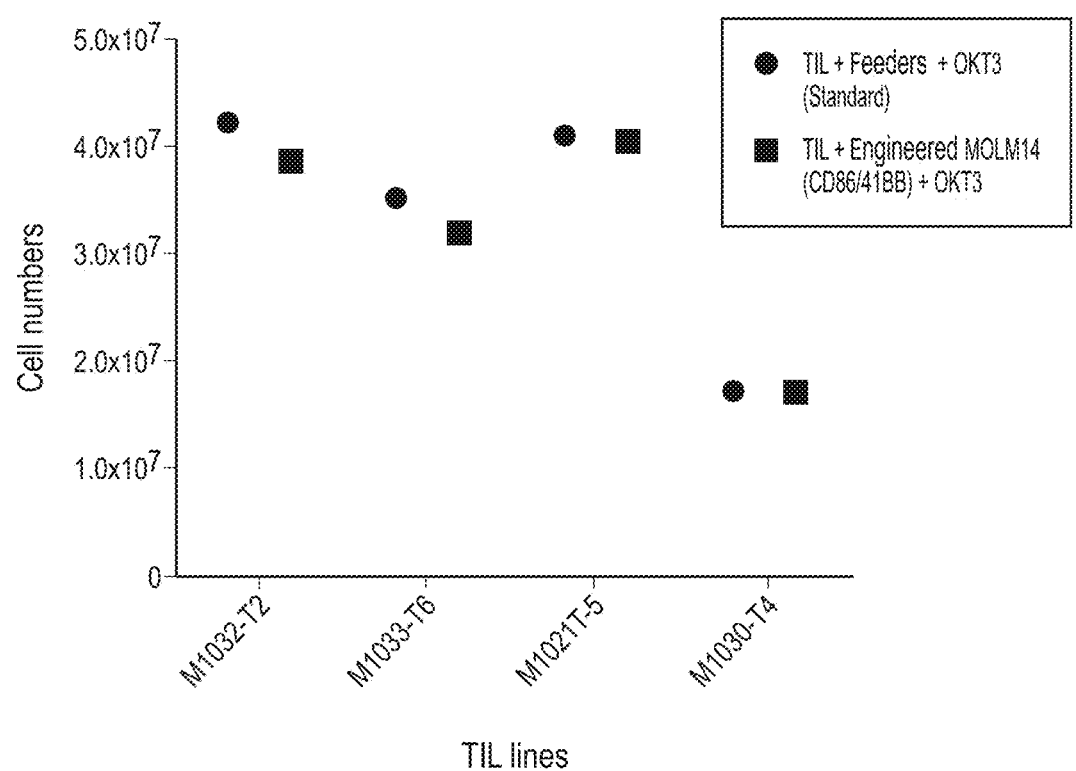
FIG. 17 illustrates the results of rapid expansions of TILs using engineered MOLM-14 cells expressing CD86 and 4-1BBL ("TIL+Engineered MOLM14 (CD86/41BB)+OKT3") or irradiated PBMC feeders ("TIL+Feeders+OKT3"). TIL were co-cultured with PBMC feeders or engineered MOLM-14 cells (aMOLM14) at 1:100 ratios plus OKT-3 (30 ng/mL) and IL-2 (3000 IU/mL). Cells were counted and split on Day 6 and 11. Each point represents cell numbers determined on Day 14.

The results at day 14 are compared in FIG. 17, where results from two additional patient TILs are shown. The results indicate that MOLM-14 cells that were engineered with CD86 and 4-1BBL showed similar TIL expansion in the rapid expansion protocol when compared with allogeneic feeder cells. However, TILs cultured with parental MOLM-14 did not expand.

In addition, TILs expanded against MOLM-14 maintained a TIL phenotype and showed potency to kill P815 cells as measured using BRLA, which is described in detail in Example 9. Briefly, luciferin-transduced P815 target cells and TILs of interest were co-cultured with and without anti-CD3 to determine whether tumor reactivity of TILs is through TCR activation (specific killing) or non-specific killing. Following 4 hours of incubation, luciferin was added to the wells and incubated for 5 minutes. After the incubation, bioluminescence intensity was read using a luminometer. The percentage cytotoxicity and percentage survival were calculated using the following formula: % Survival= (experimental survival-minimum)/(maximum signal-minimum signal)×100 or % Cytotoxicity=100−(% Survival).

Figure 18:
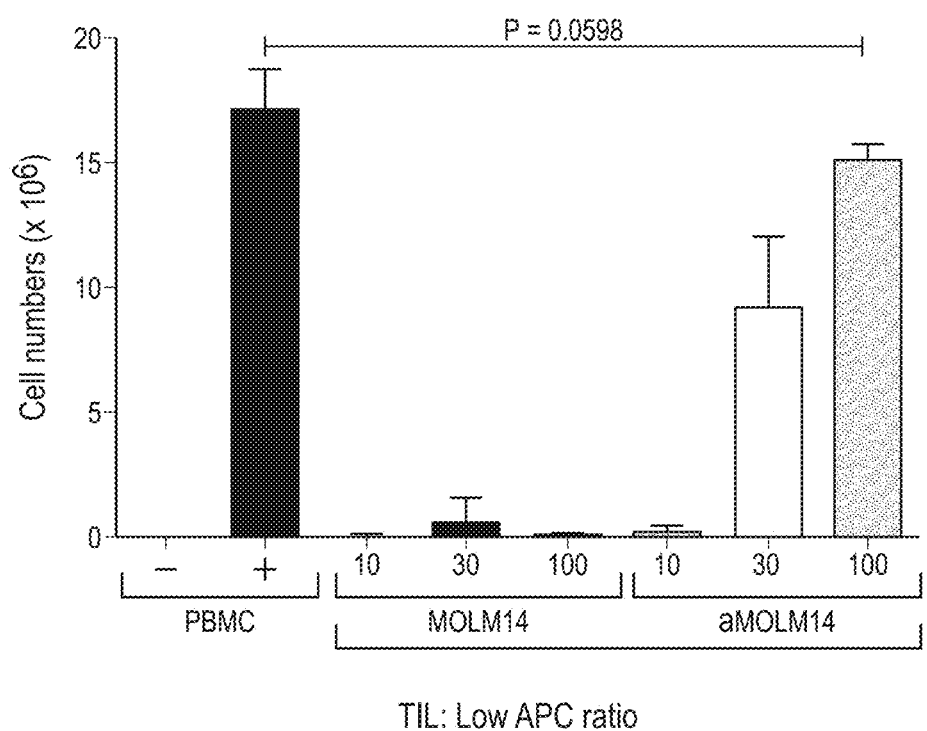
FIG. 18 illustrates the results of experiments in which TILs ($2 \times 10^4$) were cultured with different ratios (1:10, 1:30, and 1:100, denoted "10", "30", and "100", respectively) of parental MOLM-14 ("MOLM14") cells, MOLM-14 cells transduced to express CD86 and 4-1BBL ("aMOLM14"), or PBMC feeders ("PBMC+"), each with OKT-3 (30 ng/mL) and IL-2 (3000 IU/mL) in wells of a 24-well G-Rex plate. A control was performed using only OKT-3 (30 ng/mL) and IL-2 (3000 IU/mL) ("PBMC−"). Each condition was cultured in triplicate. Cultures were fed with fresh media and IL-2 on Day 4 and 7. Viable cells were counted on Day 7. The bar graph represented here shows the mean plus standard deviation (SD) of viable cell numbers counted on Day 11. The p-value was calculated by the student 't' test.

In FIG. 18, the results of expansions performed with low ratios of TILs to MOLM-14 aAPCs are shown in comparison to the results of expansions with PBMC feeders. TILs ($2\times10^4$) were cultured at different TIL to aAPC or PBMC ratios (1:10, 1:30, and 1:100, denoted "10", "30", and "100", respectively) with parental MOLM-14 ("MOLM14") cells, MOLM-14 cells transduced to express CD86 and 4-1BBL ("aMOLM14"), or PBMC feeders ("PBMC+"), each with OKT-3 (30 ng/mL) and IL-2 (3000 IU/mL) in a 24-well G-Rex plate. A control was performed using only OKT-3 (30 ng/mL) and IL-2 (3000 IU/mL) ("PBMC−"). Each condition was cultured in triplicate. Cultures were fed with fresh media and IL-2 on Day 4 and 7. Viable cells were counted on Day 7. FIG. 18 shows the mean plus standard deviation (SD) of viable cell numbers counted on Day 11, with a p-value calculated by the student t-test. Additional control experiments were performed using TILs alone, PBMCs alone, and aMOLM-14 cells alone, all of which resulted in undetectable cell numbers (data not shown). The results show that a ratio of 1:100 (TIL:aMOLM14) with OKT-3 and IL-2 yields a similar expansion when compared to PBMC feeders with OKT-3 and IL-2 (p=0.0598).

Figure 19:
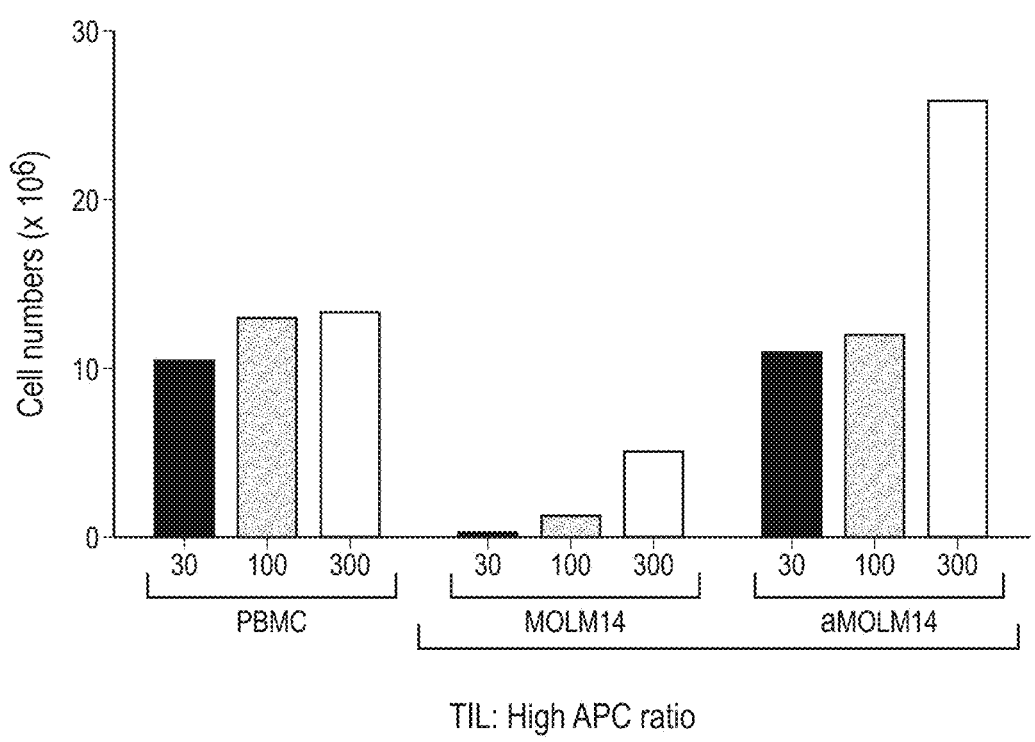
FIG. 19 illustrates the results of TILs cultured with different ratios (1:30, 1:100, and 1:300, denoted "30", "100", and "300", respectively) of PBMC feeders ("PBMC"), parental MOLM-14 cells ("MOLM14"), or MOLM-14 cells transduced to express CD86 and 4-1BBL ("aMOLM14"), each with OKT-3 (30 ng/mL) and IL-2 (3000 IU/mL) in the single 24 well G-Rex culture plates. Viable cells were counted on day 11 and plotted. Other conditions are as in FIG. 18.
Figure 20:
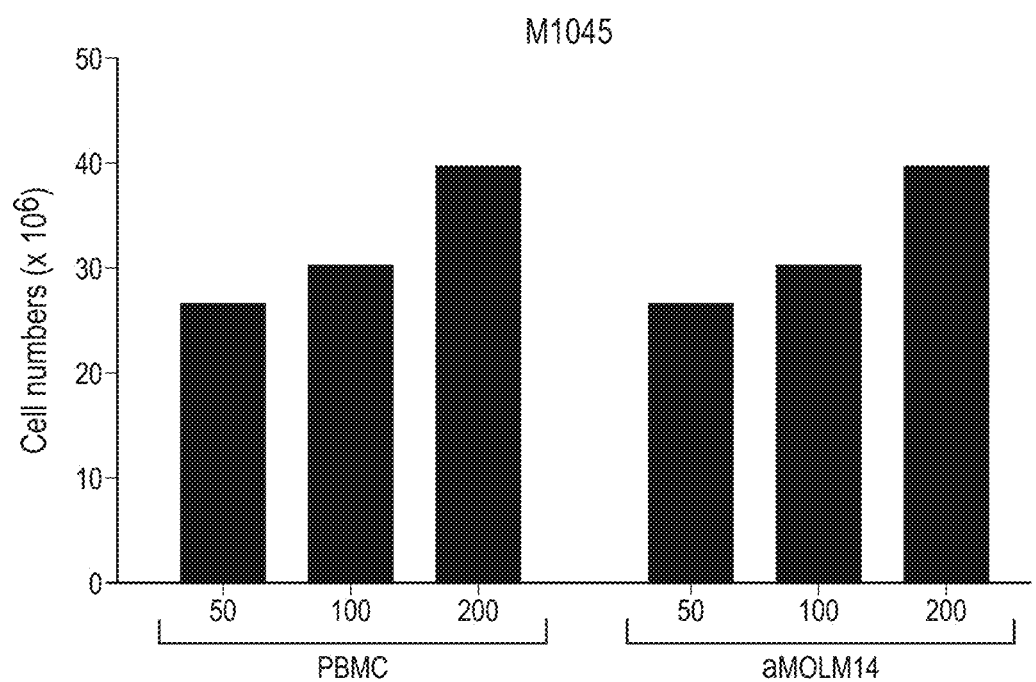
FIG. 20 illustrates the results of TILs cultured with different ratios (1:50, 1:100, and 1:200, denoted "50", "100", and "200", respectively) of PBMC feeders ("PBMC"), parental MOLM-14 cells ("MOLM14"), or MOLM-14 cells transduced to express CD86 and 4-1BBL ("aMOLM14"), each with OKT-3 (30 ng/mL) and IL-2 (3000 IU/mL) in the single 24 well G-Rex culture plates. Cells were counted on day 14. Other conditions are as in FIG. 18.
Figure 21:
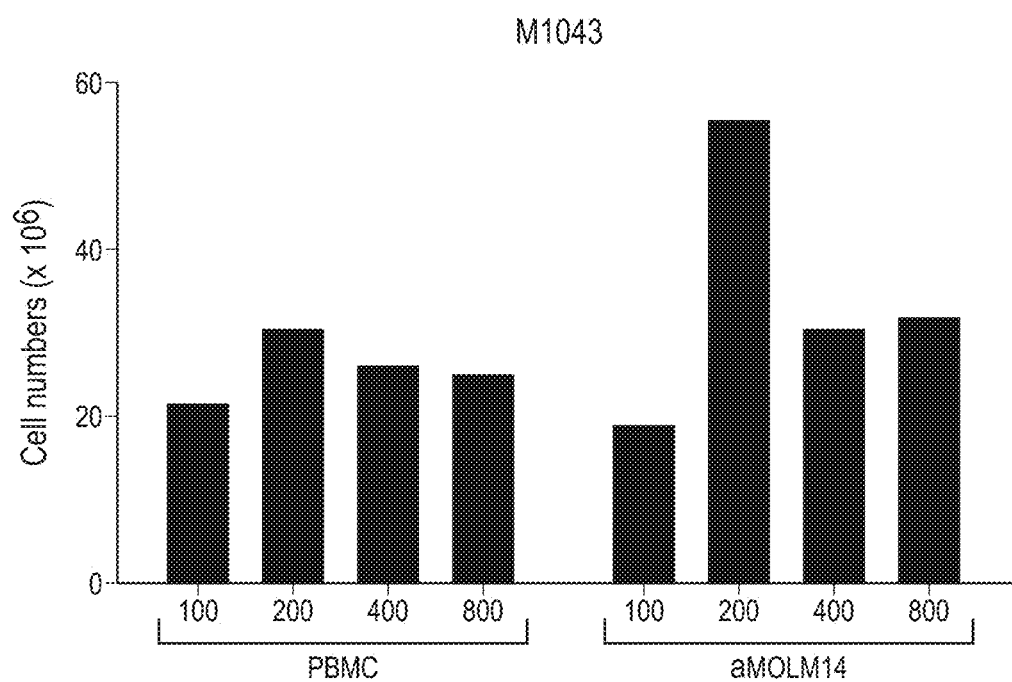
FIG. 21 illustrates the results of TILs cultured with different ratios (1:100, 1:200, 1:400, and 1:800, denoted "100", "200", "400", and "800", respectively) of PBMC feeders ("PBMC"), parental MOLM-14 cells ("MOLM14"), or MOLM-14 cells transduced to express CD86 and 4-1BBL ("aMOLM14"), each with OKT-3 (30 ng/mL) and IL-2 (3000 IU/mL) in the single 24 well G-Rex culture plates. Cells were counted on day 14. Other conditions are as in FIG. 18.

In FIG. 19, the results of expansions performed with higher ratios of TILs to MOLM-14 aAPCs, and otherwise performed as described above for FIG. 18, are shown in comparison to the results of expansions with PBMC feeders. At a ratio of 1:300, the CD86/4-1BBL modified MOLM-14 aAPCs with OKT-3 and IL-2 significantly outperform PBMC feeders with OKT-3 and IL-2. These results were verified using different TIL batches in repeat experiments shown in FIG. 20 and FIG. 21. In particular, as seen in FIG. 21, TIL to aMOLM14 ratios of 1:200 show enhanced TIL expansion compared to PBMC feeders under the same conditions. These results confirm that aMOLM14 aAPCs are unexpectedly superior in terms of expanding the TIL numbers than PBMCs particularly when using TIL:aMOLM14 ratios of 1:200 to 1:300.

Figure 22:
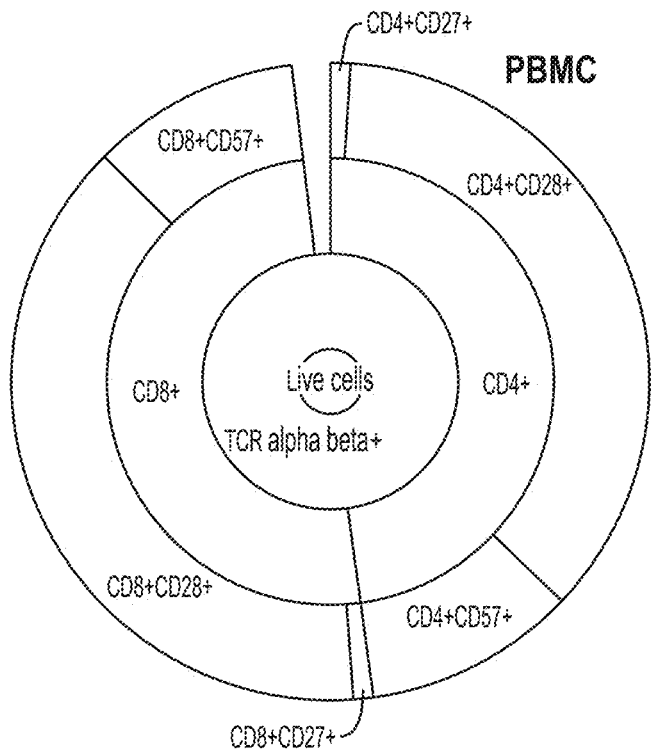
FIG. 22 illustrates a sunburst visualization showing fine distribution of Live, T cell receptor (TCR) α/β, CD4, CD8, CD27, CD28, and CD57 TILs expanded with PBMC feeders.
Figure 23:
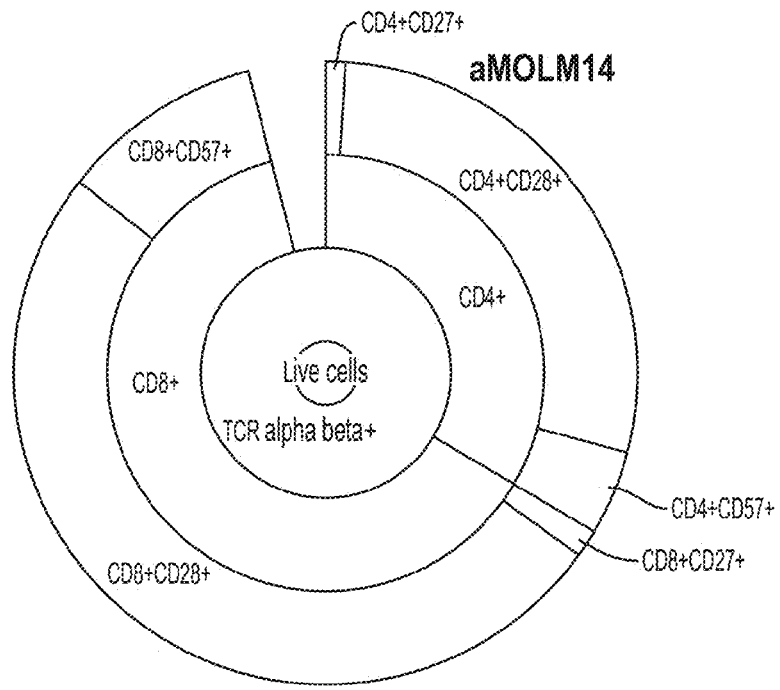
FIG. 23 illustrates a sunburst visualization showing fine distribution of Live, TCR α/β, CD4, CD8, CD27, CD28, and CD57 TILs expanded with aMOLM14 aAPCs.
Figure 24:
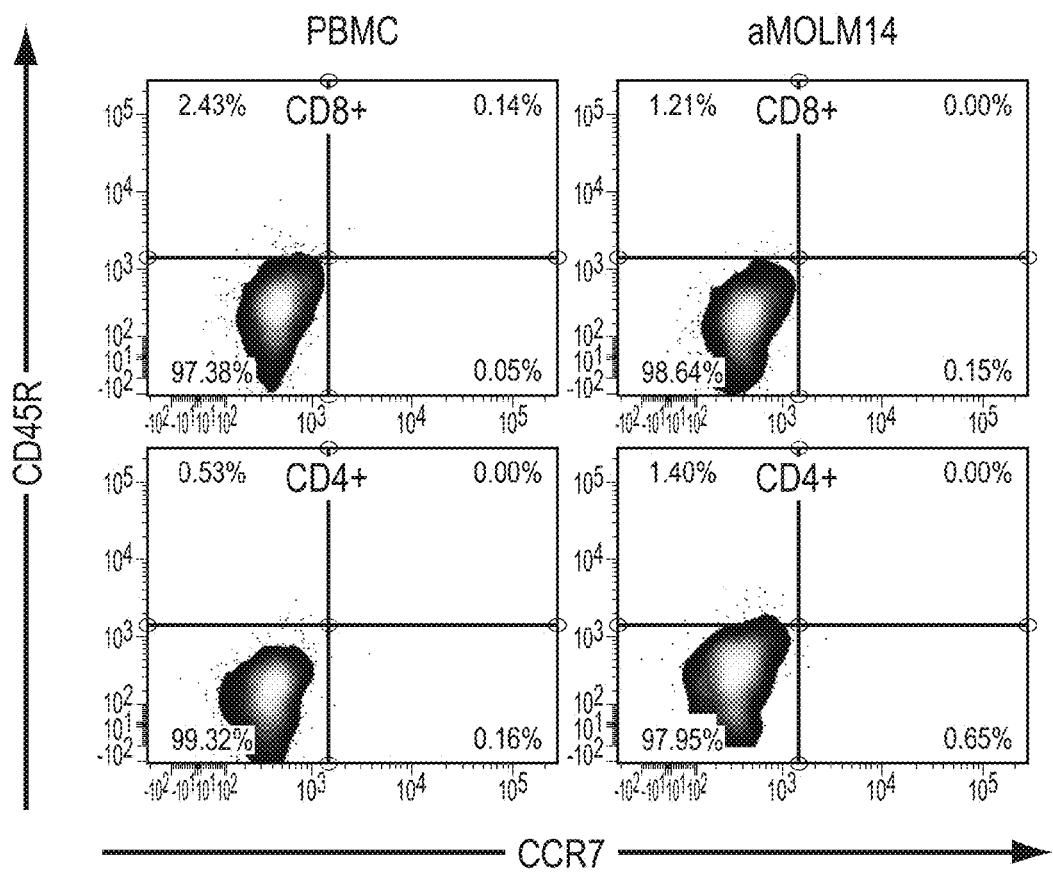
FIG. 24 depicts a flow cytometry contour plot showing memory subset (CD45RA+/−, CCR7+/−) gated on Live, TCR α/β+, CD4$^+$, or CD8$^+$ TILs.

In FIG. 22 and FIG. 23, TILs expanded with aMOLM14 or PBMC were compared by flow cytometry analysis to confirm that the TILs exhibited a similar phenotype and would be expected to perform similarly upon reinfusion into a patient. Briefly, TILs were first stained with L/D Aqua to determine viability. Next, cells were surface stained with TCR α/β PE-Cy7, CD4 FITC, CD8 PB, CD56 APC, CD28PE, CD27 APC-C7, and CD57-PerCP-Cy5.5. Phenotype analysis was done by gating 10,000 to 100,000 cells according to forward light scattering (FSC)/side light scattering (SSC) using a Canto II flow cytometer (Becton, Dickinson, and Co., Franklin Lakes, N.J., USA). Data was analyzed by Cytobank software to create sunburst diagrams and SPADE (Spanning Tree Progression of Density Normalized Event) analyses. Gates were set based on fluorescence minus one (FMO) controls. TILs expanded against aMOLM14 increases $CD8^+$ TILs when compared to PBMC feeders. Without being bound by theory, this enhanced $CD8^+$ TIL percentage may be due to the presence of 4-1BBL engineered to MOLM14. There is no difference in the expression of CD28, CD57, and CD27 differentiation markers. Additional flow cytometry data is shown in FIG. 24, and depicts a flow cytometry contour plot showing a memory subset (CD45RA+/−, CCR7+/−) gated on Live, TCR α/β+, CD4+ or CD8+ TILs, indicating that the memory subset obtained with PBMC feeders is replicated by the aMOLM14 aAPCs.

Figure 25:
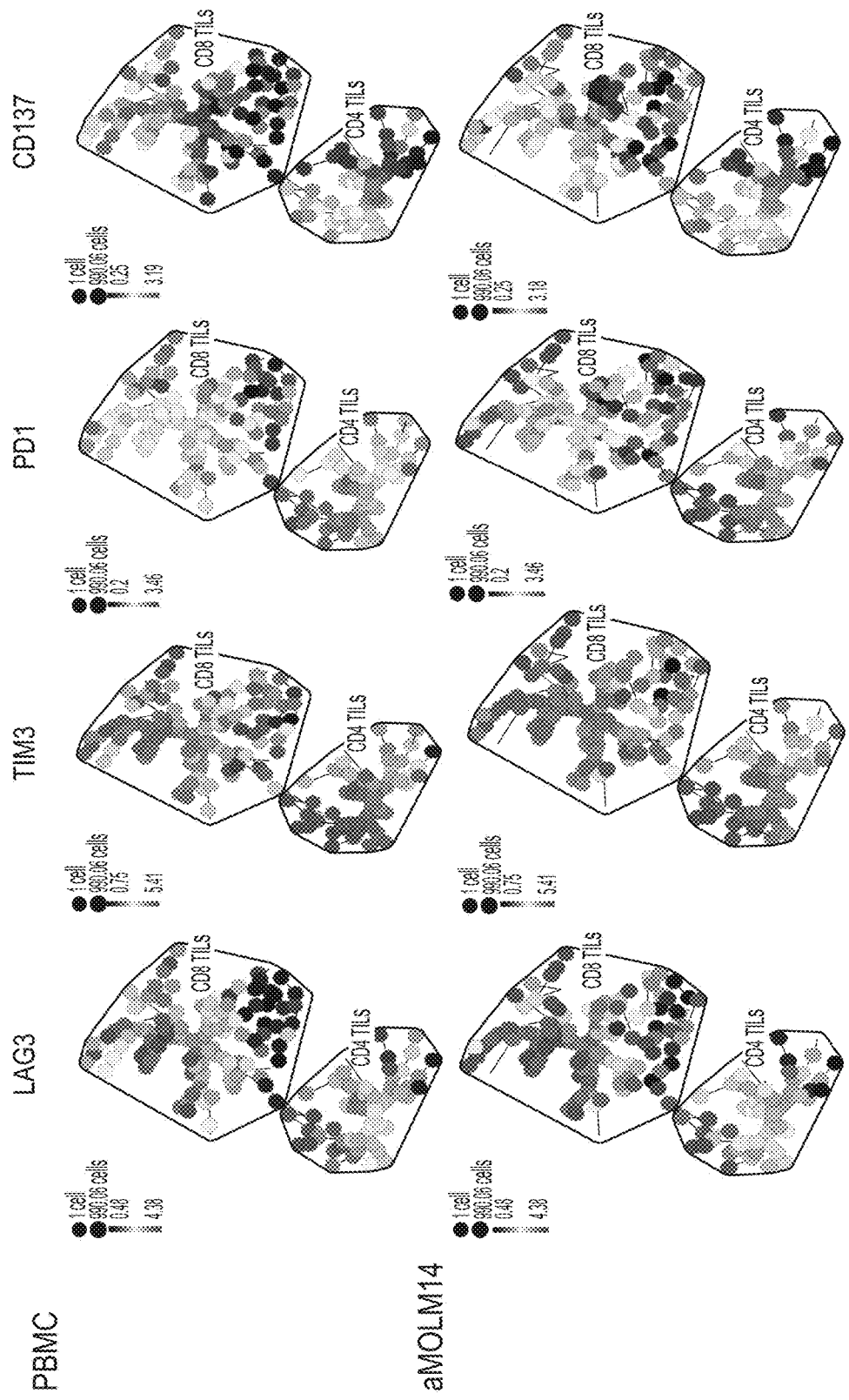
FIG. 25 illustrates phenotypic characterization of the T cell subset, CD4$^+$ and CD8$^+$ post-REP TILs (expanded with aMOLM14 aAPCs) gated on CD3$^+$ cells using a SPADE tree. The color gradient is proportional to the mean fluorescence intensity (MFI) of LAG3, TIM3, PD1, and CD137.
Figure 26:
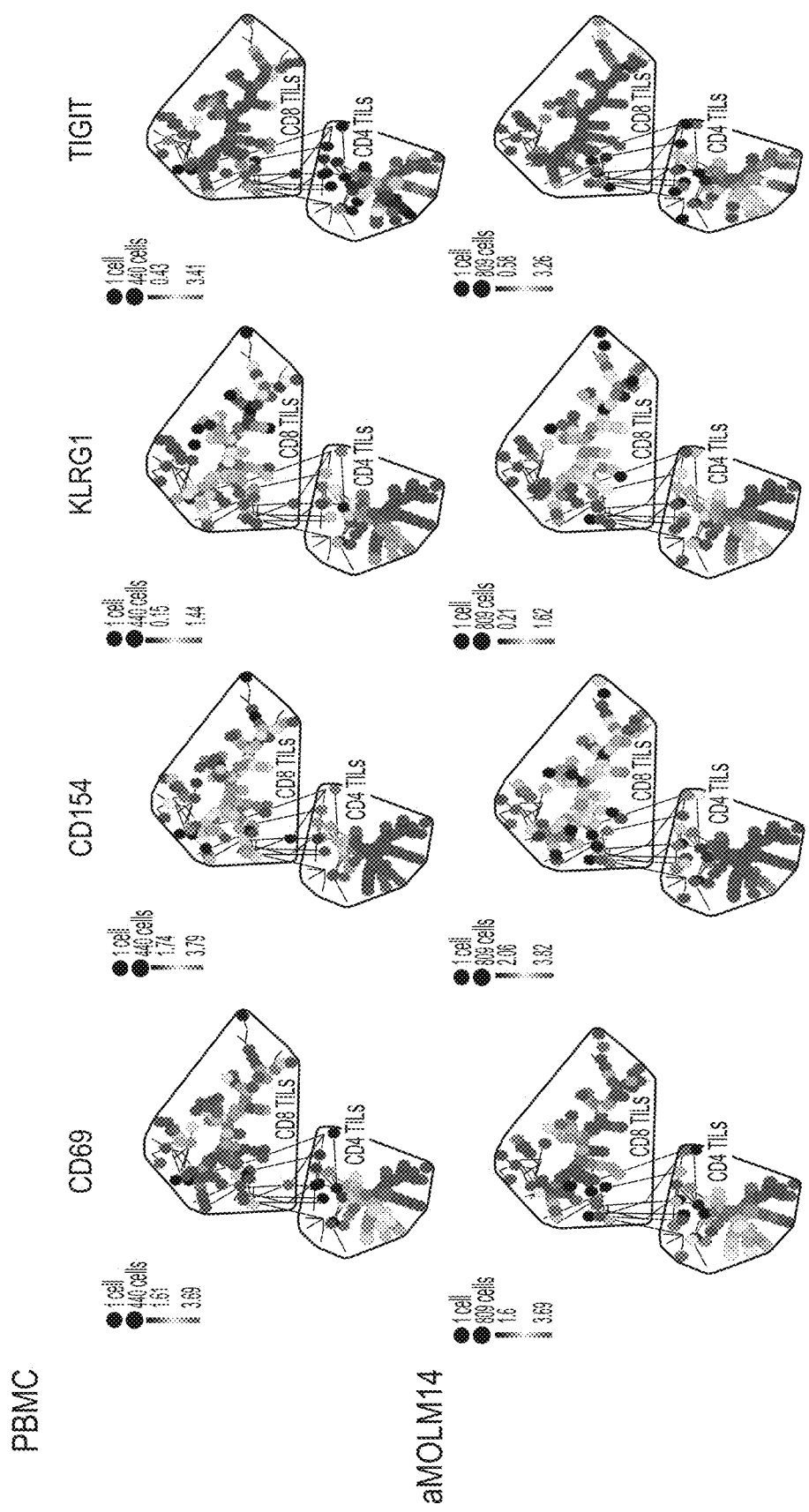
FIG. 26 illustrates phenotypic characterization of the T cell subset, CD4$^+$ and CD8$^+$ post-REP TILs (expanded with aMOLM14 aAPCs) gated on CD3$^+$ cells using a SPADE tree. The color gradient is proportional to the MFI CD69, CD154, KLRG1, and TIGIT

The CD4 and CD8 SPADE tree of TILs expanded with aMOLM14 aAPCs or PBMC feeders using CD3+ cells is shown in FIG. 25 and FIG. 26. The color gradient is proportional to the mean fluorescence intensity (MFI) of LAG3, TIL3, PD1 and CD137 or CD69, CD154, KLRG1 and TIGIT. Without being bound by theory, the results show that two batches of TILs expanded against aMOLM14 had undergone activation, but there was no difference in MFI between the aMOLM14 aAPCs and PBMC feeders, indicating that the aMOLM14 aAPCs effectively replicate the TIL phenotypic results obtained with PBMC feeders.

Figure 27:
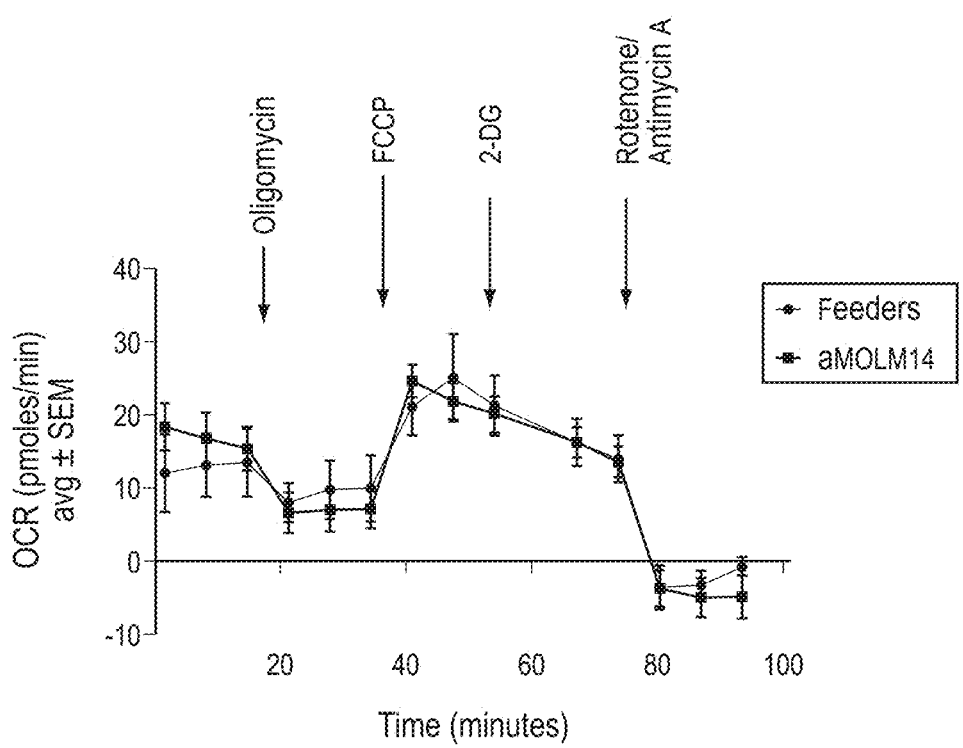
FIG. 27 illustrates oxygen consumption rate (OCR) of TIL after expansion with Feeders or aMOLM14 measured during a mitochondrial stress test. Each data point represents mean±standard error of the mean (SEM) measured in triplicate.
Figure 28:
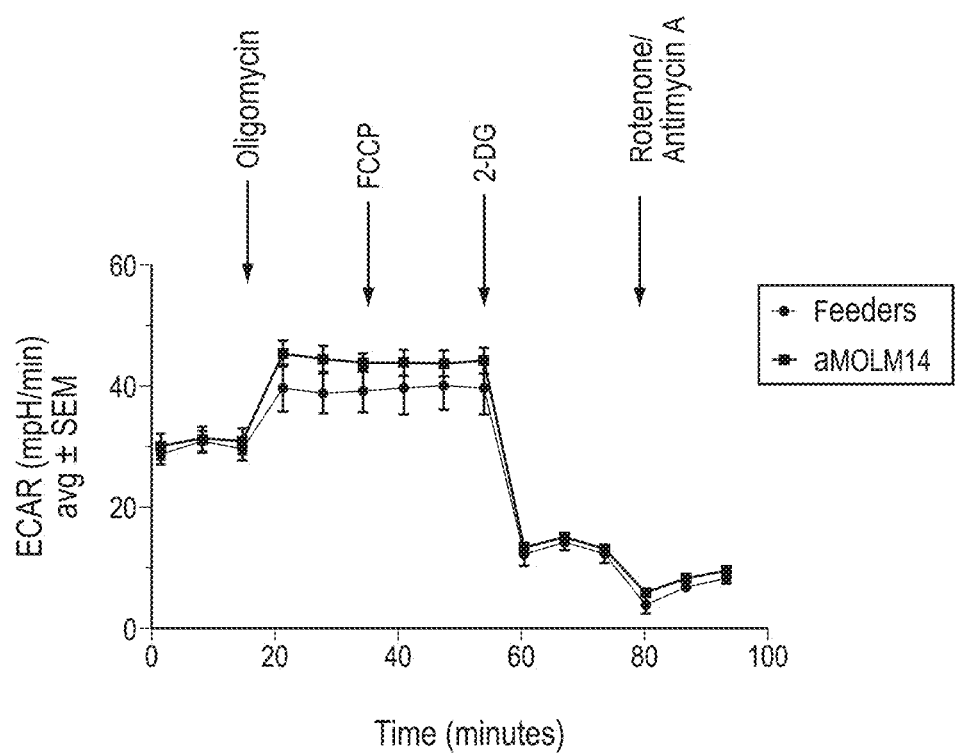
FIG. 28 illustrates extracellular acidification rate (ECAR) of TIL after expansion with Feeders or aMOLM14 measured during a mitochondrial stress test. Each data point represents mean±SEM measured in triplicate.
Figure 29:
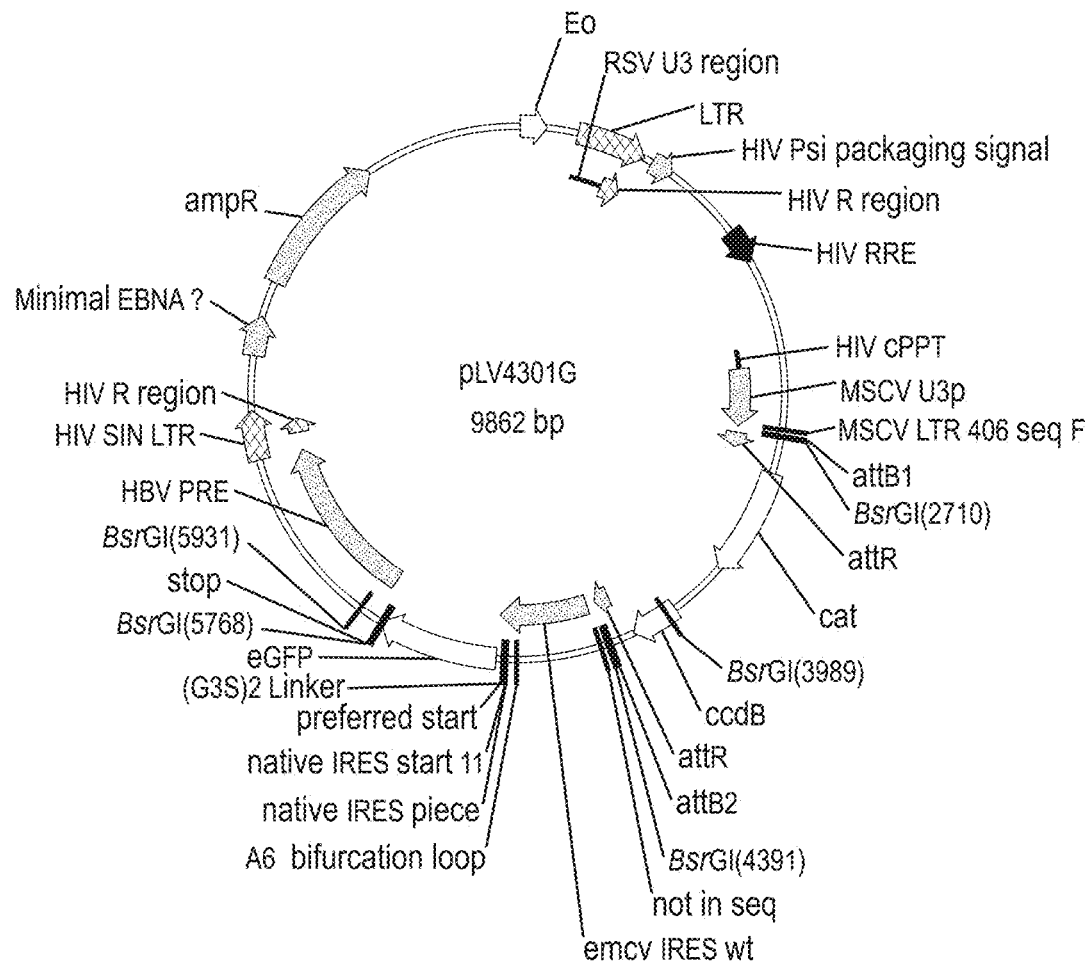
FIG. 29 illustrates a vector diagram of the destination vector pLV4301G.
Figure 30:
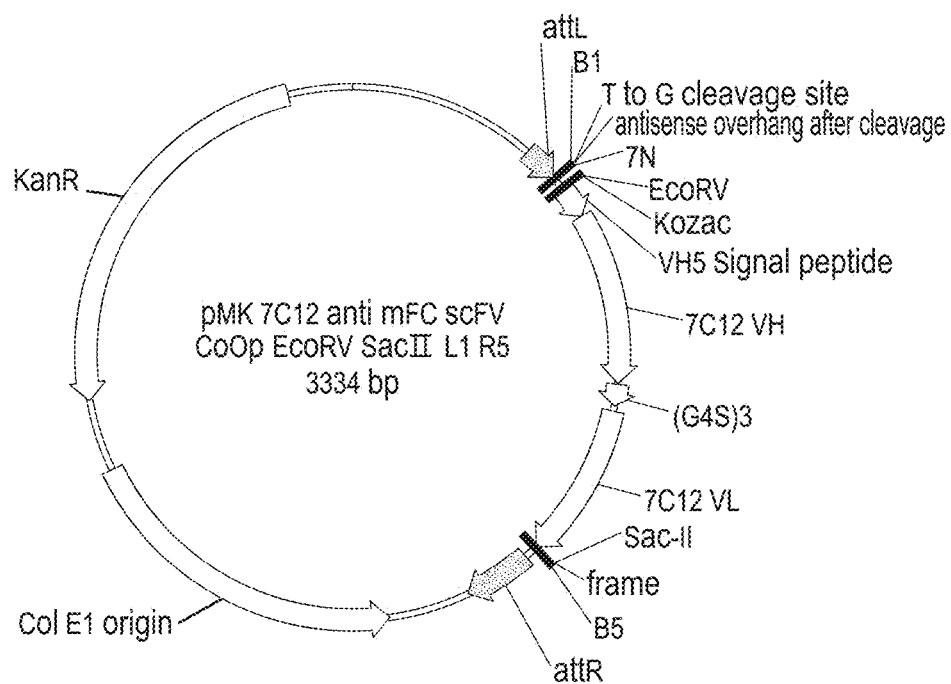
FIG. 30 illustrates a vector diagram of donor vector 1, pMK 7c12 anti mFC scFv CoOp ECORV SacII L1R5.
Figure 31:
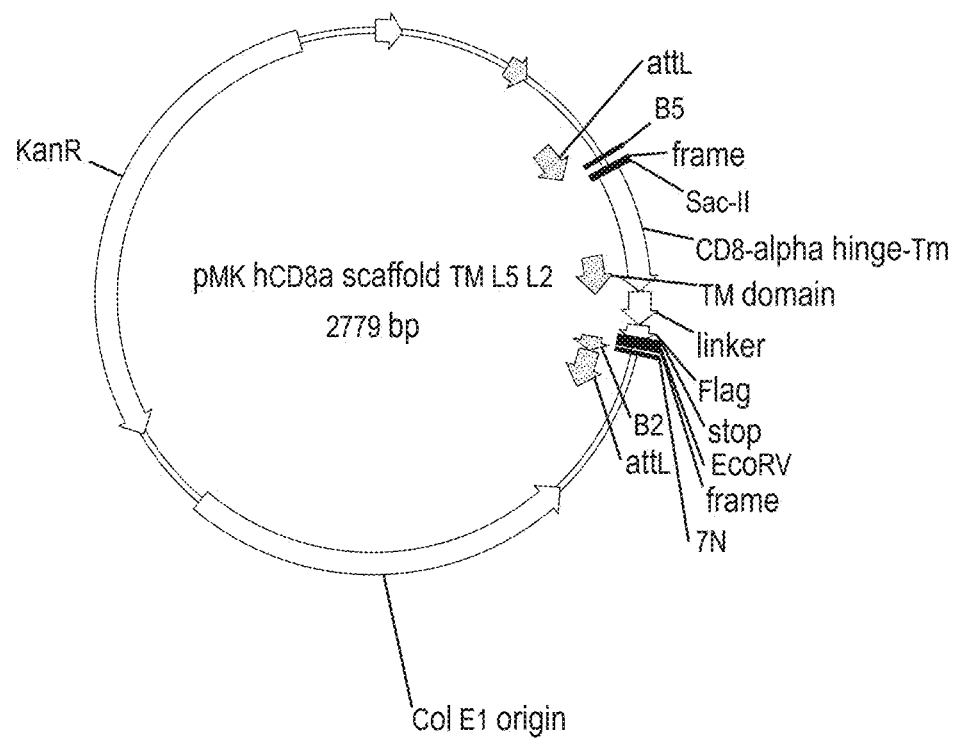
FIG. 31 illustrates a vector diagram of donor vector 2, pMK hCD8a scaffold TN L5 L2.
Figure 32:
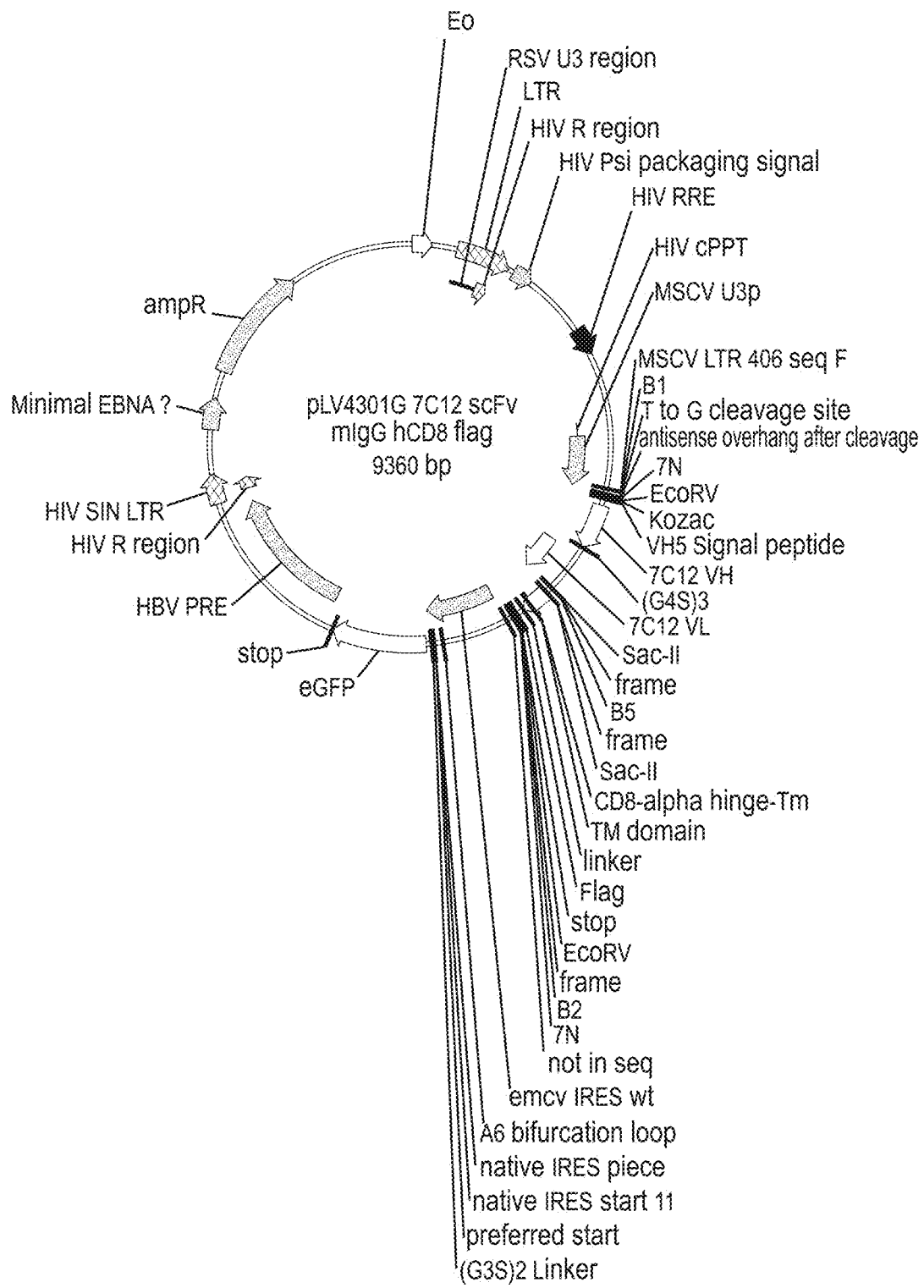
FIG. 32 illustrates a vector diagram of final vector used for lentiviral production, pLV4301G 7C12 scFv mIgG hCD8 flag.
Figure 33:
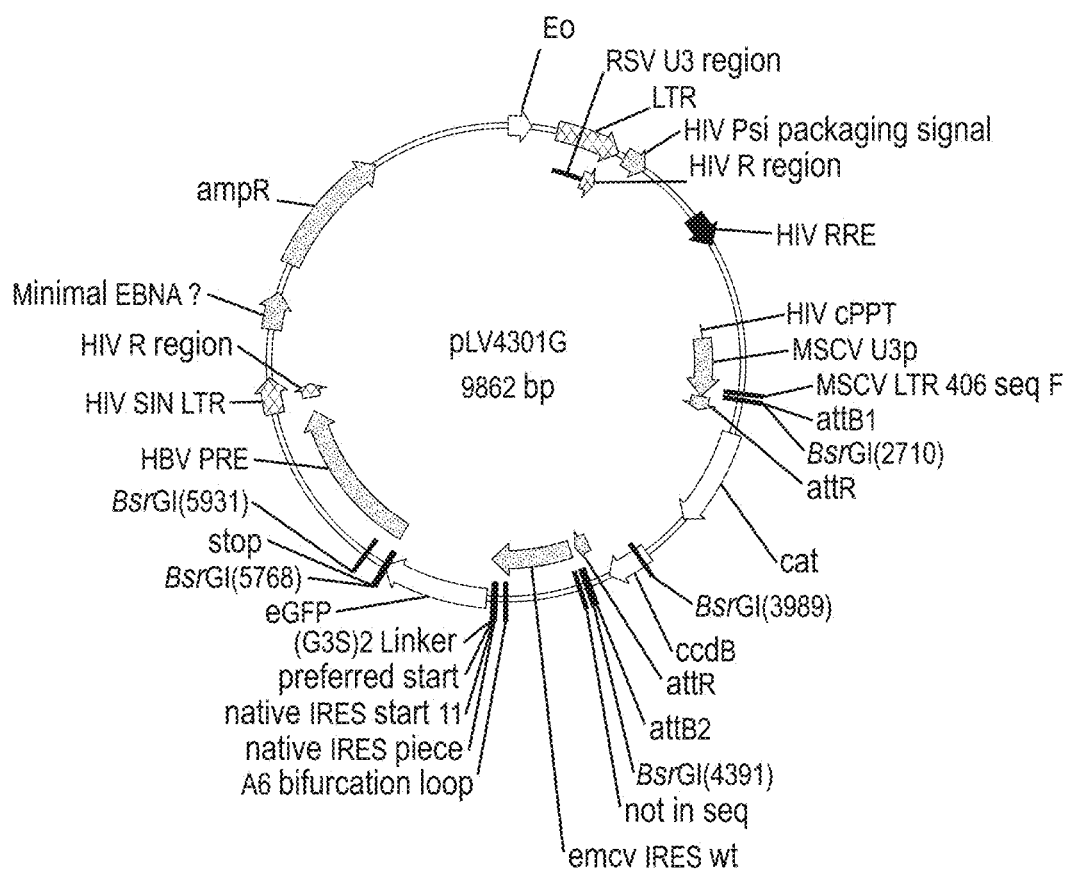
FIG. 33 illustrates a vector diagram of the destination vector pLV4301G.
Figure 34:
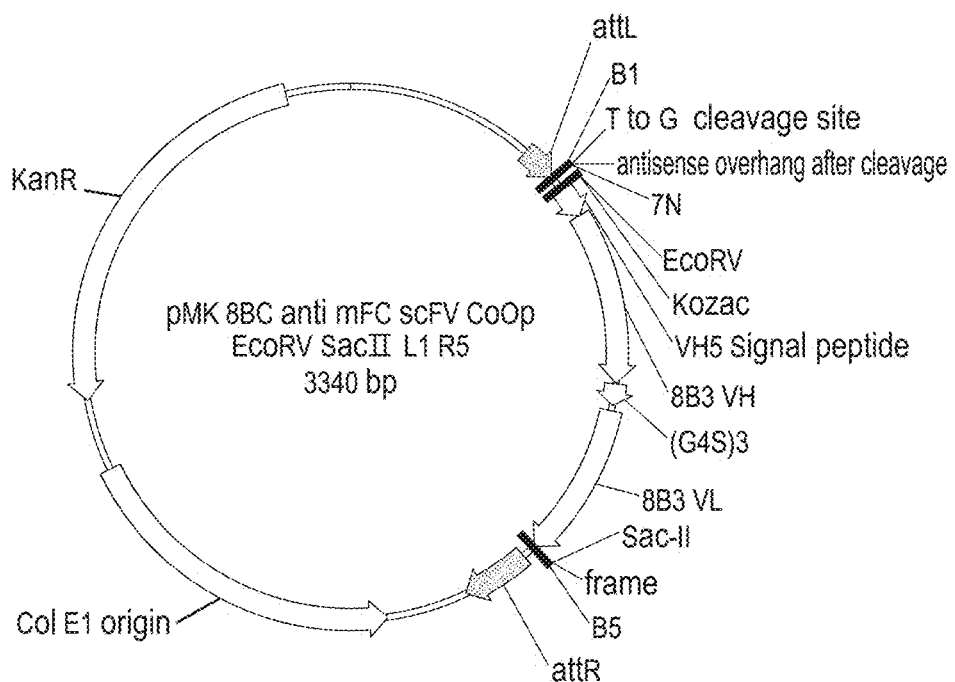
FIG. 34 illustrates a vector diagram of donor vector 1, pMK 8B3 anti mFC scFv CoOp ECORV SacII L1R5.
Figure 35:
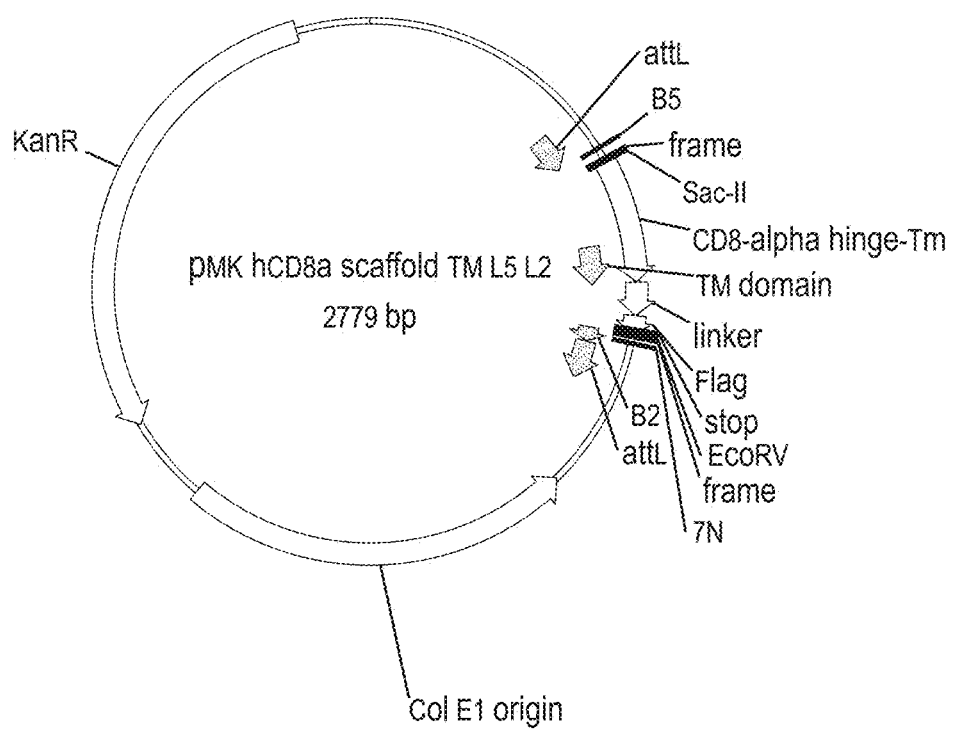
FIG. 35 illustrates a vector diagram of donor vector 2, pMK hCD8a scaffold TN L5 L2.
Figure 36:
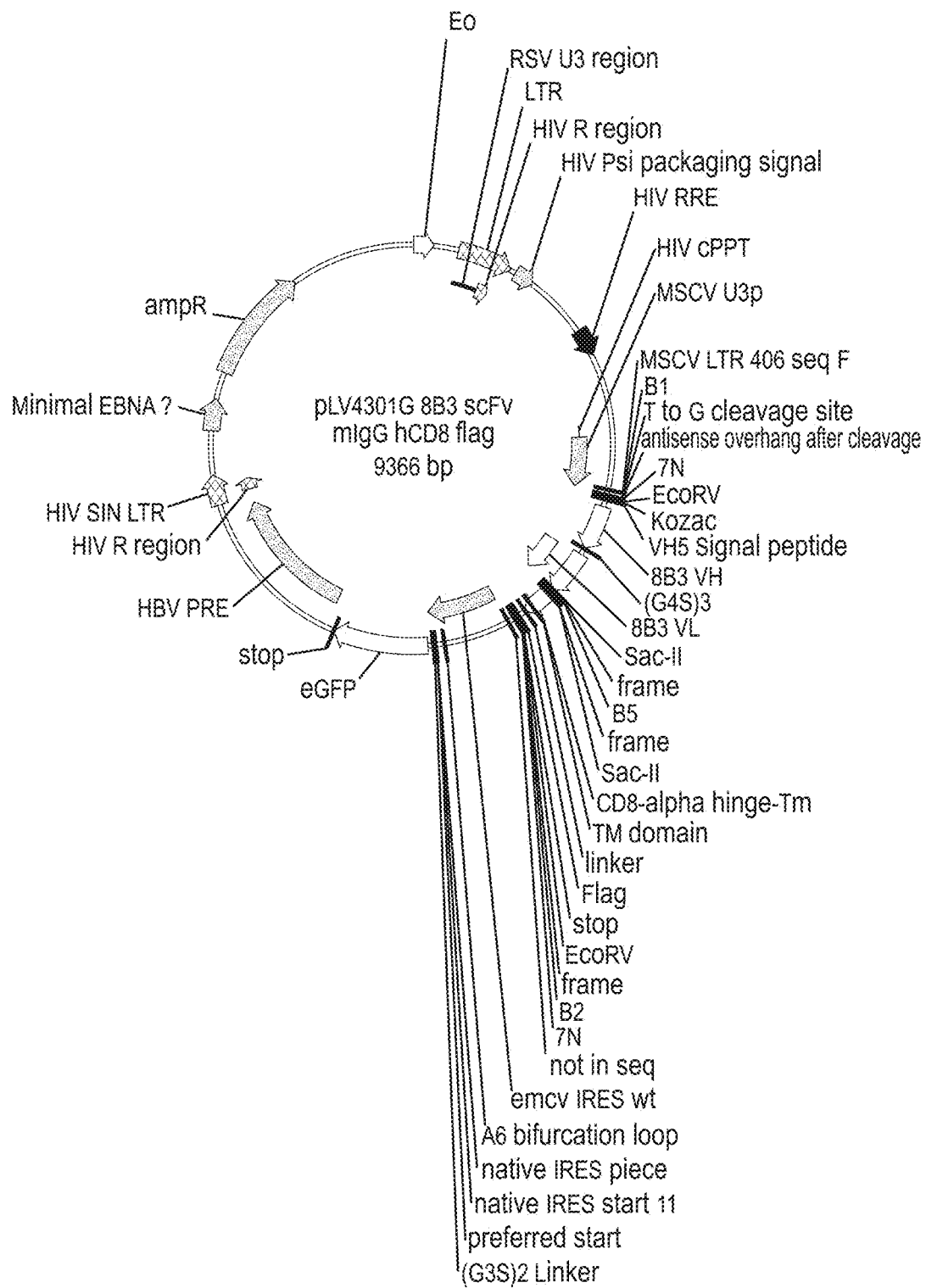
FIG. 36 illustrates a vector diagram of final vector used for lentiviral production, pLV4301G 8B3 scFv mIgG hCD8 flag.

TILs expanded against aMOLM14 or PBMC were also analyzed for metabolic profiles. Oxygen consumption rate (OCR) and extracellular acidification rate (ECAR) of TILs after expansion with irradiated PBMC feeders or aMOLM14 aAPCs were measured using a dual mitochondrial-glycolytic stress test. Briefly, cells were washed in assay medium (XF Assay Medium, Agilent Technologies, Santa Clara, Calif., USA), supplemented with 10 mM glucose, 1 mM sodium pyruvate, and 2 mM L-glutamine, at pH 7.4, and then $1\times10^5$ viable cells were plated onto an adhesive-coated (Cell-Tak™, Corning) XFp cell culture microplate. Plates were spun to adhere the cells to the plate, then equilibrated at 37° C. in a humidified, non-$CO_2$ incubator prior to analysis of cellular metabolism. Mitochondrial and glycolytic stress test experiments were performed using a Seahorse XFp Analyzer (Agilent Technologies, Santa Clara, Calif., USA), sequentially injecting the following compounds at specified intervals for simultaneous analysis of mitochondrial and glycolytic respiration of the cells: 1 µM oligomycin; 0.5 µM FCCP; 50 mM 2-deoxyglucose; and 0.5 µM each of rotenone and antimycin A. Results were analyzed using WAVE v2.3.0 software (Agilent Technologies, Santa Clara, Calif., USA) and GraphPad Prism v6.07 graphing software and are shown in FIG. 27 and FIG. 28, where points represent mean±SEM measured in triplicate. Both TILs grown with aMOLM14 aAPCs and PBMC feeders show similar oxphos and glycolysis behavior. This data suggests that aMOLM14 does not alter the metabolic programming of TILs when compared with PBMC feeders.

Example 5—Preparation of EM-3 Artificial Antigen Presenting Cells (aEM3 aAPCs)

EM-3 cells were obtained from Creative Bioarray, Inc. (Shirley, N.Y., USA). To develop an EM-3 based artificial APC, EM-3 cell lines were engineered with CD86, 4-1BBL, and antibody against IgG Fc region (Clone 7C12 or Clone 8B3). Human CD86 and human 4-1BBL/CD137 genes were cloned into commercially-available PLV430G and co-transfected with PDONR221 vectors (Invitrogen) using a lentiviral transduction method. The gateway cloning method was used as described in Katzen, *Expert Opin. Drug Disc.* 2007, 4, 571-589, to clone hCD86 and hCD137L genes onto the PLV430G and PDONR221 vectors. The 293T cell line was used for lentiviral production, and transduced to EM-3 cell lines. The transfected cells were sorted (S3e Cell Sorter, BioRad, Hercules, Calif., USA) using APC-conjugated CD86 and PE-conjugated CD137L to isolate and enrich the cells. The enriched cells were checked for purity by flow cytometry. Single-chain Fv (scFv) antibody clones designated 7C12 and 8B3 were generated against Fc of mouse IgG1, IgG2a and IgG2b (Viva Biotech Ltd., Chicago, Ill., USA). The amino acid sequences of these scFv clones are given in Table 7 (SEQ ID NO:27 and SEQ ID NO:28). The generated scFv clones were screened for Fc binding efficiency against OKT-3, engineered towards pLV4301G containing eGFP as co-reporter to produce lentivirus. The 293T cell line was used for packaging and lentiviral production. Engineered EM-3 (CD86/CD137L) cells were transduced using the lentiviral system and sorted using eGFP. EM37C12CD86CD137L and EM38B3CD86CD137L were regularly assessed for the consistent expression of each transduced molecule by flow cytometry.

TABLE 7

Amino acid sequences of scFv clones 7C12 and 8B3.

| Identifier (Description) | Sequence (One-Letter Amino Acid Symbols) | | | | | |
|---|---|---|---|---|---|---|
| SEQ ID NO: 27 (mFC-7C12 scFv) | QVQLVQSGGG | LVKPGGSLRL | SCAASGFNFN | DQYMSWIRQA | PGKGLEWVSF | ISGSGGTTYY | 60 |
| | TDSVKGRFTI | SRDNTKDSLY | LQMNSLTVED | TAVYYCARGG | NYYTSVGRGT | LVTVSAGGGG | 120 |
| | SGAPDIQMTQ | SPGTLSLSPG | ERAILSCRAS | QSVSGYLAWY | QQKPGQAPRL | LIYGASSRAT | 180 |
| | GIPDRFSGSG | SGTDFTLTIS | SLRPEDIGTY | YCKQYINAPF | TFGGGTKVEI | K | 231 |
| SEQ ID NO: 28 (mFC-8B3 scFv) | QVQLQQSGAE | VKKPGSSVKV | SCHASGGTFS | SYAISWVRQA | PGQGLEWMGW | ISPYNGNTDY | 60 |
| | AQKVQGRVTL | TTDTSTSTAY | MELRSLRSDD | TAVYYCATGG | GTWYSDLWGR | GTLVTVSAGG | 120 |
| | GGSGGGGSGG | GGSGAPEIVL | TQSPSTLSAS | VGDRVSITCR | ASQSIGGSLA | WYQQKPGKAP | 180 |
| | KLLISEASTL | ERGVPSRFSG | SGSGTDFTLT | ISSLQPEDVA | TYYCQKYNSV | PLTFGPGTKV | 240 |
| | EIK | | | | | | 243 |

A non-limiting protocol for preparation of aEM3 aAPCs, which may also be adapted for use with aMOLM14 aAPCs, is described in the following paragraphs.

Molecular cloning of plasmids of interest may be performed as follows. To generate DONR vector the following cocktail may be used: B site flanked PCR product or destination vector (e.g., Gateway-adapted lentivector) 50-100 µg; DONR vector (e.g., pDONR222) 50-100 µg; BR Clonase II (Life Technologies) 1 µL; and TE buffer ((1 mM Tris, 0.1 mM EDTA, pH 8.0, q.s. to bring volume to 5 µL). Incubate at room temperature for at least 1 hour. After incubation perform bacterial transformation either by heat shock method or electroporation. To generate destination vector, the following cocktail may be used: recombined pDONR vector (e.g., pDON222-geneX) 50-100 µg, destination vector (e.g., Gateway adapted lentivector) 50-100 µg, LR Clonase II (Life Technologies) 1 µL, and TE buffer ((1 mM Tris, 0.1 mM EDTA, pH 8.0, q.s. to bring volume to 5

µL). Incubate at room temperature for at least 1 hour. After incubation, perform bacterial transformation either by chemical competent transformation/heat shock method.

Transformation and selection of the cloned plasmid may be performed as follows. The chemical competent transformation method may be performed as follows. Prepare nutrient agar plates (LB-Lennox or YT) with antibiotic for selection. Ensure that Recovery Medium (supplied by Lucigen, Middleton, Wis., USA) is readily available at room temperature. Optionally, sterile culture tubes may be chilled on ice (e.g., 17 mm×100 mm tubes (14 mL tube)), one tube for each transformation reaction). Remove E. cloni cells (Lucigen) from an −80° C. freezer and thaw completely on wet ice (5-15 minutes). Optionally add 40 µL of E. cloni cells to the chilled culture tube. Add 1-4 µL of DNA sample to the 40 µL of cells. Flick with finger (do not pipet up and down to mix, which can introduce air bubbles and warm the cells). Incubate the cell/DNA mixture on ice for 30 minutes. Heat shock cells by placing the culture tubes in a 42° C. water bath for 45 seconds. Return the 1.7 mL tube or culture tubes to ice for 2 minutes. Add 350 µL room temperature Recovery Medium to the cells or 960 µL of room temperature Recovery Medium to the cells in the culture tube. Place the tubes in a shaking incubator at 250 rpm for 1 hour at 37° C. Plate up to 100% of the transformation mixture on LB-Lennox or YT agar plates containing the appropriate antibiotic. The plating volume may need to be optimized depending on DNA. Incubate the plates overnight at 37° C. Transformed clones can be further grown in any rich culture medium (e.g., LB or TB).

Colonies for Miniprep (Qiagen, Inc., Valencia, Calif., USA) may be grown as follows. After colonies have formed from plating recovered transformation reaction of DNA manipulation (e.g. LR reaction), add 1 mL desired TB/antibiotics into desired number of 2 mL Eppendorf microtubes with punctured caps. Pick desired number of colonies using ART LTS 20 µL soft pipette tip (VWR 89031-352) or 10 µL Denville tip. Place tip in 2 mL Eppendorf microtube with punctured cap. Cut the tip so that it fits in tube, close cap, and place tubes on shaker (purple 15 mL tube holder with VWR brand 15 mL tubes). Shake overnight (for no more than 16 hours) at 225 rpm/37° C. After overnight incubation, place each tip in a 1 mL tube in a ClavePak 96 plate from Denville with sterile water in it (to save the tip for making bacterial stock production after the plasmids are screened and selected). Perform Miniprep according to the Qiagen Mini prep kit protocol (Qiagen, Inc., Valencia, Calif., USA). Once the plasmids are eluted, restriction digestion is performed to select the right clones. After selecting the plasmids, use the tips saved from the same plasmids clone to grow the E. coli with the plasmid to make bacterial stock.

Lentiviral production may be performed as follows. The following media composition is prepared: 500 mL DMEM/F12 (Sigma); 25 mL FBS Heat Inactivated (HI) (Hyclone); 10 mM HEPES (Life Technologies); 1× Primocin (Invivogen); 1× Plasmocin (Invivogen); and 1× 2-mermactoethanol (Life Technologies). Harvest T75 flasks (Thermo Fisher Scientific) containing 90% confluent 293T cells. Aspirate media. Add 10 ml PBS, rinse gently and aspirate off. Add 2 mL TrypLE Express (Life Technologies) and evenly distribute it over the cell layer, let sit for 3-5 minutes at 37° C. (cell culture incubator). Add 10 mL media and disperse cells by pipetting up and down. Combine if there are multiple flasks. Count cells. If using a hemacytometer to determine concentration, cells/mL=(# counted cells×dilution factor×$10^4$). To split back into T75 flasks, determine the time at which the cells will need to be fully confluent and dilute accordingly. (Cells double every 16-18 hours, so 3 days=1/27 dilution). Generally, a multiplication factor of 2.5 per day may be used where confluence is $2 \times 10^5$ cells/cm$^2$. Bring volume up to 25 mL of media. To plate for titration of stocks, each well of the assay requires $5 \times 10^4$ cells in 0.4 mL of media. Adjust 293T cells to $2 \times 10^4$/mL in media. Plate 1 mL per well in a 24 well plate. For example, cells plated Monday may be infected on Tuesday and run on the flow cytometer on Friday, and cells plated Thursday are infected Friday and run on the flow cytometer on Monday. To plate for packaging transfections, seed T75 flasks with $6.8 \times 10^6$ cells one day before transfection or $1.7 \times 10^6$ cells on the morning of transfection. (Seeding on the day of transfection may reduce the variation in transfection efficiency). Bring volume in flask up to 25 mL with media. For example, flasks set up Monday are transfected Tuesday, and virus is collected on Thursday and Friday. In some cases (e.g., high titering constructs), the second collection can be omitted. To package lentiviral vectors, each T75 flask transfection requires 2 µg Baculo p35 plasmid (optional; only necessary if packaging a death gene), 2 µg VSV.G env plasmid (e.g., pMD2.G or PCIGO VSV-G); 4.7 µg Gag/polymerase plasmid (e.g., psPAX2 or pCMV-deltaR8.91), and 2.3 µg of the lentiviral vector described above. Determine the amount of VSV and R8.2/9.1 (+/−Baculo) plasmids needed for all samples (make a mixture of these DNAs if preparing many samples). Each T75 transfection requires 90 µL LipofectAmine 2000 (Thermo Fisher Scientific) in 2 mL Opti-MEM medium (Thermo Fisher Scientific). Make a mix containing enough Opti-Mem and LipofectAmine 2000 for all samples. Mix gently and let sit for 5 minutes at room temp, and label as tube A. For each transfection, add packaging DNA and specific lentiviral vector DNA to 500 µL room temperature Opti-MEM medium to a microtube and mix, and label as tube B. Add the 500 µL of DNA from tube B to the 2 mL of the LipofectAmine 2000 mix in tube A and mix gently, and incubate for 20-30 minutes at room temperature. Aspirate media from packaging flasks. Add the 2.5 mL of DNA/Lipofectamine complexes to 5 mL Opti-MEM medium and add to cells (do not pipet directly on cells since 293T cells are only semi adherent). Process plates in small groups to avoid drying. Incubate overnight and change media the next day in the morning. Collect the supernatant after 24 hours of media change. Supernatants can be harvested in a single collection, 48 hours after transfection or as 2 collections, 48 and 72 hours after transfection (in which case, harvests are pooled). If double collection is desired, collect supernatants by pipet on the first day, and replace with 20 mL of fresh media. To avoid flasks drying, work with only 5 flasks at a time. Keep collected supernatants at 4° C. until pooling the next day. Cool supernatants again on the following day and pool as appropriate. Spin the supernatants at 2000 rpm for 5 minutes to sediment any contaminating 293T cells. Filter harvested supernatants through a 0.45 µm or 0.8 µm filter unit containing a pre-filter disc. Use a large enough filtration unit so that the filtration speed is relatively fast. Store at 4° C. until ready to concentrate.

Virus may be concentrated using the PEG-it method (System Biosciences, Inc., Palo Alto, Calif. 94303) for longer-term storage at −80° C. Collect the supernatant from the transfection plates. Spin down the cell debris in the supernatant. The supernatant may also be filtered to completely remove any packaging cells. Add an amount of PEG-it solution equal to a quarter of the volume of supernatant to the supernatant. Incubate the suspension at 4° C. for overnight. Centrifuge at 3500 rpm (1500 g) at 4° C. for 30 minutes. Remove supernatant and centrifuge at 3500 rpm at 4° C. for 5 minutes. Remove remaining supernatant. Resuspend virus in desired amount of phosphate-buffered saline (PBS) and freeze aliquots at −80° C.

Transduction of cell line using lentivirus may be performed as follows. Adjust cells to be transduced to either: $1 \times 10^6$ suspension cells per well in 24 well plate (1 well per transduction) or 50% confluence for adherent cells (1 well per transduction) in 24 well plate. For suspended cells, adjust concentration of cells to $1 \times 10^7$/mL and plate 100 µL per well in 24 well plate (1 well per transduction). For adherent cells, plate to achieve 50% confluence on day of transduction based on cells/cm² (e.g., for 293T cells, confluence=$2 \times 10^5$/cm²). Total volume of transduction per well should be approximately 500 µL with 3-10 µg/mL Polybrene (Hexadimethrine bromide, Sigma-Aldrich Co., St. Louis, Miss., USA). The amount of concentrated virus added will depend on the MOI (multiplicity of infection) desired. A typical MOI is 10:1 but this may vary depending on cell type. The transfection well should contain 100 µL of standard media containing either $1 \times 10^6$ suspension cells or 50% confluent cells. For a MOI of 10:1 (e.g., virus activity is $1 \times 10^8$ IU/mL and the target is to infect $1 \times 10^6$ cells, then $1 \times 10^7$ virions or 100 µL of virus is needed). Add standard media to 500 µL. Add Polybrene to 3 µg/mL (primary cells) to 10 µg/mL (tumor cell lines). Spin plate(s) at 1800 rpm for 1.5 to 2 hours at 30° C. Incubate plate(s) at 37° C./5% $CO_2$ using a Tissue Culture incubator for 5 hours to overnight. Change media. After 72 hours of transduction, if enough cells are available, perform flow cytometric analysis to test the transduction efficiency.

Sorting of aAPCs may be performed as follows. Culture the cells in the media described above until the cell count reaches a minimum of 10-20 million. Take $1 \times 10^6$ cells for each condition and stain with the antibodies for the proteins transduced. Wash the cells and analyze by flow cytometry to test the stability of transduction. Once the expression of protein of interest has been analyzed and confirmed, prepare the rest of the cells for sorting. Sort the cells in an S3 sorter by gating on markers of interest. Culture the sorted cells using the media mentioned above. Before freezing the vial, test the stability of the protein expression of interest. Use Recovery cell culture Freezing media (Invitrogen), to make the cell bank of the same cells. Cells may be banked after each transduction and sorting procedure.

Nucleotide sequence information for the 7C12 and 8B3 scFv clones (SEQ ID NO:29 and SEQ ID NO:30) and their lentiviral vectors are given in Table 8. Sequences used for generation of the pLV4301G 7C12 scFv mIgG hCD8 flag vector are provided as SED IQ NO:31 to SEQ ID NO:34 and are depicted in FIG. 29 to FIG. 32. Sequences used for generation of the pLV4301G 8B3 scFv mIgG hCD8 flag vector are provided as SEQ ID NO:35 to SEQ ID NO:38 and are depicted in FIG. 33 to FIG. 36.

TABLE 8

Nucleotide sequences for preparation of lentivirus for transduction of aAPCs.

| Identifier (Description) | Sequence | |
|---|---|---|
| SEQ ID NO: 29 (mFC-7C12 scFv) | caggtgcagc tggtgcagtc tgggggaggc ttggtcaagc ctggagggtc cctgagactc | 60 |
| | tcctgtgcag cctctggatt caatttcaat gaccagtaca tgagttggat ccgccaggct | 120 |
| | ccagggaagg ggctggagtg ggtttcattc attagtggta gtggtggtac cacatactac | 180 |
| | acagactctg tgaagggccg gttcaccatc tccagggaca acaccaagga ctcattgtat | 240 |
| | ttgcaaatga acagcctgac agtcgaggac acggccgtgt actactgtgc gagaggaggg | 300 |
| | aattattata cttcggtggg ccggggcacc ctggtcaccg tctcggccgg tggcggcgga | 360 |
| | tctggcgcgc cagacatcca gatgacccag tctccaggca cctgtctttt gtctccaggg | 420 |
| | gaaagagcca tcctctcctg cagggccagt cagagtgtta gcggctacct agcctggtat | 480 |
| | caacagaaac ctggccaggc tcccaggctc ctcatctatg gtgcatccag cagggccact | 540 |
| | ggcatcccag acaggttcag tggcagtggg tctgggacag acttcactct caccatcagc | 600 |
| | agcctgcggc ctgaagatat tggaacatat tactgtcaac agtacattaa tgccccattc | 660 |
| | actttcggcg gcgggaccaa ggtggagatc aaa | 693 |
| SEQ ID NO: 30 (mFC-8B3 scFv) | caggtacagc tgcagcagtc aggggctgag gtgaagaagc ctggggtcctc ggtgaaggtc | 60 |
| | tcctgcaagg cttctggagg caccttcagc agctatgcta tcagctgggt gcgacaggcc | 120 |
| | cctggacaag ggcttgagtg gatgggatgg atcagcccct acaatggtaa cacagattat | 180 |
| | gcacagaagg tccagggcag agtcaccttg accacagaca tccacgag cacagcctac | 240 |
| | atggagctga ggagcctgag atccgacgac acggccgtgt attactgtgc gacaggtggc | 300 |
| | gggacctggt actccgatct ctgggggccgt ggcaccctgg tcaccgtctc ggccggtggc | 360 |
| | ggtggcagcg gcggtggtgg gtccggtggc ggcggatctg gcgcgccaga aattgtgctg | 420 |
| | actcagtctc cctccaccct gtctgcatct gtaggagaca gagtcagcat cacttgccgg | 480 |
| | gccagtcaga gtattggtgg gtcgttggcc tggtatcaac aaaagccagg gaaagcccct | 540 |
| | aagctcctga tctctactta gagagggggcg tcccatcaag attcagcggc | 600 |
| | agtggatctg ggacagattt cactctcacc atcaggagcc tgcagcctga agatgttgca | 660 |
| | acttattact gtcaaaaata taacagtgtc ccgctcactt tcggccctgg gaccaaggtg | 720 |
| | gagatcaaa | 729 |
| SEQ ID NO: 31 (destination vector pLV4301G) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |

TABLE 8-continued

Nucleotide sequences for preparation of
lentivirus for transduction of aAPCs.

| Identifier (Description) | Sequence | |
|---|---|---|
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg ggggagaatt agatcgcgat gggaaaaaat | 960 |
| | tcggttaagg ccagggggaa agaaaaaata taattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca agagaagag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac agagacagat | 2100 |
| | ccattcgatt agtgaacgga tctcgacggt atcggtttta aagaaaaagg gggattggg | 2160 |
| | gggtacagtg caggggaaag aatagtagac ataatagcaa cagacataca aactaaagaa | 2220 |
| | ttacaaaaac aaattacaaa aattcaaaat tttatcgatt ttatttagtc tccagaaaaa | 2280 |
| | gggggaatg aaagacccca cctgtaggtt tggcaagcta gcttaagtaa cgccattttg | 2340 |
| | caaggcatgg aaaatacata actgagaata gagaagttca gatcaaggtt aggaacagag | 2400 |
| | agacaggaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga aatgaccctg tgccttattt gaactaacca | 2580 |
| | atcagttcgc ttctcgcttc tgttcgcgcg cttctgctcc ccgagctcaa taaaagagcc | 2640 |
| | cacaaccccct cactcggcgc gccagtcctc cgatagactg cgtcgcccgg gtaccgatat | 2700 |
| | cacaagtttg tacaaaaaag ctgaacgaga acgtaaaat gatataaata tcaatatatt | 2760 |
| | aaattagatt ttgcataaaa aacagactac ataatactgt aaaacacaac atatccagtc | 2820 |
| | actatggcgg ccgcattagg cacccaggc tttacacttt atgcttccgg ctcgtataat | 2880 |
| | gtgtggattt tgagttagga tccgtcgaga ttttcaggag ctaaggaagc taaaatggag | 2940 |
| | aaaaaaatca ctggatatac caccgttgat atatcccaat ggcatcgtaa agaacatttt | 3000 |
| | gaggcatttc agtcagttgc tcaatgtacc tataaccaga ccgttcagct ggatattacg | 3060 |
| | gcctttttaa agaccgtaaa gaaaaataag cacaagtttt atccggcctt tattcacatt | 3120 |
| | cttgcccgcc tgatgaatgc tcatccggaa ttccgtatgg caatgaaaga cggtgagctg | 3180 |
| | gtgatatggg atagtgttca cccttgttac accgttttcc atgagcaaac tgaaacgttt | 3240 |
| | tcatcgctct ggagtgaata ccacgacgat ttccggcagt ttctacacat atattcgcaa | 3300 |
| | gatgtggcgt gttacggtga aaacctggcc tatttcccta aagggtttat tgagaatatg | 3360 |
| | tttttcgtct cagccaatcc ctgggtgagt ttcaccagtt ttgatttaaa cgtggccaat | 3420 |
| | atggacaact cttcgccccc cgttttcacc atgggcaaat attatacgca aggcgacaag | 3480 |
| | gtgctgatgc cgctggcgat tcaggttcat catgccgttt gtgatggctt ccatgtcggc | 3540 |
| | agaatgctta atgaattaca acagtactgc gatgagtggc agggcgggc gtaaatggat | 3600 |
| | ccggcttact aaaagccaga taacagtatg cgtattagcg cgctgatttt tgcggtataa | 3660 |
| | gaatatatac tgatatgtat acccgaagta tgtcaaaaag aggtatgcta tgaagcagcg | 3720 |
| | tattacagtg acagttgaca gcgacagcta tcagttgctc aaggcatata tgatgtcaat | 3780 |
| | atctccggtc tggtaagcac aaccatgcag aatgaagccc gtcgtctgcg tgccgaacgc | 3840 |
| | tggaaagcgg aaaatcagga agggatggct gaggtcgccc ggtttattga aatgaacggc | 3900 |
| | tcttttgctg acgagaacag gggctggtga aatgcagttt aaggtttaca cctataaaag | 3960 |
| | agagagccgt tatcgtctgt ttgtggatgt acagagtgat attattgaca cgcccgggcg | 4020 |
| | acggatggtg atccccctgg ccagtgcacg tctgctgtca gataaagtct cccgtgaact | 4080 |
| | ttacccggtg gtgcatatcg ggatgaaag ctggcgcatg atgaccaccg atatggccag | 4140 |
| | tgtgccggtc tccgttatcg gggaagaagt ggctgatctc agccaccgcg aaaatgacat | 4200 |
| | caaaaacgcc attaacctga tgttctgggg aatataaatg tcaggctccc ttatacacag | 4260 |
| | ccagtctgca ggtcgaccat agtgactgga tatgttgtgt tttacagtat tatgtagtct | 4320 |
| | gttttttatg caaaatctaa tttaatatat tgatatttat atcattttac gtttctcgtt | 4380 |
| | cagctttctt gtacaaagtg gtgattcgag ttaattaagt taacgaattc cccccctcc | 4440 |
| | cctccccccc cctaacgtt actggccgaa gccgcttgga ataaggccgg tgtgcgtttg | 4500 |
| | tctatatgtt attttccacc atattgccgt cttttggcaa tgtgagggcc cggaaacctg | 4560 |
| | gccctgtctt cttgacgagc attcctaggg gtctttcccc tctcgccaaa ggaatgcaag | 4620 |
| | gtctgttgaa tgtcgtgaag gaagcagttc ctctggaagc ttcttgaaga caaacaacgt | 4680 |
| | ctgtagcgac cctttgcagg cagcggaacc ccccacctgg cgacaggtgc ctctgcggcc | 4740 |
| | aaaagccacg tgtataagat acacctgcaa aggcggcaca accccagtgc cacgttgtga | 4800 |
| | gttggatagt tgtggaaaga gtcaaatggc tctcctcaag cgtattcaac aaggggctga | 4860 |
| | aggatgccca gaagtaccc cattgtatgg gatcgatct gggcctcgg tgcacatgct | 4920 |
| | ttacatgtgt ttagtcgagg ttaaaaaacg tctaggcccc ccgaaccacg ggactggt | 4980 |
| | tttcctttga aaaacacgat gataatatgg ccacaaccat gggaggcgga agcggcggag | 5040 |
| | gctcccctcg aggcaccatg gtgagcaagg gcgaggagct gttcaccggg gtggtgccca | 5100 |
| | tcctggtcga gctggacggc gacgtaaacg gccacaagtt cagcgtgtcc ggcgagggcg | 5160 |
| | agggcgatgc cacctacggc aagctgaccc tgaagttcat ctgcaccacc ggcaagctgc | 5220 |

TABLE 8-continued

Nucleotide sequences for preparation of
lentivirus for transduction of aAPCs.

| Identifier (Description) | Sequence | |
|---|---|---|
| | ccgtgccctg gcccaccctc gtgaccaccc tgacctacgg cgtgcagtgc ttcagccgct | 5280 |
| | accccgacca catgaagcag cacgacttct tcaagtccgc catgcccgaa ggctacgtcc | 5340 |
| | aggagcgcac catcttcttc aaggacgacg gcaactacaa gacccgcgcc gaggtgaagt | 5400 |
| | tcgagggcga caccctggtg aaccgcatcg agctgaaggg catcgacttc aaggaggacg | 5460 |
| | gcaacatcct ggggcacaag ctggagtaca actacaacag ccacaacgtc tatatcatgg | 5520 |
| | ccgacaagca gaagaacggc atcaaggtga acttcaagat ccgccacaac atcgaggacg | 5580 |
| | gcagcgtgca gctcgccgac cactaccagc agaacacccc catcggcgac ggccccgtgc | 5640 |
| | tgctgcccga caaccactac ctgagcaccc agtccgccct gagcaaagac cccaacgaga | 5700 |
| | agcgcgatca catggtcctg ctggagttcg tgaccgccgc cgggatcact ctcggcatgg | 5760 |
| | acgagctgta caagtaacgc gtcccgggtc tagagctagc ggtaccatgc attacgtagt | 5820 |
| | cgacgactta attaagctag cctagtgcca tttgttcagt ggttcgtagg gctttcccc | 5880 |
| | actgtttggc tttcagttat atggatgatg tggtattggg ggcaagtct gtacagcatc | 5940 |
| | ttgagtccct ttttaccgct gttaccaatt ttcttttgtc tttgggtata catttaaacc | 6000 |
| | ctaacaaaac aaagagatgg ggttactctc taaattttat gggttatgtc attggatgtt | 6060 |
| | atgggtcctt gccacaagaa cacatcatac aaaaaatcaa agaatgtttt agaaaacttc | 6120 |
| | ctattaacag gcctattgat tggaaagtat gtcaacgaat tgtgggtctt ttgggttttg | 6180 |
| | ctgccccttt tacacaatgt ggttatcctg cgttgatgcc tttgtatgca tgtattcaat | 6240 |
| | ctaagcaggc tttcactttc tcgccaactt acaaggcctt tctgtgtaaa caatacctga | 6300 |
| | acctttaccc cgttgcccgg caacggccag gtctgtgcca agtgtttgct gacgcaaccc | 6360 |
| | ccactggctg gggcttggtc atgggccatc agcgcatgcg tggaaccttt tcggctcctc | 6420 |
| | tgccgatcca tactgcggaa ctcctagccg cttgttttgc tcgcagcagg tctggagcaa | 6480 |
| | acattatcgg gactgataac tctgttgtcc tatcccgcaa atatacatcg tttccatggc | 6540 |
| | tgctaggctg tgctgccaac tggatcctgc gcgggacgtc ctttgtttac gtcccgtcgg | 6600 |
| | cgctgaatcc tgcggacgac ccttctcggg gtcgcttggg actctctcgt cccctctcc | 6660 |
| | gtctgccgtt ccgaccgacc acggggcgca cctctcttta cgcggactcc ccgtctgtgc | 6720 |
| | cttctcatct gccgaccgt gtgcacttcg cttcacctct gcacgtcgca tggagaccac | 6780 |
| | cgtgaacgcc caccaaatat tgcccaaggt cttacataag aggactcttg gactctcagc | 6840 |
| | aatgtcaacg accgacctta aggcatactt caaagactgt ttgtttaaag actgggagga | 6900 |
| | gttggggag gagattaggt taaaggtctt tgtactagga ggctgtaggc ataaattggt | 6960 |
| | ctgcgcacca gcaccatggc gcaatcacta gagcggggta cctttaagac caatgactta | 7020 |
| | caaggcagct gtagatctta gccactttt aaaagaaaag ggggactgg aagggctaat | 7080 |
| | tcactcccaa cgaagacaag atctgctttt tgcttgtact gggtctctct ggttagacca | 7140 |
| | gatctgagcc tgggagctct ctggctaact agggaaccca ctgcttaagc ctcaataaag | 7200 |
| | cttgccttga gtgcttcaag tagtgtgtgc ccgtctgttg tgtgactctg gtaactagag | 7260 |
| | atccctcaga ccccttttagt cagtgtggaa aatctctagc agtagtagtt catgtcatct | 7320 |
| | tattattcag tatttataac ttgcaaagaa atgaatatca gagagtgaga aagcttgtt | 7380 |
| | tattgcagct tataatggtt acaaataaag caatagcatc acaaatttca caaataaagc | 7440 |
| | attttttttca ctgcattcta gttgtggttt gtccaaactc atcaatgtat cttatcatgt | 7500 |
| | ctggctctag ctatcccgcc cctaactccg cccatcccgc cctaactcc gcccagttcc | 7560 |
| | gcccattctc cgccccatgg ctgactaatt tttttatttt atgcagaggc cgaggccgga | 7620 |
| | tcccttgagt ggctttcatc ctggagcaga ctttgcagtc tgtggactgc aacacaacat | 7680 |
| | tgcctttatg tgtaactctt ggctgaagct cttacaccaa tgctggggga catgtacctc | 7740 |
| | ccaggggccc aggaagacta cgggaggcta caccaacgtc aatcagaggg gcctgtgtag | 7800 |
| | ctaccgataa gcggaccctc aagagggcat tagcaatagt gtttataagg cccccttgtt | 7860 |
| | aattcttgaa gacgaaaggg cctcgtgata cgcctatttt tataggttaa tgtcatgata | 7920 |
| | ataatggttt cttagacgtc aggtggcact tttcggggaa atgtgcgcgg aacccctatt | 7980 |
| | tgtttatttt tctaaataca ttcaaatatg tatccgctca tgagacaata accctgataa | 8040 |
| | atgcttcaat aatattgaaa aaggaagagt atgagtattc aacatttccg tgtcgcccttt | 8100 |
| | attccctttt ttgcggcatt ttgccttcct gttttttgctc acccagaaac gctggtgaaa | 8160 |
| | gtaaaagatg ctgaagatca gttgggtgca cgagtgggtt acatcgaact ggatctcaac | 8220 |
| | agcggtaaga tccttgagag ttttcgcccc gaagaacgtt ttccaatgat gagcactttt | 8280 |
| | aaagttctgc tatgtggcgc ggtattatcc cgtgttgacg ccgggcaaga gcaactcggt | 8340 |
| | cgccgcatac actattctca gaatgacttg gttgagtact caccagtcac agaaaagcat | 8400 |
| | cttacggatg gcatgacagt aagagaatta tgcagtgctg ccataaccat gagtgataac | 8460 |
| | actgcggcca acttacttct gacaacgatc ggaggaccga aggagctaac gcttttttg | 8520 |
| | cacaacatgg ggatcatgt aactcgcctt gatcgttggg aaccggagct gaatgaagcc | 8580 |
| | ataccaaacg acgagcgtga caccacggta cctgcacaa tggcaacaac gttgcgcaaa | 8640 |
| | ctattaactg gcgaactact tactctagct tcccggcaac aattaataga ctggatggag | 8700 |
| | gcggataaag ttgcaggacc acttctgcgc tcggccttc cggctggctg gtttattgct | 8760 |
| | gataaatctg gagccggtga gcgtgggtct cgcggtatca ttgcagcact ggggccagat | 8820 |
| | ggtaagccct cccgtatcgt agttatctac acgacggga gtcaggcaac tatgatgaa | 8880 |
| | cgaaatagac agatcgctga gataggtgcc tcactgatta gcattggta actgtcagac | 8940 |
| | caagtttact catatatact ttagattgat ttaaaactc atttttaatt taaaaggatc | 9000 |
| | taggtgaaga tccttttttga taatctcatg accaaaatcc cttaacgtga gttttcgttc | 9060 |
| | cactgagcgt cagacccgt agaaaagatc aaaggatctt cttgagatcc tttttttctg | 9120 |
| | cgcgtaatct gctgcttgca aacaaaaaaa ccaccgctac cagcggtggt ttgtttgccg | 9180 |
| | gatcaagagc taccaactct ttttccgaag gtaactggct tcagcagagc gcagatacca | 9240 |
| | aatactgtcc ttctagtgta gccgtagtta ggccaccact tcaagaactc tgtagcaccg | 9300 |
| | cctacatacc tcgctctgct aatcctgtta ccagtggctg ctgccagtgg cgataagtcg | 9360 |
| | tgtcttaccg ggttggactc aagacgatag ttaccggata aggcgcagcg gtcgggctga | 9420 |
| | acggggggtt cgtgcacaca gcccagcttg gagcgaacga cctacaccga actgagatac | 9480 |
| | ctacagcgtg agcattgaga aagcgccacg cttcccgaag ggagaaaggc ggacaggtat | 9540 |
| | ccggtaagcg gcagggtcgg aacaggagag cgcacgaggg agcttccagg gggaaacgcc | 9600 |
| | tggtatcttt atagtcctgt cgggtttcgc cacctctgac ttgagcgtcg atttttgtga | 9660 |

TABLE 8-continued

Nucleotide sequences for preparation of
lentivirus for transduction of aAPCs.

| Identifier (Description) | Sequence | |
|---|---|---|
| | tgctcgtcag gggggcggag cctatggaaa aacgccagca acgcggcctt tttacggttc | 9720 |
| | ctggccttt gctggccttt ttgaagctgt ccctgatggt cgtcatctac ctgcctggac | 9780 |
| | agcatggcct gcaacgcggg catcccgatg ccgccggaag cgagaagaat cataatgggg | 9840 |
| | aaggccatcc agcctcgcgt cg | 9862 |
| SEQ ID NO: 32 (donor vector 1, pMK 7c12 anti mFC scFV CoOp ECORV SacII L1R5) | ctaaattgta agcgttaata ttttgttaaa attcgcgtta aattttgtt aaatcagctc | 60 |
| | atttttaac caataggccg aaatcggcaa aatcccttat aaatcaaaag aatagaccga | 120 |
| | gatagggttg agtggccgct acagggcgct cccattcgcc attcaggctg cgcaactgtt | 180 |
| | gggaagggcg tttcggtgcg ggcctcttcg ctattacgcc agctggcgaa agggggatgt | 240 |
| | gctgcaaggc gattaagttg ggtaacgcca gggttttccc agtcacgacg ttgtaaaacg | 300 |
| | acggccagtg agcgcgacgt aatacgactc actatagggc gaattgaagg aaggccgtca | 360 |
| | aggccgcata aataatgatt ttattttgac tgatagtgac ctgttcgttg caacaaattg | 420 |
| | atgagcaatg ctttttttata atgccaactt tgtacaaaaa agctgaacga tatcgccacc | 480 |
| | atgggcagca cagccattct ggccctgctg ctggcagtgc tgcagggcgt gtcagctcag | 540 |
| | gtgcagctgg tgcagtctgg cggcggactc gtgaaacctg gcggcagcct gagactgagc | 600 |
| | tgtgccgcca gcggcttcaa cttcaacgac cagtacatga gctggatccg gcaggcccct | 660 |
| | ggcaagggac tggaatgggt gtccttcatc agcggcagcg cggcaccac ctactacacc | 720 |
| | gatagcgtga agggccggtt caccatcagc cggacaacaa ccaaggacga cctgtacctg | 780 |
| | cagatgaaca gcctgaccgt ggaagatacc gccgtgtact actgcgccag aggcggcaat | 840 |
| | tactacacca gcgtgggcag aggcaccctc gtgacagtgt ctgctggcgg aggcggatca | 900 |
| | ggcggcggag gatcaggggg aggcggaagc ggagcacccg atatccagat gacacagagc | 960 |
| | cccggcaccc tgtctctgag ccctggcgaa agagccatcc tgagctgcag agccagccag | 1020 |
| | agcgtgtccg gatacctggc ttggtatcag cagaagcccg gccaggcccc cagactgctg | 1080 |
| | atctatggcg ccaggaggag agccacaggc atccccgata gattcagcgg ctctggcagc | 1140 |
| | ggcaccgact tcaccctgac aatcagctcc ctgcggcccg aggacatcgg cacctactat | 1200 |
| | tgcaagcagt acatcaacgc cccccttcacc ttcggcggag gcaccaaggt ggaaatcaag | 1260 |
| | ccgcgggcca actttgtata caaaagtgga acgagaaacg taaaatgata taaatatcaa | 1320 |
| | tatattaaat tagattttgc ataaaaaaca gactacataa tactgtaaaa cacaacatat | 1380 |
| | ccagtcacta tgaatcaact acttagatgg tattagtgac ctgtactggg cctcatgggc | 1440 |
| | cttcctttca ctgcccgctt ccagtcggg aaacctgtcg tgccagctgc attaacatgg | 1500 |
| | tcatagctgt ttccttgcgt attgggcgct ctccgcttcc tcgctcactg actcgctgcg | 1560 |
| | ctcggtcgtt cgggtaaagc ctggggtgcc taatgagcaa aaggccagca aaaggccagga | 1620 |
| | aaccgtaaaa aggccgcgtt gctggcgttt ttccataggc tccgcccccc tgacgagcat | 1680 |
| | cacaaaaatc gacgctcaag tcagaggtgg cgaaacccga caggactata agataccag | 1740 |
| | gcgtttcccc ctggaagctc cctcgtgcgc tctcctgttc cgaccctgcc gcttaccgga | 1800 |
| | tacctgtccg ccttttctccc ttcgggaagc gtggcgcttt ctcatagctc acgctgtagg | 1860 |
| | tatctcagtt cggtgtaggt cgttcgctcc aagctgggct gtgtgcacga acccccccgtt | 1920 |
| | cagcccgacc gctgcgcctt atccggtaac tatcgtcttg agtccaaccc ggtaagacac | 1980 |
| | gacttatcgc cactggcagc agccactggt aacaggatta gcagagcgag gtatgtaggc | 2040 |
| | ggtgctacag agttcttgaa gtggtggcct aactacggct acactagaag aacagtattt | 2100 |
| | ggtatctgcg ctctgctgaa gccagttacc ttcggaaaaa gagttggtag ctcttgatcc | 2160 |
| | ggcaaacaaa ccaccgctgg tagcggtggt ttttttgttt gcaagcagca gattacgcgc | 2220 |
| | agaaaaaaag gatctcaaga agatccttg atcttttcta cggggtctga cgctcagtgg | 2280 |
| | aacgaaaact cacgttaagg gattttggtc atgagattat caaaaaggat cttcacctag | 2340 |
| | atccttttaa attaaaaatg aagttttaaa tcaatctaaa gtatatatga gtaaacttgg | 2400 |
| | tctgacagtt attagaaaaa ttcatccagc agacgataaa acgcaatacg ctggctatcc | 2460 |
| | ggtgccgcaa tgccatacag caccagaaaa cgatccgccc attcgccgcc cagttcttcc | 2520 |
| | gcaatatcac gggtggccag cgcaatatcc tgataacgat ccgccacgcc cagacggccg | 2580 |
| | caatcaataa agccgctaaa acggccattt tccaccataa tgttcggcag cacgcatca | 2640 |
| | ccatgggtca ccaccagatc ttcgccatcc ggcatgctcg ctttcagacg cgcaaacagc | 2700 |
| | tctgccggtg ccaggccctg atgttcttca tccagatcat cctgatccac caggcccgct | 2760 |
| | tccatacggg tacgcgcacg ttcaatacga tgtttcgcct gatgatcaaa cggacaggtc | 2820 |
| | gccgggtcca gggtatgcag acgacgcatg gcatcgcca taatgctcac tttttctgcc | 2880 |
| | ggcgccagat ggctagacag cagatcctga cccggcactt cgcccagcag cagccaatca | 2940 |
| | cggcccgctt cggtcaccac atccagcacc gccgcacacg gaacaccgt ggtggccagc | 3000 |
| | cagctcagac gcgccgcttc atcctgcagc tcgttcagcg caccgctcag atcggtttc | 3060 |
| | acaaacagca ccggacgacc ctgcgcgctc agcgaaaca ccgccgcatc agacgagcca | 3120 |
| | atggtctgct gcgcccaatc atagccaaac agacgttcca cccacgctgc cggctaccc | 3180 |
| | gcatgcaggc catcctgttc aatcatactc ttccttttc aatattattg aagcatttat | 3240 |
| | cagggttatt gtctcatgag cggatacata tttgaatgta tttagaaaaa taaacaaata | 3300 |
| | ggggttccgc gcacatttcc ccgaaaagtg ccac | 3334 |
| SEQ ID NO: 33 (donor vector 2, pMK hCD8a scaffold TN L5 L2) | ctaaattgta agcgttaata ttttgttaaa attcgcgtta aattttgtt aaatcagctc | 60 |
| | atttttaac caataggccg aaatcggcaa aatcccttat aaatcaaaag aatagaccga | 120 |
| | gatagggttg agtggccgct acagggcgct cccattcgcc attcaggctg cgcaactgtt | 180 |
| | gggaagggcg tttcggtgcg ggcctcttcg ctattacgcc agctggcgaa agggggatgt | 240 |
| | gctgcaaggc gattaagttg ggtaacgcca gggttttccc agtcacgacg ttgtaaaacg | 300 |
| | acggccagtg agcgcgacgt aatacgactc actatagggc gaattgaagg aaggccgtca | 360 |
| | aggccgcata aataatgatt ttattttgac tgatagtgac ctgttcgttg caacaaattg | 420 |
| | atgagcaatg ctttttttata atgccaact ttgtataca aagtgcccc cggacaacaa | 480 |
| | cccctgcccc cagacctcct acccccagccc ctacaattgc cagccagcct ctgagcctga | 540 |
| | ggcccgaggc ttgtagacct gctgctggcg gagccgtgca ccagaggga ctggatttcg | 600 |
| | cctgcgacat ctacatctgg gccctctgg ccggcacatg tggcgtgctg ctgctgagcc | 660 |
| | tcgtgatcac cctgtactgc ggctccacca gcggctccgg caagcccggc tctggcgagg | 720 |

TABLE 8-continued

Nucleotide sequences for preparation of lentivirus for transduction of aAPCs.

| Identifier (Description) | Sequence | | | | | |
|---|---|---|---|---|---|---|
| | gctccaccag | cggcgactac | aaggacgacg | atgacaagta | ataggatatc | ggttcagctt | 780 |
| | tcttgtacaa | agttggcatt | ataagaaagc | attgcttatc | aatttgttgc | aacgaacagg | 840 |
| | tcactatcag | tcaaaataaa | atcattattt | ctgggcctca | tgggccttcc | tttcactgcc | 900 |
| | cgctttccag | tcggaaaacc | tgtcgtgcca | gctgcattaa | catggtcata | gctgtttcct | 960 |
| | tgcgtattgg | gcgctctccg | cttcctcgct | cactgactcg | ctgcgctcgg | tcgttcggt | 1020 |
| | aaagcctggg | gtgcctaatg | agcaaaaggc | cagcaaaagg | ccaggaaccg | taaaaaggcc | 1080 |
| | gcgttgctgg | cgttttcca | taggctccgc | ccccctgacg | agcatcacaa | aaatcgacgc | 1140 |
| | tcaagtcaga | ggtggcgaaa | cccgacagga | ctataaagat | accaggcgtt | tccccctgga | 1200 |
| | agctccctcg | tgcgctctcc | tgttccgacc | ctgccgctta | ccggatacct | gtccgccttt | 1260 |
| | ctcccttcgg | gaagcgtggc | gctttctcat | agctcacgct | gtaggtatct | cagttcggtg | 1320 |
| | taggtcgttc | gctccaagct | gggctgtgtg | cacgaacccc | ccgttcagcc | cgaccgctgc | 1380 |
| | gccttatccg | gtaactatcg | tcttgagtcc | aacccggtaa | gacacgactt | atcgccactg | 1440 |
| | gcagcagcca | ctggtaacag | gattagcaga | gcgaggtatg | taggcggtgc | tacagagttc | 1500 |
| | ttgaagtggt | ggcctaacta | cggctacact | agaagaacag | tatttggtat | ctgcgctctg | 1560 |
| | ctgaagccag | ttaccttcgg | aaaaagagtt | ggtagctctt | gatccggcaa | acaaaccacc | 1620 |
| | gctggtagcg | gtggttttt | tgtttgcaag | cagcagatta | cgcgcagaaa | aaaaggatct | 1680 |
| | caagaagatc | ctttgatctt | ttctacgggg | tctgacgctc | agtggaacga | aaactcacgt | 1740 |
| | taagggattt | tggtcatgag | attatcaaaa | aggatcttca | cctagatcct | tttaaattaa | 1800 |
| | aaatgaagtt | ttaaatcaat | ctaaagtata | tatgagtaaa | cttggtctga | cagttattag | 1860 |
| | aaaaattcat | ccagcagacg | ataaaacgca | atacgctggc | tatccggtgc | cgcaatgcca | 1920 |
| | tacagcacca | gaaaacgatc | cgcccattcg | ccgcccagtt | cttccgcaat | atcacgggtg | 1980 |
| | gccagcgcaa | tatcctgata | acgatccgcc | acgcccagac | ggccgcaatc | aataaagccg | 2040 |
| | ctaaaacggc | cattttccac | cataatgttc | ggcaggcacg | catcaccatg | ggtcaccacc | 2100 |
| | agatcttcgc | catccggcat | gctcgctttc | agacgcgcaa | acagctctgc | cggtgccagg | 2160 |
| | ccctgatgtt | cttcatccag | atcatcctga | tccaccaggc | ccgcttccat | acgggtacgc | 2220 |
| | gcacgttcaa | tacgatgttt | cgcctgatga | tcaaacggac | aggtcgccgg | gtccagggta | 2280 |
| | tgcagacgac | gcatggcatc | cgccataatg | ctcactttt | ctgccggcgc | cagatggcta | 2340 |
| | gacagcagat | cctgacccgg | cacttcgccc | agcagcagcc | aatcacggcc | cgcttcggtc | 2400 |
| | accacatcca | gcaccgccgc | acacggaaca | ccggtggtgg | ccagccagct | cagacgcgcc | 2460 |
| | gcttcatcct | gcagctcgtt | cagcgcaccg | ctcagatcgg | ttttcacaaa | cagcaccgga | 2520 |
| | cgaccctgcg | cgctcagacg | aaacaccgcc | gcatcagagc | agccaatggt | ctgctgcgcc | 2580 |
| | caatcatagc | caaacagacg | ttccacccac | gctgccgggc | taccgcatg | caggccatcc | 2640 |
| | tgttcaatca | tactcttcct | tttcaatat | tattgaagca | tttatcaggg | ttattgtctc | 2700 |
| | atgagcggat | acatatttga | atgtatttag | aaaaataaac | aaatagggt | tccgcgcaca | 2760 |
| | tttccccgaa | aagtgccac | | | | | 2779 |
| SEQ ID NO: 34 (Final vector used for lentiviral production, pLV4301G 7C12 scFV mIgG hCD8 flag) | cgataaccct | aattcgatag | catatgcttc | ccgttgggta | acatatgcta | ttgaattagg | 60 |
| | gttagtctgg | atagtatata | ctactacccg | ggaagcatat | gctaccgtt | tagggttcac | 120 |
| | cggtgatgcc | ggccacgatg | cgtccggcgt | agaggatcta | atgtgagtta | gctcactcat | 180 |
| | taggcacccc | aggctttaca | cttttatgctt | ccggctcgta | tgttgtgtgg | aattgtgagc | 240 |
| | ggataacaat | ttcacacagg | aaacagctat | gaccatgatt | acgccaagcg | cgcaattaac | 300 |
| | cctcactaaa | gggaacaaaa | gctggagctg | caagcttaat | gtagtcttat | gcaatactct | 360 |
| | tgtagtcttg | caacatggta | acgatgagtt | agcaacatgc | cttacaagga | gagaaaaagc | 420 |
| | accgtgcatg | ccgattggtg | gaagtaaggt | ggtacgtcg | tgccttatta | ggaaggcaac | 480 |
| | agacgggtct | gacatggatt | ggacgaacca | ctgaattgcc | gcattgcaga | gatattgtat | 540 |
| | ttaagtgcct | agctcgatac | ataaacgggt | ctctctggtt | agaccagatc | tgagcctggg | 600 |
| | agctctctgg | ctaactaggg | aacccactgc | ttaagcctca | ataaagcttg | ccttgagtgc | 660 |
| | ttcaagtagt | gtgtgcccgt | ctgttgtgtg | actctggtaa | ctagagatcc | ctcagaccca | 720 |
| | tttagtcagt | gtggaaaatc | tctagcagtg | gcgcccgaac | agggacttga | aagcgaaagg | 780 |
| | gaaaccagag | gagctctctc | gacgcaggac | tcggcttgct | gaagcgcgca | cggcaagagg | 840 |
| | cgaggggcgg | cgactggtga | gtacgccaaa | aattttgact | agcggaggct | agaaggagag | 900 |
| | agatgggtgc | gagagcgtca | gtattaagcg | ggggagaatt | agatcgcgat | gggaaaaaat | 960 |
| | tcggttaagg | ccagggggaa | agaaaaaata | taattaaaa | catatagtat | gggcaagcag | 1020 |
| | ggagctagaa | cgattcgcag | ttaatcctgg | cctgttagaa | acatcagaag | gctgtagaca | 1080 |
| | aatactggga | cagctacaac | catcccttca | gacaggatca | gaagaactta | gatcattata | 1140 |
| | taatacagta | gcaaccctct | attgtgtgca | tcaaggata | gagataaaag | acaccaagga | 1200 |
| | agctttagac | aagatagagg | aagagcaaaa | caaaagtaag | accaccgcac | agcaagcggc | 1260 |
| | cgctgatctt | cagacctgga | ggaggagata | tgagggacaa | ttggagaagt | gaattatata | 1320 |
| | aatataaagt | agtaaaaatt | gaaccattag | gagtagcacc | caccaaggca | aagagaagag | 1380 |
| | tggtgcagag | agaaaaaaga | gcagtgggaa | taggagcttt | gttccttggg | ttcttgggag | 1440 |
| | cagcaggaag | cactatgggc | gcagcgtcaa | tgacgctgac | ggtacaggcc | agacaattat | 1500 |
| | tgtctggtat | agtgcagcag | cagaacaatt | tgctgagggc | tattgaggcg | caacagcatc | 1560 |
| | tgttgcaact | cacagtctgg | ggcatcaagc | agctccaggc | aagaatcctg | gctgtggaaa | 1620 |
| | gatacctaaa | ggatcaacag | ctcctgggga | tttggggttg | ctctggaaaa | ctcatttgca | 1680 |
| | ccactgctgt | gccttggaat | gctagttgga | gtaataaatc | tctggaacag | atttggaatc | 1740 |
| | acacgacctg | gatggagtgg | gacagagaaa | ttaacaatta | cacaagctta | atacactcct | 1800 |
| | taattgaaga | atcgcaaaac | cagcaagaaa | agaatgaaca | agaattattg | gaattagata | 1860 |
| | aatgggcaag | tttgtggaat | tggtttaaca | taacaaattg | gctgtggtat | ataaaattat | 1920 |
| | tcataatgat | agtaggaggc | ttggtaggtt | taagaatagt | ttttgctgta | ctttctatag | 1980 |
| | tgaatagagt | taggcaggga | tattcaccat | tatcgtttca | gacccacctc | ccaacccga | 2040 |
| | ggggacccga | caggcccgaa | ggaatagaag | aagaaggtgg | agagagagac | agagacagat | 2100 |
| | ccattcgatt | agtgaacgga | tctcgacggt | atcggtttta | aagaaaagg | gggattggg | 2160 |
| | gggtacagtg | caggggaaag | aatagtagac | ataatagcaa | cagacataca | aactaaagaa | 2220 |
| | ttacaaaaac | aaattacaaa | aattcaaaat | tttatcgatt | ttatttagtc | tccagaaaaa | 2280 |

TABLE 8-continued

Nucleotide sequences for preparation of
lentivirus for transduction of aAPCs.

| Identifier (Description) | Sequence | |
|---|---|---|
| | gggggaatg aaagacccca cctgtaggtt tggcaagcta gcttaagtaa cgccattttg | 2340 |
| | caaggcatgg aaaatacata actgagaata gagaagttca gatcaaggtt aggaacagag | 2400 |
| | agacaggaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga aatgaccctg tgccttattt gaactaacca | 2580 |
| | atcagttcgc ttctcgcttc tgttcgcgcg cttctgctcc ccgagctcaa taaaagagcc | 2640 |
| | cacaacccct cactcggcgc gccagtcctc cgatagactg cgtcgcccgg gtaccgatat | 2700 |
| | caccaacttt gtacaaaaaa gctgaacgat atcgccacca tgggcagcac agccattctg | 2760 |
| | gccctgctgc tggcagtgct gcaggcgtg tcagctcagg tgcagctggt gcagtctggc | 2820 |
| | ggcggactcg tgaaacctgg cggcagcctg agactgagct gtgccgccag cggcttcaac | 2880 |
| | ttcaacgacc agtacatgag ctggatccgg caggccctg gcaagggact ggaatgggtg | 2940 |
| | tccttcatca gcggcagcgg cggcaccacc tactacaccg atagcgtgaa gggccggttc | 3000 |
| | accatcagcc gggacaacac caaggacagc ctgtacctgc agatgaacag cctgaccgtg | 3060 |
| | gaagataccg ccgtgtacta ctgcgccaga ggcggcaatt actacaccag cgtgggcaga | 3120 |
| | ggcaccctcg tgacagtgtc tgctggcgga gtcggcggag gcggcggagg atcagggga | 3180 |
| | ggcggaagcg gagcacccga tatccagatg acacagagcc ccggcaccct gtctctgagc | 3240 |
| | cctggcgaaa gagccatcct gagctgcaga gccagccaga gcgtgtccgg ataccctgct | 3300 |
| | tggtatcagc agaagcccgc ccaggccccc agactgctga tctatggcgc caggaggaga | 3360 |
| | gccacaggca tccccgatag attcagcggc tctggcagcg gcaccgactt caccctgaca | 3420 |
| | atcagctccc tgcggcccga ggacatcggc acctactatt gcaagcagta catcaacgcc | 3480 |
| | cccttcacct tcggcggagg caccaaggtg gaaatcaagc cgcgggccaa ctttgtatac | 3540 |
| | aaaagtggcc cgcggacaac aaccccctgcc cccagacctc ctaccccagc ccctacaatt | 3600 |
| | gccagccagc ctctgagcct gaggcccgag gcttgtagac ctgctgctgg cggagccgtg | 3660 |
| | cacaccagag gactggattt cgcctgcgac atctacatct gggccctct ggccggcaca | 3720 |
| | tgtggcgtgc tgctgctgag cctcgtgatc accctgtact gcggctccac cagcggctcc | 3780 |
| | ggcaagcccg gctctggcga gggctccacc agcggcgact acaaggacga cgatgacaag | 3840 |
| | taataggata tcggttcagc tttcttgtac aaagttggga ttcgagttaa ttaagttaac | 3900 |
| | gaattccccc cctctccctc ccccccccct aacgttactg gccgaagccg cttggaataa | 3960 |
| | ggccggtgtg cgtttgtcta tatgttattt tccaccatat tgccgtcttt tggcaatgtg | 4020 |
| | agggcccgga aacctgcccc tgtcttcttg acgagcattc ctaggggtct ttcccctctc | 4080 |
| | gccaaaggaa tgcaaggtct gttgaatgtc gtgaaggaag cagttcctct ggaagcttct | 4140 |
| | tgaagacaaa caacgtctgt agcgaccctt tgcaggcagc ggaaccccc acctggcgac | 4200 |
| | aggtgcctct gcggccaaaa gccacgtgta agatacac ctgcaaaggc ggcacaaccc | 4260 |
| | cagtgccacg ttgtgagttg gatagttgtg gaaagagtca aatggctctc ctcaagcgta | 4320 |
| | ttcaacaagg gctgaagga tgcccagaag gtaccccatt gtatgggatc tgatctgggg | 4380 |
| | cctcggtgca catgctttac atgtgtttag tcgaggttaa aaacgtcta ggccccccga | 4440 |
| | accacgggga cgtggttttc cttttgaaaaa cacgatgata atatggccac aaccatggga | 4500 |
| | ggcggaagcg gcggaggctc ccctcgaggc accatggtga gcaagggcga ggagctgttc | 4560 |
| | accggggtgg tgcccatcct ggtcgagctg gacggcgacg taaacggcca caagttcagc | 4620 |
| | gtgtccggcg agggcgaggg cgatgccacc tacggcaagc tgaccctgaa gttcatctgc | 4680 |
| | accaccggca agctgcccgt gccctggccc accctcgtga ccaccctgac ctacggcgtg | 4740 |
| | cagtgcttca gccgctaccc cgaccacatg aagcagcacg acttcttcaa gtccgccatg | 4800 |
| | cccgaaggct acgtccagga gcgcaccatc ttcttcaagg acgacggcaa ctacaagacc | 4860 |
| | cgcgccgagg tgaagttcga gggcgacacc ctggtgaacc gcatcgagct gaagggcatc | 4920 |
| | gacttcaagg aggacggcaa catcctgggg cacaagctgg agtacaacta caacagccac | 4980 |
| | aacgtctata tcatggccga caagcagaag aacggcatca aggtgaactt caagatccgc | 5040 |
| | cacaacatcg aggacggcag cgtgcagctc gccgaccact accagcagaa cacccccatc | 5100 |
| | ggcgacggcc ccgtgctgct gcccgacaac cactacctga gcacccagtc cgccctgagc | 5160 |
| | aaagacccca acgagaagcg cgatcacatg gtcctgctgg agttcgtgac cgccgccggg | 5220 |
| | atcactctcg gcatggacga gctgtacaag taacgcgtcc cgggtctaga gctagcggta | 5280 |
| | ccatgcatta cgtagtcgac gacttaatta agctagccta gtgccatttg ttcagtgtt | 5340 |
| | cgtagggctt tccccactg tttggctttc agttatatgg atgatgtggt attgggggcc | 5400 |
| | aagtctgtac agcatcttga gtcccttttt accgctgtta ccaattttct tttgtcttg | 5460 |
| | ggtatacatt taaaccctaa caaaacaaag atggggtt actctctaaa ttttatgggt | 5520 |
| | tatgtcattg gatgttatgt gtccttgcca caagaacaca tcatacaaaa aatcaaagaa | 5580 |
| | tgttttagaa aacttcctat taacaggcct attgattgga aagtatgtca acgaattgtg | 5640 |
| | ggtcttttgg gttttgctgc ccctttttaca caatgtggtt atcctgcgtt gatgcctttg | 5700 |
| | tatgcatgta ttcaatctaa gcaggctttc actttctcgc caacttacaa ggcctttctg | 5760 |
| | tgtaaacaat acctgaacct ttaccccgtt gcccggcaac ggccaggtct gtgccaagtg | 5820 |
| | tttgctgacg caaccccac tggctgggc ttggtcatgg gccatcagcg catgcgtgga | 5880 |
| | accttttcgg ctcctctgcc gatccatact ccggaactcc tagccgcttg ttttgctctt | 5940 |
| | agcaggtctg gagcaaacat tatcgggact gataactctg ttgtcctatc ccgcaaatat | 6000 |
| | acatcgtttc catggctgct aggctgtgct gccaactgga tcctgcgcgg gacgtccttt | 6060 |
| | gtttacgtcc cgtcggcgct gaatcctgcg gacgaccctt ctcggggtcg cttgggactc | 6120 |
| | tctcgtcccc ttctccgtct gccgttccga ccgaccacga ggcgcacctc tctttacgcg | 6180 |
| | gactcccgt ctgtgccttc tcatctgccg accgtgtgc acttcgcttc acctctgcac | 6240 |
| | gtcgcatgga gaccaccgtg aacgcccacc aaatattgcc caagtctta cataagagga | 6300 |
| | ctcttggact ctcagcaatg tcaacgaccg accttgaggc atacttcaaa gactgtttgt | 6360 |
| | ttaaagactg ggaggagttg ggggaggaga ttaggttaaa ggtctttgta ctaggaggct | 6420 |
| | gtaggcataa attggtctgc gcaccagcac catgcgcaa tcactagagc ggggtacctt | 6480 |
| | taagaccaat gacttacaag gcagctgtag atcttagcca cttttaaaa gaaaggggg | 6540 |
| | gactgaagg gctaattcac tcccaacgaa gacaagatct gcttttgct tgtactgggt | 6600 |
| | ctctctggtt agaccagatc tgagcctggg agctctctgg ctaactaggg aacccactgc | 6660 |
| | ttaagcctca ataaagcttg ccttgagtgc ttcaagtagt gtgtgcccgt ctgttgtgtg | 6720 |

TABLE 8-continued

Nucleotide sequences for preparation of
lentivirus for transduction of aAPCs.

| Identifier (Description) | Sequence | |
|---|---|---|
| | actctggtaa ctagagatcc ctcagaccct tttagtcagt gtggaaaatc tctagcagta | 6780 |
| | gtagttcatg tcatcttatt attcagtatt tataacttgc aaagaaatga atatcagaga | 6840 |
| | gtgagaggaa cttgtttatt gcagcttata atggttacaa ataaagcaat agcatcacaa | 6900 |
| | atttcacaaa taaagcattt ttttcactgc attctagttg tggtttgtcc aaactcatca | 6960 |
| | atgtatctta tcatgtctgg ctctagctat cccgccccta actccgccca tcccgcccct | 7020 |
| | aactccgccc agttccgccc attctccgcc ccatggctga ctaatttttt ttatttatgc | 7080 |
| | agaggccgag gccggatccc ttgagtggct ttcatcctgg agcagacttt gcagtctgtg | 7140 |
| | gactgcaaca caacattgcc tttatgtgta actcttggct gaagctctta caccaatgct | 7200 |
| | gggggacatg tacctcccag gggcccagga agactacggg aggctacacc aacgtcaatc | 7260 |
| | agagggggcct gtgtagctac cgataagcgg accctcaaga gggcattagc aatagtgttt | 7320 |
| | ataaggcccc cttgttaatt cttgaagacg aaagggcctc gtgatacgcc tattttttata | 7380 |
| | ggttaatgtc atgataataa tggtttctta gacgtcaggt ggcacttttc ggggaaatgt | 7440 |
| | gcgcggaacc cctatttgtt tatttttcta aatacattca aatatgtatc cgctcatgag | 7500 |
| | acaataaccc tgataaatgc ttcaataata ttgaaaaagg aagagtatga gtattcaaca | 7560 |
| | tttccgtgtc gcccttattc ccttttttgc ggcattttgc cttcctgttt ttgctcaccc | 7620 |
| | agaaacgctg gtgaaagtaa aagatgctga agatcagttg ggtgcacgag tgggttacat | 7680 |
| | cgaactggat ctcaacagcg gtaagatcct tgagagtttt cgccccgaag aacgttttcc | 7740 |
| | aatgatgagc acttttaaag ttctgctatg tggcgcggta ttatcccgtg ttgacgccgg | 7800 |
| | gcaagagcaa ctcggtcgcc gcatacacta ttctcagaat gacttggttg agtactcacc | 7860 |
| | agtcacagaa aagcatctta cggatggcat gacagtaaga gaattatgca gtgctgccat | 7920 |
| | aaccatgagt gataacactg cggccaactt acttctgaca acgatcggag gaccgaagga | 7980 |
| | gctaaccgct tttttgcaca catgggggga tcatgtaact cgccttgatc gttgggaacc | 8040 |
| | ggagctgaat gaagccatac caaacgacga gcgtgacacc acgatgcctg cagcaatggc | 8100 |
| | aacaacgttg cgcaaactat taactggcga actacttact ctagcttccc ggcaacaatt | 8160 |
| | aatagactgg atggaggcgg ataaagttgc aggaccactt ctgcgctcgg cccttccggc | 8220 |
| | tggctggttt attgctgata atctggagcc cggtgagcgt gggtctcgcg gtatcattgc | 8280 |
| | agcactgggg ccagatggta agccctcccg tatcgtagtt atctacacga cggggagtca | 8340 |
| | ggcaactatg gatgaacgaa atagacagat cgctgagata ggtgcctcac tgattaagca | 8400 |
| | ttggtaactg tcagaccaag tttactcata tatactttag attgatttaa aacttcattt | 8460 |
| | ttaatttaaa aggatctagg tgaagatcct ttttgataat ctcatgacca aaatccctta | 8520 |
| | acgtgagttt tcgttccact gagcgtcaga ccccgtagaa aagatcaaag gatcttcttg | 8580 |
| | agatccttt tttctgcgcg taatctgctg cttgcaaaca aaaaaaccac cgctaccagc | 8640 |
| | ggtggtttgt ttgccggatc aagagctacc aactcttttt ccgaaggtaa ctggcttcag | 8700 |
| | cagagcgcag ataccaaata ctgtccttct agtgtagccg tagttaggcc accacttcaa | 8760 |
| | gaactctgta gcaccgccta catacctcgc tctgctaatc ctgttaccag tggctgctgc | 8820 |
| | cagtggcgat aagtcgtgtc ttaccgggtt ggactcaaga cgatagttac cggataaggc | 8880 |
| | gcagcggtcg ggctgaacgg ggggttcgtg cacacagccc agcttggagc gaacgaccta | 8940 |
| | caccgaactg agatacctac agcgtgagca ttgagaaagc gccacgcttc ccgaagggag | 9000 |
| | aaaggcggac aggtatccgg taagcggcag ggtcggaaca ggagagcgca cgagggagct | 9060 |
| | tccagggggga aacgcctggt atctttatag tcctgtcggg tttcgccacc tctgacttga | 9120 |
| | gcgtcgattt ttgtgatgct cgtcaggggg gcggagccta tggaaaaacg ccagcaacgc | 9180 |
| | ggccttttta cggttcctgg ccttttgctg gccttttga gctgtccct gatggtcgtc | 9240 |
| | atctacctgc ctggacagca tggcctgcaa cgcgggcatc ccgatgccgc cggaagcgag | 9300 |
| | aagaatcata atggggaagg ccatccagcc tcgcgtcg | 9338 |
| SEQ ID NO: 35 (destination vector, pLV4301G) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgactcat gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaaacatg cttacaagga gagaaaaagc | 420 |
| | accgtgcatg ccgattggtg gaagtaaggt ggtacgatcg tgccttatta gaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg gggagaaatt agatcgcgat gggaaaaaat | 960 |
| | tcggttaagg ccagggggga agaaaaaata taattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaacctct attgtgtgca tcaaaggata gagataaaag acaccaaggaa | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca aagagaagag | 1380 |
| | tggtgcagag agaaaaaaga gcagtgggaa ttaggagctg gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |

TABLE 8-continued

Nucleotide sequences for preparation of
lentivirus for transduction of aAPCs.

| Identifier (Description) | Sequence | |
|---|---|---|
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac agagacagat | 2100 |
| | ccattcgatt agtgaacgga tctcgacggt atcggtttta aaagaaaagg ggggattggg | 2160 |
| | gggtacagtg caggggaaag aatagtagac ataatagcaa cagacataca aactaaagaa | 2220 |
| | ttacaaaaac aaattacaaa aattcaaaat tttatcgatt ttatttagtc tccagaaaaa | 2280 |
| | gggggggaatg aaagacccca cctgtaggtt tggcaagcta gcttaagtaa cgccattttg | 2340 |
| | caaggcatgg aaaatacata actgagaata agaaagttca gatcaaggtt aggaacagag | 2400 |
| | agacaggaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga aatgaccctg tgccttattt gaactaacca | 2580 |
| | atcagttcgc ttctcgcttc tgttcgcgcg cttctgcctc ccgagctcaa taaaagagcc | 2640 |
| | cacaacccct cactcggcgc gccagtcctc cgatagactg cgtcgcccgg gtaccgatat | 2700 |
| | cacaagtttg tacaaaaaag ctgaacgaga acgtaaaat gatataaata tcaatatatt | 2760 |
| | aaattagatt ttgcataaaa aacagactac ataatactgt aaaacacaac atatccagtc | 2820 |
| | actatgcgg ccgcattagg caccccaggc tttacatttt atgcttccgg ctcgtataat | 2880 |
| | gtgtggattt tgagttagga tccgtcgaga ttttcaggag ctaaggaagc taaaatggag | 2940 |
| | aaaaaaatca ctggatatac caccgttgat atatcccaat ggcatcgtaa agaacatttt | 3000 |
| | gaggcatttc agtcagttgc tcaatgtacc tataaccaga ccgttcagct ggatattacg | 3060 |
| | gcctttttaa agaccgtaaa gaaaaataag cacaagtttt atccggcctt tattcacatt | 3120 |
| | cttgcccgcc tgatgaatgc tcatccggaa ttccgtatgg caatgaaaga cggtgagctg | 3180 |
| | gtgatatggg atagtgttca cccttgttac accgttttcc atgagcaaac tgaaacgttt | 3240 |
| | tcatcgctct ggagtgaata ccacgacgat ttccggcagt ttctacacat atattcgcaa | 3300 |
| | gatgtggcgt gttacggtga aaacctggcc tatttcccta aagggtttat tgagaatatg | 3360 |
| | tttttcgtct cagccaatcc ctgggtgagt ttcaccagtt ttgatttaaa cgtggccaat | 3420 |
| | atggacaact tcttcgcccc cgtttcacc atgggcaaat attatacgca aggcgacaag | 3480 |
| | gtgctgatgc cgctggcgat tcaggttcat catgccgttt gtgatggctt ccatgtcggc | 3540 |
| | agaatgctta atgaattaca acagtactgc gatgagtggc agggcgggc gtaaatggat | 3600 |
| | ccggcttact aaaagccaga taacagtatg cgtatttgcg cgctgatttt tgcggtataa | 3660 |
| | gaatatatac tgatatgtat acccgaagta tgtcaaaaag aggtatgcta tgaagcagcg | 3720 |
| | tattacagtg acagttgaca gcgacagcta tcagttgctc aaggcatata tgatgtcaat | 3780 |
| | atctccggtc tggtaagcac aaccatgcag aatgaagccc gtcgtctgcg tgccgaacgc | 3840 |
| | tggaaagcgg aaaatcagga agggatggct gaggtcgccc ggtttattga aatgaacggc | 3900 |
| | tcttttgctg acgagaacag gggctggtga atgcagtttt aaggtttaca cctataaaag | 3960 |
| | agagagccgt tatcgtctgt ttgtggatgt acagagtgat attattgaca cgcccgggcg | 4020 |
| | acggatggtg atccccctgg ccagtgcacg tctgctgtca gataaagtct cccgtgaact | 4080 |
| | ttacccggtg gtgcatatcg gggatgaaag ctggcgcatg atgaccaccg atatggccag | 4140 |
| | tgtgccggtc tccgttatcg gggaagaagt ggctgatctc agccaccgcg aaaatgacat | 4200 |
| | caaaaacgcc attaacctga tgttctgggg aatataaatg tcaggctccc ttatacacag | 4260 |
| | ccagtctgca ggtcgaccat agtgactgga tatgttgtgt tttacagtat tatgtagtct | 4320 |
| | gttttttatg caaaatctaa tttaatatat tgatatttat atcattttac gtttctcgtt | 4380 |
| | cagctttctt gtacaaagtg gtgattcgag ttaattaagt taacgaattc ccccctctc | 4440 |
| | cctcccccc ccctaacgtt actggccgaa gccgcttgga ataaggccgg tgtgcgtttg | 4500 |
| | tctatatgtt attttccacc atattgccgt cttttggcaa tgtgagggcc cggaaacctg | 4560 |
| | gccctgtctt cttgacgagc attcctaggg gtcttccc tctcgccaaa ggaatgcaag | 4620 |
| | gtctgttgaa tgtcgtgaag gaagcagttc ctctggaagc ttcttgaaga caaacaacgt | 4680 |
| | ctgtagcgac cctttgcagg cagcggaacc ccccacctgg cgacaggtgc ctctgcggcc | 4740 |
| | aaaagccacg tgtataagat acacctgcaa aggcggcaca accccagtgc cacgttgtga | 4800 |
| | gttggatagt tgtggaaaga gtcaaatggc tctcctcaag cgtattcaac aaggggctga | 4860 |
| | aggatgccca gaaggtaccc cattgtatgg gatctgatct ggggcctcgg tgcacatgct | 4920 |
| | ttacatgtgt ttagtcgagg ttaaaaaacg tctaggcccc ccgaaccacg gggacggtggt | 4980 |
| | tttcctttga aaaacacgat gataatatgg ccacaaccat gggaggcgga agcggcggag | 5040 |
| | gctcccctcg aggcaccatg gtgagcaagg gcgaggagct gttcaccggg gtggtgccca | 5100 |
| | tcctggtcga gctggacggc gacgtaaacg gccacaagtt cagcgtgtcc ggcgagggcg | 5160 |
| | agggcgatgc cacctacggc aagctgaccc tgaagttcat ctgcaccacc ggcaagctgc | 5220 |
| | ccgtgccctg gcccaccctc gtgaccaccc tgacctacgg cgtgcagtgc ttcagccgct | 5280 |
| | accccgacca catgaagcag cacgacttct tcaagtccgc catgcccgaa ggctacgtcc | 5340 |
| | aggagcgcac catcttcttc aaggacgacg gcaactacaa gacccgcgcc gaggtgaagt | 5400 |
| | tcgagggcga caccctggtg aaccgcatcg agctgaaggg catcgacttc aaggaggacg | 5460 |
| | gcaacatcct ggggcacaag ctggagtaca actacaacag ccacaacgtc tatatcatgg | 5520 |
| | ccgacaagca gaagaacggc atcaaggtga acttcaagat ccgccacaac atcgaggacg | 5580 |
| | gcagcgtgca gctcgccgac cactaccagc agaacacccc catcggcgac ggccccgtgc | 5640 |
| | tgctgcccga caaccactac ctgagcaccc agtccgccct gagcaaagac cccaacgaga | 5700 |
| | agcgcgatca catggtcctg ctggagttcg tgaccgccgc cgggatcact ctcggcatgg | 5760 |
| | acgagctgta caagtaacgc gtcccgggtc tagagctagc ggtaccatgc attacgtagt | 5820 |
| | cgacgactta attaagctag cctagtgcca tttgttcagg ggttcgctta gctttcccc | 5880 |
| | actgtttggc tttcagttat atggatgatg tggtattggg ggcaagtct gtacagcatc | 5940 |
| | ttgagtccct ttttaccgct gttaccaatt ttcttttgtc tttgggtata catttaaacc | 6000 |
| | ctaacaaaac aaagagatgg ggttactctc taaatttat gggttatgtc attggatgtt | 6060 |
| | atgggtccctt gccacaagaa cacatcatac aaaaaatcaa agaatgtttt agaaaacttc | 6120 |
| | ctattaacag gcctattgat tggaaagtat gtcaacgaat tgtgggtctt ttgggttttg | 6180 |

TABLE 8-continued

Nucleotide sequences for preparation of
lentivirus for transduction of aAPCs.

| Identifier (Description) | Sequence | |
|---|---|---|
| | ctgcccctttt tacacaatgt ggttatcctg cgttgatgcc tttgtatgca tgtattcaat | 6240 |
| | ctaagcaggc tttcactttc tcgccaactt acaaggcctt tctgtgtaaa caatacctga | 6300 |
| | acctttaccc cgttgcccgg caacggccag gtctgtgcca agtgtttgct gacgcaaccc | 6360 |
| | ccactggctg gggcttggtc atgggccatc agcgcatgcg tggaacctttt tcggctcctc | 6420 |
| | tgccgatcca tactgcggaa ctcctagccg cttgttttgc tcgcagcagg tctggagcaa | 6480 |
| | acattatcgg gactgataac tctgttgtcc tatcccgcaa atatacatcg tttccatggc | 6540 |
| | tgctaggctg tgctgccaac tggatcctgc gcgggacgtc cttttgtttac gtcccgtcgg | 6600 |
| | cgctgaatcc tgccgacgac ccttctcggg gtcgcttggg actctctcgt cccctttctcc | 6660 |
| | gtctgccgtt ccgaccgacc acggggcgca cctctcttta cgcggactcc ccgtctgtgc | 6720 |
| | cttctcatct gccgaccgcgt gtgcacttcg cttcacctct gcacgtcgca tggagaccac | 6780 |
| | cgtgaacgcc caccaaatat tgcccaaggt cttacataag aggactcttg gactctcagc | 6840 |
| | aatgtcaacg accgaccttg aggcatactt caaagactgt ttgtttaaag actgggagga | 6900 |
| | gttgggggag gagattaggt taaaggtctt tgtactagga ggctgtaggc ataaattggt | 6960 |
| | ctgcgcacca gcaccatggc gcaatcacta gagcggggta cctttaagac caatgactta | 7020 |
| | caaggcagct gtagatctta gccacttttt aaaagaaaag gggggactgg aagggctaat | 7080 |
| | tcactcccaa cgaagacaag atctgctttt tgcttgtact gggtctctct ggttagacca | 7140 |
| | gatctgagcc tgggagctct ctggctaact agggaaccca ctgcttaagc ctcaataaag | 7200 |
| | cttgccttga gtgcttcaag tagtgtgtgc ccgtctgttg tgtgactctg gtaactagag | 7260 |
| | atccctcaga cccttttagt cagtgtggaa aatctctagc agtagtagtt catgtcatct | 7320 |
| | tattattcag tatttataac ttgcaaagaa atgaatatca gagagtgaga ggaacttgtt | 7380 |
| | tattgcagct tataatggtt acaaataaag caatagcatc acaaatttca caaataaagc | 7440 |
| | atttttttca ctgcattcta gttgtggttt gtccaaactc atcaatgtat cttatcatgt | 7500 |
| | ctggctctag ctatcccgcc cctaactccg cccatcccgc cctaactccg gcccagttcc | 7560 |
| | gcccattctc cgccccatgg ctgactaatt ttttttattt atgcagaggc cgaggccgga | 7620 |
| | tcccttgagt ggctttcatc ctggagcaga ctttgcagtc tgtggactgc aacacaacat | 7680 |
| | tgcctttatg tgtaactctt ggctgaagct cttacaccaa tgctggggga catgtacctc | 7740 |
| | ccaggggccc aggaagacta cgggaggcta caccaacgtc aatcagaggg gcctgtgtag | 7800 |
| | ctaccgataa gcggaccctc aagagggcat tagcaatagt gtttataagg cccccttgtt | 7860 |
| | aattcttgaa gacgaaaggg cctcgtgata cgcctatttt tataggttaa tgtcatgata | 7920 |
| | ataatggttt cttagacgtc aggtggcact tttcgggaa atgtgcgcgg aacccctatt | 7980 |
| | tgtttatttt tctaaataca ttcaaatatg tatccgctca tgagacaata accctgataa | 8040 |
| | atgcttcaat aatattgaaa aaggaagagt atgagtattc aacatttccg tgtcgccctt | 8100 |
| | attcccttttt tgcggcatt ttgccttcct gttttttgctc acccagaaac gctggtgaaa | 8160 |
| | gtaaaagatg ctgaagatca gttgggtgca cgagtgggtt acatcgaact ggatctcaac | 8220 |
| | agcggtaaga tccttgagag ttttcgcccc gaagaacgtt ttccaatgat gagcactttt | 8280 |
| | aaagttctgc tatgtggcgc ggtattatcc cgtgttgacg ccgggcaaga gcaactcggt | 8340 |
| | cgccgcatac actattctca gaatgacttg gttgagtact caccagtcac agaaaagcat | 8400 |
| | cttacgatg gcatgacagt aagagaatta tgcagtgctg ccataaccat gagtgataac | 8460 |
| | actgcggcca acttacttct gacaacgatc ggaggaccga aggagctaac cgctttttttg | 8520 |
| | cacaacatgg gggatcatgt aactcgcctt gatcgttggg aaccggagct gaatgaagcc | 8580 |
| | ataccaaacg acgagcgtga caccacgatg cctgcagcaa tggcaacaac gttgcgcaaa | 8640 |
| | ctattaactg gcgaactact tactctagct tcccggcaac aattaataga ctggatggag | 8700 |
| | gcggataaag ttgcaggacc acttctgcgc tcggcccttc cggctggctg gtttattgct | 8760 |
| | gataaatctg gagccggtga gcgtgggtct cgcggtatca ttgcagcact ggggccagat | 8820 |
| | ggtaagccct cccgtatcgt agttatctac acgacgggga gtcaggcaac tatggatgaa | 8880 |
| | cgaaatagac agatcgctga gataggtgcc tcactgatta gcattggta actgtcagac | 8940 |
| | caagtttact catatatact ttagattgat ttaaaacttc atttttaatt taaaaggatc | 9000 |
| | taggtgaaga tcctttttga taatctcatg accaaaatcc cttaacgtga ttttcgttcc | 9060 |
| | cactgagcgt cagacccccg taaaaagatc aaaggatctt cttgagatcc ttttttttctg | 9120 |
| | cgcgtaatct gctgcttgca acaaaaaaaa ccaccgctac cagcggtggt ttgtttgccg | 9180 |
| | gatcaagagc taccaactct ttttccgaag gtaactggct tcagcagagc gcagatacca | 9240 |
| | aatactgtcc ttctagtgta gccgtagtta ggccaccact tcaagaactc tgtagcaccg | 9300 |
| | cctacatacc tcgctctgct aatcctgtta ccagtggctg ctgccagtgg cgataagtcg | 9360 |
| | tgtcttaccg ggttggactc aagacgatag ttaccggata aggcgcagcg gtcgggctga | 9420 |
| | acggggggtt cgtgcacaca gcccagcttg gagcgaacga cctacaccga actgagatac | 9480 |
| | ctacagcgtg agcattgaga aagcgccacg cttcccgaag ggagaaaggc ggacaggtat | 9540 |
| | ccggtaagcg gcagggtcgg aacaggagag cgcacgaggg agcttccagg gggaaacgcc | 9600 |
| | tggtatcttt atagtcctgt cgggtttcgc cacctctgac ttgagcgtcg atttttgtga | 9660 |
| | tgctcgtcag ggggggcggag cctatggaaa aacgccagca acgcggcctt tttacggttc | 9720 |
| | ctggcctttt gctgcctttt ttgaagctgt ccctgatggt cgtcatctac ctgcctggac | 9780 |
| | agcatggcct gcaacgcggg catcccgatg ccgccggaag cgagaagaat cataatggggg | 9840 |
| | aaggccatcc agcctcgcgt cg | 9862 |
| SEQ ID NO: 36 (donor vector 1, pMK 8B3 anti mFC scFV CoOp ECORV SacII L1R5) | ctaaattgta agcgttaata ttttgttaaa attcgcgtta aattttttgtt aaatcagctc | 60 |
| | atttttttaac caataggccg aaatcggcaa aatcccttat aaatcaaaag aatagaccga | 120 |
| | gatagggttg agtggccgct acagggcgct cccattcgcc attcaggctg cgcaactgtt | 180 |
| | gggaagggcg tttcggtgcg ggcctcttcg ctattacgcc agctggcgaa aggggggatgt | 240 |
| | gctgcaaggc gattaagttg ggtaacgcca ggggtttccc agtcacgacg ttgtaaaacg | 300 |
| | acggccagtg agcgcgacgt aatacgact cactataggg gaattgaagg aaggccgtca | 360 |
| | aggccgcata aataatgatt ttattttgac tgatagtgac ctgttcgttg caacaaattg | 420 |
| | atgagcaatg cttttttata tgccaacttt gtacaaaaaa gctgaacga tatcgccacc | 480 |
| | atgggcagca cagccattct ggccctgctg ctggcagtgc tgcagggcgt gtcagctcag | 540 |
| | gtgcagctgc agcagtctgg cgccgaagtg aagaaacccg gcagcagcgt gaaggtgtcc | 600 |
| | tgcaaggcta gcggcggcac cttcaggagc tacgcccttt cttgggtgcg ccaggcccct | 660 |

US 10,415,015 B2

TABLE 8-continued

Nucleotide sequences for preparation of
lentivirus for transduction of aAPCs.

| Identifier (Description) | Sequence | |
|---|---|---|
| | ggacagggcc tggaatggat gggctggatc agcccctaca acggcaacac cgactacgcc | 720 |
| | cagaaagtgc agggcagagt gaccctgacc accgacacca gcacctccac cgcctacatg | 780 |
| | gaactgcgga gcctgagaag cgacgacacc gccgtgtact actgtgccac aggcggcgga | 840 |
| | acctggtaca gcgatctgtg gggcagaggc accctcgtga cagtgtctgc tggcggcgga | 900 |
| | ggatctggcg gaggcggaag tggcggggga ggaagcggag cacctgagat cgtgctgacc | 960 |
| | cagagcccta gcacactgag cgccagcgtg ggcgacagag tgtccatcac ctgtagagcc | 1020 |
| | agccagagca tcggaggcag cctggcctgg tatcagcaga agcctggcaa ggcccccaag | 1080 |
| | ctgctgatct ctgaggccag caccctggaa agaggcgtgc ccagcagatt ttccggcagc | 1140 |
| | ggctctggca ccgacttcac cctgacaatc agcagcctgc agcccgagga cgtggccacc | 1200 |
| | tactactgcc agaagtacaa cagcgtgccc ctgaccttcg gccctggcac caaggtggaa | 1260 |
| | atcaagccgc gggccaactt tgtatacaaa agtggaacga gaaacgtaaa atgatataaa | 1320 |
| | tatcaatata ttaaattaga ttttgcataa aaaacagact acataatact gtaaaacaca | 1380 |
| | acatatccag tcactatgaa tcaactactt agatggtatt agtgacctgt actgggcctc | 1440 |
| | atgggccttc ctttcactgc ccgcttttcca gtcgggaaac ctgtcgtgcc agctgcatta | 1500 |
| | acatggtcat agctgttttcc ttgcgtattg ggcgctctcc gcttcctcgc tcactgactc | 1560 |
| | gctgcgctcg gtcgttcggg taaagcctgg ggtgcctaat gagcaaaagg ccagcaaaag | 1620 |
| | gccaggaacc gtaaaaaggc cgcgttgctg cgttttttcc ataggctccg ccccctgac | 1680 |
| | gagcatcaca aaaatcgacg ctcaagtcag aggtggcgaa acccgacagg actataaaga | 1740 |
| | taccaggcgt ttccccctgg aagctccctc gtgcgctctc ctgttccgac cctgcgcctt | 1800 |
| | accggatacc tgtccgcctt tctcccttcg ggaagcgtgg cgctttctca tagctcacgc | 1860 |
| | tgtaggtatc tcagttcggt gtaggtcgtt cgctccaagc tgggctgtgt gcacgaaccc | 1920 |
| | cccgttcagc ccgaccgctg cgccttatcc ggtaactatc gtcttgagtc caacccggta | 1980 |
| | agacacgact tatcgccact ggcagcagcc actggtaaca ggattagcag agcgaggtat | 2040 |
| | gtaggcggtg ctacagagtt cttgaagtgg tggcctaact acggctacac tagaagaaca | 2100 |
| | gtatttggta tctgcgctct gctgaagcca gttaccttcg gaaaaagagt tggtagctct | 2160 |
| | tgatccggca aacaaaccac cgctggtagc ggtggttttt tgtttgcaa gcagcagatt | 2220 |
| | acgcgcagaa aaaaaggatc tcaagaagat cctttgatct tttctacggg gtctgacgct | 2280 |
| | cagtggaacg aaaactcacg ttaagggatt ttggtcatga gattatcaaa aaggatcttc | 2340 |
| | acctagatcc ttttaaatta aaaatgaagt tttaaatcaa tctaaagtat atatgagtaa | 2400 |
| | acttggtctg acagttatta gaaaaattca tccagcagac gataaaacgc aatacgctgg | 2460 |
| | ctatccggtg ccgcaatgcc atacagcacc agaaaacgat ccgcccattc gccgcccagt | 2520 |
| | tcttccgcaa tatcacgggt ggccagcgca atatcctgat aacgatccgc cgccccaga | 2580 |
| | cggccgcaat caataaagcc gctaaaacgg ccattttcca ccataatgtt cggcaggcac | 2640 |
| | gcatcaccat gggtcaccac cagatcttcg ccatccggca tgctcgcttt cagacgcgca | 2700 |
| | aacagctctg ccggtgccag gccctgatgt tcttcatcca gatcatcctg atccaccagg | 2760 |
| | cccgcttcca tacgggtacg cgcacgttca atacgatgtt tcgcctgatg atcaaacgga | 2820 |
| | caggtcgccg ggtccagggt atgcagacga cgcatggcat ccgccataat gctcactttt | 2880 |
| | tctgccggcg ccagatggct agacagcaga tcctgacccg gcacttcgcc cagcagcagc | 2940 |
| | caatcacggc ccgcttcggt caccacatcc agcaccgccg cacacggaac accggtgtg | 3000 |
| | gccagccagc tcagacgcgc cgcttcatcc tgcagctcgt tcagcgcacc gctcagatcg | 3060 |
| | gttttcacaa acagcaccgg acgaccctgc gcgctcagac gaaacaccgc cgcatcagag | 3120 |
| | cagccaatgg tctgctgcgc ccaatcatag ccaaacagac gttccaccca cgctgccggg | 3180 |
| | ctacccgcat gcaggccatc ctgttcaatc atactcttcc ttttcaata ttattgaagc | 3240 |
| | atttatcagg gttattgtct catgagcgga tacatatttg aatgtattta gaaaaataaa | 3300 |
| | caaataggggg ttccgcgcac atttccccga aaagtgccac | 3340 |
| SEQ ID NO: 37 (donor vector 2, pMK hCD8a scaffold TN L5 L2) | ctaaattgta agcgttaata ttttgttaaa attcgcgtta aattttttgtt aaatcagctc | 60 |
| | attttttaac caataggccg aaatcggcaa aatcccttat aaatcaaaag aatagaccga | 120 |
| | gatagggttg agtggccgct acagggcgct cccattcgcc attcaggctg cgcaactgtt | 180 |
| | gggaagggcg tttcggtgcg ggcctcttcg ctattacgcc agctggcgaa aggggggatgt | 240 |
| | gctgcaaggc gattaagttg ggtaacgcca gggttttccc agtcacgacg ttgtaaaacg | 300 |
| | acggccagtg agcgcgacgt aatacgactc actatagggc gaattgaagg aaggccgtca | 360 |
| | aggccgcata aatatgatt ttatttgtac tgatagtgac ctgttcgttg caacaaattg | 420 |
| | atgagcaatg cttttttata atgccaact tgtatacaa aagtggcccg cggacaacaa | 480 |
| | ccccctgcccc cagacctcct acccccagccc ctacaattgc cagccagcct ctgagcctga | 540 |
| | ggcccgaggc ttgtagacct gctgctggcg gagccgtgca caccagagga ctggatttcg | 600 |
| | cctgcgacat ctacatctgg gcccctctgg ccggcacatg tggcgtgctg ctgctgagcc | 660 |
| | tcgtgatcac cctgtactgc ggctccacca gcggctccgg caagcccgc tctggcgagg | 720 |
| | gctccaccag cggcgactac aaggacgacg atgacaagta ataggatatc ggttcagctt | 780 |
| | tcttgtacaa agttggcatt ataagaaagc attgcttatc aatttgttgc aacgaacagg | 840 |
| | tcactatcag tcaaaataaa atcattattt gggccttcc tttcactgc | 900 |
| | cgctttccag tcgggaaacc tgtcgtgcca gctgcattaa catggtcata gctgtttcct | 960 |
| | tgcgtattgg cgctctccg cttcctcgct cactgactcg ctgcgctcgg tcgttcggt | 1020 |
| | aaagcctggg gtgcctaatg agcaaaaggc cagcaaaagg ccaggaaccg taaaaaggcc | 1080 |
| | gcgttgctgg cgttttttcca taggctccgc ccccctgac gcatcacaaa aatcgacgc | 1140 |
| | tcaagtcaga ggtggcgaaa cccgacagga ctataaagat accaggcgtt tccccctgga | 1200 |
| | agctccctcg tgcgctctcc tgttccgacc ctgccgctta ccggatacct gtccgccttt | 1260 |
| | ctcccttcgg gaagcgtggc gctttctcat agctcacgct gtaggtatct cagttcggtg | 1320 |
| | taggtcgttc gctccaagct gggctgtgtg cacgaacccc ccgttcagcc cgaccgctgc | 1380 |
| | gccttatccg gtaactatcg tcttgagtcc aacccggtaa gacacgactt atcgccactg | 1440 |
| | gcagcagcca ctggtaacag gattagcaga gcgaggtatg taggcggtgc tacagagttc | 1500 |
| | ttgaagtggt ggcctaacta cggctacact agaagaacag tatttggtat ctgcgctctg | 1560 |
| | ctgaagccag ttaccttcgg aaaaagagtt ggtagctctt gatccggcaa acaaaccacc | 1620 |
| | gctggtagcg gtggttttt tgtttgcaag cagcagatta cgcgcagaaa aaaaggatct | 1680 |

TABLE 8-continued

Nucleotide sequences for preparation of
lentivirus for transduction of aAPCs.

| Identifier (Description) | Sequence | |
|---|---|---|
| | caagaagatc ctttgatctt ttctacgggg tctgacgctc agtggaacga aaactcacgt | 1740 |
| | taagggattt tggtcatgag attatcaaaa aggatcttca cctagatcct tttaaattaa | 1800 |
| | aaatgaagtt ttaaatcaat ctaaagtata tatgagtaaa cttggtctga cagttattag | 1860 |
| | aaaaattcat ccagcagacg ataaaacgca atacgctggc tatccggtgc cgcaatgcca | 1920 |
| | tacagcacca gaaaacgatc cgcccattcg ccgcccagtt cttccgcaat atcacgggtg | 1980 |
| | gccagcgcaa tatcctgata acgatccgcc acgcccagac ggccgcaatc aataaagccg | 2040 |
| | ctaaaacggc cattttccac cataatgttc ggcaggcacg catcaccatg ggtcaccacc | 2100 |
| | agatcttcgc catccggcat gctcgctttc agacgcgcaa acagctctgc cggtgccagg | 2160 |
| | ccctgatgtt cttcatccag atcatcctga tccaccaggc ccgcttccat acgggtacgc | 2220 |
| | gcacgttcaa tacgatgttt cgcctgatga tcaaacggac aggtcgccgg gtccagggta | 2280 |
| | tgcagacgac gcatggcatc cgccataatg ctcacttttt ctgccggcgc cagatggcta | 2340 |
| | gacaggagat cctgacccgg cacttcgccc aggaggagcc aatcacggcc cgcttcggtc | 2400 |
| | accacatcca gcaccgccgc acacggaaca ccggtggtgg ccagccagct cagacgcgcc | 2460 |
| | gcttcatcct gcagctcgtt cagcgcaccg ctcagatcgg ttttcacaaa cagcaccgga | 2520 |
| | cgaccctgcg cgctcagacg aaacaccgcc gcatcagagc agccaatggt ctgctgcgcc | 2580 |
| | caatcatagc caaacagacg ttccacccac gctgccgggc tacccgcatg caggccatcc | 2640 |
| | tgttcaatca tactcttcct ttttcaatat tattgaagca tttatcaggg ttattgtctc | 2700 |
| | atgagcggat acatatttga atgtatttag aaaaataaac aatagggggt tccgcgcaca | 2760 |
| | tttccccgaa aagtgccac | 2779 |
| SEQ ID NO: 38 (Final vector used for lentiviral production, pLV4301G 8B3 scFV mIgG hCD8 flag) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg gggagaaatt agatcgcgat gggaaaaaat | 960 |
| | tcggttaagg ccagggggaa agaaaaaata taaattaaaa catatagtat gggcaagcag | 1020 |
| | ggagctagaa cgattgcgag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca agagaagag | 1380 |
| | tggtgcagag agaaaaaaga gcagtgggaa taggagctct gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctgaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac agagacagat | 2100 |
| | ccattcgatt agtgaacgga tctcgacggt atcggtttta aagaaaagg ggggattggg | 2160 |
| | gggtacagtg caggggaaag aatagtagac cagcataca aactaaagaa | 2220 |
| | ttacaaaaac aaattacaaa aattcaaaat tttatcgatt ttatttagtc tccagaaaaa | 2280 |
| | ggggggaatg aaagacccca cctgtaggtt tggcaagcta gcttaagtaa cgccattttg | 2340 |
| | caaggcatgg aaaatacata actgagaata gagaagttca gatcaaggtt aggaacagag | 2400 |
| | agacaggaga atatggccca aacaggatat ctgtggttaa cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga aatgaccctg tgccttattt gaactaacca | 2580 |
| | atcagttcgc ttctcgcttc tgttcgcgcg cttctgctcc ccgagctcaa taaagagcc | 2640 |
| | cacaaccct cactcggcgc gccagtcctc cgatagactg cgtcgcccgg gtaccgatat | 2700 |
| | caccaactt gtacaaaaaa gctgaacgat atcgccacca tgggcagcac agccattctg | 2760 |
| | gccctgctgc tggcagtgct gcagggcgtg tcagctcagg tgcagctgca gcagtctggc | 2820 |
| | gccgaagtga agaaacccgg cagcagcgtg aaggtgtcct gcaaggctag cggcggcacc | 2880 |
| | ttcaggagct acgccttttc ttgggtgcgc caggcccgg gaatgatctg gatgggaatc | 2940 |
| | ggctggatca gccctacaa cggcaacacc gactacgccc agaaagtgca agcagagtg | 3000 |
| | accctgacca ccgacaccag cacctccacc gcctacatgg aactgcggag cctgagagc | 3060 |
| | gacgacaccg ccgtgtacta ctgtgccaca ggcggcggaa cctggtacag cgatctgtgg | 3120 |
| | ggcagaggca ccctcgtgac agtgtctgct ggcggcggag gatctggcgg aggcggaagt | 3180 |
| | ggcggggag gaagcggagc acctgagatc gtgctgaccc agagccctag cacactgagc | 3240 |

TABLE 8-continued

Nucleotide sequences for preparation of
lentivirus for transduction of aAPCs.

| Identifier (Description) | Sequence | |
|---|---|---|
| | gccagcgtgg gcgacagagt gtccatcacc tgtagagcca gccagagcat cggaggcagc | 3300 |
| | ctggcctggt atcagcagaa gcctggcaag gcccccaagc tgctgatctc tgaggccagc | 3360 |
| | accctggaaa gaggcgtgcc cagcagattt tccggcagcg gctctggcac cgacttcacc | 3420 |
| | ctgacaatca gcagcctgca gcccgaggac gtggccacct actactgcca gaagtacaac | 3480 |
| | agcgtgcccc tgaccttcgg ccctggcacc aaggtggaaa tcaagccgcg ggccaacttt | 3540 |
| | gtatacaaaa gtggcccgcg gacaacaacc cctgccccca gacctcctac cccagcccct | 3600 |
| | acaattgcca gccagcctct gagcctgagg cccgaggctt gtagacctgc tgctggcgga | 3660 |
| | gccgtgcaca ccagaggact ggatttcgcc tgcgacatct acatctgggc ccctctggcc | 3720 |
| | ggcacatgtg gcgtgctgct gctgagcctc gtgatcaccc tgtactgcgg ctccaccagc | 3780 |
| | ggctccggca agcccggctc tggcgagggc tccaccagcg gcgactacaa ggacgacgat | 3840 |
| | gacaagtaat aggatatcgg ttcagctttc ttgtacaaag ttgggattcg agttaattaa | 3900 |
| | gttaacgaat tcccccccctc tccctccccc cccctaacg ttactggccg aagccgcttg | 3960 |
| | gaataaggcc ggtgtgcgtt tgtctatatg ttattttcca ccatattgcc gtcttttggc | 4020 |
| | aatgtgaggg cccggaaacc tggccctgtc ttcttgacga gcattcctag gggtctttcc | 4080 |
| | cctctcgcca aaggaatgca aggtctgttg aatgtcgtga aggaagcagt tcctctggaa | 4140 |
| | gcttcttgaa gacaaacaac gtctgtagcg acccctttgca ggcagcggaa ccccccacct | 4200 |
| | ggcgacaggt gcctctgcgg ccaaaagcca cgtgtataag atacacctgc aaaggcggca | 4260 |
| | caaccccagt gccacgttgt gagttggata gttgtggaaa gagtcaaatg gctctcctca | 4320 |
| | agcgtattca acaaggggct gaaggatgcc cagaaggtac cccattgtat gggatctgat | 4380 |
| | ctggggcctc ggtgcacatg cttttacatgt gtttagtcga ggttaaaaaa cgtctaggcc | 4440 |
| | ccccgaacca cggggacgtg gttttccttt gaaaaacacg atgataatat ggccacaacc | 4500 |
| | atgggaggcg gaagcggcg aggctcccct cgaggcacca tggtgagcaa gggcgaggag | 4560 |
| | ctgttcaccg gggtggtgcc catcctggtc gagctggacg gcgacgtaaa cggccacaag | 4620 |
| | ttcagcgtgt ccggcgaggg cgagggcgat gccacctacg gcaagctgac cctgaagttc | 4680 |
| | atctgcacca ccggcaagct gcccgtgccc tggcccaccc tcgtgaccac cctgacctac | 4740 |
| | ggcgtgcagt gcttcagccg ctaccccgac cacatgaagc agcacgactt cttcaagtcc | 4800 |
| | gccatgcccg aaggctacgt ccaggagcgc accatcttct tcaaggacga cggcaactac | 4860 |
| | aagacccgcg ccgaggtgaa gttcgagggc gacacctgg tgaaccgcat cgagctgaag | 4920 |
| | ggcatcgact tcaaggagga cggcaacatc ctggggcaca gctggagta caactacaac | 4980 |
| | agccacaacg tctatatcat ggccgacaag cagaagaacg gcatcaaggt gaacttcaag | 5040 |
| | atccgccaca acatcgagga cggcagcgtg cagctcgccg accactacca gcagaacacc | 5100 |
| | cccatcggcg acggccccgt gctgctgccc gacaaccact acctgagcac ccagtccgcc | 5160 |
| | ctgagcaaag accccaacga gaagcgcgat cacatggtcc tgctggagtt cgtgaccgcc | 5220 |
| | gccgggatca ctctcggcat ggacgagctg tacaagtaac gcgtcccggg tctagagcta | 5280 |
| | gcggtaccat gcattacgta gtcgacgact taattaagct agcctagtgc catttgttca | 5340 |
| | gtggttcgta gggctttccc ccactgtttg gctttcagtt atatggatga tgtggtattg | 5400 |
| | ggggccaagt ctgtacagca tcttgagtcc cttttttaccg ctgttaccaa ttttcttttg | 5460 |
| | tctttgggta tacatttaaa ccctaacaaa acaaagagat ggggttactc tctaaatttt | 5520 |
| | atgggttatg tcattggatg ttatgggtcc ttgccacaag aacacatcat acaaaaaatc | 5580 |
| | aaagaatgtt ttagaaaact tcctattaac aggttggaaagt atgtcaacga | 5640 |
| | attgtgggtc ttttgggttt tgctgcccct tttacacaat gtggttatcc tgcgttgatg | 5700 |
| | cctttgtatg catgtattca atctaagcag gctttcactt tctcgccaac ttacaaggcc | 5760 |
| | tttctgtgta aacaatacct gaacctttac cccgttgccc ggcaacggcc aggtctgtgc | 5820 |
| | caagtgtttg ctgacgcaac ccccactggc tggggcttgg tcatgggcca tcagcgcatg | 5880 |
| | cgtggaacct tttcggctcc tctgccgatc catactgcgg aactcctagc cgcttgtttt | 5940 |
| | gctcgcagca ggtctgagc aaacattatc gggactgata actctgttgt cctatcccgc | 6000 |
| | aaatatacat cgtttccatg gctgctaggc tgtgctgcca actggatcct gcgcgggacg | 6060 |
| | tcctttgttt acgtcccgtc ggcgctgaat cctgcggacg accctttctcg gggtcgcttg | 6120 |
| | ggactctctc gtcccctcct ccgtctgccg ttccgaccga ccacgggggcg cacctctctt | 6180 |
| | tacgcggact ccccgtctgt gccttctcat ctgccggacc gtgtgcactt cgcttcacct | 6240 |
| | ctgcacgtcg catggagacc accgtgaacg cccaccaaat attgcccaag gtcttacata | 6300 |
| | agaggactct tggactctca gcaatgtcaa cgaccgacct tgaggcatac ttcaaagact | 6360 |
| | gtttgtttaa agactgggag gagttggggg aggagattag gttaaaggtc tttgtactag | 6420 |
| | gaggctgtag gcataaattg gtctgcgcac cagcaccatg gcgcaatcac tagagctggg | 6480 |
| | taccttaag accaatgact tacaaggcag ctgtagatct tagccacttt ttaaaagaaa | 6540 |
| | agggggact ggaagggcta attcactccc aacgaagaca agatctgctt tttgcttgta | 6600 |
| | ctgggtctct ctggttagac cagatctgag cctgggagct ctctggctaa ctagggaacc | 6660 |
| | cactgcttaa gcctcaataa agcttgcctt gagtgcttca agtagtgtgt gcccgtctgt | 6720 |
| | tgtgtgactc tggtaactag agatccctca gaccctttta gtcagtgtgg aaaatctcta | 6780 |
| | gcagtagtag ttcatgtcat cttattattc agtatttata acttgcaaag aaatgaatat | 6840 |
| | cagagagtga gaggaacttg tttattgcag cttataatgg ttacaaataa agcaatagca | 6900 |
| | tcacaaattt cacaaataaa gcatttttt cactgcattc tagttgtggt ttgtccaaac | 6960 |
| | tcatcaatgt atcttatcat gtctgctct agctatcccg ccctaactc cgcccatccc | 7020 |
| | gccctaact ccgcccagtt ccgcccattc tccgcccat ggctgactaa ttttttttat | 7080 |
| | ttatgcagag gccgaggccg gatcccttga gtggcttca tcctggagca gactttgcag | 7140 |
| | tctgtggact gcaacacaac attgccttta tgtgtaactc ttggctgaag ctcttacacc | 7200 |
| | aatgctgggg gacatgtacc tcccaggggc ccaggaagac tacgggaggc tacaccaacg | 7260 |
| | tcaatcagag gggcctgtgt agctaccgat aagcggaccc tcaagagggc attagcaata | 7320 |
| | gtgttttataa ggcccccttg ttaattcttg aagacgaaag ggcctcgtga tacgcctatt | 7380 |
| | tttataggtt aatgtcatga taataatggt ttcttagacg tcaggtggca cttttcgggg | 7440 |
| | aaatgtgcgc ggaaccccta tttgtttatt tttctaaata cattcaaata tgtatccgct | 7500 |
| | catgagacaa taaccctgat aaatgcttca ataatattga aaaggaaga gtatgagtat | 7560 |
| | tcaacatttc cgtgtcgccc ttattccctt ttttgcggca ttttgccttc ctgtttttgc | 7620 |
| | tcacccagaa acgctggtga agtaaaaga tgctgaagat cagttgggtg cacgagtggg | 7680 |

TABLE 8-continued

Nucleotide sequences for preparation of
lentivirus for transduction of aAPCs.

| Identifier (Description) | Sequence | |
|---|---|---|
| | ttacatcgaa ctggatctca acagcggtaa gatccttgag agttttcgcc ccgaagaacg | 7740 |
| | ttttccaatg atgagcactt ttaaagttct gctatgtggc gcggtattat cccgtgttga | 7800 |
| | cgccgggcaa gagcaactcg gtcgccgcat acactattct cagaatgact tggttgagta | 7860 |
| | ctcaccagtc acagaaaagc atcttacgga tggcatgaca gtaagagaat tatgcagtgc | 7920 |
| | tgccataacc atgagtgata acactgcggc caacttactt ctgacaacga tcggaggacc | 7980 |
| | gaaggagcta accgcttttt tgcacaacat gggggatcat gtaactcgcc ttgatcgttg | 8040 |
| | ggaaccggag ctgaatgaag ccataccaaa cgacgagcgt gacaccacga tgcctgcagc | 8100 |
| | aatggcaaca acgttgcgca aactattaac tggcgaacta cttactctag cttcccggca | 8160 |
| | acaattaata gactggatgg aggcggataa agttgcagga ccacttctgc gctcggccct | 8220 |
| | tccggctggc tggtttattg ctgataaatc tggagccggt gagcgtgggt ctcgcggtat | 8280 |
| | cattgcagca ctggggccag atggtaagcc ctcccgtatc gtagttatct acacgacggg | 8340 |
| | gagtcaggca actatgatg aacgaaatag acagatcgct gagataggtg cctcactgat | 8400 |
| | taagcattgg taactgtcag accaagttta ctcatatata ctttagattg atttaaaact | 8460 |
| | tcatttttaa tttaaaagga tctaggtgaa gatcctttt gataatctca tgaccaaaat | 8520 |
| | cccttaacgt gagttttcgt tccactgagc gtcagacccc gtagaaaaga tcaaaggatc | 8580 |
| | ttcttgagat cctttttttc tgcgcgtaat ctgctgcttg caaacaaaaa aaccaccgct | 8640 |
| | accagcggtg gtttgtttgc cggatcaaga gctaccaact cttttccga aggtaactgg | 8700 |
| | cttcaggaga gcgcagatac caaatactgt ccttctagtg tagccgtagt taggccacca | 8760 |
| | cttcaagaac tctgtagcac cgcctacata cctcgctctg ctaatcctgt taccagtggc | 8820 |
| | tgctgccagt ggcgataagt cgtgtcttac cgggttggac tcaagacgat agttaccgga | 8880 |
| | taaggcgcag cggtcgggct gaacggggg ttcgtgcaca gcccagct tggagcgaac | 8940 |
| | gacctacacc gaactgagat acctacagcg tgagcattga aaagcgcca cgcttcccga | 9000 |
| | agggagaaag gcggacaggt atccggtaag cggcagggtc ggaacaggag agcgcacgag | 9060 |
| | ggagcttcca gggggaaacg cctggtatct ttatagtcct gtcgggtttc gccacctctg | 9120 |
| | acttgagcgt cgatttttgt gatgctcgtc aggggggcgg agcctatgga aaaacgccag | 9180 |
| | caacgcggcc tttttacggt tcctggcctt ttgctggcct ttttgaagct gtccctgatg | 9240 |
| | gtcgtcatct acctgcctgg acagcatggc ctgcaacgcg gcatcccga tgccgccgga | 9300 |
| | agcgagaaga atcataatgg ggaaggccat ccagcctcgc gtcg | 9344 |
| SEQ ID NO: 39 (pLenti-C-Myc-DDK OX40L) | gtcgacggat cgggagatct cccgatcccc tatggtgcac tctcagtaca atctgctctg | 60 |
| | atgccgcata gttaagccag tatctgctcc ctgcttgtgt gttggaggtc gctgagtagt | 120 |
| | gcgcgagcaa aatttaagct acaacaaggc aaggcttgac cgacaattgc atgaagaatc | 180 |
| | tgcttagggt taggcgtttt gcgctgcttc gcgatgtacg ggccagatat cgcgttgaca | 240 |
| | ttgattattg actagttatt aatagtaatc aattacgggt cattagttca atagcccata | 300 |
| | tatggagttc cgcgttacat aacttacggt aaatggcccg cctggctgac cgcccaacga | 360 |
| | cccccgccca ttgacgtcaa taatgacgta tgttcccata gtaacgccaa tagggactttc | 420 |
| | ccattgacgt caatgggtgg agtatttacg gtaaactgcc cacttggcag tacatcaagt | 480 |
| | gtatcatatg ccaagtacgc cccctattga cgtcaatgac ggtaaatggc ccgcctgca | 540 |
| | ttatgcccag tacatgacct tatgggactt tcctacttgg cagtacatct acgtattagt | 600 |
| | catcgctatt accatggtga tgcggttttg gcagtacatc aatgggcgtg gatagcggtt | 660 |
| | tgactcacgg ggatttccaa gtctccaccc cattgacgtc aatgggagtt tgttttggca | 720 |
| | ccaaaatcaa cgggactttc caaaatgtcg taacaactcc gccccattga cgcaaatggg | 780 |
| | cggtaggcgt gtacggtggg aggtctatat aagcagcgcg ttttgcctgt actgggtctc | 840 |
| | tctggttaga ccagatctga gcctgggagc tctctggcta actagggaac ccactgctta | 900 |
| | agcctcaata agcttgcct tgagtgcttc aagtagtgtg tgcccgtctg ttgtgtgact | 960 |
| | ctggtaacta gagatccctc agacccttt agtcagtgtg gaaaatctct agcagtggcg | 1020 |
| | cccgaacagg gacttgaaag cgaagggaa accagaggag ctctctcgac gcaggactcg | 1080 |
| | gcttgctgaa gcgcgcacgg caagaggcga ggggcggcga ctggtgagta cgccaaaaat | 1140 |
| | tttgactagc ggaggctaga aggagagaga tgggtgcgag agcgtcagta ttaagcgggg | 1200 |
| | gagaattaga tcgcgatggg aaaaaaattcg gttaaggcca gggggaaaga aaaaatataa | 1260 |
| | attaaaacat atagtatggg caagcaggga gctagaacga ttcgcagtta atcctggcct | 1320 |
| | gttagaaaca tcagaaggct gtagacaaat actgggacag ctacaaccat cccttcagac | 1380 |
| | aggatcagaa gaacttagat cattatataa tacagtagca accctctatt gtgtgcatca | 1440 |
| | aaggatagag ataaaagaca ccaaggaagc tttagacaag atagaggaag agcaaaacaa | 1500 |
| | aagtaagacc accgcacagc aagcggccgg ccgctgatct tcagacctgg aggaggagat | 1560 |
| | atgagggaca attggagaag tgaattatat aaatataaag tagtaaaaat tgaaccatta | 1620 |
| | ggagtagcac ccaccaaggc aaagagaaga gtggtgcaga gaaaaaaag agcagtggga | 1680 |
| | ataggagctt tgttccttgg gttcttggga gcagcaggaa gcactatggg cgcagcgtca | 1740 |
| | atgacgctga cggtacaggc cagacaatta ttgtctggta tagtgcagca gcagaacaat | 1800 |
| | ttgctgaggg ctattgaggc gcaacagcat ctgttgcaac tcacagtctg gggcatcaag | 1860 |
| | cagctccagg caagaatcct ggctgtgaa agatacctaa aggatcaaca gctcctggga | 1920 |
| | atttgggt gctctggaaa actcatttgc accactgctg tgccttggaa tgctagttgg | 1980 |
| | agtaataaat ctctggaaca gatttggaat cacacgacct ggatggagtg ggacagagaa | 2040 |
| | attaacaatt acacaagctt aatacactcc ttaattgaag aatcgcaaaa ccagcaagaa | 2100 |
| | aagaatgaac aagaattatt ggaattagat aatgggcaa gtttgttgaa ttggtttaac | 2160 |
| | ataacaaatt ggctgtggta tataaaatta ttcataatga tagtaggagg cttggtaggt | 2220 |
| | ttaagaatag ttttgctgt actttctata gtgaatagag ttaggcaggg atattcacca | 2280 |
| | ttatcgtttc agacccacct cccaacccg aggggaccg acaggcccga aggaatagaa | 2340 |
| | gaagaaggtg gagagagaga cagagacaga tccattcgat tagtgaacgg atcggcactg | 2400 |
| | cgtgcgccaa ttctgcagac aaatggcagt attcatccac aatttaaaa gaaaagggg | 2460 |
| | gattgggggg tacagtgcag gggaaagaat agtagacata atagcaacag acatacaaac | 2520 |
| | taaagaatta caaaaacaaa ttacaaaaat tcaaaatttt cgggtttatt acagggacag | 2580 |
| | cagagatcca gtttggttag taccgggccc gctctagaca tgtccaatat gaccgccatg | 2640 |
| | ttgacattga ttattgacta gttattaata gtaatcaatt acggggtcat tagttcatag | 2700 |

TABLE 8-continued

Nucleotide sequences for preparation of
lentivirus for transduction of aAPCs.

| Identifier (Description) | Sequence | |
|---|---|---|
| | cccatatatg gagttccgcg ttacataact tacggtaaat ggcccgcctg gctgaccgcc | 2760 |
| | caacgacccc cgcccattga cgtcaataat gacgtatgtt cccatagtaa cgccaatagg | 2820 |
| | gactttccat tgacgtcaat gggtggagta tttacggtaa actgcccact tggcagtaca | 2880 |
| | tcaagtgtat catatgccaa gtccgccccc tattgacgtc aatgacggta aatggcccgc | 2940 |
| | ctggcattat gcccagtaca tgaccttacg ggactttcct acttggcagt acatctacgt | 3000 |
| | attagtcatc gctattacca tggtgatgcg gttttggcag tacaccaatg ggcgtggata | 3060 |
| | gcggtttgac tcacggggat ttccaagtct ccaccccatt gacgtcaatg ggagtttgtt | 3120 |
| | ttggcaccaa aatcaacggg actttccaaa atgtcgtaat aaccccgccc cgttgacgca | 3180 |
| | aatgggcggt aggcgtgtac ggtgggaggt ctatataagc agagctcgtt tagtgaaccg | 3240 |
| | tcagaatttt gtaatacgac tcactatagg gcggccggga attcgtcgac tggatccggt | 3300 |
| | accgaggaga tctgccgccg cgatcgccat ggaaaaggtc caaccctgg aagagaatgt | 3360 |
| | gggaaatgca gccaggccaa gattcgagag gaacaagcta ttgctggtgg cctctgtaat | 3420 |
| | tcagggactg gggctgctcc tgtgcttcac ctacatctgc ctgcacttct ctgctcttca | 3480 |
| | ggtatcacat cggtatcctc gaattcaaag tatcaaagta caatttaccg aatataagaa | 3540 |
| | ggagaaaggt ttcatcctca cttcccaaaa ggaggatgaa atcatgaagg tgcagaacaa | 3600 |
| | ctcagtcatc atcaactgtg atgggtttta tctcatctcc ctgaagggct acttctccca | 3660 |
| | ggaagtcaac attagccttc attaccagaa ggatgaggag cccctcttcc aactgaagaa | 3720 |
| | ggtcaggtct gtcaactcct tgatggtggc ctctctgact acaaagaca aagtctactt | 3780 |
| | gaatgtgacc actgacaata cctcccctgga tgacttccat gtgaatggcg gagaactgat | 3840 |
| | tcttatccat caaaatcctg gtgaattctg tgtccttacg cgtacgcggc cgctcgagca | 3900 |
| | gaaactcatc tcagaagagg atctggcagc aaatgatatc ctggattaca aggatgacga | 3960 |
| | cgataaggtt taaacggccg gccgcggtct gtacaagtag gattcgtcga gggacctaat | 4020 |
| | aacttcgtat agcatacatt atacgaagtt atacatgttt aagggttccg gttccactag | 4080 |
| | gtacaattcg atatcaagct tatcgataat caacctctgg attacaaaat ttgtgaaaga | 4140 |
| | ttgactggta ttcttaacta tgttgctcct tttacgctat gtggatacgc tgctttaatg | 4200 |
| | cctttgtatc atgctattgc ttcccgtatg gctttcattt tctcctcctt gtataaatcc | 4260 |
| | tggttgctgt ctctttatga ggagttgtgg cccgttgtca ggcaacgtgg cgtggtgtgc | 4320 |
| | actgtgtttg ctgacgcaac ccccactggt tggggcattg ccaccacctg tcagctccct | 4380 |
| | tccgggactt tcgctttccc cctccctatt gccacggcgg aactcatcgc cgcctgcctt | 4440 |
| | gcccgctgct ggacaggggc tcggctgttg ggcactgaca attccgtggt gttgtcgggg | 4500 |
| | aaatcatcgt cctttccttg gctgctcgcc tgtgttgcca cctggattct gcgcgggacg | 4560 |
| | tccttctgct acgtcccttc ggccctcaat ccagcggacc ttccttcccg cggcctgctg | 4620 |
| | ccggctctgc ggcctcttcc gcgtcttcgc cttcgccctc agacgagtcg gatctccctt | 4680 |
| | tgggccgcct ccccgcatcg ataccgtcga cctcgatcga gacctagaaa aacatggagc | 4740 |
| | aatcacaagt agcaatacag cagctaccaa tgctgattgt gcctggctag aagcacaaga | 4800 |
| | ggaggaggag gtgggttttc cagtcacacc tcaggtacct ttaagaccaa tgacttacaa | 4860 |
| | ggcagctgta gatcttagcc acttttttaaa agaaaagggg ggactggaag ggctaattca | 4920 |
| | ctcccaacga agacaagata tccttgatct gtggatctac cacacacaag gctacttccc | 4980 |
| | tgattggcag aactacacac cagggccagg gatcagatat ccactgacct ttggatggtg | 5040 |
| | ctacaagcta gtaccagttg agcaagagaa ggtagaagaa gccaatgaag gagagaacac | 5100 |
| | ccgcttgtta caccctgtga gcctgcatgg gatggatgac ccggagagag aagtattaga | 5160 |
| | gtggaggttt gacagccgcc tagcatttca tcacatggcc cgagagctgc atccggactg | 5220 |
| | tactgggtct ctctggttag accagatctg agcctgggag ctctctggct aactagggaa | 5280 |
| | cccactgctt aagcctcaat aaagcttgcc ttgagtgctt caagtagtgt gtgcccgtct | 5340 |
| | gttgtgtgac tctggtaact agagatccct cagacccttt tagtcagtgt ggaaaatctc | 5400 |
| | tagcagcatg tgagcaaaag gccagcaaaa ggccaggaac cgtaaaaagg ccgcgttgct | 5460 |
| | ggcgtttttc cataggctcc gcccccctga cgagcatcac aaaaatcgac gctcaagtca | 5520 |
| | gaggtggcga aacccgacag gactataaag ataccaggcg tttccccctg gaagctccct | 5580 |
| | cgtgcgctct cctgttccga ccctgccgct taccggatac ctgtccgcct ttctcccttc | 5640 |
| | gggaagcgtg gcgctttctc atagctcacg ctgtaggtat ctcagttcgg tgtaggtcgt | 5700 |
| | tcgctccaag ctgggctgtg tgcacgaacc cccgttcag cccgaccgct gcgccttatc | 5760 |
| | cggtaactat cgtcttgagt ccaacccggt aagacacgac ttatcgccac tggcagcagc | 5820 |
| | cactggtaac aggattagca gagcgaggta tgtaggcggt gctacagagt tcttgaagtg | 5880 |
| | gtggcctaac tacggctaca ctagaagaac agtatttggt atctgcgctc tgctgaagcc | 5940 |
| | agttaccttc ggaaaaagag ttggtagctc ttgatccggc aaacaaacca ccgctggtag | 6000 |
| | cggtggtttt tttgtttgca agcagcagat tacgcgcaga aaaaaggat ctcaagaaga | 6060 |
| | tcctttgatc ttttctacgg ggtctgacgc tcagtggaac gaaaactcac gttaagggat | 6120 |
| | tttggtcatg attacgcccc gccctgccac tcatcgcagt actgttgtaa ttcattaagc | 6180 |
| | attctgccga catggaagcc atcacaaacg gcatgatgaa cctgaatcgc cagcggcatc | 6240 |
| | agcaccttgt cgccttgcgt ataatatttg cccatggtga aacgggggc gaagaagttg | 6300 |
| | tccatattgg ccacgtttaa atcaaaactg gtgaaactca cccaggatt ggctgagacg | 6360 |
| | aaaaacatat tctcaataaa cccttaggg aaataggcca ggttttcacc gtaacacgcc | 6420 |
| | acatcttgcg aatatatgtg tagaaactgc cggaaatcgt cgtggtattc actccagagc | 6480 |
| | gatgaaaacg tttcagtttg ctcatggaaa acggtgtaac aaggtgaac actatcccat | 6540 |
| | atcaccagct caccgtcttt cattgccata cggaactccg atgagcatt catcaggcgg | 6600 |
| | gcaagaatgt gaataaaggc cggataaaac ttgtgcttat ttttctttac ggtctttaaa | 6660 |
| | aaggccgtaa tatccagctg aacggtctgg ttataggtac attgagcaac tgactgaaat | 6720 |
| | gcctcaaaat gttctttacg atgccattgg gatatatcaa cggtggtata tccagtgatt | 6780 |
| | tttttctcca tactcttcct ttttcaatat tattgaagca tttatcaggg ttattgtctc | 6840 |
| | atgagcggat acatatttga atgtatttag aaaaataaac aaataggggg cccgcgcaca | 6900 |
| | tttccccgaa aagtgccacc tgac | 6924 |

Figure 37:
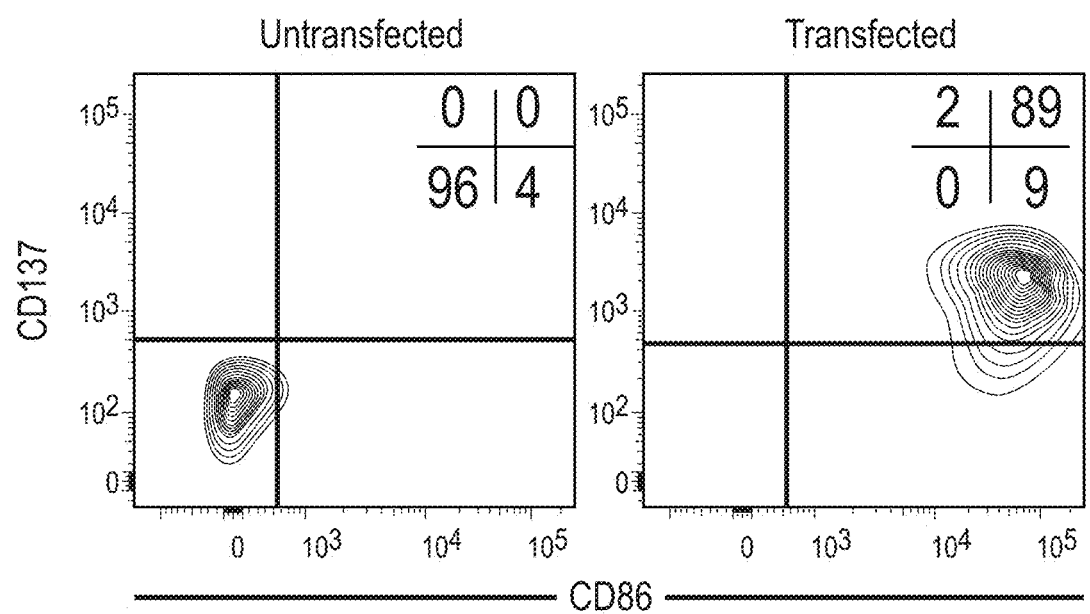
FIG. 37 illustrates the results of flow cytometry experiments on EM-3 cells before lentiviral transfection ("Untransfected") and after transfection ("Transfected"), confirming the expression of CD137 and CD86 on engineered EM-3 cells.
Figure 90:
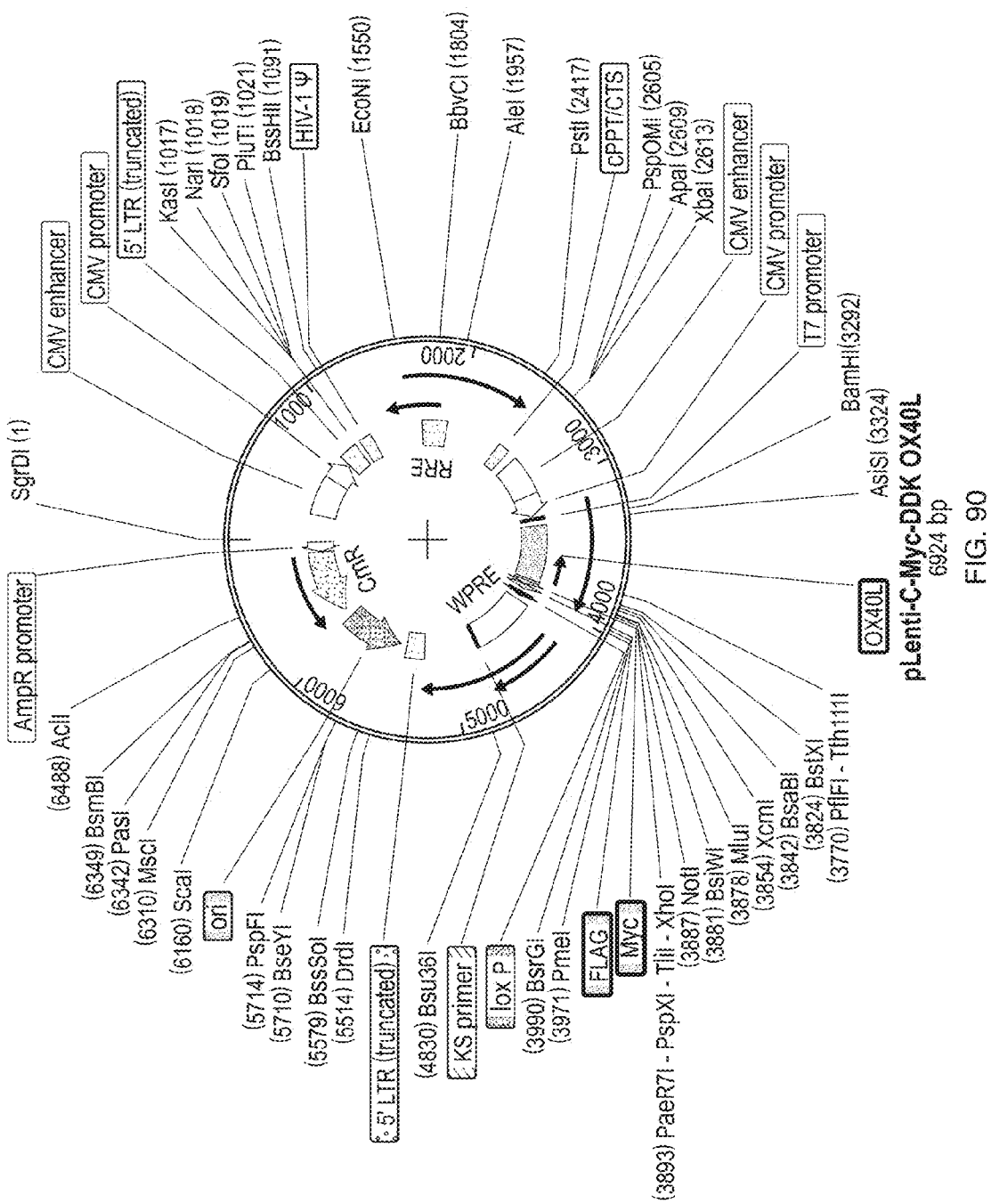
FIG. 90 illustrates a vector diagram of the pLenti-C-Myc-DDK human OX40L vector.

In the preparations of engineered EM-3 aAPCs (also referred to herein as aEM3 aAPCs) used for the experiments described herein, expression of CD86 and 4-1BBL was confirmed using flow cytometry (Canto II flow cytometer, Becton, Dickinson, and Co., Franklin Lakes, N.J., USA), with results shown in FIG. 37. aEM3 aAPCs were γ-irradiated at 100 Gy and frozen.

aEM-3 cells previously transduced to express CD86, antibody against IgG Fc region, and 4-1BBL (or optionally without 4-1BBL), as described above, were genetically engineered with a co-stimulatory human OX-40L using a similar lentiviral transduction approach. To generate lentivirus containing human OX-40L, pLenti-C-Myc-DDK OX40L (PS100064, Origene, SEQ ID NO:39, FIG. 90) vector together with the VSV-G envelope plasmid (pCIGO-VSV.G) were co-transfected into a Phoenix-GP (ATCC CRL-3215) cell line using PolyJet (Signagen Laboratories, Rockville, Md., USA). The supernatants were harvested 60 hours later and concentrated using Amicon Ultra-15 Centrifugal Filter Unit with Ultracel-100 membrane. aEM-3 cells were then infected with concentrated lentivirus and further expanded for five days. The cells were stained with PE-conjugated anti-human OX40L, Brilliant Violet 421-conjugated anti-human CD137L (if 4-1BBL is included in the prior aEM-3 cells), and PE/Cy7 conjugated anti-human CD86 and sorted based on the expression of GFP, OX40L, CD137L (when included), and CD86 using a S3e Cell Sorter (Bio-Rad, Inc., Hercules, Calif., USA). The purity of sorted cells was further validated using flow cytometry. The enriched cells were checked for purity by flow cytometry.

Figure 38:
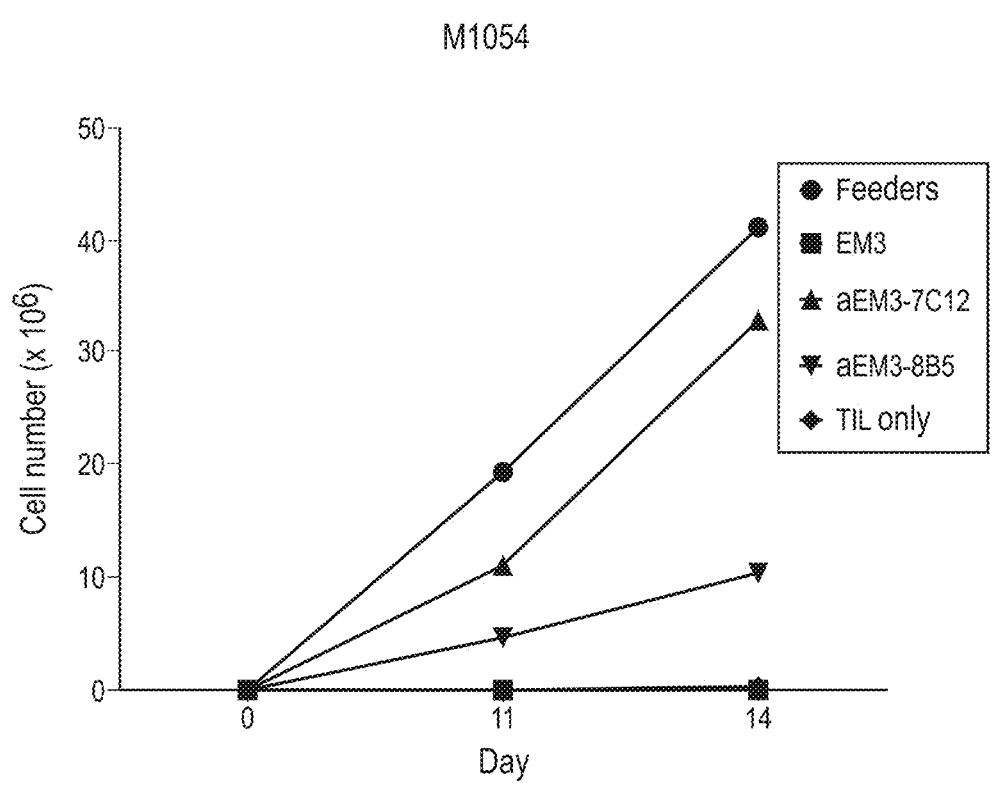
FIG. 38 illustrates the results of experiments wherein TILs were co-cultured with aEM3 (7C12 or 8B3) at a ratio of 1:100 plus OKT-3 (30 ng/mL) and IL-2 (3000 IU/mL). Cells were counted on Day 11 and 14.
Figure 39:
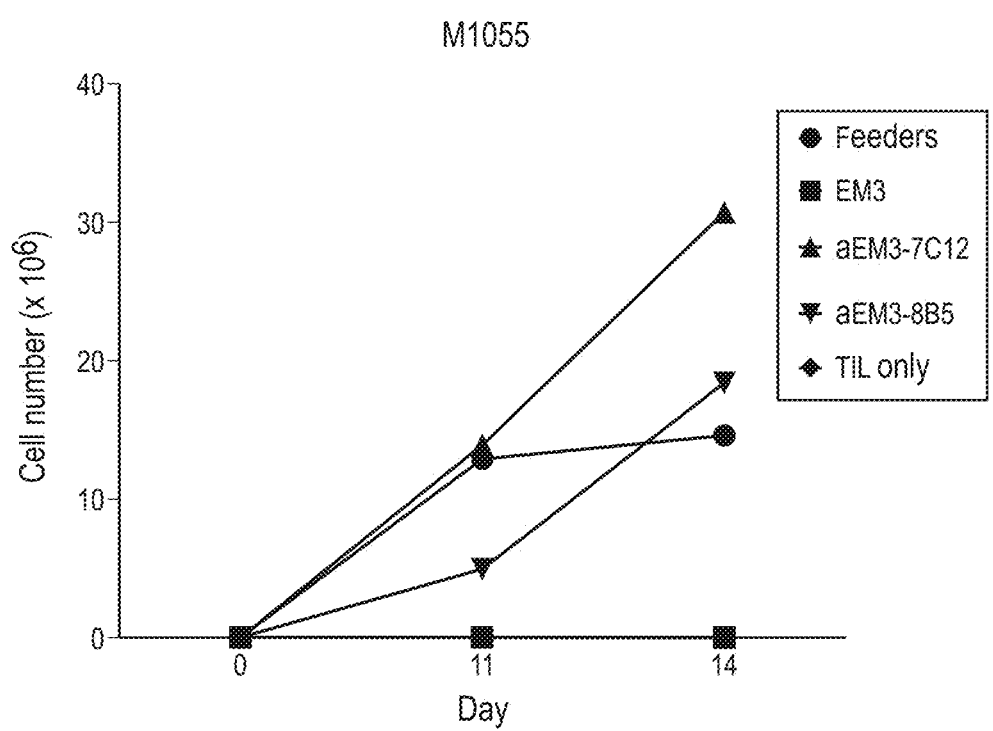
FIG. 39 illustrates the results of experiments wherein TILs were co-cultured with aEM3 (7C12 or 8B3) at a ratio of 1:100 plus OKT-3 (30 ng/mL) and IL-2 (3000 IU/mL). Cells were counted on Day 11 and 14.
Figure 40:
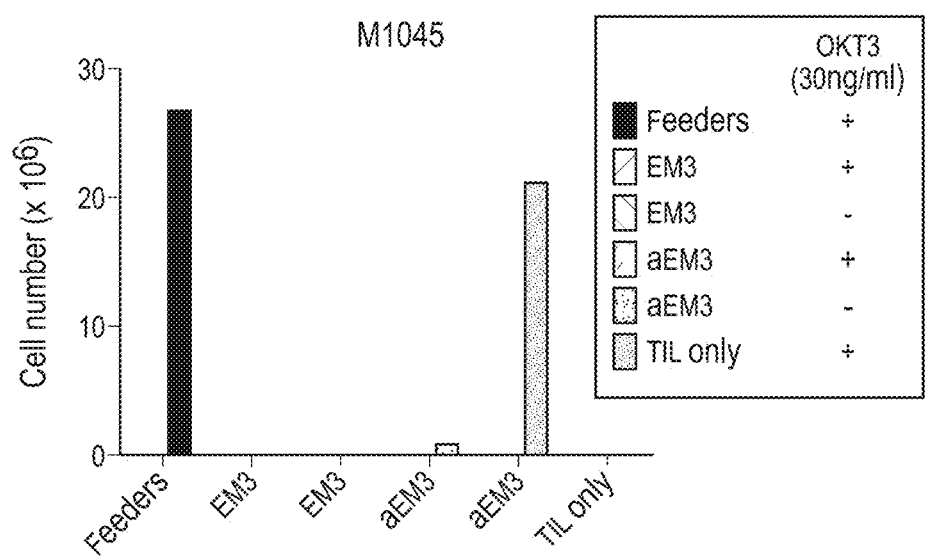
FIG. 40 illustrates the results of experiments wherein TILs were co-cultured with aEM3 or PBMC feeders at a 1:100 ratio with IL-2 (3000 IU/mL), with or without OKT-3 (30 ng/mL). The bar graph shows cell numbers determined on Day 11.

Example 6—Expansion of Tumor Infiltrating Lymphocytes Using EM-3 Artificial Antigen Presenting Cells Experiments were performed to test the ability of EM-3 aAPCs (aEM3) to expand TILs. TIL were co-cultured with aEM3 (7C12 or 8B3) at a ratio of 1:100 ratio plus OKT-3 (30 mg/mL) and IL-2 (3000 IU/mL). Cells were counted on Day 11 and 14. The results are plotted for two batches of TILs in FIG. 38 and FIG. 39. In addition, TILs were co-cultured with aEM3 or PBMC feeders at a 1:100 ratio with IL-2 (3000 IU/mL) with or without OKT-3 (30 mg/mL). The results are plotted in FIG. 40, where the bar graph shows cell numbers determined on Day 11.

Figure 41:
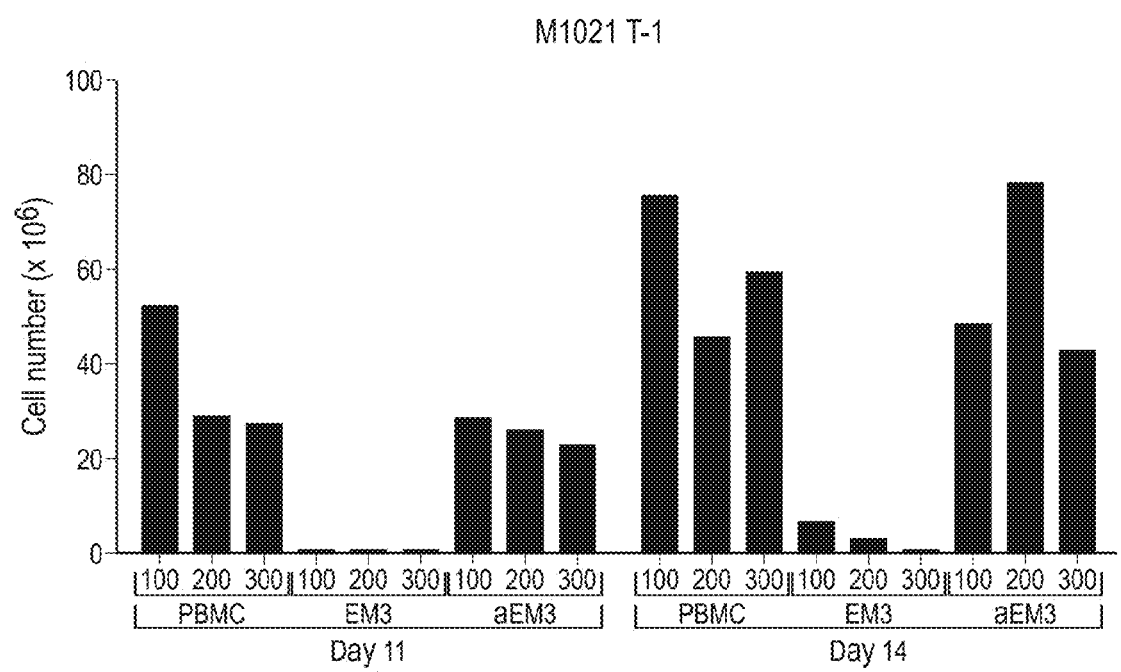
FIG. 41 illustrates the results of TIL expansions with EM-3 aAPCs at different TIL:aAPC ratios.

FIG. 41 illustrates the results of TIL expansions with EM-3 aAPCs (aEM3) at different TIL:aAPC ratios. The results show that aEM3 aAPCs perform comparably to and in some cases better than PBMCs, particularly at ratios of 1:200 at longer culture times (14 days).

Figure 42:
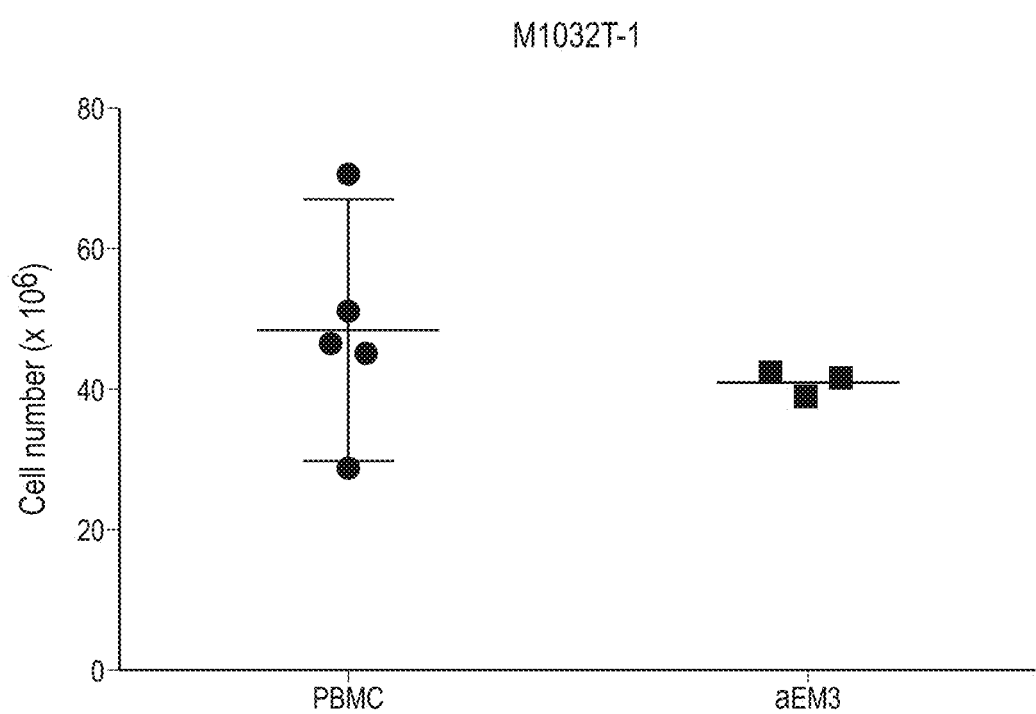
FIG. 42 illustrates the results of TIL expansions with EM-3 aAPCs. TILs (2×10$^4$) were co-cultured with five different PBMC feeder lots or aEM3 (in triplicate) at a 1:100 ratio with IL-2 (3000 IU/mL) in a G-Rex 24 well plate. Viable cells were counted on Day 14. The graph shows viable cell numbers (mean) with 95% confidence interval counted on Day 14.
Figure 43:
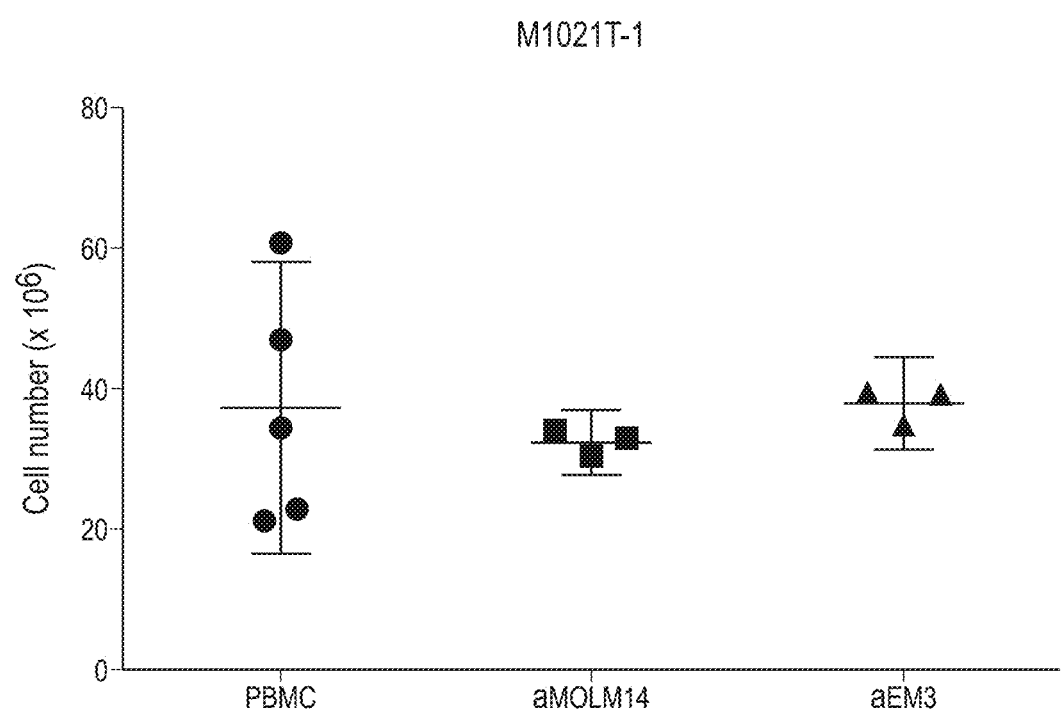
FIG. 43 illustrates the results of TIL expansions with EM-3 aAPCs and MOLM-14 aAPCs. TILs (2×10$^4$) were co-cultured with five different PBMC feeder lots or aMOLM14 (in triplicate) or aEM3 (also in triplicate) at 1:100 ratio with IL-2 (3000 IU/mL) in a G-Rex 24 well plate. The graph shows viable cell numbers (mean) with 95% confidence interval counted on Day 14.

FIG. 42 illustrates the low variability in cell counts from TIL expansions with EM-3 aAPCs (aEM3) in comparison to PBMC feeders. TILs ($2\times10^4$) were co-cultured with five different PBMC feeder lots or aEM3 (in triplicate) at 1:100 ratio with IL-2 (3000 IU/mL) in a G-Rex 24 well plate. The graph shows viable cell numbers (mean) with 95% confidence interval counted on Day 14. FIG. 43 compares the results of TIL expansions with EM-3 aAPCs and MOLM-14 aAPCs, to illustrate variability in cell counts for both aEM3 and aMOLM14 in comparison to TILs ($2\times10^4$) were co-cultured with five different PBMC feeder lots or aMOLM14 (in triplicate) or aEM3 (also in triplicate) at 1:100 ratio with IL-2 (3000 IU/mL) in a G-Rex 24 well plate. Viable cells were counted on day 14, and the graph shows viable cell numbers (mean) with 95% confidence interval. The aEM3 and aMOLM14 results indicate that much greater consistency can be obtained with both aAPCs compared to the PBMC feeder approach preferred in the prior art.

Figure 44:
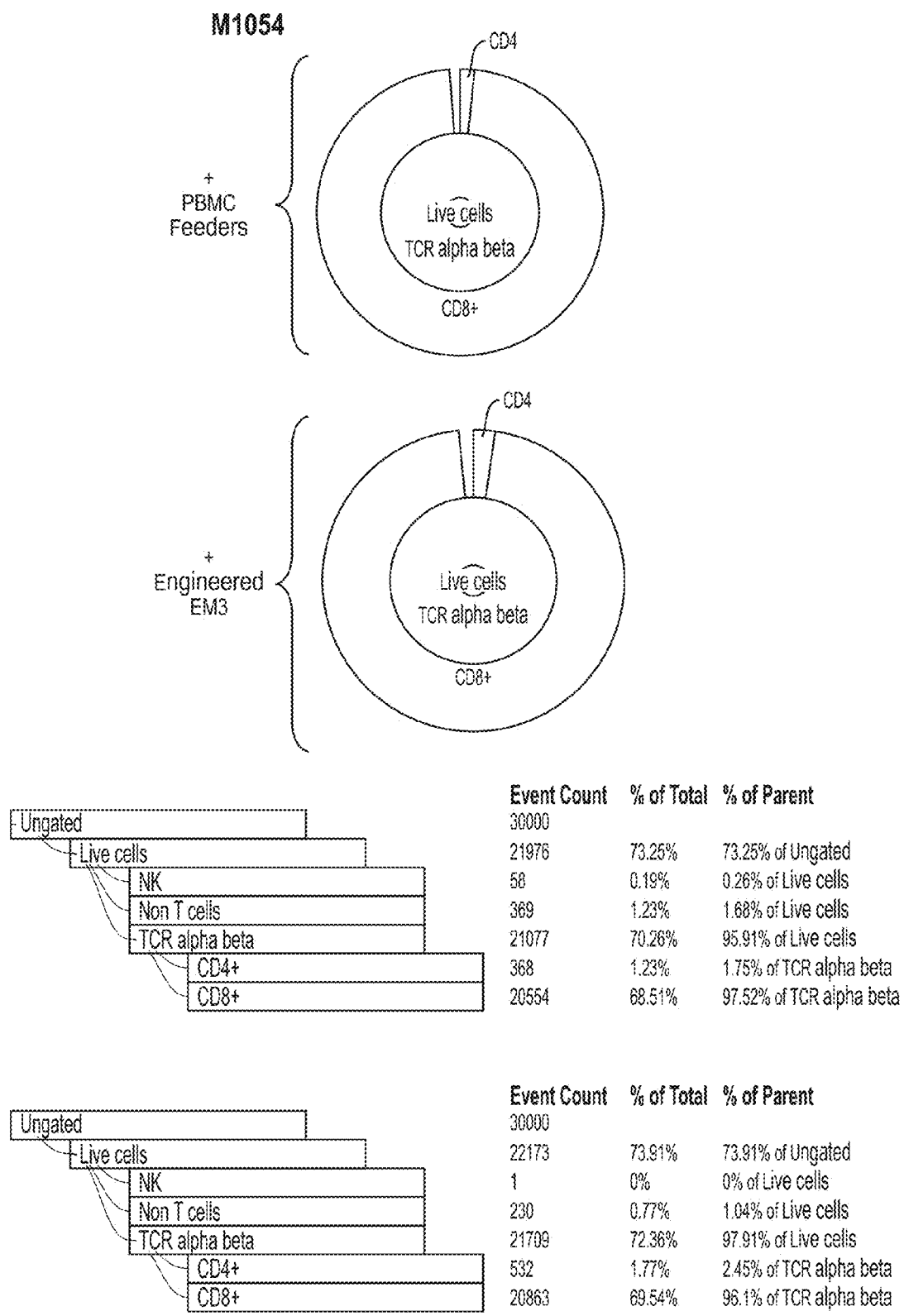
FIG. 44 illustrates a sunburst visualization to show fine distribution of Live, TCR α/β, CD4$^+$, and CD8$^+$ TILs expanded with aEM3 aAPCs or PBMC feeders (TIL batch M1054).
Figure 45:
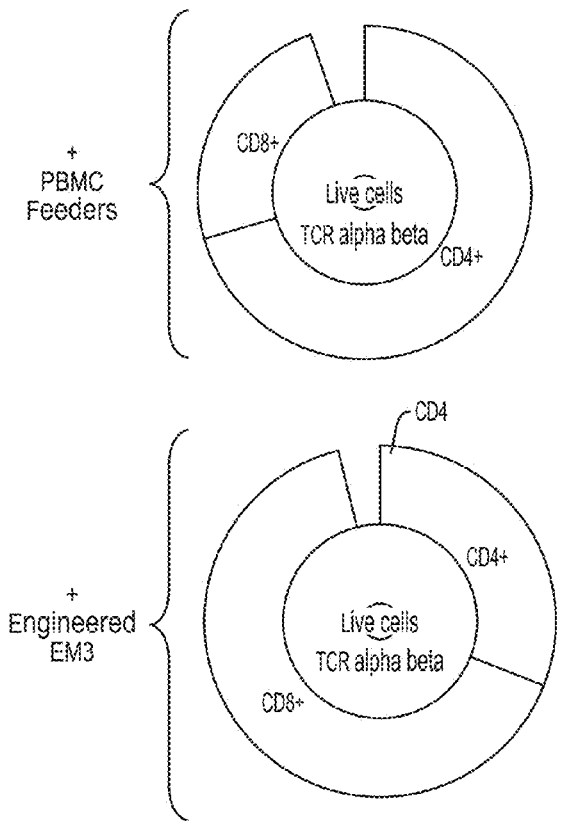
FIG. 45 illustrates the sunburst visualization to show fine distribution of Live, TCR α/β, CD4$^+$, and CD8$^+$ TILs expanded with aEM3 aAPCs or PBMC feeders (TIL batch M1055).
Figure 45:
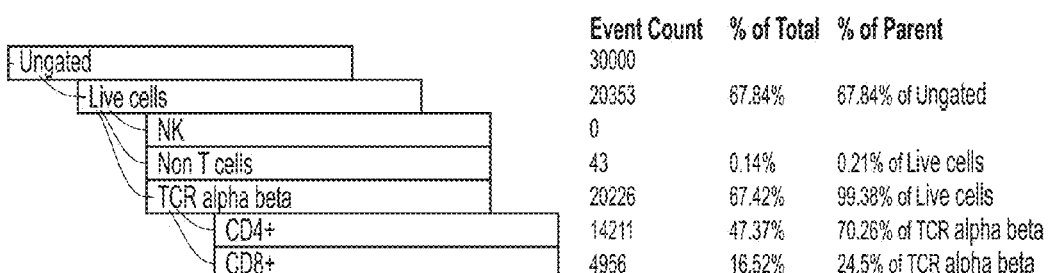
Figure 45:
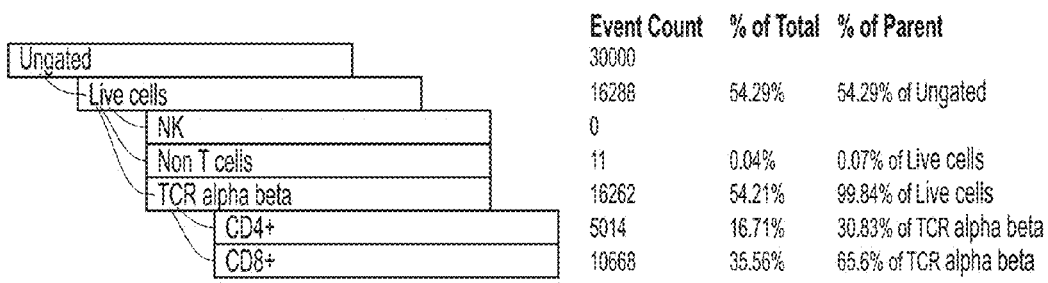

TILs expanded against aEM3 or PBMC feeders were used for flow cytometry analysis using 4 different panels (differentiation panels 1 and 2, T cell activation panels 1 and 2). Briefly, TILs were first stained with L/D Aqua to determine viability. Next, cells were surface stained with TCR α/β PE-Cy7, CD4 FITC, CD8 PB, CD56 APC, CD28 PE, CD27 APC-Cy7, and CD57-PerCP-Cy5.5 for differentiation panel 1; CD45RA PE-Cy7, CD8a PerCP/Cy5, CCR7 PE, CD4 FITC, CD3 APC-Cy7, CD38 APC, and HLA-DR PB, for differentiation panel 2; CD137 PE-Cy7, CD8a PerCP-Cy5.5, Lag3 PE, CD4 FITC, CD3 APC-Cy7, PD1 APC, and Tim-3 BV421 for T cell activation panel 1; or CD69 PE-Cy7, CD8a PerCP/Cy5.5, TIGIT PE, CD4 FITC, CD3 APC-Cy7, KLRG1 ALEXA 647, and CD154 BV421 for T cell activation panel 2. Phenotype analysis was done by gating 10,000 to 100,000 cells according to FSC/SSC using the Canto II flow cytometer. Data was analyzed using Cytobank software (Cytobank, Inc., Santa Clara, Calif., USA) to create sunburst diagrams and SPADE (Spanning-tree Progression Analysis of Density-normalized Events) plots. Gates were set based on fluorescence minus one (FMO) controls. SPADE plots were generated with the group of cells, characterized in a form of related nodes based on the expression level of surface markers. $CD4^+$ and $CD8^+$ TIL subsets were determined based on $CD3^-$ gating, and trees were generated. Sunburst visualizations are shown in FIG. 44 and FIG. 45. FIG. 44 shows that TILs expanded against aEM3 aAPCs maintained the $CD8^+$ phenotype when compared to the same TILs expanded against PBMC feeders. FIG. 45 shows the results of a second batch of TILs from a different patient expanded against aEM3 aAPCs, where a clear increase of $CD8^+$ cells (65.6%) is seen in comparison to the results from expansion using PBMC feeders (25%).

Figure 46:
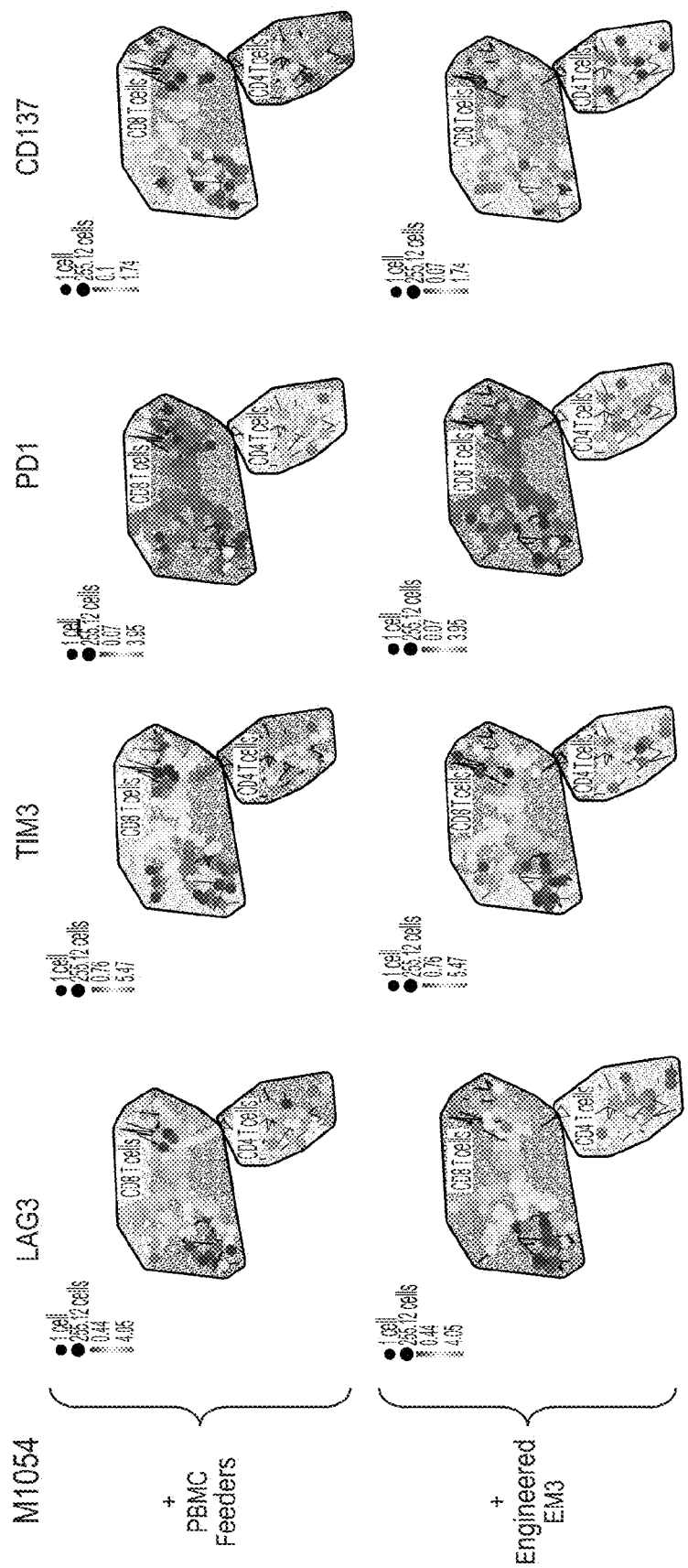
FIG. 46 illustrates the CD4$^+$ and CD8$^+$ SPADE tree of TILs expanded with aEM3 aAPCs or PBMC feeders using CD3$^+$ cells. The color gradient is proportional to the MFI of LAG-3, TIM-3, PD-1, and CD137.
Figure 47:
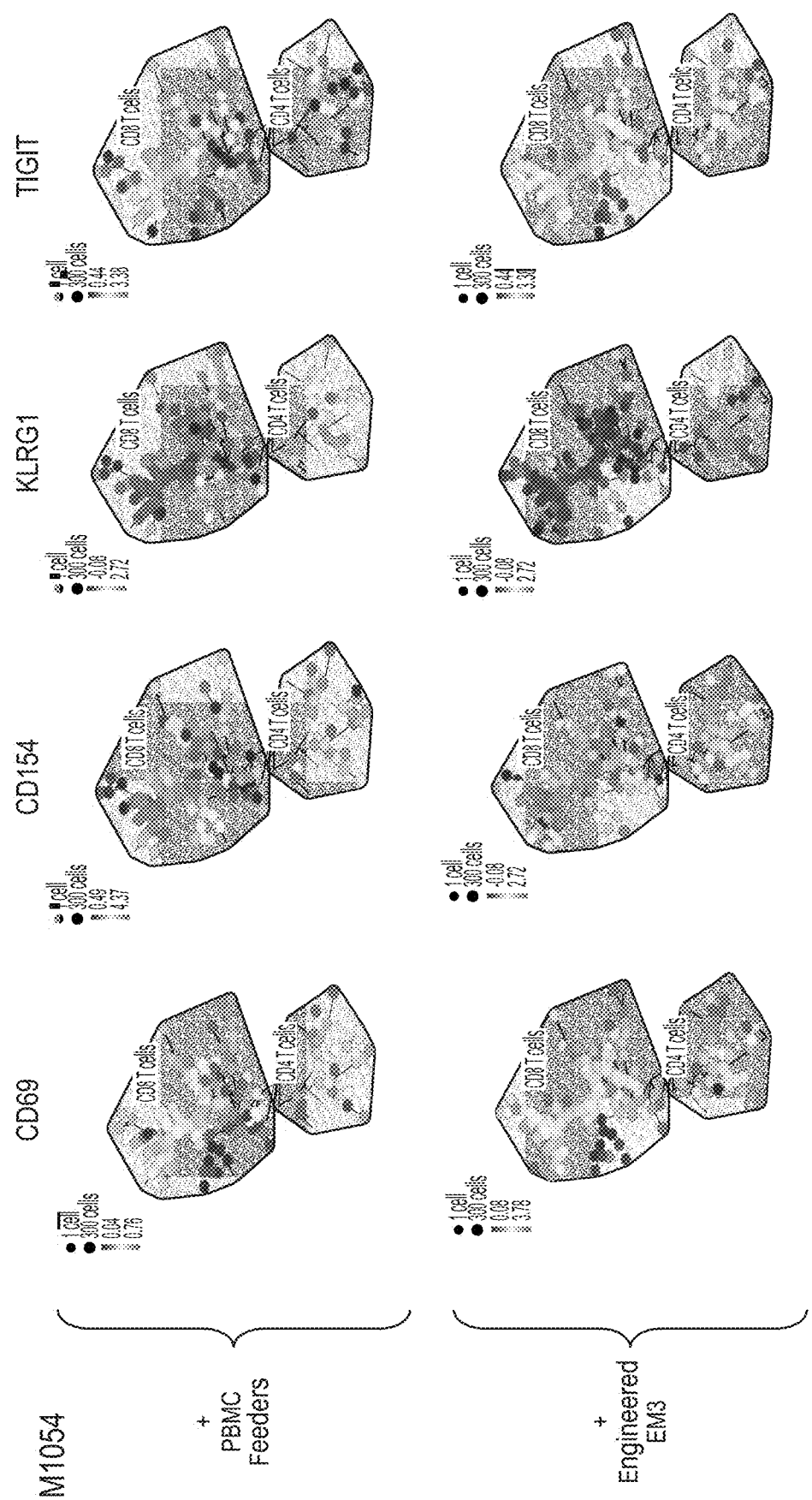
FIG. 47 illustrates the CD4$^+$ and CD8$^+$ SPADE tree of TILs expanded with aEM3 aAPCs or PBMC feeders using CD3$^+$ cells. The color gradient is proportional to the MFI of CD69, CD154, KLRG1, and TIGIT.

The CD4 and CD8 SPADE tree of TILs expanded with aEM3 aAPCs or PBMC feeders using $CD3^+$ cells is shown in FIG. 46 and FIG. 47. The color gradient is proportional to the mean fluorescence intensity (MFI) of LAG3, TIL3, PD1 and CD137 or CD69, CD154, KLRG1 and TIGIT. Without being bound by theory, the results show that TILs expanded with aEM3 aAPCs had undergone activation, but there was no difference in MFI between the aEM3 aAPCs and PBMC feeders, indicating that the aEM3 aAPCs effectively replicate the phenotypic results obtained with PBMC feeders.

Figure 48:
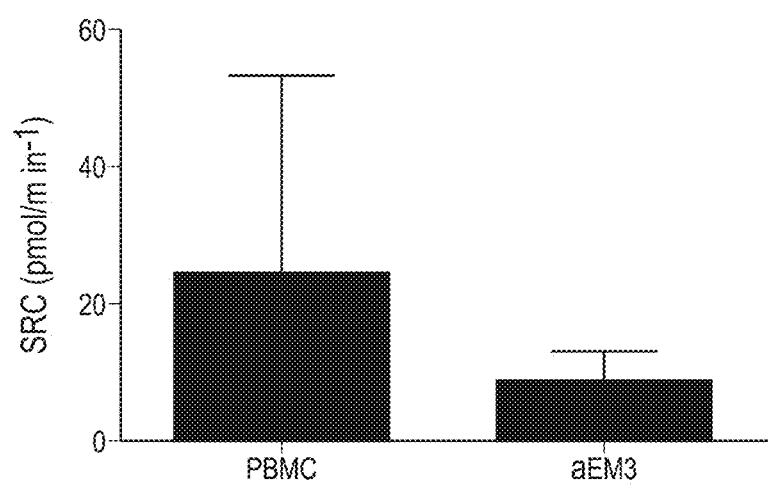
FIG. 48 illustrates a summary of spare respiratory capacity measured by the Seahorse XF Mito stress test.
Figure 49:
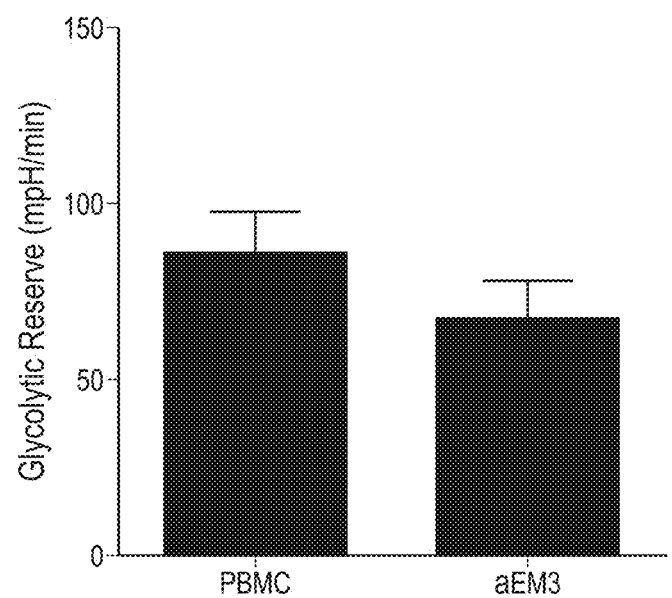
FIG. 49 illustrates a summary of glycolytic reserve measured by the Seahorse XF Mito stress test.

Spare respiratory capacity (SRC) and glycolytic reserve were also evaluated for TILs expanded with aEM3 aAPCs in comparison to PBMC feeders, with results shown in FIG. 48 and FIG. 49. The Seahorse XF Cell Mito Stress Test measures mitochondrial function by directly measuring the oxygen consumption rate (OCR) of cells, using modulators of respiration that target components of the electron transport chain in the mitochondria. The test compounds (oligomycin, FCCP, and a mix of rotenone and antimycin A, described below) are serially injected to measure ATP production, maximal respiration, and non-mitochondrial respiration, respectively. Proton leak and spare respiratory capacity are then calculated using these parameters and basal respiration. Each modulator targets a specific component of the electron transport chain. Oligomycin inhibits ATP synthase (complex V) and the decrease in OCR following injection of oligomycin correlates to the mitochondrial respiration associated with cellular ATP production. Carbonyl cyanide-4 (trifluoromethoxy) phenylhydrazone (FCCP) is an uncoupling agent that collapses the proton gradient and disrupts the mitochondrial membrane potential. As a result, electron flow through the electron transport chain is uninhibited and oxygen is maximally consumed by complex IV. The FCCP-stimulated OCR can then be used to calculate spare respiratory capacity, defined as the difference between maximal respiration and basal respiration. Spare respiratory capacity (SRC) is a measure of the ability of the cell to respond to increased energy demand. The third injection is a mix of rotenone, a complex I inhibitor, and antimycin A, a complex III inhibitor. This combination shuts down mitochondrial respiration and enables the calculation of nonmitochondrial respiration driven by processes outside the mitochondria.

Figure 50:
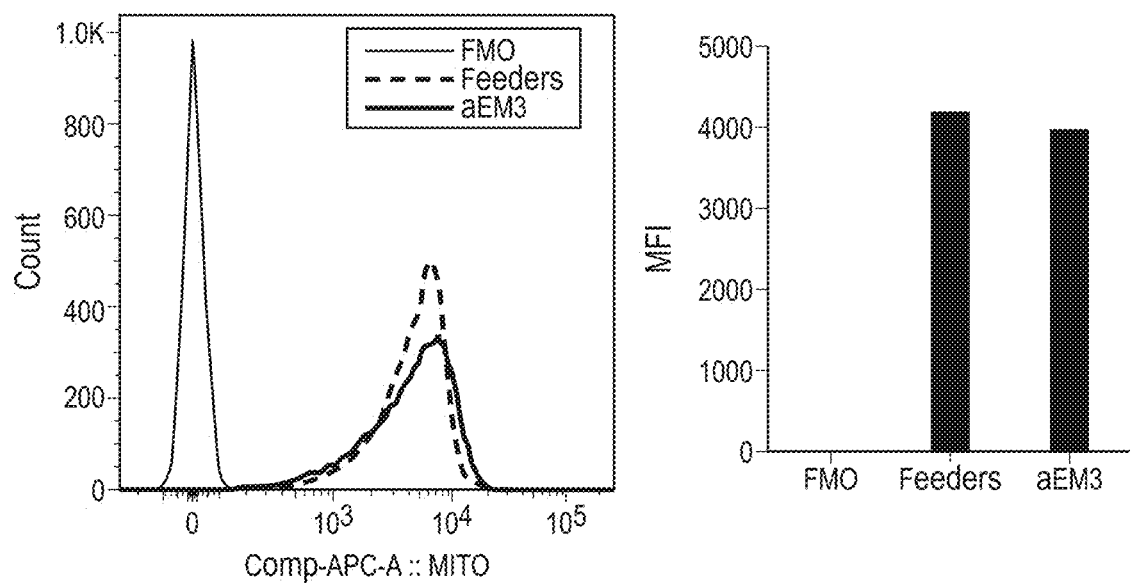
FIG. 50 illustrates a mitochondrial stain of live TILs expanded against PBMC or aEM3 using MitoTracker dye, which stains mitochondria in live cells and for which accumulation is dependent upon membrane potential. TILs expanded against PBMC or aEM3 were stained L/D Aqua followed by MitoTracker red dye. Data shown are MitoTracker positive (MFI) cells gated on live population.
Figure 51:
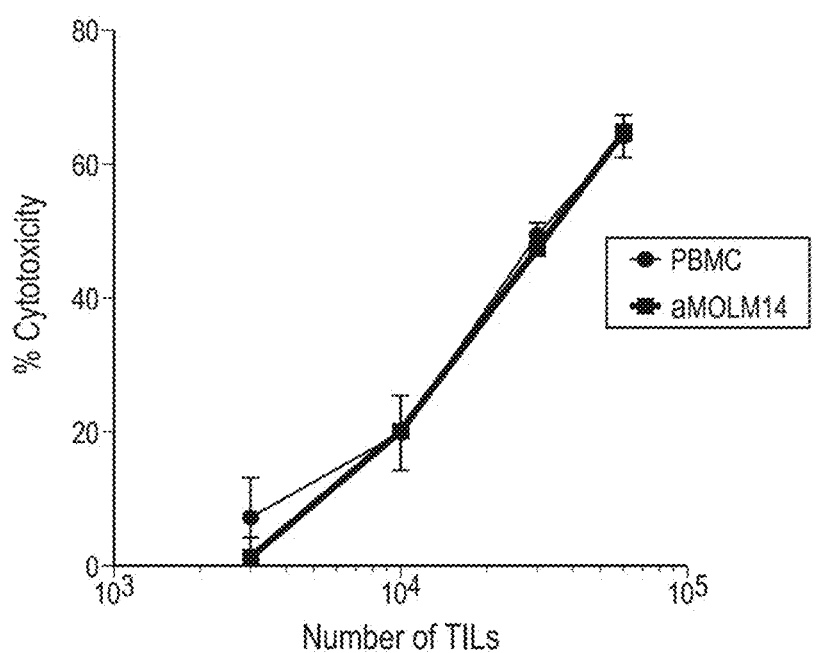
FIG. 51 illustrates results of a P815 BRLA for cytotoxic potency and functional activity, comparing TILs expanded with PBMC feeders to TILs expanded using aMOLM14 aAPCs.
Figure 52:
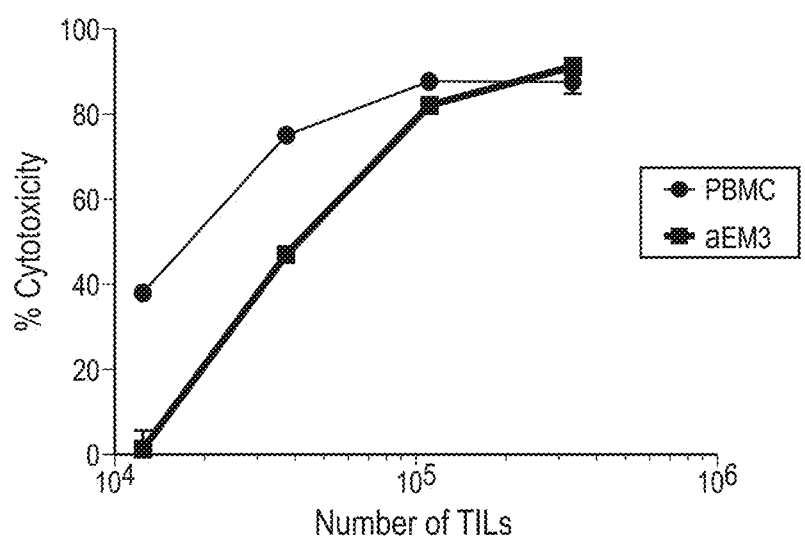
FIG. 52 illustrates results of a P815 BRLA for cytotoxic potency and functional activity, comparing TILs expanded with PBMC feeders to TILs expanded using aEM3 aAPCs.

FIG. 50 illustrates a mitochondrial stain of Live TILs expanded against PBMC feeders or aEM3 aAPCs. MitoTracker dye stains mitochondria in live cells and its accumulation is dependent upon membrane potential. TILs expanded against PBMC feeders or aEM3 were stained L/D Aqua followed by MitoTracker red dye. The data show MitoTracker positive (MFI) cells gated on live population, Example 7—Comparison of Engineered MOLM-14 (aMOLM14) and EM-3 (aEM3) aAPCs TILs expanded with PBMC feeders and aMOLM14 and aEM3 aAPCs, as described in the previous examples, were assessed for functional activity using the BRLA for cytotoxic potency. The P815 BRLA is described in detail in Example 9. The results are shown in FIG. 51 and FIG. 52, and show that TILs expanded with aAPCs have similar functional properties (and expected clinical efficacy) to those expanded with PBMC feeders.

Figure 53:
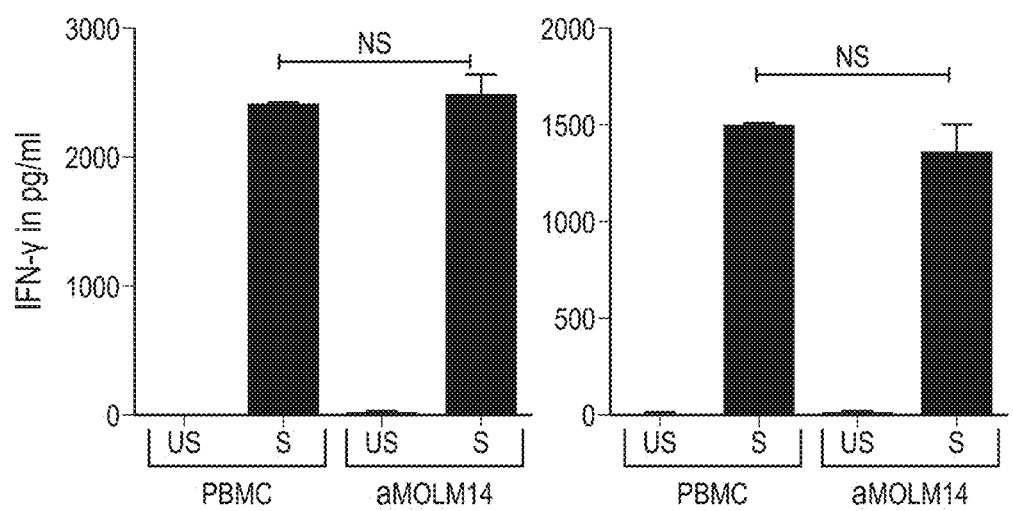
FIG. 53 illustrates IFN-γ release for two batches of TILs following overnight stimulation ("S") with microbeads coated with anti-CD3/CD28/4-1BB in comparison to unstimulated ("US") TILs, comparing TILs expanded with PBMC feeders to TILs expanded using aMOLM14 aAPCs. *p<0.05, p<0.005, *p<0.001, ns=not significant.
Figure 54:
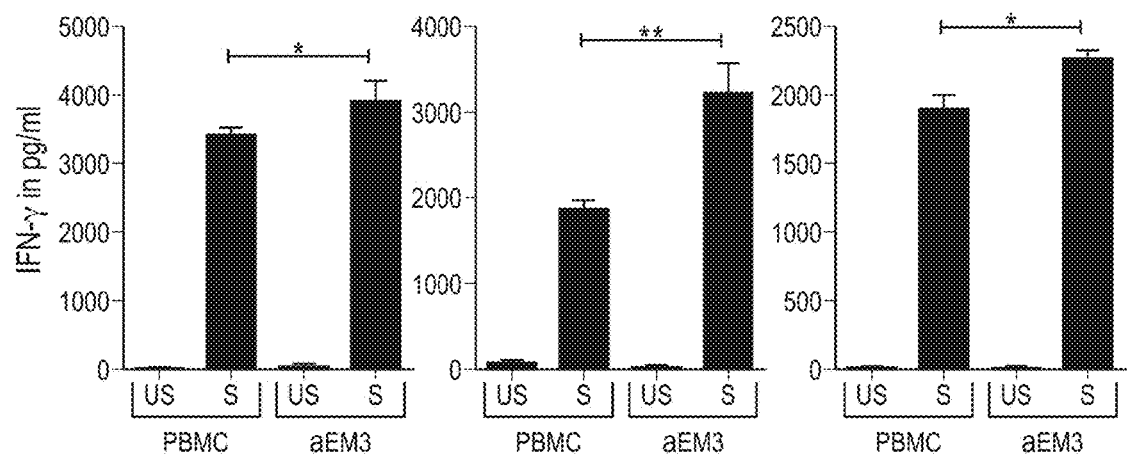
FIG. 54 illustrates IFN-γ release for three batches of TILs following overnight stimulation ("S") with microbeads coated with anti-CD3/CD28/4-1BB in comparison to unstimulated ("US") TILs, comparing TILs expanded with PBMC feeders to TILs expanded using aEM3 aAPCs. *p<0.05, p<0.005, *p<0.001, ns=not significant.
Figure 55:
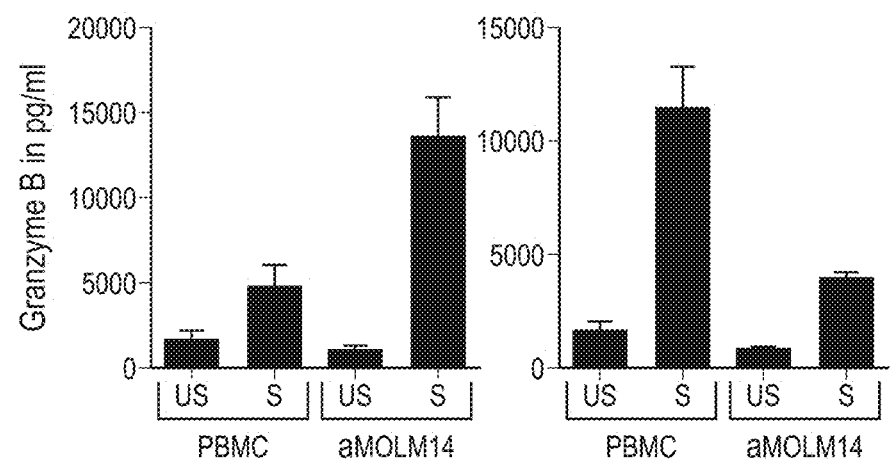
FIG. 55 illustrates Granzyme B release for two batches of TILs following overnight stimulation ("S") with microbeads coated with anti-CD3/CD28/4-1BB in comparison to unstimulated ("US") TILs, comparing TILs expanded with PBMC feeders to TILs expanded using aMOLM14 aAPCs. *p<0.05, p<0.005, *p<0.001, ns=not significant.
Figure 56:
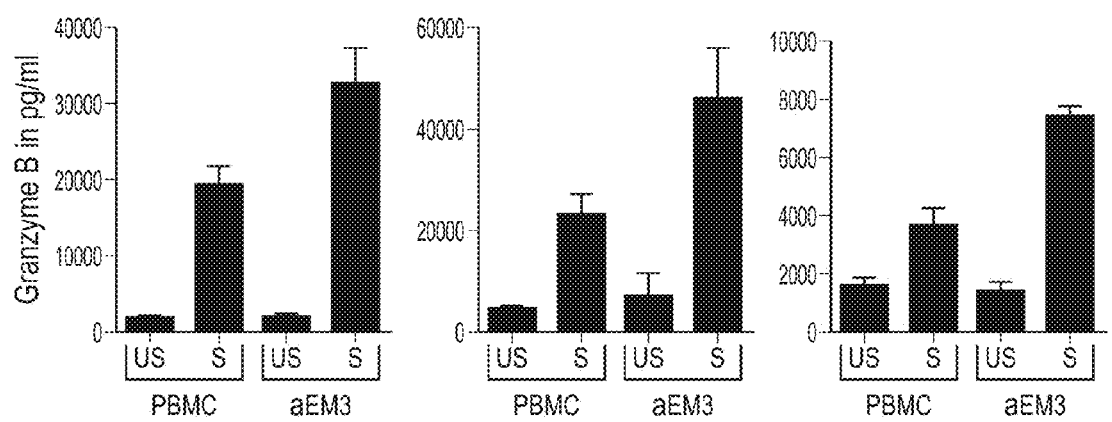
FIG. 56 illustrates Granzyme B release for three batches of TILs following overnight stimulation ("S") with microbeads coated with anti-CD3/CD28/4-1BB in comparison to unstimulated ("US") TILs, comparing TILs expanded with PBMC feeders to TILs expanded using aEM3 aAPCs. *p<0.05, p<0.005, *p<0.001, ns=not significant.

IFN-γ release and Granzyme B release from TILs expanded with PBMC feeders and aMOLM14 and aEM3 aAPCs as described above was also assessed following overnight stimulation with microbeads coated with anti-CD3/CD28/4-1BB. The IFN-γ release results are shown in FIG. 53 and FIG. 54, and the Granzyme B release results are shown in FIG. 55 and FIG. 56. Significant and surprising increases in IFN-γ release and Granzyme B release were observed for TILs expanded with aEM3 aAPCs relative to those expanded with PBMC feeders, but not for TILs expanded by aMOLM14 aAPCs. Without being bound by theory, this suggests that TILs cultured with aEM3 aAPCs may be more active in vivo as a cancer therapy. Most other differences observed were not statistically significant.

The results of TIL expansions with aEM3 and aMOLM14 aAPCs are summarized in Table 9.

Example 8—Preparation of Master Cell Banks for aEM3 and aMOLM14 aAPCs aEM3 and aMOLM14 aAPCs may be grown in the following media compositions to produce master cell banks, which may be further grown in this media for supply of aAPCs: 500 mL of Dulbecco's Modified Eagle Medium DMEM/F12 (Sigma-Aldrich, St. Louis, Miss., USA), 50 mL fetal bovine serum (FBS) Heat Inactivated (HI) (Hyclone); 10 mM 4-(2-hydroxyethyl)-1-piperazineethanesulfonic acid (HEPES buffer) (Life Technologies); 1× Primocin (Invivogen); 1× Plasmocin (Invivogen), and 1× 2-mercaptoethanol (Life Technologies).

The aAPCs described herein, including aEM3 and aMOLM14 aAPCs, may also be grown from a master cell bank using any suitable method known in the art for the growth of cells. In an embodiment, aAPCs are thawed and are then expanded in a medium of 80-90% RPMI 1640+10-20% h.i. FBS (fetal bovine serum) by splitting saturated culture 1:2 to 1:3 every 2-3 days, seeding out at about 0.5-1×10$^6$ cells/mL in 24-well plates, and maintaining at about 0.5-1.5×10$^6$ cells/mL, with incubation at 37° C. and 5% $CO_2$.

Further steps that may be employed to use the aAPCs of certain embodiments of the present invention in the production of human therapies are known in the art and include cell line characterization (HLA high resolution typing); cytokine release testing; testing of human serum to replace FBS to grow aAPC; testing freezing media to freeze aAPCs; master cell banking (including raw material testing and stability testing); standardization of irradiation (including irradiation dose (1000, 3000, 5000, 10000, 15000 rad), fresh versus frozen aAPCs, and with/without TILs); stability of aAPC; development of a panel to evaluate the contamination of aAPCs; development of molecular biology assays (qPCR, DNA sequencing); testing of TIL expansions from different tumor types, including melanoma, cervical, and head and neck cancer (using a G-Rex 5M); potency, purity, and identity testing; mycoplasma and sterility assays; microbiological testing (USP/EP sterility, bioburden and endotoxin assays); and adventitious viral agent testing.

Example 9—Methods of Expanding TILs and Treating Cancer with Expanded TILs

TILs may be expanded using the aAPCs of certain embodiments of the present invention, such as aEM3 and aMOLM14 aAPCs, using any of the expansion methods

TABLE 9

Summary of TIL expansion results with aAPCs.

Figure 57:
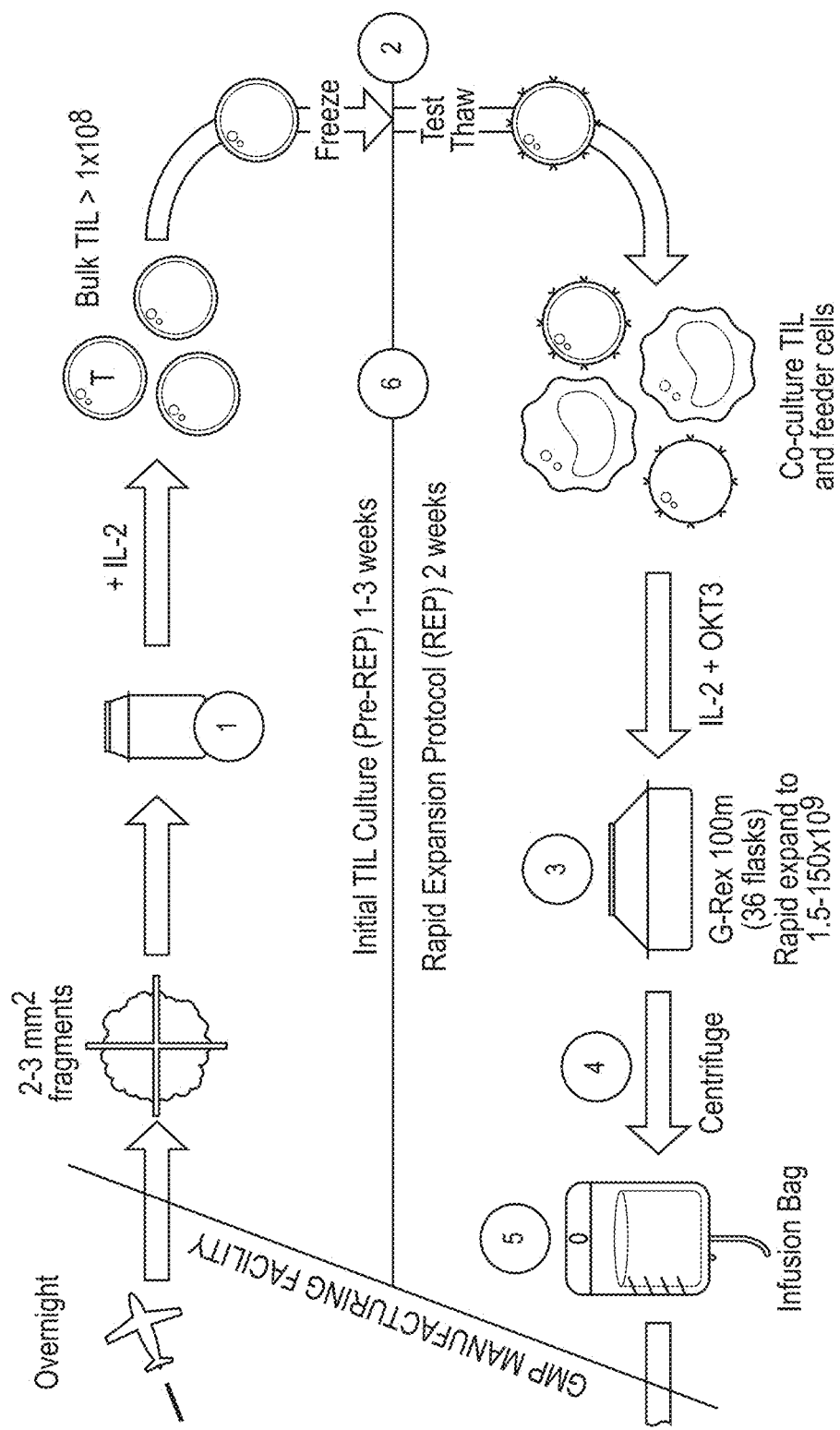
FIG. 57 illustrates a TIL expansion and treatment process. aAPCs of the present invention may be used in both the pre-REP stage (top half of figure) or REP stage (bottom half of figure) and may be added when IL-2 is added to each cell culture. Step 1 refers to the addition of 4 tumor fragments into 10 G-Rex 10 flasks. At step 2, approximately $40 \times 10^6$ TILs or greater are obtained. At step 3, a split occurs into 36 G-Rex 100 flasks for REP. TILs are harvested by centrifugation at step 4. Fresh TIL product is obtained at step 5 after a total process time of approximate 43 days, at which point TILs may be infused into a patient.
Figure 58:
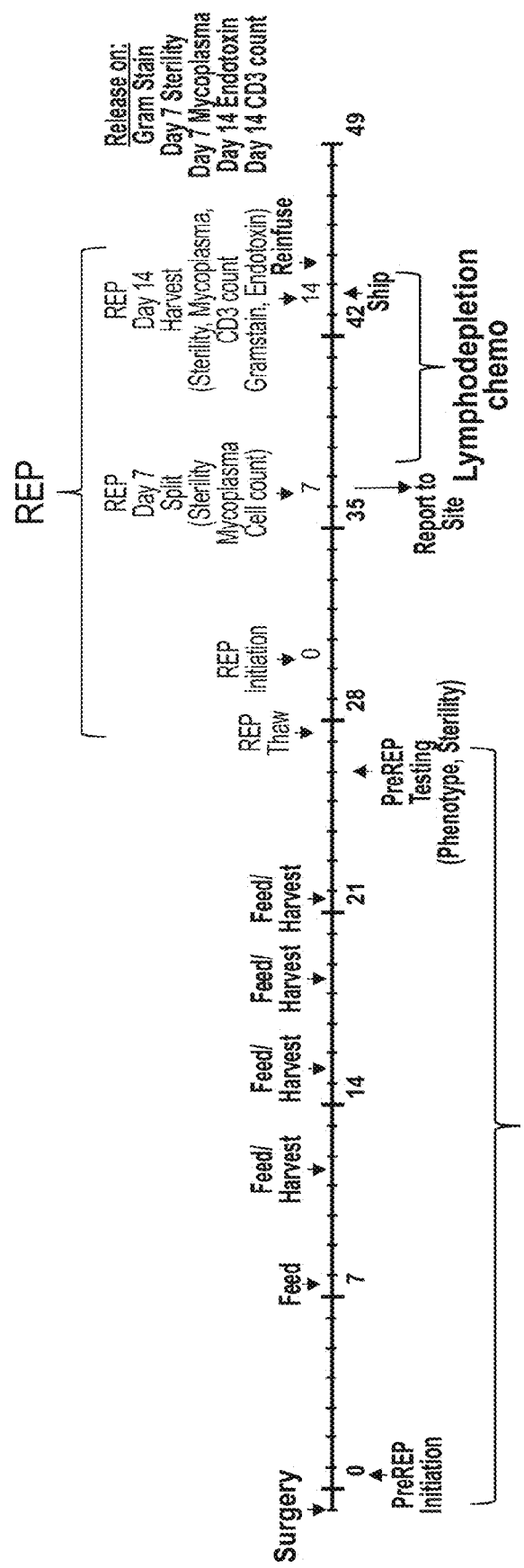
FIG. 58 illustrates a treatment protocol for use with TILs expanded with aAPCs. Surgery (and tumor resection) occurs at the start, and lymphodepletion chemo refers to non-myeloablative lymphodepletion with chemotherapy as described elsewhere herein.

| aAPC | TIL# | Fold Expansion | | Relative expansion | CD8 (%) | | CD4 (%) | | Relative CD8 | Relative CD4 |
|---|---|---|---|---|---|---|---|---|---|---|
| | | PBMC | aAPC | | PBMC | aAPC | PBMC | aAPC | | |
| aMOLM14 | M1032-T2 | 2112 | 1936 | 0.92 | 53 | 65 | 44 | 27 | 1.226 | 0.614 |
| | M1033-T6 | 1761 | 1598 | 0.91 | 50 | 57 | 36 | 40 | 1.140 | 1.111 |
| | M1021T-5 | 2053 | 2024 | 0.99 | 91 | 82 | 8 | 17 | 0.901 | 2.125 |
| | M1030T-4 | 860 | 853 | 0.99 | 46 | 78 | 51 | 12 | 1.696 | 0.235 |
| | M1045 | 858* | 758* | 0.88 | — | — | — | — | — | — |
| | M1021T-1 | 1866 | 1620 | 0.87 | — | — | — | — | — | — |
| | M1032T-1 | 2423 | 2049 | 0.85 | — | — | — | — | — | — |
| | M1042 | 1278 | 1704 | 1.33 | 8 | 8 | 88 | 89 | 0.919 | 1.015 |
| | M1043 | 1601 | 1587 | 0.99 | 90 | 87 | 5 | 5 | 0.968 | 0.947 |
| aEM3 | M1054 | 2058 | 1647 | 0.80 | 98 | 96 | 2 | 2 | 0.981 | 1.400 |
| | M1055 | 729 | 1533 | 2.10 | 25 | 66 | 70 | 31 | 2.694 | 0.441 |
| | M1021T-1 | 2985 | 2805 | 0.94 | 87 | 75 | 10 | 20 | 0.862 | 2.000 |
| | M1045 | 1336 | 1047 | 0.78 | — | — | — | — | — | — | described herein. For example, a method for expanding TILs is depicted in FIG. 57. The expansion of TILs using aAPCs may be further combined with any method of treating cancer in a patient described herein. A method for expanding TILs and treating a patient with expanded TILs, wherein the expansion makes use of aAPCs (including aEM3 and aMOLM14 aAPCs), is shown in FIG. 58.

Example 10—P815 Bioluminescent Redirected Lysis Assay

In this example, the development of a surrogate target cell line to evaluate the lytic potential of TILs in a Bioluminescent Redirected Lysis Assay (BRLA) is described. The BRLA enables assessment of T cell mediated killing in the absence of autologous tumor cells. Cytolytic activity can be assessed with and without engaging the T cell receptor in one to four hours, assessing T cell killing engaging the T cell receptor and without so-called lymphokine activated killer activities (LAK).

Mouse mastocytoma P815 cells expressing the endogenous CD16 Fc receptor can bind anti-CD3ε (OKT-3), providing a potent TCR activation signal as a target cell line. The P815 Clone G6 was transduced with a lentiviral vector based on eGFP and firefly luciferase, sorted and cloned using the BD FACSAria II. Clone G6 was selected based on eGFP intensity analyzed using an Intellicyt iQue Screener. Target cells and TILs of interest were co-cultured +/− OKT-3 to assess TCR activation (specific killing) or non-specific (lymphokine activated killing, LAK) respectively. Following 4 hours of incubation, firefly luciferin ((4S)-2-(6-hydroxy-1,3-benzothiazol-2-yl)-4,5-dihydrothiazole-4-carboxylic acid, commercially available from multiple sources) was added to the wells and incubated for 5 minutes. Bioluminescence intensity was read using a luminometer. Percent cytotoxicity and survival were calculated using the following formula: % Survival=(experimental survival−minimum)/(maximum signal−minimum signal)×100; % Cytotoxicity=100−(% Survival). Interferon gamma release in the media supernatant of co-cultured TILs was analyzed by ELISA, and LAMP1 (CD107a, clone eBioH4A3) expression on TILs was analyzed on a flow cytometer to evaluate the cytotoxic potency of TILs.

Figure 59:
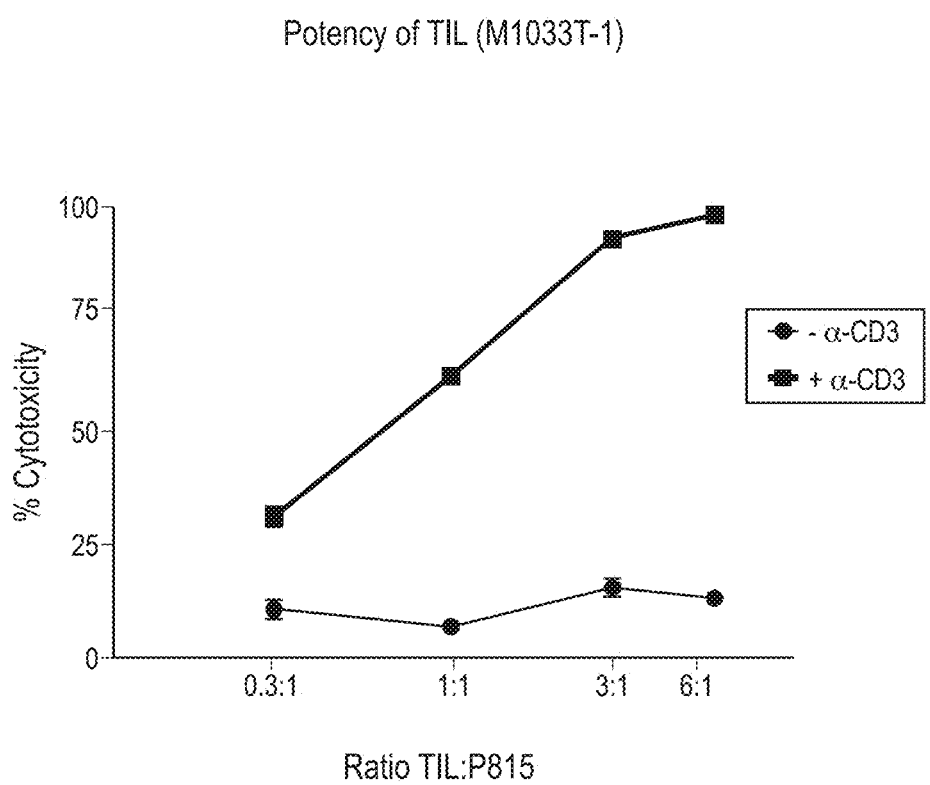
FIG. 59 illustrates Bioluminescent Redirected Lysis Assay (BRLA) results, showing percentage cytotoxicity of TIL batch M1033T-1 when co-cultured with P815 Clone G6 (with and without anti-CD3) at individual effector:target ratios.
Figure 60:
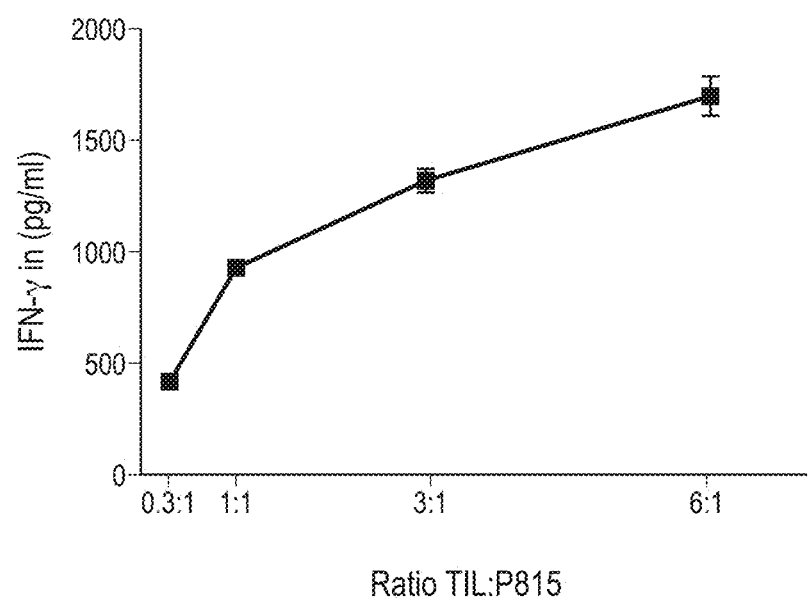
FIG. 60 illustrates enzyme-linked immunosorbent assay (ELISA) data showing amount of IFN-γ released against different ratios of effector to target cells.
Figure 61:
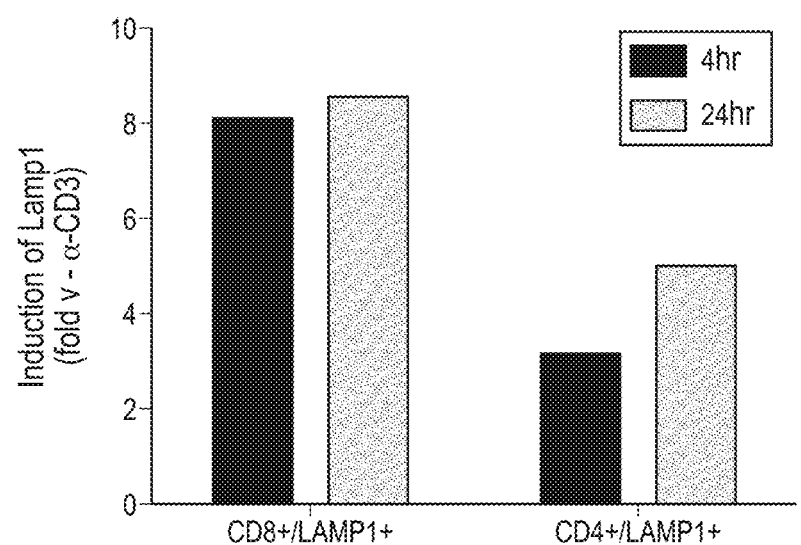
FIG. 61 illustrates LAMP1 (%) expressed by TIL batch M1033T-1 when co-cultured with P815 Clone G6 in the presence of anti-CD3 at a ratio of 1:1 effector to target cells for 4 hr and 24 hr co-culture.

Results are shown in FIG. 59 to FIG. 75. FIG. 59 illustrates percent toxicity of TIL batch M1033T-1 co-cultured with P815 Clone G6 (with and without anti-CD3) at individual effector:target ratios by BRLA. FIG. 60 illustrates enzyme-linked immunosorbent assay (ELISA) data showing the amount of IFN-γ released against different ratios of effector to target cells. FIG. 61 illustrates LAMP1 (%) expressed by TIL batch M1033T-1 when co-cultured with P815 Clone G6 in the presence of anti-CD3 at a ratio of 1:1 effector to target cells for 4 hours and 24 hours co-culture.

Figure 62:
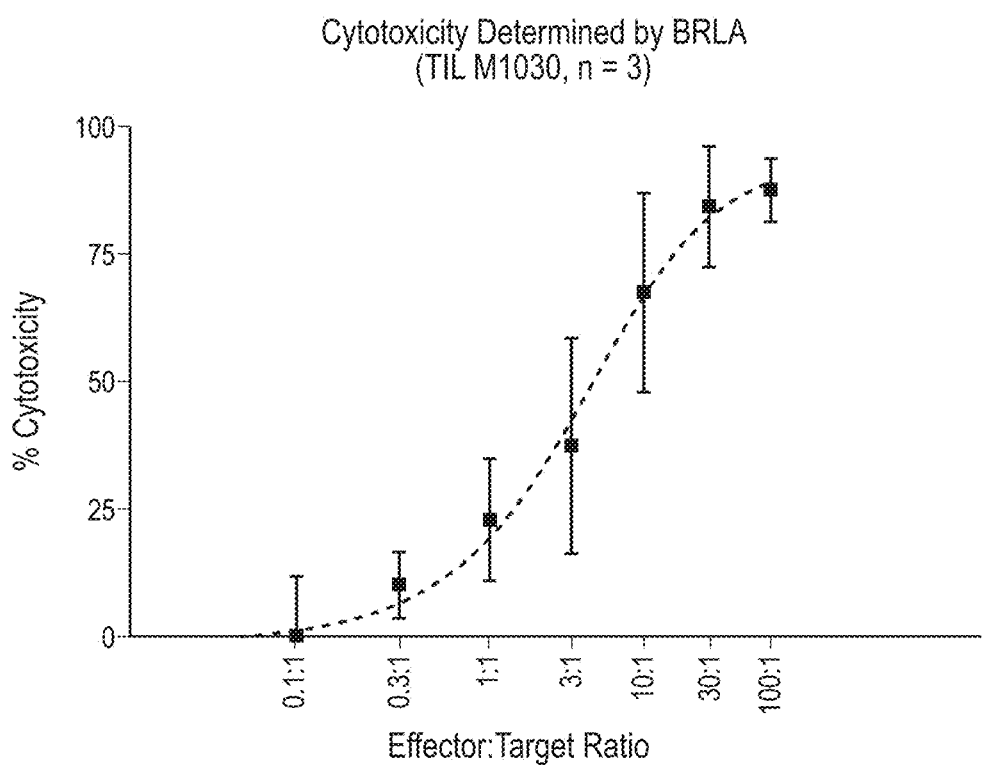
FIG. 62 illustrates BRLA results for TIL batch M1030. Cytotoxicity (measured as $LU_{50}/1 \times 10^6$ TIL) by BRLA is 26±16.
Figure 63:
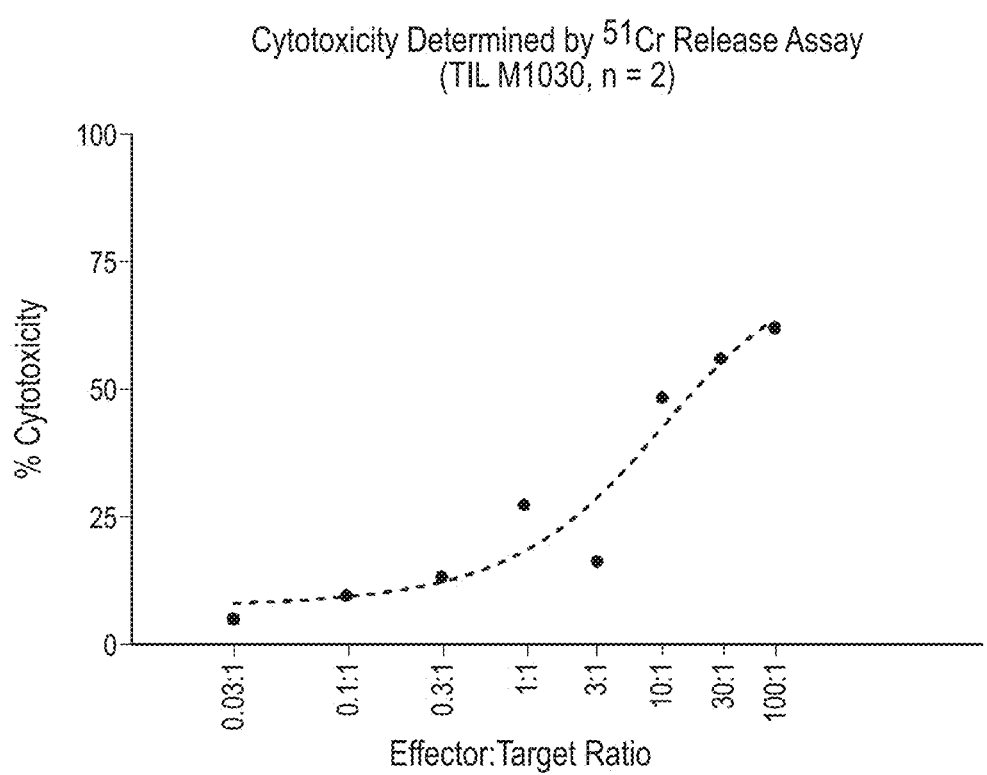
FIG. 63 illustrates standard chromium release assay for TIL batch M1030. Cytotoxicity (measured as $LU_{50}/1 \times 10^6$ TIL) by the chromium release assay is 22.

The results were confirmed using a second TIL batch as shown in FIG. 62, which illustrates BRLA for TIL batch M1030. The cytotoxicity (measured as $LU_{50}/1\times10^6$ TIL) by BRLA is 26±16. FIG. 63 illustrates the results of a standard chromium release assay for TIL batch M1030. The cytotoxicity (measured as $LU_{50}/1\times10^6$ TIL) by chromium release assay is 22.

Figure 64:
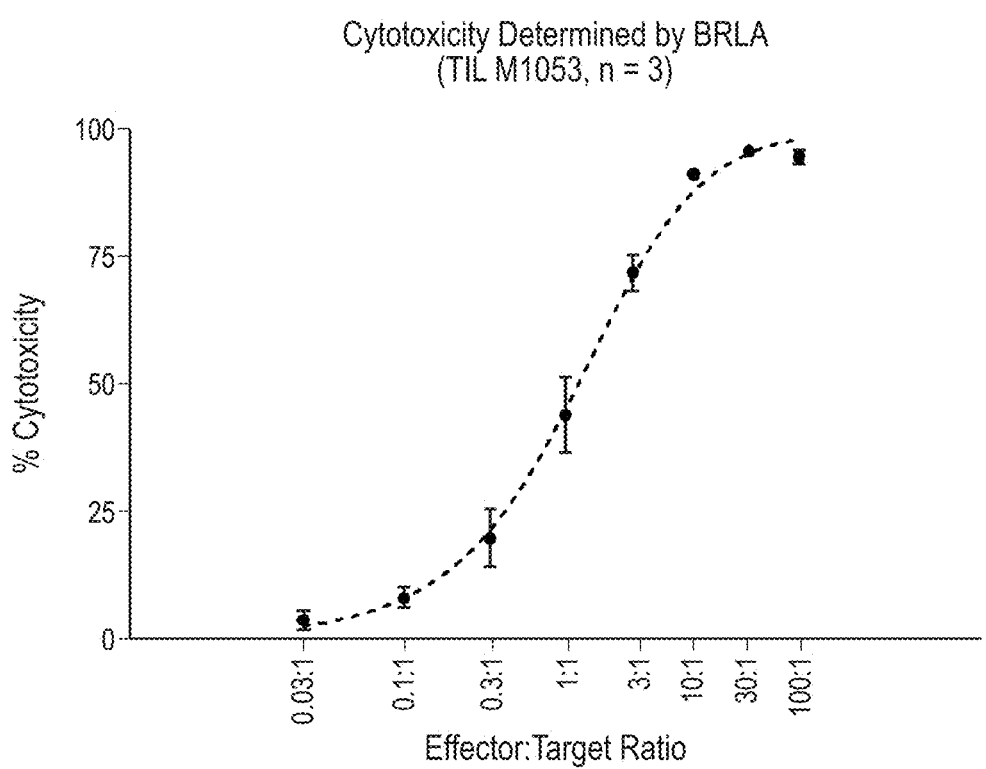
FIG. 64 illustrates BRLA results for TIL batch M1053, showing the lytic units of the TILs by BRLA as 70±17.
Figure 65:
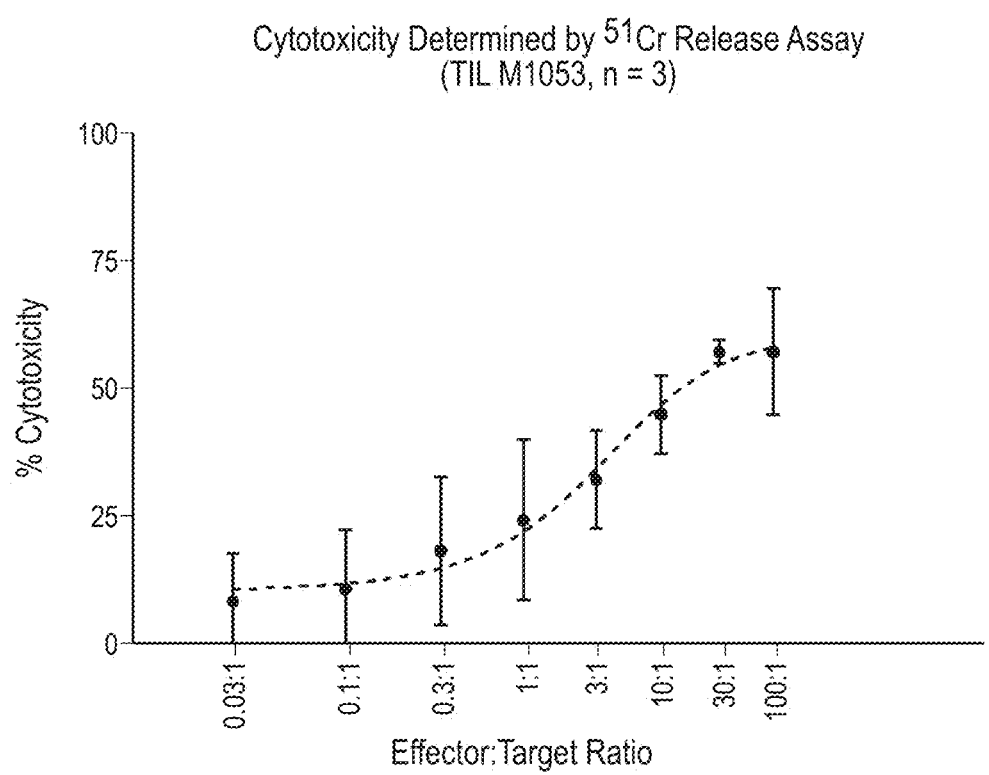
FIG. 65 illustrates standard chromium release assay results for TIL batch M1053, also showing lytic unit of the TILs by chromium assay as 14±5. Comparison of this result with FIG. 64 shows the comparable performance of the BRLA and chromium release assay.

Results were further confirmed using a third TIL batch. FIG. 64 illustrates BRLA results for TIL batch M1053, showing lytic units of the TILs by BRLA as 70±17. FIG. 65 illustrates the results of a standard chromium release assay for TIL batch M1053, showing lytic unit of the TILs by chromium assay as 14±5. Comparison of two assay results shows the comparable performance of the BRLA result to the chromium release assay result.

Figure 66:
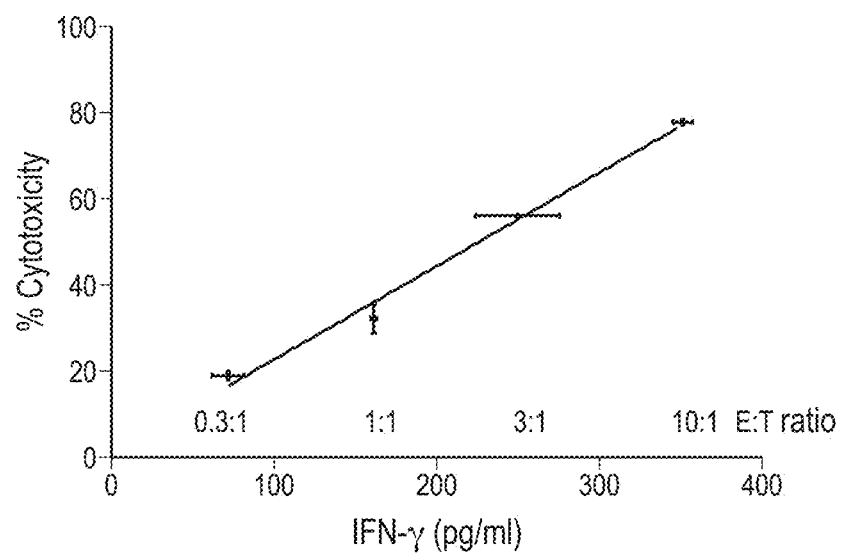
FIG. 66 illustrates the linear relationship between IFN-γ release and cytotoxic potential of TILs.
Figure 67:
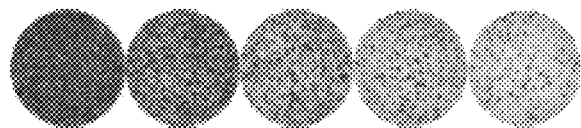
FIG. 67 illustrates ELISpot results for IFN-γ.
Figure 67:
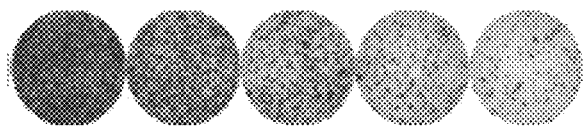
Figure 68:
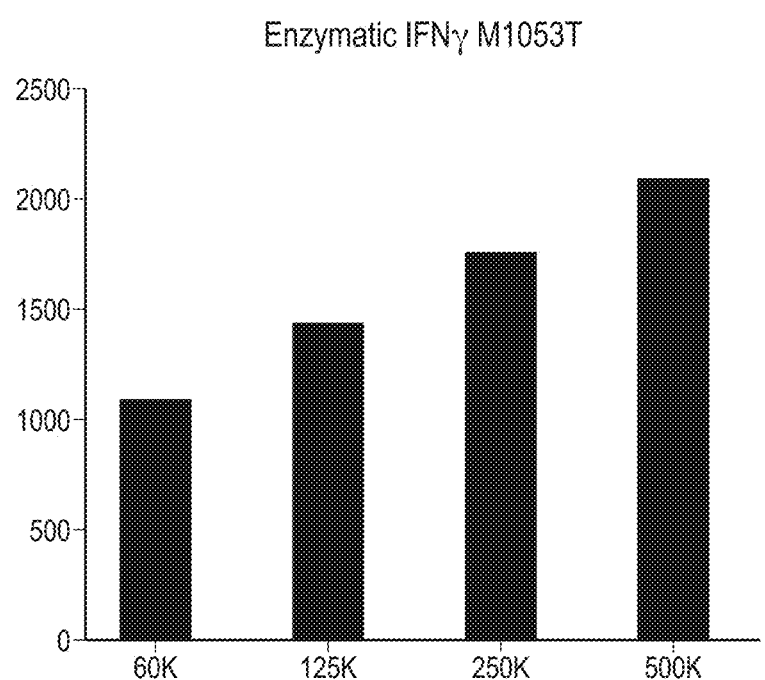
FIG. 68 illustrates enzymatic IFN-γ release for TIL batch M1053.
Figure 69:
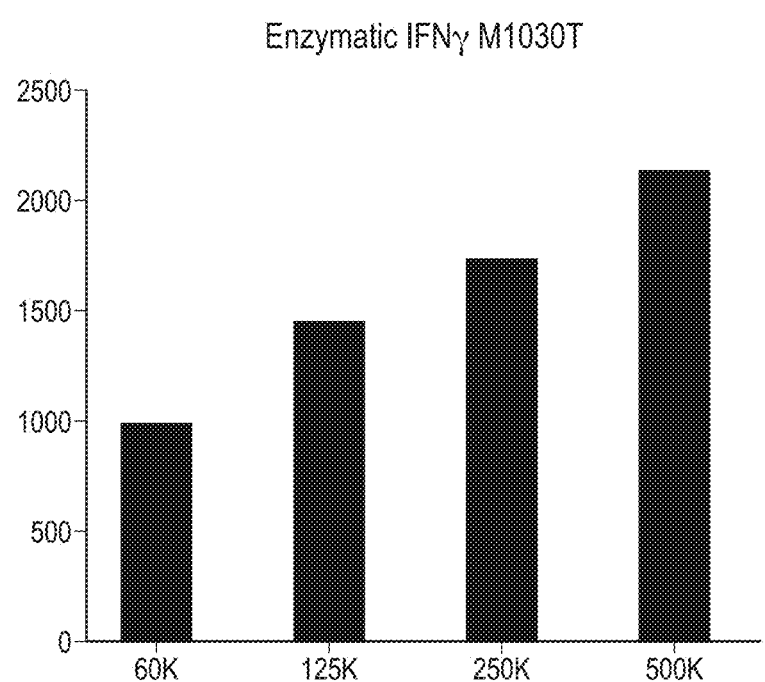
FIG. 69 illustrates enzymatic IFN-γ release for TIL batch M1030.
Figure 70:
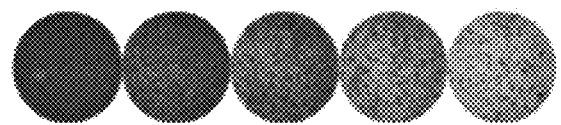
FIG. 70 illustrates ELISpot data showing Granzyme B release by M1053T and M1030T. This data confirms the potency of the TILs shown by the BRLA.
Figure 70:
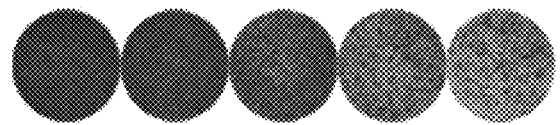
Figure 71:
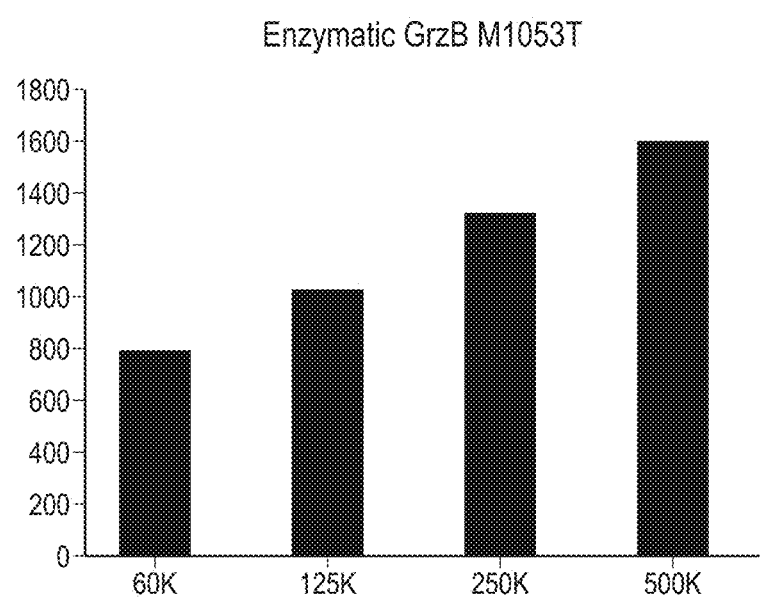
FIG. 71 illustrates enzymatic Granzyme B release for TIL batch M1053.
Figure 72:
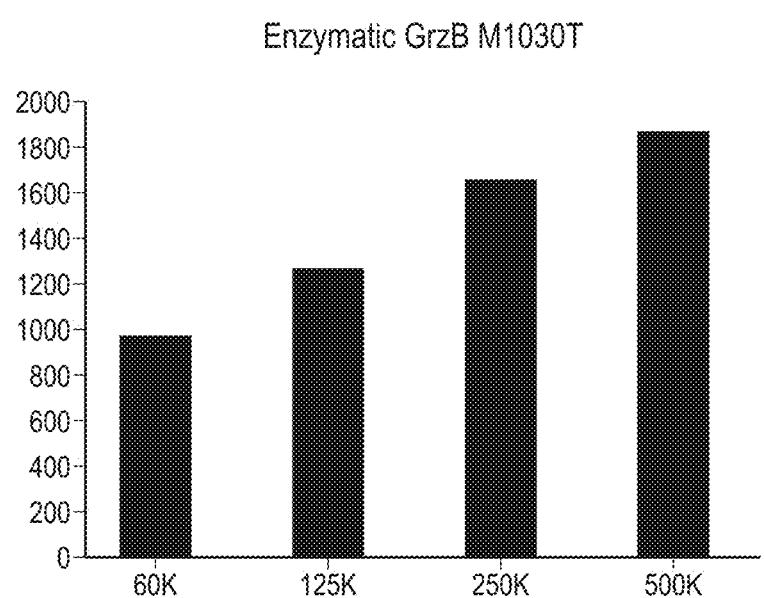
FIG. 72 illustrates enzymatic Granzyme B release for TIL batch M1030.
Figure 73:
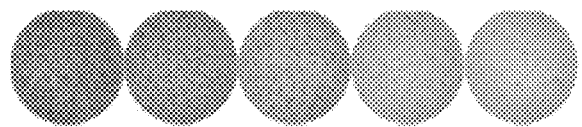
FIG. 73 illustrates ELISpot data showing TNF-α release by M1053T and M1030T. This data confirms the potency of the TILs shown by the BRLA.
Figure 73:
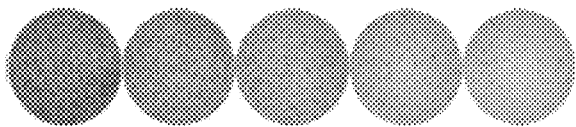
Figure 74:
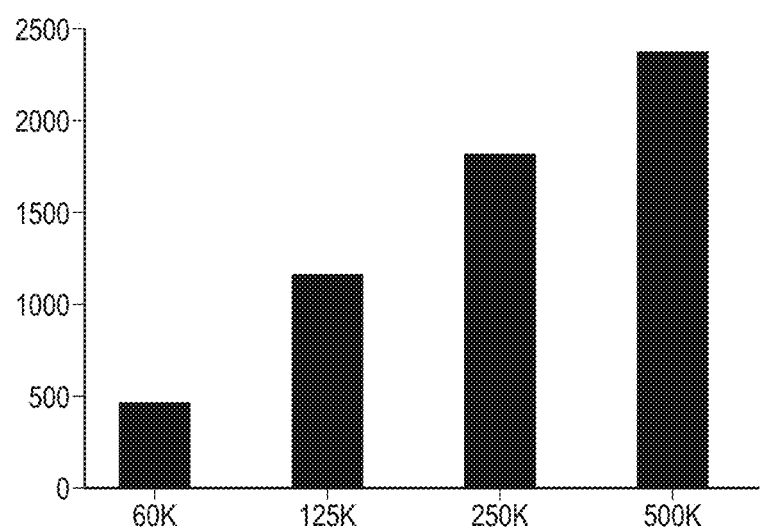
FIG. 74 illustrates enzymatic TNF-α release for TIL batch M1053.
Figure 75:
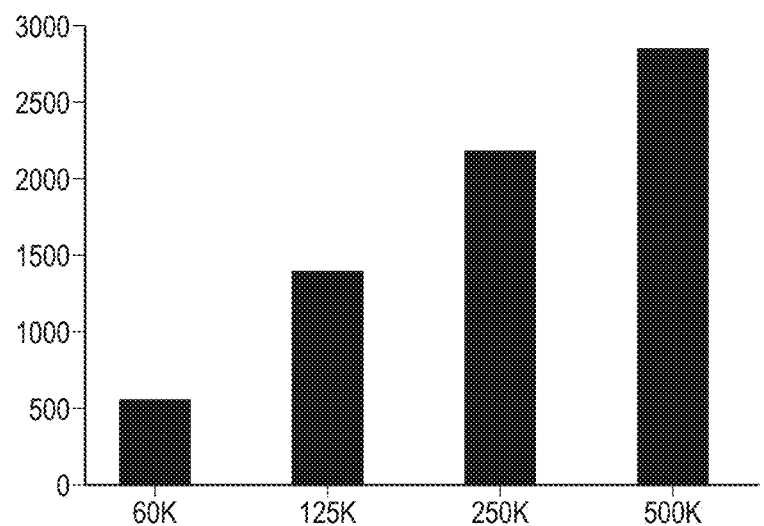
FIG. 75 illustrates enzymatic TNF-α release for TIL batch M1030.

FIG. 66 illustrates the linear relationship between IFN-γ release and cytotoxic potential of TILs. FIG. 67 illustrates ELISpot results for IFN-γ. FIG. 68 illustrates enzymatic IFN-γ release for TIL batch M1053. FIG. 69 illustrates enzymatic IFN-γ release for TIL batch M1030. FIG. 70 illustrates ELISpot data showing Granzyme B release by M1053T and M1030T. FIG. 71 illustrates enzymatic Granzyme B release for TIL batch M1053. FIG. 72 illustrates enzymatic Granzyme B release for TIL batch M1030. FIG. 73 illustrates ELISpot data showing TNF-α release by M1053T and M1030T. FIG. 74 illustrates enzymatic TNF-α release for TIL batch M1053. FIG. 75 illustrates enzymatic TNF-α release for TIL batch M1030. The data in FIG. 66 to FIG. 76 confirms the potency of these batches of TILs as also shown by the BRLA.

In conclusion, the BRLA requires no radionuclides and is as efficient and sensitive as traditional cytotoxicity assays. Flow cytometric assessment of Lamp1 expression on TILs at individual time points demonstrates degranulation of cytotoxic T cells relative to the potency shown by BRLA. The BRLA demonstrates similar to better potency than standard chromium release assay. BRLA also enables evaluation of the potency of TIL lytic activity. Comparison of BRLA with chromium release assay shows the efficiency and reliability of BRLA. BRLA has a linear relationship with IFNγ release by TILs. Release assay of IFN-γ, TNFα and Granzyme B by ELISpot is consistent with the cytotoxic efficiency of the TILs evaluated by BRLA.

Example 11—Process for Weaning EM3 Cells from FBS to hAB Serum

Figure 76:
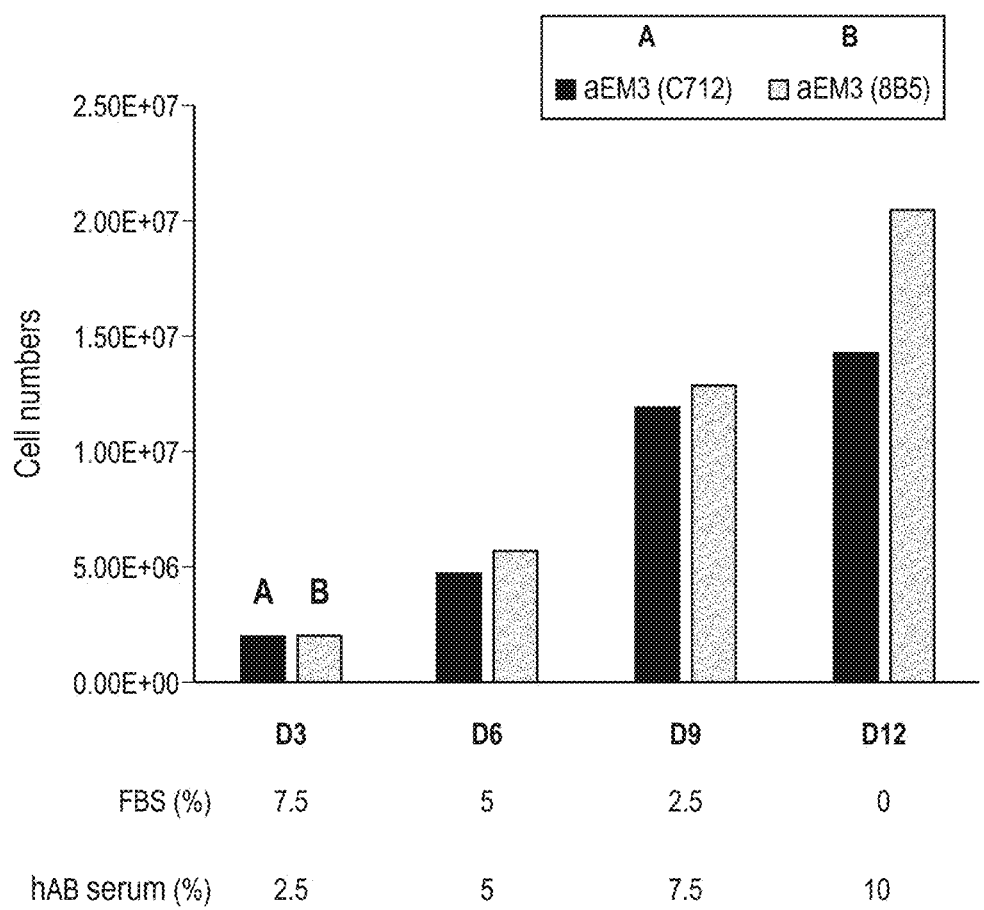
FIG. 76 illustrates changes in cell populations of aEM3 cells (C712 (A) and 8B5 (B)) when weaning such cell populations off of FBS to hAB serum media.

In order to avoid reactivity, some cell lines may need to be weaned from one medium to another. Here, EM3 cells are weaned from FBS to hAB serum to avoid reactivity. As shown in FIG. 76, aEM3 cells were successfully weaned off of FBS to hAB serum.

Example 12—Freezing Media Formulation Optimization

Figure 77:
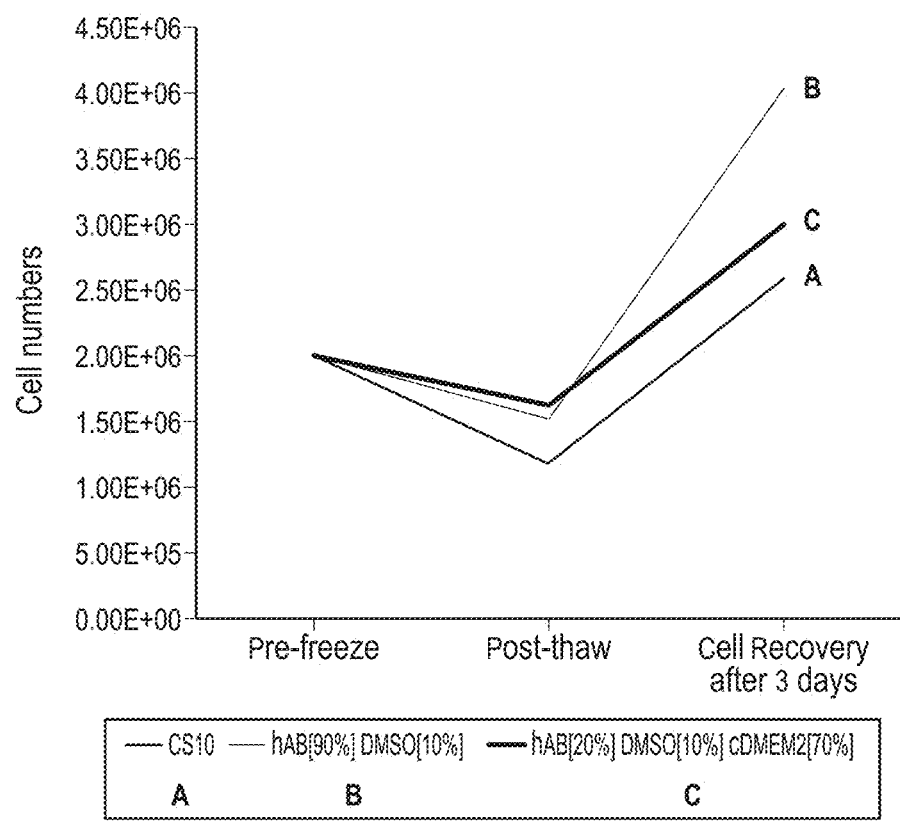
FIG. 77 illustrates changes in cell populations of during freeze-thaw-recovery cycles with aEM3 cell populations suspended in various freezing media.

To cryobank EM3 cells cultured as described herein, methods were freezing media formulation were optimized. As shown in FIG. 77, three freezing media were used and their effect on cell numbers were counted. The cell media utilized included CryStor 10 (Biolife Solutions (CS10)) (A), hAB [90%] and DMSO [10%] (B), and hAB [20%] with DMSO [10%] and cDMEM2 [70%] (C). FIG. 77 demonstrates that the formulation of human AB serum (90%) and DMSO (10%) provided for unexpectedly increased EM3 cell numbers after 3 days of recovery.

Figure 78:
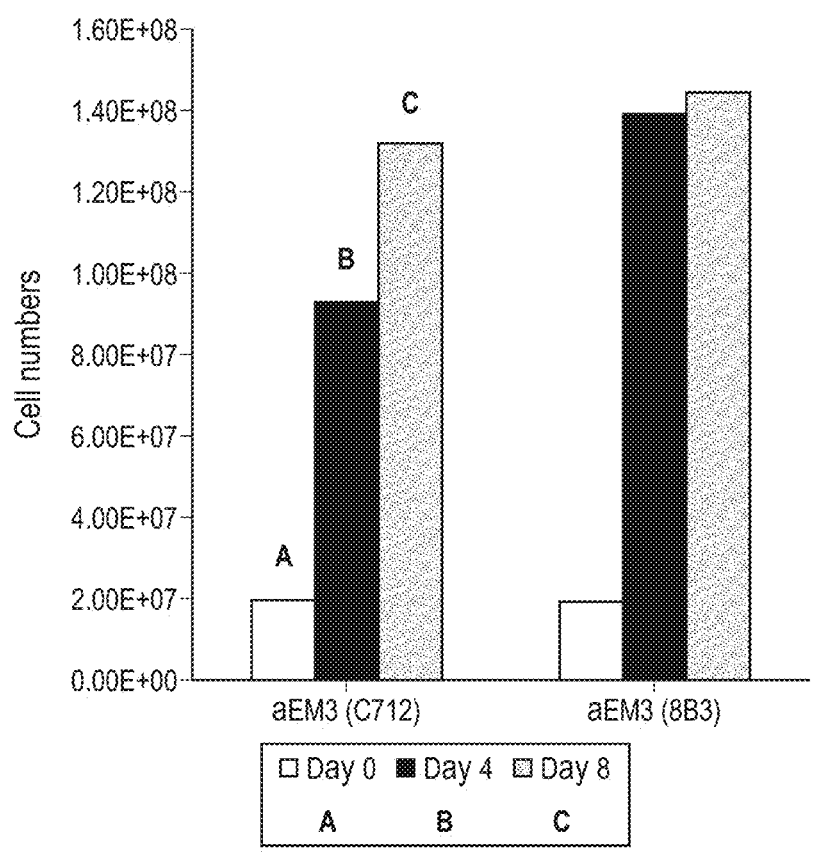
FIG. 78 illustrates the growth of aEM3 cells in gas permeable cell culture flasks over an eight-day time course.

Example 13—Growth of aEM3 Cells in GREX Flasks aEM3 cells were cultured in gas permeable cell culture flasks (i.e., GREX flasks (Wilson Wolf Manufacturing)) and the effect on cell doubling time was observed over an 8 day time course. As shown in FIG. 78, the GREX flasks provided for rapid growth of aEM3 cells.

Example 14—Flow Panel Analysis to Determine aEM3 Cell Purity

Figure 79:
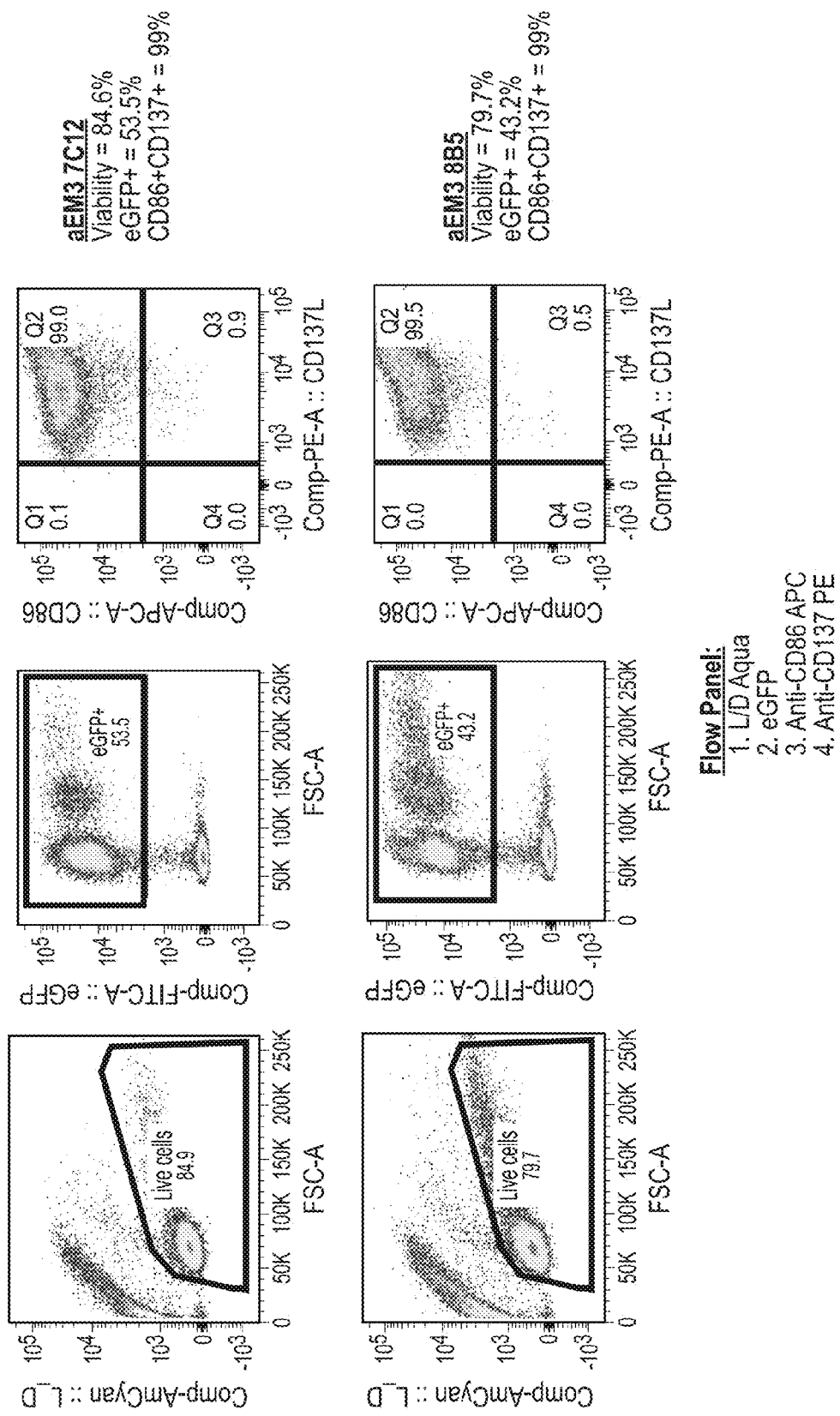
FIG. 79 illustrates a flow panel analysis to determine the purity of aEM3 cells.
Figure 80:
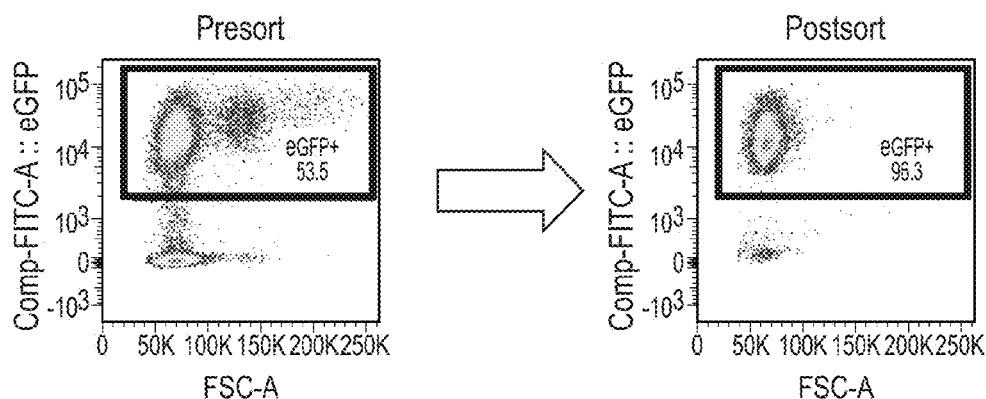
FIG. 80 illustrates the results of a flow panel analysis used to determine the purity of aEM3 cells.
Figure 80:
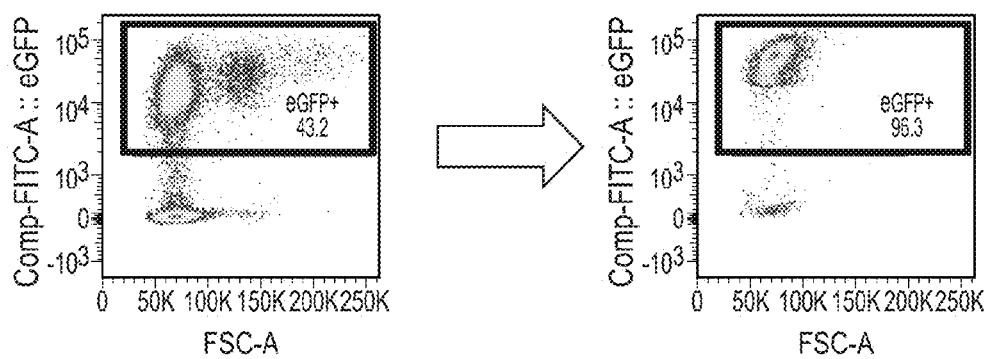

To determine the purity of cells cultured according to the processes described herein, a flow panel analysis was used to determine the purity of aEM3 aAPCs. The results of such analysis are described in FIGS. 79 and 80. As shown in FIG. 80, before sorting aEM3 cell populations were 53.5% and 43.2% eGFP+ for aEM3 7C12 and aEM3 8B5 cells, respectively. Postsorting, cell populations was improved to 96.8% and 96.3% eGFP+ for aEM3 7C12 and aEM3 8B5 cells, respectively (FIG. 80).

Example 15—aEM3 Feeder Cells as an Alternative to PBMC Feeders

Figure 81:
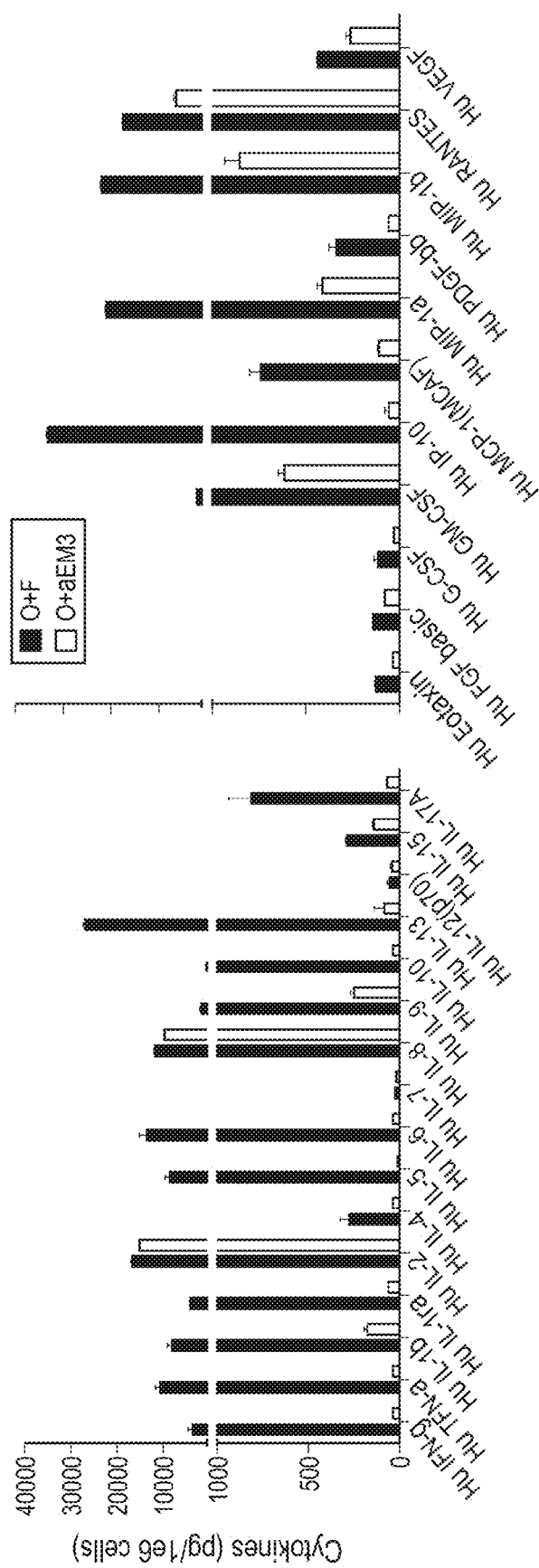
FIG. 81 illustrates the differences in cytokine expression between aEM3 feeder cells and PBMC feeders stimulated by OKT3.

As described herein, aEM3 cells may be used as an alternative for PBMC feeders, resulting in unexpectedly different properties for both TIL expansion process and the resulting TILs. To compare differences in cytokine expression, PBMCs and aEM3 cells were stimulated by treatment with OKT-3. As shown in FIG. 81, aEM3 cells displayed a comparatively different cytokine expression profile as compared to PBMCs. Surprisingly, the aEM3 cells of the present invention provide efficacious TILs (as shown herein) without reproducing the same cytokine secretion properties of TILs expanded with conventional PBMCs.

Example 16—Comparison Between Complete Media and Serum Free Media TIL Expansion

In order to optimize the TIL expansion protocols, several TIL expansion experiments were performed as described herein, but with serum free media rather than complete media (CM1).

Figure 82:
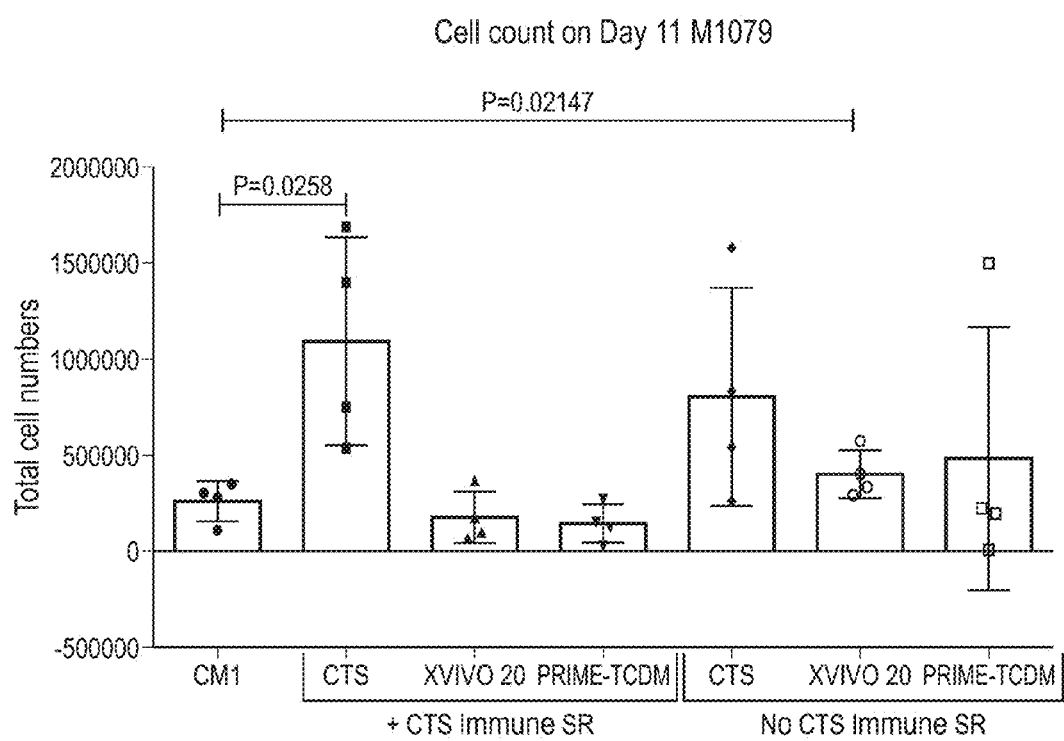
FIG. 82 illustrates that TIL may advantageously expanded (pre-REP) with serum free media (i.e., CTS Optmizer) to provide increased cell numbers as compared to CM1.

In one experiment, tissue fragments were cultured in a single well with CM1 or various serum free media with 300 IU/mL of IL-2. Cells were then counted on Day 11 before initiating REP. The various serum free media used included Prime CDM (Irvine), CTS Optimizer (ThermoFisher), and Xvivo-20 (Lonza). As shown in FIG. 82, TIL expansion (PreREP) with CTS provided increased cell numbers as compared to CM1.

Figure 83:
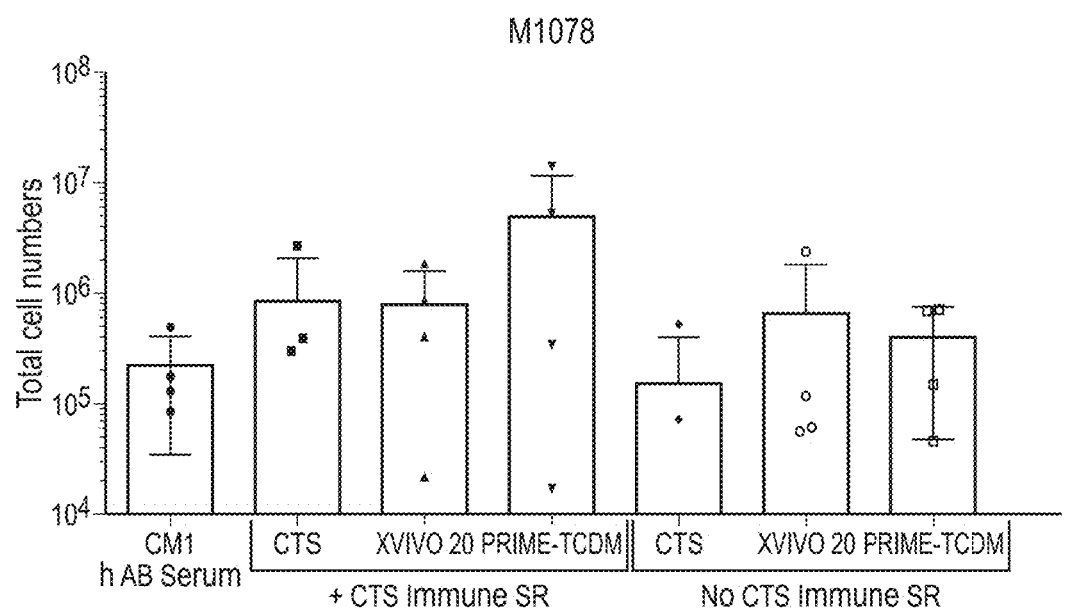
FIG. 83 and FIG. 84 illustrate that TIL may advantageously expanded with serum free media (i.e., CTS Optmizer) to provide increased cell numbers as compared to CM1 at Day 11 (PreREP) (FIG. 83) and Day 22 (Pre- and Post-REP) (FIG. 84).
Figure 84:
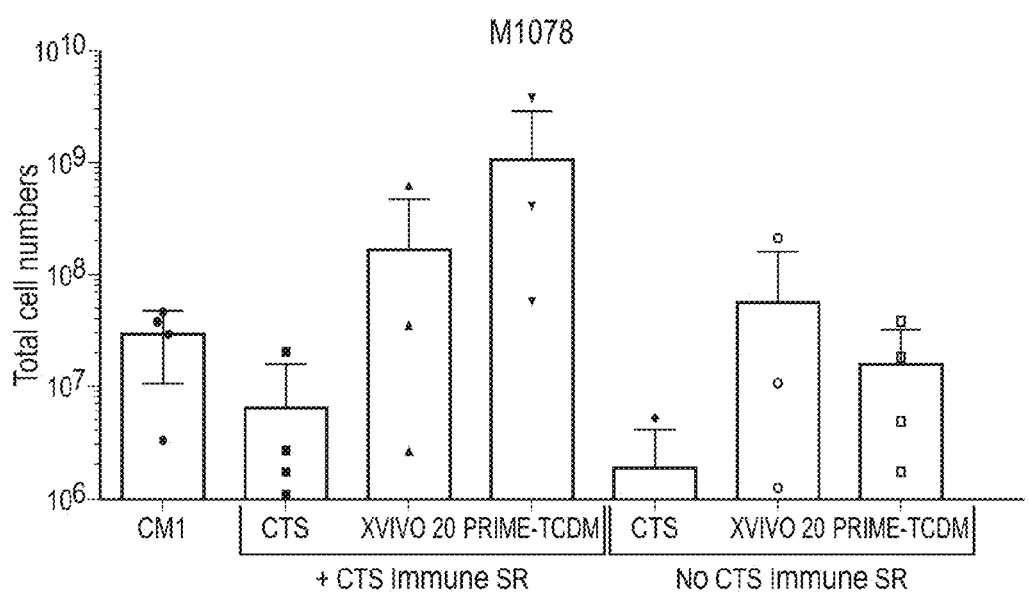

Additionally, tissue fragments were cultured with CM1 or various serum free media with 6000 IU/mL of IL-2 until Day 11. REP was then initiated on Day 11 using PBMC feeders, OKT-3, and IL-2, and culture was split on Day 16. Cultures were then terminated at the end of Day 22. The various serum free media used included Prime CDM (Irvine), CTS Optimizer (ThermoFisher), and Xvivo-20 (Lonza). As shown in FIG. 83 and FIG. 84, when counting cells at Days 11 and Day 22, respectively, TIL expansion (PreREP) with Prime CDM provided increased cell numbers as compared to CM1.

Example 17—Growth of aAPCs in Serum Free Media as Compared to Serum-Based Media

In order to optimize aAPC growth and maintenance protocols in the absence of serum, aEM3 cells were cultured using various serum free media.

aEM3 cells were cultured in 24 well plates at $1 \times 10^6$ cells per well for 3 days using general cell culture protocols as described herein, with the exception that that one group of cells were provided with serum-based media (cDMEM (10% hSerum) and the other groups of cells were provided with serum free media. The serum free media utilized for the study included CTS OpTmizer (ThermoFisher), Xvivo 20 (Lonza), Prime-TCDM (Irvine), and XFSM (MesenCult) media. Cells were then counted on Day 3.

Figure 85:
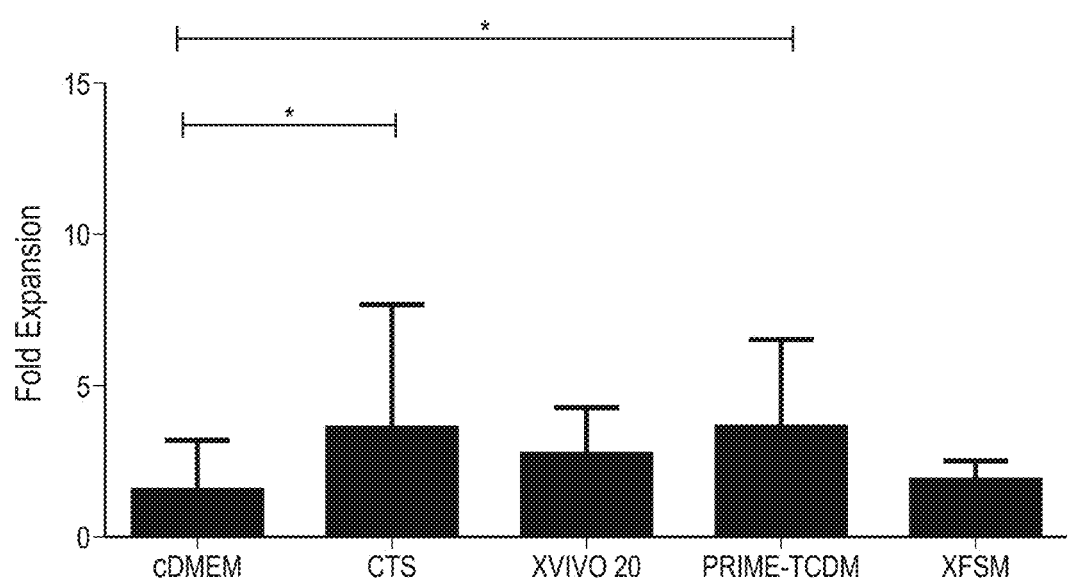
FIG. 85 illustrates that aAPC cells (i.e., aEM3 cells) can be grown and using serum free media. Specifically, CTS OpTimizer and Prime-TCDM were found to be effective in growing aEM3 as compared to cDMEM (10% hSerum). Data shown were mean+SD of five separate experiments. The p value was calculated by the student t-test. *P<0.05.

As shown in FIG. 85, CTS OpTmizer and Prime-TCDM serum free media provided cell growth that was comparable to serum-based media (i.e., cDMEM (10% hSerum). Therefore, serum free media is an effective alternative for growing and maintaining aAPCs as compared to serum-based media.

Example 18—Propagation, Maintenance, and Cryopreservation of aAPCs

In this example, procedures are provided for the preparation and preservation of aAPCs. Specifically, aEM3 cells from a cell line designated TIL-Rs3 were propagated and cryopreserved.

Thawing and recovery of aEM3 cells may be accomplished using the following non-limiting procedure. Cyropreserved aEM3 cells are warmed slowly in pre-warmed media (37° C.) that is prepared from CTS OpTmizer Basal Media (Thermo Fisher), CTS OpTmizer Cell Supplement (Thermo Fisher), Gentamicin (Lonza), and Glutamax (Life Technologies). The suspended cells are then centrifuged at 1500 rpm for 5 minutes at 4° C. The resulting supernatant is discarded and the remaining aEM3 cells are resuspended in the foregoing media and plated ($5 \times 10^6$ cells/10 mL per well of a 6 well plate).

Propagation of aEM3 cells may be accomplished using the following non-limiting procedure. Aliquots of the foregoing media are prepared in gas permeable cell culture flasks (i.e., GREX 10 flasks (Wilson Wolf Manufacturing)). The plated aEM3 cells are washed by centrifugation (i.e., 1500 rpm for 5 minutes at 4° C.), resuspended in media, and added to the GREX flasks at cell density of $1$-$2 \times 10^6$ cells/mL. The aEM3 cell suspension was diluted with 30 mL of media and the GREX flasks were then incubated for 3-4 days at 37° C. under $CO_2$. After 3-4 days, the GREX flasks were removed from the incubator and placed in a biological safety cabinet (BSC). The cultured aEM3 cells are carefully extracted from the GREX flasks by pipette and the resulting extraction is centrifuged to provide the increased number of aEM3 cells, which may be resuspended at a cell density of $10$-$20 \times 10^6$ cells per GREX 10 flask.

An alternative cryopreservation of aEM3 cells may be accomplished using the following non-limiting procedure. The foregoing GREX 10 flasks containing the aEM3 cells are removed from the incubator and placed in a BSC. The cultured aEM3 cells are carefully extracted from the GREX flasks by pipette and the resulting extraction is centrifuged to provide the increased number of aEM3 cells, which is resuspended in a volume of CryStor 10 (Biolife Solutions) to provide a concentration of $10$-$100 \times 10^6$ cells/vial in cryovials. The aEM3 cell suspensions may be placed in a freezing container and transferred to a −80° C. freezer.

Figure 86:
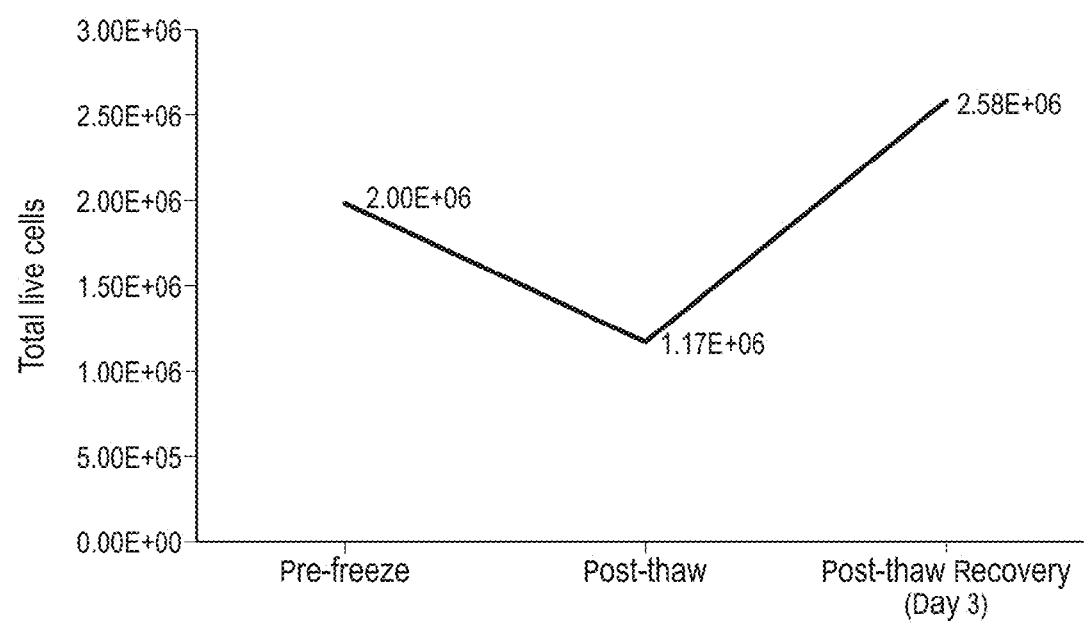
FIG. 86 and FIG. 87 illustrate the results of two experiments that demonstrate the rapid recovery of aEM3 cells from the TIL-R3 cell line on day 3 following cryopreservation.
Figure 87:
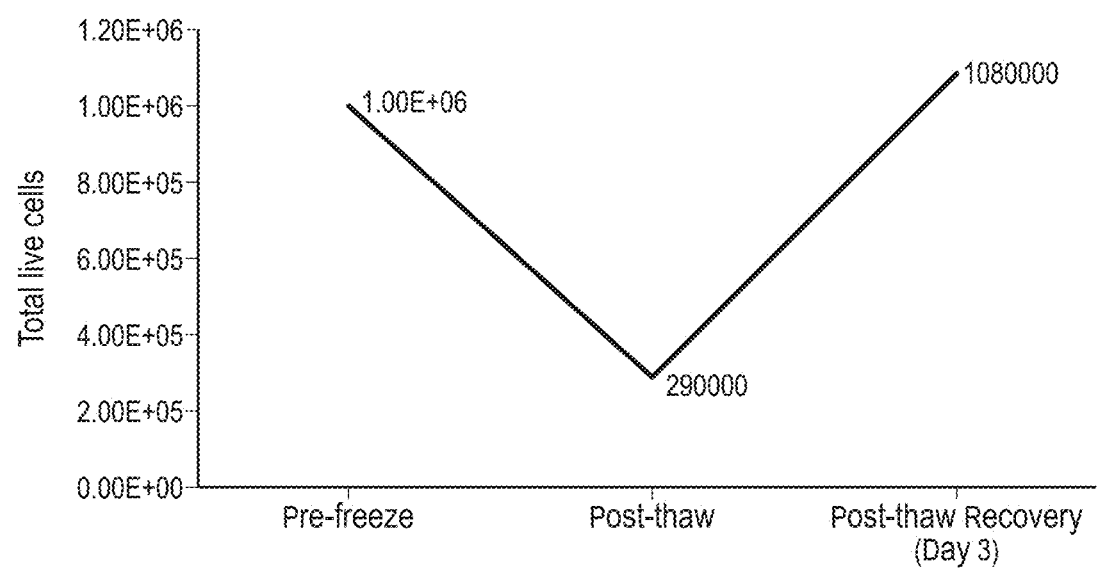

Example 19—Demonstration of Rapid Recovery of aEM3 Cells Following Cryopreservation aEM3 cells from the TIL-R3 cell line ($1$-$2 \times 10^6$ cells) were cryopreserved according to the procedure set forth in Example 18 using CS-10 cryopreservation media. Vials of such cells were then thawed and the cells were counted. Cell counts were taken pre-freeze, post-thaw, and 3 days after thaw (i.e., Post-Thaw Recovery). As shown in FIG. 86 and FIG. 87, the total live cell counts recovered rapidly post thaw in two separate experiments.

Figure 88:
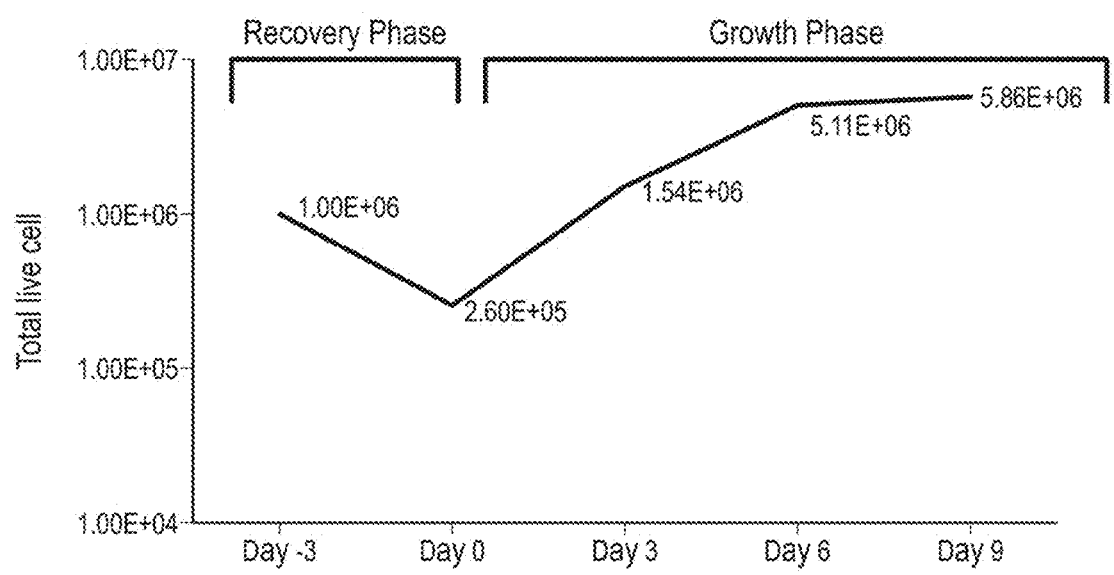
FIG. 88 illustrates the growth of aEM3 cells from the TIL-R3 cell line following cryopreservation where the cells were plated and grown for 9 days. Cell counts were measured every three days post thaw.

TIL-R3 cells ($1 \times 10^6$ cells) were thawed (Day 3 post-thaw) and plated at a density of $0.5 \times 10^6/cm^2$ in each well of a 24 well plate. On day 0 and 3, viable cells were counted and recorded. On the first passage (Day 6), cells were split at the density of $2 \times 10^6$ cells/$cm^2$ or $0.5 \times 10^6$ cells/$cm^2$. At the end of the first passage, a cell count was performed. The resulting cell counts are shown in FIG. 88, which demonstrate both a recovery phase post-thaw and a growth phase.

Figure 89:
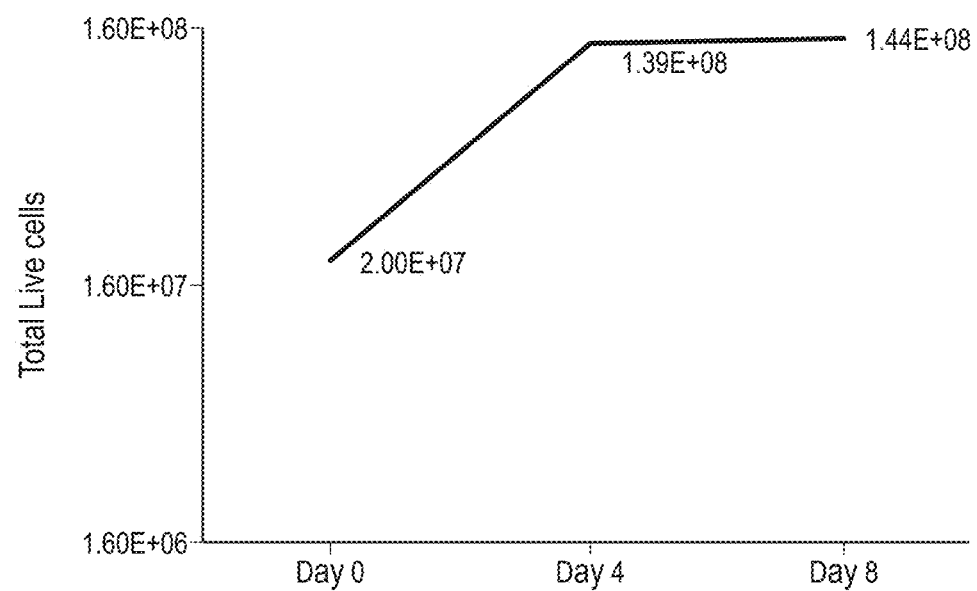
FIG. 89 illustrates the growth of aEM3 cells from the TIL-R3 cell line following cryopreservation where the cells were plated in GREX 10 flasks and grown for 8 days. Cell counts were measured every four days post thaw.

Furthermore, TIL-R3 cells (20×10⁶ cells) were cultured at a density of 2×10⁶/cm² in GREX 10 flasks according to the procedure described in Example 18. On days 4 and 8, live cells were counted and recorded. The resulting cell counts are shown in FIG. 89, which demonstrates a growth phase for the cells following cryopreservation that reaches a plateau between days 4 and 8 when the cells reached a density of 13.9×10⁶ cells/cm².

Figure 91:
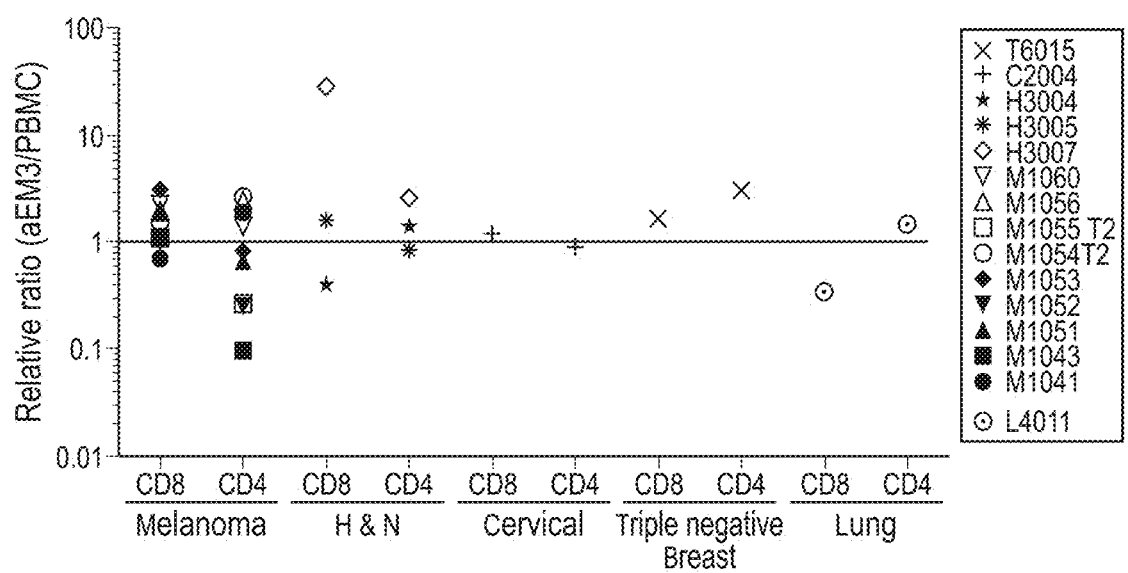
FIG. 91 illustrates the results of flow cytometry analysis of TILs expanded in a REP with the aEM3 cell line and PBMC feeders, showing that TILs cultured with aEM3 promotes CD8+ TIL skewness.
Figure 92:
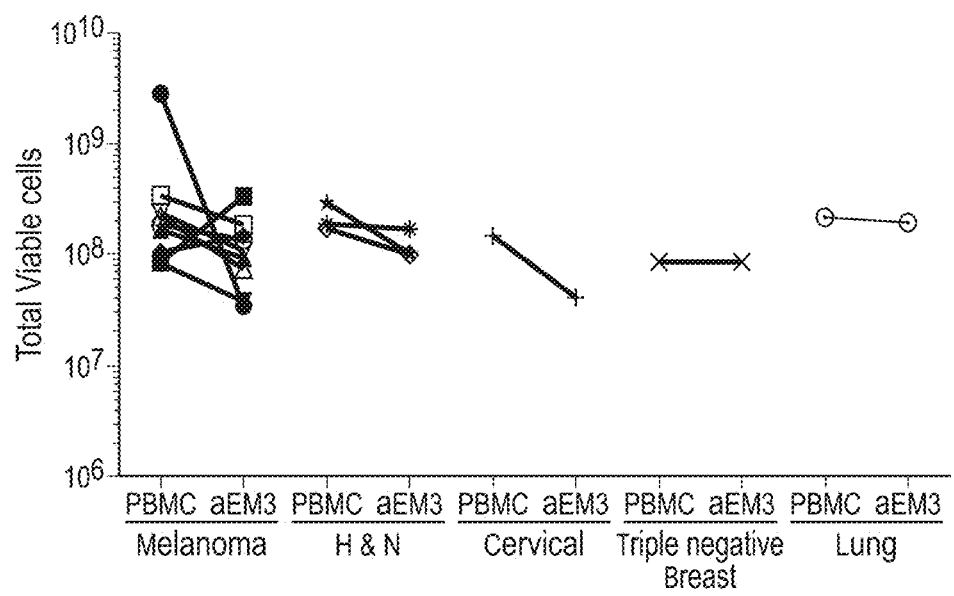
FIG. 92 illustrates the numbers of viable cells obtained from experiments wherein TILs were expanded in a REP with the aEM3 cell line and PBMC feeders.
Figure 93:
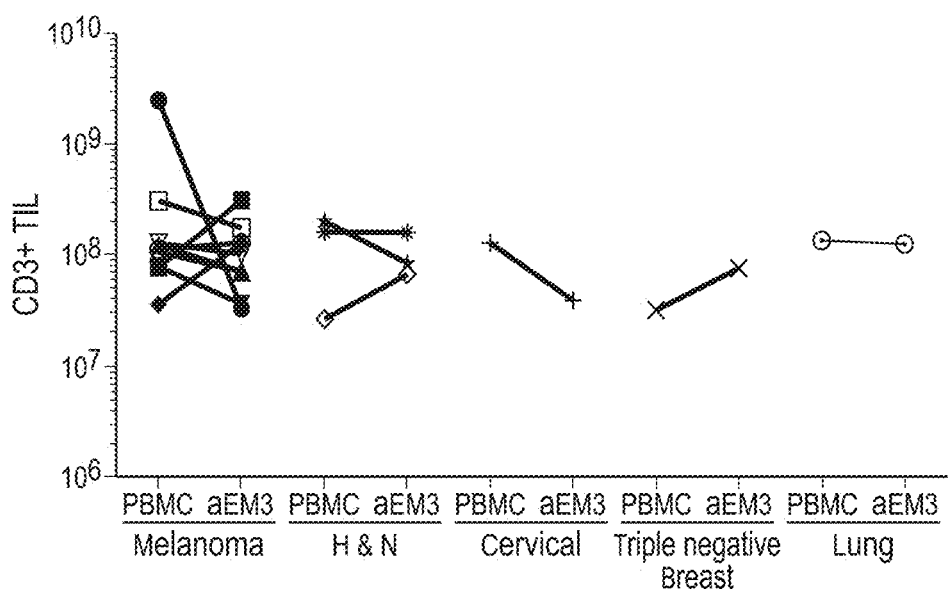
FIG. 93 illustrates the numbers of CD3+ cells obtained from experiments wherein TILs were expanded in a REP with the aEM3 cell line and PBMC feeders.
Figure 94:
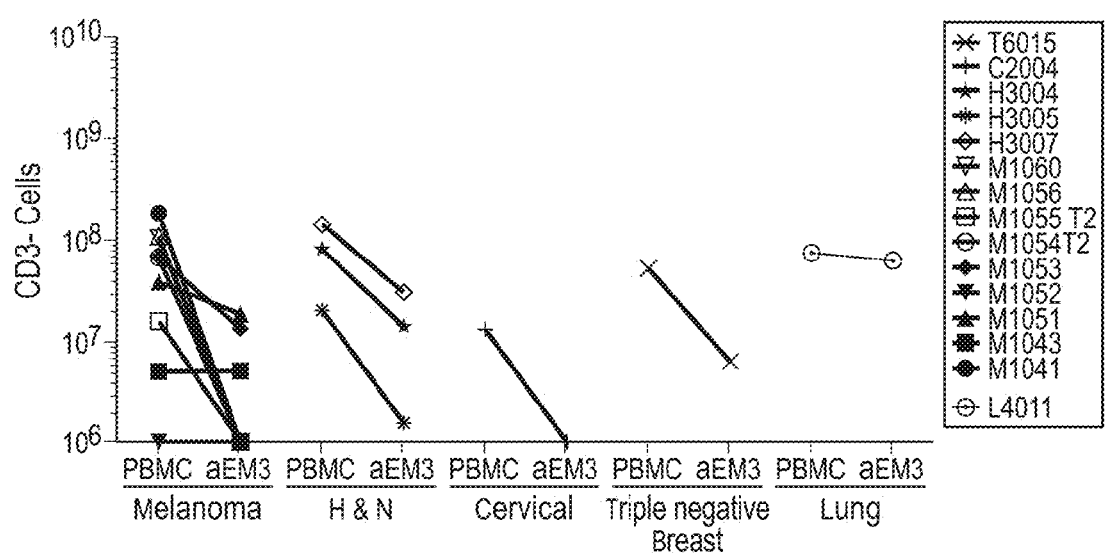
FIG. 94 illustrates the numbers of CD3− cells obtained from experiments wherein TILs were expanded in a REP with the aEM3 cell line and PBMC feeders.

Example 20—CD8 Skewness, Expansion Performance, and CD3 Contamination of TILs Cultured with aEM3 aAPCs Fifteen different PreREP TIL lines (0.4×10⁵ cells) were co-cultured with either aEM3 aAPCs (as described herein) or PBMC feeders (10×10⁶), OKT3 (30 ng/mL) and IL-2 (3000 IU/mL) and cultures were split on Day 5 using 6 well Grex plates. Cultures were sampled at day 11 and analyzed by flow cytometry. The relative ratio of CD8⁻ cells was calculated by the formula (CD8% aEM3)/(CD8% PBMC). The results shown in FIG. 91 indicate that TILs cultured with aEM3 cells surprisingly promote CD8⁺ skewing and and an improved TIL product. Additional results of these experiments are shown in FIG. 92, FIG. 93, and FIG. 94, where the results shown that TILs cultured with aEM3 aAPCs displayed comparable expansion and less non-CD3+ cell contamination in comparison to TILs cultured with PBMC feeders.

Example 21—Telomere Length Measurement

Genomic DNA was isolated from pre-REP or post-REP (magnetic bead sorted for CD3⁺) TILs for a qPCR (quantitative polymerase chain reaction) assay to measure telomere length. The real time qPCR method is described in Cawthon, *Nucleic Acids Res.* 2002, 30(10), e47; and Yang, et al., *Leukemia*, 2013, 27, 897-906. Briefly, the telomere repeat copy number to single gene copy number (T/S) ratio was determined using an PCR thermal cycler (Bio-Rad Laboratories, Inc.) in a 96-well format. Ten ng of genomic DNA was used for either the telomere or hemoglobin (hgb) PCR reaction and the primers used were as follows:

Tel-1b primer (CGG TTT GTT TGG GTT TGG GTT TGG GTT TGG GTT TGG GTT) (SEQ ID NO:40);

Tel-2b primer (GGC TTG CCT TAC CCT TAC CCT TAC CCT TAC CCT TAC CCT) (SEQ ID NO:41);

hgb1 primer (GCT TCT GAC ACA ACT GTG TTC ACT AGC) (SEQ ID NO:42); and hgb2 primer (CAC CAA CTT CAT CCA CGT TCA CC) (SEQ ID NO:43).

All samples were analyzed by both the telomere and hemoglobin reactions, and the analysis was performed in triplicate on the same plate. In addition to the test samples, each 96-well plate contained a five-point standard curve from 0.08 ng to 250 ng using genomic DNA isolated from the 1301 human T-cell leukemia cell line (available from Sigma and ATCC). The T/S ratio (–dCt) for each sample was calculated by subtracting the median hemoglobin threshold cycle (Ct) value from the median telomere Ct value. The relative T/S ratio (–ddCt) was determined by subtracting the T/S ratio of the 10.0 ng standard curve point from the T/S ratio of each unknown sample.

Figure 95:
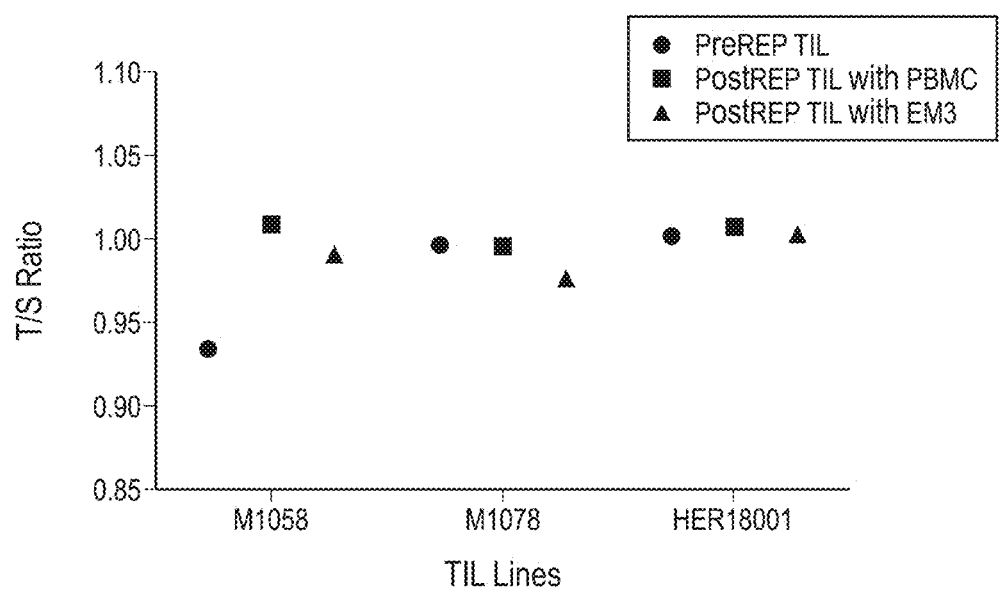
FIG. 95 illustrates the results of telomere length analysis using a qPCR method.

Results are shown in FIG. 95. Each data point shown is the median measurement of relative T/S ratio. The results indicate that TILs cultured with aEM3 maintain their telomere length.

---

We claim:

1. An isolated artificial antigen presenting cell (aAPC) comprising an EM-3 myeloid cell that endogenously expresses ICOS-L (inducible T-cell co-stimulator ligand), CD58, and one or more of HLA (human leukocyte antigen)-A, HLA-B, or HLA-C, wherein said aAPC is stably transduced with one or more viral vectors, wherein the one or more viral vectors comprise:
   (i) a nucleic acid encoding CD86;
   (ii) one or more nucleic acids encoding one or more costimulatory molecules selected from the group consisting of OX40L and 4-1BBL; and,
   (iii) a nucleic acid encoding SEQ ID NO:27;
wherein the myeloid cell expresses on its surface a protein encoded by each of the nucleic acids of (i), (ii) and (iii).

2. The aAPC of claim 1, wherein the aAPC can stimulate and expand tumor infiltrating lymphocytes (TILs) contacted with the aAPC.

3. The aAPC of claim 1, wherein the aAPC expands a population of TILs by at least 50-fold over a period of 7 days in a cell culture medium comprising IL-2 (Interleukin-2) at a concentration of about 3000 IU/mL and OKT-3 antibody at a concentration of about 30 ng/mL.

4. The aAPC of claim 1, wherein the aAPC can stimulate and expand a T cell contacted with the aAPC.

5. The aAPC of claim 1, wherein the CD86 protein comprises a sequence as set forth in SEQ ID NO:8, or a sequence comprising one or more conservative amino acid substitutions thereof.

6. The aAPC of claim 1, wherein the nucleic acid encoding CD86 comprises SEQ ID NO:19.

7. The aAPC of claim 1, wherein the one or more costimulatory molecules comprises a 4-1BBL protein.

8. The aAPC of claim 7, wherein the 4-1BBL protein comprises a sequence as set forth in SEQ ID NO:9, or a sequence comprising one or more conservative amino acid substitutions thereof.

9. The aAPC of claim 7, wherein the one or more nucleic acids encoding the 4-1BBL protein comprises SEQ ID NO:16.

10. The aAPC of claim 1, wherein the one or more costimulatory molecules comprises an OX40L protein.

11. The aAPC of claim 10, wherein the OX40L protein comprises a sequence as set forth in SEQ ID NO:10, or a sequence comprising one or more conservative amino acid substitutions thereof.

12. An isolated artificial antigen presenting cell (aAPC) comprising an EM-3 cell that endogenously expresses ICOS-L (inducible T-cell co-stimulator ligand), CD58, and one or more of HLA-A, HLA-B, or HLA-C, wherein said aAPC is stably transduced with one or more viral vectors, wherein the one or more viral vectors comprise:
   (i) a nucleic acid encoding CD86 or more conservative amino acid substitutions thereof;
   (ii) one or more nucleic acids comprising a sequence encoding one or more amino acid sequence selected from the group consisting of SEQ ID NO:9, SEQ ID NO:10, SEQ ID NO:13, and SEQ ID NO:14;
   (iii) a nucleic acid encoding SEQ ID NO:27;
wherein the EM-3 cell expresses on its surface a protein encoded by each of the nucleic acids of (i), (ii) and (iii).

* * * * *

SEQUENCE LISTING

<160> NUMBER OF SEQ ID NOS: 43

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125
```

```
Pro Leu Ala Pro Val Cys Gly Gly Thr Thr Gly Ser Ser Val Thr Leu
    130                 135                 140
Gly Cys Leu Val Lys Gly Tyr Phe Pro Glu Pro Val Thr Leu Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Val Thr Val Thr Ser Ser
            180                 185                 190
Thr Trp Pro Ser Gln Ser Ile Thr Cys Asn Val Ala His Pro Ala Ser
        195                 200                 205
Ser Thr Lys Val Asp Lys Lys Ile Glu Pro Arg Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15
Glu Lys Val Thr Met Thr Cys Ser Ala Ser Ser Ser Val Ser Tyr Met
            20                  25                  30
```

```
Asn Trp Tyr Gln Gln Lys Ser Gly Thr Ser Pro Lys Arg Trp Ile Tyr
             35                  40                  45

Asp Thr Ser Lys Leu Ala Ser Gly Val Pro Ala His Phe Arg Gly Ser
 50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
    210
```

<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2

<400> SEQUENCE: 3

```
Met Ala Pro Thr Ser Ser Ser Thr Lys Lys Thr Gln Leu Gln Leu Glu
 1               5                  10                  15

His Leu Leu Leu Asp Leu Gln Met Ile Leu Asn Gly Ile Asn Asn Tyr
                 20                  25                  30

Lys Asn Pro Lys Leu Thr Arg Met Leu Thr Phe Lys Phe Tyr Met Pro
             35                  40                  45

Lys Lys Ala Thr Glu Leu Lys His Leu Gln Cys Leu Glu Glu Glu Leu
 50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                 85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
            115                 120                 125

Ile Ile Ser Thr Leu Thr
            130
```

<210> SEQ ID NO 4
<211> LENGTH: 132
<212> TYPE: PRT
<213> ORGANISM: Artificial Sequence
<220> FEATURE:

<223> OTHER INFORMATION: aldesleukin

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 5
<211> LENGTH: 153
<212> TYPE: PRT
<213> ORGANISM: Artificial Sequence
<220> FEATURE:
<223> OTHER INFORMATION: recombinant human IL-7

<400> SEQUENCE: 5

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 6
<211> LENGTH: 115
<212> TYPE: PRT
<213> ORGANISM: Artificial Sequence
<220> FEATURE:
<223> OTHER INFORMATION: recombinant human IL-15

```
<400> SEQUENCE: 6

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 7
<211> LENGTH: 132
<212> TYPE: PRT
<213> ORGANISM: Artificial Sequence
<220> FEATURE:
<223> OTHER INFORMATION: IL-21

<400> SEQUENCE: 7

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
            20                  25                  30

Ala Pro Glu Asp Val Glu Thr Asn Cys Glu Trp Ser Ala Phe Ser Cys
        35                  40                  45

Phe Gln Lys Ala Gln Leu Lys Ser Ala Asn Thr Gly Asn Asn Glu Arg
    50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
    130

<210> SEQ ID NO 8
<211> LENGTH: 323
<212> TYPE: PRT
<213> ORGANISM: Artificial Sequence
<220> FEATURE:
<223> OTHER INFORMATION: human CD86

<400> SEQUENCE: 8

Met Gly Leu Ser Asn Ile Leu Phe Val Met Ala Phe Leu Leu Ser Gly
1               5                   10                  15

Ala Ala Pro Leu Lys Ile Gln Ala Tyr Phe Asn Glu Thr Ala Asp Leu
            20                  25                  30
```

-continued

```
Pro Cys Gln Phe Ala Asn Ser Gln Asn Gln Ser Leu Ser Glu Leu Val
            35                  40                  45

Val Phe Trp Gln Asp Gln Glu Asn Leu Val Leu Asn Glu Val Tyr Leu
 50                  55                  60

Gly Lys Glu Lys Phe Asp Ser Val His Ser Lys Tyr Met Gly Arg Thr
 65                  70                  75                  80

Ser Phe Asp Ser Asp Ser Trp Thr Leu Arg Leu His Asn Leu Gln Ile
                 85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
            115                 120                 125

Asn Phe Ser Gln Pro Glu Ile Val Pro Ile Ser Asn Ile Thr Glu Asn
130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
            195                 200                 205

Thr Ile Phe Cys Ile Leu Glu Thr Asp Lys Thr Arg Leu Leu Ser Ser
210                 215                 220

Pro Phe Ser Ile Glu Leu Glu Asp Pro Gln Pro Pro Pro Asp His Ile
225                 230                 235                 240

Pro Trp Ile Thr Ala Val Leu Pro Thr Val Ile Ile Cys Val Met Val
                245                 250                 255

Phe Cys Leu Ile Leu Trp Lys Trp Lys Lys Lys Arg Pro Arg Asn
            260                 265                 270

Ser Tyr Lys Cys Gly Thr Asn Thr Met Glu Arg Glu Glu Ser Glu Gln
            275                 280                 285

Thr Lys Lys Arg Glu Lys Ile His Ile Pro Glu Arg Ser Asp Glu Ala
290                 295                 300

Gln Arg Val Phe Lys Ser Ser Lys Thr Ser Ser Cys Asp Lys Ser Asp
305                 310                 315                 320

Thr Cys Phe

<210> SEQ ID NO 9
<211> LENGTH: 254
<212> TYPE: PRT
<213> ORGANISM: Artificial Sequence
<220> FEATURE:
<223> OTHER INFORMATION: human 4-1BBL

<400> SEQUENCE: 9

Met Glu Tyr Ala Ser Asp Ala Ser Leu Asp Pro Glu Ala Pro Trp Pro
 1               5                  10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
             35                  40                  45

Leu Ala Cys Pro Trp Ala Val Ser Gly Ala Arg Ala Ser Pro Gly Ser
 50                  55                  60

Ala Ala Ser Pro Arg Leu Arg Glu Gly Pro Glu Leu Ser Pro Asp Asp
```

```
            65                  70                  75                  80
Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 10
<211> LENGTH: 183
<212> TYPE: PRT
<213> ORGANISM: Artificial Sequence
<220> FEATURE:
<223> OTHER INFORMATION: human OX40L

<400> SEQUENCE: 10

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
        130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
```

-continued

```
                180

<210> SEQ ID NO 11
<211> LENGTH: 220
<212> TYPE: PRT
<213> ORGANISM: Artificial Sequence
<220> FEATURE:
<223> OTHER INFORMATION: human CD28

<400> SEQUENCE: 11

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 12
<211> LENGTH: 223
<212> TYPE: PRT
<213> ORGANISM: Artificial Sequence
<220> FEATURE:
<223> OTHER INFORMATION: human CTLA-4

<400> SEQUENCE: 12

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80
```

-continued

Val Thr Glu Val Cys Ala Ala Thr Tyr Met Met Gly Asn Glu Leu Thr
            85                  90                  95

Phe Leu Asp Asp Ser Ile Cys Thr Gly Thr Ser Ser Gly Asn Gln Val
        100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
        210                 215                 220

<210> SEQ ID NO 13
<211> LENGTH: 255
<212> TYPE: PRT
<213> ORGANISM: Artificial Sequence
<220> FEATURE:
<223> OTHER INFORMATION: human 4-1BB

<400> SEQUENCE: 13

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 14
<211> LENGTH: 277
<212> TYPE: PRT
<213> ORGANISM: Artificial Sequence
<220> FEATURE:
<223> OTHER INFORMATION: human OX40

<400> SEQUENCE: 14

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 15
<211> LENGTH: 7569
<212> TYPE: DNA
<213> ORGANISM: Artificial Sequence
<220> FEATURE:
<223> OTHER INFORMATION: pLV430G human 4-1BBL vector

<400> SEQUENCE: 15

```
cgataacccct aattcgatag catatgcttc ccgttgggta acatatgcta ttgaattagg      60
gttagtctgg atagtatata ctactacccg ggaagcatat gctacccgtt tagggttcac     120
cggtgatgcc ggccacgatg cgtccggcgt agaggatcta atgtgagtta gctcactcat     180
taggcacccc aggctttaca ctttatgctt ccggctcgta tgttgtgtgg aattgtgagc     240
ggataacaat ttcacacagg aaacagctat gaccatgatt acgccaagcg cgcaattaac     300
cctcactaaa gggaacaaaa gctggagctg caagcttaat gtagtcttat gcaatactct     360
tgtagtcttg caacatggta acgatgagtt agcaacatgc cttacaagga gagaaaaagc     420
accgtgcatg ccgattggtg gaagtaaggt ggtacgatcg tgccttatta ggaaggcaac     480
agacgggtct gacatggatt ggacgaacca ctgaattgcc gcattgcaga gatattgtat     540
ttaagtgcct agctcgatac ataaacgggt ctctctggtt agaccagatc tgagcctggg     600
agctctctgg ctaactaggg aacccactgc ttaagcctca ataaagcttg ccttgagtgc     660
ttcaagtagt gtgtgcccgt ctgttgtgtg actctggtaa ctagagatcc ctcagaccct     720
tttagtcagt gtggaaaatc tctagcagtg gcgcccgaac agggacttga agcgaaagg     780 gaaaccagag gagctctctc gacgcaggac tcggcttgct gaagcgcgca cggcaagagg     840
cgaggggcgg cgactggtga gtacgccaaa aattttgact agcggaggct agaaggagag     900
agatgggtgc gagagcgtca gtattaagcg ggggagaatt agatcgcgat gggaaaaaat     960
tcggttaagg ccaggggaa agaaaaaata taaattaaaa catatagtat gggcaagcag    1020
ggagctagaa cgattcgcag ttaatcctgg cctgttagaa acatcagaag gctgtagaca    1080
aatactggga cagctacaac catcccttca gacaggatca aagaacttta gatcattata    1140
taatacagta gcaaccctct attgtgtgca tcaaaggata gagataaaag acaccaagga    1200
agctttagac aagatagagg aagagcaaaa caaaagtaag accaccgcac agcaagcggc    1260
cgctgatctt cagacctgga ggaggagata tgagggacaa ttggagaagt gaattatata    1320
aatataaagt agtaaaaatt gaaccattag gagtagcacc caccaaggca aagagaagag    1380
tggtgcagag agaaaaaaga gcagtgggaa taggagcttt gttccttggg ttcttgggag    1440
cagcaggaag cactatgggc gcagcgtcaa tgacgctgac ggtacaggcc agacaattat    1500
tgtctggtat agtgcagcag cagaacaatt gctgagggc tattgaggcg caacagcatc    1560
tgttgcaact cacagtctgg ggcatcaagc agctccaggc aagaatcctg gctgtggaaa    1620
gatacctaaa ggatcaacag ctcctgggga tttggggttg ctctggaaaa ctcatttgca    1680
ccactgctgt gccttggaat gctagttgga gtaataaatc tctggaacag atttggaatc    1740
acacgacctg gatggagtgg gacagagaaa ttaacaatta cacaagctta atacactcct    1800
taattgaaga atcgcaaaac cagcaagaaa agaatgaaca agaattattg gaattagata    1860
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc ccaaccccga    2040
ggggacccga caggcccgaa ggaatagaag aagaaggtgg agagagagac agagacagat    2100
ccattcgatt agtgaacgga tctcgacggt atcggtttta aagaaaagg ggggattggg    2160 gggtacagtg caggggaaag aatagtagac ataatagcaa cagacataca aactaaagaa    2220
ttacaaaaac aaattacaaa aattcaaaat tttatcgatt ttatttagtc tccagaaaaa    2280
ggggggaatg aaagacccca cctgtaggtt tggcaagcta gcttaagtaa cgccattttg    2340
```

-continued

```
caaggcatgg aaaatacata actgagaata gagaagttca gatcaaggtt aggaacagag    2400
agacagcaga atatgggcca aacaggatat ctgtggtaag cagttcctgc cccggctcag    2460
ggccaagaac agatggtccc cagatgcggt cccgccctca gcagtttcta gagaaccatc    2520
agatgtttcc agggtgcccc aaggacctga aatgaccctg tgccttattt gaactaacca    2580
atcagttcgc ttctcgcttc tgttcgcgcg cttctgctcc ccgagctcaa taaaagagcc    2640
cacaacccct cactcggcgc gccagtcctc cgatagactg cgtcgcccgg gtaccgatat    2700
caacaagttt gtacaaaaaa gcaggcttcg ccaccatgga atacgcctct gatgccagcc    2760
tggaccccga agctccttgg cctcctgccc ctagagccag agcctgtaga gtgctgcctt    2820
gggctctggt ggctggcctt ctccttctgc tgctgctggc cgctgcctgc gctgtgtttc    2880
tggcttgtcc ttgggccgtg tcaggcgcca gagcttctcc tggatctgcc gccagcccca    2940
gactgagaga gggacctgag ctgagccccg atgatcctgc cggactgctg gatctgagac    3000
agggcatgtt cgcccagctg gtggcccaga acgtgctgct gatcgatggc cccctgagct    3060
ggtacagcga tcctggactg gctggcgtgt cactgacagg cggcctgagc tacaaagagg    3120
acaccaaaga actggtggtg gccaaggccg gcgtgtacta cgtgttcttt cagctggaac    3180
tgcggagagt ggtggccggc gaaggatccg gctctgtgtc tctggcactg catctgcagc    3240
ccctgagatc tgctgcaggc gctgctgcac tggccctgac agtggacctg cctccagcct    3300
ctagcgaggc cagaaactcc gcattcgggt tcaaggcag actgctgcac ctgtctgccg    3360
gccagagact gggagtgcat ctgcacacag aggccagagc cagacacgcc tggcagctga    3420
cacagggcgc tacagtgctg ggcctgttca gagtgacccc cgaaattcca gccggcctgc    3480
ccagccctag aagcgagtag gacccagctt tcttgtacaa agtggtgatt cgagttaatt    3540
aagctagcct agtgccattt gttcagtggt tcgtagggct ttcccccact gtttggcttt    3600
cagttatatg gatgatgtgg tattggggc caagtctgta cagcatcttg agtcccttt    3660 taccgctgtt accaattttc ttttgtcttt gggtatacat ttaaacccta acaaaacaaa    3720
gagatggggt tactctctaa attttatggg ttatgtcatt ggatgttatg ggtccttgcc    3780
acaagaacac atcatacaaa aaatcaaaga atgttttaga aaacttccta ttaacaggcc    3840
tattgattgg aaagtatgtc aacgaattgt gggtcttttg ggttttgctg cccctttac    3900 acaatgtggt tatcctgcgt tgatgccttt gtatgcatgt attcaatcta agcaggcttt    3960
cactttctcg ccaacttaca aggccttct gtgtaaacaa tacctgaacc tttacccgt    4020 tgcccggcaa cggccaggtc tgtgccaagt gtttgctgac gcaaccccca ctggctgggg    4080
cttggtcatg ggccatcagc gcatgcgtgg aaccttttcg gctcctctgc cgatccatac    4140
tgcggaactc ctagccgctt gttttgctcg cagcaggtct ggagcaaaca ttatcgggac    4200
tgataactct gttgtcctat cccgcaaata tacatcgttt ccatggctgc taggctgtgc    4260
tgccaactgg atcctgcgcg ggacgtcctt tgtttacgtc ccgtcggcgc tgaatcctgc    4320
ggacgaccct tctcggggtc gcttgggact ctctcgtccc cttctccgtc tgccgttccg    4380
accgaccacg gggcgcacct ctctttacgc ggactccccg tctgtgcctt ctcatctgcc    4440
ggaccgtgtg cacttcgctt cacctctgca cgtcgcatgg agaccaccgt gaacgcccac    4500
caaatattgc ccaaggtctt acataagagg actcttggac tctcagcaat gtcaacgacc    4560
gaccttgagg catacttcaa agactgtttg tttaaagact gggaggagtt gggggaggag    4620
attaggttaa aggtctttgt actaggaggc tgtaggcata aattggtctg cgcaccagca    4680
ccatggcgca atcactagag cggggtacct ttaagaccaa tgacttacaa ggcagctgta    4740
```

```
gatcttagcc acttttaaaa agaaaagggg ggactggaag ggctaattca ctcccaacga    4800
agacaagatc tgcttttgc ttgtactggg tctctctggt tagaccagat ctgagcctgg     4860
gagctctctg gctaactagg gaacccactg cttaagcctc aataaagctt gccttgagtg    4920
cttcaagtag tgtgtgcccg tctgttgtgt gactctggta actagagatc cctcagaccc    4980
ttttagtcag tgtggaaaat ctctagcagt agtagttcat gtcatcttat tattcagtat    5040
ttataacttg caaagaaatg aatatcagag agtgagagga acttgtttat tgcagcttat    5100
aatggttaca aataaagcaa tagcatcaca aatttcacaa ataaagcatt tttttcactg    5160
cattctagtt gtggtttgtc caaactcatc aatgtatctt atcatgtctg gctctagcta    5220
tcccgcccct aactccgccc atcccgccc taactccgcc cagttccgcc cattctccgc     5280
cccatggctg actaatttt tttatttatg cagaggccga ggccggatcc cttgagtggc     5340
tttcatcctg gagcagactt tgcagtctgt ggactgcaac acaacattgc ctttatgtgt    5400
aactcttggc tgaagctctt acaccaatgc tggggacat gtacctccca ggggcccagg     5460
aagactacgg gaggctacac caacgtcaat cagagggcc tgtgtagcta ccgataagcg     5520
gaccctcaag agggcattag caatagtgtt tataaggccc ccttgttaat tcttgaagac    5580
gaaagggcct cgtgatacgc ctattttat aggttaatgt catgataata atggttcctt     5640
agacgtcagg tggcactttt cggggaaatg tgcgcggaac ccctatttgt ttatttttct    5700
aaatacattc aaatatgtat ccgctcatga acaataacc ctgataaatg cttcaataat     5760
attgaaaaag gaagagtatg agtattcaac atttccgtgt cgcccttatt ccctttttg     5820 cggcattttg ccttcctgtt tttgctcacc cagaaacgct ggtgaaagta aaagatgctg    5880
aagatcagtt gggtgcacga gtgggttaca tcgaactgga tctcaacagc ggtaagatcc    5940
ttgagagttt tcgccccgaa gaacgttttc caatgatgag cacttttaaa gttctgctat    6000
gtggcgcggt attatcccgt gttgacgccg ggcaagagca actcggtcgc cgcatacact    6060
attctcagaa tgacttggtt gagtactcac cagtcacaga aaagcatctt acggatggca    6120
tgacagtaag agaattatgc agtgctgcca taaccatgag tgataacact gcggccaact    6180
tacttctgac aacgatcgga ggaccgaagg agctaaccgc ttttttgcac aacatggggg    6240
atcatgtaac tcgccttgat cgttgggaac cggagctgaa tgaagccata ccaaacgacg    6300
agcgtgacac cacgatgcct gcagcaatgg caacaacgtt gcgcaaacta ttaactggcg    6360
aactacttac tctagcttcc cggcaacaat taatagactg gatggaggcg gataaagttg    6420
caggaccact tctgcgctcg gcccttccgg ctggctggtt tattgctgat aaatctggag    6480
ccggtgagcg tgggtctcgc ggtatcattg cagcactggg gccagatggt aagccctccc    6540
gtatcgtagt tatctacacg acggggagtc aggcaactat ggatgaacga atagacaga    6600 tcgctgagat aggtgcctca ctgattaagc attggtaact gtcagaccaa gtttactcat    6660
atatacttta gattgattta aaacttcatt tttaatttaa aaggatctag gtgaagatcc    6720
tttttgataa tctcatgacc aaaatccctt aacgtgagtt ttcgttccac tgagcgtcag    6780
accccgtaga aaagatcaaa ggatcttctt gagatccttt ttttctgcgc gtaatctgct    6840
gcttgcaaac aaaaaaacca ccgctaccag cggtggtttg tttgccggat caagagctac    6900
caactctttt tccgaaggta actggcttca gcagagcgca gataccaaat actgtccttc    6960
tagtgtagcc gtagttaggc caccacttca agaactctgt agcaccgcct acatacctcg    7020
ctctgctaat cctgttacca gtggctgctg ccagtggcga taagtcgtgt cttaccgggt    7080
```

-continued

```
tggactcaag acgatagtta ccggataagg cgcagcggtc gggctgaacg gggggttcgt    7140
gcacacagcc cagcttggag cgaacgacct acaccgaact gagataccta cagcgtgagc    7200
attgagaaag cgccacgctt cccgaaggga gaaaggcgga caggtatccg gtaagcggca    7260
gggtcggaac aggagagcgc acgagggagc ttccaggggg aaacgcctgg tatctttata    7320
gtcctgtcgg gtttcgccac ctctgacttg agcgtcgatt tttgtgatgc tcgtcagggg    7380
ggcggagcct atggaaaaac gccagcaacg cggccttttt acggttcctg gccttttgct    7440
ggccttttg aagctgtccc tgatggtcgt catctacctg cctggacagc atggcctgca    7500
acgcgggcat cccgatgccg ccggaagcga aagaatcat aatggggaag gccatccagc    7560
ctcgcgtcg                                                            7569
```

<210> SEQ ID NO 16
<211> LENGTH: 765
<212> TYPE: DNA
<213> ORGANISM: Artificial Sequence
<220> FEATURE:
<223> OTHER INFORMATION: 4-1BBL CoOP

<400> SEQUENCE: 16

```
atggaatacg cctctgatgc cagcctggac cccgaagctc cttggcctcc tgcccctaga     60
gccagagcct gtagagtgct gccttgggct ctggtgctg gccttctcct tctgctgctg    120
ctggccgctg cctgcgctgt gtttctggct tgtccttggg ccgtgtcagg cgccagagct    180
tctcctggat ctgccgccag ccccagactg agagagggac ctgagctgag ccccgatgat    240
cctgccggac tgctggatct gagacagggc atgttcgccc agctggtggc ccagaacgtg    300
ctgctgatcg atggccccct gagctggtac agcgatcctg gactggctgg cgtgtcactg    360
acaggcggcc tgagctacaa agaggacacc aaagaactgg tggtggccaa ggccggcgtg    420
tactacgtgt tctttcagct ggaactgcgg agagtggtgg ccggcgaagg atccggctct    480
gtgtctctgg cactgcatct gcagcccctg agatctgctg caggcgctgc tgcactggcc    540
ctgacagtgg acctgcctcc agcctctagc gaggccagaa actccgcatt cgggtttcaa    600
ggcagactgc tgcacctgtc tgccggccag agactgggag tgcatctgca cacagaggcc    660
agagccagac acgcctggca gctgacacag ggcgctacag tgctgggcct gttcagagtg    720
acccccgaaa ttccagccgg cctgcccagc cctagaagcg agtag                    765
```

<210> SEQ ID NO 17
<211> LENGTH: 832
<212> TYPE: DNA
<213> ORGANISM: Artificial Sequence
<220> FEATURE:
<223> OTHER INFORMATION: 4-1BBL PRCP

<400> SEQUENCE: 17

```
ggggacaagt ttgtacaaaa aagcaggctt cgccaccatg gaatacgcct ctgatgccag     60
cctggacccc gaagctcctt ggcctcctgc cctagagcc agagcctgta gagtgctgcc    120
ttgggctctg gtgctggcc ttctccttct gctgctgctg ccgctgcct gcgctgtgtt    180
tctggcttgt ccttgggccg tgtcaggcgc cagagcttct cctggatctg ccgccagccc    240
cagactgaga gagggacctg agctgagccc cgatgatcct gccggactgc tggatctgag    300
acagggcatg ttcgcccagc tggtggccca gaacgtgctg ctgatcgatg gccccctgag    360
ctggtacagc gatcctggac tggctggcgt gtcactgaca ggcggcctga gctacaaaga    420
ggacaccaaa gaactggtgg tggccaaggc cggcgtgtac tacgtgttct ttcagctgga    480
```

```
actgcggaga gtggtggccg gcgaaggatc cggctctgtg tctctggcac tgcatctgca    540 gccccctgaga tctgctgcag gcgctgctgc actggccctg acagtggacc tgcctccagc   600
ctctagcgag gccagaaact ccgcattcgg gtttcaaggc agactgctgc acctgtctgc   660
cggccagaga ctgggagtgc atctgcacac agaggccaga gccagacacg cctggcagct   720
gacacagggc gctacagtgc tgggcctgtt cagagtgacc cccgaaattc agccggcct    780 gcccagccct agaagcgagt aggacccagc tttcttgtac aaagtggtcc cc           832
```

<210> SEQ ID NO 18
<211> LENGTH: 7776
<212> TYPE: DNA
<213> ORGANISM: Artificial Sequence
<220> FEATURE:
<223> OTHER INFORMATION: pLV430G human CD86 vector

<400> SEQUENCE: 18

```
cgataaccct aattcgatag catatgcttc ccgttgggta acatatgcta ttgaattagg    60
gttagtctgg atagtatata ctactacccg ggaagcatat gctacccgtt tagggttcac   120
cggtgatgcc ggccacgatg cgtccggcgt agaggatcta atgtgagtta gctcactcat   180
taggcacccc aggctttaca ctttatgctt ccggctcgta tgttgtgtgg aattgtgagc   240
ggataacaat ttcacacagg aaacagctat gaccatgatt acgccaagcg cgcaattaac   300
cctcactaaa gggaacaaaa gctggagctg caagcttaat gtagtcttat gcaatactct   360
tgtagtcttg caacatggta acgatgagtt agcaacatgc cttacaagga gagaaaaagc   420
accgtgcatg ccgattggtg gaagtaaggt ggtacgatcg tgccttatta ggaaggcaac   480
agacgggtct gacatggatt ggacgaacca ctgaattgcc gcattgcaga gatattgtat   540
ttaagtgcct agctcgatac ataaacgggt ctctctggtt agaccagatc tgagcctggg   600
agctctctgg ctaactaggg aacccactgc ttaagcctca ataaagcttg ccttgagtgc   660
ttcaagtagt gtgtgcccgt ctgttgtgtg actctggtaa ctagagatcc ctcagaccct   720
tttagtcagt gtggaaaatc tctagcagtg gcgcccgaac agggacttga aagcgaaagg   780
gaaaccagag gagctctctc gacgcaggac tcggcttgct gaagcgcgca cggcaagagg   840
cgaggggcgg cgactggtga gtacgccaaa aattttgact agcggaggct agaaggagag   900
agatgggtgc gagagcgtca gtattaagcg gggagaatt agatcgcgat gggaaaaaat   960
tcggttaagg ccagggggaa agaaaaaata taaattaaaa catatagtat gggcaagcag  1020
ggagctagaa cgattcgcag ttaatcctgg cctgttagaa acatcagaag gctgtagaca  1080
aatactggga cagctacaac catcccttca gacaggatca gaagaactta gatcattata  1140
taatacagta gcaaccctct attgtgtgca tcaaaggata gagataaaag acaccaagga  1200
agctttagac aagatagagg aagagcaaaa caaaagtaag accaccgcac agcaagcggc  1260
cgctgatctt cagacctgga ggaggagata tgagggacaa ttggagaagt gaattatata  1320
aatataaagt agtaaaaatt gaaccattag gagtagcacc caccaaggca agagaagag  1380 tggtgcagag agaaaaaaga gcagtgggaa taggagcttt gttccttggg ttcttgggag  1440
cagcaggaag cactatgggc gcagcgtcaa tgacgctgac ggtacaggcc agacaattat  1500
tgtctggtat agtgcagcag cagaacaatt tgctgagggc tattgaggcg caacagcatc  1560
tgttgcaact cacagtctgg ggcatcaagc agctccaggc aagaatcctg gctgtggaaa  1620
gatacctaaa ggatcaacag ctcctgggga tttggggttg ctctggaaaa ctcatttgca  1680
```

```
ccactgctgt gccttggaat gctagttgga gtaataaatc tctggaacag atttggaatc    1740
acacgacctg gatggagtgg gacagagaaa ttaacaatta cacaagctta atacactcct    1800
taattgaaga atcgcaaaac cagcaagaaa agaatgaaca agaattattg gaattagata    1860
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc ccaaccccga    2040
ggggacccga caggcccgaa ggaatagaag aagaaggtgg agagagagac agagacagat    2100
ccattcgatt agtgaacgga tctcgacggt atcggtttta aaagaaaagg ggggattggg    2160
gggtacagtg caggggaaag aatagtagac ataatagcaa cagacataca aactaaagaa    2220
ttacaaaaac aaattacaaa aattcaaaat tttatcgatt ttatttagtc tccagaaaaa    2280
gggggggaatg aaagacccca cctgtaggtt tggcaagcta gcttaagtaa cgccattttg    2340
caaggcatgg aaaatacata actgagaata gagaagttca gatcaaggtt aggaacagag    2400
agacagcaga atatgggcca aacaggatat ctgtggtaag cagttcctgc cccggctcag    2460
ggccaagaac agatggtccc cagatgcggt cccgccctca gcagtttcta gagaaccatc    2520
agatgtttcc agggtgcccc aaggacctga aatgaccctg tgccttattt gaactaacca    2580
atcagttcgc ttctcgcttc tgttcgcgcg cttctgctcc ccgagctcaa taaaagagcc    2640
cacaccccct cactcggcgc gccagtcctc cgatagactg cgtcgcccgg gtaccgatat    2700
caacaagttt gtacaaaaaa gcaggcttcg ccaccatggg cctgagcaac atcctgttcg    2760
tgatggcctt cctgctgtcc ggagccgccc tctgaagat ccaggcctac ttcaacgaga    2820
ccgccgacct gccctgccag ttcgccaaca gccagaacca gagcctgagc gaactggtgg    2880
tgttctggca ggaccaggaa aacctggtcc tgaacgaggt gtacctgggc aaagaaaagt    2940
tcgacagcgt gcacagcaag tacatgggcc ggaccagctt cgacagcgac agctggaccc    3000
tgcggctgca caacctgcag atcaaggaca agggcctgta ccagtgcatc atccaccaca    3060
agaaacccac cggcatgatc agaatccacc agatgaacag cgagctgtcc gtgctggcca    3120
acttcagcca gcccgagatc gtgcccatca gcaacatcac cgagaacgtg tacatcaacc    3180
tgacctgcag cagcatccac ggctacccg agcccaagaa aatgagcgtg ctgctgcgga    3240
ccaagaacag caccatcgag tacgacggcg tgatgcagaa aagccaggac aacgtgaccg    3300
agctgtacga cgtgagcatc agcctgagcg tgagcttccc cgacgtgacc agcaacatga    3360
ccatcttttg catcctggaa accgacaaga cccggctgct gtccagcccc ttcagcatcg    3420
agctggaaga tcccagccc cctcccgacc acatccctg gatcaccgcc gtgctgccca    3480
ccgtgatcat ctgcgtgatg gtgttctgcc tgatcctgtg gaagtggaag aagaagaagc    3540
ggcctaggaa cagctacaag tgcggcacca acaccatgga acgggaggaa agcgagcaga    3600
ccaagaagcg ggagaagatc cacatccccg agcggagcga cgaggccag cgggtgttca    3660
agagcagcaa gaccagcagc tgcgacaaga gcgacacctg cttctaggac ccagcttttct   3720
tgtacaaagt ggtgattcga gttaattaag ctagcctagt gccatttgtt cagtggttcg    3780
tagggctttc ccccactgtt tggctttcag ttatatggat gatgtggtat tgggggccaa    3840
gtctgtacag catcttgagt ccctttttac cgctgttacc aattttcttt tgtctttggg    3900
tatacattta aaccctaaca aaacaaagag atggggttac tctctaaatt ttatgggtta    3960
tgtcattgga tgttatgggt ccttgccaca agaaacatc atacaaaaaa tcaaagaatg    4020
ttttagaaaa cttcctatta acaggcctat tgattggaaa gtatgtcaac gaattgtggg    4080
```

```
tcttttgggt tttgctgccc cttttacaca atgtggttat cctgcgttga tgcctttgta    4140
tgcatgtatt caatctaagc aggctttcac tttctcgcca acttacaagg cctttctgtg    4200
taaacaatac ctgaacctt  accccgttgc ccggcaacgg ccaggtctgt gccaagtgtt    4260
tgctgacgca accccactg  gctgggctt  ggtcatgggc catcagcgca tgcgtggaac    4320
cttttcggct cctctgccga tccatactgc ggaactccta gccgcttgtt ttgctcgcag    4380
caggtctgga gcaaacatta tcgggactga taactctgtt gtcctatccc gcaaatatac    4440
atcgtttcca tggctgctag gctgtgctgc caactggatc ctgcgcggga cgtcctttgt    4500
ttacgtcccg tcggcgctga atcctgcgga cgacccttct cggggtcgct tgggactctc    4560
tcgtcccctt ctccgtctgc cgttccgacc gaccacgggg cgcacctctc tttacgcgga    4620
ctccccgtct gtgccttctc atctgccgga ccgtgtgcac ttcgcttcac ctctgcacgt    4680
cgcatggaga ccaccgtgaa cgcccaccaa atattgccca aggtcttaca taagaggact    4740
cttggactct cagcaatgtc aacgaccgac cttgaggcat acttcaaaga ctgtttgttt    4800
aaagactggg aggagttggg ggaggagatt aggttaaagg tctttgtact aggaggctgt    4860
aggcataaat tggtctgcgc accagcacca tggcgcaatc actagagcgg ggtacccttta   4920 agaccaatga cttacaaggc agctgtagat cttagccact ttttaaaaga aaggggggga    4980
ctggaagggc taattcactc ccaacgaaga caagatctgc ttttttgcttg tactgggtct    5040 ctctggttag accagatctg agcctgggag ctctctggct aactagggaa cccactgctt    5100
aagcctcaat aaagcttgcc ttgagtgctt caagtagtgt gtgcccgtct gttgtgtgac    5160
tctggtaact agagatccct cagacccttt tagtcagtgt ggaaaatctc tagcagtagt    5220
agttcatgtc atcttattat tcagtattta aacttgcaa  agaaatgaat atcagagagt    5280
gagaggaact tgtttattgc agcttataat ggttacaaat aaagcaatag catcacaaat    5340
ttcacaaata aagcattttt ttcactgcat tctagttgtg gtttgtccaa actcatcaat    5400
gtatcttatc atgtctggct ctagctatcc cgcccctaac tccgcccatc ccgcccctaa    5460
ctccgcccag ttccgcccat tctccgcccc atggctgact aatttttttt atttatgcag    5520
aggccgaggc cggatccctt gagtggcttt catcctggag cagactttgc agtctgtgga    5580
ctgcaacaca acattgcctt tatgtgtaac tcttggctga agctcttaca ccaatgctgg    5640
gggacatgta cctcccaggg gcccaggaag actacggag  gctacaccaa cgtcaatcag    5700
aggggcctgt gtagctaccg ataagcggac cctcaagagg gcattagcaa tagtgtttat    5760 aaggcccccct tgttaattct tgaagacgaa agggcctcgt gatacgccta ttttttatagg   5820 ttaatgtcat gataataatg gtttcttaga cgtcaggtgg cacttttcgg ggaaatgtgc    5880 gcggaaccc  tatttgttta ttttttctaaa tacattcaaa tatgtatccg ctcatgagac    5940
aataaccctg ataaatgctt caataatatt gaaaaaggaa gagtatgagt attcaacatt    6000
tccgtgtcgc ccttattccc ttttttgcgg cattttgcct tcctgttttt gctcacccag    6060
aaacgctggt gaaagtaaaa gatgctgaag atcagttggg tgcacgagtg ggttacatcg    6120
aactggatct caacagcggt aagatccttg agagttttcg ccccgaagaa cgttttccaa    6180
tgatgagcac ttttaaagtt ctgctatgtg gcgcggtatt atcccgtgtt gacgccgggc    6240
aagagcaact cggtcgccgc atacactatt ctcagaatga cttggttgag tactcaccag    6300
tcacagaaaa gcatcttacg gatggcatga cagtaagaga attatgcagt gctgccataa    6360
ccatgagtga taacactgcg gccaacttac ttctgacaac gatcggagga ccgaaggagc    6420
```

```
taaccgcttt tttgcacaac atgggggatc atgtaactcg ccttgatcgt tgggaaccgg    6480
agctgaatga agccatacca aacgacgagc gtgacaccac gatgcctgca gcaatggcaa    6540
caacgttgcg caaactatta actggcgaac tacttactct agcttcccgg caacaattaa    6600
tagactggat ggaggcggat aaagttgcag gaccacttct cgcgtcggcc cttccggctg    6660
gctggtttat tgctgataaa tctggagccg gtgagcgtgg gtctcgcggt atcattgcag    6720
cactggggcc agatggtaag ccctcccgta tcgtagttat ctacacgacg gggagtcagg    6780
caactatgga tgaacgaaat agacagatcg ctgagatagg tgcctcactg attaagcatt    6840
ggtaactgtc agaccaagtt tactcatata ctttagat tgatttaaaa cttcattttt    6900
aatttaaaag gatctaggtg aagatccttt ttgataatct catgaccaaa atcccttaac    6960
gtgagttttc gttccactga gcgtcagacc ccgtagaaaa gatcaaagga tcttcttgag    7020 atccttttt tctgcgcgta atctgctgct tgcaaacaaa aaaaccaccg ctaccagcgg    7080
tggtttgttt gccggatcaa gagctaccaa ctcttttcc gaaggtaact ggcttcagca    7140
gagcgcagat accaaatact gtccttctag tgtagccgta gttaggccac cacttcaaga    7200
actctgtagc accgcctaca tacctcgctc tgctaatcct gttaccagtg gctgctgcca    7260
gtggcgataa gtcgtgtctt accgggttgg actcaagacg atagttaccg gataaggcgc    7320
agcggtcggg ctgaacgggg gttcgtgca cacagcccag cttggagcga acgacctaca    7380
ccgaactgag atacctacag cgtgagcatt gagaaagcgc cacgcttccc gaagggagaa    7440
aggcggacag gtatccggta agcggcaggg tcggaacagg agagcgcacg agggagcttc    7500
cagggggaaa cgcctggtat ctttatagtc ctgtcgggtt tcgccacctc tgacttgagc    7560
gtcgattttt gtgatgctcg tcaggggggc ggagcctatg gaaaaacgcc agcaacgcgg    7620 ccttttacg gttcctggcc ttttgctggc cttttgaag ctgtccctga tggtcgtcat    7680
ctacctgcct ggacagcatg gcctgcaacg cgggcatccc gatgccgccg aagcgagaa    7740 gaatcataat ggggaaggcc atccagcctc gcgtcg                             7776
```

```
<210> SEQ ID NO 19
<211> LENGTH: 969
<212> TYPE: DNA
<213> ORGANISM: Artificial Sequence
<220> FEATURE:
<223> OTHER INFORMATION: CD86 CoOP

<400> SEQUENCE: 19
```

```
atgggcctga gcaacatcct gttcgtgatg gccttcctgc tgtccggagc cgcccctctg     60
aagatccagg cctacttcaa cgagaccgcc gacctgccct gccagttcgc caacagccag    120
aaccagagcc tgagcgaact ggtggtgttc tggcaggacc aggaaaacct ggtcctgaac    180
gaggtgtacc tgggcaaaga aaagttcgac agcgtgcaca gcaagtacat gggccggacc    240
agcttcgaca cgacagctg gaccctgcgc ctgcacaacc tgcagatcaa ggacaagggc    300
ctgtaccagt gcatcatcca ccacaagaaa cccaccggca tgatcagaat ccaccagatg    360
aacagcgagc tgtccgtgct ggccaacttc agccagcccg agatcgtgcc catcagcaac    420
atcaccgaga acgtgtacat caacctgacc tgcagcagca tccacggcta ccccgagccc    480
aagaaaatga gcgtgctgct gcgaccaag aacagcacca tcgagtacga cggcgtgatg    540
cagaaaagcc aggacaacgt gaccgagctg tacgacgtga gcatcagcct gagcgtgagc    600
ttccccgacg tgaccagcaa catgaccatc ttttgcatcc tggaaccga caagacccgg    660 ctgctgtcca gccccttcag catcgagctg gaagatcccc agccccctcc cgaccacatc    720
```

```
cctggatca  ccgccgtgct  gcccaccgtg  atcatctgcg  tgatggtgtt  ctgcctgatc      780
ctgtggaagt  ggaagaagaa  gaagcggcct  aggaacagct  acaagtgcgg  caccaacacc      840
atggaacggg  aggaaagcga  gcagaccaag  aagcgggaga  gatccacat   ccccgagcgg      900 agcgacgagg  cccagcgggt  gttcaagagc  agcaagacca  gcagctgcga  caagagcgac      960
acctgcttc                                                                   969
```

<210> SEQ ID NO 20
<211> LENGTH: 1039
<212> TYPE: DNA
<213> ORGANISM: Artificial Sequence
<220> FEATURE:
<223> OTHER INFORMATION: CD86 PCRP

<400> SEQUENCE: 20

```
ggggacaagt  ttgtacaaaa  aagcaggctt  cgccaccatg  ggcctgagca  acatcctgtt       60
cgtgatggcc  ttcctgctgt  ccggagccgc  ccctctgaag  atccaggcct  acttcaacga      120
gaccgccgac  ctgccctgcc  agttcgccaa  cagccagaac  cagagcctga  gcgaactggt      180
ggtgttctgg  caggaccagg  aaaacctggt  cctgaacgag  gtgtacctgg  gcaaagaaaa      240
gttcgacagc  gtgcacagca  gtacatgggg  ccggaccagc  ttcgacagcg  acagctggac      300
cctgcggctg  cacaacctgc  agatcaagga  caagggcctg  taccagtgca  tcatccacca      360
caagaaaccc  accggcatga  tcagaatcca  ccagatgaac  agcgagctgt  ccgtgctggc      420
caacttcagc  cagcccgaga  tcgtgcccat  cagcaacatc  accgagaacg  tgtacatcaa      480
cctgacctgc  agcagcatcc  acggctaccc  cgagcccaag  aaaatgagcg  tgctgctgcg      540
gaccaagaac  agcaccatcg  agtacgacgg  cgtgatgcag  aaaagccagg  acaacgtgac      600
cgagctgtac  gacgtgagca  tcagcctgag  cgtgagcttc  cccgacgtga  ccagcaacat      660
gaccatcttt  tgcatcctgg  aaaccgacaa  gacccggctg  ctgtccagcc  ccttcagcat      720
cgagctggaa  gatcccagc   ccctcccga   ccacatcccc  tggatcaccg  ccgtgctgcc      780
caccgtgatc  atctgcgtga  tggtgttctg  cctgatcctg  tggaagtgga  agaagaagaa      840
gcggcctagg  aacagctaca  agtgcggcac  caacaccatg  gaacgggagg  aaagcgagca      900
gaccaagaag  cgggagaaga  tccacatcccc  cgagcggagc  gacgaggccc  agcgggtgtt      960
caagagcagc  aagaccagca  gctgcgacaa  gagcgacacc  tgcttctagg  acccagcttt     1020
cttgtacaaa  gtggtcccc                                                     1039
```

<210> SEQ ID NO 21
<211> LENGTH: 3526
<212> TYPE: DNA
<213> ORGANISM: Artificial Sequence
<220> FEATURE:
<223> OTHER INFORMATION: pDONR221 CD86 vector

<400> SEQUENCE: 21

```
ctttcctgcg  ttatcccctg  attctgtgga  taaccgtatt  accgcctttg  agtgagctga       60
taccgctcgc  cgcagccgaa  cgaccgagcg  cagcgagtca  gtgagcgagg  aagcggaaga      120
gcgcccaata  cgcaaaccgc  ctctccccgc  gcgttggccg  attcattaat  gcagctggca      180
cgacaggttt  cccgactgga  aagcgggcag  tgagcgcaac  gcaattaata  cgcgtaccgc      240
tagccaggaa  gagtttgtag  aaacgcaaaa  aggccatccg  tcaggatggc  cttctgctta      300
gtttgatgcc  tggcagttta  tggcgggcgt  cctgcccgcc  accctccggg  ccgttgcttc      360
```

-continued

```
acaacgttca aatccgctcc cggcggattt gtcctactca ggagagcgtt caccgacaaa      420
caacagataa aacgaaaggc ccagtcttcc gactgagcct ttcgttttat ttgatgcctg      480
gcagttccct actctcgcgt taacgctagc atggatgttt cccagtcac gacgttgtaa       540 aacgacggcc agtcttaagc tcgggcccca aataatgatt ttattttgac tgatagtgac      600
ctgttcgttg caacacattg atgagcaatg ctttttttata atgcacaagt ttgtacaaaa     660
aagcaggctt cgccaccatg ggcctgagca acatcctgtt cgtgatggcc ttcctgctgt      720
ccggagccgc ccctctgaag atccaggcct acttcaacga gaccgccgac ctgccctgcc     780
agttcgccaa cagccagaac cagagcctga gcgaactggt ggtgttctgg caggaccagg     840
aaaacctggt cctgaacgag gtgtacctgg gcaaagaaaa gttcgacagc gtgcacagca     900
agtacatggg ccggaccagc ttcgacagcg acagctggac cctgcggctg cacaacctgc     960
agatcaagga caagggcctg taccagtgca tcatccacca caagaaaccc accggcatga    1020
tcagaatcca ccagatgaac agcgagctgt ccgtgctggc caacttcagc cagcccgaga    1080
tcgtgcccat cagcaacatc accgagaacg tgtacatcaa cctgacctgc agcagcatcc    1140
acggctaccc cgagcccaag aaaatgagcg tgctgctgcg gaccaagaac agcaccatcg    1200
agtacgacgg cgtgatgcag aaaagccagg acaacgtgac cgagctgtac gacgtgagca    1260
tcagcctgag cgtgagcttc cccgacgtga ccagcaacat gaccatcttt tgcatcctgg    1320
aaaccgacaa gacccggctg ctgtccagcc ccttcagcat cgagctggaa gatccccagc    1380
cccctcccga ccacatcccc tggatcaccg ccgtgctgcc caccgtgatc atctgcgtga    1440
tggtgttctg cctgatcctg tggaagtgga agaagaagaa gcggcctagg aacagctaca    1500
agtgcggcac caacaccatg gaacgggagg aaagcgagca gaccaagaag cgggagaaga    1560
tccacatccc cgagcggagc gacgaggccc agcgggtgtt caagagcagc aagaccagca    1620
gctgcgacaa gagcgacacc tgcttctagg acccagcttt cttgtacaaa gtggtcatta    1680
taagaaagca ttgcttatca atttgttgca acgaacaggt cactatcagt caaaataaaa    1740
tcattatttg ccatccagct gatatcccct atagtgagtc gtattacatg gtcatagctg    1800
tttcctggca gctctggccc gtgtctcaaa atctctgatg ttacattgca caagataaaa    1860
taatatcatc atgaacaata aaactgtctg cttacataaa cagtaataca aggggtgtta    1920
tgagccatat tcaacgggaa acgtcgaggc cgcgattaaa ttccaacatg gatgctgatt    1980
tatatgggta taaatgggct cgcgataatg tcgggcaatc aggtgcgaca atctatcgct    2040
tgtatgggaa gcccgatgcg ccagagttgt ttctgaaaca tggcaaaggt agcgttgcca    2100
atgatgttac agatgagatg gtcagactaa actggctgac ggaatttatg cctcttccga    2160
ccatcaagca tttatccgt actcctgatg atgcatggtt actcaccact gcgatccccg    2220
gaaaaacagc attccaggta ttagaagaat atcctgattc aggtgaaaat attgttgatg    2280
cgctggcagt gttcctgcgc cggttgcatt cgattcctgt ttgtaattgt ccttttaaca    2340
gcgatcgcgt atttcgtctc gctcaggcgc aatcacgaat gaataacggt ttggttgatg    2400
cgagtgattt tgatgacgag cgtaatggct ggcctgttga acaagtctgg aaagaaatgc    2460
ataaactttt gccattctca ccggattcag tcgtcactca tggtgatttc tcacttgata    2520
accttatttt tgacgagggg aaattaatag gttgtattga tgttggacga gtcggaatcg    2580
cagaccgata ccaggatctt gccatcctat ggaactgcct cggtgagttt tctccttcat    2640
tacagaaacg ctttttcaa aaatatggta ttgataatcc tgatatgaat aaattgcagt    2700
ttcatttgat gctcgatgag ttttttctaat cagaattggt taattggttg taacactggc    2760
```

```
agagcattac gctgacttga cgggacggcg caagctcatg accaaaatcc cttaacgtga    2820
gttacgcgtc gttccactga gcgtcagacc ccgtagaaaa gatcaaagga tcttcttgag    2880 atccttttt tctgcgcgta atctgctgct tgcaaacaaa aaaaccaccg ctaccagcgg     2940
tggtttgttt gccggatcaa gagctaccaa ctcttttcc gaaggtaact ggcttcagca     3000
gagcgcagat accaaatact gttcttctag tgtagccgta gttaggccac cacttcaaga    3060
actctgtagc accgcctaca tacctcgctc tgctaatcct gttaccagtg gctgctgcca    3120
gtggcgataa gtcgtgtctt accgggttgg actcaagacg atagttaccg gataaggcgc    3180
agcggtcggg ctgaacgggg ggttcgtgca cacagcccag cttggagcga acgacctaca    3240
ccgaactgag atacctacag cgtgagctat gagaaagcgc cacgcttccc gaagggagaa    3300
aggcggacag gtatccggta agcggcaggg tcggaacagg agagcgcacg agggagcttc    3360 caggggaaa cgcctggtat ctttatagtc ctgtcgggtt tcgccacctc tgacttgagc     3420
gtcgattttt gtgatgctcg tcaggggggc ggagcctatg gaaaaacgcc agcaacgcgg    3480
cctttttacg gttcctggcc ttttgctggc cttttgctca catgtt                   3526
```

<210> SEQ ID NO 22
<211> LENGTH: 3319
<212> TYPE: DNA
<213> ORGANISM: Artificial Sequence
<220> FEATURE:
<223> OTHER INFORMATION: pDONR221 4-1BBL vector

<400> SEQUENCE: 22

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca atccgctcc cggcggattt gtcctactca ggagagcgtt caccgacaaa     420
caacagataa aacgaaaggc ccagtcttcc gactgagcct tcgttttat ttgatgcctg     480 gcagttccct actctcgcgt taacgctagc atggatgttt tcccagtcac gacgttgtaa    540
aacgacggcc agtcttaagc tcgggcccca ataatgatt ttattttgac tgatagtgac     600
ctgttcgttg caaacacttg atgagcaatg ctttttata atgcacaagt ttgtacaaaa     660
aagcaggctt cgccaccatg aatacgcct ctgatgccag cctggacccc gaagctcctt     720
ggcctcctgc cctagagcc agagcctgta gagtgctgcc ttgggctctg gtggctggcc     780
ttctccttct gctgctgctg gccgctgcct gcgctgtgtt tctggcttgt ccttgggccg    840
tgtcaggcgc cagagcttct cctggatctg ccgccagccc cagactgaga gagggacctg    900
agctgagccc cgatgatcct gccggactgc tggatctgag acagggcatg ttcgcccagc    960
tggtggccca gaacgtgctg ctgatcgatg gccccctgag ctggtacagc gatcctggac    1020
tggctggcgt gtcactgaca gcggcctga gctacaaaga ggacaccaaa gaactggtgg    1080
tggccaaggc cggcgtgtac tacgtgttct tcagctgga actgcggaga gtggtggccg    1140
gcgaaggatc cggctctgtg tctctggcac tgcatctgca gccctgaga tctgctgcag    1200 gcgctgctgc actggccctg acagtggacc tgcctccagc ctctagcgag gccagaaact    1260
```

```
ccgcattcgg gtttcaaggc agactgctgc acctgtctgc cggccagaga ctgggagtgc   1320
atctgcacac agaggccaga gccagacacg cctggcagct gacacagggc gctacagtgc   1380
tgggcctgtt cagagtgacc cccgaaattc agccggcct gcccagccct agaagcgagt    1440
aggacccagc tttcttgtac aaagtggtca ttataagaaa gcattgctta tcaatttgtt   1500
gcaacgaaca ggtcactatc agtcaaaata aaatcattat ttgccatcca gctgatatcc   1560
cctatagtga gtcgtattac atggtcatag ctgtttcctg gcagctctgg cccgtgtctc   1620
aaaatctctg atgttacatt gcacaagata aataatatc atcatgaaca ataaaactgt    1680
ctgcttacat aaacagtaat acaaggggtg ttatgagcca tattcaacgg gaaacgtcga   1740
ggccgcgatt aaattccaac atggatgctg atttatatgg gtataaatgg gctcgcgata   1800
atgtcgggca atcaggtgcg acaatctatc gcttgtatgg gaagcccgat gcgccagagt   1860
tgtttctgaa acatggcaaa ggtagcgttg ccaatgatgt tacagatgag atggtcagac   1920
taaactggct gacggaattt atgcctcttc cgaccatcaa gcattttatc cgtactcctg   1980
atgatgcatg gttactcacc actgcgatcc ccggaaaaac agcattccag gtattagaag   2040
aatatcctga ttcaggtgaa aatattgttg atgcgctggc agtgttcctg cgccggttgc   2100
attcgattcc tgtttgtaat tgtccttta acagcgatcg cgtatttcgt ctcgctcagg    2160
cgcaatcacg aatgaataac ggtttggttg atgcgagtga ttttgatgac gagcgtaatg   2220
gctggcctgt tgaacaagtc tggaaagaaa tgcataaact tttgccattc tcaccggatt   2280
cagtcgtcac tcatggtgat ttctcacttg ataaccttat ttttgacgag gggaaattaa   2340
taggttgtat tgatgttgga cgagtcggaa tcgcagaccg ataccaggat cttgccatcc   2400
tatggaactg cctcggtgag ttttctcctt cattacagaa acggcttttt caaaaatatg   2460
gtattgataa tcctgatatg aataaattgc agtttcattt gatgctcgat gagttttcct   2520
aatcagaatt ggttaattgg ttgtaacact ggcagagcat tacgctgact tgacgggacg   2580
gcgcaagctc atgaccaaaa tcccttaacg tgagttacgc gtcgttccac tgagcgtcag   2640
accccgtaga aaagatcaaa ggatcttctt gagatccttt ttttctgcgc gtaatctgct   2700
gcttgcaaac aaaaaaacca ccgctaccag cggtggtttg tttgccggat caagagctac   2760
caactctttt tccgaaggta actggcttca gcagagcgca gataccaaat actgttcttc   2820
tagtgtagcc gtagttaggc caccacttca agaactctgt agcaccgcct acatacctcg   2880
ctctgctaat cctgttacca gtggctgctg ccagtggcga taagtcgtgt cttaccgggt   2940
tggactcaag acgatagtta ccggataagg cgcagcggtc gggctgaacg gggggttcgt   3000
gcacacagcc cagcttggag cgaacgacct acaccgaact gagatacta cagcgtgagc    3060
tatgagaaag cgccacgctt cccgaaggga gaaaggcgga caggtatccg gtaagcggca   3120
gggtcggaac aggagagcgc acgagggagc ttccaggggg aaacgcctgg tatctttata   3180
gtcctgtcgg gtttcgccac ctctgacttg agcgtcgatt tttgtgatgc tcgtcagggg   3240
ggcggagcct atggaaaaac gccagcaacg cggcctttt acggttcctg gccttttgct   3300
ggccttttgc tcacatgtt                                               3319
```

<210> SEQ ID NO 23
<211> LENGTH: 8449
<212> TYPE: DNA
<213> ORGANISM: Artificial Sequence
<220> FEATURE:
<223> OTHER INFORMATION: pLV430G vector

<400> SEQUENCE: 23

| | |
|---|---|
| cgataaccct aattcgatag catatgcttc ccgttgggta acatatgcta ttgaattagg | 60 |
| gttagtctgg atagtatata ctactacccg ggaagcatat gctacccgtt tagggttcac | 120 |
| cggtgatgcc ggccacgatg cgtccggcgt agaggatcta atgtgagtta gctcactcat | 180 |
| taggcacccc aggctttaca ctttatgctt ccggctcgta tgttgtgtgg aattgtgagc | 240 |
| ggataacaat ttcacacagg aaacagctat gaccatgatt acgccaagcg cgcaattaac | 300 |
| cctcactaaa gggaacaaaa gctggagctg caagcttaat gtagtcttat gcaatactct | 360 |
| tgtagtcttg caacatggta acgatgagtt agcaacatgc cttacaagga gagaaaaagc | 420 |
| accgtgcatg ccgattggtg gaagtaaggt ggtacgatcg tgccttatta ggaaggcaac | 480 |
| agacgggtct gacatggatt ggacgaacca ctgaattgcc gcattgcaga gatattgtat | 540 |
| ttaagtgcct agctcgatac ataaacgggt ctctctggtt agaccagatc tgagcctggg | 600 |
| agctctctgg ctaactaggg aacccactgc ttaagcctca ataaagcttg ccttgagtgc | 660 |
| ttcaagtagt gtgtgcccgt ctgttgtgtg actctggtaa ctagagatcc ctcagaccct | 720 |
| tttagtcagt gtggaaaatc tctagcagtg gcgcccgaac agggacttga aagcgaaagg | 780 |
| gaaaccagag gagctctctc gacgcaggac tcggcttgct gaagcgcgca cggcaagagg | 840 |
| cgaggggcgg cgactggtga gtacgccaaa aattttgact agcggaggct agaaggagag | 900 |
| agatgggtgc gagagcgtca gtattaagcg ggggagaatt agatcgcgat gggaaaaaat | 960 |
| tcggttaagg ccagggggaa agaaaaaata taaattaaaa catatagtat gggcaagcag | 1020 |
| ggagctagaa cgattcgcag ttaatcctgg cctgttagaa acatcagaag gctgtagaca | 1080 |
| aatactggga cagctacaac catcccttca gacaggatca aagaacttta gatcattata | 1140 |
| taatacagta gcaaccctct attgtgtgca tcaaaggata gagataaaag acaccaagga | 1200 |
| agctttagac aagatagagg aagagcaaaa caaaagtaag accaccgcac agcaagcggc | 1260 |
| cgctgatctt cagacctgga ggaggagata tgagggacaa ttggagaagt gaattatata | 1320 |
| aatataaagt agtaaaaatt gaaccattag gagtagcacc caccaaggca aagagaagag | 1380 |
| tggtgcagag agaaaaaaga gcagtgggaa taggagcttt gttccttggg ttcttgggag | 1440 |
| cagcaggaag cactatgggc gcagcgtcaa tgacgctgac ggtacaggcc agacaattat | 1500 |
| tgtctggtat agtgcagcag cagaacaatt tgctgagggc tattgaggcg caacagcatc | 1560 |
| tgttgcaact cacagtctgg ggcatcaagc agctccaggc aagaatcctg gctgtggaaa | 1620 |
| gatacctaaa ggatcaacag ctcctgggga tttggggttg ctctggaaaa ctcatttgca | 1680 |
| ccactgctgt gccttggaat gctagttgga gtaataaatc tctggaacag atttggaatc | 1740 |
| acacgacctg gatggagtgg gacagagaaa ttaacaatta cacaagctta atacactcct | 1800 |
| taattgaaga atcgcaaaac cagcaagaaa agaatgaaca agaattattg gaattagata | 1860 |
| aatgggcaag tttgtggaat tggtttaaca taacaaattg gctgtggtat ataaaattat | 1920 |
| tcataatgat agtaggaggc ttggtaggtt taagaatagt ttttgctgta ctttctatag | 1980 |
| tgaatagagt taggcaggga tattcaccat tatcgtttca gacccacctc ccaaccccga | 2040 |
| ggggacccga caggcccgaa ggaatagaag aagaaggtgg agagagagac agagacagat | 2100 |
| ccattcgatt agtgaacgga tctcgacggt atcggtttta aagaaaagg ggggattggg | 2160 |
| gggtacagtg caggggaaag aatagtagac ataatagcaa cagacataca aactaaagaa | 2220 |
| ttacaaaaac aaattacaaa aattcaaaat tttatcgatt ttatttagtc tccagaaaaa | 2280 |
| ggggggaatg aaagacccca cctgtaggtt tggcaagcta gcttaagtaa cgccattttg | 2340 |

```
caaggcatgg aaaatacata actgagaata gagaagttca gatcaaggtt aggaacagag   2400
agacagcaga atatgggcca aacaggatat ctgtggtaag cagttcctgc cccggctcag   2460
ggccaagaac agatggtccc cagatgcggt cccgccctca gcagtttcta gagaaccatc   2520
agatgtttcc agggtgcccc aaggacctga aatgaccctg tgccttattt gaactaacca   2580
atcagttcgc ttctcgcttc tgttcgcgcg cttctgctcc ccgagctcaa taaaagagcc   2640
cacaacccct cactcggcgc gccagtcctc cgatagactg cgtcgcccgg gtaccgatat   2700
cacaagtttg tacaaaaaag ctgaacgaga acgtaaaat gatataaata tcaatatatt   2760
aaattagatt ttgcataaaa aacagactac ataatactgt aaaacacaac atatccagtc   2820
actatggcgg ccgcattagg cacccccaggc tttacacttt atgcttccgg ctcgtataat   2880
gtgtggattt tgagttagga tccgtcgaga ttttcaggag ctaaggaagc taaaatggag   2940
aaaaaaatca ctggatatac caccgttgat atatcccaat ggcatcgtaa agaacatttt   3000
gaggcatttc agtcagttgc tcaatgtacc tataaccaga ccgttcagct ggatattacg   3060
gcctttttaa agaccgtaaa gaaaaataag cacaagtttt atccggcctt tattcacatt   3120
cttgcccgcc tgatgaatgc tcatccggaa ttccgtatgg caatgaaaga cggtgagctg   3180
gtgatatggg atagtgttca cccttgttac accgttttcc atgagcaaac tgaaacgttt   3240
tcatcgctct ggagtgaata ccacgacgat ttccggcagt ttctacacat atattcgcaa   3300
gatgtggcgt gttacggtga aaacctggcc tatttcccta aagggtttat tgagaatatg   3360 ttttcgtct cagccaatcc ctgggtgagt ttcaccagtt ttgatttaaa cgtggccaat   3420
atggacaact tcttcgcccc cgttttcacc atgggcaaat attatacgca aggcgacaag   3480
gtgctgatgc cgctggcgat tcaggttcat catgccgttt gtgatggctt ccatgtcggc   3540
agaatgctta atgaattaca acagtactgc gatgagtggc agggcgggc gtaaacgcgt   3600 ggatccggct tactaaaagc cagataacag tatgcgtatt tgcgcgctga ttttgcggt   3660 ataagaatat atactgatat gtatacccga agtatgtcaa aaagaggtat gctatgaagc   3720
agcgtattac agtgacagtt gacagcgaca gctatcagtt gctcaaggca tatatgatgt   3780
caatatctcc ggtctggtaa gcacaaccat gcagaatgaa gcccgtcgtc tgcgtgccga   3840
acgctggaaa gcggaaaatc aggaagggat ggctgaggtc gcccggttta ttgaaatgaa   3900
cggctctttt gctgacgaga acaggggctg gtgaaatgca gtttaaggtt tacacctata   3960
aaagagagag ccgttatcgt ctgtttgtgg atgtacagag tgatattatt gacacgcccg   4020
ggcgacggat ggtgatcccc ctggccagtg cacgtctgct gtcagataaa gtctcccgtg   4080
aactttaccc ggtggtgcat atcggggatg aaagctggcg catgatgacc accgatatgg   4140
ccagtgtgcc ggtctccgtt atcggggaag aagtggctga tctcagccac cgcgaaaatg   4200
acatcaaaaa cgccattaac ctgatgttct ggggaatata aatgtcaggc tcccttatac   4260
acagccagtc tgcaggtcga ccatagtgac tggatatgtt gtgttttaca gtattatgta   4320
gtctgttttt tatgcaaaat ctaatttaat atattgatat ttatatcatt ttacgtttct   4380
cgttcagctt tcttgtacaa agtggtgatt cgagttaatt aagctagcct agtgccattt   4440
gttcagtggt tcgtagggct ttcccccact gtttggcttt cagttatatg gatgatgtgg   4500
tattgggggc caagtctgta cagcatcttg agtcccttt taccgctgtt accaattttc   4560
ttttgtcttt gggtatacat ttaaacccta acaaaacaaa gagatggggt tactctctaa   4620
attttatggg ttatgtcatt ggatgttatg ggtccttgcc acaagaacac atcatacaaa   4680
aaatcaaaga atgttttaga aaacttccta ttaacaggcc tattgattgg aaagtatgtc   4740
```

```
aacgaattgt gggtcttttg ggttttgctg cccctttac acaatgtggt tatcctgcgt   4800
tgatgccttt gtatgcatgt attcaatcta agcaggcttt cactttctcg ccaacttaca   4860
aggcctttct gtgtaaacaa tacctgaacc tttaccccgt tgcccggcaa cggccaggtc   4920
tgtgccaagt gtttgctgac gcaaccccca ctggctgggg cttggtcatg gccatcagc    4980
gcatgcgtgg aaccttttcg gctcctctgc cgatccatac tgcggaactc ctagccgctt   5040
gttttgctcg cagcaggtct ggagcaaaca ttatcgggac tgataactct gttgtcctat   5100
cccgcaaata tacatcgttt ccatggctgc taggctgtgc tgccaactgg atcctgcgcg   5160
ggacgtcctt tgtttacgtc ccgtcggcgc tgaatcctgc ggacgaccct tctcggggtc   5220
gcttgggact ctctcgtccc cttctccgtc tgccgttccg accgaccacg gggcgcacct   5280
ctctttacgc ggactccccg tctgtgcctt ctcatctgcc ggaccgtgtg cacttcgctt   5340
cacctctgca cgtcgcatgg agaccaccgt gaacgcccac caaatattgc ccaaggtctt   5400
acataagagg actcttggac tctcagcaat gtcaacgacc gaccttgagg catacttcaa   5460
agactgtttg tttaaagact gggaggagtt gggggaggag attaggttaa aggtctttgt   5520
actaggaggc tgtaggcata aattggtctg cgcaccagca ccatggcgca atcactagag   5580
cggggtacct ttaagaccaa tgacttacaa ggcagctgta gatcttagcc acttttttaaa  5640
agaaaagggg ggactggaag ggctaattca ctcccaacga agacaagatc tgcttttttgc  5700
ttgtactggg tctctctggt tagaccagat ctgagcctgg gagctctctg gctaactagg   5760
gaacccactg cttaagcctc aataaagctt gccttgagtg cttcaagtag tgtgtgcccg   5820
tctgttgtgt gactctggta actagagatc cctcagaccc ttttagtcag tgtggaaaat   5880
ctctagcagt agtagttcat gtcatcttat tattcagtat ttataacttg caaagaaatg   5940
aatatcagag agtgagagga acttgtttat tgcagcttat aatggttaca aataaagcaa   6000
tagcatcaca aatttcacaa ataaagcatt ttttttcactg cattctagtt gtggtttgtc   6060
caaactcatc aatgtatctt atcatgtctg gctctagcta tcccgcccct aactccgccc   6120
atcccgcccc taactccgcc cagttccgcc cattctccgc cccatggctg actaattttt   6180
tttatttatg cagaggccga ggccggatcc cttgagtggc tttcatcctg gagcagactt   6240
tgcagtctgt ggactgcaac acaacattgc ctttatgtgt aactcttggc tgaagctctt   6300
acaccaatgc tgggggacat gtacctccca ggggcccagg aagactacgg gaggctacac   6360
caacgtcaat cagaggggcc tgtgtagcta ccgataagcg gaccctcaag agggcattag   6420
caatagtgtt tataaggccc ccttgttaat tcttgaagac gaaagggcct cgtgatacgc   6480
ctatttttat aggttaatgt catgataata atggtttctt agacgtcagg tggcacttt   6540
cggggaaatg tgcgcggaac ccctatttgt ttatttttct aaatacattc aaatatgtat   6600
ccgctcatga cacaataacc ctgataaatg cttcaataat attgaaaaag gaagagtatg   6660
agtattcaac atttccgtgt cgcccttatt cccttttttg cggcattttg ccttcctgtt   6720
tttgctcacc cagaaacgct ggtgaaagta aaagatgctg aagatcagtt gggtgcacga   6780
gtgggttaca tcgaactgga tctcaacagc ggtaagatcc ttgagagttt cgccccgaa    6840
gaacgttttc caatgatgag cacttttaaa gttctgctat gtggcgcggt attatcccgt   6900
gttgacgccg ggcaagagca actcggtcgc cgcatacact attctcagaa tgacttggtt   6960
gagtactcac cagtcacaga aaagcatctt acgatggca tgcagtaag agaattatgc      7020
agtgctgcca taaccatgag tgataacact gcggccaact tacttctgac aacgatcgga   7080
```

| | |
|---|---|
| ggaccgaagg agctaaccgc ttttttgcac aacatggggg atcatgtaac tcgccttgat | 7140 |
| cgttgggaac cggagctgaa tgaagccata ccaaacgacg agcgtgacac cacgatgcct | 7200 |
| gcagcaatgg caacaacgtt gcgcaaacta ttaactggcg aactacttac tctagcttcc | 7260 |
| cggcaacaat taatagactg gatggaggcg gataaagttg caggaccact tctgcgctcg | 7320 |
| gcccttccgg ctggctggtt tattgctgat aaatctggag ccggtgagcg tgggtctcgc | 7380 |
| ggtatcattg cagcactggg gccagatggt aagccctccc gtatcgtagt tatctacacg | 7440 |
| acggggagtc aggcaactat ggatgaacga atagacaga tcgctgagat aggtgcctca | 7500 |
| ctgattaagc attggtaact gtcagaccaa gtttactcat atatacttta gattgattta | 7560 |
| aaacttcatt tttaatttaa aaggatctag gtgaagatcc ttttttgataa tctcatgacc | 7620 |
| aaaatccctt aacgtgagtt ttcgttccac tgagcgtcag accccgtaga aaagatcaaa | 7680 |
| ggatcttctt gagatccttt ttttctgcgc gtaatctgct gcttgcaaac aaaaaaacca | 7740 |
| ccgctaccag cggtggtttg tttgccggat caagagctac caactctttt tccgaaggta | 7800 |
| actggcttca gcagagcgca gataccaaat actgtccttc tagtgtagcc gtagttaggc | 7860 |
| caccacttca agaactctgt agcaccgcct acatacctcg ctctgctaat cctgttacca | 7920 |
| gtggctgctg ccagtggcga taagtcgtgt cttaccgggt tggactcaag acgatagtta | 7980 |
| ccggataagg cgcagcggtc gggctgaacg gggggttcgt gcacacagcc cagcttggag | 8040 |
| cgaacgacct acaccgaact gagatacta cagcgtgagc attgagaaag cgccacgctt | 8100 |
| cccgaaggga gaaaggcgga caggtatccg gtaagcggca gggtcggaac aggagagcgc | 8160 |
| acgagggagc ttccagggg aaacgcctgg tatctttata gtcctgtcgg gtttcgccac | 8220 |
| ctctgacttg agcgtcgatt tttgtgatgc tcgtcagggg ggcggagcct atggaaaaac | 8280 |
| gccagcaacg cggccttttt acggttcctg gccttttgct ggccttttg aagctgtccc | 8340 |
| tgatggtcgt catctacctg cctggacagc atggcctgca acgcgggcat cccgatgccg | 8400 |
| ccggaagcga agaatcat aatggggaag gccatccagc ctcgcgtcg | 8449 |

<210> SEQ ID NO 24
<211> LENGTH: 4761
<212> TYPE: DNA
<213> ORGANISM: Artificial Sequence
<220> FEATURE:
<223> OTHER INFORMATION: pDONR221 vector

<400> SEQUENCE: 24

| | |
|---|---|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt tcccagtcac gacgttgtaa | 540 |
| aacgacggcc agtcttaagc tcgggcccca aataatgatt ttattttgac tgatagtgac | 600 |
| ctgttcgttg caacacattg atgagcaatg cttttttata tgccaacttt gtacaaaaaa | 660 |
| agctgaacga gaaacgtaaa atgatataaa tatcaatata ttaaattaga ttttgcataa | 720 |

```
aaaacagact acataatact gtaaaacaca acatatccag tcactatgaa tcaactactt    780
agatggtatt agtgacctgt agtcgaccga cagccttcca aatgttcttc gggtgatgct    840
gccaacttag tcgaccgaca gccttccaaa tgttcttctc aaacggaatc gtcgtatcca    900
gcctactcgc tattgtcctc aatgccgtat taaatcataa aaagaaataa gaaaaagagg    960
tgcgagcctc ttttttgtgt gacaaaataa aaacatctac ctattcatat acgctagtgt   1020
catagtcctg aaaatcatct gcatcaagaa caatttcaca actcttatac ttttctctta   1080
caagtcgttc ggcttcatct ggattttcag cctctatact tactaaacgt gataaagttt   1140
ctgtaatttc tactgtatcg acctgcagac tggctgtgta taagggagcc tgacatttat   1200
attccccaga acatcaggtt aatggcgttt ttgatgtcat tttcgcggtg gctgagatca   1260
gccacttctt ccccgataac ggagaccggc acactggcca tatcggtggt catcatgcgc   1320
cagctttcat ccccgatatg caccaccggg taaagttcac gggagacttt atctgacagc   1380
agacgtgcac tggccagggg gatcaccatc cgtcgcccgg gcgtgtcaat aatatcactc   1440
tgtacatcca caaacagacg ataacggctc tctcttttat aggtgtaaac cttaaactgc   1500
atttcaccag cccctgttct cgtcagcaaa agagccgttc atttcaataa accgggcgac   1560
ctcagccatc ccttcctgat tttccgcttt ccagcgttcg gcacgcagac gacgggcttc   1620
attctgcatg ttgtgctta ccagaccgga gatattgaca tcatatatgc cttgagcaac   1680
tgatagctgt cgctgtcaac tgtcactgta atacgctgct tcatagcata cctcttttg   1740
acatacttcg ggtatacata tcagtatata ttcttatacc gcaaaaatca gcgcgcaaat   1800
acgcatactg ttatctggct tttagtaagc cggatccacg cggcgtttac gccccgccct   1860
gccactcatc gcagtactgt tgtaattcat taagcattct gccgacatgg aagccatcac   1920
agacggcatg atgaacctga atcgccagcg gcatcagcac cttgtcgcct tgcgtataat   1980
atttgcccat ggtgaaaacg ggggcgaaga agttgtccat attggccacg tttaaatcaa   2040
aactggtgaa actcacccag ggattggctg agacgaaaaa catattctca ataaaccctt   2100
tagggaaata ggccaggttt tcaccgtaac acgccacatc ttgcgaatat atgtgtagaa   2160
actgccggaa atcgtcgtgg tattcactcc agagcgatga aaacgtttca gtttgctcat   2220
ggaaaacggt gtaacaaggg tgaacactat cccatatcac cagctcaccg tctttcattg   2280
ccatacgaa ttccggatga gcattcatca ggcgggcaag aatgtgaata aaggccggat   2340
aaaacttgtg cttattttc tttacggtct ttaaaaggc cgtaatatcc agctgaacgg   2400
tctggttata ggtacattga gcaactgact gaaatgcctc aaaatgttct ttacgatgcc   2460
attgggatat atcaacggtg gtatatccag tgatttttt ctccatttta gcttccttag   2520
ctcctgaaaa tctcgataac tcaaaaaata cgcccgtag tgatcttatt tcattatggt   2580
gaaagttgga acctcttacg tgccgatcaa cgtctcattt tcgccaaaag ttggcccagg   2640
gcttcccggt atcaacaggg acaccaggat ttattattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg ttttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000
tcccctatag tgagtcgtat tacatggtca tagctgtttc ctggcagctc tggcccgtgt   3060
```

```
ctcaaaatct ctgatgttac attgcacaag ataaaataat atcatcatga acaataaaac    3120
tgtctgctta cataaacagt aatacaaggg gtgttatgag ccatattcaa cgggaaacgt    3180
cgaggccgcg attaaattcc aacatggatg ctgatttata tgggtataaa tgggctcgcg    3240
ataatgtcgg gcaatcaggt gcgacaatct atcgcttgta tgggaagccc gatgcgccag    3300
agttgtttct gaaacatggc aaaggtagcg ttgccaatga tgttacagat gagatggtca    3360
gactaaactg gctgacggaa tttatgcctc ttccgaccat caagcatttt atccgtactc    3420
ctgatgatgc atggttactc accactgcga tccccggaaa aacagcattc caggtattag    3480
aagaatatcc tgattcaggt gaaaatattg ttgatgcgct ggcagtgttc ctgcgccggt    3540
tgcattcgat tcctgtttgt aattgtcctt ttaacagcga tcgcgtattt cgtctcgctc    3600
aggcgcaatc acgaatgaat aacggtttgg ttgatgcgag tgattttgat gacgagcgta    3660
atggctggcc tgttgaacaa gtctggaaag aaatgcataa acttttgcca ttctcaccgg    3720
attcagtcgt cactcatggt gatttctcac ttgataacct tatttttgac gaggggaaat    3780
taataggttg tattgatgtt ggacgagtcg gaatcgcaga ccgataccag gatcttgcca    3840
tcctatggaa ctgcctcggt gagttttctc cttcattaca gaaacggctt tttcaaaaat    3900
atggtattga taatcctgat atgaataaat tgcagtttca tttgatgctc gatgagtttt    3960
tctaatcaga attggttaat tggttgtaac actggcagag cattacgctg acttgacggg    4020
acggcgcaag ctcatgacca aaatccctta acgtgagtta cgcgtcgttc cactgagcgt    4080
cagaccccgt agaaaagatc aaaggatctt cttgagatcc ttttttttctg cgcgtaatct    4140
gctgcttgca acaaaaaaa ccaccgctac cagcggtggt ttgtttgccg gatcaagagc    4200
taccaactct tttccgaag gtaactggct tcagcagagc gcagatacca atactgttc    4260
ttctagtgta gccgtagtta ggccaccact tcaagaactc tgtagcaccg cctacatacc    4320
tcgctctgct aatcctgtta ccagtggctg ctgccagtgg cgataagtcg tgtcttaccg    4380
ggttggactc aagacgatag ttaccggata aggcgcagcg gtcgggctga acggggggtt    4440
cgtgcacaca gcccagcttg gagcgaacga cctacaccga actgagatac ctacagcgtg    4500
agctatgaga aagcgccacg cttcccgaag ggagaaaggc ggacaggtat ccggtaagcg    4560
gcagggtcgg aacaggagag cgcacgaggg agcttccagg gggaaacgcc tggtatcttt    4620
atagtcctgt cgggtttcgc cacctctgac ttgagcgtcg atttttgtga tgctcgtcag    4680
gggggcggag cctatggaaa aacgccagca acgcggcctt tttacggttc ctggccttt    4740
gctggccttt tgctcacatg t                                             4761
```

<210> SEQ ID NO 25
<211> LENGTH: 10703
<212> TYPE: DNA
<213> ORGANISM: Artificial Sequence
<220> FEATURE:
<223> OTHER INFORMATION: psPAX2 plasmid

<400> SEQUENCE: 25

```
aaaaggatct tcacctagat ccttttaaat taaaaatgaa gttttaaatc aatctaaagt      60
atatatgagt aaacttggtc tgacagttac caatgcttaa tcagtgaggc acctatctca     120
gcgatctgtc tatttcgttc atccatagtt gcctgactcc ccgtcgtgta gataactacg     180
atacgggagg gcttaccatc tggccccagt gctgcaatga taccgcgaga cccacgctca     240
ccggctccag atttatcagc aataaaccag ccagccggaa gggccgagcg cagaagtggt     300
cctgcaactt tatccgcctc catccagtct attaattgtt gccgggaagc tagagtaagt     360
```

```
agttcgccag ttaatagttt gcgcaacgtt gttgccattg ctacaggcat cgtggtgtca    420
cgctcgtcgt ttggtatggc ttcattcagc tccggttccc aacgatcaag gcagttaca     480 tgatccccca tgttgtgcaa aaaagcggtt agctccttcg gtcctccgat cgttgtcaga    540
agtaagttgg ccgcagtgtt atcactcatg gttatggcag cactgcataa ttctcttact    600
gtcatgccat ccgtaagatg cttttctgtg actggtgagt actcaaccaa gtcattctga    660
gaatagtgta tgcggcgacc gagttgctct tgcccggcgt caatacggga taataccgcg    720
ccacatagca gaactttaaa agtgctcatc attggaaaac gttcttcggg gcgaaaactc    780
tcaaggatct taccgctgtt gagatccagt tcgatgtaac ccactcgtgc acccaactga    840
tcttcagcat cttttacttt caccagcgtt tctgggtgag caaaaacagg aaggcaaaat    900
gccgcaaaaa agggaataag ggcgacacgg aaatgttgaa tactcatact cttcctttt     960 caatattatt gaagcattta tcagggttat tgtctcatga gcggatacat atttgaatgt   1020
atttagaaaa ataaacaaat aggggttccg cgcacatttc cccgaaaagt gccacctggt   1080
cgacattgat tattgactag ttattaatag taatcaatta cggggtcatt agttcatagc   1140
ccatatatgg agttccgcgt tacataactt acggtaaatg gcccgcctgg ctgaccgccc   1200
aacgaccccc gcccattgac gtcaataatg acgtatgttc ccatagtaac gccaataggg   1260
actttccatt gacgtcaatg ggtggactat ttacggtaaa ctgcccactt ggcagtacat   1320
caagtgtatc atatgccaag tacgccccct attgacgtca atgacggtaa atggcccgcc   1380
tggcattatg cccagtacat gaccttatgg gactttccta cttggcagta catctacgta   1440
ttagtcatcg ctattaccat gggtcgaggt gagccccacg ttctgcttca ctctccccat   1500
ctcccccccc tccccacccc caattttgta tttatttatt ttttaattat tttgtgcagc   1560 gatggggggcg gggggggggg ggcgcgcgc caggcgggc gggcggggc gaggggcggg    1620 gcggggcgag gcgagaggt gcggcggcag ccaatcagag cggcgcgctc cgaaagtttc   1680 ctttatggc gaggcggcgg cggcggcggc cctataaaaa gcgaagcgcg cggcgggcgg   1740
gagtcgctgc gttgccttcg ccccgtgccc cgctccgcgc cgcctcgcgc cgcccgcccc   1800
ggctctgact gaccgcgtta ctcccacagg tgagcgggcg gacggcccct tctcctccgg   1860
gctgtaatta gcgcttggtt taatgacggc tcgtttcttt tctgtggctg cgtgaaagcc   1920
ttaaagggct ccgggagggc cctttgtgcg ggggggagcg gctcgggggg tgcgtgcgtg   1980
tgtgtgtgcg tggggagcgc cgcgtgcggc ccgcgctgcc cggcggctgt gagcgctgcg   2040
ggcgcggcgc ggggctttgt gcgctccgcg tgtgcgcgag gggagcgcgg ccggggcggg   2100
tgccccgcgg tgcgggggg ctgcgagggg aacaaaggct gcgtgcgggg tgtgtgcgtg   2160 gggggtgag caggggtgt gggcgcgcg gtcgggctgt aaccccccc tgcaccccc      2220 tccccgagtt gctgagcacg gcccggcttc gggtgcgggg ctccgtgcgg ggcgtggcgc   2280
ggggctcgcc gtgccgggcg gggggtggcg gcaggtgggg gtgccgggcg gggcggggcc   2340
gcctcgggcc ggggagggct cggggggaggg gcgcggcggc cccggagcgc cggcggctgt   2400
cgaggcgcgg cgagccgcag ccattgcctt ttatggtaat cgtgcgagag ggcgcaggga   2460
cttcctttgt cccaaatctg gcggagccga atctgggag gcgccgccgc accccctcta   2520
gcgggcgcgg gcgaagcggt gcggcgccgg caggaaggaa atgggcgggg agggccttcg   2580
tgcgtcgccg cgccgccgtc cccttctcca tctccagcct cggggctgcc gcaggggac    2640 ggctgccttc gggggggacg gggcagggcg gggttcggct tctggcgtgt gaccggcggc   2700
```

```
tctagagcct ctgctaacca tgttcatgcc ttcttctttt tcctacagct cctgggcaac   2760
gtgctggtta ttgtgctgtc tcatcatttt ggcaaagaat tcgggccggc cgcgttgacg   2820
cgcacggcaa gaggcgaggg gcggcgactg gtgagagatg ggtgcgagag cgtcagtatt   2880
aagcggggga gaattagatc gatgggaaaa aattcggtta aggccagggg gaaagaaaaa   2940
atataaatta aaacatatag tatgggcaag cagggagcta gaacgattcg cagttaatcc   3000
tggcctgtta gaaacatcag aaggctgtag acaaatactg ggacagctac aaccatccct   3060
tcagacagga tcagaagaac ttagatcatt atataataca gtagcaaccc tctattgtgt   3120
gcatcaaagg atagagataa aagacaccaa ggaagcttta gacaagatag aggaagagca   3180
aaacaaaagt aagaaaaaag cacagcaagc agcagctgac acaggacaca gcaatcaggt   3240
cagccaaaat taccctatag tgcagaacat ccagggcaa atggtacatc aggccatatc   3300
acctagaact ttaaatgcat gggtaaaagt agtagaagag aaggctttca gcccagaagt   3360
gatacccatg ttttcagcat tatcagaagg agccacccca caagatttaa acaccatgct   3420
aaacacagtg gggggacatc aagcagccat gcaaatgtta aaagagacca tcaatgagga   3480
agctgcagaa tgggatagag tgcatccagt gcatgcaggg cctattgcac caggccagat   3540
gagagaacca aggggaagtg acatagcagg aactactagt acccttcagg aacaaatagg   3600
atggatgaca cataatccac ctatcccagt aggagaaatc tataaaagat ggataatcct   3660
gggattaaat aaaatagtaa gaatgtatag ccctaccagc attctggaca taagacaagg   3720
accaaaggaa cccctttaga g actatgtaga ccgattctat aaaactctaa gagccgagca   3780
agcttcacaa gaggtaaaaa attggatgac agaaaccttg ttggtccaaa atgcgaaccc   3840
agattgtaag actatttaa aagcattggg accaggagcg acactagaag aaatgatgac   3900
agcatgtcag ggagtggggg gacccggcca taaagcaaga gttttggctg aagcaatgag   3960
ccaagtaaca aatccagcta ccataatgat acagaaaggc aattttagga accaaagaaa   4020
gactgttaag tgtttcaatt gtggcaaaga agggcacata gccaaaaatt gcagggcccc   4080
taggaaaaag ggctgttgga atgtgggaaa ggaaggacac caaatgaaag attgtactga   4140
gagacaggct aattttttag ggaagatctg gccttccac aagggaaggc cagggaattt   4200
tcttcagagc agaccagagc caacagcccc accagaagag agcttcaggt ttggggaaga   4260
gacaacaact ccctctcaga agcaggagcc gatagacaag gaactgtatc ctttagcttc   4320
cctcagatca ctctttggca gcgaccctc gtcacaataa agatagggg gcaattaaag   4380 gaagctctat tagatacagg agcagatgat acagtattag aagaaatgaa tttgccagga   4440
agatggaaac caaaaatgat aggggggaatt ggaggtttta tcaaagtagg acagtatgat   4500
cagatactca tagaaatctg cggacataaa gctataggta cagtattagt aggacctaca   4560
cctgtcaaca taattggaag aaatctgttg actcagattg gctgcacttt aaattttccc   4620
attagtccta ttgagactgt accagtaaaa ttaaagccag gaatggatgg cccaaaagtt   4680
aaacaatggc cattgacaga agaaaaaata aaagcattag tagaaatttg tacagaaatg   4740
gaaaaggaag gaaaaatttc aaaaattggg cctgaaaatc catacaatac tccagtattt   4800
gccataaaga aaaagacag tactaaatgg agaaaattag tagatttcag agaacttaat   4860
aagagaactc aagatttctg ggaagttcaa ttaggaatac cacatcctgc agggttaaaa   4920
cagaaaaaat cagtaacagt actggatgtg ggcgatgcat atttttcagt tcccttagat   4980
aaagacttca ggaagtatac tgcatttacc atacctagta taaacaatga gacaccaggg   5040
attagatatc agtacaatgt gcttccacag ggatggaaag gatcaccagc aatattccag   5100
```

-continued

```
tgtagcatga caaaaatctt agagccttt agaaaacaaa atccagacat agtcatctat    5160
caatacatgg atgatttgta tgtaggatct gacttagaaa tagggcagca tagaacaaaa    5220
atagaggaac tgagacaaca tctgttgagg tggggattta ccacaccaga caaaaaacat    5280
cagaaagaac ctccattcct ttggatgggt tatgaactcc atcctgataa atggacagta    5340
cagcctatag tgctgccaga aaaggacagc tggactgtca atgacataca gaaattagtg    5400
ggaaaattga attgggcaag tcagatttat gcagggatta agtaaggca attatgtaaa     5460
cttcttaggg gaaccaaagc actaacagaa gtagtaccac taacagaaga agcagagcta    5520
gaactggcag aaaacaggga gattctaaaa gaaccggtac atggagtgta ttatgaccca    5580
tcaaaagact aatagcaga atacagaag caggggcaag gccaatggac atatcaaatt     5640
tatcaagagc catttaaaaa tctgaaaaca ggaaaatatg caagaatgaa gggtgcccac    5700
actaatgatg tgaaacaatt aacagaggca gtacaaaaaa tagccacaga aagcatagta    5760
atatggggaa agactcctaa atttaaatta cccatacaaa aggaaacatg ggaagcatgg    5820
tggacagagt attggcaagc cacctggatt cctgagtggg agtttgtcaa tacccctccc    5880
ttagtgaagt tatggtacca gttagagaaa gaacccataa taggagcaga aactttctat    5940
gtagatgggg cagccaatag ggaaactaaa ttaggaaaag caggatatgt aactgacaga    6000
ggaagacaaa aagttgtccc cctaacggac acaacaaatc agaagactga gttacaagca    6060
attcatctag ctttgcagga ttcgggatta gaagtaaaca tagtgacaga ctcacaatat    6120
gcattgggaa tcattcaagc acaaccagat aagagtgaat cagagttagt cagtcaaata    6180
atagagcagt taataaaaaa ggaaaaagtc tacctggcat gggtaccagc acacaaagga    6240
attggaggaa atgaacaagt agatggggttg gtcagtgctg gaatcaggaa agtactattt    6300
ttagatggaa tagataaggc ccaagaagaa catgagaaat atcacagtaa ttggagagca    6360
atggctagtg attttaacct accacctgta gtagcaaaag aaatagtagc cagctgtgat    6420
aaatgtcagc taaaagggga agccatgcat ggacaagtag actgtagccc aggaatatgg    6480
cagctagatt gtacacattt agaaggaaaa gttatcttgg tagcagttca tgtagccagt    6540
ggatatatag aagcagaagt aattccagca gagacagggc aagaaacagc atacttcctc    6600
ttaaaattag caggaagatg gccagtaaaa acagtacata cagacaatgg cagcaatttc    6660
accagtacta cagttaaggc cgcctgttgg tgggcgggga tcaagcagga atttggcatt    6720
ccctacaatc cccaaagtca aggagtaata gaatctatga ataaagaatt aagaaaaatt    6780
ataggacagg taagagatca ggctgaacat cttaagacag cagtacaaat ggcagtattc    6840
atccacaatt ttaaaagaaa agggggggatt ggggggtaca gtgcagggga agaatagta    6900
gacataatag caacagacat acaaactaaa gaattacaaa acaaattac aaaaattcaa    6960
aattttcggg tttattacag ggacagcaga gatccagttt ggaaaggacc agcaaagctc    7020
ctctggaaag gtgaagggc agtagtaata caagataata gtgacataaa agtagtgcca    7080
agaagaaaag caaagatcat cagggattat ggaaaacaga tggcaggtga tgattgtgtg    7140
gcaagtagac aggatgagga ttaacacatg gaattctgca acaactgctg tttatccatt    7200
tcagaattgg gtgtcgacat agcagaatag gcgttactcg acagaggaga gcaagaaatg    7260
gagccagtag atcctagact agagccctgg aagcatccag gaagtcagcc taaaactgct    7320
tgtaccaatt gctattgtaa aaagtgttgc tttcattgcc aagtttgttt catgacaaaa    7380
gccttaggca tctcctatgg caggaagaag cggagacagc gacgaagagc tcatcagaac    7440
```

```
agtcagactc atcaagcttc tctatcaaag cagtaagtag tacatgtaat gcaacctata    7500
atagtagcaa tagtagcatt agtagtagca ataataatag caatagttgt gtggtccata    7560
gtaatcatag aatataggaa aatggccgct gatcttcaga cctggaggag agatatgag     7620 ggacaattgg agaagtgaat tatataaata taaagtagta aaaattgaac cattaggagt    7680
agcacccacc aaggcaaaga gaagagtggt gcagagagaa aaaagagcag tgggaatagg    7740
agctttgttc cttgggttct gggagcagc aggaagcact atgggcgcag cctcaatgac     7800
gctgacggta caggccagac aattattgtc tggtatagtg cagcagcaga acaatttgct    7860
gagggctatt gaggcgcaac agcatctgtt gcaactcaca gtctggggca tcaagcagct    7920
ccaagcaaga atcctagctg tggaaagata cctaaaggat caacagctcc tagggatttg    7980
gggttgctct ggaaaactca tttgcaccac tgctgtgcct tggaatgcta gttggagtaa    8040
taaatctctg gaacagatct ggaatcacac gacctggatg gagtgggaca gagaaattaa    8100
caattcacaa agcttaatac actccttaat tgaagaatcg caaaaccagc aagaaaagaa    8160
tgaacaagaa ttattggaat tagataaatg gcaagtttg tggaattggt ttaacataac     8220
aaattggctg tggtatataa aattattcat aatgatagta ggaggcttgg taggtttaag    8280
aatagttttt gctgtacttt ctatagtgaa tagagttagg cagggatatt caccattatc    8340
gtttcagacc cacctcccaa tcccgagggg acccgacagg cccgaaggaa tagaagaaga    8400
aggtggagag agacagag acagatccat tcgattagtg aacggatcct ggcacttat      8460 ctgggacgat ctgcggagcc tgtgcctctt cagctaccac cgcttgagag acttactctt    8520
gattgtaacg aggattgtgg aacttctggg acgcaggggg tgggaagccc tcaaatattg    8580
gtggaatctc ctacaatatt ggagtcagga gctaaagaat agtgctgtta gcttgctcaa    8640
tgccacagcc atagcagtag ctgaggggac agatagggtt atagaagtag tacaaggagc    8700
ttgtagagct attcgccaca tacctagaag aataagacag gcttggaaa ggattttgct     8760 ataagctcga acaaccggt acctctagaa ctatagctag cagatctttt tccctctgcc     8820
aaaaattatg gggacatcat gaagcccctt gagcatctga cttctggcta ataaaggaaa    8880 tttatttca ttgcaatagt gtgttggaat ttttgtgtc tctcactcgg aaggacatat       8940
gggagggcaa atcatttaaa acatcagaat gagtatttgg tttagagttt ggcaacatat    9000
gccatatgct ggctgccatg aacaaaggtg gctataaaga ggtcatcagt atatgaaaca    9060 gcccctgct gtccattcct tattccatag aaaagccttg acttgaggtt agatttttt       9120 tatatttgt tttgtgttat tttttctctt aacatccctta aaattttcct tacatgttt      9180 actagccaga ttttcctcc tctcctgact actcccagtc atagctgtcc ctcttctctt      9240
atgaagatcc ctcgacctgc agcccaagct tggcgtaatc atggtcatag ctgtttcctg    9300
tgtgaaattg ttatccgctc acaattccac acaacatacg agccggaagc ataaagtgta    9360
aagcctgggg tgcctaatga gtgagctaac tcacattaat tgcgttgcgc tcactgcccg    9420
ctttccagtc gggaaacctg tcgtgccagc ggatccgcat tcaattagt cagcaaccat      9480 agtcccgccc ctaactccgc ccatcccgcc cctaactccg cccagttccg cccattctcc    9540
gccccatggc tgactaattt tttttattta tgcagaggcc gaggccgcct cggcctctga    9600
gctattccag aagtagtgag gaggcttttt tggaggccta ggcttttgca aaaagctaac    9660
ttgtttattg cagcttataa tggttacaaa taaagcaata gcatcacaaa tttcacaaat    9720
aaagcatttt tttcactgca ttctagttgt ggtttgtcca aactcatcaa tgtatcttat    9780
catgtctgga tccgctgcat taatgaatcg gccaacgcgc ggggagaggc ggtttgcgta    9840
```

```
ttgggcgctc ttccgcttcc tcgctcactg actcgctgcg ctcggtcgtt cggctgcggc    9900
gagcggtatc agctcactca aaggcggtaa tacggttatc cacagaatca ggggataacg    9960
caggaaagaa catgtgagca aaaggccagc aaaaggccag gaaccgtaaa aaggccgcgt   10020
tgctggcgtt tttccatagg ctccgccccc ctgacgagca tcacaaaaat cgacgctcaa   10080
gtcagaggtg gcgaaacccg acaggactat aaagatacca ggcgtttccc cctggaagct   10140
ccctcgtgcg ctctcctgtt ccgaccctgc cgcttaccgg atacctgtcc gcctttctcc   10200
cttcgggaag cgtggcgctt tctcaatgct cacgctgtag gtatctcagt tcggtgtagg   10260
tcgttcgctc caagctgggc tgtgtgcacg aaccccccgt tcagcccgac cgctgcgcct   10320
tatccggtaa ctatcgtctt gagtccaacc cggtaagaca cgacttatcg ccactggcag   10380
cagccactgg taacaggatt agcagagcga ggtatgtagg cggtgctaca gagttcttga   10440
agtggtggcc taactacggc tacactagaa ggacagtatt tggtatctgc gctctgctga   10500
agccagttac cttcggaaaa agagttggta gctcttgatc cggcaaacaa accaccgctg   10560
gtagcggtgg tttttttgtt tgcaagcagc agattacgcg cagaaaaaaa ggatctcaag   10620
aagatccttt gatcttttct acggggtctg acgctcagtg gaacgaaaac tcacgttaag   10680
ggattttggt catgagatta tca                                           10703
```

<210> SEQ ID NO 26
<211> LENGTH: 7298
<212> TYPE: DNA
<213> ORGANISM: Artificial Sequence
<220> FEATURE:
<223> OTHER INFORMATION: pCIGO-VSV.G plasmid

<400> SEQUENCE: 26

```
gtcgacggat cgggagatca attccggcac ctgtcctacg agttgcatga taaagaagac     60
agtcataagt gcggcgacga tagtcatgcc ccgcgcccac cggaaggagc tgactgggtt    120
gaaggctctc aagggcatcg gtcgatgcag gaaaaggaca agcagcgaaa attcacgccc    180
ccttgggagg tggcggcata tgcaaaggat agcactccca ctctactact gggtatcata    240
tgctgactgt atatgcatga ggatagcata tgctacccgg atacagatta ggatagcata    300
tactacccag atatagatta ggatagcata tgctacccag atatagatta ggatagccta    360
tgctacccag atataaatta ggatagcata tactacccag atatagatta ggatagcata    420
tgctacccag atatagatta ggatagccta tgctacccag atatagatta ggatagcata    480
tgctacccag atatagatta ggatagccta tgctatccag atatttgggt agtatatgct    540
acccagatat aaattaggat agcatatact accctaatct ctattaggat agcatatgct    600
acccggatac agattaggat agcatatact acccagatat agattaggat agcatatgct    660
acccagatat agattaggat agcctatgct acccagatat aaattaggat agcatatact    720
acccagatat agattaggat agcatatgct acccagatat agattaggat agcctatgct    780
acccagatat agattaggat agcatatgct atccagatat ttgggtagta tatgctaccc    840
atggcaacat tagcccaccg tgctctcagc gacctcgtga atatgaggac caacaaccct    900
gtgcttggcg ctcaggcgca agtgtgtgta atttgtcctc cagatcgcag caatcgcgcc    960
cctatcttgg cccgcccacc tacttatgca ggtattcccc gggtgccat tagtggtttt   1020 gtgggcaagt ggtttgaccg cagtggttag cggggttaca atcagccaag ttattacacc   1080 cttatttttac agtccaaaac cgcagggcgg cgtgtggggg ctgacgcgtg cccccactcc   1140
```

```
acaatttcaa aaaaaagagt ggccacttgt ctttgtttat gggccccatt ggcgtggagc   1200
cccgtttaat tttcgggggt gttagagaca accagtggag tccgctgctg tcggcgtcca   1260
ctctctttcc ccttgttaca aatagagtgt aacaacatgg ttcacctgtc ttggtccctg   1320
cctgggacac atcttaataa ccccagtatc atattgcact aggattatgt gttgcccata   1380
gccataaatt cgtgtgagat ggacatccag tctttacggc ttgtccccac ccatggatt    1440
tctattgtta aagatattca gaatgtttca ttcctacact agtatttatt gcccaagggg   1500
tttgtgaggg ttatattggt gtcatagcac aatgccacca ctgaaccccc cgtccaaatt   1560
ttattctggg ggcgtcacct gaaaccttgt tttcgagcac ctcacataca ccttactgtt   1620
cacaactcag cagttattct attagctaaa cgaaggagaa tgaagaagca ggcgaagatt   1680
caggagagtt cactgcccgc tccttgatct tcagccactg cccttgtgac taaaatggtt   1740
cactaccctc gtggaatcct gaccccatgt aaataaaacc gtgacagctc atggggtggg   1800
agatatcgct gttccttagg acccttttac taacccctaat tcgatagcat atgcttcccg   1860
ttgggtaaca tatgctattg aattagggtt agtctggata gtatatacta ctacccggga   1920
agcatatgct accgtttag ggttaacaag ggggccttat aaacactatt gctaatgccc     1980
tcttgagggt ccgcttatcg gtagctacac aggcccctct gattgacgtt ggtgtagcct   2040
cccgtagtct tcctgggccc ctgggaggta catgtccccc agcattggtg taagagcttc   2100
agccaagagt tacacataaa ggcaatgttg tgttgcagtc cacagactgc aaagtctgct   2160
ccaggatgaa agccactcaa gggatcttca atattggcca ttagccatat tattcattgg   2220
ttatatagca taaatcaata ttggctattg gccattgcat acgttgtatc tatatcataa   2280
tatgtacatt tatattggct catgtccaat atgaccgcca tgttggcatt gattattgac   2340
tagttattaa tagtaatcaa ttacggggtc attagttcat agcccatata tggagttccg   2400
cgttacataa cttacggtaa atggcccgcc tggctgaccg cccaacgacc cccgcccatt   2460
gacgtcaata atgacgtatg ttcccatagt aacgccaata gggactttcc attgacgtca   2520
atgggtggag tatttacggt aaactgccca cttggcagta catcaagtgt atcatatgcc   2580
aagtccgccc cctattgacg tcaatgacgg taaatggccc gcctggcatt atgcccagta   2640
catgacctta cgggactttc ctacttggca gtacatctac gtattagtca tcgctattac   2700
catggtgatg cggttttggc agtacaccaa tgggcgtgga tagcggtttg actcacgggg   2760
atttccaagt ctccacccca ttgacgtcaa tgggagtttg ttttggcacc aaaatcaacg   2820
ggactttcca aaatgtcgta ataaccccgc cccgttgacg caaatgggcg gtaggcgtgt   2880
acggtgggag gtctatataa gcagagctcg tttagtgaac cgtcagatca ctagaagctt   2940
tattgcggta gtttatcaca gttaaattgc taacgcagtc agtgcttctg acacaacagt   3000
ctcgaactta agctgcagaa gttggtcgtg aggcactggg caggtaagta tcaaggttac   3060
aagacaggtt taaggagacc aatagaaact gggcttgtcg agacagagaa gactcttgcg   3120
tttctgatag gcacctattg gtcttactga catccacttt gcctttctct ccacaggtgt   3180
ccactcccag ttcaattaca gctcttaagg ctagagtact taatacgact cactataggc   3240
tagcggtacc gagctcggat ccactagtaa cggccgccag tgtgctggaa ttcaacagag   3300
atcgatctgt ttccttgaca ctatgaagtg ccttttgtac ttagcctttt tattcattgg   3360
ggtgaattgc aagttcacca tagttttttcc acacaaccaa aaaggaaact ggaaaaatgt   3420
tccttctaat taccattatt gcccgtcaag ctcagattta aattggcata atgacttaat   3480
aggcacagcc atacaagtca aaatgcccaa gagtcacaag gctattcaag cagacggttg   3540
```

```
gatgtgtcat gcttccaaat gggtcactac ttgtgatttc cgctggtatg gaccgaagta    3600
tataacacag tccatccgat ccttcactcc atctgtagaa caatgcaagg aaagcattga    3660
acaaacgaaa caaggaactt ggctgaatcc aggcttccct cctcaaagtt gtggatatgc    3720
aactgtgacg gatgccgaag cagtgattgt ccaggtgact cctcaccatg tgctggttga    3780
tgaatacaca ggagaatggg ttgattcaca gttcatcaac ggaaaatgca gcaattacat    3840
atgccccact gtccataact ctacaacctg cattctgac  tataaggtca aagggctatg    3900
tgattctaac ctcatttcca tggacatcac cttcttctca gaggacggag agctatcatc    3960
cctgggaaag gagggcacag ggttcagaag taactacttt gcttatgaaa ctggaggcaa    4020
ggcctgcaaa atgcaatact gcaagcattg gggagtcaga ctcccatcag gtgtctggtt    4080
cgagatggct gataaggatc tctttgctgc agccagattc cctgaatgcc agaagggtc     4140 aagtatctct gctccatctc agacctcagt ggatgtaagt ctaattcagg acgttgagag    4200
gatcttggat tattccctct gccaagaaac ctggagcaaa atcagagcgg tcttccaat     4260 ctctccagtg gatctcagct atcttgctcc taaaaaccca ggaaccggtc ctgctttcac    4320
cataatcaat ggtaccctaa atactttga ggaccagatac atcagagtcg atattgctgc    4380
tccaatcctc tcaagaatgg tcggaatgat cagtggaact accacagaaa gggaactgtg    4440
ggatgactgg gcaccatatg aagacgtgga aattggaccc aatggagttc tgaggaccag    4500
ttcaggatat aagtttcctt tatacatgat tggacatggt atgttggact ccgatcttca    4560
tcttagctca aaggctcagg tgttcgaaca tcctcacatt caagacgctg cttcgcaact    4620
tcctgatgat gagagtttat tttttggtga tactgggcta tccaaaaatc caatcgagct    4680
tgtagaaggt tggttcagta gttggaaaag ctctattgcc tctttttct  ttatcatagg    4740 gttaatcatt ggactattct tggttctccg agttggtatc catctttgca ttaaattaaa    4800
gcacaccaag aaaagacaga tttatacaga catagagatg aaccgacttg gaaagtaact    4860
caaatcctgc acaacagatt cttcatgttt ggaccaaatc aacttgtgat accatgctca    4920
aagaggcctc aattatattt gagtttttaa ttttttatgga attctgcaga tatccatcac    4980
actggcggcc gctcgagcat gcatctagag ggccctattc tatagtgtca cctaaatgct    5040
agagctcgct gatcagcctc gactgtgcct tctagttgcc agccatctgt tgtttgcccc    5100 tccccgtgc cttccttgac cctggaaggt gccactccca ctgtcctttc ctaataaaat    5160
gaggaaattg catcgcattg tctgagtagg tgtcattcta ttctgggggg tggggtgggg    5220
caggacagca aggggagga ttgggaagac aatagcaggc atgctggga tgcggtgggc     5280 tctatggctt ctgaggcgga agaaccagc tgcattaatg aatcggccaa cgcgcgggga    5340
gaggcggttt gcgtattggg cgctcttccg cttcctcgct cactgactcg ctgcgctcgg    5400
tcgttcggct gcggcgagcg gtatcagctc actcaaaggc ggtaatacgg ttatccacag    5460
aatcagggga taacgcagga aagaacatgt gagcaaaagg ccagcaaaag gccaggaacc    5520
gtaaaaaggc cgcgttgctg gcgtttttcc ataggctccg ccccctgac  gagcatcaca    5580 aaaatcgacg ctcaagtcag aggtggcgaa acccgacagg actataaaga taccaggcgt    5640
ttccccctgg aagctccctc gtgcgctctc ctgttccgac cctgccgctt accggatacc    5700
tgtccgcctt tctcccttcg ggaagcgtgg cgctttctca atgctcacgc tgtaggtatc    5760
tcagttcggt gtaggtcgtt cgctccaagc tgggctgtgt gcacgaaccc cccgttcagc    5820
ccgaccgctg cgccttatcc ggtaactatc gtcttgagtc caacccggta agacacgact    5880
```

```
tatcgccact ggcagcagcc actggtaaca ggattagcag agcgaggtat gtaggcggtg   5940
ctacagagtt cttgaagtgg tggcctaact acggctacac tagaaggaca gtatttggta   6000
tctgcgctct gctgaagcca gttaccttcg aaaaagagt tggtagctct tgatccggca    6060
aacaaaccac cgctggtagc ggtggttttt ttgtttgcaa gcagcagatt acgcgcagaa   6120
aaaaggatc tcaagaagat cctttgatct tttctacggg gtctgacgct cagtggaacg    6180
aaaactcacg ttaagggatt ttggtcatga gattatcaaa aaggatcttc acctagatcc    6240
ttttaaatta aaaatgaagt tttaaatcaa tctaaagtat atatgagtaa acttggtctg    6300
acagttacca atgcttaatc agtgaggcac ctatctcagc gatctgtcta tttcgttcat    6360
ccatagttgc ctgactcccc gtcgtgtaga taactacgat acgggagggc ttaccatctg    6420
gccccagtgc tgcaatgata ccgcgagacc cacgctcacc ggctccagat ttatcagcaa    6480
taaaccagcc agccggaagg gccgagcgca gaagtggtcc tgcaacttta tccgcctcca    6540
tccagtctat taattgttgc cgggaagcta gagtaagtag ttcgccagtt aatagtttgc    6600
gcaacgttgt tgccattgct acaggcatcg tggtgtcacg ctcgtcgttt ggtatggctt    6660
cattcagctc cggttcccaa cgatcaaggc gagttacatg atcccccatg ttgtgcaaaa    6720
aagcggttag ctccttcggt cctccgatcg ttgtcagaag taagttggcc gcagtgttat    6780
cactcatggt tatggcagca ctgcataatt ctcttactgt catgccatcc gtaagatgct    6840
tttctgtgac tggtgagtac tcaaccaagt cattctgaga atagtgtatg cggcgaccga    6900
gttgctcttg cccggcgtca atacgggata ataccgcgcc acatagcaga actttaaaag    6960
tgctcatcat tggaaaacgt tcttcggggc gaaaactctc aaggatctta ccgctgttga    7020
gatccagttc gatgtaaccc actcgtgcac ccaactgatc ttcagcatct tttactttca    7080
ccagcgtttc tgggtgagca aaaacaggaa ggcaaaatgc cgcaaaaaag gaataagggg    7140
cgacacggaa atgttgaata ctcatactct tcctttttca atattattga agcatttatc    7200
agggttattg tctcatgagc ggatacatat ttgaatgtat ttagaaaaat aaacaaatag    7260
gggttccgcg cacatttccc cgaaaagtgc cacctgac                            7298
```

<210> SEQ ID NO 27
<211> LENGTH: 231
<212> TYPE: PRT
<213> ORGANISM: Artificial Sequence
<220> FEATURE:
<223> OTHER INFORMATION: mFC-7C12 scFv

<400> SEQUENCE: 27

```
Gln Val Gln Leu Val Gln Ser Gly Gly Gly Leu Val Lys Pro Gly Gly
1               5                   10                  15
Ser Leu Arg Leu Ser Cys Ala Ala Ser Gly Phe Asn Phe Asn Asp Gln
            20                  25                  30
Tyr Met Ser Trp Ile Arg Gln Ala Pro Gly Lys Gly Leu Glu Trp Val
        35                  40                  45
Ser Phe Ile Ser Gly Ser Gly Gly Thr Thr Tyr Tyr Thr Asp Ser Val
    50                  55                  60
Lys Gly Arg Phe Thr Ile Ser Arg Asp Asn Thr Lys Asp Ser Leu Tyr
65                  70                  75                  80
Leu Gln Met Asn Ser Leu Thr Val Glu Asp Thr Ala Val Tyr Tyr Cys
                85                  90                  95
Ala Arg Gly Gly Asn Tyr Tyr Thr Ser Val Gly Arg Gly Thr Leu Val
            100                 105                 110
```

```
Thr Val Ser Ala Gly Gly Gly Ser Gly Ala Pro Asp Ile Gln Met
            115                 120                 125

Thr Gln Ser Pro Gly Thr Leu Ser Leu Ser Pro Gly Glu Arg Ala Ile
130                 135                 140

Leu Ser Cys Arg Ala Ser Gln Ser Val Ser Gly Tyr Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Ser Leu Arg Pro Glu Asp Ile Gly
        195                 200                 205

Thr Tyr Tyr Cys Lys Gln Tyr Ile Asn Ala Pro Phe Thr Phe Gly Gly
    210                 215                 220

Gly Thr Lys Val Glu Ile Lys
225                 230

<210> SEQ ID NO 28
<211> LENGTH: 243
<212> TYPE: PRT
<213> ORGANISM: Artificial Sequence
<220> FEATURE:
<223> OTHER INFORMATION: mFC-8B3 scFv

<400> SEQUENCE: 28

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ser Pro Tyr Asn Gly Asn Thr Asp Tyr Ala Gln Lys Val
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Gly Gly Gly Thr Trp Tyr Ser Asp Leu Trp Gly Arg Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Pro Glu Ile Val Leu Thr Gln Ser Pro
    130                 135                 140

Ser Thr Leu Ser Ala Ser Val Gly Asp Arg Val Ser Ile Thr Cys Arg
145                 150                 155                 160

Ala Ser Gln Ser Ile Gly Gly Ser Leu Ala Trp Tyr Gln Gln Lys Pro
                165                 170                 175

Gly Lys Ala Pro Lys Leu Leu Ile Ser Glu Ala Ser Thr Leu Glu Arg
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Val Ala Thr Tyr Tyr Cys
    210                 215                 220

Gln Lys Tyr Asn Ser Val Pro Leu Thr Phe Gly Pro Gly Thr Lys Val
225                 230                 235                 240
```

<210> SEQ ID NO 29
<211> LENGTH: 693
<212> TYPE: DNA
<213> ORGANISM: Artificial Sequence
<220> FEATURE:
<223> OTHER INFORMATION: mFC-7C12 scFv

<400> SEQUENCE: 29

```
caggtgcagc tggtgcagtc tggggggaggc ttggtcaagc ctggagggtc cctgagactc      60
tcctgtgcag cctctggatt caatttcaat gaccagtaca tgagttggat ccgccaggct     120
ccagggaagg ggctggagtg ggtttcattc attagtggta gtggtggtac cacatactac     180
acagactctg tgaagggccg gttcaccatc tccaggaca acaccaagga ctcattgtat      240
ttgcaaatga acagcctgac agtcgaggac acggccgtgt actactgtgc gagaggaggg     300
aattattata cttcggtggg ccggggcacc ctggtcaccg tctcggcgg tggcggcgga      360
tctggcgcgc cagacatcca gatgacccag tctccaggca ccctgtcttt gtctccaggg     420
gaaagagcca tcctctcctg cagggccagt cagagtgtta gcggctacct agcctggtat     480
caacagaaac tggccaggc tcccaggctc ctcatctatg gtgcatccag cagggccact      540
ggcatcccag acaggttcag tggcagtggg tctgggacag acttcactct caccatcagc    600
agcctgcggc ctgaagatat tgaacatat actgtaaac agtacattaa tgccccattc       660
actttcggcg gcgggaccaa ggtggagatc aaa                                  693
```

<210> SEQ ID NO 30
<211> LENGTH: 729
<212> TYPE: DNA
<213> ORGANISM: Artificial Sequence
<220> FEATURE:
<223> OTHER INFORMATION: mFC-8B3 scFv

<400> SEQUENCE: 30

```
caggtacagc tgcagcagtc aggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggatgg atcagccctt acaatggtaa cacagattat     180
gcacagaagg tccagggcag agtcaccttg accacagaca catccacgag cacagcctac     240
atggagctga ggagcctgag atccgacgac acggccgtgt attactgtgc gacaggtggc     300
gggacctggt actccgatct ctggggccgt ggcaccctgg tcaccgtctc ggccggtggc     360
ggtggcagcg gcggtggtgg gtccggtggc ggcggatctg gcgcgccaga aattgtgctg    420
actcagtctc cctccaccct gtctgcatct gtaggagaca gagtcagcat cacttgccgg    480
gccagtcaga gtattggtgg gtcgttggcc tggtatcaac aaaagccagg gaaagcccct    540
aagctcctga tctctgaggc gtctacttta gagaggggcg tcccatcaag attcagcggc    600
agtggatctg gacagattt cactctcacc atcagcagcc tgcagcctga agatgttgca     660
acttattact gtcaaaaata taacagtgtc ccgctcactt tcggccctgg gaccaaggtg    720
gagatcaaa                                                              729
```

<210> SEQ ID NO 31
<211> LENGTH: 9862
<212> TYPE: DNA
<213> ORGANISM: Artificial Sequence
<220> FEATURE:
<223> OTHER INFORMATION: destination vector pLV4301G

<400> SEQUENCE: 31

```
cgataaccct aattcgatag catatgcttc ccgttgggta acatatgcta ttgaattagg    60
gttagtctgg atagtatata ctactacccg ggaagcatat gctacccgtt tagggttcac   120
cggtgatgcc ggccacgatg cgtccggcgt agaggatcta atgtgagtta gctcactcat   180
taggcacccc aggctttaca ctttatgctt ccggctcgta tgttgtgtgg aattgtgagc   240
ggataacaat ttcacacagg aaacagctat gaccatgatt acgccaagcg cgcaattaac   300
cctcactaaa gggaacaaaa gctggagctg caagcttaat gtagtcttat gcaatactct   360
tgtagtcttg caacatggta acgatgagtt agcaacatgc cttacaagga gagaaaaagc   420
accgtgcatg ccgattggtg gaagtaaggt ggtacgatcg tgccttatta ggaaggcaac   480
agacgggtct gacatggatt ggacgaacca ctgaattgcc gcattgcaga gatattgtat   540
ttaagtgcct agctcgatac ataaacgggt ctctctggtt agaccagatc tgagcctggg   600
agctctctgg ctaactaggg aacccactgc ttaagcctca ataaagcttg ccttgagtgc   660
ttcaagtagt gtgtgcccgt ctgttgtgtg actctggtaa ctagagatcc ctcagaccct   720
tttagtcagt gtggaaaatc tctagcagtg gcgcccgaac agggacttga aagcgaaagg   780
gaaaccagag gagctctctc gacgcaggac tcggcttgct gaagcgcgca cggcaagagg   840
cgaggggcgg cgactggtga gtacgccaaa aattttgact agcggaggct agaaggagag   900
agatgggtgc gagagcgtca gtattaagcg ggggagaatt agatcgcgat gggaaaaaat   960
tcggttaagg ccaggggaa agaaaaaata taaattaaaa catatagtat gggcaagcag  1020
ggagctagaa cgattcgcag ttaatcctgg cctgttagaa acatcagaag gctgtagaca  1080
aatactggga cagctacaac catcccttca gacaggatca gaagaactta gatcattata  1140
taatacagta gcaaccctct attgtgtgca tcaaggata gagataaaag acaccaagga  1200
agctttagac aagataagg aagagcaaaa caaaagtaag accaccgcac agcaagcggc  1260
cgctgatctt cagacctgga ggaggagata tgagggacaa ttggagaagt gaattatata  1320
aatataaagt agtaaaaatt gaaccattag gagtagcacc caccaaggca agagaagag  1380
tggtgcagag agaaaaaaga gcagtgggaa taggagcttt gttccttggg ttcttgggag  1440
cagcaggaag cactatgggc gcagcgtcaa tgacgctgac ggtacaggcc agacaattat  1500
tgtctggtat agtgcagcag cagaacaatt tgctgagggc tattgaggcg caacagcatc  1560
tgttgcaact cacagtctgg ggcatcaagc agctccaggc aagaatcctg gctgtggaaa  1620
gatacctaaa ggatcaacag ctcctgggga tttggggttg ctctggaaaa ctcatttgca  1680
ccactgctgt gccttggaat gctagttgga gtaataaatc tctggaacag atttggaatc  1740
acacgacctg gatggagtgg gacagagaaa ttaacaatta cacaagctta atacactcct  1800
taattgaaga atcgcaaaac cagcaagaaa agaatgaaca agaattattg gaattagata  1860
aatgggcaag tttgtggaat tggtttaaca aacaaattg gctgtggtat ataaaattat  1920
tcataatgat agtaggaggc ttggtaggtt taagaatagt ttttgctgta ctttctatag  1980
tgaatagagt taggcaggga tattcaccat tatcgtttca gacccacctc ccaaccccga  2040
ggggacccga caggcccgaa ggaatagaag aagaggtgg agagagagac agagacagat  2100
ccattcgatt agtgaacgga tctcgacggt atcggtttta aagaaaagg ggggattggg  2160
gggtacagtg caggggaaag aatagtagac ataatagcaa cagacataca aactaaagaa  2220
ttacaaaaac aaattacaaa aattcaaaat tttatcgatt ttatttagtc tccagaaaaa  2280
```

```
gggggaatg aaagacccca cctgtaggtt tggcaagcta gcttaagtaa cgccattttg      2340
caaggcatgg aaaatacata actgagaata gagaagttca gatcaaggtt aggaacagag      2400
agacagcaga atatgggcca acaggatat ctgtggtaag cagttcctgc cccggctcag      2460
ggccaagaac agatggtccc cagatgcggt cccgccctca gcagtttcta gagaaccatc      2520
agatgtttcc agggtgcccc aaggacctga aatgaccctg tgccttattt gaactaacca      2580
atcagttcgc ttctcgcttc tgttcgcgcg cttctgctcc ccgagctcaa taaaagagcc      2640
cacaacccct cactcggcgc gccagtcctc cgatagactg cgtcgcccgg gtaccgatat      2700
cacaagtttg tacaaaaaag ctgaacgaga acgtaaaat gatataaata tcaatatatt      2760
aaattagatt ttgcataaaa aacagactac ataatactgt aaaacacaac atatccagtc      2820
actatggcgg ccgcattagg cacccccaggc tttacacttt atgcttccgg ctcgtataat      2880
gtgtggattt tgagttagga tccgtcgaga ttttcaggag ctaaggaagc taaaatggag      2940
aaaaaaatca ctggatatac caccgttgat atatcccaat ggcatcgtaa agaacatttt      3000
gaggcatttc agtcagttgc tcaatgtacc tataaccaga ccgttcagct ggatattacg      3060
gcctttttaa agaccgtaaa gaaaaataag cacaagtttt atccggcctt tattcacatt      3120
cttgcccgcc tgatgaatgc tcatccggaa ttccgtatgg caatgaaaga cggtgagctg      3180
gtgatatggg atagtgttca cccttgttac accgttttcc atgagcaaac tgaaacgttt      3240
tcatcgctct ggagtgaata ccacgacgat ttccggcagt ttctacacat atattcgcaa      3300
gatgtggcgt gttacggtga aaacctggcc tatttcccta aagggtttat tgagaatatg      3360
tttttcgtct cagccaatcc ctgggtgagt ttcaccagtt ttgatttaaa cgtggccaat      3420
atggacaact tcttcgcccc cgttttcacc atgggcaaat attatacgca aggcgacaag      3480
gtgctgatgc cgctggcgat tcaggttcat catgccgttt gtgatggctt ccatgtcggc      3540
agaatgctta atgaattaca acagtactgc gatgagtggc agggcggggc gtaaatggat      3600
ccggcttact aaaagccaga taacagtatg cgtatttgcg cgctgatttt tgcggtataa      3660
gaatatatac tgatatgtat acccgaagta tgtcaaaaag aggtatgcta tgaagcagcg      3720
tattacagtg acagttgaca gcgacagcta tcagttgctc aaggcatata tgatgtcaat      3780
atctccggtc tggtaagcac aaccatgcag aatgaagccc gtcgtctgcg tgccgaacgc      3840
tggaaagcgg aaaatcagga agggatggct gaggtcgccc ggtttattga atgaacggc      3900 tcttttgctg acgagaacag gggctggtga atgcagtttt aaggtttaca cctataaaag      3960
agagagccgt tatcgtctgt tgtggatgt acagagtgat attattgaca cgcccgggcg      4020
acggatggtg atcccctgg ccagtgcacg tctgctgtca gataaagtct cccgtgaact      4080
ttacccggtg gtgcatatcg gggatgaaag ctggcgcatg atgaccaccg atatggccag      4140
tgtgccggtc tccgttatcg gggaagaagt ggctgatctc agccaccgcg aaaatgacat      4200
caaaaacgcc attaacctga tgttctgggg aatataaatg tcaggctccc ttatacacag      4260
ccagtctgca ggtcgaccat agtgactgga tatgttgtgt tttacagtat tatgtagtct      4320
gttttttatg caaaatctaa tttaatatat tgatatttat atcattttac gtttctcgtt      4380
cagctttctt gtacaaagtg gtgattcgag ttaattaagt taacgaattc ccccctctc      4440 cctcccccc cctaacgtt actggccgaa gccgcttgga ataaggccgg tgtgcgtttg      4500
tctatatgtt attttccacc atattgccgt cttttggcaa tgtgagggcc cggaaacctg      4560
gccctgtctt cttgacgagc attcctaggg gtctttcccc tctcgccaaa ggaatgcaag      4620
gtctgttgaa tgtcgtgaag gaagcagttc ctctggaagc ttcttgaaga caaacaacgt      4680
```

```
ctgtagcgac cctttgcagg cagcggaacc ccccacctgg cgacaggtgc ctctgcggcc    4740
aaaagccacg tgtataagat acacctgcaa aggcggcaca accccagtgc cacgttgtga    4800
gttggatagt tgtggaaaga gtcaaatggc tctcctcaag cgtattcaac aaggggctga    4860
aggatgccca gaaggtaccc cattgtatgg gatctgatct ggggcctcgg tgcacatgct    4920
ttacatgtgt ttagtcgagg ttaaaaaacg tctaggcccc ccgaaccacg gggacgtggt    4980
tttcctttga aaaacacgat gataatatgg ccacaaccat gggaggcgga agcggcggag    5040
gctcccctcg aggcaccatg gtgagcaagg gcgaggagct gttcaccggg gtggtgccca    5100
tcctggtcga gctggacggc gacgtaaacg gccacaagtt cagcgtgtcc ggcgagggcg    5160
agggcgatgc cacctacggc aagctgaccc tgaagttcat ctgcaccacc ggcaagctgc    5220
ccgtgccctg gcccaccctc gtgaccaccc tgacctacgg cgtgcagtgc ttcagccgct    5280
accccgacca catgaagcag cacgacttct tcaagtccgc catgcccgaa ggctacgtcc    5340
aggagcgcac catcttcttc aaggacgacg gcaactacaa gacccgcgcc gaggtgaagt    5400
tcgagggcga caccctggtg aaccgcatcg agctgaaggg catcgacttc aaggaggacg    5460
gcaacatcct ggggcacaag ctggagtaca actacaacag ccacaacgtc tatatcatgg    5520
ccgacaagca gaagaacggc atcaaggtga acttcaagat ccgccacaac atcgaggacg    5580
gcagcgtgca gctcgccgac cactaccagc agaacacccc catcggcgac ggccccgtgc    5640
tgctgcccga caaccactac ctgagcaccc agtccgccct gagcaaagac cccaacgaga    5700
agcgcgatca catggtcctg ctggagttcg tgaccgccgc cgggatcact ctcggcatgg    5760
acgagctgta caagtaacgc gtcccgggtc tagagctagc ggtaccatgc attacgtagt    5820
cgacgactta attaagctag cctagtgcca tttgttcagt ggttcgtagg ctttccccc    5880
actgtttggc tttcagttat atggatgatg tggtattggg ggccaagtct gtacagcatc    5940
ttgagtccct ttttaccgct gttaccaatt ttcttttgtc tttgggtata catttaaacc    6000
ctaacaaaac aaagagatgg ggttactctc taaattttat gggttatgtc attggatgtt    6060
atgggtcctt gccacaagaa cacatcatac aaaaaatcaa agaatgtttt agaaaacttc    6120
ctattaacag gcctattgat tggaaagtat gtcaacgaat gtgggtcttt tgggttttg    6180
ctgccccttt tacacaatgt ggttatcctg cgttgatgcc tttgtatgca tgtattcaat    6240
ctaagcaggc tttcactttc tcgccaactt acaaggcctt tctgtgtaaa caatacctga    6300
acctttaccc cgttgcccgg caacggccag gtctgtgcca agtgtttgct gacgcaaccc    6360
ccactggctg gggcttggtc atgggccatc agcgcatgcg tggaaccttt tcggctcctc    6420
tgccgatcca tactgcggaa ctcctagccg cttgttttgc tcgcagcagg tctggagcaa    6480
acattatcgg gactgataac tctgttgtcc tatcccgcaa atatacatcg tttccatggc    6540
tgctaggctg tgctgccaac tggatcctgc gcgggacgtc ctttgtttac gtcccgtcgg    6600
cgctgaatcc tgcggacgac ccttctcggg gtcgcttggg actctctcgt cccttctcc    6660
gtctgccgtt ccgaccgacc acggggcgca cctctcttta cgcggactcc ccgtctgtgc    6720
cttctcatct gccggaccgt gtgcacttcg cttcacctct gcacgtcgca tggagaccac    6780
cgtgaacgcc caccaaatat tgcccaaggt cttacataag aggactcttg gactctcagc    6840
aatgtcaacg accgaccttg aggcatactt caaagactgt ttgtttaaag actgggagga    6900
gttggggggag gagattaggt taaaggtctt tgtactagga ggctgtaggc ataaattggt    6960
ctgcgcacca gcaccatggc gcaatcacta gagcgggta cctttaagac caatgactta    7020
```

```
caaggcagct gtagatctta gccactttt  aaaagaaaag ggggactgg  aagggctaat   7080
tcactcccaa cgaagacaag atctgctttt tgcttgtact gggtctctct ggttagacca   7140
gatctgagcc tgggagctct ctggctaact agggaaccca ctgcttaagc ctcaataaag   7200
cttgccttga gtgcttcaag tagtgtgtgc ccgtctgttg tgtgactctg gtaactagag   7260
atccctcaga ccctttagt  cagtgtggaa aatctctagc agtagtagtt catgtcatct   7320
tattattcag tatttataac ttgcaaagaa atgaatatca gagagtgaga ggaacttgtt   7380
tattgcagct tataatggtt acaaataaag caatagcatc acaaatttca caaataaagc   7440
atttttttca ctgcattcta gttgtggttt gtccaaactc atcaatgtat cttatcatgt   7500
ctggctctag ctatcccgcc cctaactccg cccatcccgc cctaactcc  gcccagttcc   7560
gcccattctc cgccccatgg ctgactaatt ttttttattt atgcagaggc cgaggccgga   7620
tcccttgagt ggctttcatc ctggagcaga cttttgcagtc tgtggactgc aacacaacat   7680
tgcctttatg tgtaactctt ggctgaagct cttacaccaa tgctggggga catgtacctc   7740
ccaggggccc aggaagacta cgggaggcta caccaacgtc aatcagaggg gcctgtgtag   7800
ctaccgataa gcggaccctc aagagggcat tagcaatagt gtttataagg ccccccttgtt  7860
aattcttgaa gacgaaaggg cctcgtgata cgcctattt  tataggttaa tgtcatgata   7920
ataatggttt cttagacgtc aggtggcact tttcggggaa atgtgcgcgg aaccccctatt  7980
tgtttatttt tctaaataca ttcaaatatg tatccgctca tgagacaata accctgataa   8040
atgcttcaat aatattgaaa aggaagagt  atgagtattc aacatttccg tgtcgccctt   8100
attccctttt ttgcggcatt ttgccttcct gttttttgctc acccagaaac gctggtgaaa   8160
gtaaaagatg ctgaagatca gttgggtgca cgagtgggtt acatcgaact ggatctcaac   8220
agcggtaaga tccttgagag ttttcgcccc gaagaacgtt ttccaatgat gagcactttt   8280
aaagttctgc tatgtggcgc ggtattatcc cgtgttgacg ccgggcaaga gcaactcggt   8340
cgccgcatac actattctca gaatgacttg gttgagtact caccagtcac agaaaagcat   8400
cttacggatg gcatgacagt aagagaatta tgcagtgctg ccataaccat gagtgataac   8460
actgcggcca acttacttct gacaacgatc ggaggaccga aggagctaac cgcttttttg   8520
cacaacatgg gggatcatgt aactcgcctt gatcgttggg aaccggagct gaatgaagcc   8580
ataccaaacg acgagcgtga caccacgatg cctgcagcaa tggcaacaac gttgcgcaaa   8640
ctattaactg gcgaactact tactctagct tcccggcaac aattaataga ctggatggag   8700
gcggataaag ttgcaggacc acttctgcgc tcggcccttc cggctggctg gtttattgct   8760
gataaatctg gagccggtga gcgtgggtct cgcggtatca ttgcagcact ggggccagat   8820
ggtaagccct cccgtatcgt agttatctac acgacgggga gtcaggcaac tatggatgaa   8880
cgaaatagac agatcgctga gataggtgcc tcactgatta agcattggta actgtcagac   8940
caagtttact catatatact ttagattgat ttaaaacttc attttaatt  taaaaggatc   9000
taggtgaaga tcctttttga taatctcatg accaaaatcc cttaacgtga gttttcgttc   9060
cactgagcgt cagaccccgt agaaaagatc aaaggatctt cttgagatcc ttttttctg   9120
cgcgtaatct gctgcttgca acaaaaaaa  ccaccgctac cagcggtggt ttgtttgccg   9180
gatcaagagc taccaactct ttttccgaag gtaactggct tcagcagagc gcagatacca   9240
aatactgtcc ttctagtgta gccgtagtta ggccaccact tcaagaactc tgtagcaccg   9300
cctacatacc tcgctctgct aatcctgtta ccagtggctg ctgccagtgg cgataagtcg   9360
tgtcttaccg ggttggactc aagacgatag ttaccggata aggcgcagcg gtcgggctga   9420
```

| | |
|---|---|
| acgggggtt cgtgcacaca gcccagcttg gagcgaacga cctacaccga actgagatac | 9480 |
| ctacagcgtg agcattgaga aagcgccacg cttcccgaag ggagaaaggc ggacaggtat | 9540 |
| ccggtaagcg gcagggtcgg aacaggagag cgcacgaggg agcttccagg gggaaacgcc | 9600 |
| tggtatcttt atagtcctgt cgggtttcgc cacctctgac ttgagcgtcg attttttgtga | 9660 |
| tgctcgtcag gggggcggag cctatggaaa aacgccagca acgcggcctt tttacggttc | 9720 |
| ctggccttt gctggccttt ttgaagctgt ccctgatggt cgtcatctac ctgcctggac | 9780 |
| agcatggcct gcaacgcggg catcccgatg ccgccggaag cgagaagaat cataatgggg | 9840 |
| aaggccatcc agcctcgcgt cg | 9862 |

<210> SEQ ID NO 32
<211> LENGTH: 3334
<212> TYPE: DNA
<213> ORGANISM: Artificial Sequence
<220> FEATURE:
<223> OTHER INFORMATION: donor vector 1, pMK 7c12 anti mFC scFV CoOp
    ECORV SacII L1R5

<400> SEQUENCE: 32

| | |
|---|---|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattgaagg aaggccgtca | 360 |
| aggccgcata ataatgatt ttattttgac tgatagtgac ctgttcgttg caacaaattg | 420 |
| atgagcaatg cttttttata atgccaactt tgtacaaaaa agctgaacga tatcgccacc | 480 |
| atgggcagca cagccattct ggccctgctg ctggcagtgc tgcagggcgt gtcagctcag | 540 |
| gtgcagctgg tgcagtctgg cggcggactc gtgaaacctg gcggcagcct gagactgagc | 600 |
| tgtgccgcca gcggcttcaa cttcaacgac cagtacatga gctggatccg gcaggccct | 660 |
| ggcaagggac tggaatgggt gtccttcatc agcggcagcg gcggcaccac ctactacacc | 720 |
| gatagcgtga agggccggtt caccatcagc cgggacaaca ccaaggacag cctgtacctg | 780 |
| cagatgaaca gcctgaccgt ggaagatacc gccgtgtact actgcgccag aggcggcaat | 840 |
| tactacacca gcgtgggcag aggcacccct gtgacagtgt ctgctggcgg aggcggatca | 900 |
| ggcggcggag gatcaggggg aggcggaagc ggagcacccg atatccagat gacacagagc | 960 |
| cccggcaccc tgtctctgag ccctggcgaa agagccatcc tgagctgcag agccagccag | 1020 |
| agcgtgtccg gatacctggc ttggtatcag cagaagcccg gccaggcccc cagactgctg | 1080 |
| atctatggcg ccagcagcag agccacaggc atccccgata gattcagcgg ctctggcagc | 1140 |
| ggcaccgact tcaccctgac aatcagctcc ctgcggcccg aggacatcgg cacctactat | 1200 |
| tgcaagcagt acatcaacgc ccccttcacc ttcggcggag gcaccaaggt ggaaatcaag | 1260 |
| ccgcgggcca actttgtata caaaagtgga acgagaaacg taaatgata taaatatcaa | 1320 |
| tatattaaat tagattttgc ataaaaaaca gactacataa tactgtaaaa cacaacatat | 1380 |
| ccagtcacta tgaatcaact acttagatgg tattagtgac ctgtactggg cctcatgggc | 1440 |
| cttcctttca ctgcccgctt tccagtcggg aaacctgtcg tgccagctgc attaacatgg | 1500 |
| tcatagctgt ttccttgcgt attgggcgct ctccgcttcc tcgctcactg actcgctgcg | 1560 |

```
ctcggtcgtt cgggtaaagc ctggggtgcc taatgagcaa aaggccagca aaaggccagg    1620
aaccgtaaaa aggccgcgtt gctggcgttt ttccataggc tccgcccccc tgacgagcat    1680
cacaaaaatc gacgctcaag tcagaggtgg cgaaacccga caggactata aagataccag    1740
gcgtttcccc ctggaagctc cctcgtgcgc tctcctgttc cgaccctgcc gcttaccgga    1800
tacctgtccg cctttctccc ttcgggaagc gtggcgcttt ctcatagctc acgctgtagg    1860
tatctcagtt cggtgtaggt cgttcgctcc aagctgggct gtgtgcacga accccccgtt    1920
cagcccgacc gctgcgcctt atccggtaac tatcgtcttg agtccaaccc ggtaagacac    1980
gacttatcgc cactggcagc agccactggt aacaggatta gcagagcgag gtatgtaggc    2040
ggtgctacag agttcttgaa gtggtggcct aactacggct acactagaag aacagtattt    2100
ggtatctgcg ctctgctgaa gccagttacc ttcggaaaaa gagttggtag ctcttgatcc    2160
ggcaaacaaa ccaccgctgg tagcggtggt ttttttgttt gcaagcagca gattacgcgc    2220
agaaaaaaag gatctcaaga agatcctttg atcttttcta cggggtctga cgctcagtgg    2280
aacgaaaact cacgttaagg gattttggtc atgagattat caaaaaggat cttcacctag    2340
atccttttaa attaaaaatg aagttttaaa tcaatctaaa gtatatatga gtaaacttgg    2400
tctgacagtt attagaaaaa ttcatccagc agacgataaa acgcaatacg ctggctatcc    2460
ggtgccgcaa tgccatacag caccagaaaa cgatccgccc attcgccgcc cagttcttcc    2520
gcaatatcac gggtggccag cgcaatatcc tgataacgat ccgccacgcc cagacggccg    2580
caatcaataa agccgctaaa acggccattt ccaccataa tgttcggcag gcacgcatca    2640
ccatgggtca ccaccagatc ttcgccatcc ggcatgctcg ctttcagacg cgcaaacagc    2700
tctgccggtg ccaggccctg atgttcttca tccagatcat cctgatccac caggcccgct    2760
tccatacggg tacgcgcacg ttcaatacga tgtttcgcct gatgatcaaa cggacaggtc    2820
gccgggtcca gggtatgcag acgacgcatg gcatccgcca taatgctcac tttttctgcc    2880
ggcgccagat ggctagacag cagatcctga cccggcactt cgcccagcag cagccaatca    2940
cggcccgctt cggtcaccac atccagcacc gccgcacacg gaacaccggt ggtggccagc    3000
cagctcagac gcgccgcttc atcctgcagc tcgttcagcg caccgctcag atcggttttc    3060
acaaacagca ccggacgacc ctgcgcgctc agacgaaaca ccgccgcatc agagcagcca    3120
atggtctgct gcgcccaatc atagccaaac agacgttcca cccacgctgc cgggctaccc    3180
gcatgcaggc catcctgttc aatcatactc ttccttttc aatattattg aagcatttat    3240
cagggttatt gtctcatgag cggatacata tttgaatgta tttagaaaaa taaacaaata    3300
ggggttccgc gcacatttcc ccgaaaagtg ccac                                3334
```

<210> SEQ ID NO 33
<211> LENGTH: 2779
<212> TYPE: DNA
<213> ORGANISM: Artificial Sequence
<220> FEATURE:
<223> OTHER INFORMATION: donor vector 2, pMK hCD8a scaffold TN L5 L2

<400> SEQUENCE: 33

```
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
```

```
gctgcaaggc gattaagttg ggtaacgcca gggttttccc agtcacgacg ttgtaaaacg    300
acggccagtg agcgcgacgt aatacgactc actatagggc gaattgaagg aaggccgtca    360
aggccgcata aataatgatt ttattttgac tgatagtgac ctgttcgttg caacaaattg    420
atgagcaatg cttttttata atgcccaact ttgtatacaa aagtggcccg cggacaacaa    480
cccctgcccc cagacctcct accccagccc ctacaattgc cagccagcct ctgagcctga    540
ggcccgaggc ttgtagacct gctgctggcg gagccgtgca caccgaggga ctggatttcg    600
cctgcgacat ctacatctgg gcccctctgg ccggcacatg tggcgtgctg ctgctgagcc    660
tcgtgatcac cctgtactgc ggctccacca gcggctccgg caagcccggc tctggcgagg    720
gctccaccag cggcgactac aaggacgacg atgacaagta ataggatatc ggttcagctt    780
tcttgtacaa agttggcatt ataagaaagc attgcttatc aatttgttgc aacgaacagg    840
tcactatcag tcaaaataaa atcattattt ctgggcctca tgggccttcc tttcactgcc    900
cgcttttccag tcgggaaacc tgtcgtgcca gctgcattaa catggtcata gctgtttcct    960
tgcgtattgg gcgctctccg cttcctcgct cactgactcg ctgcgctcgg tcgttcgggt   1020
aaagcctggg gtgcctaatg agcaaaaggc cagcaaaagg ccaggaaccg taaaaaggcc   1080
gcgttgctgg cgttttttcca taggctccgc ccccctgacg agcatcacaa aaatcgacgc   1140
tcaagtcaga ggtggcgaaa cccgacagga ctataaagat accaggcgtt ccccctggaa   1200
agctccctcg tgcgctctcc tgttccgacc ctgccgctta ccggatacct gtccgccttt   1260
ctcccttcgg gaagcgtggc gctttctcat agctcacgct gtaggtatct cagttcggtg   1320
taggtcgttc gctccaagct gggctgtgtg cacgaacccc ccgttcagcc cgaccgctgc   1380
gccttatccg gtaactatcg tcttgagtcc aacccggtaa gacacgactt atcgccactg   1440
gcagcagcca ctggtaacag gattagcaga gcgaggtatg taggcggtgc tacagagttc   1500
ttgaagtggt ggcctaacta cggctacact agaagaacag tatttggtat ctgcgctctg   1560
ctgaagccag ttaccttcgg aaaaagagtt ggtagctctt gatccggcaa acaaaccacc   1620
gctggtagcg gtggtttttt tgtttgcaag cagcagatta cgcgcagaaa aaaggatct    1680
caagaagatc ctttgatctt ttctacgggg tctgacgctc agtggaacga aaactcacgt   1740
taagggattt tggtcatgag attatcaaaa aggatcttca cctagatcct tttaaattaa   1800
aaatgaagtt ttaaatcaat ctaaagtata tatgagtaaa cttggtctga cagttattag   1860
aaaaattcat ccagcagacg ataaaacgca atacgctggc tatccggtgc cgcaatgcca   1920
tacagcacca gaaaacgatc cgcccattcg ccgcccagtt cttccgcaat atcacgggtg   1980
gccagcgcaa tatcctgata acgatccgcc acgcccagac ggccgcaatc aataaagccg   2040
ctaaaacggc cattttccac cataatgttc ggcaggcacg catcaccatg gtcaccacc    2100
agatcttcgc catccggcat gctcgctttc agacgcgcaa acagctctgc cggtgccagg   2160
ccctgatgtt cttcatccag atcatcctga tccaccaggc ccgcttccat acgggtacgc   2220
gcacgttcaa tacgatgttt cgcctgatga tcaaacggac aggtcgccgg gtccagggta   2280
tgcagacgac gcatggcatc cgccataatg ctcacttttt ctgccggcgc cagatggcta   2340
gacagcagat cctgacccgg cacttcgccc agcagcagcc aatcacgccc gcttcggtc    2400
accacatcca gcaccgccgc acacggaaca ccggtggtgg ccagccagct cagacgcgcc   2460
gcttcatcct gcagctcgtt cagcgcaccg ctcagatcgg ttttcacaaa cagcaccgga   2520
cgaccctgcg cgctcagacg aaacaccgcc gcatcagagc agccaatggt ctgctgcgcc   2580
caatcatagc caaacagacg ttccacccac gctgccgggc tacccgcatg caggccatcc   2640
```

```
tgttcaatca tactcttcct ttttcaatat tattgaagca tttatcaggg ttattgtctc      2700
atgagcggat acatatttga atgtatttag aaaaataaac aaataggggt tccgcgcaca      2760
tttccccgaa aagtgccac                                                  2779
```

<210> SEQ ID NO 34
<211> LENGTH: 9338
<212> TYPE: DNA
<213> ORGANISM: Artificial Sequence
<220> FEATURE:
<223> OTHER INFORMATION: Final vector used for lentiviral production,
      pLV4301G 7C12 scFV mIgG hCD8 flag

<400> SEQUENCE: 34

```
cgataaccct aattcgatag catatgcttc ccgttgggta acatatgcta ttgaattagg        60
gttagtctgg atagtatata ctactacccg ggaagcatat gctacccgtt tagggttcac       120
cggtgatgcc ggccacgatg cgtccggcgt agaggatcta atgtgagtta gctcactcat       180
taggcacccc aggctttaca ctttatgctt ccggctcgta tgttgtgtgg aattgtgagc       240
ggataacaat ttcacacagg aaacagctat gaccatgatt acgccaagcg cgcaattaac       300
cctcactaaa gggaacaaaa gctggagctg caagcttaat gtagtcttat gcaatactct       360
tgtagtcttg caacatggta acgatgagtt agcaacatgc cttacaagga gagaaaaagc       420
accgtgcatg ccgattggtg gaagtaaggt ggtacgatcg tgccttatta ggaaggcaac       480
agacgggtct gacatggatt ggacgaacca ctgaattgcc gcattgcaga gatattgtat       540
ttaagtgcct agctcgatac ataaacgggt ctctctggtt agaccagatc tgagcctggg       600
agctctctgg ctaactaggg aacccactgc ttaagcctca ataaagcttg ccttgagtgc       660
ttcaagtagt gtgtgcccgt ctgttgtgtg actctggtaa ctagagatcc ctcagaccct       720
tttagtcagt gtggaaaatc tctagcagtg gcgcccgaac agggacttga agcgaaagg       780 gaaaccagag gagctctctc gacgcaggac tcggcttgct gaagcgcgca cggcaagagg       840
cgaggggcgg cgactggtga gtacgccaaa aattttgact agcggaggct agaaggagag       900
agatgggtgc gagagcgtca gtattaagcg gggagaatt agatcgcgat gggaaaaaat       960
tcggttaagg ccagggggaa agaaaaaata taaattaaaa catatagtat gggcaagcag      1020
ggagctagaa cgattcgcag ttaatcctgg cctgttagaa acatcagaag gctgtagaca      1080
aatactggga cagctacaac catcccttca gacaggatca agaaaactta gatcattata      1140
taatacagta gcaaccctct attgtgtgca tcaaaggata gagataaaag acaccaagga      1200
agctttagac aagatagagg aagagcaaaa caaaagtaag accaccgcac agcaagcggc      1260
cgctgatctt cagacctgga ggaggagata tgagggacaa ttggagaagt gaattatata      1320
aatataaagt agtaaaaatt gaaccattag gagtagcacc caccaaggca agagaagag      1380 tggtgcagag agaaaaaaga gcagtgggaa taggagcttt gttccttggg ttcttgggag      1440
cagcaggaag cactatgggc gcagcgtcaa tgacgctgac ggtacaggcc agacaattat      1500
tgtctggtat agtgcagcag cagaacaatt tgctgagggc tattgaggcg caacagcatc      1560
tgttgcaact cacagtctgg ggcatcaagc agctccaggc aagaatcctg gctgtggaaa      1620
gataccctaa ggatcaacag ctcctgggga tttggggttg ctctggaaaa ctcatttgca      1680
ccactgctgt gccttggaat gctagttgga gtaataaatc tctggaacag atttggaatc      1740
acacgacctg gatggagtgg gacagagaaa ttaacaatta cacaagctta atacactcct      1800
taattgaaga atcgcaaaac cagcaagaaa agaatgaaca agaattattg gaattagata      1860
```

-continued

```
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc ccaaccccga    2040
ggggacccga caggcccgaa ggaatagaag aagaaggtgg agagagagac agagacagat    2100
ccattcgatt agtgaacgga tctcgacggt atcggtttta aaagaaaagg ggggattggg    2160
gggtacagtg caggggaaag aatagtagac ataatagcaa cagacataca aactaaagaa    2220
ttacaaaaac aaattacaaa aattcaaaat tttatcgatt ttatttagtc tccagaaaaa    2280
ggggggaatg aaagacccca cctgtaggtt tggcaagcta gcttaagtaa cgccattttg    2340
caaggcatgg aaaatacata actgagaata gagaagttca gatcaaggtt aggaacagag    2400
agacagcaga atatgggcca aacaggatat ctgtggtaag cagttcctgc cccggctcag    2460
ggccaagaac agatggtccc cagatgcggt cccgccctca gcagtttcta gagaaccatc    2520
agatgtttcc agggtgcccc aaggacctga aatgaccctg tgccttattt gaactaacca    2580
atcagttcgc ttctcgcttc tgttcgcgcg cttctgctcc ccgagctcaa taaaagagcc    2640
cacaacccct cactcggcgc gccagtcctc cgatagactg cgtcgcccgg gtaccgatat    2700
caccaacttt gtacaaaaaa gctgaacgat atcgccacca tgggcagcac agccattctg    2760
gccctgctgc tggcagtgct gcagggcgtg tcagctcagg tgcagctggt gcagtctggc    2820
ggcggactcg tgaaacctgg cggcagcctg agactgagct gtgccgccag cggcttcaac    2880
ttcaacgacc agtacatgag ctggatccgg caggcccctg gcaagggact ggaatgggtg    2940
tccttcatca gcggcagcgg cggcaccacc tactacaccg atagcgtgaa gggccggttc    3000
accatcagcc gggacaacac caaggacagc ctgtacctgc agatgaacag cctgaccgtg    3060
gaagataccg ccgtgtacta ctgcgccaga ggcggcaatt actacaccag cgtgggcaga    3120
ggcaccctcg tgacagtgtc tgctggcgga ggcggatcag gcggcggagg atcagggga    3180
ggcggaagcg gagcacccga tatccagatg acacagagcc ccggcaccct gtctctgagc    3240
cctggcgaaa gagccatcct gagctgcaga gccagccaga gcgtgtccgg ataccctggct    3300
tggtatcagc agaagcccgg ccaggccccc agactgctga tctatggcgc cagcagcaga    3360
gccacaggca tccccgatag attcagcggc tctggcagcg gcaccgactt caccctgaca    3420
atcagctccc tgcggcccga ggacatcggc acctactatt gcaagcagta catcaacgcc    3480
cccttcaccc tcggcggagg caccaaggtg gaaatcaagc gcgggccaa ctttgtatac    3540
aaaagtggcc cgcggacaac aaccccctgcc cccagacctc ctaccccagc ccctacaatt    3600
gccagccagc ctctgagcct gaggcccgag gcttgtagac ctgctgctgg cggagccgtg    3660
cacaccagag gactggattt cgcctgcgac atctacatct gggcccctct ggccggcaca    3720
tgtggcgtgc tgctgctgag cctcgtgatc accctgtact gcggctccac cagcggctcc    3780
ggcaagcccg gctctggcga gggctccacc agcggcgact acaaggacga cgatgacaag    3840
taataggata tcggttcagc tttcttgtac aaagttggga ttcgagttaa ttaagttaac    3900
gaattccccc cctctccctc ccccccccct aacgttactg gccgaagccg cttggaataa    3960
ggccggtgtg cgtttgtcta tatgttattt tccaccatat gccgtctttt ggcaatgtg    4020
agggcccgga aacctggccc tgtcttcttg acgagcattc ctaggggtct ttcccctctc    4080
gccaaaggaa tgcaaggtct gttgaatgtc gtgaaggaag cagttcctct ggaagcttct    4140
tgaagacaaa caacgtctgt agcgaccctt tgcaggcagc ggaaccccc acctggcgac    4200
```

-continued

```
aggtgcctct gcggccaaaa gccacgtgta aagatacac ctgcaaaggc ggcacaaccc    4260
cagtgccacg ttgtgagttg gatagttgtg gaaagagtca aatggctctc ctcaagcgta    4320
ttcaacaagg ggctgaagga tgcccagaag gtaccccatt gtatgggatc tgatctgggg    4380
cctcggtgca catgctttac atgtgtttag tcgaggttaa aaaacgtcta ggccccccga    4440
accacgggga cgtggttttc cttttgaaaaa cacgatgata atatggccac aaccatggga    4500
ggcggaagcg gcggaggctc ccctcgaggc accatggtga gcaagggcga ggagctgttc    4560
accggggtgg tgcccatcct ggtcgagctg gacggcgacg taaacggcca caagttcagc    4620
gtgtccggcg agggcgaggg cgatgccacc tacggcaagc tgaccctgaa gttcatctgc    4680
accaccggca agctgcccgt gccctggccc accctcgtga ccaccctgac ctacggcgtg    4740
cagtgcttca gccgctaccc cgaccacatg aagcagcacg acttcttcaa gtccgccatg    4800
cccgaaggct acgtccagga gcgcaccatc ttcttcaagg acgacggcaa ctacaagacc    4860
cgcgccgagg tgaagttcga gggcgacacc ctggtgaacc gcatcgagct gaagggcatc    4920
gacttcaagg aggacggcaa catcctgggg cacaagctgg agtacaacta caacagccac    4980
aacgtctata tcatggccga caagcagaag aacggcatca aggtgaactt caagatccgc    5040
cacaacatcg aggacggcag cgtgcagctc gccgaccact accagcagaa cacccccatc    5100
ggcgacggcc ccgtgctgct gcccgacaac cactacctga gcacccagtc cgccctgagc    5160
aaagacccca acgagaagcg cgatcacatg gtcctgctgg agttcgtgac cgccgccggg    5220
atcactctcg gcatggacga gctgtacaag taacgcgtcc cgggtctaga gctagcggta    5280
ccatgcatta cgtagtcgac gacttaatta agctagccta gtgccatttg ttcagtggtt    5340
cgtagggctt tcccccactg tttggctttc agttatatgg atgatgtggt attggggggcc    5400
aagtctgtac agcatcttga gtccctttttt accgctgtta ccaatttttct tttgtctttg    5460
ggtatacatt taaaccctaa caaaacaaag agatggggtt actctctaaa ttttatgggt    5520
tatgtcattg gatgttatgg gtccttgcca caagaacaca tcatacaaaa aatcaaagaa    5580
tgttttagaa aacttcctat taacaggcct attgattgga aagtatgtca acgaattgtg    5640
ggtcttttgg gttttgctgc cccttttaca caatgtggtt atcctgcgtt gatgcctttg    5700
tatgcatgta ttcaatctaa gcaggctttc actttctcgc caacttacaa ggcctttctg    5760
tgtaaacaat acctgaacct ttaccccgtt gcccggcaac ggccaggtct gtgccaagtg    5820
tttgctgacg caacccccac tggctggggc ttggtcatgg gccatcagcg catgcgtgga    5880
acctttcgg ctcctctgcc gatccatact gcggaactcc tagccgcttg ttttgctcgc    5940
agcaggtctg gagcaaacat tatcgggact gataactctg ttgtcctatc ccgcaaatat    6000
acatcgtttc catggctgct aggctgtgct gccaactgga tcctgcgcgg gacgtccttt    6060
gtttacgtcc cgtcggcgct gaatcctgcg gacgacccttt ctcggggtcg cttgggactc    6120
tctcgtcccc ttctccgtct gccgttccga ccgaccacgg ggcgcacctc tctttacgcg    6180
gactcccgt ctgtgccttc tcatctgccg gaccgtgtgc acttcgcttc acctctgcac    6240
gtcgcatgga gaccaccgtg aacgcccacc aaatattgcc caaggtctta cataagagga    6300
ctcttggact ctcagcaatg tcaacgaccg accttgaggc atacttcaaa gactgtttgt    6360
ttaaagactg ggaggagttg ggggaggaga ttaggttaaa ggtctttgta ctaggaggct    6420
gtaggcataa attggtctgc gcaccagcac catggcgcaa tcactagagc ggggtacctt    6480
taagaccaat gacttacaag gcagctgtag atccttagcca ctttttaaaa gaaaaggggg    6540
gactggaagg gctaattcac tcccaacgaa gacaagatct gcttttttgct tgtactgggt    6600
```

```
ctctctggtt agaccagatc tgagcctggg agctctctgg ctaactaggg aacccactgc    6660
ttaagcctca ataaagcttg ccttgagtgc ttcaagtagt gtgtgcccgt ctgttgtgtg    6720
actctggtaa ctagagatcc ctcagaccct tttagtcagt gtggaaaatc tctagcagta    6780
gtagttcatg tcatcttatt attcagtatt tataacttgc aaagaaatga atatcagaga    6840
gtgagaggaa cttgtttatt gcagcttata atggttacaa ataaagcaat agcatcacaa    6900
atttcacaaa taaagcattt ttttcactgc attctagttg tggtttgtcc aaactcatca    6960
atgtatctta tcatgtctgg ctctagctat cccgccccta actccgccca tcccgcccct    7020
aactccgccc agttccgccc attctccgcc ccatggctga ctaattttt tttatttatgc    7080 agaggccgag gccggatccc ttgagtggct ttcatcctgg agcagacttt gcagtctgtg    7140
gactgcaaca caacattgcc tttatgtgta actcttggct gaagctctta caccaatgct    7200
gggggacatg tacctcccag gggcccagga agactacggg aggctacacc aacgtcaatc    7260
agaggggcct gtgtagctac cgataagcgg accctcaaga gggcattagc aatagtgttt    7320
ataaggcccc cttgttaatt cttgaagacg aaagggcctc gtgatacgcc tatttttata    7380
ggttaatgtc atgataataa tggtttctta gacgtcaggt ggcactttc ggggaaatgt    7440 gcgcggaacc cctatttgtt tatttttcta aatacattca aatatgtatc cgctcatgag    7500
acaataaccc tgataaatgc ttcaataata ttgaaaaagg aagagtatga gtattcaaca    7560
tttccgtgtc gcccttattc cctttttgc ggcattttgc cttcctgttt ttgctcaccc    7620
agaaacgctg gtgaaagtaa aagatgctga agatcagttg ggtgcacgag tgggttacat    7680
cgaactggat ctcaacagcg gtaagatcct tgagagtttt cgccccgaag aacgttttcc    7740
aatgatgagc acttttaaag ttctgctatg tggcgcggta ttatcccgtg ttgacgccgg    7800
gcaagagcaa ctcggtcgcc gcatacacta ttctcagaat gacttggttg agtactcacc    7860
agtcacagaa aagcatctta cggatggcat gacagtaaga gaattatgca gtgctgccat    7920
aaccatgagt gataacactg cggccaactt acttctgaca acgatcggag gaccgaagga    7980
gctaaccgct tttttgcaca acatggggga tcatgtaact cgccttgatc gttgggaacc    8040
ggagctgaat gaagccatac caaacgacga gcgtgacacc acgatgcctg cagcaatggc    8100
aacaacgttg cgcaaactat taactggcga actacttact ctagcttccc ggcaacaatt    8160
aatagactgg atggaggcgg ataaagttgc aggaccactt ctgcgctcgg cccttccggc    8220
tggctggttt attgctgata aatctggagc cggtgagcgt gggtctcgcg gtatcattgc    8280
agcactgggg ccagatggta agccctcccg tatcgtagtt atctacacga cggggagtca    8340
ggcaactatg gatgaacgaa atagacagat cgctgagata ggtgcctcac tgattaagca    8400
ttggtaactg tcagaccaag tttactcata tactttag attgatttaa aacttcattt    8460
ttaatttaaa aggatctagg tgaagatcct ttttgataat ctcatgacca aaatccctta    8520
acgtgagttt cgttccact gagcgtcaga ccccgtagaa aagatcaaag gatcttcttg    8580
agatcctttt tttctgcgcg taatctgctg cttgcaaaca aaaaaaccac cgctaccagc    8640
ggtggtttgt ttgccggatc aagagctacc aactctttt ccgaaggtaa ctggcttcag    8700
cagagcgcag ataccaaata ctgtccttct agtgtagccg tagttaggcc accacttcaa    8760
gaactctgta gcaccgccta catacctcgc tctgctaatc ctgttaccag tggctgctgc    8820
cagtggcgat aagtcgtgtc ttaccgggtt ggactcaaga cgatagttac cggataaggc    8880
gcagcggtcg ggctgaacgg ggggttcgtg cacacagccc agcttggagc gaacgaccta    8940
```

```
caccgaactg agatacctac agcgtgagca ttgagaaagc gccacgcttc ccgaagggag   9000
aaaggcggac aggtatccgg taagcggcag ggtcggaaca ggagagcgca cgagggagct   9060
tccaggggga aacgcctggt atctttatag tcctgtcggg tttcgccacc tctgacttga   9120
gcgtcgattt ttgtgatgct cgtcaggggg cggagccta tggaaaaacg ccagcaacgc    9180 ggcctttttta cggttcctgg cctttttgctg gccttttttga agctgtccct gatggtcgtc  9240
atctacctgc ctggacagca tggcctgcaa cgcgggcatc ccgatgccgc cggaagcgag   9300
aagaatcata atggggaagg ccatccagcc tcgcgtcg                            9338
```

<210> SEQ ID NO 35
<211> LENGTH: 9862
<212> TYPE: DNA
<213> ORGANISM: Artificial Sequence
<220> FEATURE:
<223> OTHER INFORMATION: destination vector, pLV4301G

<400> SEQUENCE: 35

```
cgataaccct aattcgatag catatgcttc ccgttgggta acatatgcta ttgaattagg     60
gttagtctgg atagtatata ctactacccg ggaagcatat gctaccgtt tagggttcac    120 cggtgatgcc ggccacgatg cgtccggcgt agaggatcta atgtgagtta gctcactcat   180
taggcacccc aggctttaca ctttatgctt ccggctcgta tgttgtgtgg aattgtgagc   240
ggataacaat ttcacacagg aaacagctat gaccatgatt acgccaagcg cgcaattaac   300
cctcactaaa gggaacaaaa gctggagctg caagcttaat gtagtcttat gcaatactct   360
tgtagtcttg caacatggta acgatgagtt agcaacatgc cttacaagga gagaaaaagc   420
accgtgcatg ccgattggtg gaagtaaggt ggtacgatcg tgccttatta ggaaggcaac   480
agacgggtct gacatggatt ggacgaacca ctgaattgcc gcattgcaga gatattgtat   540
ttaagtgcct agctcgatac ataaacgggt ctctctggtt agaccagatc tgagcctggg   600
agctctctgg ctaactaggg aacccactgc ttaagcctca ataaagcttg ccttgagtgc   660
ttcaagtagt gtgtgcccgt ctgttgtgtg actctggtaa ctagagatcc ctcagaccct   720
tttagtcagt gtggaaaatc tctagcagtg gcgcccgaac agggacttga aagcgaaagg   780
gaaaccagag gagctctctc gacgcaggac tcggcttgct gaagcgcgca cggcaagagg   840
cgaggggcgg cgactggtga gtacgccaaa aattttgact agcggaggct agaaggagag   900
agatgggtgc gagagcgtca gtattaagcg ggggagaatt agatcgcgat gggaaaaaat   960
tcggttaagg ccaggggga agaaaaaata taaattaaaa catatagtat gggcaagcag  1020
ggagctagaa cgattcgcag ttaatcctgg cctgttagaa acatcagaag gctgtagaca  1080
aatactggga cagctacaac catcccttca gacaggatca aagaactta gatcattata  1140 taatacagta gcaaccctct attgtgtgca tcaaaggata gagataaaag acaccaagga  1200
agctttagac aagatagagg aagagcaaaa caaaagtaag accaccgcac agcaagcggc  1260
cgctgatctt cagacctgga ggaggagata tgagggacaa ttggagaagt gaattatata  1320
aatataaagt agtaaaaatt gaaccattag gagtagcacc caccaaggca agagaagag  1380 tggtgcagag agaaaaaaga gcagtgggaa taggagcttt gttccttggg ttcttggag  1440 cagcaggaag cactatgggc gcagcgtcaa tgacgctgac ggtacaggcc agacaattat  1500
tgtctggtat agtgcagcag cagaacaatt tgctgagggc tattgaggcg caacagcatc  1560
tgttgcaact cacagtctgg ggcatcaagc agctccaggc aagaatcctg gctgtggaaa  1620 gataccctaaa ggatcaacag ctcctgggga tttggggttg ctctggaaaa ctcatttgca  1680
```

```
ccactgctgt gccttggaat gctagttgga gtaataaatc tctggaacag atttggaatc    1740
acacgacctg gatggagtgg gacagagaaa ttaacaatta cacaagctta atacactcct    1800
taattgaaga atcgcaaaac cagcaagaaa agaatgaaca agaattattg gaattagata    1860
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc caacccccga    2040
ggggacccga caggcccgaa ggaatagaag aagaaggtgg agagagagac agagacagat    2100
ccattcgatt agtgaacgga tctcgacggt atcggtttta aaagaaaagg ggggattggg    2160
gggtacagtg caggggaaag aatagtagac ataatagcaa cagacataca aactaaagaa    2220
ttacaaaaac aaattacaaa aattcaaaat tttatcgatt ttatttagtc tccagaaaaa    2280 gggggaatg aaagacccca cctgtaggtt tggcaagcta gcttaagtaa cgccattttg     2340
caaggcatgg aaaatacata actgagaata gagaagttca gatcaaggtt aggaacagag    2400
agacagcaga atatgggcca acaggatat ctgtggtaag cagttcctgc cccggctcag     2460
ggccaagaac agatggtccc cagatgcggt cccgccctca gcagtttcta gagaaccatc    2520
agatgtttcc agggtgcccc aaggacctga aatgaccctg tgccttattt gaactaacca    2580
atcagttcgc ttctcgcttc tgttcgcgcg cttctgctcc ccgagctcaa taaaagagcc    2640
cacaacccct cactcggcgc gccagtcctc cgatagactg cgtcgcccgg gtaccgatat    2700
cacaagtttg tacaaaaaag ctgaacgaga acgtaaaat gatataaata tcaatatatt    2760
aaattagatt ttgcataaaa aacagactac ataatactgt aaaacacaac atatccagtc    2820
actatggcgg ccgcattagg cacccccaggc tttacacttt atgcttccgg ctcgtataat    2880
gtgtggattt tgagttagga tccgtcgaga ttttcaggag ctaaggaagc taaaatggag    2940
aaaaaaatca ctggatatac caccgttgat atatcccaat ggcatcgtaa agaacatttt    3000
gaggcatttc agtcagttgc tcaatgtacc tataaccaga ccgttcagct ggatattacg    3060 gccttttaa agaccgtaaa gaaaaataag cacaagtttt atccggcctt tattcacatt    3120
cttgcccgcc tgatgaatgc tcatccggaa ttccgtatgg caatgaaaga cggtgagctg    3180
gtgatatggg atagtgttca cccttgttac accgttttcc atgagcaaac tgaaacgttt    3240
tcatcgctct ggagtgaata ccacgacgat ttccggcagt ttctacacat atattcgcaa    3300
gatgtggcgt gttacggtga aaacctggcc tatttcccta aagggtttat tgagaatatg    3360
tttttcgtct cagccaatcc ctgggtgagt ttcaccagtt ttgatttaaa cgtggccaat    3420
atggacaact tcttcgcccc cgttttcacc atgggcaaat attatacgca aggcgacaag    3480
gtgctgatgc cgctggcgat tcaggttcat catgccgttt gtgatggctt ccatgtcggc    3540
agaatgctta atgaattaca acagtactgc gatgagtggc agggcggggc gtaaatggat    3600
ccggcttact aaaagccaga taacagtatg cgtatttgcg cgctgatttt tgcggtataa    3660
gaatatatac tgatatgtat acccgaagta tgtcaaaaag aggtatgcta tgaagcagcg    3720
tattacagtg acagttgaca gcgacagcta tcagttgctc aaggcatata tgatgtcaat    3780
atctccggtc tggtaagcac aaccatgcag aatgaagccc gtcgtctgcg tgccgaacgc    3840
tggaaagcgg aaaatcagga agggatggct gaggtcgccc ggtttattga aatgaacggc    3900
tcttttgctg acgagaacag gggctggtga aatgcagttt aaggtttaca cctataaaag    3960
agagagccgt tatcgtctgt ttgtggatgt acagagtgat attattgaca cgcccgggcg    4020
```

```
acggatggtg atcccctgg ccagtgcacg tctgctgtca gataaagtct cccgtgaact    4080
ttacccggtg gtgcatatcg gggatgaaag ctggcgcatg atgaccaccg atatggccag   4140
tgtgccggtc tccgttatcg gggaagaagt ggctgatctc agccaccgcg aaaatgacat   4200
caaaaacgcc attaacctga tgttctgggg aatataaatg tcaggctccc ttatacacag   4260
ccagtctgca ggtcgaccat agtgactgga tatgttgtgt tttacagtat tatgtagtct   4320
gttttttatg caaaatctaa tttaatatat tgatatttat atcattttac gtttctcgtt   4380
cagctttctt gtacaaagtg gtgattcgag ttaattaagt taacgaattc ccccctctc    4440
cctccccccc ccctaacgtt actggccgaa gccgcttgga ataaggccgg tgtgcgtttg   4500
tctatatgtt attttccacc atattgccgt cttttggcaa tgtgagggcc cggaaacctg   4560
gccctgtctt cttgacgagc attcctaggg gtctttcccc tctcgccaaa ggaatgcaag   4620
gtctgttgaa tgtcgtgaag gaagcagttc ctctggaagc ttcttgaaga caaacaacgt   4680
ctgtagcgac cctttgcagg cagcggaacc cccacctgg cgacaggtgc ctctgcggcc    4740
aaaagccacg tgtataagat acacctgcaa aggcggcaca ccccagtgc cacgttgtga    4800
gttggatagt tgtggaaaga gtcaaatggc tctcctcaag cgtattcaac aaggggctga   4860
aggatgccca gaaggtaccc cattgtatgg gatctgatct ggggcctcgg tgcacatgct   4920
ttacatgtgt ttagtcgagg ttaaaaaacg tctaggcccc ccgaaccacg gggacgtggt   4980
tttcctttga aaaacacgat gataatatgg ccacaaccat gggaggcgga agcggcggag   5040
gctcccctcg aggcaccatg gtgagcaagg gcgaggagct gttcaccggg gtggtgccca   5100
tcctggtcga gctggacggc gacgtaaacg gccacaagtt cagcgtgtcc ggcgagggcg   5160
agggcgatgc cacctacggc aagctgaccc tgaagttcat ctgcaccacc ggcaagctgc   5220
ccgtgccctg gcccaccctc gtgaccaccc tgacctacgg cgtgcagtgc ttcagccgct   5280
accccgacca catgaagcag cacgacttct tcaagtccgc catgcccgaa ggctacgtcc   5340
aggagcgcac catcttcttc aaggacgacg gcaactacaa gacccgcgcc gaggtgaagt   5400
tcgagggcga caccctggtg aaccgcatcg agctgaaggg catcgacttc aaggaggacg   5460
gcaacatcct gggcacaag ctggagtaca actacaacag ccacaacgtc tatatcatgg    5520
ccgacaagca gaagaacggc atcaaggtga acttcaagat ccgccacaac atcgaggacg   5580
gcagcgtgca gctcgccgac cactaccagc agaacacccc catcggcgac ggccccgtgc   5640
tgctgcccga caaccactac ctgagcaccc agtccgccct gagcaaagac cccaacgaga   5700
agcgcgatca catggtcctg ctggagttcg tgaccgccgc cgggatcact ctcggcatgg   5760
acgagctgta caagtaacgc gtcccgggtc tagagctagc ggtaccatgc attacgtagt   5820
cgacgactta attaagctag cctagtgcca tttgttcagt ggttcgtagg gctttccccc   5880
actgtttggc tttcagttat atggatgatg tggtattggg ggccaagtct gtacagcatc   5940
ttgagtccct ttttaccgct gttaccaatt ttcttttgtc tttgggtata catttaaacc   6000
ctaacaaaac aaagagatgg ggttactctc taaattttat gggttatgtc attggatgtt   6060
atgggtcctt gccacaagaa cacatcatac aaaaaatcaa agaatgtttt agaaaacttc   6120
ctattaacag gcctattgat tggaaagtat gtcaacgaat tgtgggtctt ttgggttttg   6180
ctgccccttt tacacaatgt ggttatcctg cgttgatgcc tttgtatgca tgtattcaat   6240
ctaagcaggc tttcactttc tcgccaactt acaaggcctt tctgtgtaaa caatacctga   6300
accttacccc cgttgcccgg caacggccag gtctgtgcca agtgtttgct gacgcaaccc   6360
ccactggctg gggcttggtc atgggccatc agcgcatgcg tggaaccttt tcggctcctc   6420
```

-continued

```
tgccgatcca tactgcggaa ctcctagccg cttgttttgc tcgcagcagg tctggagcaa   6480
acattatcgg gactgataac tctgttgtcc tatcccgcaa atatacatcg tttccatggc   6540
tgctaggctg tgctgccaac tggatcctgc gcgggacgtc ctttgtttac gtcccgtcgg   6600
cgctgaatcc tgcggacgac ccttctcggg gtcgcttggg actctctcgt ccccttctcc   6660
gtctgccgtt ccgaccgacc acggggcgca cctctcttta cgcggactcc ccgtctgtgc   6720
cttctcatct gccggaccgt gtgcacttcg cttacctct gcacgtcgca tggagaccac    6780
cgtgaacgcc caccaaatat tgcccaaggt cttacataag aggactcttg gactctcagc   6840
aatgtcaacg accgaccttg aggcatactt caaagactgt ttgtttaaag actgggagga   6900
gttgggggag gagattaggt taaaggtctt tgtactagga ggctgtaggc ataaattggt   6960
ctgcgcacca gcaccatggc gcaatcacta gagcggggta cctttaagac caatgactta   7020
caaggcagct gtagatctta gccactttt aaaagaaaag gggggactgg aagggctaat    7080
tcactcccaa cgaagacaag atctgctttt tgcttgtact gggtctctct ggttagacca   7140
gatctgagcc tgggagctct ctggctaact agggaaccca ctgcttaagc ctcaataaag   7200
cttgccttga gtgcttcaag tagtgtgtgc ccgtctgttg tgtgactctg gtaactagag   7260
atccctcaga ccctttagt cagtgtggaa aatctctagc agtagtagtt catgtcatct     7320
tattattcag tatttataac ttgcaaagaa atgaatatca gagagtgaga ggaacttgtt   7380
tattgcagct tataatggtt acaaataaag caatagcatc acaaatttca caaataaagc   7440 attttttca ctgcattcta gttgtggttt gtccaaactc atcaatgtat cttatcatgt     7500
ctggctctag ctatcccgcc cctaactccg cccatcccgc cctaactcc gcccagttcc    7560 gcccattctc cgccccatgg ctgactaatt tttttattt atgcagaggc cgaggccgga    7620
tcccttgagt ggctttcatc ctggagcaga cttttgcagtc tgtggactgc aacacaacat   7680 tgccttatg tgtaactctt ggctgaagct cttacaccaa tgctggggga catgtacctc     7740
ccaggggccc aggaagacta cgggaggcta caccaacgtc aatcagaggg gcctgtgtag    7800
ctaccgataa gcggaccctc aagagggcat tagcaatagt gtttataagg cccccttgtt    7860
aattcttgaa gacgaaaggg cctcgtgata cgcctatttt tataggttaa tgtcatgata    7920
ataatggttt cttagacgtc aggtggcact tttcggggaa atgtgcgcgg aaccccctatt   7980 tgtttatttt tctaaataca ttcaaatatg tatccgctca tgagacaata accctgataa    8040
atgcttcaat aatattgaaa aaggaagagt atgagtattc aacatttccg tgtcgccctt    8100 attcccttt ttgcggcatt ttgccttcct gttttttgctc acccagaaac gctggtgaaa    8160
gtaaaagatg ctgaagatca gttgggtgca cgagtgggtt acatcgaact ggatctcaac    8220
agcggtaaga tccttgagag ttttcgcccc gaagaacgtt ttccaatgat gagcactttt   8280
aaagttctgc tatgtggcgc ggtattatcc cgtgttgacg ccgggcaaga gcaactcggt   8340
cgccgcatac actattctca gaatgacttg gttgagtact caccagtcac agaaaagcat   8400
cttacggatg gcatgacagt aagagaatta tgcagtgctg ccataaccat gagtgataac   8460
actgcggcca acttacttct gacaacgatc ggaggaccga aggagctaac cgcttttttg   8520
cacaacatgg gggatcatgt aactcgcctt gatcgttggg aaccggagct gaatgaagcc   8580
ataccaaacg acgagcgtga ccacgatg cctgcagcaa tggcaacaac gttgcgcaaa     8640
ctattaactg gcgaactact tactctagct tcccggcaac aattaataga ctggatggag   8700
gcggataaag ttgcaggacc acttctgcgc tcggcccttc cggctggctg gtttattgct   8760
```

```
gataaatctg gagccggtga gcgtgggtct cgcggtatca ttgcagcact ggggccagat    8820
ggtaagccct cccgtatcgt agttatctac acgacgggga gtcaggcaac tatggatgaa    8880
cgaaatagac agatcgctga gataggtgcc tcactgatta agcattggta actgtcagac    8940
caagttract catatatact ttagattgat ttaaaacttc atttttaatt taaaaggatc    9000
taggtgaaga tccttttga taatctcatg accaaaatcc cttaacgtga gttttcgttc    9060
cactgagcgt cagaccccgt agaaaagatc aaaggatctt cttgagatcc ttttttctg    9120 cgcgtaatct gctgcttgca acaaaaaaaa ccaccgctac cagcggtggt ttgtttgccg    9180
gatcaagagc taccaactct ttttccgaag gtaactggct tcagcagagc gcagatacca    9240
aatactgtcc ttctagtgta gccgtagtta ggccaccact tcaagaactc tgtagcaccg    9300
cctacatacc tcgctctgct aatcctgtta ccagtggctg ctgccagtgg cgataagtcg    9360
tgtcttaccg ggttggactc aagacgatag ttaccggata aggcgcagcg gtcgggctga    9420
acggggggtt cgtgcacaca gcccagcttg gagcgaacga cctacaccga actgagatac    9480
ctacagcgtg agcattgaga aagcgccacg cttcccgaag ggagaaaggc ggacaggtat    9540
ccggtaagcg gcagggtcgg aacaggagag cgcacgaggg agcttccagg gggaaacgcc    9600
tggtatcttt atagtcctgt cgggtttcgc cacctctgac ttgagcgtcg attttgtga    9660 tgctcgtcag ggggcggag cctatggaaa aacgccagca acgcggcctt tttacggttc    9720 ctggccttt gctggccttt tgaagctgt ccctgatggt cgtcatctac ctgcctggac    9780
agcatggcct gcaacgcggg catcccgatg ccgccggaag cgagaagaat cataatgggg    9840
aaggccatcc agcctcgcgt cg                                              9862
```

<210> SEQ ID NO 36  
<211> LENGTH: 3340  
<212> TYPE: DNA  
<213> ORGANISM: Artificial Sequence  
<220> FEATURE:  
<223> OTHER INFORMATION: donor vector 1, pMK 8B3 anti mFC scFV CoOp  
    ECORV SacII L1R5

<400> SEQUENCE: 36

```
ctaaattgta agcgttaata ttttgttaaa attcgcgtta aattttttgtt aaatcagctc      60 attttttaac caataggccg aaatcggcaa atcccttat aaatcaaaag aatagaccga      120
gatagggttg agtggccgct acagggcgct cccattcgcc attcaggctg cgcaactgtt      180
gggaagggcg tttcggtgcg ggcctcttcg ctattacgcc agctggcgaa aggggggatgt     240 gctgcaaggc gattaagttg gtaacgcca gggttttccc agtcacgacg ttgtaaaacg      300
acggccagtg agcgcgacgt aatacgactc actatagggc gaattgaagg aaggccgtca     360
aggccgcata aataatgatt ttattttgac tgatagtgac ctgttcgttg caacaaattg      420
atgagcaatg cttttttata atgccaactt tgtacaaaaa agctgaacga tatcgccacc      480
atgggcagca cagccattct ggccctgctg ctggcagtgc tgcagggcgt gtcagctcag      540
gtgcagctgc agcagtctgg cgccgaagtg aagaaacccg gcagcagcgt gaaggtgtcc     600
tgcaaggcta gcggcggcac cttcagcagc tacgccattt cttgggtgcg ccaggccct      660 ggacagggcc tggaatggat gggctggatc agcccctaca acggcaacac cgactacgcc     720
cagaaagtgc agggcagagt gaccctgacc accgacacca gcacctccac cgcctacatg     780
gaactgcgga gcctgagaag cgacgacacc gccgtgtact actgtgccac aggcggcgga     840
acctggtaca gcgatctgtg gggcagaggc accctcgtga cagtgtctgc tggcggcgga     900
```

```
ggatctggcg gaggcggaag tggcggggga ggaagcggag cacctgagat cgtgctgacc      960
cagagcccta gcacactgag cgccagcgtg ggcgacagag tgtccatcac ctgtagagcc     1020
agccagagca tcggaggcag cctggcctgg tatcagcaga agcctggcaa ggcccccaag     1080
ctgctgatct ctgaggccag caccctggaa agaggcgtgc ccagcagatt tccggcagc     1140
ggctctggca ccgacttcac cctgacaatc agcagcctgc agcccgagga cgtggccacc     1200
tactactgcc agaagtacaa cagcgtgccc ctgaccttcg gcctggcac caaggtggaa     1260
atcaagccgc gggccaactt tgtatacaaa agtggaacga gaaacgtaaa atgatataaa     1320
tatcaatata ttaaattaga ttttgcataa aaaacagact acataatact gtaaaacaca     1380
acatatccag tcactatgaa tcaactactt agatggtatt agtgacctgt actgggcctc     1440
atgggccttc ctttcactgc ccgctttcca gtcgggaaac ctgtcgtgcc agctgcatta     1500
acatggtcat agctgtttcc ttgcgtattg ggcgctctcc gcttcctcgc tcactgactc     1560
gctgcgctcg gtcgttcggg taaagcctgg ggtgcctaat gagcaaaagg ccagcaaaag     1620
gccaggaacc gtaaaaaggc cgcgttgctg gcgttttccc ataggctccg ccccctgac     1680
gagcatcaca aaaatcgacg ctcaagtcag aggtggcgaa acccgacagg actataaaga     1740
taccaggcgt ttccccctgg aagctccctc gtgcgctctc ctgttccgac cctgccgctt     1800
accggatacc tgtccgcctt tctcccttcg ggaagcgtgg cgctttctca tagctcacgc     1860
tgtaggtatc tcagttcggt gtaggtcgtt cgctccaagc tgggctgtgt gcacgaaccc     1920
cccgttcagc ccgaccgctg cgccttatcc ggtaactatc gtcttgagtc aacccggta     1980
agacacgact tatcgccact ggcagcagcc actggtaaca ggattagcag agcgaggtat     2040
gtaggcggtg ctacagagtt cttgaagtgg tggcctaact acggctacac tagaagaaca     2100
gtatttggta tctgcgctct gctgaagcca gttaccttcg gaaaaagagt tggtagctct     2160
tgatccggca acaaaccac cgctggtagc ggtggttttt tgttgcaa gcagcagatt     2220
acgcgcagaa aaaaggatc tcaagaagat cctttgatct tttctacggg gtctgacgct     2280
cagtggaacg aaaactcacg ttaagggatt ttggtcatga gattatcaaa aaggatcttc     2340
acctagatcc ttttaaatta aaaatgaagt tttaaatcaa tctaaagtat atatgagtaa     2400
acttggtctg acagttatta gaaaaattca tccagcagac gataaaacgc aatacgctgg     2460
ctatccggtg ccgcaatgcc atacagcacc agaaaacgat ccgcccattc gccgccagt     2520
tcttccgcaa tatcacgggt ggccagcgca atatcctgat aacgatccgc cacgcccaga     2580
cggccgcaat caataaagcc gctaaaacgg ccatttttcca ccataatgtt cggcaggcac     2640
gcatcaccat gggtcaccac cagatcttcg ccatccggca tgctcgcttt cagacgcgca     2700
aacagctctg ccggtgccag gccctgatgt tcttcatcca gatcatcctg atccaccagg     2760
cccgcttcca tacgggtacg cgcacgttca atacgatgtt tcgcctgatg atcaaacgga     2820
caggtcgccg ggtccagggt atgcagacga cgcatggcat ccgccataat gctcactttt     2880
tctgccggcg ccagatggct agacagcaga tcctgacccg gcacttcgcc cagcagcagc     2940
caatcacggc ccgcttcggt caccacatcc agcaccgccg cacacggaac accggtggtg     3000
gccagccagc tcgacgcgc cgcttcatcc tgcagctcgt tcagcgcacc gctcagatcg     3060
gttttcacaa acagcaccgg acgaccctgc gcgctcagac gaaacaccgc cgcatcagag     3120
cagccaatgg tctgctgcgc ccaatcatag ccaaacagac gttccaccca cgctgccggg     3180
ctacccgcat gcaggccatc ctgttcaatc atactcttcc ttttttcaata ttattgaagc     3240
atttatcagg gttattgtct catgagcgga tacatatttg aatgtattta gaaaaataaa     3300
```

```
caaatagggg ttccgcgcac atttccccga aaagtgccac            3340
```

<210> SEQ ID NO 37
<211> LENGTH: 2779
<212> TYPE: DNA
<213> ORGANISM: Artificial Sequence
<220> FEATURE:
<223> OTHER INFORMATION: donor vector 2, pMK hCD8a scaffold TN L5 L2

<400> SEQUENCE: 37

```
ctaaattgta agcgttaata ttttgttaaa attcgcgtta aattttttgtt aaatcagctc     60
attttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa aggggggatgt    240
gctgcaaggc gattaagttg ggtaacgcca gggttttccc agtcacgacg ttgtaaaacg    300
acggccagtg agcgcgacgt aatacgactc actatagggc gaattgaagg aaggccgtca    360
aggccgcata ataatgattt tattttgac tgatagtgac ctgttcgttg caacaaattg    420
atgagcaatg cttttttata tgcccaact ttgtatacaa aagtgccccg cggacaacaa    480
cccctgcccc cagacctcct accccagccc ctacaattgc cagccagcct ctgagcctga    540
ggcccgagcc ttgtagacct gctgctggcg gagccgtgca caccgagga ctggatttcg    600
cctgcgacat ctacatctgg gcccctctgg ccggcacatg tggcgtgctg ctgctgagcc    660
tcgtgatcac cctgtactgc ggctccacca gcggctccgg caagcccggc tctggcgagg    720
gctccaccag cggcgactac aaggacgacg atgacaagta ataggatatc ggttcagctt    780
tcttgtacaa agttggcatt ataagaaagc attgcttatc aatttgttgc aacgaacagg    840
tcactatcag tcaaaataaa atcattattt ctgggcctca tgggccttcc tttcactgcc    900
cgcttttccag tcgggaaacc tgtcgtgcca gctgcattaa catggtcata gctgtttcct    960
tgcgtattgg gcgctctccg cttcctcgct cactgactcg ctgcgctcgg tcgttcgggt   1020
aaagcctggg gtgcctaatg agcaaaaggc cagcaaaagg ccaggaaccg taaaaaggcc   1080
gcgttgctgg cgttttttcca taggctccgc cccctgacg agcatcacaa aaatcgacgc   1140
tcaagtcaga ggtggcgaaa cccgacagga ctataaagat accaggcgtt tcccctggaa   1200
agctccctcg tgcgctctcc tgttccgacc ctgccgctta ccggatacct gtccgccttt   1260
ctcccttcgg gaagcgtggc gctttctcat agctcacgct gtaggtatct cagttcggtg   1320
taggtcgttc gctccaagct gggctgtgtg cacgaacccc ccgttcagcc cgaccgctgc   1380
gccttatccg gtaactatcg tcttgagtcc aacccggtaa gacacgactt atcgccactg   1440
gcagcagcca ctggtaacag gattagcaga gcgaggtatg taggcggtgc tacagagttc   1500
ttgaagtggt ggcctaacta cggctacact agaagaacag tatttggtat ctgcgctctg   1560
ctgaagccag ttaccttcgg aaaaagagtt ggtagctctt gatccggcaa acaaaccacc   1620
gctggtagcg gtggttttt tgtttgcaag cagcagatta cgcgcagaaa aaaggatct   1680
caagaagatc ctttgatctt ttctacgggg tctgacgctc agtggaacga aaactcacgt   1740
taagggattt tggtcatgag attatcaaaa aggatcttca cctagatcct ttttaattaa   1800
aaatgaagtt ttaaatcaat ctaaagtata tatgagtaaa cttggtctga cagttattag   1860
aaaaattcat ccagcagacg ataaaacgca atacgctggc tatccggtgc cgcaatgcca   1920
tacagcacca gaaaacgatc cgcccattcg ccgcccagtt cttccgcaat atcacgggtg   1980
```

```
gccagcgcaa tatcctgata acgatccgcc acgcccagac ggccgcaatc aataaagccg    2040
ctaaaacggc catttccac cataatgttc ggcaggcacg catcaccatg ggtcaccacc     2100
agatcttcgc catccggcat gctcgctttc agacgcgcaa acagctctgc cggtgccagg    2160
ccctgatgtt cttcatccag atcatcctga tccaccaggc ccgcttccat acgggtacgc    2220
gcacgttcaa tacgatgttt cgcctgatga tcaaacggac aggtcgccgg gtccagggta    2280
tgcagacgac gcatggcatc cgccataatg ctcacttttt ctgccggcgc cagatggcta    2340
gacagcagat cctgacccgg cacttcgccc agcagcagc aatcacggcc cgcttcggtc     2400
accacatcca gcaccgccgc acacggaaca ccggtggtgg ccagccagct cagacgcgcc    2460
gcttcatcct gcagctcgtt cagcgcaccg ctcagatcgg ttttcacaaa cagcaccgga    2520
cgaccctgcg cgctcagacg aaacaccgcc gcatcagagc agccaatggt ctgctgcgcc    2580
caatcatagc caaacagacg ttccacccac gctgccgggc tacccgcatg caggccatcc    2640
tgttcaatca tactcttcct tttcaatat tattgaagca tttatcaggg ttattgtctc     2700
atgagcggat acatattga atgtatttag aaaataaac aatagggt ccgcgcaca         2760 tttccccgaa aagtgccac                                                 2779
```

<210> SEQ ID NO 38
<211> LENGTH: 9344
<212> TYPE: DNA
<213> ORGANISM: Artificial Sequence
<220> FEATURE:
<223> OTHER INFORMATION: Final vector used for lentiviral production,
      pLV4301G 8B3 scFV mIgG hCD8 flag

<400> SEQUENCE: 38

```
cgataaccct aattcgatag catatgcttc ccgttgggta acatatgcta ttgaattagg      60
gttagtctgg atagtatata ctactacccg ggaagcatat gctacccgtt tagggttcac    120
cggtgatgcc ggccacgatg cgtccggcgt agaggatcta atgtgagtta gctcactcat    180
taggcacccc aggctttaca ctttatgctt ccggctcgta tgttgtgtgg aattgtgagc    240
ggataacaat ttcacacagg aaacagctat gaccatgatt acgccaagcg cgcaattaac    300
cctcactaaa gggaacaaaa gctggagctg caagcttaat gtagtcttat gcaatactct    360
tgtagtcttg caacatggta acgatgagtt agcaacatgc cttacaagga gagaaaaagc    420
accgtgcatg ccgattggtg gaagtaaggt ggtacgatcg tgccttatta ggaaggcaac    480
agacgggtct gacatggatt ggacgaacca ctgaattgcc gcattgcaga gatattgtat    540
ttaagtgcct agctcgatac ataaacgggt ctctctggtt agaccagatc tgagcctggg    600
agctctctgg ctaactaggg aacccactgc ttaagcctca ataaagcttg ccttgagtgc    660
ttcaagtagt gtgtgcccgt ctgttgtgtg actctggtaa ctagagatcc ctcagaccct    720
tttagtcagt gtggaaaatc tctagcagtg gcgcccgaac agggacttga aagcgaaagg    780
gaaaccagag gagctctctc gacgcaggac tcggcttgct gaagcgcgca cggcaagagg    840
cgaggggcgg cgactggtga gtacgccaaa aattttgact agcggaggct agaaggagag    900
agatgggtgc gagagcgtca gtattaagcg gggagaatt agatcgcgat gggaaaaaat    960
tcggttaagg ccagggggaa agaaaaaata taaattaaaa catatagtat gggcaagcag   1020
ggagctagaa cgattcgcag ttaatcctgg cctgttagaa acatcagaag gctgtagaca   1080
aatactggga cagctacaac catcccttca gacaggatca gaagaactta gatcattata   1140
taatacagta gcaaccctct attgtgtgca tcaaaggata gagataaaag acaccaagga   1200
```

```
agctttagac aagatagagg aagagcaaaa caaaagtaag accaccgcac agcaagcggc   1260
cgctgatctt cagacctgga ggaggagata tgagggacaa ttggagaagt gaattatata   1320
aatataaagt agtaaaaatt gaaccattag gagtagcacc caccaaggca aagagaagag   1380
tggtgcagag agaaaaaaga gcagtgggaa taggagcttt gttccttggg ttcttgggag   1440
cagcaggaag cactatgggc gcagcgtcaa tgacgctgac ggtacaggcc agacaattat   1500
tgtctggtat agtgcagcag cagaacaatt tgctgagggc tattgaggcg caacagcatc   1560
tgttgcaact cacagtctgg ggcatcaagc agctccaggc aagaatcctg gctgtggaaa   1620
gatacctaaa ggatcaacag ctcctgggga tttggggttg ctctggaaaa ctcatttgca   1680
ccactgctgt gccttggaat gctagttgga gtaataaatc tctggaacag atttggaatc   1740
acacgacctg gatggagtgg gacagagaaa ttaacaatta cacaagctta atacactcct   1800
taattgaaga atcgcaaaac cagcaagaaa agaatgaaca agaattattg gaattagata   1860
aatgggcaag tttgtggaat tggtttaaca taacaaattg gctgtggtat ataaaattat   1920
tcataatgat agtaggaggc ttggtaggtt taagaatagt ttttgctgta ctttctatag   1980
tgaatagagt taggcaggga tattcaccat tatcgtttca gacccacctc ccaaccccga   2040
ggggacccga caggcccgaa ggaatagaag aagaaggtgg agagagagac agagacagat   2100
ccattcgatt agtgaacgga tctcgacggt atcggtttta aagaaaaggg gggattggg   2160
gggtacagtg caggggaaag aatagtagac ataatagcaa cagacataca aactaaagaa   2220
ttacaaaaac aaattacaaa aattcaaaat tttatcgatt ttatttagtc tccagaaaaa   2280
gggggggaatg aaagacccca cctgtaggtt tggcaagcta gcttaagtaa cgccattttg   2340
caaggcatgg aaaatacata actgagaata gagaagttca gatcaaggtt aggaacagag   2400
agacagcaga atatgggcca aacaggatat ctgtggtaag cagttcctgc cccggctcag   2460
ggccaagaac agatggtccc cagatgcggt cccgccctca gcagtttcta gagaaccatc   2520
agatgtttcc agggtgcccc aaggacctga aatgaccctg tgccttattt gaactaacca   2580
atcagttcgc ttctcgcttc tgttcgcgcg cttctgctcc ccgagctcaa taaaagagcc   2640
cacaacccct cactcggcgc gccagtcctc cgatagactg cgtcgcccgg gtaccgatat   2700
caccaacttt gtacaaaaaa gctgaacgat atcgccacca tgggcagcac agccattctg   2760
gccctgctgc tggcagtgct gcagggcgtg tcagctcagg tgcagctgca gcagtctggc   2820
gccgaagtga agaaacccgg cagcagcgtg aaggtgtcct gcaaggctag cggcggcacc   2880
ttcagcagct acgccatttc ttgggtgcgc caggcccctg gacagggcct ggaatggatg   2940
ggctggatca gcccctacaa cggcaacacc gactacgccc agaaagtgca gggcagagtg   3000
accctgacca ccgacaccag cacctccacc gcctacatgg aactgcggag cctgagaagc   3060
gacgacaccg ccgtgtacta ctgtgccaca ggcggcggaa cctggtacag cgatctgtgg   3120
ggcagaggca cctcgtgac agtgtctgct ggcggcggag gatctggcgg aggcggaagt   3180
ggcgggggag gaagcggagc acctgagatc gtgctgaccc agagccctag cacactgagc   3240
gccagcgtgg gcgacagagt gtccatcacc tgtagagcca gcagagcat cggaggcagc   3300
ctggcctggt atcagcagaa gcctggcaag gcccccaagc tgctgatctc tgaggccagc   3360
accctggaaa gaggcgtgcc cagcagattt tccggcagcg gctctggcac cgacttcacc   3420
ctgacaatca gcagcctgca gcccgaggac gtggccacct actactgcca gaagtacaac   3480
agcgtgcccc tgaccttcgg ccctggcacc aaggtggaaa tcaagccgcg ggccaacttt   3540
gtatacaaaa gttgggccgcg gacaacaacc cctgccccca gacctcctac cccagcccct   3600
```

```
acaattgcca gccagcctct gagcctgagg cccgaggctt gtagacctgc tgctggcgga   3660
gccgtgcaca ccagaggact ggatttcgcc tgcgacatct acatctgggc ccctctggcc   3720
ggcacatgtg gcgtgctgct gctgagcctc gtgatcaccc tgtactgcgg ctccaccagc   3780
ggctccggca agcccggctc tggcgagggc tccaccagcg gcgactacaa ggacgacgat   3840
gacaagtaat aggatatcgg ttcagctttc ttgtacaaag ttgggattcg agttaattaa   3900
gttaacgaat tcccccctc tccctccccc ccctaacg ttactggccg aagccgcttg     3960
gaataaggcc ggtgtgcgtt tgtctatatg ttattttcca ccatattgcc gtcttttggc   4020
aatgtgaggg cccggaaacc tggccctgtc ttcttgacga gcattcctag ggtctttcc    4080 cctctcgcca aggaatgca aggtctgttg aatgtcgtga aggaagcagt tcctctggaa    4140
gcttcttgaa gacaaacaac gtctgtagcg acccttgca ggcagcggaa ccccccacct    4200
ggcgacaggt gcctctgcgg ccaaaagcca cgtgtataag atacacctgc aaaggcggca   4260
caaccccagt gccacgttgt gagttggata gttgtggaaa gagtcaaatg gctctcctca   4320
agcgtattca caaggggct gaaggatgcc cagaaggtac cccattgtat gggatctgat    4380
ctggggcctc ggtgcacatg ctttacatgt gtttagtcga ggttaaaaaa cgtctaggcc   4440
ccccgaacca cggggacgtg gttttccttt gaaaaacacg atgataatat ggccacaacc   4500
atgggaggcg gaagcggcgg aggctcccct cgaggcacca tggtgagcaa gggcgaggag   4560
ctgttcaccg gggtggtgcc catcctggtc gagctggacg gcgacgtaaa cggccacaag   4620
ttcagcgtgt ccggcgaggg cgagggcgat gccacctacg gcaagctgac cctgaagttc   4680
atctgcacca ccggcaagct gcccgtgccc tggcccaccc tcgtgaccac cctgacctac   4740
ggcgtgcagt gcttcagccg ctaccccgac cacatgaagc agcacgactt cttcaagtcc   4800
gccatgcccg aaggctacgt ccaggagcgc accatcttct tcaaggacga cggcaactac   4860
aagacccgcg ccgaggtgaa gttcgagggc gacaccctgg tgaaccgcat cgagctgaag   4920
ggcatcgact tcaaggagga cggcaacatc ctggggcaca gctggagta caactacaac    4980 agccacaacg tctatatcat ggccgacaag cagaagaacg gcatcaaggt gaacttcaag   5040
atccgccaca acatcgagga cggcagcgtg cagctcgccg accactacca gcagaacacc   5100
cccatcggcg acggccccgt gctgctgccc gacaaccact acctgagcac ccagtccgcc   5160
ctgagcaaag accccaacga gaagcgcgat cacatggtcc tgctggagtt cgtgaccgcc   5220
gccgggatca ctctcggcat ggacgagctg tacaagtaac gcgtcccggg tctagagcta   5280
gcggtaccat gcattacgta gtcgacgact taattaagct agcctagtgc catttgttca   5340
gtggttcgta gggctttccc ccactgtttg gctttcagtt atatggatga tgtggtattg   5400
ggggccaagt ctgtacagca tcttgagtcc cttttaccg ctgttaccaa ttttcttttg    5460
tctttgggta tacatttaaa ccctaacaaa acaagagat ggggttactc tctaaatttt    5520
atgggttatg tcattggatg ttatgggtcc ttgccacaag aacacatcat acaaaaaatc   5580
aaagaatgtt ttagaaaact tcctattaac aggcctattg attggaaagt atgtcaacga   5640
attgtgggtc ttttgggttt tgctgcccct tttacacaat gtggttatcc tgcgttgatg   5700
cctttgtatg catgtattca atctaagcag gctttcactt tctcgccaac ttacaaggcc   5760
tttctgtgta aacaatacct gaacctttac cccgttgccc ggcaacggcc aggtctgtgc   5820
caagtgtttg ctgacgcaac ccccactggc tggggcttgg tcatgggcca tcagcgcatg   5880
cgtggaacct tttcggctcc tctgccgatc catactgcgg aactcctagc cgcttgtttt   5940
```

```
gctcgcagca ggtctggagc aaacattatc gggactgata actctgttgt cctatcccgc    6000
aaatatacat cgtttccatg gctgctaggc tgtgctgcca actggatcct gcgcgggacg    6060
tcctttgttt acgtcccgtc ggcgctgaat cctgcggacg acccttctcg gggtcgcttg    6120
ggactctctc gtccccttct ccgtctgccg ttccgaccga ccacggggcg cacctctctt    6180
tacgcggact ccccgtctgt gccttctcat ctgccggacc gtgtgcactt cgcttcacct    6240
ctgcacgtcg catggagacc accgtgaacg cccaccaaat attgcccaag gtcttacata    6300
agaggactct tggactctca gcaatgtcaa cgaccgacct tgaggcatac ttcaaagact    6360
gtttgtttaa agactgggag gagttggggg aggagattag gttaaaggtc tttgtactag    6420
gaggctgtag gcataaattg gtctgcgcac cagcaccatg gcgcaatcac tagagcgggg    6480
tacctttaag accaatgact acaaggcag ctgtagatct tagccacttt ttaaaagaaa     6540
agggggact ggaagggcta attcactccc aacgaagaca agatctgctt tttgcttgta     6600
ctgggtctct ctggttagac cagatctgag cctgggagct ctctggctaa ctagggaacc    6660
cactgcttaa gcctcaataa agcttgcctt gagtgcttca agtagtgtgt gcccgtctgt    6720
tgtgtgactc tggtaactag agatccctca gaccctttta gtcagtgtgg aaaatctcta    6780
gcagtagtag ttcatgtcat cttattattc agtatttata acttgcaaag aaatgaatat    6840
cagagagtga gaggaacttg tttattgcag cttataatgg ttacaaataa agcaatagca    6900
tcacaaattt cacaaataaa gcattttttt cactgcattc tagttgtggt ttgtccaaac    6960
tcatcaatgt atcttatcat gtctggctct agctatcccg ccccctaactc cgcccatccc    7020
gcccctaact ccgcccagtt ccgcccattc tccgccccat ggctgactaa ttttttttat    7080
ttatgcagag gccgaggccg gatcccttga gtggctttca tcctggagca gactttgcag    7140
tctgtggact gcaacacaac attgccttta tgtgtaactc ttggctgaag ctcttacacc    7200
aatgctgggg gacatgtacc tcccaggggc ccaggaagac tacgggaggc tacaccaacg    7260
tcaatcagag gggcctgtgt agctaccgat aagcggaccc tcaagagggc attagcaata    7320
gtgtttataa ggccccctg ttaattcttg aagacgaaag ggcctcgtga tacgcctatt    7380
tttataggtt aatgtcatga taataatggt ttcttagacg tcaggtggca cttttcgggg    7440
aaatgtgcgc ggaaccccta tttgtttatt tttctaaata cattcaaata tgtatccgct    7500
catgagacaa taaccctgat aaatgcttca ataatattga aaaggaaga gtatgagtat    7560
tcaacatttc cgtgtcgccc ttattccctt ttttgcggca ttttgccttc ctgttttgc     7620
tcacccagaa acgctggtga agtaaaaga tgctgaagat cagttgggtg cacgagtggg    7680
ttacatcgaa ctggatctca acagcggtaa gatccttgag agttttcgcc ccgaagaacg    7740
ttttccaatg atgagcactt ttaaagttct gctatgtggc gcggtattat cccgtgttga    7800
cgccgggcaa gagcaactcg gtcgccgcat acactattct cagaatgact tggttgagta    7860
ctcaccagtc acagaaaagc atcttacgga tggcatgaca gtaagagaat tatgcagtgc    7920
tgccataacc atgagtgata acactgcggc caacttactt ctgacaacga tcggaggacc    7980
gaaggagcta accgcttttt tgcacaacat ggggatcat gtaactcgcc ttgatcgttg     8040
ggaaccggag ctgaatgaag ccataccaaa cgacgagcgt gacaccacga tgcctgcagc    8100
aatggcaaca acgttgcgca aactattaac tggcgaacta cttactctag cttcccggca    8160
acaattaata gactggatgg aggcggataa agttgcagga ccacttctgc gctcggccct    8220
tccggctggc tggtttattg ctgataaatc tggagccggt gagcgtgggt ctcgcggtat    8280
cattgcagca ctggggccag atggtaagcc ctcccgtatc gtagttatct acacgacggg    8340
```

```
gagtcaggca actatggatg aacgaaatag acagatcgct gagataggtg cctcactgat    8400
taagcattgg taactgtcag accaagttta ctcatatata ctttagattg atttaaaact    8460
tcatttttaa tttaaaagga tctaggtgaa gatcctttt gataatctca tgaccaaaat     8520
cccttaacgt gagttttcgt tccactgagc gtcagacccc gtagaaaaga tcaaaggatc    8580
ttcttgagat ccttttttc tgcgcgtaat ctgctgcttg caaacaaaaa aaccaccgct      8640
accagcggtg tttgtttgc cggatcaaga gctaccaact ctttttccga aggtaactgg      8700
cttcagcaga gcgcagatac caaatactgt ccttctagtg tagccgtagt taggccacca    8760
cttcaagaac tctgtagcac cgcctacata cctcgctctg ctaatcctgt taccagtggc    8820
tgctgccagt ggcgataagt cgtgtcttac cgggttggac tcaagacgat agttaccgga    8880
taaggcgcag cggtcgggct gaacggggg ttcgtgcaca cagcccagct tggagcgaac      8940
gacctacacc gaactgagat acctacagcg tgagcattga gaaagcgcca cgcttcccga    9000
agggagaaag gcggacaggt atccggtaag cggcagggtc ggaacaggag agcgcacgag    9060
ggagcttcca gggggaaacg cctggtatct ttatagtcct gtcgggtttc gccacctctg    9120
acttgagcgt cgatttttgt gatgctcgtc aggggggcgg agcctatgga aaaacgccag    9180
caacgcggcc tttttacggt tcctggcctt ttgctggcct ttttgaagct gtccctgatg    9240
gtcgtcatct acctgcctgg acagcatggc ctgcaacgcg ggcatcccga tgccgccgga    9300
agcgagaaga atcataatgg ggaaggccat ccagcctcgc gtcg                     9344

<210> SEQ ID NO 39
<211> LENGTH: 6924
<212> TYPE: DNA
<213> ORGANISM: Artificial Sequence
<220> FEATURE:
<223> OTHER INFORMATION: pLenti-C-Myc-DDK OX40L

<400> SEQUENCE: 39
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat cgcgttgaca     240
ttgattattg actagttatt aatagtaatc aattacgggg tcattagttc atagcccata     300
tatggagttc cgcgttacat aacttacggt aaatggcccg cctggctgac cgcccaacga     360 ccccccgccca ttgacgtcaa taatgacgta tgttcccata gtaacgccaa tagggacttt   420
ccattgacgt caatgggtgg agtatttacg gtaaactgcc cacttggcag tacatcaagt    480
gtatcatatg ccaagtacgc ccccattga cgtcaatgac ggtaaatggc ccgcctggca     540
ttatgcccag tacatgacct tatgggactt tcctacttgg cagtacatct acgtattagt    600
catcgctatt accatggtga tgcggttttg gcagtacatc aatgggcgtg atagcggtt    660 tgactcacgg ggatttccaa gtctccaccc cattgacgtc aatgggagtt tgttttggca    720
ccaaaatcaa cgggactttc caaaatgtcg taacaactcc gccccattga cgcaaatggg    780
cggtaggcgt gtacggtggg aggtctatat aagcagcgcg ttttgcctgt actgggtctc    840
tctggttaga ccagatctga gcctgggagc tctctggcta actagggaac ccactgctta    900
agcctcaata aagcttgcct tgagtgcttc aagtagtgtg tgcccgtctg ttgtgtgact    960
ctggtaacta gagatccctc agaccctttt agtcagtgtg gaaaatctct agcagtggcg   1020
```

```
cccgaacagg gacttgaaag cgaaagggaa accagaggag ctctctcgac gcaggactcg   1080
gcttgctgaa gcgcgcacgg caagaggcga ggggcggcga ctggtgagta cgccaaaaat   1140
tttgactagc ggaggctaga aggagagaga tgggtgcgag agcgtcagta ttaagcgggg   1200
gagaattaga tcgcgatggg aaaaaattcg gttaaggcca ggggggaaaga aaaaatataa   1260 attaaaacat atagtatggg caagcaggga gctagaacga ttcgcagtta atcctggcct   1320
gttagaaaca tcagaaggct gtagacaaat actgggacag ctacaaccat cccttcagac   1380
aggatcagaa gaacttagat cattatataa tacagtagca accctctatt gtgtgcatca   1440
aaggatagag ataaaagaca ccaaggaagc tttagacaag atagaggaag agcaaaacaa   1500
aagtaagacc accgcacagc aagcggccgg ccgctgatct tcagacctgg aggaggagat   1560
atgagggaca attggagaag tgaattatat aaatataaag tagtaaaaat tgaaccatta   1620
ggagtagcac ccaccaaggc aaagagaaga gtggtgcaga gagaaaaaag agcagtggga   1680
ataggagctt tgttccttgg gttcttggga gcagcaggaa gcactatggg cgcagcgtca   1740
atgacgctga cggtacaggc cagacaatta ttgtctggta tagtgcagca gcagaacaat   1800
ttgctgaggg ctattgaggc gcaacagcat ctgttgcaac tcacagtctg ggcatcaag   1860 cagctccagg caagaatcct ggctgtggaa agatacctaa aggatcaaca gctcctgggg   1920
atttggggtt gctctggaaa actcatttgc accactgctg tgccttggaa tgctagttgg   1980
agtaataaat ctctgaaca gatttggaat cacacgacct ggatggagtg ggacagagaa   2040
attaacaatt acacaagctt aatacactcc ttaattgaag aatcgcaaaa ccagcaagaa   2100
aagaatgaac aagaattatt ggaattagat aaatgggcaa gtttgtggaa ttggtttaac   2160
ataacaaatt ggctgtggta tataaaatta ttcataatga tagtaggagg cttggtaggt   2220
ttaagaatag ttttttgctgt actttctata gtgaatagag ttaggcaggg atattcacca   2280
ttatcgtttc agacccacct cccaaccccg aggggacccg acaggcccga aggaatagaa   2340
gaagaaggtg gagagagaga cagagacaga tccattcgat tagtgaacgg atcggcactg   2400
cgtgcgccaa ttctgcagac aaatggcagt attcatccac aattttaaaa gaaaaggggg   2460
gattgggggg tacagtgcag gggaaagaat agtagacata atagcaacag acatacaaac   2520
taaagaatta caaaaacaaa ttacaaaaat tcaaaatttt cgggtttatt acagggacag   2580
cagagatcca gtttggttag taccgggccc gctctagaca tgtccaatat gaccgccatg   2640
ttgacattga ttattgacta gttattaata gtaatcaatt acgggtcat agttcatag   2700 cccatatatg gagttccgcg ttacataact tacggtaaat ggcccgcctg gctgaccgcc   2760
caacgacccc cgcccattga cgtcaataat gacgtatgtt cccatagtaa cgccaatagg   2820
gactttccat tgacgtcaat gggtggagta tttacggtaa actgcccact ggcagtaca   2880 tcaagtgtat catatgccaa gtccgccccc tattgacgtc aatgacggta aatggcccgc   2940
ctggcattat gcccagtaca tgaccttacg ggactttcct acttggcagt acatctacgt   3000
attagtcatc gctattacca tggtgatgcg gttttggcag tacaccaatg ggcgtggata   3060
gcggtttgac tcacggggat ttccaagtct ccaccccatt gacgtcaatg ggagtttgtt   3120
ttggcaccaa aatcaacggg actttccaaa atgtcgtaat aaccccgccc cgttgacgca   3180
aatgggcggt aggcgtgtac ggtgggaggt ctatataagc agagctcgtt tagtgaaccg   3240
tcagaatttt gtaatacgac tcactatagg gcggccggga attcgtcgac tggatccggt   3300
accgaggaga tctgccgccg cgatcgccat ggaaagggtc caacccctgg aagagaatgt   3360
gggaaatgca gccaggccaa gattcgagag gaacaagcta ttgctggtgg cctctgtaat   3420
```

```
tcagggactg gggctgctcc tgtgcttcac ctacatctgc ctgcacttct ctgctcttca    3480
ggtatcacat cggtatcctc gaattcaaag tatcaaagta caatttaccg aatataagaa    3540
ggagaaaggt ttcatcctca cttcccaaaa ggaggatgaa atcatgaagg tgcagaacaa    3600
ctcagtcatc atcaactgtg atgggtttta tctcatctcc ctgaagggct acttctccca    3660
ggaagtcaac attagccttc attaccagaa ggatgaggag cccctcttcc aactgaagaa    3720
ggtcaggtct gtcaactcct tgatggtggc ctctctgact tacaaagaca agtctactt     3780
gaatgtgacc actgacaata cctccctgga tgacttccat gtgaatggcg agaactgat     3840
tcttatccat caaaatcctg gtgaattctg tgtccttacg cgtacgcggc cgctcgagca    3900
gaaactcatc tcagaagagg atctggcagc aaatgatatc ctggattaca aggatgacga    3960
cgataaggtt taaacggccg ccgcgggtct gtacaagtag gattcgtcga gggacctaat    4020
aacttcgtat agcatacatt atacgaagtt atacatgttt aagggttccg gttccactag    4080
gtacaattcg atatcaagct tatcgataat caacctctgg attacaaaat tgtgaaaga    4140
ttgactggta ttcttaacta tgttgctcct tttacgctat gtggatacgc tgctttaatg    4200
cctttgtatc atgctattgc ttcccgtatg gctttcattt tctcctcctt gtataaatcc    4260
tggttgctgt ctctttatga ggagttgtgg cccgttgtca ggcaacgtgg cgtggtgtgc    4320
actgtgtttg ctgacgcaac ccccactggt tggggcattg ccaccacctg tcagctcctt    4380
tccgggactt tcgctttccc cctccctatt gccacggcgg aactcatcgc cgcctgcctt    4440
gcccgctgct ggacagggc tcggctgttg ggcactgaca attccgtggt gttgtcgggg    4500
aaatcatcgt cctttccttg gctgctcgcc tgtgttgcca cctggattct gcgcgggacg    4560
tccttctgct acgtcccttc ggccctcaat ccagcggacc ttccttcccg cggcctgctg    4620
ccggctctgc ggcctcttcc gcgtcttcgc cttcgccctc agacgagtcg atctccctt    4680
tgggccgcct ccccgcatcg ataccgtcga cctcgatcga gacctagaaa acatggagc    4740
aatcacaagt agcaatacag cagctaccaa tgctgattgt gcctggctag aagcacaaga    4800
ggaggaggag gtgggttttc cagtcacacc tcaggtacct ttaagaccaa tgacttacaa    4860
ggcagctgta gatcttagcc actttttaaa agaaaagggg ggactggaag gctaattca    4920
ctcccaacga agacaagata tccttgatct gtggatctac cacacacaag ctacttccc     4980
tgattggcag aactacacac cagggccagg gatcagatat ccactgacct ttggatggtg    5040
ctacaagcta gtaccagttg agcaagagaa ggtagaagaa gccaatgaag agagaacac    5100
ccgcttgtta caccctgtga gcctgcatgg gatggatgac ccggagagag aagtattaga    5160
gtggaggttt gacagccgcc tagcatttca tcacatggcc cgagagctgc atccggactg    5220
tactgggtct ctctggttag accagatctg agcctgggag ctctctggct aactaggaa     5280
cccactgctt aagcctcaat aaagcttgcc ttgagtgctt caagtagtgt gtgcccgtct    5340
gttgtgtgac tctggtaact agagatccct cagaccctt tagtcagtgt ggaaaatctc     5400
tagcagcatg tgagcaaaag gccagcaaaa ggccaggaac cgtaaaaagg ccgcgttgct    5460
ggcgttttc cataggctcc gcccccctga cgagcatcac aaaaatcgac gctcaagtca    5520
gaggtggcga aacccgacag gactataaag ataccaggcg tttccccctg gaagctccct    5580
cgtgcgctct cctgttccga ccctgccgct taccggatac ctgtccgcct ttctcccttc    5640
gggaagcgtg gcgctttctc atagctcacg ctgtaggtat ctcagttcgg tgtaggtcgt    5700
tcgctccaag ctgggctgtg tgcacgaacc ccccgttcag cccgaccgct gcgccttatc    5760
```

```
cggtaactat cgtcttgagt ccaacccggt aagacacgac ttatcgccac tggcagcagc    5820
cactggtaac aggattagca gagcgaggta tgtaggcgt gctacagagt tcttgaagtg     5880
gtggcctaac tacggctaca ctagaagaac agtatttggt atctgcgctc tgctgaagcc    5940
agttaccttc ggaaaaagag ttggtagctc ttgatccggc aaacaaacca ccgctggtag    6000
cggtggtttt tttgtttgca agcagcagat tacgcgcaga aaaaaggat ctcaagaaga     6060 tcctttgatc ttttctacgg ggtctgacgc tcagtggaac gaaaactcac gttaagggat    6120
tttggtcatg attacgcccc gccctgccac tcatcgcagt actgttgtaa ttcattaagc    6180
attctgccga catggaagcc atcacaaacg gcatgatgaa cctgaatcgc cagcggcatc    6240
agcaccttgt cgccttgcgt ataatatttg cccatggtga aacgggggc gaagaagttg     6300 tccatattgg ccacgtttaa atcaaaactg gtgaaactca cccagggatt ggctgagacg    6360
aaaaacatat tctcaataaa ccctttaggg aataggcca ggttttcacc gtaacacgcc     6420
acatcttgcg aatatatgtg tagaaactgc cggaaatcgt cgtggtattc actccagagc    6480
gatgaaaacg tttcagtttg ctcatggaaa acggtgtaac aagggtgaac actatcccat    6540
atcaccagct caccgtcttt cattgccata cggaactccg gatgagcatt catcaggcgg    6600
gcaagaatgt gaataaaggc cggataaaac ttgtgcttat ttttctttac ggtctttaaa    6660
aaggccgtaa tatccagctg aacggtctgg ttataggtac attgagcaac tgactgaaat    6720
gcctcaaaat gttctttacg atgccattgg gatatatcaa cggtggtata tccagtgatt    6780 ttttctcca tactcttcct ttttcaatat tattgaagca tttatcaggg ttattgtctc     6840
atgagcggat acatatttga atgtatttag aaaaataaac aaatagggt cccgcgcaca     6900 tttccccgaa aagtgccacc tgac                                           6924
```

```
<210> SEQ ID NO 40
<211> LENGTH: 39
<212> TYPE: DNA
<213> ORGANISM: Artificial Sequence
<220> FEATURE:
<223> OTHER INFORMATION: Tel-1b primer

<400> SEQUENCE: 40
cggtttgttt gggtttgggt ttgggtttgg gtttgggtt                           39

<210> SEQ ID NO 41
<211> LENGTH: 39
<212> TYPE: DNA
<213> ORGANISM: Artificial Sequence
<220> FEATURE:
<223> OTHER INFORMATION: Tel-2b primer

<400> SEQUENCE: 41
ggcttgcctt acccttaccc ttaccttac ccttaccct                            39

<210> SEQ ID NO 42
<211> LENGTH: 27
<212> TYPE: DNA
<213> ORGANISM: Artificial Sequence
<220> FEATURE:
<223> OTHER INFORMATION: hgb1 primer

<400> SEQUENCE: 42
gcttctgaca caactgtgtt cactagc                                        27

<210> SEQ ID NO 43
<211> LENGTH: 23
```

```
<212> TYPE: DNA
<213> ORGANISM: Artificial Sequence
<220> FEATURE:
<223> OTHER INFORMATION: hgb2 primer

<400> SEQUENCE: 43
caccaacttc atccacgttc acc                                              23
```